US012447207B2

(12) United States Patent
Liu et al.

(10) Patent No.: US 12,447,207 B2
(45) **Date of Patent: *Oct. 21, 2025**

(54) HUMAN CYTOMEGALOVIRUS gB POLYPEPTIDE

(71) Applicant: Pfizer Inc., New York, NY (US)

(72) Inventors: Yuhang Liu, South Glastonbury, CT (US); Ye Che, Niantic, CT (US); Xiaoyuan Sherry Chi, Tenafly, NJ (US); Philip Ralph Dormitzer, Sherborn, MA (US); Jennifer Anne Nicki, Gales Ferry, CT (US); Xiaojie Yao, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/506,578

(22) Filed: Nov. 10, 2023

(65) Prior Publication Data

US 2024/0100153 A1 Mar. 28, 2024

Related U.S. Application Data

(63) Continuation of application No. 17/350,008, filed on Jun. 17, 2021, now Pat. No. 11,857,622.

(60) Provisional application No. 63/208,457, filed on Jun. 8, 2021, provisional application No. 63/041,945, filed on Jun. 21, 2020.

(51) Int. Cl.

| | |
|---|---|
| ***A61K 39/245*** | (2006.01) |
| ***C07K 14/045*** | (2006.01) |
| ***C12N 7/00*** | (2006.01) |

(52) U.S. Cl.

CPC .......... *A61K 39/245* (2013.01); *C07K 14/045* (2013.01); *C12N 7/00* (2013.01); *C12N 2710/16134* (2013.01)

(58) Field of Classification Search

CPC .... A61K 39/245; A61K 39/12; C07K 14/045; C07K 14/005; C12N 7/00; C12N 2710/16134; C12N 2710/16122; A61P 31/22

See application file for complete search history.

(56) References Cited

U.S. PATENT DOCUMENTS

| | | | | |
|---|---|---|---|---|
| 11,857,622 | B2 | 1/2024 | Liu et al. | |
| 2013/0216613 | A1 | 8/2013 | Baudoux et al. | |
| 2019/0314493 | A1 * | 10/2019 | Ciaramella | C12N 7/00 |

OTHER PUBLICATIONS

Zhu Y, Shen R, Vuong I, Reynolds RA, Shears MJ, Yao ZC, Hu Y, Cho WJ, Kong J, Reddy SK, Murphy SC, Mao HQ. Multi-step screening of DNA/lipid nanoparticles and co-delivery with siRNA to enhance and prolong gene expression. Nat Commun. Jul. 25, 2022;13(1):4282. (Year: 2022).*

Quagliarini E, Wang J, Renzi S, Cui L, Digiacomo L, Ferri G, Pesce L, De Lorenzi V, et, al. Mechanistic Insights into the Superior DNA Delivery Efficiency of Multicomponent Lipid Nanoparticles: An In Vitro and In Vivo Study. ACS Appl Mater Interfaces. Dec. 28, 2022;14(51):56666-56677. Epub Dec. 16, 2022. (Year: 2022).*

Cárdenas M, Campbell RA, Yanez Arteta M, Lawrence MJ, Sebastiani F. Review of structural design guiding the development of lipid nanoparticles for nucleic acid delivery. Curr Op Colloid & Interface Sci. vol. 66, 2023:101705, 1-16. (Year: 2023).*

Brown DW, Wee P, Bhandari P, Bukhari A, Grin L, Vega H, Hejazi M, Sosnowski D, Ablack J, Clancy EK, Pink D, Kumar J, Solis Ares MP, Lamb S, Quevedo R, et al. Safe and effective in vivo delivery of DNA and RNA using proteolipid vehicles. Cell. Sep. 19, 2024;187(19):5357-5375.e24. Epub Sep. 10, 2024. (Year: 2024).*

Filipovich et al., Biochemical Bases of Human Life; Moscow, VLADOS Humanitarian Publishing Center 2005, pp. 49-50 (English translation).

Pakula & Sauer, "Genetic Analysis of Protein Stability and Function", Annual Review of Genetics 23:289-310 (1989).

* cited by examiner

*Primary Examiner* — Rachel B Gill

(74) *Attorney, Agent, or Firm* — Rebecca Wright

(57) ABSTRACT

Polypeptides and cytomegalovirus (CMV) antigens that include at least two introduced amino acid mutations relative to the amino acid sequence of the wild-type HCMV glycoprotein B (gB). For example, polypeptides stabilized in a conformation alternative to the gB postfusion conformation. Compositions including the polypeptides and uses thereof.

20 Claims, 79 Drawing Sheets

Specification includes a Sequence Listing.

2D projections from a postfusion gB structure 2D class averages

FIG. 2

```
1   MESRIWCLVV CVNLCIVCLG AAVSSSSTRG TSATHSHHSS HTTSAAHSRS GSVSQRVTSS
    MESRIWCLVV CVNLCIVCLG AAVSSSSTRG TSATHSHHSS HTTSAAHSRS GSVSQRVTSS

61  QTVSHGVNET IYNTTLKYGD VVGVNTTKYP YRVCSMAQGT DLIRFERNIV CTSMKPINED
    QTVSHGVNET IYNTTLKYGD VVGVNTTKYP YRVCSMAQGT DLIRFERNIV CTSMKPINED

121 LDEGIMVVYK RNIVAHTFKV RVYQKVLTFR RSYAYIHTTY LLGSNTEYVA PPMWEIHHIN
    LDEGIMVVYK RNIVAHTFKV RVYQKVLTFR RSYAYIHTTY LLGSNTEYVA PPMWEIHHIN

181 SHSQCYSSYS RVIAGTVFVA YHRDSYENKT MQLMPDDYSN THSTRYVTV K DQWHSRGSTW
    SHSQCYSSYS RVIAGTVFVA YHRDSYENKT MQLMPDDYSN THSTRYVTVK DQWHSRGSTW

241 LYRETCNLNC MVTITTARSK YPYHFFATST GDVVDISPFY NGTNRNASYF GENADKFFIF
    LYRETCNLNC MVTITTARSK YPYHFFATST GDVVDISPFY NGTNRNASYF GENADKFFIF

301 PNYTIVSDFG RPNSALETHR LVAFLERADS VISWDIQDEK NVTCQLTFWE ASERTIRSEA
    PNYTIVSDFG RPNSALETHR LVAFLERADS VISWDIQDEK NVTCQLTFWE ASERTIRSEA

361 EDSYHFSSAK MTATFLSKKQ EVNMSDSALD CVRDEAINKL QQIFNTSYNQ TYEKYGNVSV
    EDSYHFSSAK MTATFLSKKQ EVNMSDSALD CVRDEAINKL QQIFNTSYNQ TYEKYGNVSV

421 FETTGGLVVF WQGIKQKSLV ELERLANRSS LNLTHNRTKR STDGNNATHL SNMESVHNLV
    FETTGGLVVF WQGIKQKSLV ELERLANRSS LNLTHNRTKR STDGNNATHL SNMESVHNLV

481 YAQLQFTYDT LRGYINRALA QIAEAWCVDQ RRTLEVFKEL SKINPSAILS AIYNKPIAAR
    YAQLQFTYDT LRGYINRALA QIAEAWCVDQ RRTLEVFKEL SKINPSAILS AIYNKPIAAR

541 FMGDVLGLAS CVTINQTSVK VLRDMNVKES PGRCYSRPVV IFNFANSSYV QYGQLGEDNE
    FMGDVLGLAS CVTINQTSVK VLRDMNVKES PGRCYSRPVV IFNFANSSYV QYGQLGEDNE

601 ILLGNHRTEE CQLPSLKIFI AGNSAYEYVD YLFKRMIDLS SISTVDSMIA LDIDPLENTD
    ILLGNHRTEE CQLPSLKIFI AGNSAYEYVD YLFKRMIDLS SISTVDSMIA LDIDPLENTD

661 FRVLELYSQK ELRSSNVFDL EEIMREFNSY KQRVKYVEDK VVDPLPPYLK GLDDLMSGLG
    FRVLELYSQK ELRSSNVFDL EEIMREFNSY KQRVKYVEDK VVDPLPPYLK GLDDLMSGLG

721 AAGKAVGVAI GAVGGAVASV VEGVATFLKN PFGAFTIILV AIAVVIIIYL IYTRQRRLCM
    AAGKAVGVAI GAVGGAVASV VEGVATFLKN PFGAFTIILV AIAVVIIIYL IYTRQRRLCM

781 QPLQNLFPYL VSADGTTVTS GNTKDTSLQA PPSYEESVYN SGRKGPGPPS SDASTAAPPY
    QPLQNLFPYL VSADGTTVTS GNTKDTSLQA PPSYEESVYN SGRKGPGPPS SDASTAAPPY

841 TNEQAYQMLL ALVRLDAEQR AQQNGTDSLD GQTGT  QDKGQ KPNLLDRLRH RKNGYRHLKD
    TNEQAYQMLL ALVRLDAEQR AQQNGTDSLD GQTGTQDKGQ KPNLLDRLRH RKNGYRHLKD

901 SDEEENV
    SDEEENV
```

Prefusion

Extended Intermediate

Postfusion

FIG. 8

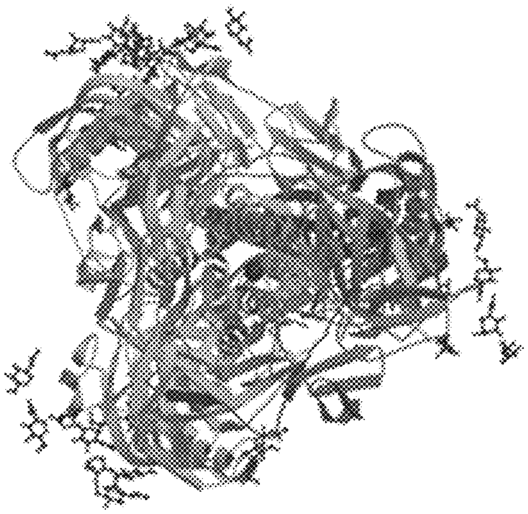

>5CXF:A|PDBID|CHAIN|SEQUENCE
YGDVVGVNTTKYPYRVCSMAQGTDLIRFERNIICTSMKPINEDLDEGIMVVYKRNIVAHTFKVRVYQKVLTFRRSYAGHR
TTYLLGSNTEYVAPPMWEIHHINKFAQCYSSYSRVIGGTVFVAYHRDSHENKTMQLIPDDYSNTHSTRYVTVKDQWHSRG
STATHRETCNLNCMLTITTARSKYPYHFFATSTGDVVYISPFYNGTNRNASYFGENADKFFIFPNYTIVSDFGRPNAAPE
THRLVAFLERADSVISWDIQDEKNVTCQLTFWEASERTIRSEAEDSYHFSSAKMTATFLSKKQEVNMSDSALDCVRDEAI
NKLQQIFNTSYNQTYEKYGNVSVFETSGGLVVFWQGIKQKSLVELERLANRSSLNITHDDDDKSTSDNNTTHLSSMESVH
NLVYAQLQFTYDTLRGYINRALAQIAEAWCVDQRRTLEVFKELSKINPSAILSAIYNKPIAARFMGDVLGLASCVTINQT
SVKVLRDMNVKESPGRCYSRPVVIFNFANSSYVQYGQLGEDNEILLGNHRTEECQLPSLKIFIAGNSAYEYVDYLFKRMI
DLSSISTVDSMIALDIDPLENTDFRVLELYSQKELRSSNVFDLEEIMREFNSYKQRVKYVEDKVVDPLPP (SEQ ID NO: 107)

>5CXF:B|PDBID|CHAIN|SEQUENCE
YGDVVGVNTTKYPYRVCSMAQGTDLIRFERNIICTSMKPINEDLDEGIMVVYKRNIVAHTFKVRVYQKVLTFRRSYAGHR
TTYLLGSNTEYVAPPMWEIHHINKFAQCYSSYSRVIGGTVFVAYHRDSHENKTMQLIPDDYSNTHSTRYVTVKDQWHSRG
STATHRETCNLNCMLTITTARSKYPYHFFATSTGDVVYISPFYNGTNRNASYFGENADKFFIFPNYTIVSDFGRPNAAPE
THRLVAFLERADSVISWDIQDEKNVTCQLTFWEASERTIRSEAEDSYHFSSAKMTATFLSKKQEVNMSDSALDCVRDEAI
NKLQQIFNTSYNQTYEKYGNVSVFETSGGLVVFWQGIKQKSLVELERLANRSSLNITHDDDDKSTSDNNTTHLSSMESVH
NLVYAQLQFTYDTLRGYINRALAQIAEAWCVDQRRTLEVFKELSKINPSAILSAIYNKPIAARFMGDVLGLASCVTINQT
SVKVLRDMNVKESPGRCYSRPVVIFNFANSSYVQYGQLGEDNEILLGNHRTEECQLPSLKIFIAGNSAYEYVDYLFKRMI
DLSSISTVDSMIALDIDPLENTDFRVLELYSQKELRSSNVFDLEEIMREFNSYKQRVKYVEDKVVDPLPP (SEQ ID NO: 108)

>5CXF:C|PDBID|CHAIN|SEQUENCE
YGDVVGVNTTKYPYRVCSMAQGTDLIRFERNIICTSMKPINEDLDEGIMVVYKRNIVAHTFKVRVYQKVLTFRRSYAGHR
TTYLLGSNTEYVAPPMWEIHHINKFAQCYSSYSRVIGGTVFVAYHRDSHENKTMQLIPDDYSNTHSTRYVTVKDQWHSRG
STATHRETCNLNCMLTITTARSKYPYHFFATSTGDVVYISPFYNGTNRNASYFGENADKFFIFPNYTIVSDFGRPNAAPE
THRLVAFLERADSVISWDIQDEKNVTCQLTFWEASERTIRSEAEDSYHFSSAKMTATFLSKKQEVNMSDSALDCVRDEAI
NKLQQIFNTSYNQTYEKYGNVSVFETSGGLVVFWQGIKQKSLVELERLANRSSLNITHDDDDKSTSDNNTTHLSSMESVH
NLVYAQLQFTYDTLRGYINRALAQIAEAWCVDQRRTLEVFKELSKINPSAILSAIYNKPIAARFMGDVLGLASCVTINQT
SVKVLRDMNVKESPGRCYSRPVVIFNFANSSYVQYGQLGEDNEILLGNHRTEECQLPSLKIFIAGNSAYEYVDYLFKRMI
DLSSISTVDSMIALDIDPLENTDFRVLELYSQKELRSSNVFDLEEIMREFNSYKQRVKYVEDKVVDPLPP (SEQ ID NO: 109)

FIG. 9

>HAN13 gi|242345614|gb|GQ221973.1|:81988-84705 Human herpesvirus 5 strain HAN13, complete genome reverse complement
MESRIWCLVVCVNLCIVCLGAAVSSSSTSHATSSAHNGSHTSRTTSAQTRSVSSQHVTSS
EAVSHRANETIYNTTLKYGDVVGVNTTKYPYRVCSMAQGTDLIRFERNIVCTPMKPINED
LDEGIMVVYKRNIVAHTFKVRVYQKVLTFRRSYAYIHTTYLLGSNTEYVAPPMWEIHHIN
RHSQCYSSYSRVIAGTVFVAYHRDSYENKTMQLMLDDYSNTHSTRYVTVKDQWHSRGSTW
LYRETCNLNCMVTITTARSKYPYHFFATSTGDVVDISPFYNGTNRNTSYFGENADKFFIF
PNYTIVSDFGRANSAPETHRLVAFLERADSVISWDIQDEKNVTCQLTFWEASERTIRSEA
EDSYHFSSAKMTATFLSKKQEVNMSDPVLDCVRDQALNKLQQIFNASYNQTYEKYGNVSV
FETTGGLVVFWQGIKQKSLLELERLANSSGVNSTRRTKRSTGNTTTLSLESESVRNVLYA
QLQFTYDTLRSYINRALAQIAEAWCVDQRRTLEVFKELSKINPSAILSAIYNKPIAARFM
GDVLGLASCVTINQTSVKVLRDMNVKESPGRCYSRPVVIFNFVNSSYVQYGQLGEDNEIL
LGNHRTEECQFPSLKIFIAGNSAYEYVDYLFKRMIDLSSISTVDSMIALDIDPLENTDFR
VLELYSQKELRSSNVFDLEEIMREFNSYKQRVKYVEDKVVDPLPPYLKGLDDLMSGLGAA
GKAVGVAIGAVGGAVASVVEGVATFLKNPFGAFTIILVAIAVVIIIYLIYTRQRRLCMQP
LQNLFPYLVSADGTTVTSGNTKDTSLQAPPSYEESVYNSGRKGPGPPSSDASTAAPPYTN
EQAYQMLLALARLDAEQRAQQNGTDSLDGQTGTQDKGQKPNLLDRLRHRKNGYRHLKDSD
EEENV (SEQ ID NO: 110)

>VR1814 gi|270355759|gb|GU179289.1|:81925-84642 Human herpesvirus 5 strain VR1814, complete genome reverse complement
MESRIWCLVVCVNLCIVCLGAVVSSSSTSHATSSAHNGSHTSRTTSAQTRSVSSQHVTSS
EAVSHRANETIYNTTLKYGDVVGVNTTKYPYRVCSMAQGTDLIRFERNIVCTPMKPINED
LDEGIMVVYKRNIVAHTFKVRVYQKVLTFRRSYAYIHTTYLLGSNTEYVAPPMWEIHHIN
RHSQCYSSYSRVIAGTVFVAYHRDSYENKTMQLMLDDYSNTHSTRYVTVKDQWHSRGSTW
LYRETCNLNCMVTITTARSKYPYHFFATSTGDVVDISPFYNGTNRNTSYFGENADKFFIF
PNYTIVSDFGRANSAPETHRLVAFLERADSVISWDIQDEKNVTCQLTFWEASERTIRSEA
EDSYHFSSAKMTATFLSKKQEVNMSDPVLDCVRDQALNKLQQIFNASYNQTYEKYGNVSV
FETTGGLVVFWQGIKQKSLLELERLANSSGVNSTRRTKRSTGNTTTLSLESESVRNVLYA
QLQFTYDTLRSYINRALAQIAEAWCVDQRRTLEVFKELSKINPSAILSAIYNKPIAARFM
GDVLGLASCVTINQTSVKVLRDMNVKESPGRCYSRPVVIFNFVNSSYVQYGQLGEDNEIL
LGNHRTEECQFPSLKIFIAGNSAYEYVDYLFKRMIDLSSISTVDSMIALDIDPLENTDFR
VLELYSQKELRSSNVFDLEEIMREFNSYKQRVKYVEDKVVDPLPPYLKGLDDLMSGLGAA
GKAVGVAIGAVGGAVASVVEGVATFLKNPFGAFTIILVAIAVVIIIYLIYTRQRRLCMQP
LQNLFPYLVSADGTTVTSGNTKDTSLQAPPSYEESVYNSGRKGPGPPSSDASTAAPPYTN
EQAYQMLLALARLDAEQRAQQNGTDSLDGQTGTQDKGQKPNLLDRLRHRKNGYRHLKDSD
EEENV (SEQ ID NO: 111)

FIG. 10

Original HCMV gB (Towne) sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 1)

gB-001 Q98C, G271C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMACGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST CDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 2)

FIG. 10 (Continued)

gB-002 Q98C, I653C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMACGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDCDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 3)

gB-003 G99C, A267C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQCT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFCTST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 4)

FIG. 10 (Continued)

gB-004 T100C, A267C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGC DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFCTST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 5)

gB-005 T100C, S269C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGC DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATCT GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 6)

FIG. 10 (Continued)

gB-006 T100C, L651C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGC DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA CDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 7)

gB-007 D217C, F584C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDCYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNCANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 8)

FIG. 10 (Continued)

gB-008 Y218C, A585C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDCSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFCNSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 9)

gB-009 S219C, D654C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYCN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDICPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 10)

FIG. 10 (Continued)

gB-010 N220C, D652C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSC THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LCIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 11)

gB-011 T221C, D652C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN CHSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LCIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 12)

FIG. 10 (Continued)

gB-012 W240C, G718C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTC
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSCLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 13)

gB-013 Y242C, K710C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LCRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLC GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 14)

FIG. 10 (Continued)

gB-014 Y242C, D714C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LCRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDCLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 15)

gB-015 S269C, I653C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATCT GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDCDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 16)

FIG. 10 (Continued)

gB-016 G271C, P614C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST CDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLCSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 17)

gB-017 S367C, L499C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFCSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRACA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 18)

FIG. 10 (Continued)

gB-018 T372C, W506C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MCATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEACCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 19)

gB-019 F541C, Q669C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 CMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSCK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 20)

FIG. 10 (Continued)

gB-020 L548C, A650C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGCAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIC LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 21)

gB-021 A549C, I653C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLCS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDCDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 22)

FIG. 10 (Continued)

gB-022 S550C, D652C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAC CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LCIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 23)

gB-023 G604C, F661C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLCNHRTEE CQLPSLKIFI AGNSAYEYVD YLFKRMIDLS SISTVDSMIA LDIDPLENTD
661 CRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 24)

FIG. 10 (Continued)

gB-024 N605C, E665C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGCHRTEE CQLPSLKIFI AGNSAYEYVD YLFKRMIDLS SISTVDSMIA LDIDPLENTD
661 FRVLCLYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 25)

gB-025 R607C, S675C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHCTEE CQLPSLKIFI AGNSAYEYVD YLFKRMIDLS SISTVDSMIA LDIDPLENTD
661 FRVLELYSQK ELRSCNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 26)

FIG. 10 (Continued)

gB-026 T608C, D679C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRCEE CQLPSLKIFI AGNSAYEYVD YLFKRMIDLS SISTVDSMIA LDIDPLENTD
661 FRVLELYSQK ELRSSNVFCL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 27)

gB-027 E609C, F678C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTCE CQLPSLKIFI AGNSAYEYVD YLFKRMIDLS SISTVDSMIA LDIDPLENTD
661 FRVLELYSQK ELRSSNVCDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 28)

FIG. 10 (Continued)

gB-028 R673C, S674C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELCCSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 29)

gB-029 N676C, V677C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSCCFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 30)

FIG. 10 (Continued)

gB-030 L680C, E681C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDC CEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 31)

gB-031 I683C, M684C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EECCREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 32)

FIG. 10 (Continued)

gB-032 F687C, N688C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMRECCSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 33)

gB-033 Y690C, K691C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSC CQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 34)

FIG. 10 (Continued)

gB-034 K695C, K724C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVCYVEDK VVDPLPPYLK GLDDLMSGLG
721 AAGCAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 35)

gB-035 T746C, F747C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVACCLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 36)

FIG. 10 (Continued)

gB-036 K749C, N750C

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLCC PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 37)

gB-037 K670L

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQL ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 38)

FIG. 10 (Continued)

gB-038 K670F

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQF ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 39)

gB-039 R673L

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELLSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 40)

FIG. 10 (Continued)

gB-040 R673F

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELFSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 41)

gB-041 K691L

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY LQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 42)

FIG. 10 (Continued)

gB-042 K691F

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY FQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 43)

gB-043 M96C, D660C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSCAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTC
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 47)

FIG. 10 (Continued)

gB-044 Q98C, N658C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMACGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLECTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 48)

gB-045 T100C, R258C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGC DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTACSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 49)

FIG. 10 (Continued)

gB-046 T100C, L656C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGC DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPCENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 50)

gB-047 T100C, N658C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGC DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLECTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 51)

FIG. 10 (Continued)

gB-048 I117C, T406C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPCNED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNCSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 52)

gB-049 I117C, S407C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPCNED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTCYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 53)

FIG. 10 (Continued)

gB-050 Y153C, L712C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSCAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GCDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 54)

gB-051 L162C, M716C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LCGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLCSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 55)

FIG. 10 (Continued)

gB-052 D217C, S587C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDCYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANCSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 56)

gB-053 D217C, Y589C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDCYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSCV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 57)

FIG. 10 (Continued)

gB-054 S219C, F584C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYCN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNCANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 58)

gB-055 S219C, A585C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYCN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFCNSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 59)

FIG. 10 (Continued)

gB-056 S219C, N586C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYCN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFACSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 60)

gB-057 N220C, T659C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSC THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENCD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 61)

FIG. 10 (Continued)

gB-058 S223C, T659C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THCTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENCD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 62)

gB-059 W240C, A732C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTC
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GCVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 63)

FIG. 10 (Continued)

gB-060 W240C, G735C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTC
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGCAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 64)

gB-061 Y242C, V728C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LCRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGCAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 65)

FIG. 10 (Continued)

gB-062 Y242C, G731C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LCRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI CAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 66)

gB-063 R258C, L656C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTACSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPCENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 67)

FIG. 10 (Continued)

gB-064 S269C, L656C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATCT GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPCENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 68)

gB-065 S269C, N658C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATCT GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLECTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 69)

FIG. 10 (Continued)

gB-066 D272C, P614C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GCVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLCSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 70)

gB-067 V273C, V629C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDCVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYCD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 71)

FIG. 10 (Continued)

gB-068 W349C, A650C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFCE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIC LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 72)

gB-069 S367C, A500C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFCSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALC QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 73)

FIG. 10 (Continued)

gB-070 S367C, A503C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFCSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QICEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 74)

gB-071 K370C, Q501C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAC MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA CIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 75)

FIG. 10 (Continued)

gB-072 K522C, I683C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SCINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EECMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 76)

gB-073 I523C, I683C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKCNPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EECMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 77)

FIG. 10 (Continued)

gB-074 I523C, M684C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKCNPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEICREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 78)

gB-075 N524C, M684C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKICPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEICREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 79)

FIG. 10 (Continued)

gB-076 P525C, E681C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINCSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL CEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 80)

gB-077 R540C, L680C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAC
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDC EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 81)

FIG. 10 (Continued)

gB-078 F541C, L680C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 CMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDC EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 82)

gB-079 L548C, P655C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGCAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDCLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 83)

FIG. 10 (Continued)

gB-080 A549C, N658C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLCS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLECTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 84)

gB-081 S550C, P655C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAC CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDCLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 85)

FIG. 10 (Continued)

gB-082 S550C, E657C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAC CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLCNTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 86)

gB-083 Q591C, S668C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV CYGQLGEDNE
601 ILLGNHRTEE CQLPSLKIFI AGNSAYEYVD YLFKRMIDLS SISTVDSMIA LDIDPLENTD
661 FRVLELYCQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 87)

FIG. 10 (Continued)

gB-084 L603C, Y667C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILCGNHRTEE CQLPSLKIFI AGNSAYEYVD YLFKRMIDLS SISTVDSMIA LDIDPLENTD
661 FRVLELCSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 88)

gB-085 G604C, L672C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLCNHRTEE CQLPSLKIFI AGNSAYEYVD YLFKRMIDLS SISTVDSMIA LDIDPLENTD
661 FRVLELYSQK ECRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 89)

FIG. 10 (Continued)

gB-086 R607C, N688C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHCTEE CQLPSLKIFI AGNSAYEYVD YLFKRMIDLS SISTVDSMIA LDIDPLENTD
661 FRVLELYSQK ELRSSNVFDL EEIMREFCSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 90)

gB-087 T608C, Q692C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRCEE CQLPSLKIFI AGNSAYEYVD YLFKRMIDLS SISTVDSMIA LDIDPLENTD
661 FRVLELYSQK ELRSSNVFDL EEIMREFNSY KCRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 91)

FIG. 10 (Continued)

gB-088 E609C, K691C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTCE CQLPSLKIFI AGNSAYEYVD YLFKRMIDLS SISTVDSMIA LDIDPLENTD
661 FRVLELYSQK ELRSSNVFDL EEIMREFNSY CQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 92)

gB-089 E610C, S674C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEC CQLPSLKIFI AGNSAYEYVD YLFKRMIDLS SISTVDSMIA LDIDPLENTD
661 FRVLELYSQK ELRCSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 93)

FIG. 10 (Continued)

gB-090 E610C, S675C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEC CQLPSLKIFI AGNSAYEYVD YLFKRMIDLS SISTVDSMIA LDIDPLENTD
661 FRVLELYSQK ELRSCNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 94)

gB-091 Q612C, V663C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CCLPSLKIFI AGNSAYEYVD YLFKRMIDLS SISTVDSMIA LDIDPLENTD
661 FRCLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 95)

FIG. 10 (Continued)

gB-092 V737C, F755C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGACASV VEGVATFLKN PFGACTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 96)

gB-093 V741C, A754C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV CEGVATFLKN PFGCFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 97)

FIG. 10 (Continued)

gB-094 V741C, F755C sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV CEGVATFLKN PFGACTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 98)

gB-095 D679S sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFSL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 99)

FIG. 10 (Continued)

gB-096 D679N sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFNL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 100)

gB-097 E682S sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL ESIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 101)

FIG. 10 (Continued)

gB-098 E682Q sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EQIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 102)

gB-099 E686S sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMRSFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 103)

FIG. 10 (Continued)

gB-100 E686Q sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMRQFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 104)

gB-101 N118P sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPIPED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVDSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 105)

FIG. 10 (Continued)

gB-102 D646P sequence

1 MESRIWCLVV CVNLCIVCLG AAVSSSSTRG TSATHSHHSS HTTSAAHSRS GSVSQRVTSS
61 QTVSHGVNET IYNTTLKYGD VVGVNTTKYP YRVCSMAQGT DLIRFERNIV CTSMKPINED
121 LDEGIMVVYK RNIVAHTFKV RVYQKVLTFR RSYAYIHTTY LLGSNTEYVA PPMWEIHHIN
181 SHSQCYSSYS RVIAGTVFVA YHRDSYENKT MQLMPDDYSN THSTRYVTVK DQWHSRGSTW
241 LYRETCNLNC MVTITTARSK YPYHFFATST GDVVDISPFY NGTNRNASYF GENADKFFIF
301 PNYTIVSDFG RPNSALETHR LVAFLERADS VISWDIQDEK NVTCQLTFWE ASERTIRSEA
361 EDSYHFSSAK MTATFLSKKQ EVNMSDSALD CVRDEAINKL QQIFNTSYNQ TYEKYGNVSV
421 FETTGGLVVF WQGIKQKSLV ELERLANRSS LNLTHNRTKR STDGNNATHL SNMESVHNLV
481 YAQLQFTYDT LRGYINRALA QIAEAWCVDQ RRTLEVFKEL SKINPSAILS AIYNKPIAAR
541 FMGDVLGLAS CVTINQTSVK VLRDMNVKES PGRCYSRPVV IFNFANSSYV QYGQLGEDNE
601 ILLGNHRTEE CQLPSLKIFI AGNSAYEYVD YLFKRMIDLS SISTVPSMIA LDIDPLENTD
661 FRVLELYSQK ELRSSNVFDL EEIMREFNSY KQRVKYVEDK VVDPLPPYLK GLDDLMSGLG
721 AAGKAVGVAI GAVGGAVASV VEGVATFLKN PFGAFTIILV AIAVVIIIYL IYTRQRRLCM
781 QPLQNLFPYL VSADGTTVTS GNTKDTSLQA PPSYEESVYN SGRKGPGPPS SDASTAAPPY
841 TNEQAYQMLL ALVRLDAEQR AQQNGTDSLD GQTGTQDKGQ KPNLLDRLRH RKNGYRHLKD
901 SDEEENV (SEQ ID NO: 106)

FIG. 25C
gB2555 GCN4 1666
+(M371,W506)
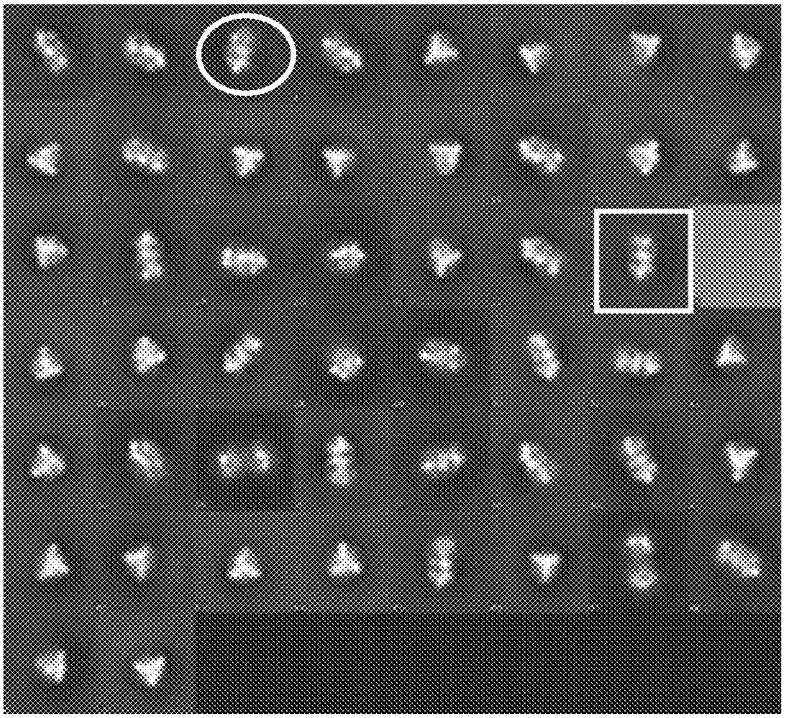
FIG. 25D
gB2556 GCN4 1666
+(N524,M684)
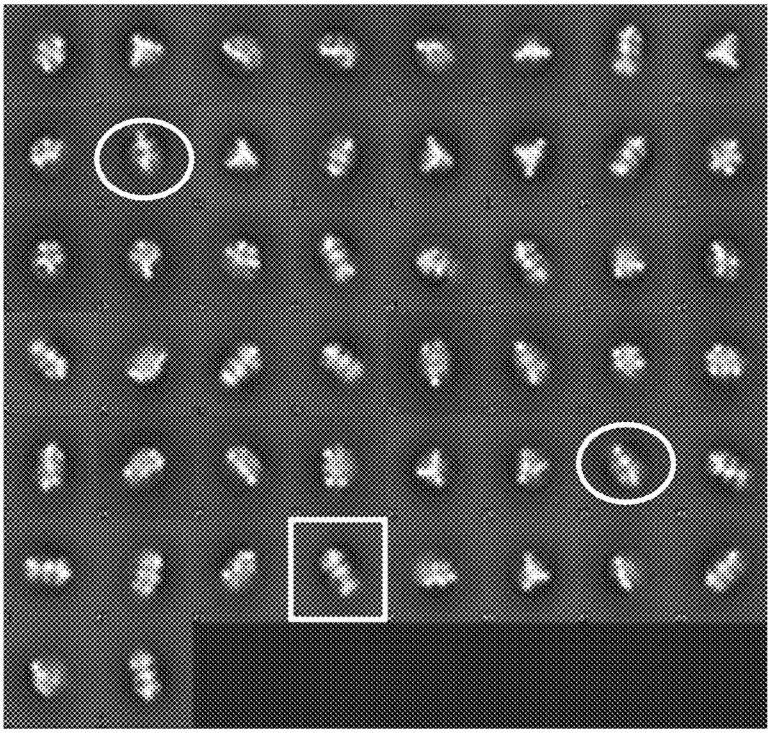

HUMAN CYTOMEGALOVIRUS gB POLYPEPTIDE

RELATED APPLICATIONS

This application claims priority to U.S. Provisional Application No. 63/041,945 filed Jun. 21, 2020 and U.S. Provisional Application No. 63/208,457 filed Jun. 8, 2021. The entire content of each of the foregoing applications is herein incorporated by reference in its entirety.

REFERENCE TO SEQUENCE LISTING

This application is being filed electronically via EFS-Web and includes an electronically submitted sequence listing in .xml format. The .xml file contains a sequence listing entitled "PC072639B Sequence Listing—Updated 21May2025.xml" created on May 21, 2025 and having a size of 641 KB. The sequence listing contained in this .xml file is part of the specification and is herein incorporated by reference in its entirety.

FIELD OF THE INVENTION

The present invention relates to human cytomegalovirus (HCMV) compositions and methods thereof.

BACKGROUND OF THE INVENTION

Human cytomegalovirus (HCMV) is a double stranded DNA virus of the β-herpesvirus family. HCMV is the leading cause of congenital and neonatal hearing loss resulting from vertical virus transmission following infection or reactivation of latent virus in pregnant women. In addition, HCMV is a common opportunistic pathogen affecting immunosuppressed patients, such as solid organ and stem cell transplant patients, AIDS patients, etc. Though development of a vaccine against HCMV has been listed as a top priority by the Institute of Medicine, none has been licensed to date.

The HCMV genome encodes several envelope glycoproteins, one of which is glycoprotein B (gB). Glycoprotein B is a fusogen that is required for virus entry into cells and an important target for neutralizing antibody (nAb) responses to infection. HCMV vaccines that incorporate gB subunit antigens have been under development. Clinical studies have shown that some gB subunit-based vaccine candidates are safe and immunogenic, though improvements in protective efficacy and durability of protection are desirable.

Accordingly, safe and effective immunogenic compositions to protect against HCMV infection are needed. Diagnostic reagents to detect immune responses to HCMV, to guide the design of gB-based HCMV vaccines, and to support the development of therapeutic or prophylactic antibodies against HCMV are also needed.

SUMMARY OF THE INVENTION

To meet these and other needs, in one aspect, the present invention relates to a polypeptide that may be included in an immunogenic composition as an antigen to elicit an immune response to HCMV.

This invention provides a mutant of a wild-type cytomegalovirus (CMV) glycoprotein B (gB) protein, which mutant comprises at least two amino acid mutations relative to the amino acid sequence of the wild-type CMV gB protein, and wherein the amino acid mutation is selected from the group consisting of:

(1) an engineered disulfide bond mutation;
(2) an additional mutation; and
(3) a combination of at least one engineered disulfide mutation and at least one additional mutation.

In one aspect, the amino acid mutations comprise a combination of at least two engineered disulfide mutations and at least one additional mutation. In another aspect, the mutant of a wild-type CMV gB protein is in the form of a trimer.

In another aspect of the invention, the engineered disulfide mutation is selected from the group consisting of: D217C and Y589C; M371C and W506C; and N524C and M684C.

In a further aspect of the invention, the additional mutation is selected from the group consisting of:

(1) substitution of YIH at positions 155-157 with GHR;
(2) substitution of W at position 240 with A;
(3) substitution of C at position 246 with S;
(4) substitution of P at position 655 with S;
(5) substitution of F at position 678 with S; and
(6) substitution of L at position 680 with T;
(7) substitution of R at position 685 with A;
(8) substitution of MIALDI (SEQ ID NO: 275) at positions 648-653 with GSGKDG (SEQ ID NO: 276);
(9) substitution of R at position 693 with V;
(10) substitution of I at position 675 with S;
(11) substitution of I at positions 767 and 768 with C;
(12) substitution of D at position 703 and P at position 704 with C; and
(13) substitution of Y at position 696 and V at position 697 with C.

In another aspect of the invention, the mutant is secreted. In another aspect of the invention, the mutant is soluble.

This invention also provides a pharmaceutical composition comprising (i) a CMV gB protein mutant according to the embodiments and aspects described herein and (ii) a pharmaceutically acceptable carrier. In one aspect, the pharmaceutical composition is a vaccine.

This invention also provides a method of reducing CMV infection in a subject comprising administering to the subject an effective amount of the vaccine set forth in the embodiments herein.

This invention also provides a method of eliciting an immune response to CMV infection in a subject comprising administering to the subject an effective amount of the vaccine set forth in the embodiments herein.

This invention also provides a method of preventing CMV infection in a subject comprising administering to the subject an effective amount of the vaccine set forth in the embodiments herein.

In another aspect, the invention relates to a polypeptide including at least one introduced amino acid mutation relative to the amino acid sequence of the wild-type HCMV glycoprotein B (gB). In some embodiments, the polypeptide includes a conformation that is not an HCMV gB postfusion conformation.

In another aspect, the invention relates to a polypeptide that binds to an HCMV gB prefusion-specific antibody.

In another aspect, the invention relates to a polypeptide that binds to a bis(aryl)thiourea compound. In some embodiments, the compound is N-{4-[({(1S)-1-[3,5-bis(trifluoromethyl)phenyl]ethyl}carbamothioyl)amino]phenyl}-1,3-thiazole-4-carboxamide.

In some embodiments, the polypeptide is characterized by structure coordinates including a root mean square deviation (RMSD) of conserved residue backbone atoms when superimposed on backbone atoms described by structural coordinates of Table 1A, i.e., pdb file, "Table1A-prefusion_gB_121918pdb," which is incorporated herein by reference in its entirety.

In some embodiments, the polypeptide is characterized by structure coordinates including a root mean square deviation (RMSD) of conserved residue backbone atoms when superimposed on backbone atoms described by structural coordinates of Table 1B, i.e., the pdb file, "Table1B-refine_apply_ncs_14pdb," which is incorporated herein by reference in its entirety.

In one aspect, the invention relates to a polypeptide including at least one amino acid mutation relative to the amino acid sequence of the wild-type HCMV gB polypeptide, wherein the amino acid mutation includes a cysteine substitution.

In another aspect, the invention relates to a polypeptide including at least one amino acid mutation relative to the amino acid sequence of the wild-type HCMV gB polypeptide, wherein the amino acid mutation includes a mutation that allows a disulfide bond to form.

In another aspect, the invention relates to a polypeptide including at least one amino acid mutation relative to the amino acid sequence of the wild-type HCMV gB polypeptide, wherein the amino acid mutation includes an electrostatic mutation.

In another aspect, the invention relates to a polypeptide including at least one amino acid mutation relative to the amino acid sequence of the wild-type HCMV gB polypeptide, wherein the amino acid mutation includes a phenylalanine substitution.

In another aspect, the invention relates to a polypeptide including at least one amino acid mutation relative to the amino acid sequence of the wild-type HCMV gB polypeptide, wherein the amino acid mutation includes a leucine substitution.

In another aspect, the invention relates to a polypeptide including at least one amino acid mutation relative to the amino acid sequence of the wild-type HCMV gB polypeptide, wherein the mutation stabilizes prefusion conformation of the polypeptide, and wherein the polypeptide specifically binds to an HCMV gB prefusion-specific antibody.

In another aspect, the invention relates to a polypeptide including a cysteine at any one of the amino acid positions listed in column (ii) of Table 2, as compared to SEQ ID NO: 1.

In another aspect, the invention relates to a polypeptide including an amino acid substitution at any one of the amino acid positions listed in column (ii) of Table 3, as compared to SEQ ID NO: 1.

In another aspect, the invention relates to a polypeptide including the mutations Q98C and I653C according to the numbering of SEQ ID NO: 1. In another aspect, the invention relates to a polypeptide including the mutations T100C and S269C according to the numbering of SEQ ID NO: 1. In another aspect, the invention relates to a polypeptide including the mutations D217C and F584C according to the numbering of SEQ ID NO: 1. In another aspect, the invention relates to a polypeptide including the mutations Y242C and K710C according to the numbering of SEQ ID NO: 1. In another aspect, the invention relates to a polypeptide including the mutations Y242C and D714C according to the numbering of SEQ ID NO: 1. In another aspect, the invention relates to a polypeptide including the mutations S367C and L499C according to the numbering of SEQ ID NO: 1. In another aspect, the invention relates to a polypeptide including the mutations T372C and W506C according to the numbering of SEQ ID NO: 1. In another aspect, the invention relates to a polypeptide including the mutations S550C and D652C according to the numbering of SEQ ID NO: 1. In another aspect, the invention relates to a polypeptide including the mutations T608C and D679C according to the numbering of SEQ ID NO: 1. In another aspect, the invention relates to a polypeptide including the mutations K695C and K724C according to the numbering of SEQ ID NO: 1. In another aspect, the invention relates to a polypeptide including an amino acid sequence that is at least about 90% identical to the amino acid sequence set forth in any one of SEQ ID NOs: 1-43, wherein the polypeptide includes a mutation as compared to SEQ ID NO: 1.

In some embodiments, the polypeptide does not include a mutation at any one of the following positions: R562, P577, S587, Y588, G592, G595, L601/H605, C610, L612, P613, Y625, Y627, F632, and K633.

In some embodiments, the polypeptide does not include the cytoplasmic tail of HCMV gB. In some embodiments, the polypeptide does not include the transmembrane region. In some embodiments, the polypeptide includes the cytoplasmic tail of HCMV gB and does not include the transmembrane region.

In some embodiments, the polypeptide does not contain an insect cell pattern of glycosylation.

In some embodiments, the polypeptide exhibits improved solubility or stability, as compared to a native gB in a postfusion conformation.

In some embodiments, the polypeptide is immunogenic.

In another aspect, the invention relates to a nucleic acid encoding the polypeptide according to any one of embodiments described herein. In some embodiments, the nucleic acid includes a self-replicating RNA molecule. In some embodiments, the nucleic acid includes a modified RNA molecule. In another aspect, the invention relates to a composition including a nucleic acid according to any one of the embodiments described herein.

In another aspect, the invention relates to a composition including the polypeptide according to any one of embodiments described herein, and further including a CMV antigen. In some embodiments, the composition further includes any one of the following polypeptides: gO, gH, gL, pUL128, pUL130, pUL131, and any combination thereof. In some embodiments, the composition further includes a diluent. In some embodiments, the composition further includes an adjuvant. In some embodiments, the composition is immunogenic. In some embodiments, the composition is for use in eliciting an immune response against cytomegalovirus.

In another aspect, the invention relates to a method of eliciting an immune response in a mammal. The method includes administering to the mammal an effective amount of the polypeptide according to any one of the embodiments described herein.

In another aspect, the invention relates to a method for reducing cytomegalovirus viral shedding in a mammal. The method includes administering to the mammal an effective amount of the polypeptide according to any one of the embodiments described herein.

In another aspect, the invention relates to a composition including a polynucleotide that may elicit an immune response in a mammal. The polynucleotide encodes at least one polypeptide of interest, e.g., an antigen. Antigens disclosed herein may be wild type (i.e., derived from the infectious agent) or preferably modified (e.g., engineered, designed or artificial). The nucleic acid molecules described herein, specifically polynucleotides, in some embodiments, encode one or more peptides or polypeptides of interest. Such peptides or polypeptides may serve as an antigen or antigenic molecule. The term “nucleic acid” includes any compound that includes a polymer of nucleotides. These polymers are referred to as “polynucleotides.” Exemplary nucleic acids or polynucleotides of the invention include, but are not limited to, ribonucleic acids (RNAs), including mRNA, and deoxyribonucleic acids (DNAs).

In some embodiments, the composition includes DNA encoding a polypeptide or fragment thereof described herein. In some embodiments, the composition includes RNA encoding a polypeptide or fragment thereof described herein. In some embodiments, the composition includes an mRNA polynucleotide encoding a polypeptide or fragment thereof described herein. Such compositions may produce the appropriate protein conformation upon translation.

In one aspect, the invention relates to a composition that includes at least one polynucleotide encoding a polypeptide including at least one amino acid mutation relative to the amino acid sequence of the wild-type HCMV gB.

In some embodiments, the invention relates to a composition that includes at least one polynucleotide encoding at least one hCMV gB polypeptide or an immunogenic fragment or epitope thereof.

In some embodiments, the composition includes at least one polynucleotide encoding two or more additional polypeptides or an immunogenic fragment or epitope thereof. In some embodiments, the composition includes two or more polynucleotides encoding two or more additional polypeptides or immunogenic fragments or epitopes thereof. The one or more additional polypeptides may be encoded on a single polynucleotide or may be encoded individually on multiple (e.g., two or more) polynucleotides.

In another aspect, the invention relates to a composition that includes (a) a polypeptide including at least one introduced amino acid mutation relative to the amino acid sequence of the wild-type HCMV glycoprotein B (gB); and (b) an additional polypeptide, preferably an HCMV polypeptide, more preferably an HCMV antigenic polypeptide. The additional polypeptide may be selected from gH, gL, gB, gO, gN, and gM and an immunogenic fragment or epitope thereof. In some embodiments, the additional polypeptide is pp65. In some embodiments, the additional polypeptide may be selected from gH, gL, gO, gM, gN, UL128, UL130, and UL131A, and fragments thereof. In another aspect, the invention relates to a composition that includes (a) a polynucleotide encoding a polypeptide including at least one introduced amino acid mutation relative to the amino acid sequence of the wild-type HCMV glycoprotein B (gB); and (b) a polynucleotide encoding an additional polypeptide, preferably an HCMV antigenic polypeptide. The additional polypeptide may be selected from HCMV gH, gL, gB, gO, gN, and gM and an immunogenic fragment or epitope thereof. In some embodiments, the additional polypeptide is HCMV pp65. In some embodiments, the additional polypeptide may be selected from HCMV gH, gL, gO, gM, gN, UL128, UL130, and UL131A, and fragments thereof.

In another aspect, the invention relates to methods of inducing an immune response in a mammal, including administering to the mammal a composition in an amount effective to induce an immune response, wherein the composition includes a polynucleotide encoding a polypeptide including at least one introduced amino acid mutation relative to the amino acid sequence of the wild-type HCMV gB. The composition disclosed herein may be formulated in an effective amount to produce an antigen specific immune response in a mammal.

BRIEF DESCRIPTION OF THE DRAWINGS

FIG. 1A depicts the 2D projections from a postfusion gB structure. Projection images of an electron cryomicroscopy structure of postfusion gB bound with antibody Fabs are shown. FIG. 1B depicts 2D class averages. Two-dimensional class averages from electron cryomicroscopy images obtained from a preparation of gB extracted from CMV virions after treatment with a fusion inhibitor and a cross-linker and binding of an antibody fragment are shown on the right. Class averaged images that do not resemble any of the reference postfusion gB two dimensional projections are identified by circles.

FIG. 2 describes glycoprotein B amino acids (SEQ ID NO: 1) included in the prefusion and postfusion gB-Fab complex models from our electron cryomicroscopy structures. The amino acids that can be modeled in the electron cryomicroscopy density maps are highlighted with the domain color codes (Domain I (italics only, i.e., upper sequence (prefusion) residues 133-344; lower sequence (post-fusion) residues 133-344); Domain II (bold and underlined, i.e., upper sequence (prefusion) residues 121-132 and 345-436; lower sequence (post-fusion) residues 121-132 and 345-439); Domain III (bold only, i.e., upper sequence (prefusion) residues 86-120 and 483-550; lower sequence (post-fusion) residues 86-120 and 474-550); Domain IV (italics and underlined, i.e., upper sequence (prefusion) residues 551-641; lower sequence (post-fusion) residues 551-641); Domain V (italics and bold, i.e., upper sequence (prefusion) residues 642-724; lower sequence (post-fusion) residues 642-697); MPR (underline only, i.e., upper sequence (prefusion) residues 25-7507; lower sequence (post-fusion) no residues); TM (italics, bold, and underlined, i.e., upper sequence (prefusion) residues 751-769; lower sequence (post-fusion) no residues)). The upper and lower sequences are for the prefusion and postfusion structure models, respectively.

FIG. 5A depicts the location of fusion inhibitor compound N-{4-[({(1S)-1-[3,5-bis(trifluoromethyl)phenyl]ethyl}carbamothioyl)amino]phenyl}-1,3-thiazole-4-carboxamide in the prefusion gB model is shown in black. The chemical structure of the compound is shown in FIG. 5D. FIG. 5B: A close view of the electron density around the compound (grey transparent surface). Nearby amino acid residues are shown and domains are labeled. FIG. 5C: The interacting residues around the compound are shown.

FIG. 6A (prefusion) depicts a prefusion conformation; FIG. 6B (Extended intermediate) depicts an extended intermediate conformation; FIG. 6C (postfusion) depicts a postfusion conformation.

FIG. 8 depicts information from Research Collaboratory for Structural Bioinformatics Protein Data Bank (RCSB PDB) file: 5CXF, Crystal structure of the extracellular domain of glycoprotein B from Human Cytomegalovirus, from Human cytomegalovirus (strain AD169), deposited 2015 Jul. 28; DOI: 10.2210/pdb5CXF/pdb.

Unit Cell:

Length (Å) Angle (°)

a=92.183 α=90.00 b=133.930 β=90.00 c=295.376 γ=90.00

FIG. 9 depicts sequences of gB from clinical and laboratory-adapted HCMV strains (SEQ ID NO: 110-SEQ ID NO: 111). Additional sequences may be found in an amino acid sequence alignment of gB from clinical and laboratory-adapted HCMV found in S4 Fig., from Burke et al., PLoS Pathog. 2015 Oct. 20; 11(10):e1005227. According to Burke et al. sixty HCMV gB sequences from clinical and laboratory-adapted strains, downloaded from NCBI's RefSeq data base, were aligned and analyzed using ClustalW2 and ESPript 3.x. Identical residues are shown as white text on red background, and similar residues are highlighted in yellow in S4 Fig. of Burke et al., said S4 Fig. and the description thereof is incorporated herein by reference in its entirety.

FIG. 10 depicts the amino acid sequences for SEQ ID NOs: 1-43 and SEQ ID NOs: 47-106.

Figure 11:
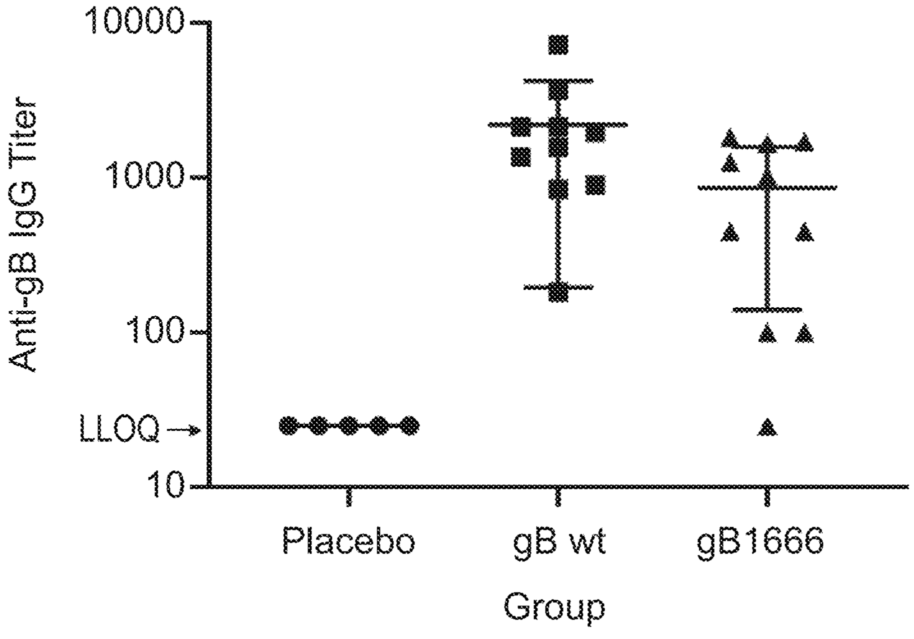

FIG. 11 depicts the dose-dependent IgG responses in both gB1666 and wild type gB (Towne) immunized mice. The graph shows that 10 out of 10 mice immunized with wild type gB DNA, and 9 out of 10 mice immunized with gB1666 DNA generated detectable anti-gB IgG titers. Mean±SD, LLOQ=25.

Figure 12:
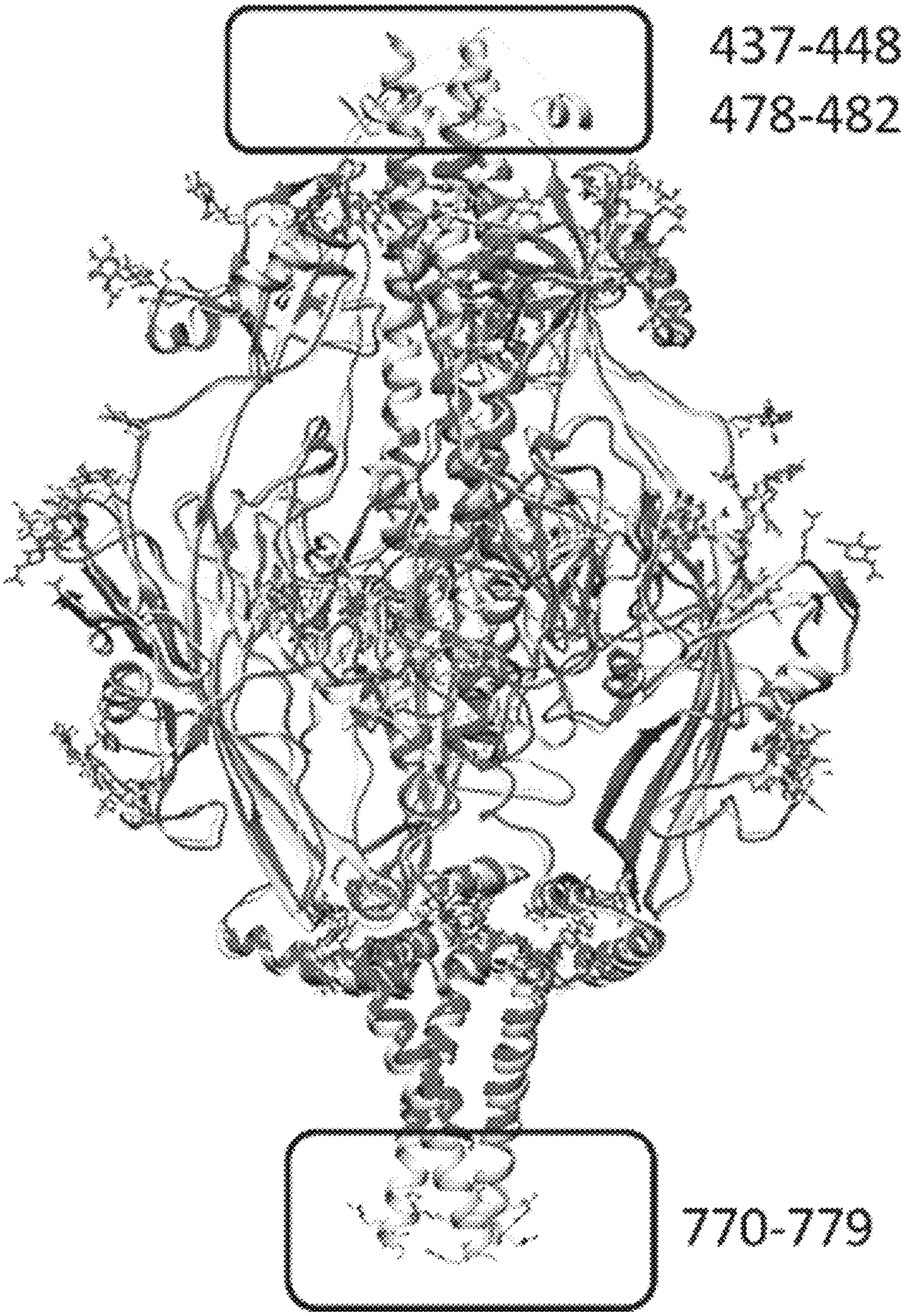

FIG. 12 depicts the structural model of engineered gB1666 (light gray, structure code:P-GB-002) is overlaid with the structural model of wild type HCMV gB (dark gray, structure code:P-GB-001). The new structure allows modeling of additional residues, 437-448 and 478-482 at the membrane distal end of the molecule and 770-779 in the transmembrane domain.

Figure 13:
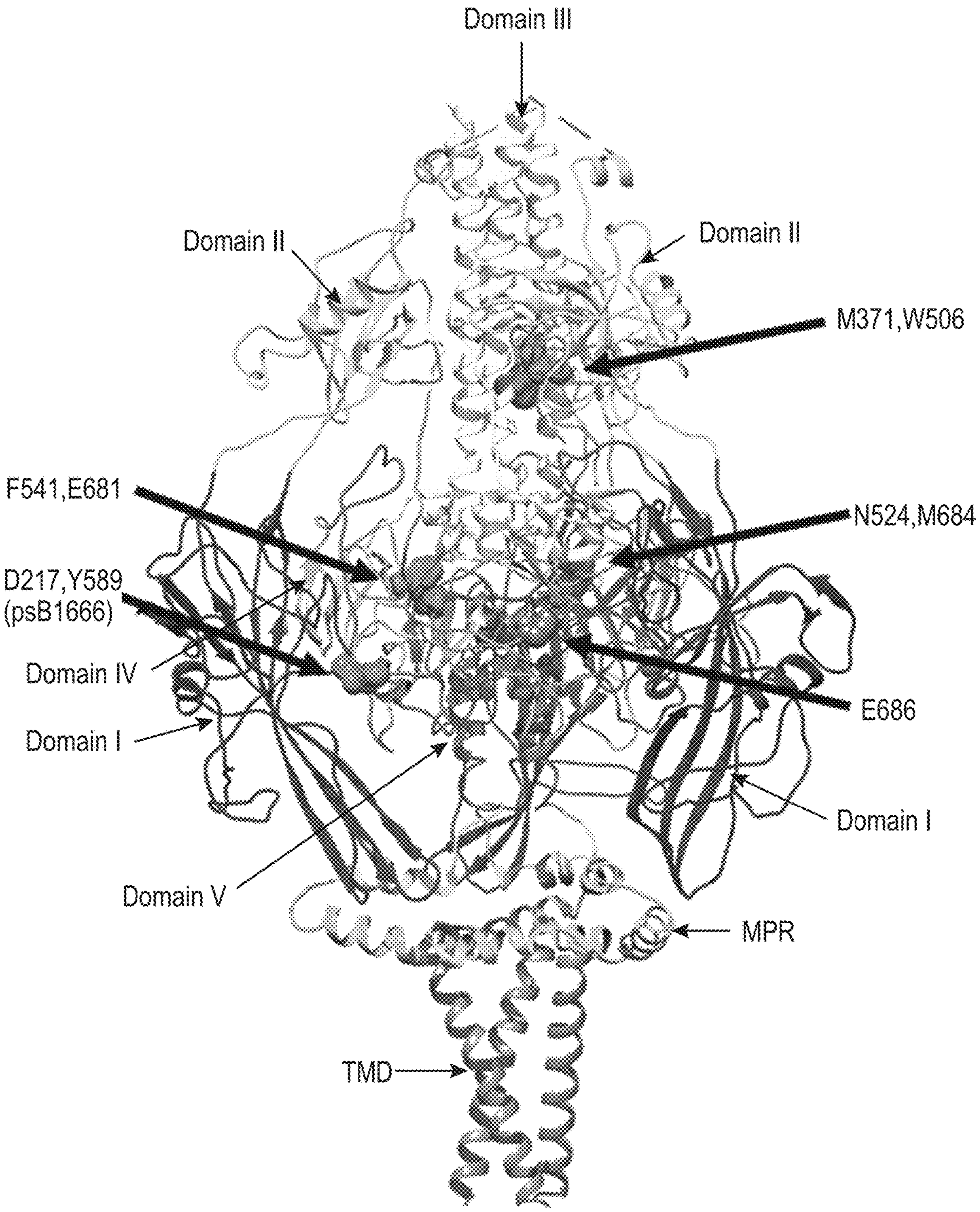

FIG. 13 depicts an example of the combinations of additional mutation combinations on the pSB1666 background that could further stabilize prefusion gB. Disulfide bond at M371, W506 could link domains II and III. Disulfide bonds at N524, M684 and F541, E681 could link domains IV and V. Mutations of negatively charged patches at E686 to hydrophobic residues could further stabilize gB in prefusion conformation. Each domain is identified. Abbreviations: membrane proximal region (MPR), and transmembrane domain (TMD).

Figure 14:
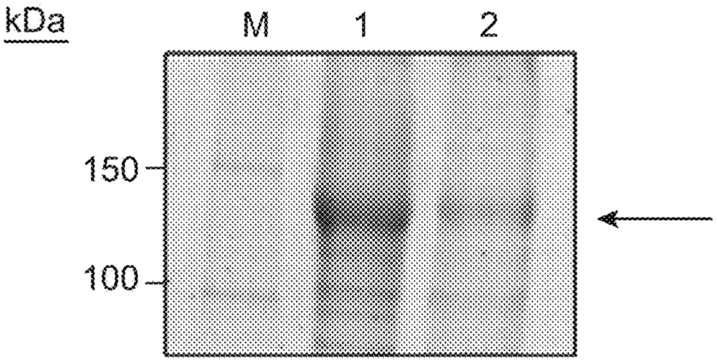

FIG. 14 depicts a SDS-PAGE documenting the expression and purification of recombinant gB2459 protein. The pSB2459 expression plasmid was transiently transfected into Expi293F cells. The cell pellets were harvested 68 hours after transfection, and the glycoprotein product gB2459 was purified in 25 mM HEPES pH 7.5, 250 mM NaCl, 0.02% n-Dodecyl 0-D-maltoside (DDM), 0.002% cholesteryl hemi-succinate (CHS) through a series of processes of solubilization, affinity and size exclusion chromatography. This figure shows the purified protein analyzed by stain-free 4-20% SDS-PAGE under reducing conditions. The smearing of the protein band is consistent with gB2459 being heavily glycosylated. Lane M: protein marker; Lane 1: gB2457; and Lane 2: gB2459.

Figure 15:
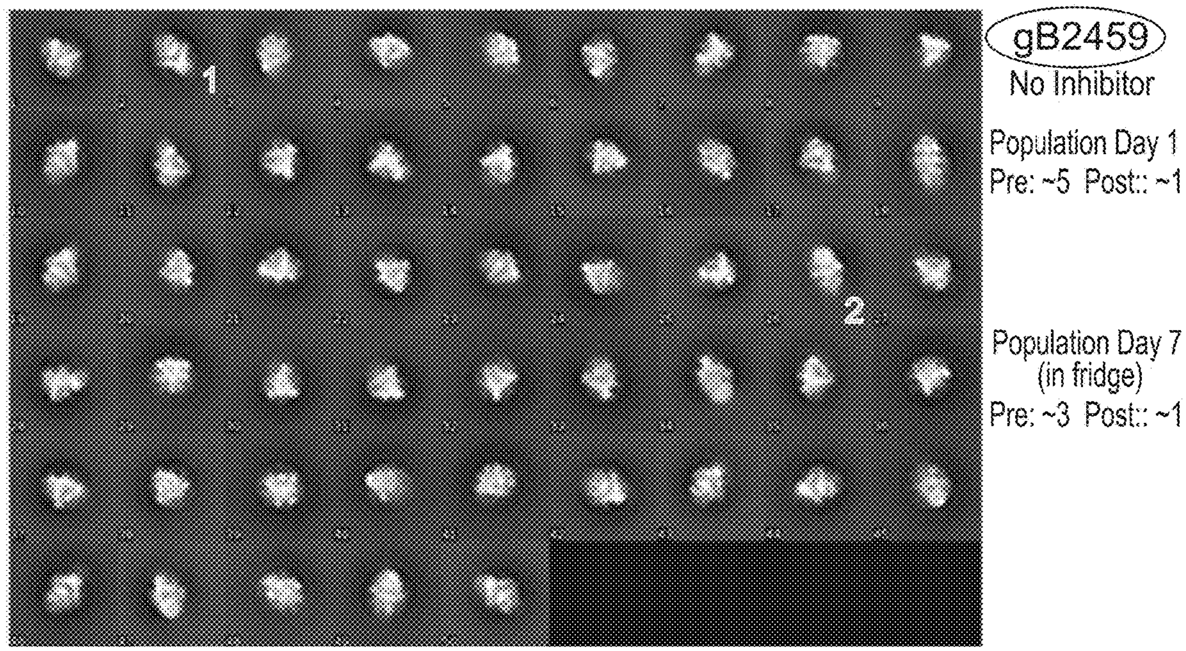

FIG. 15 depicts the construct pSB2459 which contains N524C and M684C mutations on the pSB1666 background. The protein product gB2459 was purified through affinity tags without the presence of any fusion inhibitors. There are prefusion classes observed in the 2D class averaged images (two classes with obvious prefusion features are indicated with the numbers 1 and 2). In addition, the prefusion gB2459 is stable over a period of a few days. Sample solution of gB2459 was stored at 4° C., aliquots of the sample were obtained at day 1 and day 7 to prepare the negative stained grids. An images dataset was collected and processed on these two grids. For each dataset, the particle populations in the prefusion and postfusion 2D classes were counted: the ratio between prefusion and postfusion conformation was 5:1 for the sample at day 1 and 3:1 at day 7.

Figure 16A:
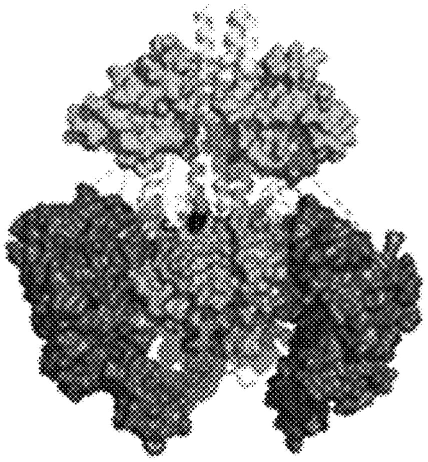
Figure 16B:
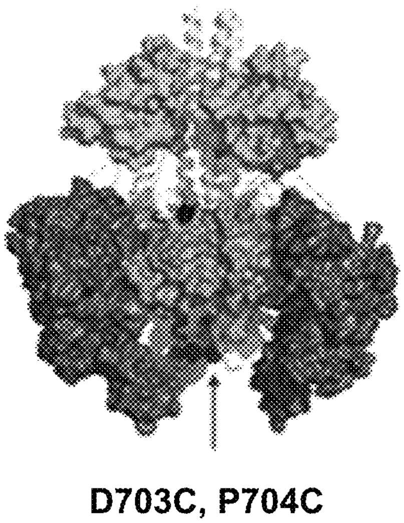
Figure 16C:
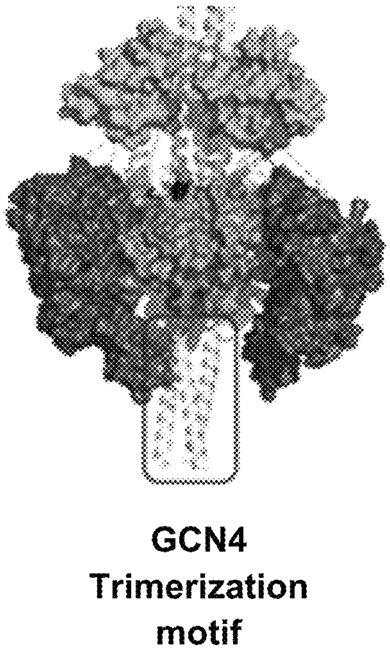
Figure 16D:
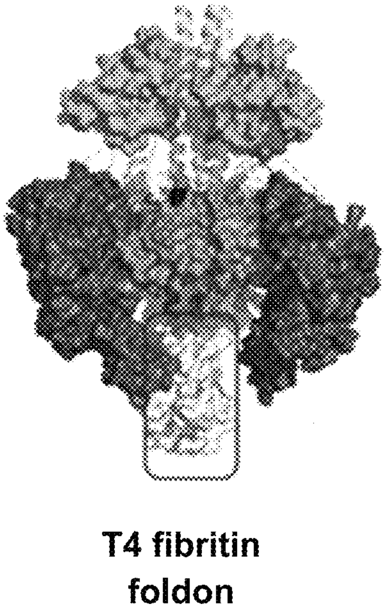

FIG. 16A-16D depict the design of soluble, detergent-free gB ectodomains. FIG. 16A shows gB ectodomain (1-707) with MPR, TM and CT regions removed. FIG. 16B shows gB ectodomain stabilized with additional cysteine mutations, e.g. D703C and P704C, in Domain V. FIG. 16C shows gB ectodomain fused to a C-terminal GCN4 trimerization motif. FIG. 16D shows gB ectodomain fused to a C-terminal T4 fibritin foldon domain. Legend: Domain I (residues 134-344)—dark gray 3D volume structure; Domain II (residues 121-133 and 345-436)—light gray 3D volume structure; Domain III (residues 97-111, 475-539 and 640-648)—top center light gray vertical coils; Domain V (residues 649-707)—bottom internal dark gray coils (see arrow FIG. 16B); and rectangle—trimerization location.

Figure 17:
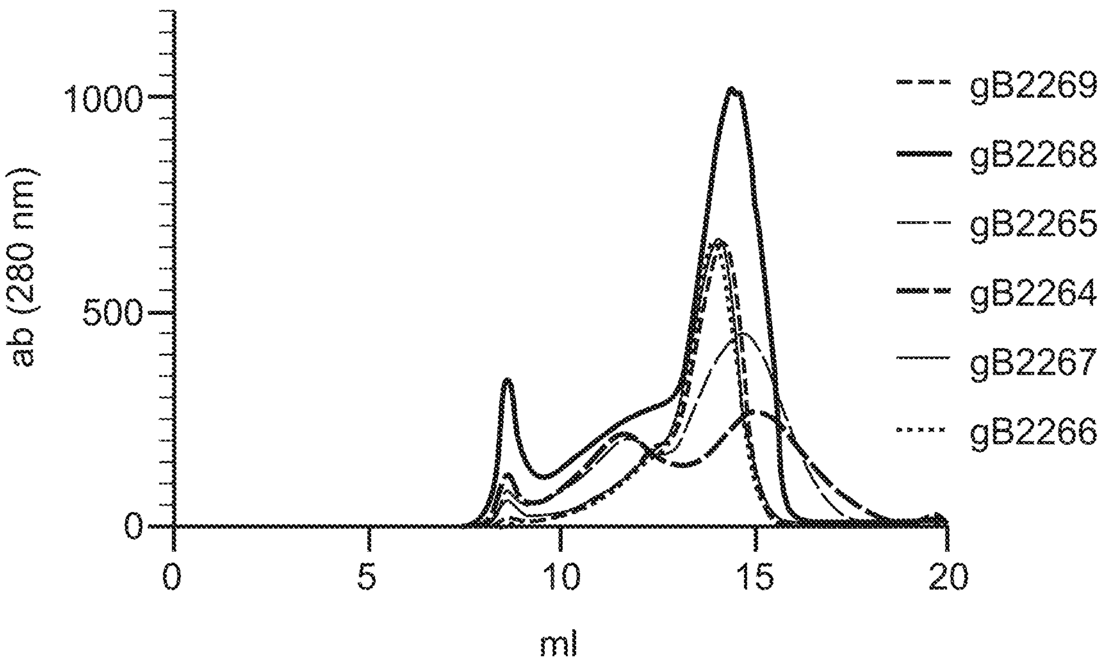

FIG. 17 depicts gel-filtration profiles of purified gB ectodomains, gB2264-gB2269, analyzed by Superose 6 Increase 10/300 in 20 mM HEPES pH 7.5, 250 mM NaCl.

Figure 18A:
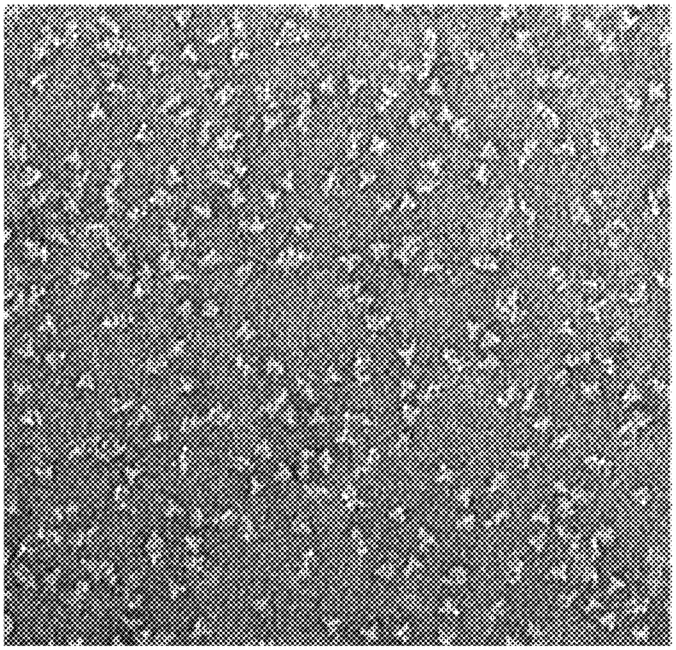
Figure 18B:
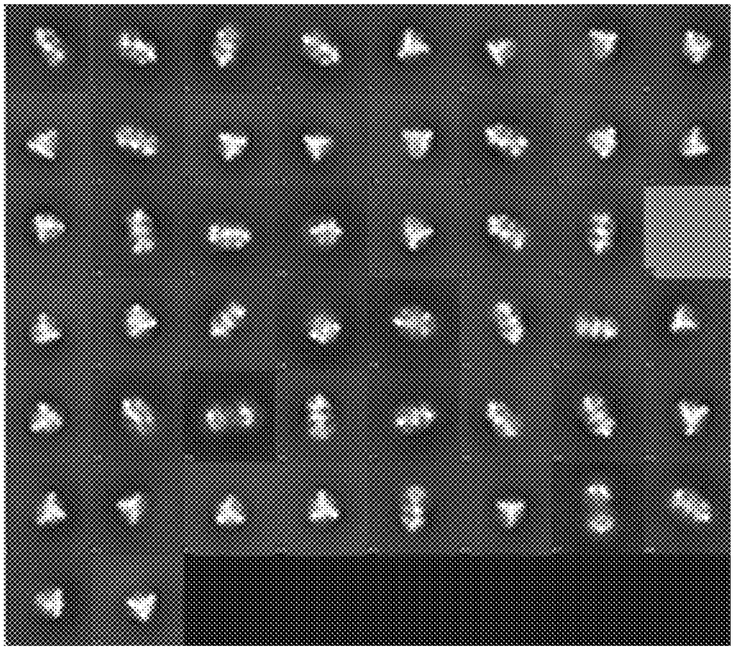

FIG. 18A-18B depict a Negative stain EM image (FIG. 18A) and representative 2D class averages (FIG. 18B) from negative stain EM of recombinant gB2555 without bound fusion inhibitor, which show monodispersed gB proteins are suitable to use as a framework to add more stabilizing mutations towards a prefusion form of gB in the absence of inhibitor and detergents.

Figure 19A:
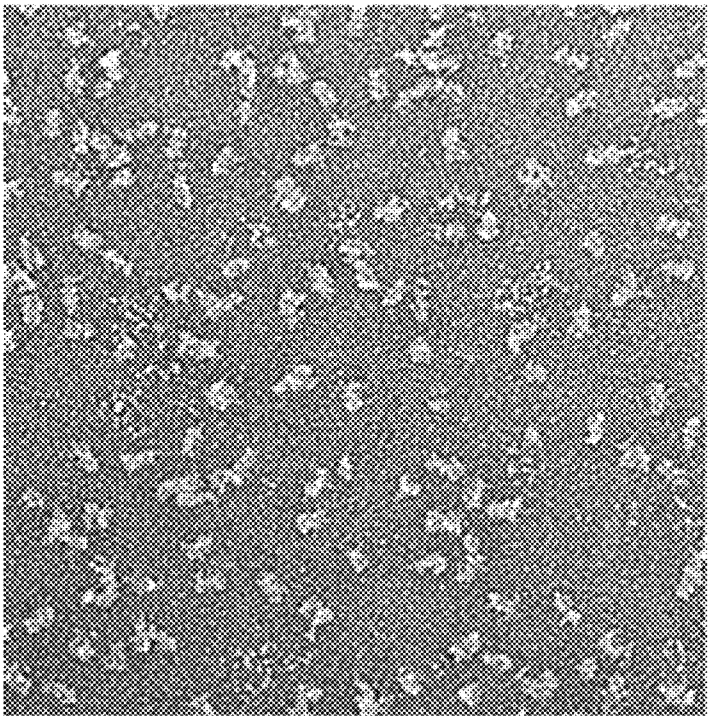
Figure 19B:
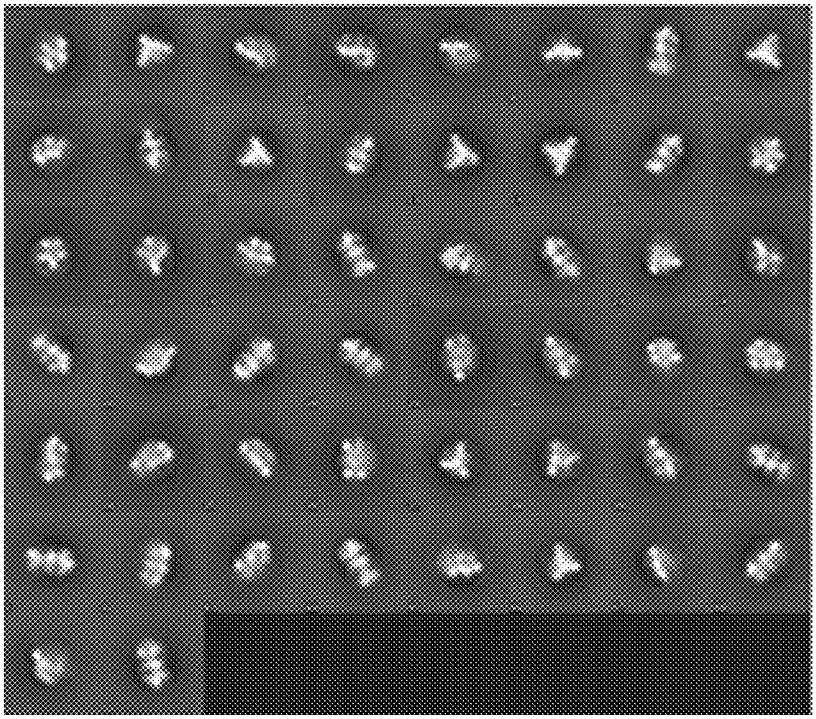

FIG. 19A-19B depict a Negative stain EM image (FIG. 19A) and representative 2D class averages (FIG. 19B) from negative stain EM of recombinant gB2556 without bound fusion inhibitor, which show monodispersed gB proteins are suitable to use as a framework to add more stabilizing mutations towards a prefusion form of gB in the absence of inhibitor and detergents.

Figure 20A:
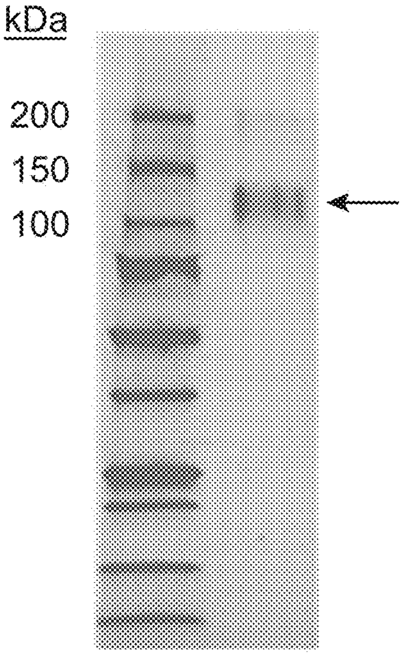
Figure 20B:
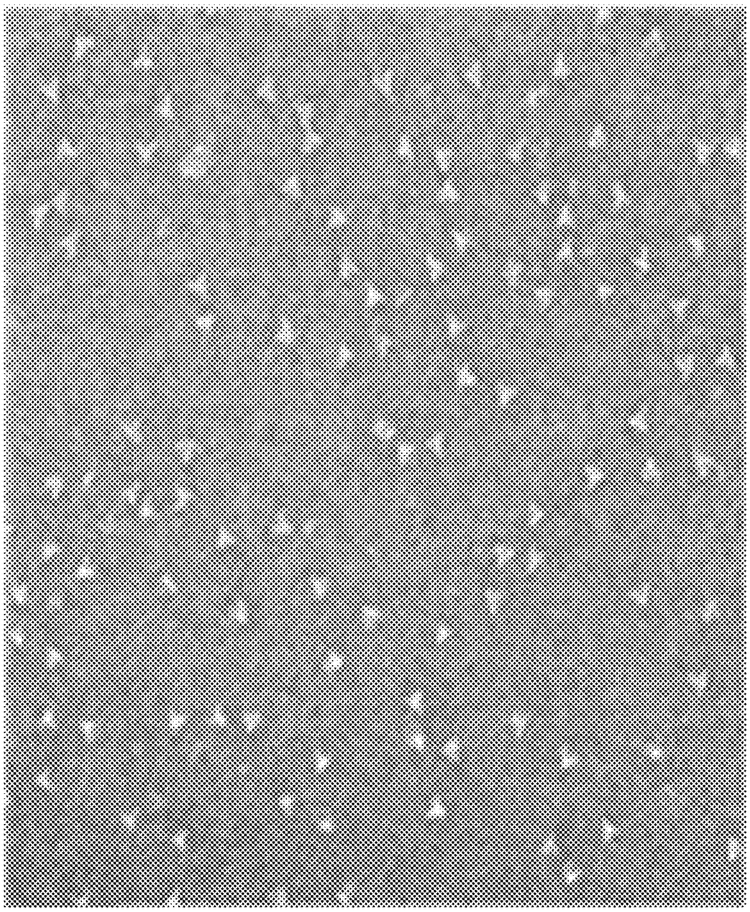

FIG. 20A-20B depict: the purified protein analyzed on 4-20% Mini-PROTEAN® TGX STAIN-FREE® Protein Gels (Biorad) in Tris/glycine/SDS buffer under reducing conditions (arrow shows protein on gel) (FIG. 20A); and the image of the negatively stained protein by electron microscopy (FIG. 20B).

Figure 21:
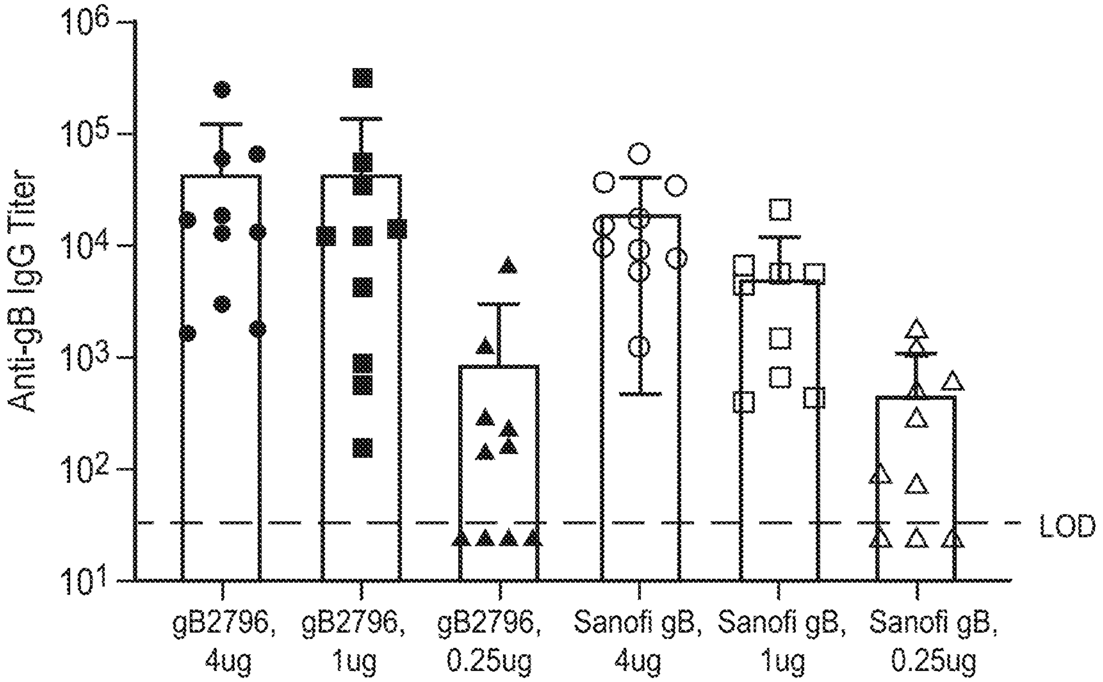

FIG. 21 depicts the dose-dependent IgG responses to gB in both gB2796 and Sanofi gB immunized mice.

Figure 22A:
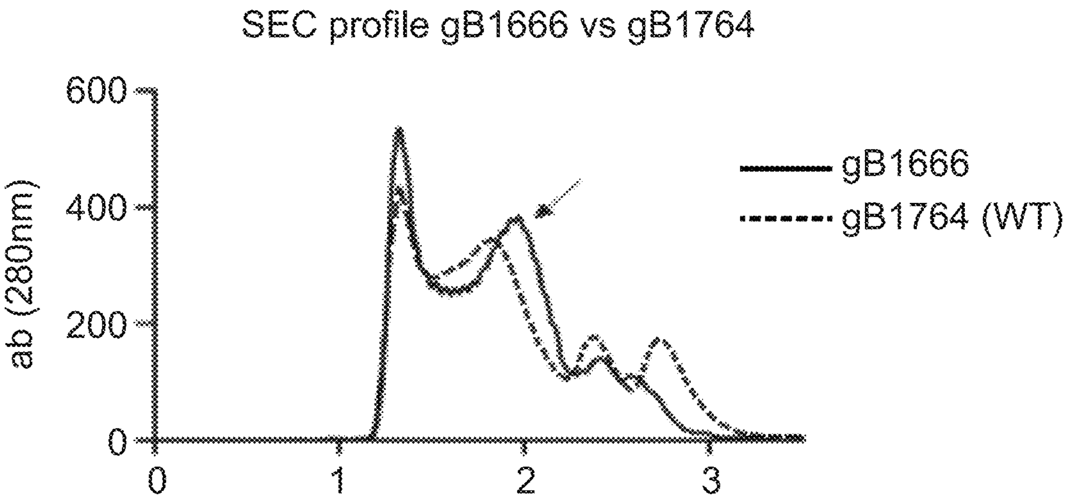
Figure 22B:
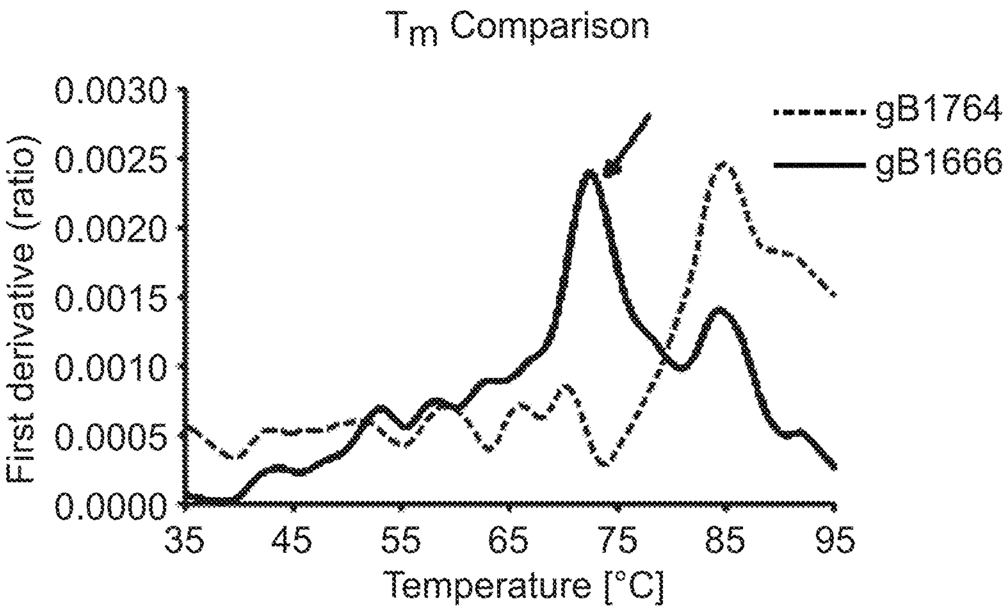

FIG. 22A-22B depict (i) FIG. 22A: the SEC profile comparison between gB1666 and gB1764 (the wild type CMVgB) (SEC is run on Superose6 increase 5/150 column in buffer 25 mM HEPES pH 7.5, 250 mM NaCl, 0.02% DDM, 0.002% CHS, 3 ug/ml WAY-174865); and (ii) FIG. 22B: thermal stability comparison between gB1666 and gB1764 (the assay is run on Tycho NT.6 with 20° C./min heating rate).

Figure 23A:
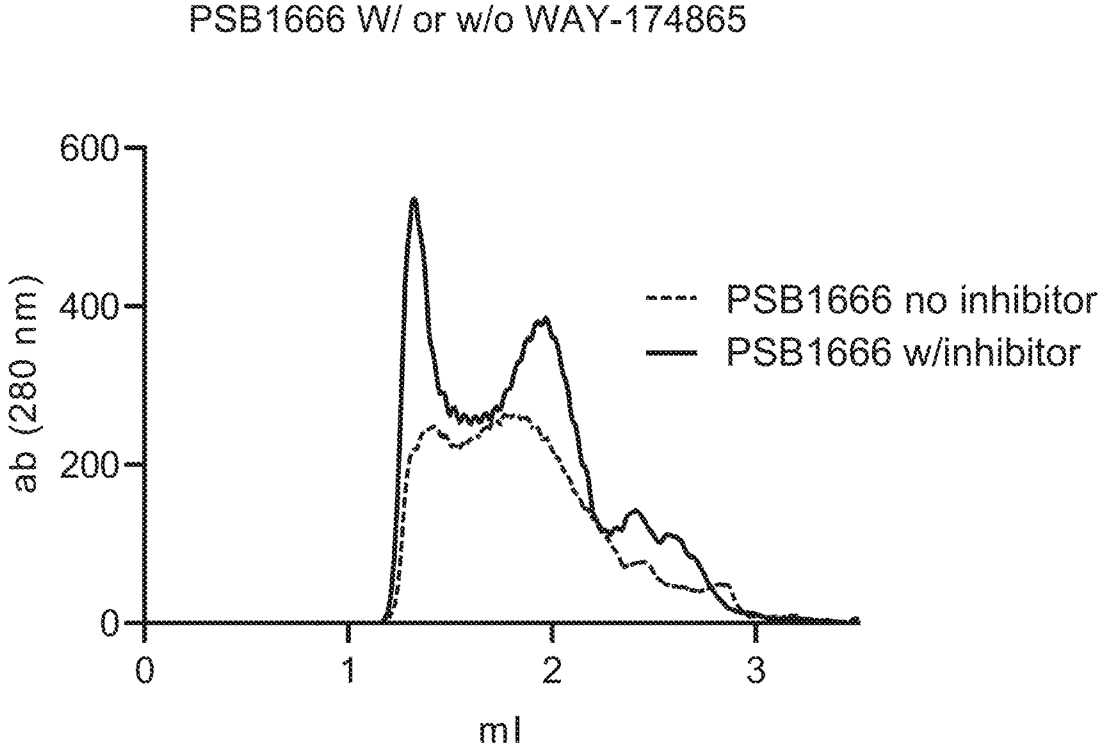
Figure 23B:
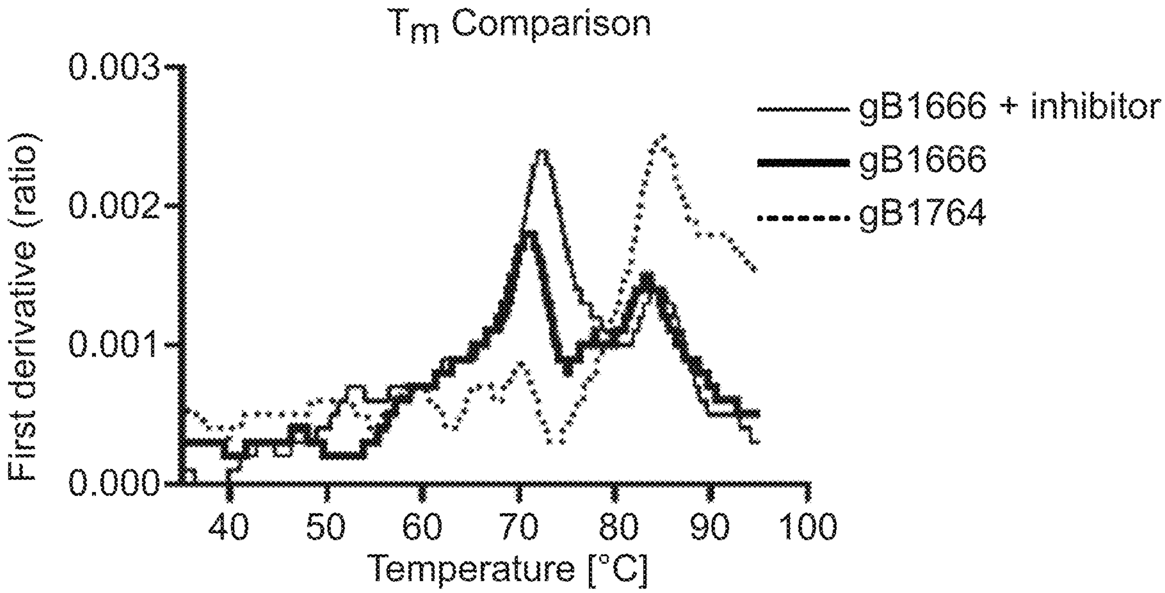

FIG. 23A-23B depict (i) FIG. 23A: SEC profile of gB1666 with or without the inhibitor WAY-174865 (SEC is run on Superose6 increase 5/150 column in buffer 25 mM HEPES pH 7.5, 250 mM NaCl, 0.02% DDM, 0.002% CHS, 3 ug/ml WAY-174865); and (ii) FIG. 23B: thermal stability comparison among gB1666, gB1666 with inhibitor and gB1764 (the assay is run on Tycho NT.6 with 20° C./min heating rate).

Figure 24A:
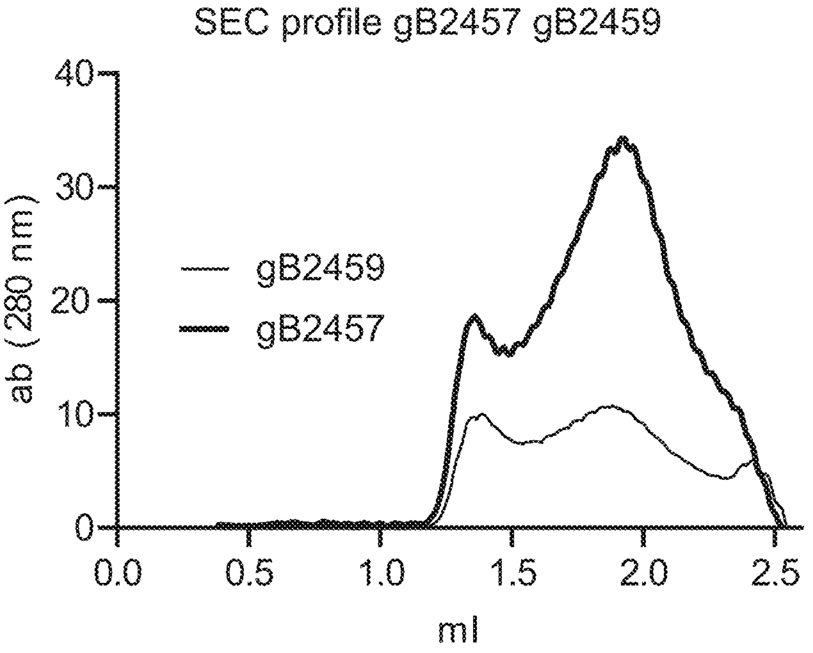
Figure 24B:
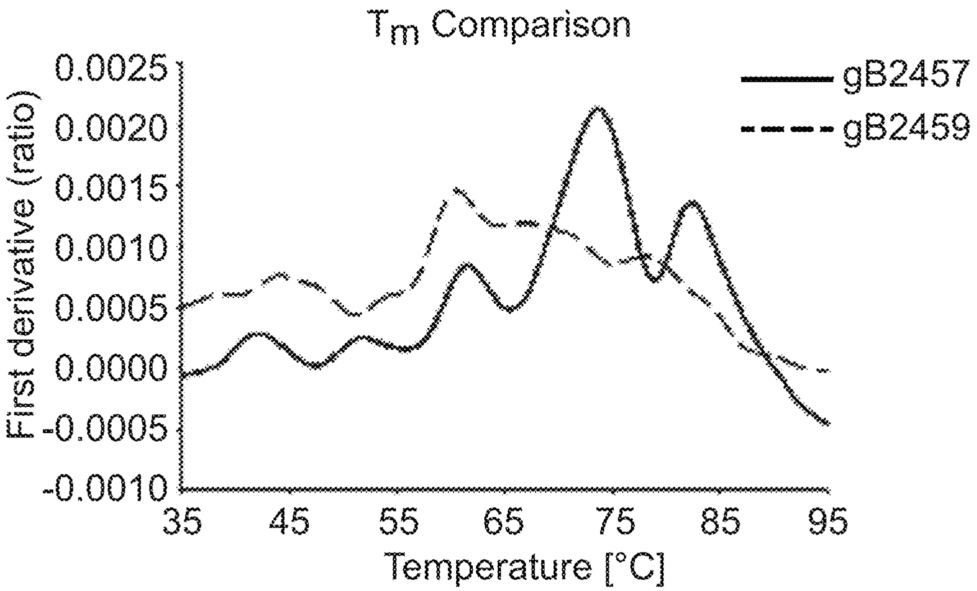

FIG. 24A-24B depict (i) FIG. 24A: SEC profile comparison of gB2457 and gB2459 (SEC is run on Superose6 increase 5/150 column in buffer 25 mM HEPES pH 7.5, 250 mM NaCl, 0.02% DDM, 0.002% CHS); and (ii) FIG. 24B: thermal stability comparison between gB2457 and gB2459 (the assay is run on Tycho NT.6 with 20° C./min heating rate).

Figure 25A:
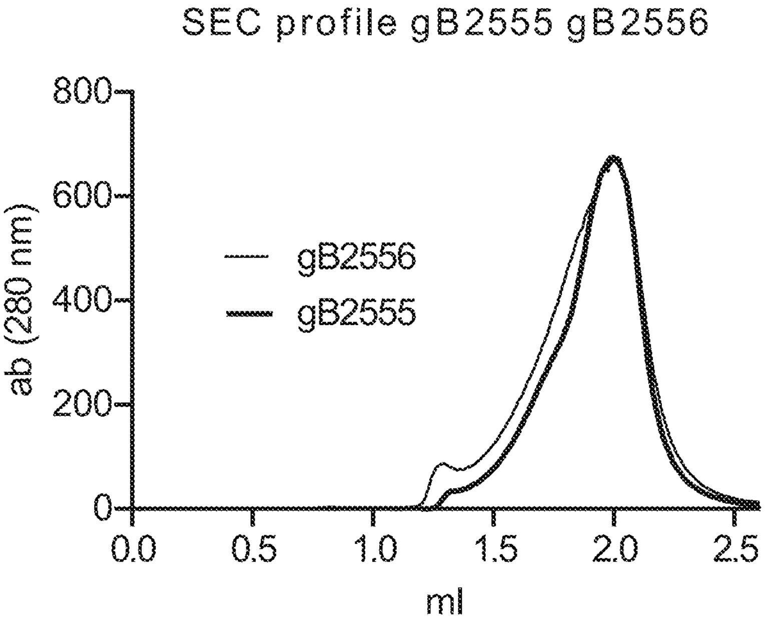

FIG. 25A-25D depict (i) FIG. 25A: SEC profile comparison of gB2555 and gB2556 (SEC is run on Superose6 increase 5/150 column in buffer 20 mM HEPES pH 7.5, 250 mM NaCl); (ii) FIG. 25B: thermal stability comparison between gB2555 and gB2556 (the assay is run on Tycho NT.6 with 20° C./min heating rate); (iii) FIG. 25C: 2D class averaged from negatively stained EM images of gB2555; and (iv) FIG. 25D: 2D class averaged from negatively stained EM images of gB2556. In FIGS. 25C and 25D, representative classes for prefusion gB (tapered shape) are indicated with a circle and postfusion gB are indicated with a square.

Figure 26A:
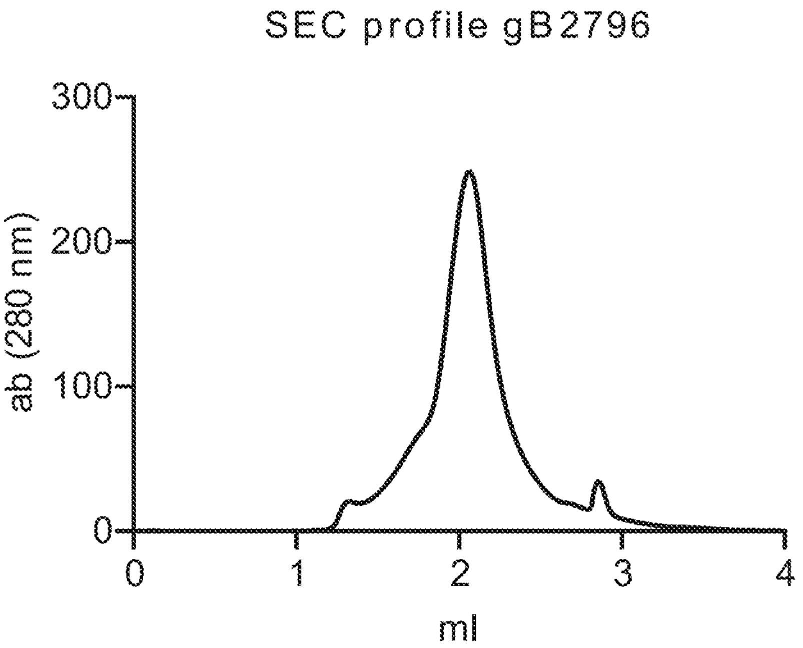
Figure 26B:
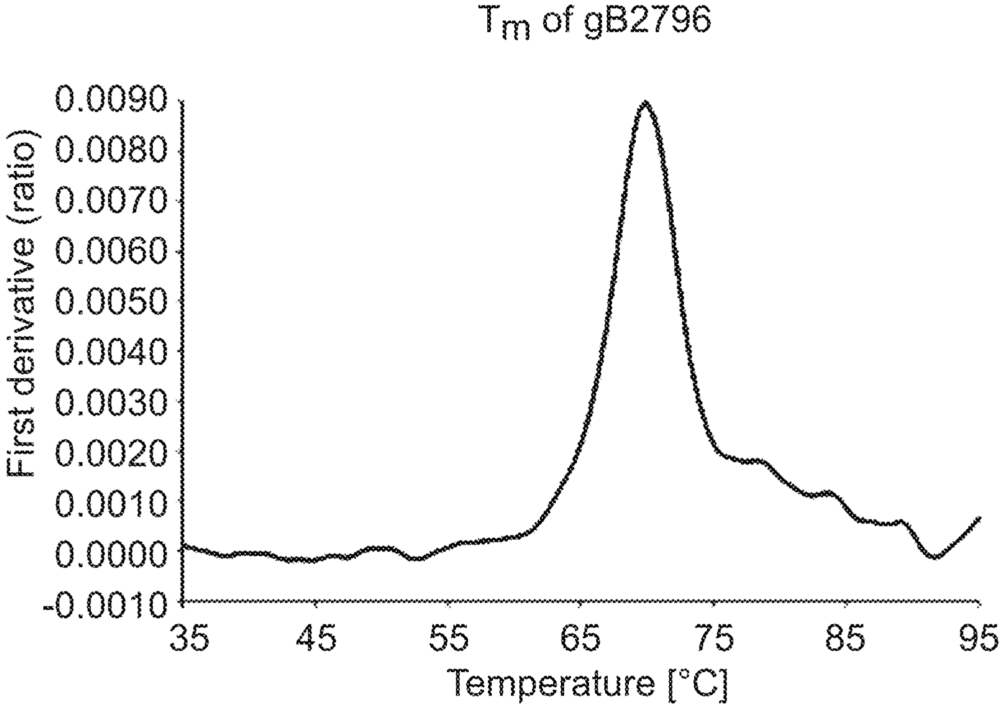

FIG. 26A-26B depict (i) FIG. 26A: SEC profile comparison of gB2796 (SEC is run on Superose6 increase 5/150 column in buffer 20 mM HEPES pH 7.5, 250 mM NaCl); and FIG. 26B: thermal stability of gB2796 (the assay is run on Tycho NT.6 with 20° C./min heating rate).

SEQUENCE IDENTIFIERS

SEQ ID NO: 1 sets forth an amino acid sequence derived from a native HCMV gB (strain Towne).

SEQ ID NO: 2 sets forth the amino acid sequence of SEQ ID NO: 1, wherein the following mutations are included: Q98C, G271C.

SEQ ID NO: 3 sets forth the amino acid sequence of SEQ ID NO: 1, wherein the following mutations are included: Q98C, I653C.

SEQ ID NO: 4 sets forth the amino acid sequence of SEQ ID NO: 1, wherein the following mutations are included: G99C, A267C.

SEQ ID NO: 5 sets forth the amino acid sequence of SEQ ID NO: 1, wherein the following mutations are included: T100C, A267C.

SEQ ID NO: 6 sets forth the amino acid sequence of SEQ ID NO: 1, wherein the following mutations are included: T100C, S269C.

SEQ ID NO: 7 sets forth the amino acid sequence of SEQ ID NO: 1, wherein the following mutations are included: T100C, L651C.

SEQ ID NO: 8 sets forth the amino acid sequence of SEQ ID NO: 1, wherein the following mutations are included: D217C, F584C.

SEQ ID NO: 9 sets forth the amino acid sequence of SEQ ID NO: 1, wherein the following mutations are included: Y218C, A585C.

SEQ ID NO: 10 sets forth the amino acid sequence of SEQ ID NO: 1, wherein the following mutations are included: S219C, D654C.

SEQ ID NO: 11 sets forth the amino acid sequence of SEQ ID NO: 1, wherein the following mutations are included: N220C, D652C.

SEQ ID NO: 12 sets forth the amino acid sequence of SEQ ID NO: 1, wherein the following mutations are included: T221C, D652C.

SEQ ID NO: 13 sets forth the amino acid sequence of SEQ ID NO: 1, wherein the following mutations are included: W240C, G718C.

SEQ ID NO: 14 sets forth the amino acid sequence of SEQ ID NO: 1, wherein the following mutations are included: Y242C, K710C.

SEQ ID NO: 15 sets forth the amino acid sequence of SEQ ID NO: 1, wherein the following mutations are included: Y242C, D714C.

SEQ ID NO: 16 sets forth the amino acid sequence of SEQ ID NO: 1, wherein the following mutations are included: S269C, I653C.

SEQ ID NO: 17 sets forth the amino acid sequence of SEQ ID NO: 1, wherein the following mutations are included: G271C, P614C.

SEQ ID NO: 18 sets forth the amino acid sequence of SEQ ID NO: 1, wherein the following mutations are included: S367C, L499C.

SEQ ID NO: 19 sets forth the amino acid sequence of SEQ ID NO: 1, wherein the following mutations are included: T372C, W506C.

SEQ ID NO: 20 sets forth the amino acid sequence of SEQ ID NO: 1, wherein the following mutations are included: F541C, Q669C.

SEQ ID NO: 21 sets forth the amino acid sequence of SEQ ID NO: 1, wherein the following mutations are included: L548C, A650C.

SEQ ID NO: 22 sets forth the amino acid sequence of SEQ ID NO: 1, wherein the following mutations are included: A549C, I653C.

SEQ ID NO: 23 sets forth the amino acid sequence of SEQ ID NO: 1, wherein the following mutations are included: S550C, D652C.

SEQ ID NO: 24 sets forth the amino acid sequence of SEQ ID NO: 1, wherein the following mutations are included: G604C, F661C.

SEQ ID NO: 25 sets forth the amino acid sequence of SEQ ID NO: 1, wherein the following mutations are included: N605C, E665C.

SEQ ID NO: 26 sets forth the amino acid sequence of SEQ ID NO: 1, wherein the following mutations are included: R607C, S675C.

SEQ ID NO: 27 sets forth the amino acid sequence of SEQ ID NO: 1, wherein the following mutations are included: T608C, D679C.

SEQ ID NO: 28 sets forth the amino acid sequence of SEQ ID NO: 1, wherein the following mutations are included: E609C, F678C.

SEQ ID NO: 29 sets forth the amino acid sequence of SEQ ID NO: 1, wherein the following mutations are included: R673C, S674C.

SEQ ID NO: 30 sets forth the amino acid sequence of SEQ ID NO: 1, wherein the following mutations are included: N676C, V677C.

SEQ ID NO: 31 sets forth the amino acid sequence of SEQ ID NO: 1, wherein the following mutations are included: L680C, E681C.

SEQ ID NO: 32 sets forth the amino acid sequence of SEQ ID NO: 1, wherein the following mutations are included: I683C, M684C.

SEQ ID NO: 33 sets forth the amino acid sequence of SEQ ID NO: 1, wherein the following mutations are included: F687C, N688C.

SEQ ID NO: 34 sets forth the amino acid sequence of SEQ ID NO: 1, wherein the following mutations are included: Y690C, K691C.

SEQ ID NO: 35 sets forth the amino acid sequence of SEQ ID NO: 1, wherein the following mutations are included: K695C, K724C.

SEQ ID NO: 36 sets forth the amino acid sequence of SEQ ID NO: 1, wherein the following mutations are included: T746C, F747C.

SEQ ID NO: 37 sets forth the amino acid sequence of SEQ ID NO: 1, wherein the following mutations are included: K749C, N750C.

SEQ ID NO: 38 sets forth the amino acid sequence of SEQ ID NO: 1, wherein the following mutation is included: K670L.

SEQ ID NO: 39 sets forth the amino acid sequence of SEQ ID NO: 1, wherein the following mutation is included: K670F.

SEQ ID NO: 40 sets forth the amino acid sequence of SEQ ID NO: 1, wherein the following mutation is included: R673L.

SEQ ID NO: 41 sets forth the amino acid sequence of SEQ ID NO: 1, wherein the following mutation is included: R673F.

SEQ ID NO: 42 sets forth the amino acid sequence of SEQ ID NO: 1, wherein the following mutation is included: K691L.

SEQ ID NO: 43 sets forth the amino acid sequence of SEQ ID NO: 1, wherein the following mutation is included: K691F.

SEQ ID NO: 44 sets forth the amino acid sequence for a native HCMV gB (AD169; PDB: 5CXF) that folds into a postfusion conformation when expressed.

SEQ ID NO: 45 sets forth the amino acid sequence for an HCMV gB variant (gB705) that folds into a postfusion conformation when expressed.

SEQ ID NO: 46 sets forth the amino acid sequence for a native HCMV gB (Merlin strain) that folds into a postfusion conformation when expressed.

SEQ ID NO: 47 sets forth the amino acid of SEQ ID NO: 1, wherein the following mutations are included: M96C and D660C.

SEQ ID NO: 48 sets forth the amino acid of SEQ ID NO: 1, wherein the following mutations are included: Q98C and N658C.

SEQ ID NO: 49 sets forth the amino acid of SEQ ID NO: 1, wherein the following mutations are included: T1000 and R258C.

SEQ ID NO: 50 sets forth the amino acid of SEQ ID NO: 1, wherein the following mutations are included: T100C and L656C.

SEQ ID NO: 51 sets forth the amino acid of SEQ ID NO: 1, wherein the following mutations are included: T1000 and N658C.

SEQ ID NO: 52 sets forth the amino acid of SEQ ID NO: 1, wherein the following mutations are included: I117C and T406C.

SEQ ID NO: 53 sets forth the amino acid of SEQ ID NO: 1, wherein the following mutations are included: I117C and S407C.

SEQ ID NO: 54 sets forth the amino acid of SEQ ID NO: 1, wherein the following mutations are included: Y153C and L712C.

SEQ ID NO: 55 sets forth the amino acid of SEQ ID NO: 1, wherein the following mutations are included: L162C and M716C.

SEQ ID NO: 56 sets forth the amino acid of SEQ ID NO: 1, wherein the following mutations are included: D217C and S587C.

SEQ ID NO: 57 sets forth the amino acid of SEQ ID NO: 1, wherein the following mutations are included: D217C and Y589C.

SEQ ID NO: 58 sets forth the amino acid of SEQ ID NO: 1, wherein the following mutations are included: S219C and F584C.

SEQ ID NO: 59 sets forth the amino acid of SEQ ID NO: 1, wherein the following mutations are included: S219C and A585C.

SEQ ID NO: 60 sets forth the amino acid of SEQ ID NO: 1, wherein the following mutations are included: S219C and N586C.

SEQ ID NO: 61 sets forth the amino acid of SEQ ID NO: 1, wherein the following mutations are included: N220C and T659C.

SEQ ID NO: 62 sets forth the amino acid of SEQ ID NO: 1, wherein the following mutations are included: S223C and T659C.

SEQ ID NO: 63 sets forth the amino acid of SEQ ID NO: 1, wherein the following mutations are included: W240C and A732A.

SEQ ID NO: 64 sets forth the amino acid of SEQ ID NO: 1, wherein the following mutations are included: W240C and G735C.

SEQ ID NO: 65 sets forth the amino acid of SEQ ID NO: 1, wherein the following mutations are included: Y242C and V728C.

SEQ ID NO: 66 sets forth the amino acid of SEQ ID NO: 1, wherein the following mutations are included: Y242C and G731C.

SEQ ID NO: 67 sets forth the amino acid of SEQ ID NO: 1, wherein the following mutations are included: R258C and L656C.

SEQ ID NO: 68 sets forth the amino acid of SEQ ID NO: 1, wherein the following mutations are included: S269C and L656C.

SEQ ID NO: 69 sets forth the amino acid of SEQ ID NO: 1, wherein the following mutations are included: S269C and N658C.

SEQ ID NO: 70 sets forth the amino acid of SEQ ID NO: 1, wherein the following mutations are included: D272C and P614C.

SEQ ID NO: 71 sets forth the amino acid of SEQ ID NO: 1, wherein the following mutations are included: V273C and V629C.

SEQ ID NO: 72 sets forth the amino acid of SEQ ID NO: 1, wherein the following mutations are included: W349C and A650C.

SEQ ID NO: 73 sets forth the amino acid of SEQ ID NO: 1, wherein the following mutations are included: S367C and A500C.

SEQ ID NO: 74 sets forth the amino acid of SEQ ID NO: 1, wherein the following mutations are included: S367C and A503C.

SEQ ID NO: 75 sets forth the amino acid of SEQ ID NO: 1, wherein the following mutations are included: K370C and Q501C.

SEQ ID NO: 76 sets forth the amino acid of SEQ ID NO: 1, wherein the following mutations are included: K522C and I683C.

SEQ ID NO: 77 sets forth the amino acid of SEQ ID NO: 1, wherein the following mutations are included: I523C and I683C.

SEQ ID NO: 78 sets forth the amino acid of SEQ ID NO: 1, wherein the following mutations are included: I523C and M684C.

SEQ ID NO: 79 sets forth the amino acid of SEQ ID NO: 1, wherein the following mutations are included: N524C and M684C.

SEQ ID NO: 80 sets forth the amino acid of SEQ ID NO: 1, wherein the following mutations are included: P525C and E681C.

SEQ ID NO: 81 sets forth the amino acid of SEQ ID NO: 1, wherein the following mutations are included: R540C and L680C.

SEQ ID NO: 82 sets forth the amino acid of SEQ ID NO: 1, wherein the following mutations are included: F541C and L680C.

SEQ ID NO: 83 sets forth the amino acid of SEQ ID NO: 1, wherein the following mutations are included: L548C and P655C.

SEQ ID NO: 84 sets forth the amino acid of SEQ ID NO: 1, wherein the following mutations are included: A549C and N658C.

SEQ ID NO: 85 sets forth the amino acid of SEQ ID NO: 1, wherein the following mutations are included: S550C and P655C.

SEQ ID NO: 86 sets forth the amino acid of SEQ ID NO: 1, wherein the following mutations are included: S550C and E657C.

SEQ ID NO: 87 sets forth the amino acid of SEQ ID NO: 1, wherein the following mutations are included: Q591C and S668C.

SEQ ID NO: 88 sets forth the amino acid of SEQ ID NO: 1, wherein the following mutations are included: L603C and Y667C.

SEQ ID NO: 89 sets forth the amino acid of SEQ ID NO: 1, wherein the following mutations are included: G604C and L672C.

SEQ ID NO: 90 sets forth the amino acid of SEQ ID NO: 1, wherein the following mutations are included: R607C and N688C.

SEQ ID NO: 91 sets forth the amino acid of SEQ ID NO: 1, wherein the following mutations are included: T608C and Q692C.

SEQ ID NO: 92 sets forth the amino acid of SEQ ID NO: 1, wherein the following mutations are included: E609C and K691C.

SEQ ID NO: 93 sets forth the amino acid of SEQ ID NO: 1, wherein the following mutations are included: E610C and S674C.

SEQ ID NO: 94 sets forth the amino acid of SEQ ID NO: 1, wherein the following mutations are included: E610C and S675C.

SEQ ID NO: 95 sets forth the amino acid of SEQ ID NO: 1, wherein the following mutations are included: Q612C and V663C.

SEQ ID NO: 96 sets forth the amino acid of SEQ ID NO: 1, wherein the following mutations are included: V737C and F755C.

SEQ ID NO: 97 sets forth the amino acid of SEQ ID NO: 1, wherein the following mutations are included: V741C and A754C.

SEQ ID NO: 98 sets forth the amino acid of SEQ ID NO: 1, wherein the following mutations are included: V741C and F755C.

SEQ ID NO: 99 sets forth the amino acid of SEQ ID NO: 1, wherein the following mutation is included: D679S.

SEQ ID NO: 100 sets forth the amino acid of SEQ ID NO: 1, wherein the following mutation is included: D679N.

SEQ ID NO: 101 sets forth the amino acid of SEQ ID NO: 1, wherein the following mutation is included: E682S.

SEQ ID NO: 102 sets forth the amino acid of SEQ ID NO: 1, wherein the following mutation is included: E682Q.

SEQ ID NO: 103 sets forth the amino acid of SEQ ID NO: 1, wherein the following mutation is included: E686S.

SEQ ID NO: 104 sets forth the amino acid of SEQ ID NO: 1, wherein the following mutation is included: E686Q.

SEQ ID NO: 105 sets forth the amino acid of SEQ ID NO: 1, wherein the following mutation is included: N118P.

SEQ ID NO: 106 sets forth the amino acid of SEQ ID NO: 1, wherein the following mutation is included: D646P.

SEQ ID NO: 107 sets forth the amino acid sequence for >5CXF:A|PDBID|CHAIN|SEQUENCE, from FIG. 8.

SEQ ID NO: 108 sets forth the amino acid sequence for >5CXF:B|PDBID|CHAIN|SEQUENCE, from FIG. 8.

SEQ ID NO: 109 sets forth the amino acid sequence for >5CXF:C|PDBID|CHAIN|SEQUENCE, from FIG. 8.

SEQ ID NO: 110 sets forth the amino acid sequence for a gB polypeptide from HAN13 gi|242345614|gb|GQ221973.1|:81988-84705 Human herpesvirus 5 strain HAN13, complete genome reverse complement, referenced in the description for FIG. 9.

SEQ ID NOs: 111 sets forth the amino acid sequence for a gB polypeptide from VR1814 gi|270355759|gb|GU179289.1|:81925-84642 Human herpesvirus 5 strain VR1814, complete genome reverse complement, referenced in the description for FIG. 9.

SEQ ID NOs: 112-140 sets forth the amino acid sequence for a gB polypeptide from various CMV gB strains described in FIG. 9.

SEQ ID NO: 141-SEQ ID NO: 210 set forth a polynucleotide sequence encoding a polypeptide derived from HCMV, such as for example, gH, gL, UL128, UL130, UL131, gB or pp65.

SEQ ID NO: 211-SEQ ID NO: 223 set forth an amino acid sequence for a polypeptide derived from HCMV, such as for example, gH, gL, UL128, UL130, UL131, gB or pp65. SEQ ID NO: 224 sets forth an amino acid sequence for a polypolypeptide derived from HCMV.

SEQ ID NO: 225-SEQ ID NO: 254 set forth a polynucleotide sequence encoding a polypolypeptide derived from HCMV.

SEQ ID NO: 255 sets forth the amino acid sequence of CMV gB1666, residues V23 to V907 of SEQ ID NO: 1 (Towne) having the following mutations: D217C, Y589C, and I675S. Does not include the signal sequence (residues M1-A22 of SEQ ID NO: 1).

SEQ ID NO: 256 sets forth the nucleic acid sequence of CMV gB1666 encoding residues V23 to V907 of SEQ ID NO: 1 (Towne) having the following mutations: D217C, Y589C, and I675S. Does not include nucleotides encoding the signal sequence (residues M1-A22 of SEQ ID NO: 1).

SEQ ID NO: 257 sets forth the amino acid sequence of CMV gB2457 (Prefusion, Full length), residues V23 to V907 of SEQ ID NO: 1 (Towne) having the following mutations: D217C, M371C, W506C, Y589C, and I675S. Does not include the signal sequence (residues M1-A22 of SEQ ID NO: 1).

SEQ ID NO: 258 sets forth the nucleic acid sequence of CMV gB2457 (Prefusion, Full length) encoding residues V23 to V907 of SEQ ID NO: 1 (Towne) having the following mutations: D217C, M371C, W506C, Y589C, and I675S. Does not include nucleotides encoding the signal sequence (residues M1-A22 of SEQ ID NO: 1).

SEQ ID NO: 259 sets forth the amino acid sequence of CMV gB2459 (Prefusion, Full length), residues V23 to V907 of SEQ ID NO: 1 (Towne) having the following mutations: D217C, N524C, Y589C, M684C, and I675S. Does not include the signal sequence (residues M1-A22 of SEQ ID NO: 1).

SEQ ID NO: 260 sets forth the nucleic acid sequence of CMV gB2459 (Prefusion, Full length) encoding residues V23 to V907 of SEQ ID NO: 1 (Towne) having the following mutations: D217C, N524C, Y589C, M684C, and I675S. Does not include nucleotides encoding the signal sequence (residues M1-A22 of SEQ ID NO: 1).

SEQ ID NO: 261 sets forth the amino acid sequence of CMV gB2555 (Prefusion, including trimerization domain (GCN4 CC tri2)), residues V23 to V702 of SEQ ID NO: 1 (Towne) having the following mutations: YIH to GHR (155-157), D217C, W240A, M371C, C246S, W506C, Y589C, and I675S. Does not include the signal sequence (residues M1-A22 of SEQ ID NO: 1).

SEQ ID NO: 262 sets forth the nucleic acid sequence of CMV gB2555 (Prefusion, including trimerization domain (GCN4 CC tri2)) encoding residues V23 to V702 of SEQ ID NO: 1 (Towne) having the following mutations: YIH to GHR (155-157), D217C, W240A, M371C, C246S, W506C, Y589C, and I675S. Does not include nucleotides encoding the signal sequence (residues M1-A22 of SEQ ID NO: 1).

SEQ ID NO: 263 sets forth the amino acid sequence of CMV gB2556 (Prefusion, including trimerization domain (GCN4 CC tri2)), residues V23 to V702 of SEQ ID NO: 1 (Towne) having the following mutations: YIH to GHR (155-157), D217C, W240A, C246S, N524C, Y589C, I675S, and M684C. Does not include the signal sequence (residues M1-A22 of SEQ ID NO: 1).

SEQ ID NO: 264 sets forth the nucleic acid sequence of CMV gB2556 (Prefusion, including trimerization domain (GCN4 CC tri2)) encoding residues V23 to V702 of SEQ ID NO: 1 (Towne) having the following mutations: YIH to GHR (155-157), D217C, W240A, C246S, N524C, Y589C, I675S, and M684C. Does not include nucleotides encoding the signal sequence (residues M1-A22 of SEQ ID NO: 1).

SEQ ID NO: 265 sets forth the amino acid sequence of CMV gB2796 (Prefusion, ectodomain), residues V23 to D646 of SEQ ID NO:1 (Towne) having the following mutations: YIH to GHR (155-157), D217C, W240A, C246S, M371C, W506C, and Y589C. Does not include the signal sequence (residues M1-A22 of SEQ ID NO: 1).

SEQ ID NO: 266 sets forth the nucleic acid sequence of CMV gB2796 (Prefusion, ectodomain) encoding amino acids V23 to D646 of SEQ ID NO:1 (Towne) having the following amino acid mutations: YIH to GHR (155-157), D217C, W240A, C246S, M371C, W506C, and Y589C. Does not include the nucleotides encoding the signal sequence (residues M1-A22 of SEQ ID NO: 1).

SEQ ID NO: 267 sets for the CMV gB ectodomain, V23 to P707 of SEQ ID NO:1 (Towne strain).

SEQ ID NO: 268 sets forth the amino acid sequence of the signal sequence of wt HCMV gB (Towne).

SEQ ID NO: 269 sets forth the amino acid sequence of GCN4 CC tri2 trimerization domain (see Table 9).

SEQ ID NO: 270 sets forth the nucleic acid sequence encoding the GCN4 CC tri2 trimerization domain.

SEQ ID NO: 271 sets forth the amino acid sequence of T4 fibritin foldon domain (see Table 9).

SEQ ID NO: 272-273 sets forth the amino acid sequences of various GCN4 trimerization domains.

SEQ ID NO: 274 sets forth the amino acid sequences of C-terminal fusion sequence described in Table 9.

SEQ ID NO: 275 sets forth the amino acid sequence MIALDI.

SEQ ID NO: 276 sets forth the amino acid sequence GSGKDG.

DETAILED DESCRIPTION

As described herein, the inventors elucidated a three-dimensional structure of a HCMV glycoprotein B (gB) polypeptide in a conformation that differs from the postfusion conformation and which we refer to as a prefusion conformation. Mutations to stabilize the polypeptide in a prefusion conformation were also discovered. The structures may be used to generate HCMV neutralizing antibody responses greater than those achieved with prior HCMV gB-based immunogens. The polypeptides described herein, and the nucleic acids that encode the polypeptides, may be used, for example, as potential immunogens in a vaccine against HCMV and as diagnostic tools, among other uses.

The inventors further discovered mutations that can be introduced into a cytomegalovirus (CMV) gB polypeptide, which can, among other things, greatly facilitate the production and subsequent purification of a gB antigen stabilized in the prefusion conformation; significantly improve the efficiency of production of a gB polypeptide in the prefusion conformation; alter the antigenicity of a gB polypeptide, as compared to the wild-type gB polypeptide; facilitate a focused immune response to prefusion gB; and reduce and/or eliminate steric occlusion of neutralizing epitopes of gB.

Definitions

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen."

As used herein, the term "additional mutation" shall include, but not be limited to, an amino acid substitution that introduces electrostatic mutations, fill cavities, alter the packing of residues, introduce N-linked glycosylation sites, introduce inter-protomer disulfide bonds, and combinations thereof, including consersatvie substitutions thereof, as compared to a native HCMV gB. Examples of an "additional mutation" may be found throughout this description but most specifically are set forth in Tables 3 and 4 and the Examples.

The term "adjuvant" refers to a substance capable of enhancing, accelerating, or prolonging the body's immune response to an immunogen or immunogenic composition, such as a vaccine (although it is not immunogenic by itself). An adjuvant may be included in the immunogenic composition, such as a vaccine, or may be administered separately from the immunogenic composition.

The term "administration" refers to the introduction of a substance or composition into a subject by a chosen route. Administration can be local or systemic. For example, if the chosen route is intramuscular, the composition (such as a composition including a disclosed immunogen) is administered by introducing the composition into a muscle of the subject.

The term "antigen" refers to a molecule that can be recognized by an antibody. Examples of antigens include polypeptides, peptides, lipids, polysaccharides, and nucleic acids containing antigenic determinants, such as those recognized by an immune cell.

The term "conservative substitution" refers to the substitution of an amino acid with a chemically similar amino acid. Conservative amino acid substitutions providing functionally similar amino acids are well known in the art. The following six groups each contain amino acids that are conservative substitutions for one another:

1) alanine (A), serine (S), threonine (T);
2) aspartic acid (D), glutamic acid (E);
3) asparagine (N), glutamine (Q);
4) arginine (R), lysine (K);
5) isoleucine (I), leucine (L), methionine (M), valine (V); and
6) phenylalanine (F), tyrosine (Y), tryptophan (W).

The term "degenerate variant" of a reference polynucleotide refers to a polynucleotide that differs in the nucleotide sequence from the reference polynucleotide but encodes the same polypeptide sequence as encoded by the reference polynucleotide. There are 20 natural amino acids, most of which are specified by more than one codon. For instance, the codons CGU, CGC, CGA, CGG, AGA, and AGG all encode the amino acid arginine. Thus, at every position where an arginine is specified within a protein encoding sequence, the codon can be altered to any of the corresponding codons described without altering the encoded protein. Because of the degeneracy of the genetic code, a large number of functionally identical nucleic acids encode any given polypeptide.

The term "effective amount" refers to an amount of agent that is sufficient to generate a desired response. For instance, this can be the amount necessary to inhibit viral replication or to measurably alter outward symptoms of the viral infection.

The term "epitope" (or "antigenic determinant" or "antigenic site") refers to the region of an antigen to which an antibody, B cell receptor, or T cell receptor binds or responds. Epitopes can be formed from contiguous amino acids or noncontiguous amino acids juxtaposed by secondary, tertiary, or quaternary folding of a protein. Epitopes formed from contiguous amino acids are typically retained on exposure to denaturing solvents whereas epitopes formed by higher order folding are typically lost on treatment with denaturing solvents.

The term "subject" refers to either a human or a non-human mammal. The term "mammal" refers to any animal species of the Mammalia class. Examples of mammals include: humans; non-human primates such as monkeys; laboratory animals such as rats, mice, guinea pigs; domestic animals such as cats, dogs, rabbits, cattle, sheep, goats, horses, and pigs; and captive wild animals such as lions, tigers, elephants, and the like.

The term "glycoprotein" refers to a protein that contains oligosaccharide chains (glycans) covalently attached to polypeptide side-chains. The carbohydrate is attached to the protein in a cotranslational or posttranslational modification known as glycosylation. The term "glycosylation site" refers to an amino acid sequence on the surface of a polypeptide, such as a protein, which accommodates the attachment of a glycan. An N-linked glycosylation site is triplet sequence of NX(S/T) in which N is asparagine, X is any residue except proline, and (S/T) is a serine or threonine residue. A glycan is a polysaccharide or oligosaccharide. Glycan may also be used to refer to the carbohydrate portion of a glycoconjugate, such as a glycoprotein, glycolipid, or a proteoglycan.

The term "host cells" refers to cells in which a vector can be propagated and its DNA or RNA expressed. The cell may be prokaryotic or eukaryotic.

The term "identical" or percent "identity," in the context of two or more nucleic acid or polypeptide sequences, refers to two or more sequences or subsequences that are the same or have a specified percentage of amino acid residues or nucleotides that are the same, when compared and aligned for maximum correspondence. Methods of alignment of sequences for comparison are well known in the art. Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166+1554*100=75.0).

Optimal alignment of sequences for comparison can be conducted, e.g., by the local homology algorithm of Smith and Waterman, Adv. Appl. Math. 2:482, 1981, by the homology alignment algorithm of Needleman and Wunsch, Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Sambrook et al. (Molecular Cloning: A Laboratory Manual, 4th ed, Cold Spring Harbor, New York, 2012) and Ausubel et al. (In Current Protocols in Molecular Biology, John Wiley and Sons, New York, through supplement 104, 2013).

The term "immunogen" refers to a compound, composition, or substance that is immunogenic as defined herein below.

The term "immunogenic" refers to the ability of a substance to cause, elicit, stimulate, or induce an immune response against a particular antigen, in a subject, whether in the presence or absence of an adjuvant.

The term "immune response" refers to any detectable response of a cell or cells of the immune system of a host mammal to a stimulus (such as an immunogen), including, but not limited to, innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids). Examples of immune responses include an alteration (e.g., increase) in Toll-like receptor activation, lymphokine (e.g., cytokine (e.g., Th1, Th2 or Th17 type cytokines) or chemokine) expression or secretion, macrophage activation, dendritic cell activation, T cell (e.g., CD4+ or CD8+ T cell) activation, NK cell activation, B cell activation (e.g., antibody generation and/or secretion), binding of an immunogen (e.g., antigen (e.g., immunogenic polypeptide)) to an MHC molecule, induction of a cytotoxic T lymphocyte ("CTL") response, induction of a B cell response (e.g., antibody production), and, expansion (e.g., growth of a population of cells) of cells of the immune system (e.g., T cells and B cells), and increased processing and presentation of antigen by antigen presenting cells. The term "immune response" also encompasses any detectable response to a particular substance (such as an antigen or immunogen) by one or more components of the immune system of a vertebrate animal in vitro.

The term 'immunogenic composition" refers to a composition comprising an immunogen.

The term "mutation" refers to deletion, addition, or substitution of amino acid residues in the amino acid sequence of a protein or polypeptide as compared to the amino acid sequence of a reference protein or polypeptide. Throughout the specification and claims, the substitution of an amino acid at one particular location in the protein sequence is referred to using a notation "(amino acid residue in wild type protein)(amino acid position)(amino acid residue in engineered protein)". For example, a notation Y75A refers to a substitution of a tyrosine (Y) residue at the 75th position of the amino acid sequence of the reference protein by an alanine (A) residue (in a mutant of the reference protein). In cases where there is variation in the amino acid residue at the same position among different wild-type sequences, the amino acid code preceding the position number may be omitted in the notation, such as "75A." The term "native" or "wild-type" protein, sequence, or polypeptide refers to a naturally existing protein, sequence, or polypeptide that has not been artificially modified by selective mutations.

The term "pharmaceutically acceptable carriers" refers to a material or composition which, when combined with an active ingredient, is compatible with the active ingredient and does not cause toxic or otherwise unwanted reactions when administered to a subject, particularly a mammal. Examples of pharmaceutically acceptable carriers include solvents, surfactants, suspending agents, buffering agents, lubricating agents, emulsifiers, absorbants, dispersion media, coatings, and stabilizers.

The term "pre-fusion-specific antibody" refers to an antibody that specifically binds to the CMV gB glycoprotein in a pre-fusion conformation, but does not bind to the CMV gB protein in a post-fusion conformation.

The term "pre-fusion trimer-specific antibody" refers to an antibody that specifically binds to the CMV gB glycoprotein in a pre-fusion, trimeric conformation, but does not bind to the CMV gB protein in a post-fusion conformation or in a pre-fusion conformation that is not also trimeric. "Pre-fusion trimer-specific antibodies" are a subset of "pre-fusion-specific antibodies."

The term "prime-boost vaccination" refers to an immunotherapy regimen that includes administration of a first immunogenic composition (the primer vaccine) followed by administration of a second immunogenic composition (the booster vaccine) to a subject to induce an immune response. The primer vaccine and the booster vaccine typically contain the same immunogen and are presented in the same or similar format. However, they may also be presented in different formats, for example one in the form of a vector and the other in the form of a naked DNA plasmid. The skilled artisan will understand a suitable time interval between administration of the primer vaccine and the booster vaccine. Further, the primer vaccine, the booster vaccine, or both primer vaccine and the booster vaccine additionally include an adjuvant.

The term "soluble protein" refers to a protein capable of dissolving in aqueous liquid and remaining dissolved. The solubility of a protein may change depending on the concentration of the protein in the water-based liquid, the buffering condition of the liquid, the concentration of other solutes in the liquid, for example salt and protein concentrations, and the temperature of the liquid.

The term "specifically bind," in the context of the binding of an antibody to a given target molecule, refers to the binding of the antibody with the target molecule with higher affinity than its binding with other tested substances. For example, an antibody that specifically binds to the CMV gB protein in pre-fusion conformation is an antibody that binds CMV gB protein in pre-fusion conformation with higher affinity than it binds to the CMV gB protein in the post-fusion conformation.

The term "therapeutically effective amount" refers to the amount of agent that is sufficient to prevent, treat (including prophylaxis), reduce and/or ameliorate the symptoms and/or underlying causes of a disorder.

The term "vaccine" refers to a pharmaceutical composition comprising an immunogen that is capable of eliciting a prophylactic or therapeutic immune response in a subject. Typically, a vaccine elicits an antigen-specific immune response to an antigen of a pathogen, for example a viral pathogen.

The term "vector" refers to a nucleic acid molecule capable of transporting or transferring a foreign nucleic acid molecule. The term encompasses both expression vectors and transcription vectors. The term "expression vector" refers to a vector capable of expressing the insert in the target cell, and generally contains control sequences, such as enhancer, promoter, and terminator sequences, that drive expression of the insert. The term "transcription vector" refers to a vector capable of being transcribed but not translated. Transcription vectors are used to amplify their insert. The foreign nucleic acid molecule is referred to as "insert" or "transgene." A vector generally consists of an insert and a larger sequence that serves as the backbone of the vector. Based on the structure or origin of vectors, major types of vectors include plasmid vectors, cosmid vectors, phage vectors such as lambda phage, viral vectors such as adenovirus (Ad) vectors, and artificial chromosomes.

Native HCMV gB

Native HCMV gB is synthesized as a 906 or 907 amino acid polypeptide (depending upon the strain of CMV) that undergoes extensive posttranslational modification, including glycosylation at N- and O-linked sites and cleavage by ubiquitous cellular endoproteases into amino- and carboxy-terminal fragments. The N- and C-terminal fragments of gB, gp116 and gp55, respectively, are covalently connected by disulfide bonds, and the mature, glycosylated gB assumes a trimeric configuration. The gB polypeptide contains a large ectodomain (which is cleaved into gp116 and the ectodomain of gp55), a transmembrane domain (TM), and the intraviral (or cytoplasmic) domain (cytodomain).

Native HCMV gBs from various strains are known. For example, at least sixty HCMV gB sequences from clinical and laboratory-adapted strains are available from NCBI's RefSeq database as described in Burke et al., "Crystal Structure of the Human Cytomegalovirus Glycoprotein B." *PLoS Pathog.* 2015 Oct. 20; 11(10):e1005227, see S4 Fig., which is hereby incorporated herein in its entirety.

Accordingly, the term "CMV gB" polypeptide or "HCMV gB" polypeptide as used herein is to be understood as the native HCMV gB polypeptide from any human HCMV strain (not limited to the Towne strain). The actual residue position number may need to be adjusted for gBs from other human CMV strains depending on the actual sequence alignment. However, one of skill in the art will understand how to align sequences from different strains in order to identify the corresponding residue position from one strain to another.

HCMV gB is encoded by the UL55 gene of HCMV genome. It is an envelope glycoprotein that mediates the fusion of the HCMV viral membrane with a host cell membrane. The protein undergoes a series of conformational changes from a prefusion to a postfusion form. The crystal structure of gB in its postfusion form is available (PDB accession code 5CXF), and the prefusion conformation is set forth herein.

Conformations

A HCMV gB postfusion conformation refers to a structural conformation adopted by HCMV gB subsequent to the fusion of the virus envelope with the host cellular membrane. The native HCMV gB may also assume the postfusion conformation outside the context of a fusion event, for example, under stress conditions such as exposure to heat, extraction from a membrane, expression as an ectodomain or storage. More specifically, the gB postfusion conformation is described, for example, in Burke et al., Crystal Structure of the Human Cytomegalovirus Glycoprotein B. *PLoS Pathog.* 2015 Oct. 20; 11(10): e1005227. See also, Research Collaboratory for Structural Bioinformatics Protein Data Bank (RCSB PDB): 5CXF, Crystal structure of the extracellular domain of glycoprotein B from Human Cytomegalovirus, from Human cytomegalovirus (strain AD169), deposited 2015 Jul. 28; DOI: 10.2210/pdb5CXF/pdb; and Burke et al., *PLoS Pathog.* 2015 Oct. 20; 11(10):e1005227. A sequence of a protein that when expressed, can fold into a postfusion conformation, is provided as SEQ ID NO: 44. Another example of a protein that when expressed folds into a postfusion conformation is provided as SEQ ID NO: 45. The postfusion conformation is about 165 Å tall and 65 Å wide.

As used herein, a "prefusion conformation" refers to a structural conformation adopted by the polypeptide that differs from the HCMV gB postfusion conformation at least in terms of molecular dimensions or three-dimensional coordinates. The prefusion conformation refers to a structural conformation adopted by HCMV gB prior to triggering of the fusogenic event that leads to transition of gB to the postfusion conformation. Isolating HCMV gB in a stable prefusion conformation may be useful in informing and directing development of improved vaccines and immunogenic compositions to address the important public health problem of cytomegalovirus infections. In some embodiments, a prefusion conformation includes a conformation that can bind to a prefusion-specific antibody. In some embodiments, a prefusion conformation includes a conformation that is characterized by coordinates set forth in Table 1A, which is incorporated by reference herein in its entirety. In some embodiments, the polypeptide is characterized by structure coordinates comprising a root mean square deviation (RMSD) of conserved residue backbone atoms when superimposed on backbone atoms described by structural coordinates set forth in Table 1A. In some embodiments, a prefusion conformation includes a conformation that is characterized by coordinates set forth in Table 1B, which is incorporated by reference herein in its entirety. In some embodiments, the polypeptide is characterized by structure coordinates comprising a root mean square deviation (RMSD) of conserved residue backbone atoms when superimposed on backbone atoms described by structural coordinates set forth in Table 1B. In some embodiments, a polypeptide having a HCMV gB prefusion conformation refers to a polypeptide that includes a trimeric helix bundle, centered on the three-fold axis of the trimer and comprising residues L479 to K522 of each protomer, wherein the direction of the bundle from N-terminal to C-terminal along the three-fold axis (shown by the arrows in FIGS. 4A and 4B) is towards the point on the three-fold axis intersected by the plane defined by residue W240 of each protomer, which is in a fusion loop near the tip of each Domain I of the trimer. In some embodiments, the helix bundle comprises the residues between L479 and K522, according to the numbering of SEQ ID NO: 1.

Polypeptides of the Invention

The present invention relates to polypeptides that include amino acid mutations relative to the amino acid sequence of the corresponding wild-type HCMV gB. The amino acid mutations include amino acid substitutions, deletions, or additions relative to a wild-type HCMV gB. Accordingly, the polypeptides are mutants of wild-type HCMV gBs.

In some embodiments, the polypeptides possess certain beneficial characteristics, such as being immunogenic. In some embodiments, the polypeptides possess increased immunogenic properties or improved stability in the prefusion conformation, as compared to the corresponding wild-type HCMV gB. Stability refers to the degree to which a transition of the HCMV gB conformation from prefusion to postfusion is hindered or prevented. In still other embodiments, the present disclosure provides polypeptides that display one or more introduced mutations as described herein, which may also result in improved stability in the prefusion conformation. The introduced amino acid mutations in the HCMV gB include amino acid substitutions, deletions, or additions. In some embodiments, the only mutations in the amino acid sequences of the mutants are amino acid substitutions relative to a wild-type HCMV gB.

Several modes of stabilizing the polypeptide conformation include amino acid substitutions that introduce disulfide bonds, introduce electrostatic mutations, fill cavities, alter the packing of residues, introduce N-linked glycosylation sites, and combinations thereof, as compared to a native HCMV gB.

Figure 3A:
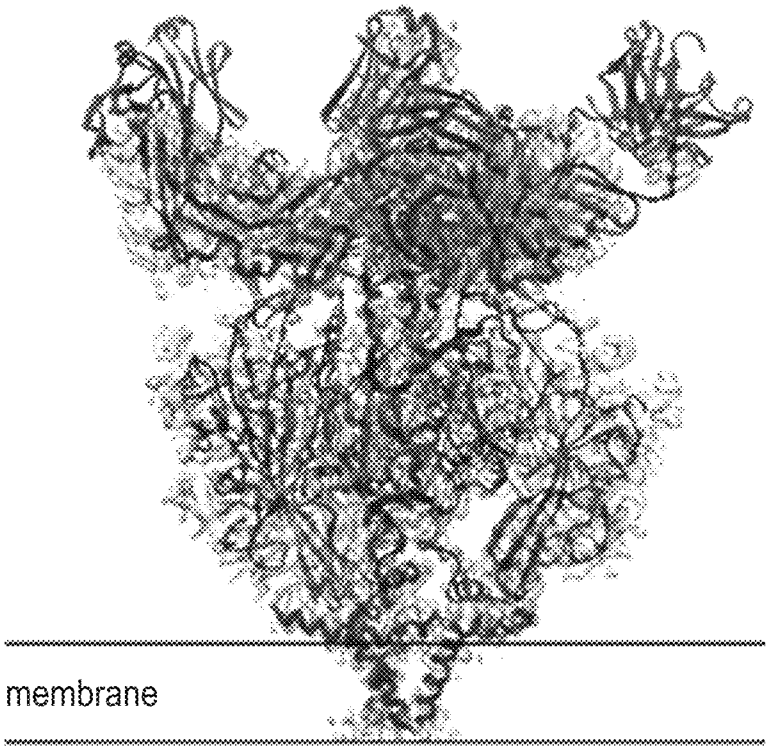
FIG. 3A-3B depict the fitting of models into the density maps. The models of inhibitor compound stabilized prefusion (FIG. 3A) and postfusion gB conformation (FIG. 3B) are fitted into the light gray density maps. gB components are dark gray, and SM5-1 fab components are black. Approximate position of the virus envelope as determined by the position of the TM region in the prefusion structure is indicated by black horizontal lines.

In one aspect, the invention relates to a polypeptide that exhibits a conformation that is not the postfusion conformation. That is, the polypeptide exhibits a prefusion conformation as described above and does not exhibit a postfusion conformation. See, for example, the prefusion conformation illustrated in FIG. 3A, as compared to the postfusion conformation illustrated in FIG. 3B; FIG. 4A, as compared to the postfusion conformation illustrated in FIG. 4B; and FIG. 6A, as compared to the postfusion conformation illustrated in FIG. 6C. In some embodiments, the polypeptide is characterized by structure coordinates comprising a root mean square deviation (RMSD) of conserved residue backbone atoms when superimposed on backbone atoms described by structural coordinates of Table 1A. In some embodiments, the polypeptide is characterized by structure coordinates comprising a root mean square deviation (RMSD) of conserved residue backbone atoms when superimposed on backbone atoms described by structural coordinates of Table 1B.

In some embodiments, the polypeptides are isolated, i.e., separated from HCMV gB polypeptides having a postfusion conformation. Thus, the polypeptide may be, for example, at least 80% isolated, at least 90%, 95%, 98%, 99%, or even 99.9% isolated from HCMV gB polypeptides in a postfusion conformation. In one aspect, the invention relates to a polypeptide that specifically binds to an HCMV gB prefusion-specific antibody.

It will be understood that a homogeneous population of polypeptides in a particular conformation can include variations (such as polypeptide modification variations, e.g., glycosylation state), that do not alter the conformational state of the polypeptide. In several embodiments, the population of polypeptides remains homogeneous over time. For example, in some embodiments, the polypeptide, when dissolved in aqueous solution, forms a population of polypeptides stabilized in the prefusion conformation for at least 12 hours, such as at least 24 hours, at least 48 hours, at least one week, at least two weeks, or more.

Without being bound by theory, the polypeptides disclosed herein are believed to facilitate a stabilized prefusion conformation of an HCMV gB polypeptide. The polypeptides include at least one mutation as compared to a corresponding native HCMV gB polypeptide. A person of ordinary skill in the art will appreciate that the polypeptides are useful to elicit immune responses in mammals to CMV.

The native HCMV gB is conserved among the HCMV entry glycoproteins and is required for entry into all cell types. In view of the substantial conservation of HCMV gB sequences, the amino acid positions amongst different native HCMV gB sequences may be compared to identify corresponding HCMV gB amino acid positions among different HCMV strains. Thus, the conservation of native HCMV gB sequences across strains allows use of a reference HCMV gB sequence for comparison of amino acids at particular positions in the HCMV gB polypeptide. Accordingly, unless expressly indicated otherwise, the polypeptide amino acid positions provided herein refer to the reference sequence of the HCMV gB polypeptide set forth in SEQ ID NO: 1.

However, it should be noted that different native HCMV gB sequences may have different numbering systems from SEQ ID NO: 1, for example, there may be additional amino acid residues added or removed as compared to SEQ ID NO: 1 in a native HCMV gB sequence derived from a strain other than Towne. As such, it is to be understood that when specific amino acid residues are referred to by their number, the description is not limited to only amino acids located at precisely that numbered position when counting from the beginning of a given amino acid sequence, but rather that the equivalent or corresponding amino acid residue in any and all HCMV gB sequences is intended even if that residue is not at the same precise numbered position, for example if the HCMV sequence is shorter (e.g., a fragment) or longer than SEQ ID NO: 1, or has insertions or deletions as compared to SEQ ID NO: 1.

In some embodiments, the polypeptide is full-length, wherein the polypeptide includes the same number of amino acid residues as the mature full-length wild-type HCMV gB. In some embodiments, the polypeptide is a fragment, wherein the polypeptide includes less than the total number of amino acid residues as the mature full-length wild-type HCMV gB. As used herein the term "fragment" and "truncated" are interchangeable. In some embodiments, the truncated gB polypeptide includes only the ectodomain sequence.

1. Cysteine (C) Substitutions

In some embodiments, the polypeptide includes cysteine substitutions that are introduced, as compared to a native HCMV gB. In some embodiments, the polypeptide includes any one of 1, 2, 3, 4, 5, 6, 7, 8, 9, or 10 cysteine substitutions. Without being bound by theory or mechanism, the cysteine substitutions described herein are believed to facilitate stability of the polypeptide in a conformation that is not the HCMV gB postfusion conformation. The introduced cysteine substitutions may be introduced by protein engineering, for example, by including one or more substituted cysteine residues that form a disulfide bond. In several embodiments, the amino acid positions of the cysteines are within a sufficiently close distance for formation of a disulfide bond in the prefusion, and not postfusion, conformation of the HCMV gB.

The cysteine residues that form a disulfide bond can be introduced into native HCMV gB sequence by two or more amino acid substitutions. For example, in some embodiments, two cysteine residues are introduced into a native HCMV gB sequence to form a disulfide bond.

In some embodiments, the polypeptide includes a recombinant HCMV gB stabilized in a prefusion conformation by a disulfide bond between cysteines that are introduced into a pair of amino acid positions that are close to each other in the prefusion conformation and more distant in the postfusion conformation.

Exemplary cysteine substitutions as compared to a native HCMV gB include any mutation selected from Table 2, the numbering of which based on the numbering of SEQ ID NO: 1.

TABLE 2

Exemplary cysteine pairs for bond stabilization

| Row | (i) Mutant ID | (ii) HCMV gB residue pairs for cysteine substitution, according to the numbering of SEQ ID NO: 1 | (iii) Substitutions corresponding to SEQ ID NO: 1 | (iv) Exemplary sequence that includes the mutations is set forth in: |
|---|---|---|---|---|
| 1 | gB-001; pSB01582 | 98 and 271 | Q98C and G271C | SEQ ID NO: 2 |
| 2 | gB-002 | 98 and 653 | Q98C and I653C | SEQ ID NO: 3 |
| 3 | gB-003; pSB01579 | 99 and 267 | G99C and A267C | SEQ ID NO: 4 |
| 4 | gB-004; pSB01580 | 100 and 267 | T100C and A267C | SEQ ID NO: 5 |
| 5 | gB-005; pSB01581 | 100 and 269 | T100C and S269C | SEQ ID NO: 6 |

TABLE 2-continued

| Exemplary cysteine pairs for bond stabilization | | | | |
|---|---|---|---|---|
| Row | (i) Mutant ID | (ii) HCMV gB residue pairs for cysteine substitution, according to the numbering of SEQ ID NO: 1 | (iii) Substitutions corresponding to SEQ ID NO: 1 | (iv) Exemplary sequence that includes the mutations is set forth in: |
| 6 | gB-006 | 100 and 651 | T100C and L651C | SEQ ID NO: 7 |
| 7 | gB-007 | 217 and 584 | D217C and F584C | SEQ ID NO: 8 |
| 8 | gB-008 | 218 and 585 | Y218C and A585C | SEQ ID NO: 9 |
| 9 | gB-009 | 219 and 654 | S219C and D654C | SEQ ID NO: 10 |
| 10 | gB-010 | 220 and 652 | N220C and D652C | SEQ ID NO: 11 |
| 11 | gB-011 | 221 and 652 | T221C and D652C | SEQ ID NO: 12 |
| 12 | gB-012 | 240 and 718 | W240C and G718C | SEQ ID NO: 13 |
| 13 | gB-013 | 242 and 710 | Y242C and K710C | SEQ ID NO: 14 |
| 14 | gB-014 | 242 and 714 | Y242C and D714C | SEQ ID NO: 15 |
| 15 | gB-015 | 269 and 653 | S269C and I653C | SEQ ID NO: 16 |
| 16 | gB-016 | 271 and 614 | G271C and P614C | SEQ ID NO: 17 |
| 17 | gB-017 | 367 and 499 | S367C and L499C | SEQ ID NO: 18 |
| 18 | gB-018 | 372 and 506 | T372C and W506C | SEQ ID NO: 19 |
| 19 | gB-019 | 541 and 669 | F541C and Q669C | SEQ ID NO: 20 |
| 20 | gB-020 | 548 and 650 | L548C and A650C | SEQ ID NO: 21 |
| 21 | gB-021 | 549 and 653 | A549C and 1653C | SEQ ID NO: 22 |
| 22 | gB-022 | 550 and 652 | S550C and D652C | SEQ ID NO: 23 |
| 23 | gB-023 | 604 and 661 | G604C and F661C | SEQ ID NO: 24 |
| 24 | gB-024 | 605 and 665 | N605C and E665C | SEQ ID NO: 25 |
| 25 | gB-025 | 607 and 675 | R607C and S675C | SEQ ID NO: 26 |
| 26 | gB-026 | 608 and 679 | T608C and D679C | SEQ ID NO: 27 |
| 27 | gB-027 | 609 and 678 | E609C and F678C | SEQ ID NO: 28 |
| 28 | gB-028 | 673 and 674 | R673C and S674C | SEQ ID NO: 29 |
| 29 | gB-029 | 676 and 677 | N676C and V677C | SEQ ID NO: 30 |
| 30 | gB-030 | 680 and 681 | L680C and E681C | SEQ ID NO: 31 |
| 31 | gB-031 | 683 and 684 | I683C and M684C | SEQ ID NO: 32 |
| 32 | gB-032 | 687 and 688 | F687C and N688C | SEQ ID NO: 33 |
| 33 | gB-033 | 690 and 691 | Y690C and K691C | SEQ ID NO: 34 |
| 34 | gB-034 | 695 and 724 | K695C and K724C | SEQ ID NO: 35 |
| 35 | gB-035 | 746 and 747 | T746C and F747C | SEQ ID NO: 36 |
| 36 | gB-036 | 749 and 750 | K749C and N750C | SEQ ID NO: 37 |
| 37 | gB-043; pSB01656 | 96 and 660 | M96C and D660C | SEQ ID NO: 47 |
| 38 | gB-044; pSB01657 | 98 and 658 | Q98C and N658C | SEQ ID NO: 48 |
| 39 | gB-045; pSB01658 | 100 and 258 | T100C and R258C | SEQ ID NO: 49 |
| 40 | gB-046; pSB01659 | 100 and 656 | T100C and L656C | SEQ ID NO: 50 |
| 41 | gB-047; pSB01660 | 100 and 658 | T100C and N658C | SEQ ID NO: 51 |
| 42 | gB-048; pSB01661 | 117 and 406 | I117C and T406C | SEQ ID NO: 52 |
| 43 | gB-049; pSB01662 | 117 and 407 | I117C and S407C | SEQ ID NO: 53 |
| 44 | gB-050; pSB01663 | 153 and 712 | Y153C and L712C | SEQ ID NO: 54 |
| 45 | gB-051; pSB01664 | 162 and 716 | L162C and M716C | SEQ ID NO: 55 |
| 46 | gB-052; pSB01665 | 217 and 587 | D217C and S587C | SEQ ID NO: 56 |
| 47 | gB-053; pSB01666 | 217 and 589 | D217C and Y589C | SEQ ID NO: 57 |
| 48 | gB-054; pSB01667 | 219 and 584 | S219C and F584C | SEQ ID NO: 58 |
| 49 | gB-055; pSB01668 | 219 and 585 | S219C and A585C | SEQ ID NO: 59 |
| 50 | gB-056; pSB01669 | 219 and 586 | S219C and N586C | SEQ ID NO: 60 |
| 51 | gB-057; pSB01670 | 220 and 659 | N220C and T659C | SEQ ID NO: 61 |
| 52 | gB-058; pSB01671 | 223 and 659 | S223C and T659C | SEQ ID NO: 62 |
| 53 | gB-059; pSB01672 | 240 and 732 | W240C and A732C | SEQ ID NO: 63 |
| 54 | gB-060; pSB01673 | 240 and 735 | W240C and G735C | SEQ ID NO: 64 |
| 55 | gB-061; pSB01674 | 242 and 728 | Y242C and V728C | SEQ ID NO: 65 |

TABLE 2-continued

Exemplary cysteine pairs for bond stabilization

| Row | (i) Mutant ID | (ii) HCMV gB residue pairs for cysteine substitution, according to the numbering of SEQ ID NO: 1 | (iii) Substitutions corresponding to SEQ ID NO: 1 | (iv) Exemplary sequence that includes the mutations is set forth in: |
|---|---|---|---|---|
| 56 | gB-062; pSB01675 | 242 and 731 | Y242C and G731C | SEQ ID NO: 66 |
| 57 | gB-063 | 258 and 656 | R258C and L656C | SEQ ID NO: 67 |
| 58 | gB-064 | 269 and 656 | S269C and L656C | SEQ ID NO: 68 |
| 59 | gB-065; pSB01678 | 269 and 658 | S269C and N658C | SEQ ID NO: 69 |
| 60 | gB-066; pSB01679 | 272 and 614 | D272C and P614C | SEQ ID NO: 70 |
| 61 | gB-067; pSB01680 | 273 and 629 | V273C and V629C | SEQ ID NO: 71 |
| 62 | gB-068; pSB01681 | 349 and 650 | W349C and A650C | SEQ ID NO: 72 |
| 63 | gB-069; pSB01682 | 367 and 500 | S367C and A500C | SEQ ID NO: 73 |
| 64 | gB-070; pSB01683 | 367 and 503 | S367C and A503C | SEQ ID NO: 74 |
| 65 | gB-071; pSB01684 | 370 and 501 | K370C and Q501C | SEQ ID NO: 75 |
| 66 | gB-072; pSB01685 | 522 and 683 | K522C and I683C | SEQ ID NO: 76 |
| 67 | gB-073; pSB01686 | 523 and 683 | I523C and I683C | SEQ ID NO: 77 |
| 68 | gB-074; pSB01687 | 523 and 684 | I523C and M684C | SEQ ID NO: 78 |
| 69 | gB-075; pSB01688 | 524 and 684 | N524C and M684C | SEQ ID NO: 79 |
| 70 | gB-076 | 525 and 681 | P525C and E681C | SEQ ID NO: 80 |
| 71 | gB-077 | 540 and 680 | R540C and L680C | SEQ ID NO: 81 |
| 72 | gB-078; pSB01691 | 541 and 680 | F541C and L680C | SEQ ID NO: 82 |
| 73 | gB-079; pSB01692 | 548 and 655 | L548C and P655C | SEQ ID NO: 83 |
| 74 | gB-080; pSB01693 | 549 and 658 | A549C and N658C | SEQ ID NO: 84 |
| 75 | gB-081; pSB01694 | 550 and 655 | S550C and P655C | SEQ ID NO: 85 |
| 76 | gB-082; pSB01695 | 550 and 657 | S550C and E657C | SEQ ID NO: 86 |
| 77 | gB-083; pSB01696 | 591 and 668 | Q591C and S668C | SEQ ID NO: 87 |
| 78 | gB-084; pSB01697 | 603 and 667 | L603C and Y667C | SEQ ID NO: 88 |
| 79 | gB-085; pSB01698 | 604 and 672 | G604C and L672C | SEQ ID NO: 89 |
| 80 | gB-086; pSB01699 | 607 and 688 | R607C and N688C | SEQ ID NO: 90 |
| 81 | gB-087; pSB01700 | 608 and 692 | T608C and Q692C | SEQ ID NO: 91 |
| 82 | gB-088; pSB01701 | 609 and 691 | E609C and K691C | SEQ ID NO: 92 |
| 83 | gB-089; pSB01702 | 610 and 674 | E610C and S674C | SEQ ID NO: 93 |
| 84 | gB-090; pSB01703 | 610 and 675 | E610C and S675C | SEQ ID NO: 94 |
| 85 | gB-091; pSB01704 | 612 and 663 | Q612C and V663C | SEQ ID NO: 95 |
| 86 | gB-092; pSB01705 | 737 and 755 | V737C and F755C | SEQ ID NO: 96 |
| 87 | gB-093; pSB01706 | 741 and 754 | V741C and A754C | SEQ ID NO: 97 |
| 88 | gB-094; pSB01707 | 741 and 755 | V741C and F755C | SEQ ID NO: 98 |
| 89 | | 356 and 500 | I356C and A500C | |
| 90 | | 371 and 505 | M371C and A505C | |
| 91 | | 371 and 506 | M371C and W506C | |
| 92 | | 374 and 503 | T374C and A503C | |
| 93 | | 160 and 708 | Y160C and Y708C | |
| 94 | | 221 and 657 | T221C and E657C | |
| 95 | | 541 and 681 | F541C and E681C | |
| 96 | | 605 and 670 | N605C and K670C | |

TABLE 2-continued

| Row | (i) Mutant ID | (ii) HCMV gB residue pairs for cysteine substitution, according to the numbering of SEQ ID NO: 1 | (iii) Substitutions corresponding to SEQ ID NO: 1 | (iv) Exemplary sequence that includes the mutations is set forth in: |
|---|---|---|---|---|
| | Exemplary cysteine pairs for bond stabilization | | | |
| 97 | | 219 and 587 | S219C and S587C | |
| 98 | | 219 and 588 | S219C and S588C | |
| 99 | | 219 and 589 | S219C and Y589C | |
| 100 | | 217 and 586 | D217C and N586C | |
| 101 | | 217 and 588 | D217C and S588C | |

In some embodiments, the polypeptide includes one or more (such as 2, 3, 4, 5, 6, 7, 8, 9 or 10) cysteine substitutions at any one of the positions listed in one or more of rows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or 101 of column (ii) of Table 2, wherein the resulting polypeptide does not exhibit an HCMV postfusion conformation.

In some embodiments, the polypeptide includes one or more (such as 2, 3, 4, 5, 6, 7, 8, 9 or 10) cysteine substitutions at any one of the positions listed in one or more of rows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 47, 69 or 91 of column (ii) of Table 2, wherein the resulting polypeptide does not exhibit an HCMV postfusion conformation.

In some embodiments, the polypeptide includes two cysteine substitutions as listed at any one of rows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or 101 of column (ii) of Table 2. In an embodiment, the resulting polypeptide does not exhibit an HCMV postfusion conformation. In an embodiment, the resulting polypeptide exhibits an HCMV prefusion conformation.

In a preferred embodiment, the polypeptide includes cysteine substitutions at positions 98 and 653 (listed in row 2, column (ii) of Table 2) according to the numbering of SEQ ID NO: 1, relative to the amino acid sequence of the wild-type HCMV gB. In another preferred embodiment, the polypeptide includes cysteine substitutions at positions 100 and 269 (listed in row 5, column (ii) of Table 2) according to the numbering of SEQ ID NO: 1, relative to the amino acid sequence of the wild-type HCMV gB. In a further preferred embodiment, the polypeptide includes cysteine substitutions at positions 217 and 584 (listed in row 7, column (ii) of Table 2) according to the numbering of SEQ ID NO: 1, relative to the amino acid sequence of the wild-type HCMV gB. In a preferred embodiment, the polypeptide includes cysteine substitutions at positions 242 and 710 (listed in row 13, column (ii) of Table 2) according to the numbering of SEQ ID NO: 1, relative to the amino acid sequence of the wild-type HCMV gB. In another preferred embodiment, the polypeptide includes cysteine substitutions at positions 242 and 714 (listed in row 14, column (ii) of Table 2) according to the numbering of SEQ ID NO: 1, relative to the amino acid sequence of the wild-type HCMV gB. In a further preferred embodiment, the polypeptide includes cysteine substitutions at positions 367 and 499 (listed in row 17, column (ii) of Table 2) according to the numbering of SEQ ID NO: 1, relative to the amino acid sequence of the wild-type HCMV gB. In a preferred embodiment, the polypeptide includes cysteine substitutions at positions 372 and 506 (listed in row 18, column (ii) of Table 2) according to the numbering of SEQ ID NO: 1, relative to the amino acid sequence of the wild-type HCMV gB. In another preferred embodiment, the polypeptide includes cysteine substitutions at positions 550 and 652 (listed in row 22, column (ii) of Table 2) according to the numbering of SEQ ID NO: 1, relative to the amino acid sequence of the wild-type HCMV gB. In a further preferred embodiment, the polypeptide includes cysteine substitutions at positions 608 and 679 (listed in row 26, column (ii) of Table 2) according to the numbering of SEQ ID NO: 1, relative to the amino acid sequence of the wild-type HCMV gB. In a preferred embodiment, the polypeptide includes cysteine substitutions at positions 695 and 724 (listed in row 34, column (ii) of Table 2) according to the numbering of SEQ ID NO: 1, relative to the amino acid sequence of the wild-type HCMV gB.

In some embodiments, the polypeptide includes one or more (such as 2, 3, 4, 5, 6, 7, 8, 9 or 10) disulfide bonds between pairs of cysteine residues substituted at any one of the pairs of positions listed in one or more of rows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 and 101 of column (ii) of Table 2. In a preferred embodiment, the polypeptide includes a disulfide bond between a pair of cysteine residues substituted at positions 98 and 653 (listed in row 2, column (ii) of Table 2) according to the numbering of SEQ ID NO: 1, relative to the amino acid sequence of the wild-type HCMV gB. In another preferred embodiment, the polypeptide includes a disulfide bond between a pair of cysteine residues substituted at positions 100 and 269 (listed in row 5, column (ii) of Table 2) according to the numbering of SEQ ID NO: 1, relative to the amino acid sequence of the wild-type HCMV gB. In a further preferred embodiment, the polypeptide includes a disulfide bond between a pair of cysteine residues substituted at positions 217 and 584 (listed in row 7, column (ii) of Table 2) according to the numbering of SEQ ID NO: 1, relative to the amino acid sequence of the wild-type HCMV gB. In a preferred embodiment, the polypeptide includes a disulfide bond between a pair of cysteine residues substituted at positions 242 and 710 (listed in row 13, column (ii) of Table 2) according to the numbering of SEQ ID NO: 1, relative to the amino acid sequence of the wild-type HCMV gB. In another preferred embodiment, the polypeptide includes a disulfide bond between a pair of cysteine residues substituted at positions 242 and 714 (listed in row 14, column (ii) of Table 2) according to the numbering of SEQ ID NO: 1, relative to the amino acid sequence of the wild-type HCMV gB. In a further preferred embodiment, the polypeptide includes a disulfide bond between a pair of cysteine residues substituted at positions 367 and 499 (listed in row 17, column (ii) of Table 2) according to the numbering of SEQ ID NO: 1, relative to the amino acid sequence of the wild-type HCMV gB. In a preferred embodiment, the polypeptide includes a disulfide bond between a pair of cysteine residues substituted at positions 372 and 506 (listed in row 18, column (ii) of Table 2) according to the numbering of SEQ ID NO: 1, relative to the amino acid sequence of the wild-type HCMV gB. In another preferred embodiment, the polypeptide includes a disulfide bond between a pair of cysteine residues substituted at positions 550 and 652 (listed in row 22, column (ii) of Table 2) according to the numbering of SEQ ID NO: 1, relative to the amino acid sequence of the wild-type HCMV gB. In a further preferred embodiment, the polypeptide includes a disulfide bond between a pair of cysteine residues substituted at positions 608 and 679 (listed in row 26, column (ii) of Table 2) according to the numbering of SEQ ID NO: 1, relative to the amino acid sequence of the wild-type HCMV gB. In a preferred embodiment, the polypeptide includes a disulfide bond between a pair of cysteine residues substituted at positions 695 and 724 (listed in row 34, column (ii) of Table 2) according to the numbering of SEQ ID NO: 1, relative to the amino acid sequence of the wild-type HCMV gB. In a preferred embodiment, the polypeptide includes a disulfide bond between a pair of cysteine residues substituted at positions 217 and 589 (listed in row 47, column (ii) of Table 2) according to the numbering of SEQ ID NO: 1, relative to the amino acid sequence of the wild-type HCMV gB. In a preferred embodiment, the polypeptide includes a disulfide bond between a pair of cysteine residues substituted at positions 524 and 684 (listed in row 69, column (ii) of Table 2) according to the numbering of SEQ ID NO: 1, relative to the amino acid sequence of the wild-type HCMV gB. In a preferred embodiment, the polypeptide includes a disulfide bond between a pair of cysteine residues substituted at positions 371 and 506 (listed in row 91, column (ii) of Table 2) according to the numbering of SEQ ID NO: 1, relative to the amino acid sequence of the wild-type HCMV gB.

In further embodiments, the polypeptide includes one or more (such as 2, 3, 4, 5, 6, 7, 8, 9 or 10) disulfide bonds between pairs of cysteine residues that are introduced by cysteine amino acid substitutions at any one of the pairs of positions listed in one or more of rows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 of column (iii) of Table 2, wherein the polypeptide does not exhibit an HCMV postfusion conformation.

In further embodiments, the polypeptide includes one or more (such as 2, 3, 4, 5, 6, 7, 8, 9 or 10) disulfide bonds between pairs of cysteine residues that are introduced by cysteine amino acid substitutions at any one of the pairs of positions listed in one or more of rows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 70, 71 72, 73, 74, 75, 76, 77, 78, 79, 80, 81, 82, 83, 84, 85, 86, 87, 88, 89, 90, 91, 92, 93, 94, 95, 96, 97, 98, 99, 100 or 101 of column (iii) of Table 2, wherein the polypeptide does not exhibit an HCMV postfusion conformation.

In some embodiments, the polypeptide includes a disulfide bond between pairs of cysteine residues substituted at any one of the pairs of positions listed at any one of rows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or 101 of column (ii) of Table 2. In an embodiment, the resulting polypeptide does not exhibit an HCMV postfusion conformation. In an embodiment, the resulting polypeptide exhibits an HCMV prefusion conformation.

In a preferred embodiment, the polypeptide includes cysteine substitutions at Q98C and I653C (listed in row 2, column (iii) of Table 2) according to the numbering of SEQ ID NO: 1, relative to the amino acid sequence of the wild-type HCMV gB. In another preferred embodiment, the polypeptide includes cysteine substitutions at T100C and S269C (listed in row 5, column (iii) of Table 2) according to the numbering of SEQ ID NO: 1, relative to the amino acid sequence of the wild-type HCMV gB. In a further preferred embodiment, the polypeptide includes cysteine substitutions at D217C and F584C (listed in row 7, column (iii) of Table 2) according to the numbering of SEQ ID NO: 1, relative to the amino acid sequence of the wild-type HCMV gB. In a preferred embodiment, the polypeptide includes cysteine substitutions at Y242C and K710C (listed in row 13, column (iii) of Table 2) according to the numbering of SEQ ID NO: 1, relative to the amino acid sequence of the wild-type HCMV gB. In another preferred embodiment, the polypeptide includes cysteine substitutions at Y242C and D714C (listed in row 14, column (iii) of Table 2) according to the numbering of SEQ ID NO: 1, relative to the amino acid sequence of the wild-type HCMV gB. In a further preferred embodiment, the polypeptide includes cysteine substitutions at S367C and L499C (listed in row 17, column (iii) of Table 2) according to the numbering of SEQ ID NO: 1, relative to the amino acid sequence of the wild-type HCMV gB. In a preferred embodiment, the polypeptide includes cysteine substitutions at T372C and W506C (listed in row 18, column (iii) of Table 2) according to the numbering of SEQ ID NO: 1, relative to the amino acid sequence of the wild-type HCMV gB. In another preferred embodiment, the polypeptide includes cysteine substitutions at S550C and D652C (listed in row 22, column (iii) of Table 2) according to the numbering of SEQ ID NO: 1, relative to the amino acid sequence of the wild-type HCMV gB. In a further preferred embodiment, the polypeptide includes cysteine substitutions at T608C and D679C (listed in row 26, column (iii) of Table 2) according to the numbering of SEQ ID NO: 1, relative to the amino acid sequence of the wild-type HCMV gB. In a preferred embodiment, the polypeptide includes cysteine substitutions at K695C and K724C (listed in row 34, column (iii) of Table 2) according to the numbering of SEQ ID NO: 1, relative to the amino acid sequence of the wild-type HCMV gB. In a preferred embodiment, the polypeptide includes cysteine substitutions at D217C and Y589C (listed in row 47, column (ili) of Table 2) according to the numbering of SEQ ID NO: 1, relative to the amino acid sequence of the wild-type HCMV gB. In a preferred embodiment, the polypeptide includes cysteine substitutions at N524C and M684C (listed in row 69, column (iil) of Table 2) according to the numbering of SEQ ID NO: 1, relative to the amino acid sequence of the wild-type HCMV gB. In a preferred embodiment, the polypeptide includes cysteine substitutions at M371C and W506C (listed in row 91, column (ili) of Table 2) according to the numbering of SEQ ID NO: 1, relative to the amino acid sequence of the wild-type HCMV gB.

In a preferred embodiment, the polypeptide includes a disulfide bond between a pair of cysteine residues substituted at positions 96 and 660 according to the numbering of SEQ ID NO: 1, relative to the amino acid sequence of the wild-type HCMV gB. In another preferred embodiment, the polypeptide includes a disulfide bond between a pair of cysteine residues substituted at positions 98 and 658 according to the numbering of SEQ ID NO: 1, relative to the amino acid sequence of the wild-type HCMV gB. In a further preferred embodiment, the polypeptide includes a disulfide bond between a pair of cysteine residues substituted at positions 100 and 258 according to the numbering of SEQ ID NO: 1, relative to the amino acid sequence of the wild-type HCMV gB. In a preferred embodiment, the polypeptide includes a disulfide bond between a pair of cysteine residues substituted at positions 100 and 656 according to the numbering of SEQ ID NO: 1, relative to the amino acid sequence of the wild-type HCMV gB. In another preferred embodiment, the polypeptide includes a disulfide bond between a pair of cysteine residues substituted at positions 100 and 658 according to the numbering of SEQ ID NO: 1, relative to the amino acid sequence of the wild-type HCMV gB. In a further preferred embodiment, the polypeptide includes a disulfide bond between a pair of cysteine residues substituted at positions 117 and 406 according to the numbering of SEQ ID NO: 1, relative to the amino acid sequence of the wild-type HCMV gB. In a preferred embodiment, the polypeptide includes a disulfide bond between a pair of cysteine residues substituted at positions 117 and 407 according to the numbering of SEQ ID NO: 1, relative to the amino acid sequence of the wild-type HCMV gB. In a preferred embodiment, the polypeptide includes a disulfide bond between a pair of cysteine residues substituted at positions 153 and 712 according to the numbering of SEQ ID NO: 1, relative to the amino acid sequence of the wild-type HCMV gB. In a preferred embodiment, the polypeptide includes a disulfide bond between a pair of cysteine residues substituted at positions 162 and 716 according to the numbering of SEQ ID NO: 1, relative to the amino acid sequence of the wild-type HCMV gB. In a preferred embodiment, the polypeptide includes a disulfide bond between a pair of cysteine residues substituted at positions 217 and 587 according to the numbering of SEQ ID NO: 1, relative to the amino acid sequence of the wild-type HCMV gB. In a preferred embodiment, the polypeptide includes a disulfide bond between a pair of cysteine residues substituted at positions 217 and 589 according to the numbering of SEQ ID NO: 1, relative to the amino acid sequence of the wild-type HCMV gB. In a preferred embodiment, the polypeptide includes a disulfide bond between a pair of cysteine residues substituted at positions 219 and 584 according to the numbering of SEQ ID NO: 1, relative to the amino acid sequence of the wild-type HCMV gB. In a preferred embodiment, the polypeptide includes a disulfide bond between a pair of cysteine residues substituted at positions 219 and 585 according to the numbering of SEQ ID NO: 1, relative to the amino acid sequence of the wild-type HCMV gB. In a preferred embodiment, the polypeptide includes a disulfide bond between a pair of cysteine residues substituted at positions 219 and 586 according to the numbering of SEQ ID NO: 1, relative to the amino acid sequence of the wild-type HCMV gB. In a preferred embodiment, the polypeptide includes a disulfide bond between a pair of cysteine residues substituted at positions 220 and 659 according to the numbering of SEQ ID NO: 1, relative to the amino acid sequence of the wild-type HCMV gB. In a preferred embodiment, the polypeptide includes a disulfide bond between a pair of cysteine residues substituted at positions 223 and 659 according to the numbering of SEQ ID NO: 1, relative to the amino acid sequence of the wild-type HCMV gB. In a preferred embodiment, the polypeptide includes a disulfide bond between a pair of cysteine residues substituted at positions 240 and 732 according to the numbering of SEQ ID NO: 1, relative to the amino acid sequence of the wild-type HCMV gB. In a preferred embodiment, the polypeptide includes a disulfide bond between a pair of cysteine residues substituted at positions 240 and 735 according to the numbering of SEQ ID NO: 1, relative to the amino acid sequence of the wild-type HCMV gB. In a preferred embodiment, the polypeptide includes a disulfide bond between a pair of cysteine residues substituted at positions 242 and 728 according to the numbering of SEQ ID NO: 1, relative to the amino acid sequence of the wild-type HCMV gB. In a preferred embodiment, the polypeptide includes a disulfide bond between a pair of cysteine residues substituted at positions 242 and 731 according to the numbering of SEQ ID NO: 1, relative to the amino acid sequence of the wild-type HCMV gB. In a preferred embodiment, the polypeptide includes a disulfide bond between a pair of cysteine residues substituted at positions 258 and 656 according to the numbering of SEQ ID NO: 1, relative to the amino acid sequence of the wild-type HCMV gB. In a preferred embodiment, the polypeptide includes a disulfide bond between a pair of cysteine residues substituted at positions 269 and 656 according to the numbering of SEQ ID NO: 1, relative to the amino acid sequence of the wild-type HCMV gB. In a preferred embodiment, the polypeptide includes a disulfide bond between a pair of cysteine residues substituted at positions 269 and 658 according to the numbering of SEQ ID NO: 1, relative to the amino acid sequence of the wild-type HCMV gB. In a preferred embodiment, the polypeptide includes a disulfide bond between a pair of cysteine residues substituted at positions 272 and 614 according to the numbering of SEQ ID NO: 1, relative to the amino acid sequence of the wild-type HCMV gB. In a preferred embodiment, the polypeptide includes a disulfide bond between a pair of cysteine residues substituted at positions 273 and 629 according to the numbering of SEQ ID NO: 1, relative to the amino acid sequence of the wild-type HCMV gB. In a preferred embodiment, the polypeptide includes a disulfide bond between a pair of cysteine residues substituted at positions 349 and 650 according to the numbering of SEQ ID NO: 1, relative to the amino acid sequence of the wild-type HCMV gB. In a preferred embodiment, the polypeptide includes a disulfide bond between a pair of cysteine residues substituted at positions 367 and 500 according to the numbering of SEQ ID NO: 1, relative to the amino acid sequence of the wild-type HCMV gB. In a preferred embodiment, the polypeptide includes a disulfide bond between a pair of cysteine residues substituted at positions 367 and 503 according to the numbering of SEQ ID NO: 1, relative to the amino acid sequence of the wild-type HCMV gB. In a preferred embodiment, the polypeptide includes a disulfide bond between a pair of cysteine residues substituted at positions 370 and 501 according to the numbering of SEQ ID NO: 1, relative to the amino acid sequence of the wild-type HCMV gB. In a preferred embodiment, the polypeptide includes a disulfide bond between a pair of cysteine residues substituted at positions 522 and 683 according to the numbering of SEQ ID NO: 1, relative to the amino acid sequence of the wild-type HCMV gB. In a preferred embodiment, the polypeptide includes a disulfide bond between a pair of cysteine residues substituted at positions 523 and 683 according to the numbering of SEQ ID NO: 1, relative to the amino acid sequence of the wild-type HCMV gB. In a preferred embodiment, the polypeptide includes a disulfide bond between a pair of cysteine residues substituted at positions 523 and 684 according to the numbering of SEQ ID NO: 1, relative to the amino acid sequence of the wild-type HCMV gB. In a preferred embodiment, the polypeptide includes a disulfide bond between a pair of cysteine residues substituted at positions 524 and 684 according to the numbering of SEQ ID NO: 1, relative to the amino acid sequence of the wild-type HCMV gB. In a preferred embodiment, the polypeptide includes a disulfide bond between a pair of cysteine residues substituted at positions 525 and 681 according to the numbering of SEQ ID NO: 1, relative to the amino acid sequence of the wild-type HCMV gB. In a preferred embodiment, the polypeptide includes a disulfide bond between a pair of cysteine residues substituted at positions 540 and 680 according to the numbering of SEQ ID NO: 1, relative to the amino acid sequence of the wild-type HCMV gB. In a preferred embodiment, the polypeptide includes a disulfide bond between a pair of cysteine residues substituted at positions 541 and 680 according to the numbering of SEQ ID NO: 1, relative to the amino acid sequence of the wild-type HCMV gB. In a preferred embodiment, the polypeptide includes a disulfide bond between a pair of cysteine residues substituted at positions 548 and 655 according to the numbering of SEQ ID NO: 1, relative to the amino acid sequence of the wild-type HCMV gB. In a preferred embodiment, the polypeptide includes a disulfide bond between a pair of cysteine residues substituted at positions 549 and 658 according to the numbering of SEQ ID NO: 1, relative to the amino acid sequence of the wild-type HCMV gB. In a preferred embodiment, the polypeptide includes a disulfide bond between a pair of cysteine residues substituted at positions 550 and 655 according to the numbering of SEQ ID NO: 1, relative to the amino acid sequence of the wild-type HCMV gB. In a preferred embodiment, the polypeptide includes a disulfide bond between a pair of cysteine residues substituted at positions 550 and 657 according to the numbering of SEQ ID NO: 1, relative to the amino acid sequence of the wild-type HCMV gB. In a preferred embodiment, the polypeptide includes a disulfide bond between a pair of cysteine residues substituted at positions 591 and 668 according to the numbering of SEQ ID NO: 1, relative to the amino acid sequence of the wild-type HCMV gB. In a preferred embodiment, the polypeptide includes a disulfide bond between a pair of cysteine residues substituted at positions 603 and 667 according to the numbering of SEQ ID NO: 1, relative to the amino acid sequence of the wild-type HCMV gB. In a preferred embodiment, the polypeptide includes a disulfide bond between a pair of cysteine residues substituted at positions 604 and 672 according to the numbering of SEQ ID NO: 1, relative to the amino acid sequence of the wild-type HCMV gB. In a preferred embodiment, the polypeptide includes a disulfide bond between a pair of cysteine residues substituted at positions 607 and 688 according to the numbering of SEQ ID NO: 1, relative to the amino acid sequence of the wild-type HCMV gB. In a preferred embodiment, the polypeptide includes a disulfide bond between a pair of cysteine residues substituted at positions 608 and 692 according to the numbering of SEQ ID NO: 1, relative to the amino acid sequence of the wild-type HCMV gB. In a preferred embodiment, the polypeptide includes a disulfide bond between a pair of cysteine residues substituted at positions 609 and 691 according to the numbering of SEQ ID NO: 1, relative to the amino acid sequence of the wild-type HCMV gB. In a preferred embodiment, the polypeptide includes a disulfide bond between a pair of cysteine residues substituted at positions 610 and 674 according to the numbering of SEQ ID NO: 1, relative to the amino acid sequence of the wild-type HCMV gB. In a preferred embodiment, the polypeptide includes a disulfide bond between a pair of cysteine residues substituted at positions 610 and 675 according to the numbering of SEQ ID NO: 1, relative to the amino acid sequence of the wild-type HCMV gB. In a preferred embodiment, the polypeptide includes a disulfide bond between a pair of cysteine residues substituted at positions 612 and 663 according to the numbering of SEQ ID NO: 1, relative to the amino acid sequence of the wild-type HCMV gB. In a preferred embodiment, the polypeptide includes a disulfide bond between a pair of cysteine residues substituted at positions 737 and 755 according to the numbering of SEQ ID NO: 1, relative to the amino acid sequence of the wild-type HCMV gB. In a preferred embodiment, the polypeptide includes a disulfide bond between a pair of cysteine residues substituted at positions 741 and 754 according to the numbering of SEQ ID NO: 1, relative to the amino acid sequence of the wild-type HCMV gB. In a preferred embodiment, the polypeptide includes a disulfide bond between a pair of cysteine residues substituted at positions 741 and 755 according to the numbering of SEQ ID NO: 1, relative to the amino acid sequence of the wild-type HCMV gB.

In some embodiments, the polypeptide includes a combination of two or more of the disulfide bonds between cysteine residues listed in Table 2. In some embodiments, the polypeptide includes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% identity to any sequence selected from: SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; and SEQ ID NO: 37.

In some embodiments, the polypeptide includes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% identity to any sequence selected from: SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, and SEQ ID NO: 98.

In some embodiments, the polypeptide includes an amino acid sequence having at least 80%, 81%, 82%, 83%, 84%, 85%, 86%, 87%, 88%, 89%, 90%, 91%, 92%, 93%, 94%, 95%, 96%, 97%, 98%, preferably 99%, or 100% identity to any sequence selected from SEQ ID NO: 56, SEQ ID NO: 57, SEQ ID NO: 58, and SEQ ID NO: 60.

In some embodiments, the polypeptide includes an amino acid sequence having at least 80%, 81%, 82%, 83%, 84%, 85%, 86%, 87%, 88%, 89%, 90%, 91%, 92%, 93%, 94%, 95%, 96%, 97%, 98%, preferably 99%, or 100% identity to any sequence selected from SEQ ID NO: 51, SEQ ID NO: 73, SEQ ID NO: 70, and SEQ ID NO: 78.

In some embodiments, the composition preferably does not include a polypeptide having the sequence set forth in any one of SEQ ID NO: 59, SEQ ID NO: 75, SEQ ID NO: 76, SEQ ID NO: 71, SEQ ID NO: 52, SEQ ID NO: 96, and SEQ ID NO: 50.

In additional embodiments, the polypeptide includes the amino acid sequence as set forth in any one of the SEQ ID NOs listed in column (iv) of Table 2. That is, an exemplary polypeptide includes a polypeptide having the amino acid sequence selected from any one of: SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; and SEQ ID NO: 37.

In some embodiments, the polypeptide has the amino acid sequence selected from any one of SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, and SEQ ID NO: 98.

In a preferred embodiment, the polypeptide includes the amino acid sequence as set forth in any one of SEQ ID NO: 3; SEQ ID NO: 6; SEQ ID NO: 8; SEQ ID NO: 14; SEQ ID NO: 15; SEQ ID NO: 18; SEQ ID NO: 19; SEQ ID NO: 23; SEQ ID NO: 27; and SEQ ID NO: 35.

In some embodiments, the polypeptide comprises an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to amino acids 23 to 907 of SEQ ID NO: 1. In an embodiment, the polypeptide comprises an amino acid sequence having at least 90% identity to amino acids 23 to 907 of SEQ ID NO: 1. In an embodiment, the polypeptide comprises an amino acid sequence having at least 94% identity to amino acids 23 to 907 of SEQ ID NO: 1. In an embodiment, the polypeptide comprises an amino acid sequence having at least 95% identity to amino acids 23 to 907 of SEQ ID NO: 1. In an embodiment, the polypeptide comprises an amino acid sequence having at least 96% identity to amino acids 23 to 907 of SEQ ID NO: 1. In an embodiment, the polypeptide comprises an amino acid sequence having at least 97% identity to amino acids 23 to 907 of SEQ ID NO: 1. In an embodiment, the polypeptide comprises an amino acid sequence having at least 97% identity to amino acids 23 to 907 of SEQ ID NO: 1. In an embodiment, the polypeptide comprises an amino acid sequence having at least 98% identity to amino acids 23 to 907 of SEQ ID NO: 1. In an embodiment, the polypeptide comprises an amino acid sequence having at least 99% identity to amino acids 23 to 907 of SEQ ID NO: 1. In an embodiment, the polypeptide comprises an amino acid sequence having at least 99.5% identity to amino acids 23 to 907 of SEQ ID NO: 1. In an embodiment, the polypeptide comprises an amino acid sequence having at least 99.6% identity to amino acids 23 to 907 of SEQ ID NO: 1. In an embodiment, the polypeptide comprises an amino acid sequence having at least 99.7% identity to amino acids 23 to 907 of SEQ ID NO: 1. In an embodiment, the polypeptide comprises an amino acid sequence having at least 99.8% identity to amino acids 23 to 907 of SEQ ID NO: 1. In an embodiment, the polypeptide comprises an amino acid sequence having at least 99.85% identity to amino acids 23 to 907 of SEQ ID NO: 1.

In some embodiments, the polypeptide comprises an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to amino acids 23 to 707 of SEQ ID NO: 1. In an embodiment, the polypeptide comprises an amino acid sequence having at least 90% identity to amino acids 23 to 707 of SEQ ID NO: 1. In an embodiment, the polypeptide comprises an amino acid sequence having at least 94% identity to amino acids 23 to 707 of SEQ ID NO: 1. In an embodiment, the polypeptide comprises an amino acid sequence having at least 95% identity to amino acids 23 to 707 of SEQ ID NO: 1. In an embodiment, the polypeptide comprises an amino acid sequence having at least 96% identity to amino acids 23 to 707 of SEQ ID NO: 1. In an embodiment, the polypeptide comprises an amino acid sequence having at least 97% identity to amino acids 23 to 707 of SEQ ID NO: 1. In an embodiment, the polypeptide comprises an amino acid sequence having at least 97% identity to amino acids 23 to 707 of SEQ ID NO: 1. In an embodiment, the polypeptide comprises an amino acid sequence having at least 98% identity to amino acids 23 to 707 of SEQ ID NO: 1. In an embodiment, the polypeptide comprises an amino acid sequence having at least 99% identity to amino acids 23 to 707 of SEQ ID NO: 1. In an embodiment, the polypeptide comprises an amino acid sequence having at least 99.5% identity to amino acids 23 to 707 of SEQ ID NO: 1. In an embodiment, the polypeptide comprises an amino acid sequence having at least 99.6% identity to amino acids 23 to 707 of SEQ ID NO: 1. In an embodiment, the polypeptide comprises an amino acid sequence having at least 99.7% identity to amino acids 23 to 707 of SEQ ID NO: 1. In an embodiment, the polypeptide comprises an amino acid sequence having at least 99.8% identity to amino acids 23 to 707 of SEQ ID NO: 1. In an embodiment, the polypeptide comprises an amino acid sequence having at least 99.85% identity to amino acids 23 to 707 of SEQ ID NO: 1.

In some embodiments, the polypeptide comprises an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to amino acids 23 to 646 of SEQ ID NO: 1. In an embodiment, the polypeptide comprises an amino acid sequence having at least 90% identity to amino acids 23 to 646 of SEQ ID NO: 1. In an embodiment, the polypeptide comprises an amino acid sequence having at least 94% identity to amino acids 23 to 646 of SEQ ID NO: 1. In an embodiment, the polypeptide comprises an amino acid sequence having at least 95% identity to amino acids 23 to 646 of SEQ ID NO: 1. In an embodiment, the polypeptide comprises an amino acid sequence having at least 96% identity to amino acids 23 to 646 of SEQ ID NO: 1. In an embodiment, the polypeptide comprises an amino acid sequence having at least 97% identity to amino acids 23 to 646 of SEQ ID NO: 1. In an embodiment, the polypeptide comprises an amino acid sequence having at least 97% identity to amino acids 23 to 646 of SEQ ID NO: 1. In an embodiment, the polypeptide comprises an amino acid sequence having at least 98% identity to amino acids 23 to 646 of SEQ ID NO: 1. In an embodiment, the polypeptide comprises an amino acid sequence having at least 99% identity to amino acids 23 to 646 of SEQ ID NO: 1. In an embodiment, the polypeptide comprises an amino acid sequence having at least 99.5% identity to amino acids 23 to 646 of SEQ ID NO: 1. In an embodiment, the polypeptide comprises an amino acid sequence having at least 99.6% identity to amino acids 23 to 646 of SEQ ID NO: 1. In an embodiment, the polypeptide comprises an amino acid sequence having at least 99.7% identity to amino acids 23 to 646 of SEQ ID NO: 1. In an embodiment, the polypeptide comprises an amino acid sequence having at least 99.8% identity to amino acids 23 to 646 of SEQ ID NO: 1. In an embodiment, the polypeptide comprises an amino acid sequence having at least 99.85% identity to amino acids 23 to 646 of SEQ ID NO: 1.

In some embodiments, amino acids can be inserted (or deleted) from the native HCMV gB sequence to adjust the alignment of residues in the polypeptide structure, such that particular residue pairs are within a sufficiently close distance to form a disulfide bond in the prefusion, but not postfusion, conformation. In several such embodiments, the polypeptide includes a disulfide bond between cysteine residues located at any of the pairs of positions listed in one or more of rows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or 101 of column (ii) of Table 2, in addition to including at least one amino acid insertion.

In some embodiments, the polypeptide includes a phenylalanine substitution as compared to a native HCMV gB. In some embodiments, the polypeptide includes a leucine substitution as compared to a native HCMV gB. In some embodiments, the polypeptide may be stabilized by amino acid mutations (such as, for example, phenylalanine (F) and leucine (L) substitutions) that decrease ionic repulsion between resides that are proximate to each other in the folded structure of the polypeptide, as compared to a HCMV gB polypeptide in postfusion conformation. In some embodiments, the polypeptide may be stabilized by amino acid mutations that increase ionic attraction between residues that are proximate to each other in the folded structure of the polypeptide, as compared to a HCMV gB in postfusion conformation.

Exemplary mutations include any mutation selected from Table 3, according to the numbering of SEQ ID NO: 1 as compared to a native HCMV gB:

TABLE 3

Exemplary Phenylalanine (F) and Leucine (L) Substitutions

| Row | (i) Mutant ID | (ii) Mutated residue position, according to the numbering of SEQ ID NO: 1 | (iii) Substitutions corresponding to SEQ ID NO: 1 | (iv) Exemplary sequence that includes the mutation is set forth in: |
|---|---|---|---|---|
| 1 | gB-037 | 670 | K670L | SEQ ID NO: 38 |
| 2 | gB-038 | 670 | K670F | SEQ ID NO: 39 |
| 3 | gB-039 | 673 | R673L | SEQ ID NO: 40 |
| 4 | gB-040 | 673 | R673F | SEQ ID NO: 41 |
| 5 | gB-041 | 691 | K691L | SEQ ID NO: 42 |
| 6 | gB-042 | 691 | K691F | SEQ ID NO: 43 |
| 7 | pSB02041 | 686 | E686F | |
| 8 | | 686 | E686L | |
| 9 | | 354 | R354F | |
| 10 | | 573 | R573F | |
| 11 | | 101 and 260 | D101L and K260L | |

TABLE 4

Additional substitutions

| Row | (i) Mutant ID | (ii) Mutated residue position, according to the numbering of SEQ ID NO: 1 | (iii) Substitutions corresponding to SEQ ID NO: 1 | (iv) Exemplary sequence that includes the mutation is set forth in: |
|---|---|---|---|---|
| 1 | gB-095; pSB01708 | 679 | D679S | SEQ ID NO: 99 |
| 2 | gB-096; pSB01709 | 679 | D679N | SEQ ID NO: 100 |
| 3 | gB-097 | 682 | E682S | SEQ ID NO: 101 |
| 4 | gB-098 | 682 | E682Q | SEQ ID NO: 102 |
| 5 | gB-099; pSB01712 | 686 | E686S | SEQ ID NO: 103 |
| 6 | gB-100; pSB01713 | 686 | E686Q | SEQ ID NO: 104 |

TABLE 4-continued

| Additional substitutions | | | | |
|---|---|---|---|---|
| Row | (i) Mutant ID | (ii) Mutated residue position, according to the numbering of SEQ ID NO: 1 | (iii) Substitutions corresponding to SEQ ID NO: 1 | (iv) Exemplary sequence that includes the mutation is set forth in: |
| 7 | gB-101 | 118 | N118P | SEQ ID NO: 105 |
| 8 | gB-102; pSB01715 | 646 | D646P | SEQ ID NO: 106 |
| 9 | | 240 | W240A | |
| 10 | | 246 | C246S | |
| 11 | | 675 | I675S | |
| 12 | | 155-157 | Y155G I156H H157R | |
| 13 | pSB02043 | 686 | E6861 | |
| 14 | pSB02044 | 686 | E686V | |
| 15 | | 679 | D679A | |
| 16 | | 696 and 697 | Y696C and V697C | |
| 17 | | 703 and 704 | D703C and P704C | |
| 18 | | 767 and 768 | I767C and I768C | |
| 19 | | 217, 589, 703, and 704 | D217C, Y589C, D703C, and P704C | |
| 20 | | 217, 589, 696, and 697 | D217C, Y589C, Y696C, and V697C | |
| 21 | pSB2795 | 217, 371, 506, 524 and 589 | D217C, M371C, W506C, N524C and Y589C | |
| 22 | pSB2796 | 217, 371, 506, and 589 | D217C, M371C, W506C, and Y589C | |
| 23 | | 217, 524, 589, and 684 | D217C, N524C, Y589C, M684C | |
| 24 | | 217, 524, 589, 684, 703, and 704 | D217C, N524C, Y589C, M684C, D703C, and P704C | |
| 25 | | 655 | P655S | |
| 26 | pSB2797; pSB2968 | 217, 371, 506, 524 589 and 684 | D217C, M371C, W506C, N524C Y589C and M684C | |
| 27 | pSB2797; pSB2968 | 648 -653 | M648G I649S A650G L651K D652D 1653G | |
| 28 | | 693 | R693V | |
| 29 | | 685 | R685A | |
| 30 | | 678 | F678S | |
| 31 | | 680 | L680T | |

In some embodiments, the polypeptide includes one or more (such as 2, 3, 4, 5, 6, 7, 8, 9 or 10) residues substituted at any one of the positions listed in one or more of rows 1, 2, 3, 4, 5, 6, 7, 8, 9, 10 or 11 of column (ii) of Table 3, wherein the polypeptide does not exhibit an HCMV gB postfusion conformation. In an embodiment, the resulting polypeptide exhibits an HCMV gB prefusion conformation.

In some embodiments, the polypeptide includes one or more (such as 2, 3, 4, 5, 6, 7, 8, 9 or 10) residues substituted at any one of the positions listed in one or more of rows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 of column (ii) of Table 4, wherein the polypeptide does not exhibit an HCMV gB postfusion conformation. In an embodiment, the resulting polypeptide exhibits an HCMV gB prefusion conformation.

In some embodiments, the polypeptide includes a mutation at position 670 (listed in rows 1 and 2, column (ii) of Table 3) according to the numbering of SEQ ID NO: 1. In some embodiments, the polypeptide includes a mutation at position 673 (listed in rows 3 and 4, column (ii) of Table 3) according to the numbering of SEQ ID NO: 1. In some embodiments, the polypeptide includes a mutation at position 691 (listed in rows 5 and 6, column (ii) of Table 3) according to the numbering of SEQ ID NO: 1.

In some embodiments, the polypeptide includes a mutation at position 670 according to the numbering of SEQ ID NO: 1. In some embodiments, the polypeptide includes a mutation at position 682 according to the numbering of SEQ ID NO: 1. In some embodiments, the polypeptide includes a mutation at position 686 according to the numbering of SEQ ID NO: 1. In some embodiments, the polypeptide includes a mutation at position 118 according to the numbering of SEQ ID NO: 1. In some embodiments, the polypeptide includes a mutation at position 646 according to the numbering of SEQ ID NO: 1.

In further embodiments, the polypeptide includes an electrostatic mutation that is introduced by substitutions at any one of the positions listed in one or more of rows 1, 2, 3, 4, 5, 6, 7, 8, 9, 10 or 11 of column (iii) of Table 3, wherein the polypeptide does not exhibit an HCMV postfusion conformation.

In a preferred embodiment, the polypeptide includes a substitution K670L (listed in row 1, column (iii) of Table 3) according to the numbering of SEQ ID NO: 1. In another preferred embodiment, the polypeptide includes a substitution K670F (listed in row 2, column (iii) of Table 3) according to the numbering of SEQ ID NO: 1. In a further preferred embodiment, the polypeptide includes a substitution R673L (listed in row 3, column (iii) of Table 3) according to the numbering of SEQ ID NO: 1. In a preferred embodiment, the polypeptide includes a substitution R673F (listed in row 4, column (iii) of Table 3) according to the numbering of SEQ ID NO: 1. In another preferred embodiment, the polypeptide includes a substitution K691L (listed in row 5, column (iii) of) Table 3 according to the numbering of SEQ ID NO: 1. In a further preferred embodiment, the polypeptide includes a substitution K691F (listed in row 6, column (iii) of Table 3) according to the numbering of SEQ ID NO: 1. In a further preferred embodiment, the polypeptide includes a substitution K691F (listed in row 7, column (iii) of Table 3) according to the numbering of SEQ ID NO: 1. In a further preferred embodiment, the polypeptide includes a substitution K691F (listed in row 8, column (iii) of Table 3) according to the numbering of SEQ ID NO: 1. In a further preferred embodiment, the polypeptide includes a substitution K691F (listed in row 9, column (iii) of Table 3) according to the numbering of SEQ ID NO: 1. In a further preferred embodiment, the polypeptide includes a substitution K691F (listed in row 10, column (iii) of Table 3) according to the numbering of SEQ ID NO: 1. In a further preferred embodiment, the polypeptide includes a substitution K691F (listed in row 11, column (iii) of Table 3) according to the numbering of SEQ ID NO: 1.

In some embodiments, the polypeptide includes a combination of two or more of the phenylalanine (F) and leucine (L) substitutions listed in Table 3.

In a preferred embodiment, the polypeptide includes a substitution D679S according to the numbering of SEQ ID NO: 1. In another preferred embodiment, the polypeptide includes a substitution D679N according to the numbering of SEQ ID NO: 1. In another preferred embodiment, the polypeptide includes a substitution E682S according to the numbering of SEQ ID NO: 1. In another preferred embodiment, the polypeptide includes a substitution E682Q according to the numbering of SEQ ID NO: 1. In another preferred embodiment, the polypeptide includes a substitution E686S according to the numbering of SEQ ID NO: 1. In another preferred embodiment, the polypeptide includes a substitution E686Q according to the numbering of SEQ ID NO: 1. In another preferred embodiment, the polypeptide includes a substitution N118P according to the numbering of SEQ ID NO: 1. In another preferred embodiment, the polypeptide includes a substitution D646P according to the numbering of SEQ ID NO: 1.

In some embodiments, the polypeptide includes a combination of two or more of the phenylalanine (F) and leucine (L) substitutions listed in Table 3. In some embodiments, the polypeptide includes an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any sequence selected from: SEQ ID NO: 38; SEQ ID NO: 39; SEQ ID NO: 40; SEQ ID NO: 41; SEQ ID NO: 42; and SEQ ID NO: 43.

In some embodiments, the polypeptide includes an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any sequence selected from: SEQ ID NO: 99; SEQ ID NO: 100, SEQ ID NO: 102, SEQ ID NO: 103, SEQ ID NO: 104, SEQ ID NO: 105, and SEQ ID NO: 106.

In additional embodiments, the polypeptide includes the amino acid sequence as set forth in any one of the SEQ ID NOs listed in column (iv) of Table 3. That is, an exemplary polypeptide includes a polypeptide having the amino acid sequence selected from any one of: SEQ ID NO: 38; SEQ ID NO: 39; SEQ ID NO: 40; SEQ ID NO: 41; SEQ ID NO: 42; and SEQ ID NO: 43. In some embodiments, the polypeptide has the amino acid sequence selected from any one of: SEQ ID NO: 99; SEQ ID NO: 100, SEQ ID NO: 102, SEQ ID NO: 103, SEQ ID NO: 104, SEQ ID NO: 105, and SEQ ID NO: 106.

In some embodiments, the polypeptide includes one or more (such as 2, 3, 4, 5, 6, 7, 8, 9 or 10) residues substituted at any one of the positions listed in one or more of rows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 of column (iii) of Table 4, wherein the polypeptide does not exhibit an HCMV gB postfusion conformation. In an embodiment, the resulting polypeptide exhibits an HCMV gB prefusion conformation.

In some embodiments, amino acids can be inserted (or deleted) from the native HCMV gB sequence to adjust the alignment of residues in the polypeptide structure, such that particular residue pairs are within a sufficiently close distance to form a desired electrostatic interaction in the prefusion, but not postfusion, conformation. In several such embodiments, the polypeptide includes a desired electrostatic interaction at any of the positions listed in one or more of rows 1, 2, 3, 4, 5, 6, 7, 8, 9, 10, or 11 of column (ii) of Table 3, wherein the polypeptide does not exhibit an HCMV postfusion conformation.

This invention provides a mutant of a wild-type cytomegalovirus (CMV) glycoprotein B (gB) protein, which mutant comprises at least two amino acid mutations relative to the amino acid sequence of the wild-type CMV gB protein, and wherein the amino acid mutation is selected from the group consisting of:

(1) an engineered disulfide bond mutation;
(2) an additional mutation; and
(3) a combination of at least one engineered disulfide mutation and at least one additional mutation.

In one aspect, the amino acid mutations comprise a combination of at least two engineered disulfide mutations and at least one additional mutation. In another aspect, the mutant of a wild-type CMV gB protein is in the form of a trimer.

In another aspect, the mutant of a wild-type CMV gB protein has increased stability in prefusion form as compared with the corresponding wild-type CMV gB protein, wherein the stability is measured by binding of a prefusion-specific antibody, thermal shift assay or EM imaging.

In another aspect, the mutant of the wild-type CMV gB is Towne strain.

In another aspect of the invention, the engineered disulfide mutation is selected from the group consisting of: D217C and Y589C; M371C and W506C; and N524C and M684C.

In a further aspect of the invention, the additional mutation is selected from the group consisting of:

(1) substitution of YIH at positions 155-157 with GHR;
(2) substitution of W at position 240 with A;
(3) substitution of C at position 246 with S;
(4) substitution of P at position 655 with S;
(5) substitution of F at position 678 with S; and
(6) substitution of L at position 680 with T;
(7) substitution of R at position 685 with A;
(8) substitution of MIALDI (SEQ ID NO: 275) at positions 648-653 with GSGKDG (SEQ ID NO: 276);
(9) substitution of R at position 693 with V;
(10) substitution of I at position 675 with S;
(11) substitution of I at positions 767 and 768 with C;
(12) substitution of D at position 703 and P at position 704 with C; and

(13) substitution of Y at position 696 and V at position 697 with C.

In another aspect of the invention, the additional mutation is selected from the group consisting of:

(1) substitution of YIH at positions 155-157 with GHR;
(2) substitution of W at position 240 with A;
(3) substitution of C at position 246 with S; and
(4) substitution of I at position 675 with S.

In another aspect of the invention, the amino acid mutation is a combination of at least two engineered disulfide mutations and at least one additional mutation, and wherein:

(i) the engineered disulfide mutations are selected from the group consisting of: D217C and Y589C; M371C and W506C; and N524C and M684C; and
(ii) the additional mutation is selected from the group consisting of:
  (1) substitution of YIH at positions 155-157 with GHR;
  (2) substitution of W at position 240 with A;
  (3) substitution of C at position 246 with S;
  (4) substitution of P at position 655 with S;
  (5) substitution of F at position 678 with S; and
  (6) substitution of L at position 680 with T;
  (7) substitution of R at position 685 with A;
  (8) substitution of MIALDI (SEQ ID NO: 275) at positions 648-653 with GSGKDG (SEQ ID NO: 276);
  (9) substitution of R at position 693 with V;
  (10) substitution of I at position 675 with S;
  (11) substitution of I at positions 767 and 768 with C;
  (12) substitution of D at position 703 and P at position 704 with C; and
  (13) substitution of Y at position 696 and V at position 697 with C.

In another aspect of the invention, the amino acid mutations are a combination of mutations selected from the group consisting of:

(1) combination of D217C and Y589C, M371C and W506C, and I675S;
(2) combination of D217C and Y589C, N524C and M684C, and I675S;
(3) combination of D217C and Y589C, M371C and W506C, Y155G I156H H157R, W240A, C246S and I675S; and
(4) combination of D217C and Y589C, N524C and M684C, Y155G I156H H157R, W240A, C246S and I675S.

In another aspect of the invention, the mutant comprises a cysteine (C) at position 217 (217C) and at position 589 (589C), a cysteine (C) at position 371 (371C) and at position 506 (506C), and a serine (S) at position 675 (675S), and wherein the mutant is selected from the group consisting of:

(1) a mutant comprising the amino acid sequence set forth in SEQ ID NO:257; and
(2) a mutant comprising an amino acid sequence that is at least 97%, 98% or 99% identical to the amino acid sequence of SEQ ID NO:257.

In another aspect of the invention, the mutant comprises a cysteine (C) at position 217 (217C) and at position 589 (589C), a cysteine (C) at position 524 (524C) and at position 684 (684C), and a serine (S) at position 675 (675S), and wherein the mutant is selected from the group consisting of:

(1) a mutant comprising the amino acid sequence of SEQ ID NO: 259; and
(2) a mutant comprising an amino acid sequence that is at least 97%, 98% or 99% identical to the amino acid sequence of SEQ ID NO: 259.

In another aspect of the invention, the mutant comprises a cysteine (C) at position 217 (217C) and at position 589 (589C), a cysteine (C) at position 371 (371C) and at position 506 (506C), a serine (S) at position 675 (675S), a glycine (G) at position 155 (155G), a histidine at position 156 (156H), an arginine at position 157 (157R), an alanine at position 240 (240A), and a serine at position 246 (246S), and wherein the mutant is selected from the group consisting of:

(1) a mutant comprising the amino acid sequence set forth in SEQ ID NO:261; and
(2) a mutant comprising an amino acid sequence that is at least 97%, 98% or 99% identical to the amino acid sequence of SEQ ID NO: 261; (1) a mutant comprising the amino acid sequence set forth in SEQ ID NO: 261;
(3) a mutant comprising the amino acid sequence set forth in SEQ ID NO: 265; and
(4) a mutant comprising an amino acid sequence that is at least 97%, 98% or 99% identical to the amino acid sequence of SEQ ID NO:265.

In another aspect of the invention, the mutant comprises a cysteine (C) at position 217 (217C) and at position 589 (589C), a cysteine (C) at position 524 (524C) and at position 684 (684C), a serine (S) at position 675 (675S), a glycine (G) at position 155 (155G), a histidine at position 156 (156H), an arginine at position 157 (157R), an alanine at position 240 (240A), and a serine at position 246 (246S), and wherein the mutant is selected from the group consisting of:

(1) a mutant comprising the amino acid sequence of SEQ ID NO: 263; and
(2) a mutant comprising an amino acid sequence that is at least 97%, 98% or 99% identical to the amino acid sequence of SEQ ID NO:263.

In another aspect of the invention, the amino acid sequence of the wildtype CMV gB polypeptide is set forth in SEQ ID NO: 1.

In another aspect of the invention, the amino acid sequence of the mutant does not comprise a signal sequence. In another aspect of the invention, the mutant comprises residues 23-907 of SEQ ID NO: 1.

In another aspect of the invention, the amino acid sequence of the mutant does not comprise an MPR, TM or CT domain. In another aspect of the invention, the mutant comprises residues 23-707 of SEQ ID NO: 1.

In another aspect of the invention, the amino acid sequence of the mutant comprises a truncated Domain V region. In another aspect of the invention, the mutant comprises residues 23-702 or 23-703 of SEQ ID NO: 1.

In another aspect of the invention, the amino acid sequence of the mutant does not comprise a Domain V region. In another aspect of the invention, the mutant comprises residues 23-646 of SEQ ID NO: 1.

In another aspect of the invention, the mutant further comprises a trimerization motif linked to the C terminus of the mutant. In another aspect of the invention, the trimerization motif is selected from the group consisting of:

(i) an inter-protomer disulfide ring;
(ii) GCN4;
(iii) T4 fibritin foldon; and
(iv) C-terminus fusion sequence.

In another aspect of the invention, (i) the GCN4 comprises an amino acid sequence as set forth in SEQ ID NOs: 269, 272 or 273;
(ii) the T4 fibritin foldon comprises an amino acid sequence as set forth in SEQ ID NO: 271; or
(iii) the C-terminus fusion sequence comprises an amino acid sequence as set forth in SEQ ID NO: 274.

In another aspect of the invention, the inter-protomer disulfide ring comprises at least two engineered cysteine mutations selected from:

(i) 696C and 697C;

(ii) 703C and 704C; or (iii) 767C and 768C.

Several exogenous multimerization domains that promote formation of stable trimers of soluble proteins are known in the art. Examples of such multimerization domains that can be linked to a mutant provided by the present disclosure include, but are not limited to: (1) the GCN4 leucine zipper (Harbury et al. 1993 Science 262: 1401-1407); (2) the trimerization motif from the lung surfactant protein (Hoppe et al. 1994 FEB S Lett 344: 191-195); (3) collagen (McAlinden et al. 2003 Biol Chem 278:42200-42207); and (4) the phage T4 fibritin foldon (Miroshnikov et al. 1998 Protein Eng 11:329-414). In some embodiments, a multimerization domain is linked to a CMV gB mutant at the C-terminus. In specific embodiments, the trimerization domain is set forth in SEQ ID NOs: 269-274. Methods for connecting the multimerization domain to the gB polypeptide are well known in the art.

As used herein, "inter-protomer disulfide ring" shall mean a covalent ring formation between three helices achieved by three interhelical disulfide bonds formed by a ring system comprising pairs of adjacent cysteine residues, which establishes a functional topology and stabilization of the multimer (e.g. trimer). See, Stewart-Jones G B E, et al. (2015) A Cysteine Zipper Stabilizes a Pre-Fusion F Glycoprotein Vaccine for Respiratory Syncytial Virus. PLoS ONE 10(6): e0128779. doi:10.1371/journal.pone.0128779.

In another aspect of the invention, the mutant is secreted. In another aspect of the invention, the mutant is soluble.

In another aspect of the invention, the wildtype CMV gB polypeptide sequence is selected from SEQ ID NOs: 107-140 or 224.

In another aspect of the invention, the wildtype CMV gB polypeptide sequence is encoded by the polynucleotide sequences set forth in SEQ ID NOs: 225-254.

This invention also provides a nucleic acid molecule comprising nucleotides that encode an amino acid sequence of a CMV gB protein mutant according to the embodiment and aspects described herein.

In one aspect, the nucleic acid comprises nucleotides having a sequence set forth in SEQ ID NOs: 225-254.

This invention also provides a pharmaceutical composition comprising (i) a CMV gB protein mutant according to the embodiments and aspects described herein and (ii) a pharmaceutically acceptable carrier.

In one aspect, the pharmaceutical composition is a vaccine.

This invention also provides a method of reducing CMV infection in a subject comprising administering to the subject an effective amount of the vaccine set forth in the embodiments herein.

This invention also provides a method of eliciting an immune response to CMV infection in a subject comprising administering to the subject an effective amount of the vaccine set forth in the embodiments herein.

This invention also provides a method of preventing CMV infection in a subject comprising administering to the subject an effective amount of the vaccine set forth in the embodiments herein.

In one aspect, the subject is a human.

2. Further Embodiments of the Polypeptide

In some embodiments, the polypeptide does not include a mutation at any one of the following amino acid positions: 280, 281, 283, 284, 285, 286, 290, 292, 295, 297, 298, 299, or any combinations thereof, according to the numbering of reference sequence SEQ ID NO: 46. In some exemplary embodiments, the polypeptide does not include a substitution of any one of the following residues, according to the numbering of reference sequence SEQ ID NO: 46: Y280; N281; T283; N284; R285; N286; F290; E292; N293; F297; F298; I299; F298; and any combinations thereof. Without being bound by theory or mechanism, residues important for neutralizing antibodies may include Y280/N284 and Y280/N293/D295. Accordingly, in a preferred embodiment, the polypeptide does not include mutations at Y280, N293, N284, and D295, as compared to reference sequence SEQ ID NO: 46.

In some embodiments, the polypeptide does not include a mutation at any one of the following amino acid positions: R562, P577, S587, Y588, G592, G595, L601/H605, C610, L612, P613, Y625, Y627, F632, and K633, and any combinations thereof, according to the numbering of reference sequence SEQ ID NO: 44. In some embodiments, the polypeptide does not include any one of the following amino acid mutations: R562C, P577L, S587L, Y588C, G592S, G595D, L601P/H605N, C610Y, L612F, P613Y, Y625C, Y627C, F632L, and K633T, or any combinations thereof, according to the numbering of reference sequence SEQ ID NO: 44. Without being bound by theory or mechanism, P577 and Y627 are believed to be located next to each other within the domain IV core while C610 participates in a conserved disulfide bond. Thus, all three residues may help maintain the position of domain IV in the prefusion structure and, therefore, the stability of entire antigenic site AD-1. Moreover, without being bound by theory or mechanism, F632 and G595 are believed to be exposed on the surface of the prefusion form of gB. Accordingly, in a preferred embodiment, the polypeptide does not include a mutation at P577, Y627, C610, F632, and G595, or any combinations thereof, according to the numbering of reference sequence SEQ ID NO: 44.

3. Cavity Filling Mutations

In still other embodiments, the polypeptide includes amino acid mutations that are one or more cavity filling mutations. Examples of amino acids that may be replaced with the goal of cavity filling include small aliphatic (e.g. Gly, Ala, and Val) or small polar amino acids (e.g. Ser and Thr) and amino acids that are buried in the pre-fusion conformation, but exposed to solvent in the post-fusion conformation. Examples of the replacement amino acids include large aliphatic amino acids (lie, Leu and Met) or large aromatic amino acids (His, Phe, Tyr and Trp).

4. Combination of Mutations

In another aspect, the present invention relates to a polypeptide that includes a combination of two or more different types of mutations selected from at least two engineered disulfide bond mutations, and at least one additional mutation such as a cavity filling mutation, anelectrostatic mutation, an inter-protomer disulfide ring each as described herein. In some embodiments, the polypeptide includes at least two disulfide bond mutations and at least one electrostatic mutation. More specifically, in some embodiments, the polypeptide includes at least two cysteine substitutions and at least one phenylalanine substitution. In some embodiments, the polypeptide includes at least two cysteine substitutions and at least one leucine substitution.

In some further embodiments, the polypeptide includes at least two mutations selected from any one of the mutations in Table 2 and at least one mutation selected from any one of the mutations in Table 3. In some further embodiments, the polypeptide includes at least two mutations selected from any one of the mutations in Table 2 and at least one mutation selected from any one of the mutations in Table 4. In some further embodiments, the polypeptide includes at least two mutations selected from any one of the mutations in Table 2, at least one mutation selected from any one of the mutations in Table 3 and at least one mutation selected from any one of the mutations in Table 4.

Preparation of the Polypeptide

The polypeptides described herein may be prepared by routine methods known in the art, such as by expression in a recombinant host system using a suitable vector. Suitable recombinant host cells include, for example, insect cells, mammalian cells, avian cells, bacteria, and yeast cells. Examples of suitable insect cells include, for example, Sf9 cells, Sf21 cells, Tn5 cells, Schneider S2 cells, and HIGH FIVE cells (a clonal isolate derived from the parental *Trichoplusia ni* BTI-TN-5B1-4 cell line). Examples of suitable mammalian cells include Chinese hamster ovary (CHO) cells, human embryonic kidney cells (HEK293 or Expi 293 cells, typically transformed by sheared adenovirus type 5 DNA), NIH-3T3 cells, 293-T cells, Vero cells, and HeLa cells. Suitable avian cells include, for example, chicken embryonic stem cells (e.g., EBx® cells), chicken embryonic fibroblasts, chicken embryonic germ cells, quail fibroblasts (e.g. ELL-O), and duck cells. Suitable insect cell expression systems, such as baculovirus-vectored systems, are known to those of skill in the art. Materials and methods for baculovirus/insect cell expression systems are commercially available in kit form from. Avian cell expression systems are also known to those of skill in the art. Similarly, bacterial and mammalian cell expression systems are also known in the art.

A number of suitable vectors for expression of recombinant proteins in insect or mammalian cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable baculovirus expression vector, such as PFASTBAC, is used to produce recombinant baculovirus particles. The baculovirus particles are amplified and used to infect insect cells to express recombinant protein. For expression in mammalian cells, a vector that will drive expression of the construct in the desired mammalian host cell (e.g., Chinese hamster ovary cells) is used.

The polypeptide can be purified using any suitable methods. For example, methods for purifying a polypeptide by immunoaffinity chromatography are known in the art. Suitable methods for purifying desired polypeptides including precipitation and various types of chromatography, such as hydrophobic interaction, ion exchange, affinity, chelating and size exclusion are known in the art. Suitable purification schemes can be created using two or more of these or other suitable methods. If desired, the polypeptide may include a "tag" that facilitates purification, such as an epitope tag or a histidine tag. Such tagged polypeptides can be purified, for example from conditioned media, by chelating chromatography or affinity chromatography.

Nucleic Acids Encoding polypeptides

In another aspect, the invention relates to nucleic acid molecules that encode a polypeptide described herein. These nucleic acid molecules include DNA, cDNA, and RNA sequences. Nucleic acid molecules that encode only the ectodomain of the polypeptide are also encompassed by the invention. The nucleic acid molecule can be incorporated into a vector, such as an expression vector.

In some embodiments, the nucleic acid includes a self-replicating RNA molecule. In some embodiments, the nucleic acid includes a modified RNA molecule. In another aspect, the invention relates to a composition including a nucleic acid according to any one of the embodiments described herein.

Compound-Stabilized Polypeptide

The inventors discovered a polypeptide stabilized in a prefusion conformation that can be identified by, for example, the binding of a bis(aryl)thiourea compound to an HCMV gB. Bis(aryl)thiourea compounds, as exemplified by structures 1a,b (Formula I), are highly potent and specific inhibitors of CMV. In one aspect, the invention relates to a polypeptide that is capable of binding to a bis(aryl)thiourea compound. In preferred embodiments, the compound does not bind to a postfusion conformation of the HCMV gB polypeptide.

(Formula I)

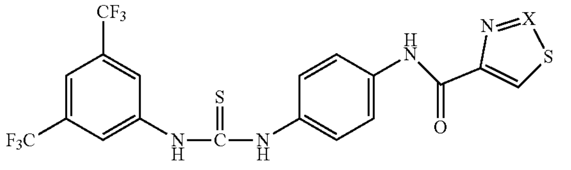

1a (X = CH)
1b (X = N)

In a preferred embodiment, the compound is a bis(aryl) thiourea thioziole analog thereof. Most preferably, in some embodiments, the compound is N-{4-[({(1S)-1-[3,5-bis(trifluoromethyl)phenyl]ethyl}carbamothioyl)amino]phenyl}-1,3-thiazole-4-carboxamide, having the following structure:

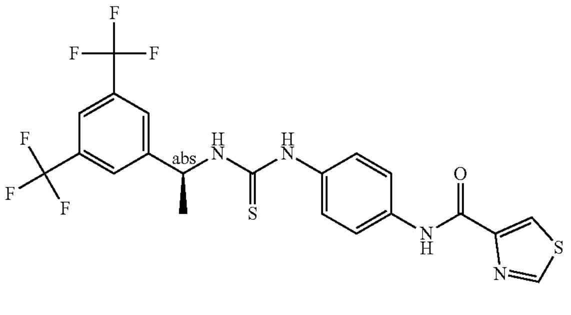 [SMILES: C[C@H](NC(=S)Nc1ccc(NC(=O)c2cscn2)cc1)c1cc(C(F)(F)F)cc(C(F)(F)F)c1]

In another embodiment, the compound has the following structure:

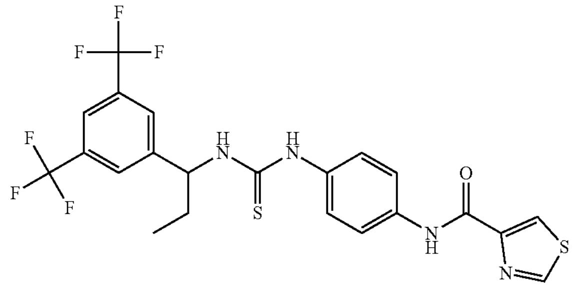 [SMILES: CCC(NC(=S)Nc1ccc(NC(=O)c2cscn2)cc1)c1cc(C(F)(F)F)cc(C(F)(F)F)c1]

In several embodiments, the polypeptide includes an HCMV gB prefusion epitope, which is not present in a native HCMV gB a postfusion conformation.

In some embodiments, at least about 90% of the polypeptides (such as at least about 91%, 92%, 93%, 94%, 95%, 96%, 97%, 98%, 99% or 99.9% of the polypeptides in the homogeneous population are bound by a bis(aryl)thiourea compound (e.g., such as a thiazole analog of bis(aryl) thiourea compounds, more preferably N-{4-[({(1S)-1-[3,5-bis(trifluoromethyl)phenyl]ethyl}carbamothioyl) amino] phenyl}-1,3-thiazole-4-carboxamide). In some embodiments, the polypeptide that can bind to the bis(aryl) thiourea compound does not have a postfusion conformation. Rather, the polypeptide has a prefusion conformation, such as an HCMV gB prefusion conformation.

In another embodiment, the polypeptide can be at least 80% isolated, at least 90%, 95%, 98%, 99%, or preferably 99.9% isolated from HCMV gB polypeptides that are not specifically bound by a bis(aryl)thiourea compound.

Compositions Including a Polypeptide and Methods of Use Thereof

The invention relates to compositions and methods of using the polypeptide described herein, or a nucleic acid encoding such polypeptide described herein. For example, the polypeptide of the invention can be delivered directly as a component of an immunogenic composition. Alternatively, nucleic acids that encode the polypeptide of the invention can be administered to produce the polypeptide or immunogenic fragment in vivo. Certain preferred embodiments, such as protein formulations, recombinant nucleic acids (e.g., DNA, RNA, self-replicating RNA, or any variation thereof) and viral vectors (e.g., live, single-round, non-replicative assembled virions, or otherwise virus-like particles, or alphavirus VRP) that contain sequences encoding polypeptides are further described herein and may be included in the composition.

In one aspect, the invention provides an immunogenic composition comprising the polypeptide described herein. The immunogenic composition can include additional CMV proteins, such as gO, gH, gL, pUL128, pUL130, pUL131, pp65, an immunogenic fragment thereof, or a combination thereof. For example, the polypeptide can be combined with CMV pentameric complex comprising: gH or a pentamer-forming fragment thereof, gL or a pentamer-forming fragment thereof, pUL128 or a pentamer-forming fragment thereof, pUL130 or a pentamer-forming fragment thereof, and pUL131 or a pentamer-forming fragment thereof. The polypeptide of the invention can also be combined with CMV trimeric complex comprising: gH or a trimer-forming fragment thereof, gL or a trimer-forming fragment thereof, and gO or a trimer-forming fragment thereof.

In another aspect, the invention relates to a composition including a polynucleotide that may elicit an immune response in a mammal. The polynucleotide encodes at least one polypeptide of interest, e.g., an antigen. Antigens disclosed herein may be wild type (i.e., derived from the infectious agent) or preferably modified (e.g., engineered, designed or artificial). The nucleic acid molecules described herein, specifically polynucleotides, in some embodiments, encode one or more peptides or polypeptides of interest. Such peptides or polypeptides may serve as an antigen or antigenic molecule. The term "nucleic acid" includes any compound that includes a polymer of nucleotides. These polymers are referred to as "polynucleotides." Exemplary nucleic acids or polynucleotides of the invention include, but are not limited to, ribonucleic acids (RNAs), including mRNA, and deoxyribonucleic acids (DNAs).

In some embodiments, the composition includes DNA encoding a polypeptide or fragment thereof described herein. In some embodiments, the composition includes RNA encoding a polypeptide or fragment thereof described herein. In some embodiments, the composition includes an mRNA polynucleotide encoding a polypeptide or fragment thereof described herein. Such compositions may produce the appropriate protein conformation upon translation.

In one aspect, the invention relates to a composition that includes at least one polynucleotide encoding a polypeptide including at least one amino acid mutation relative to the amino acid sequence of the wild-type HCMV gB.

In one aspect, the invention relates to a composition that includes at least one DNA polynucleotide encoding a polypeptide including at least one amino acid mutation relative to the amino acid sequence of the wild-type HCMV gB.

In one aspect, the invention relates to a composition that includes at least one RNA polynucleotide encoding a polypeptide including at least one amino acid mutation relative to the amino acid sequence of the wild-type HCMV gB.

In some embodiments, the invention relates to a composition that includes at least one polynucleotide encoding at least one hCMV gB polypeptide or an immunogenic fragment or epitope thereof.

In some embodiments, the composition includes at least one polynucleotide encoding two or more antigenic polypeptides or an immunogenic fragment or epitope thereof. In some embodiments, the composition includes two or more polynucleotides encoding two or more antigenic polypeptides or immunogenic fragments or epitopes thereof. The one or more antigenic polypeptides may be encoded on a single polynucleotide or may be encoded individually on multiple (e.g., two or more) polynucleotides.

In another aspect, the invention relates to a composition that includes (a) a polynucleotide encoding a polypeptide including at least one introduced amino acid mutation relative to the amino acid sequence of the wild-type HCMV glycoprotein B (gB); and (b) a polynucleotide encoding an additional polypeptide.

In another aspect, the invention relates to a composition that includes (a) a polynucleotide encoding a polypeptide including at least one introduced amino acid mutation relative to the amino acid sequence of the wild-type HCMV glycoprotein B (gB); and (b) a polynucleotide encoding an additional polypeptide, preferably an HCMV antigenic polypeptide. The additional polypeptide may be selected from HCMV gH, gL, gB, gO, gN, and gM and an immunogenic fragment or epitope thereof. In some embodiments, the additional polypeptide is HCMV pp65. In some embodiments, the additional polypeptide may be selected from gH, gL, gO, gM, gN, UL128, UL130, and UL131A, and fragments thereof. In some embodiments, the additional polypeptide is HCMV gH polypeptide. In some embodiments, the additional polypeptide is an HCMV gL polypeptide. In some embodiments, the additional polypeptide is an HCMV gB polypeptide. In some embodiments, the additional polypeptide is an HCMV gO polypeptide. In some embodiments, the additional polypeptide is an HCMV gN polypeptide. In some embodiments, the additional polypeptide is an HCMV gM polypeptide. In some embodiments, the additional polypeptide is a variant gH polypeptide, a variant gL polypeptide, or a variant gB polypeptide. In some embodiments, the variant HCMV gH, gL, or gB polypeptide is a truncated polypeptide lacking one or more of the following domain sequences: (1) the hydrophobic membrane proximal domain, (2) the transmembrane domain, and (3) the cytoplasmic domain. In some embodiments, the truncated HCMV gH, gL, or gB polypeptide lacks the hydrophobic membrane proximal domain, the transmembrane domain, and the cytoplasmic domain. In some embodiments, the truncated HCMV gH, gL, or gB polypeptide includes only the ectodomain sequence. In some embodiments, an antigenic polypeptide is an HCMV protein selected from UL83, UL123, UL128, UL130 and UL131A or an immunogenic fragment or epitope thereof. In some embodiments, the antigenic polypeptide is an HCMV UL83 polypeptide. In some embodiments, the antigenic polypeptide is an HCMV UL123 polypeptide. In some embodiments, the antigenic polypeptide is an HCMV UL128 polypeptide. In some embodiments, the antigenic polypeptide is an HCMV UL130 polypeptide. In some embodiments, the antigenic polypeptide is an HCMV UL131 polypeptide.

In another aspect, the invention relates to a composition that includes (a) a polynucleotide encoding a polypeptide including at least two introduced amino acid mutations relative to the amino acid sequence of the wild-type HCMV glycoprotein B (gB); and (b) a polynucleotide encoding an additional polypeptide having any one of the amino acid sequences set forth in SEQ ID NOs: 211-223. In another aspect, the invention relates to a composition that includes (a) a polynucleotide encoding a polypeptide including at least two introduced amino acid mutations relative to the amino acid sequence of the wild-type HCMV glycoprotein B (gB); and (b) a polynucleotide having any one of the sequences selected from SEQ ID NOs: 141-210. In another aspect, the invention relates to a composition that includes (a) a polynucleotide encoding a polypeptide including at least two introduced amino acid mutations relative to the amino acid sequence of the wild-type HCMV glycoprotein B (gB); and (b) an additional polypeptide having any one of the amino acid sequences selected from SEQ ID NOs: 211-223. In some embodiments, the polynucleotide encoding the additional polypeptide includes at least one nucleic acid sequence selected from any of SEQ ID NOs: 225-254. In some embodiments, the polynucleotide encoding the additional polypeptide includes at least one nucleic acid sequence selected from any of SEQ ID NOs: 141-147. In some embodiments, the polynucleotide encoding the additional polypeptide has at least one sequence selected from any of SEQ ID NOs: 220-223.

In some embodiments, the antigenic polypeptide includes two or more HCMV proteins, fragments, or epitopes thereof. In some embodiments, the antigenic polypeptide includes two or more glycoproteins, fragments, or epitopes thereof. In some embodiments, the antigenic polypeptide includes at least one HCMV polypeptide, fragment or epitope thereof and at least one other HCMV protein, fragment or epitope thereof. In some embodiments, the two or more HCMV polypeptides are encoded by a single RNA polynucleotide. In some embodiments, the two or more HCMV polypeptides are encoded by two or more RNA polynucleotides, for example, each HCMV polypeptide is encoded by a separate RNA polynucleotide. In some embodiments, the two or more HCMV polypeptides can be any combination of HCMV gH, gL, gB, gO, gN, and gM polypeptides or immunogenic fragments or epitopes thereof. In some embodiments, the two or more glycoproteins includes pp65 or immunogenic fragments or epitopes thereof; and any combination of HCMV gH, gL, gB, gO, gN, and gM polypeptides or immunogenic fragments or epitopes thereof. In some embodiments, the two or more glycoproteins can be any combination of HCMV gB and one or more HCMV polypeptides selected from gH, gL, gO, gN, and gM polypeptides or immunogenic fragments or epitopes thereof. In some embodiments, the two or more glycoproteins can be any combination of HCMV gH and one or more HCMV polypeptides selected from gL, gO, gN, and gM polypeptides or immunogenic fragments or epitopes thereof. In some embodiments, the two or more glycoproteins can be any combination of HCMV gL and one or more HCMV polypeptides selected from gB, gH, gO, gN, and gM polypeptides or immunogenic fragments or epitopes thereof. In some embodiments, the two or more HCMV polypeptides are gB and gH. In some embodiments, the two or more HCMV polypeptides are gB and gL. In some embodiments, the two or more HCMV polypeptides are gH and gL. In some embodiments, the two or more HCMV polypeptides are gB, gL, and gH. In some embodiments, the two or more HCMV proteins can be any combination of HCMV UL83, UL123, UL128, UL130, and UL131A polypeptides or immunogenic fragments or epitopes thereof. In some embodiments, the two or more HCMV polypeptides are UL123 and UL130. In some embodiments, the two or more HCMV polypeptides are UL123 and 131 A. In some embodiments, the two or more HCMV polypeptides are UL130 and 131 A. In some embodiments, the two or more HCMV polypeptides are UL 128, UL130 and 131 A. In some embodiments, the two or more HCMV proteins can be any combination of HCMV gB, gH, gL, gO, gM, gN, UL83, UL123, UL128, UL130, and UL131A polypeptides or immunogenic fragments or epitopes thereof. In some embodiments, the two or more glycoproteins can be any combination of HCMV gH and one or more HCMV polypeptides selected from gL, UL128, UL130, and UL131A polypeptides or immunogenic fragments or epitopes thereof. In some embodiments, the two or more glycoproteins can be any combination of HCMV gL and one or more HCMV polypeptides selected from gH, UL128, UL130, and UL131A polypeptides or immunogenic fragments or epitopes thereof. In some embodiments, the two or more HCMV polypeptides are gL, gH, UL 128, UL130 and 131 A. In any of these embodiments in which the composition includes two or more HCMV proteins, the HCMV gH may be a variant gH, such as any of the variant HCMV gH glycoproteins disclosed herein, for example, any of the variant HCMV gH disclosed herein. In any of these embodiments in which the composition includes two or more HCMV proteins, the HCMV gB may be a variant gB, such as any of the variant HCMV gB glycoproteins disclosed herein, for example, any of the variant HCMV gB disclosed herein. In any of these embodiments in which the composition includes two or more HCMV gL proteins, the HCMV gL may be a variant gL, such as any of the variant HCMV gL glycoproteins disclosed herein, for example, any of the variant HCMV gL disclosed herein.

In certain embodiments in which the compostion includes two or more RNA polynucleotides encoding two or more HCMV antigenic polypeptides or an immunogenic fragment or epitope thereof (either encoded by a single RNA polynucleotide or encoded by two or more RNA polynucleotides, for example, each protein encoded by a separate RNA polynucleotide), the two or more HCMV proteins are a variant gB, for example, any of the variant gB polypeptides disclosed herein, and an HCMV protein selected from gH, gL, gO, gM, gN, UL128, UL130, and UL131 polypeptides or immunogenic fragments or epitopes thereof. In some embodiments, the two or more HCMV proteins are a variant gH, for example, any of the variant gH polypeptides disclosed herein, and an HCMV protein selected from gH, gL, gO, gM, gN, UL128, UL130, and UL131A polypeptides or immunogenic fragments or epitopes thereof. In some embodiments, the two or more HCMV proteins are a variant gH, for example, any of the variant gH polypeptides disclosed herein, and an HCMV protein selected from gH, gL, gO, gM, gN, UL128, UL130, and UL131 polypeptides or immunogenic fragments or epitopes thereof. In some embodiments in which the variant HCMV proteins are variant HCMV gB, variant HCMV gL, and variant HCMV gH, the variant HCMV polypeptide is a truncated polypeptide selected from the following truncated polypeptides: lacks the hydrophobic membrane proximal domain; lacks the transmembrane domain; lacks the cytoplasmic domain; lacks two or more of the hydrophobic membrane proximal, transmembrane, and cytoplasmic domains; and includes only the ectodomain. In some embodiments, the composition includes multimeric RNA polynucleotides encoding at least one HCMV antigenic polypeptide or an immunogenic fragment or epitope thereof. In some embodiments, the composition includes at least one RNA polynucleotide encoding at least one HCMV antigenic polypeptide or an immunogenic fragment or epitope thereof, wherein the 5'UTR of the RNA polynucleotide includes a patterned UTR. In some embodiments, the patterned UTR has a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level. In some embodiments, the 5' UTR of the RNA polynucleotide (e.g., a first nucleic acid) has regions of complementarity with a UTR of another RNA polynucleotide (a second nucleic acid). For example, UTR nucleotide sequences of two polynucleotides sought to be joined (e.g., in a multimeric molecule) can be modified to include a region of complementarity such that the two UTRs hybridize to form a multimeric molecule. In some embodiments, the 5' UTR of an RNA polynucleotide encoding an HCMV antigenic polypeptide is modified to allow the formation of a multimeric sequence. In some embodiments, the 5' UTR of an RNA polynucleotide encoding an HCMV protein selected from UL128, UL130, UL131 is modified to allow the formation of a multimeric sequence. In some embodiments, the 5' UTR of an RNA polynucleotide encoding an HCMV polypeptide is modified to allow the formation of a multimeric sequence. In some embodiments, the 5' UTR of an RNA polynucleotide encoding an HCMV polypeptide selected from gH, gL, gB, gO, gM, and gN is modified to allow the formation of a multimeric sequence. In any of these embodiments, the multimer may be a dimer, a trimer, pentamer, hexamer, heptamer, octamer nonamer, or decamer. Thus, in some embodiments, the 5' UTR of an RNA polynucleotide encoding an HCMV protein selected from gH, gL, gB, gO, gM, gN, UL128, UL130, and UL131 is modified to allow the formation of a dimer. In some embodiments, the 5' UTR of an RNA polynucleotide encoding an HCMV protein selected from gH, gL, gB, gO, gM, gN, UL128, UL130, and UL131A is modified to allow the formation of a trimer. In some embodiments, the 5' UTR of an RNA polynucleotide encoding an HCMV protein selected from gH, gL, gB, gO, gM, gN, UL128, UL130, and UL131 is modified to allow the formation of a pentamer. In some embodiments, the composition includes at least one RNA polynucleotide having a single open reading frame encoding two or more (for example, two, three, four, five, or more) HCMV antigenic polypeptides or an immunogenic fragment or epitope thereof. In some embodiments, the composition includes at least one RNA polynucleotide having more than one open reading frame, for example, two, three, four, five or more open reading frames encoding two, three, four, five or more HCMV antigenic polypeptides. In either of these embodiments, the at least one RNA polynucleotide may encode two or more HCMV antigenic polypeptides selected from gH, gB, gL, gO, gM, gN, UL83, UL123, UL128, UL130, UL131A, and fragments or epitopes thereof. In some embodiments, the at least one RNA polynucleotide encodes UL83 and UL123. In some embodiments, the at least one RNA polynucleotide encodes gH and gL. In some embodiments, the at least one RNA polynucleotide encodes UL128, UL130, and UL131. In some embodiments, the at least one RNA polynucleotide encodes gH, gL, UL128, UL130, and UL131. In some embodiments, in which the at least one RNA polynucleotide has a single open reading frame encoding two or more (for example, two, three, four, five, or more) HCMV antigenic polypeptides, the RNA polynucleotide further comprises additional sequence, for example, a linker sequence or a sequence that aids in the processing of the HCMV RNA transcripts or polypeptides, for example a cleavage site sequence. In some embodiments, the additional sequence may be a protease sequence, such as a furin sequence. In some embodiments, the additional sequence may be self-cleaving 2A peptide, such as a P2A, E2A, F2A, and T2A sequence. In some embodiments, the linker sequences and cleavage site sequences are interspersed between the sequences encoding HCMV polypeptides.

In some embodiments, at least one RNA polynucleotide includes any nucleic acid sequence selected from any one of nucleic acid sequences disclosed herein, or homologs thereof having at least 80% (e.g., 85%, 90%, 95%, 98%, 99%) identity with a nucleic acid sequence disclosed herein. In some embodiments, the open reading frame is encoded is codon-optimized. Some embodiments include a composition that includes at least one RNA polynucleotide encoding at least one HCMV antigenic polypeptide or an immunogenic fragment thereof and at least one 5' terminal cap. In some embodiments, a 5' terminal cap is 7mG(5')ppp(5')NlmpNp.

In some embodiments, the at least one polynucleotide includes a nucleic acid sequence selected from any one of SEQ ID NOs: 141-210. In some embodiments, the at least one polynucleotide encodes a polypeptide having at least 90% identity to any one of the amino acid sequences of SEQ ID NOs: 211-223. In some preferred embodiments, the composition does not include a polypeptide having the amino acid sequence SEQ ID NO: 216. In some preferred embodiments, the composition does not include a polynucleotide encoding the amino acid sequence SEQ ID NO: 216.

In some preferred embodiments, the composition does not include a polynucleotide having the sequence SEQ ID NO: 152.

In some embodiments, the composition includes at least one polynucleotide, wherein the at least one polynucleotide has at least one chemical modification. In some embodiments, the at least one polynucleotide further includes a second chemical modification. Preferably, the polynucleotide is RAN. In some embodiments, the at least one polynucleotide having at least one chemical modification has a 5' terminal cap. In some embodiments, the at least one chemical modification is selected from pseudouridine, N1-methylpseudouridine, N1-ethylpseudouridine, N1-ethylpseudouridine, 2-thiouridine, 4'-thiouridine, 5-methylcytosine, 2-thio-I-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-0-methyl uridine. In some embodiments, the composition includes at least one polynucleotide, wherein at least 80% (e.g., 85%, 90%, 95%, 98%, 99%, 100%) of the uracil in the open reading frame has a chemical modification, optionally wherein the composition is formulated in a lipid nanoparticle. In some embodiments, 100% of the uracil in the open reading frame has a chemical modification. In some embodiments, a chemical modification is in the 5-position of the uracil. In some embodiments, a chemical modification is a N1-methyl pseudouridine.

In some embodiments, the additional polypeptides or immunogenic fragments encoded by the polynucleotide (e.g., in an mRNA composition) are selected from gB, gH, gL, gO, gM, gN, UL83, UL123, UL128, UL130, UL131A, pp65 and IE1 antigens.

In some embodiments, a first composition and a second composition are administered to the mammal. In some embodiments, a first composition includes a polynucleotide encoding a polypeptide including at least one introduced amino acid mutation relative to the amino acid sequence of the wild-type HCMV gB; and a second composition includes a polynucleotide encoding HCMV pp65 or an antigenic fragment or epitope thereof. In some embodiments, a first composition includes a polynucleotide encoding a polypeptide including at least one introduced amino acid mutation relative to the amino acid sequence of the wild-type HCMV gB; and a second composition includes a polynucleotide encoding at least one polynucleotide encoding an additional polypeptide selected from HCMV gH, gL, UL128, UL130, and UL131, or antigenic fragments or epitopes thereof.

In another aspect, the invention relates to methods of inducing an immune response in a mammal, including administering to the mammal a composition in an amount effective to induce an immune response, wherein the composition includes a polynucleotide encoding a polypeptide including at least two introduced amino acid mutations relative to the amino acid sequence of the wild-type HCMV gB.

In some embodiments, the immune response includes a T cell response or a B cell response. In some embodiments, the immune response includes a T cell response and a B cell response. In some embodiments, the method involves a single administration of the composition. In some embodiments, a method further includes administering to the subject a booster dose of the composition. The composition including a polynucleotide disclosed herein may be formulated in an effective amount to produce an antigen specific immune response in a mammal.

The immunogenic composition may include an adjuvant. Exemplary adjuvants to enhance effectiveness of the composition include: (1) aluminum salts (alum), such as aluminum hydroxide, aluminum phosphate, aluminum sulfate, etc.; (2) oil-in-water emulsion formulations (with or without other specific adjuvants such as muramyl peptides (see below) or bacterial cell wall components), such as for example (a) MF59 (PCT Publ. No. WO 90/14837), containing 5% Squalene, 0.5% TWEEN 80, and 0.5% Span 85 formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DETOX™); (3) saponin adjuvants, such as QS-21, STIMULON™ (Cambridge Bioscience, Worcester, Mass.), which may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; and (6) other substances that act as adjuvants to enhance the effectiveness of the composition. In a preferred embodiment, the adjuvant is a saponin adjuvant, namely QS-21. In some embodiments, the composition does not include an adjuvant. In some embodiments, the composition further includes a lipid nanoparticle. In some embodiments, the composition is formulated in a nanoparticle. In some embodiments, the composition further includes a cationic or polycationic compounds, including protamine or other cationic peptides or proteins, such as poly-L-lysine (PLL).

Each of the immunogenic compositions discussed herein may be used alone or in combination with one or more other antigens, the latter either from the same viral pathogen or from another pathogenic source or sources. These compositions may be used for prophylactic (to prevent infection) or therapeutic (to treat disease after infection) purposes.

In one embodiment, the composition may include a "pharmaceutically acceptable carrier," which includes any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as adjuvants. Furthermore, the antigen may be conjugated to a bacterial toxoid, such as a toxoid from diphtheria, tetanus, cholera, *H. pylori*, and etc. pathogens.

In one embodiment, the composition includes a diluent, such as water, saline, glycerol, ethanol, etc. Additionally, auxiliary substances, such as wetting or emulsifying agents, pH buffering substances, and the like, may be present in such vehicles.

The compositions described herein may include an immunologically effective amount of the polypeptide or polynucleotide, as well as any other of the above-mentioned components, as needed. By "immunologically effective amount," it is meant that the administration of that amount to an individual, either in a single dose or as part of a series, is effective for eliciting an immune response. The immune response elicited may be sufficient, for example, for treatment and/or prevention and/or reduction in incidence of illness, infection or disease. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The composition may be administered parenterally, e.g., by injection, either subcutaneously or intramuscularly. In some embodiments, the composition is administered to the mammal by intradermal or intramuscular injection. Additional formulations suitable for other modes of administration include oral and pulmonary formulations, nasal formulations, suppositories, and transdermal applications. Oral formulations may be preferred for certain viral proteins. Dosage treatment may be a single dose schedule or a multiple dose schedule. The immunogenic composition may be administered in conjunction with other immunoregulatory agents.

In another aspect, the invention provides a method of eliciting an immune response against cytomegalovirus, comprising administering to a subject in need thereof an immunologically effective amount of the polypeptide and/or an immunogenic composition described herein, which comprises the proteins, DNA molecules, RNA molecules (e.g., self-replicating RNA molecules), or VRPs as described above. In certain embodiments, the immune response comprises the production of neutralizing antibodies against CMV.

The immune response can comprise a humoral immune response, a cell-mediated immune response, or both. In some embodiments an immune response is induced against each delivered CMV protein. A cell-mediated immune response can comprise a Helper T-cell (Th) response, a CD8+ cytotoxic T-cell (CTL) response, or both. In some embodiments the immune response comprises a humoral immune response, and the antibodies are neutralizing antibodies.

Neutralizing antibodies block viral infection of cells. CMV infects epithelial cells and also fibroblast cells. In some embodiments the immune response reduces or prevents infection of both cell types. Neutralizing antibody responses can be complement-dependent or complement-independent. In some embodiments the neutralizing antibody response is complement-independent. In some embodiments the neutralizing antibody response is cross-neutralizing; i.e., an antibody generated against an administered composition neutralizes a CMV virus of a strain other than the strain used in the composition.

The polypeptide and/or immunogenic composition described herein may also elicit an effective immune response to reduce the likelihood of a CMV infection of a non-infected mammal, or to reduce symptoms in an infected mammal, e.g., reduce the number of outbreaks, CMV shedding, and risk of spreading the virus to other mammals.

In one aspect, the invention relates to a method for reducing CMV viral shedding in a mammal. In some embodiments, the invention relates to a method for reducing CMV viral shedding in urine in a mammal. In some embodiments, the invention relates to a method for reducing CMV viral shedding in saliva in a mammal. In another aspect, the invention relates to a method for reducing CMV viral titers in a mammal. In one aspect, the invention relates to a method for reducing CMV nucleic acids in serum in a mammal. The term "viral shedding" is used herein according to its plain ordinary meaning in medicine and virology and refers to the production and release of virus from an infected cell. In some embodiments, the virus is released from a cell of a mammal. In some embodiments, virus is released into the environment from an infected mammal. In some embodiments the virus is released from a cell within a mammal.

In one aspect, the invention relates to a method for reducing CMV viral shedding in a mammal. The method includes administering the modified CMV gB polypeptide and/or immunogenic composition described herein to the mammal that is infected with or is at risk of a CMV infection. In one embodiment, the reduction in CMV viral shedding in a mammal is as compared to the viral shedding in mammals that were not administered the modified CMV gB. In another embodiment, the reduction in CMV viral shedding in a mammal is as compared to the viral shedding following an administration of a CMV pentamer alone or following an administration of a CMV pentamer in the absence of the polypeptide.

In some embodiments, the mammal is a human. In some embodiments, the human is a child, such as an infant. In some other embodiments, the human is female, including an adolescent female, a female of childbearing age, a female who is planning pregnancy, a pregnant female, and females who recently gave birth. In some embodiments, the human is a transplant patient.

In one embodiment, the challenge cytomegalovirus strain is a human CMV strain. In one embodiment, the challenge cytomegalovirus strain is homologous to the CMV strain from which the polypeptide is derived. In another embodiment, the challenge cytomegalovirus strain is homologous to the CMV strain VR1814. In another embodiment, the challenge cytomegalovirus strain is homologous to the CMV strain Towne.

In one embodiment, the challenge cytomegalovirus strain is a human CMV strain that is heterologous to the CMV strain from which the modified CMV gB polypeptide is derived. In another embodiment, the challenge cytomegalovirus strain is a human CMV strain that is heterologous to the VR1814 CMV strain. In another embodiment, the challenge cytomegalovirus strain is the VR1814 CMV strain. In another embodiment, the challenge cytomegalovirus strain is a human CMV strain that is heterologous to the CMV strain Towne. In another embodiment, the challenge cytomegalovirus strain is the CMV strain Towne.

In another embodiment, the challenge cytomegalovirus strain is a rhesus CMV strain homologous to the macacine herpesvirus 3 isolate 21252 CMV strain. In another embodiment, the challenge cytomegalovirus strain is the macacine herpesvirus 3 isolate 21252 CMV strain.

A useful measure of antibody potency in the art is "50% neutralization titer." Another useful measure of antibody potency is any one of the following: a "60% neutralization titer"; a "70% neutralization titer"; a "80% neutralization titer"; and a "90% neutralization titer." To determine, for example, a 50% neutralizing titer, serum from immunized animals is diluted to assess how dilute serum can be yet retain the ability to block entry of 50% of infectious viruses into cells. For example, a titer of 700 means that serum retained the ability to neutralize 50% of infectious virus after being diluted 700-fold. Thus, higher titers indicate more potent neutralizing antibody responses. In some embodiments, this titer is in a range having a lower limit of about 200, about 400, about 600, about 800, about 1000, about 1500, about 2000, about 2500, about 3000, about 3500, about 4000, about 4500, about 5000, about 5500, about 6000, about 6500, or about 7000. The 50%, 60%, 70%, 80%, or 90% neutralization titer range can have an upper limit of about 400, about 600, about 800, about 1000, about 1500, about 2000, about 2500, about 3000, about 3500, about 4000, about 4500, about 5000, about 5500, about 6000, about 6500, about 7000, about 8000, about 9000, about 10000, about 11000, about 12000, about 13000, about 14000, about 15000, about 16000, about 17000, about 18000, about 19000, about 20000, about 21000, about 22000, about 23000, about 24000, about 25000, about 26000, about 27000, about 28000, about 29000, or about 30000. For example, the 50% neutralization titer can be about 3000 to about 6500. "About" means plus or minus 10% of the recited value. Neutralization titer can be measured as described in the specific examples, below.

An immune response can be stimulated by administering proteins, DNA molecules, RNA molecules (e.g., self-replicating RNA molecules or nucleoside modified RNA molecules), or VRPs to an individual, typically a mammal, including a human. In some embodiments the immune response induced is a protective immune response, i.e., the response reduces the risk or severity of or clinical consequences of a CMV infection. Stimulating a protective immune response is particularly desirable in some populations particularly at risk from CMV infection and disease. For example, at-risk populations include solid organ transplant (SOT) patients, bone marrow transplant patients, and hematopoietic stem cell transplant (HSCT) patients. VRPs can be administered to a transplant donor pre-transplant, or a transplant recipient pre- and/or post-transplant. Because vertical transmission from mother to child is a common source of infecting infants, administering VRPs to a woman who is pregnant or can become pregnant is particularly useful.

Administration of the compositions provided by the present disclosure, such as pharmaceutical compositions, can be carried out using standard routes of administration. Any suitable route of administration can be used. For example, a composition can be administered intramuscularly, intraperitoneally, subcutaneously, or transdermally. Some embodiments will be administered through an intra-mucosal route such as intra-orally, intra-nasally, intra-vaginally, and intra-rectally. Compositions can be administered according to any suitable schedule.

Also provided herein is a method of inhibiting cytomegalovirus entry into a cell, comprising contacting the cell with the immunogenic composition described herein.

In one aspect, the invention relates to compositions that include a polypeptide described above. In another aspect, the invention relates to compositions that include a nucleic acid molecule or vector encoding such polypeptide. In a further aspect, the invention relates to compositions that include a polypeptide described above and a nucleic acid molecule or vector encoding such polypeptide.

In some embodiments, the composition is an immunogenic composition capable of eliciting an immune response against CMV in a subject. In some particular embodiments, the immunogenic composition is a pharmaceutical composition, which includes a polypeptide provided by the present disclosure and a pharmaceutically acceptable carrier. In still other embodiments, the pharmaceutical composition is a vaccine.

In some embodiments, a composition, such as an immunogenic composition or a vaccine, includes two or more different polypeptides described above. The two or more different polypeptides may include the same introduced amino acid mutations but may be derived from gB from different HCMV strains or subtypes. In another embodiment, the two or more different polypeptides may include amino acid mutations, as compared to a native HCMV gB, that differ from one another.

In preferred embodiments, the polypeptide is soluble in aqueous solution. In some embodiments, the polypeptide is soluble in a solution that lacks detergent.

Antibodies and Diagnostic Uses

The polypeptides described above may be used to produce antibodies, both polyclonal and monoclonal. If polyclonal antibodies are desired, a selected mammal (e.g., mouse, rabbit, goat, guinea pig, horse, etc.) is immunized with an immunogenic polypeptide bearing a CMV epitope(s). Serum from the immunized animal is collected and treated according to known procedures. If serum containing polyclonal antibodies to a CMV epitope contains antibodies to other antigens, the polyclonal antibodies can be purified by immunoaffinity chromatography. Techniques for producing and processing polyclonal antisera are known in the art.

Monoclonal antibodies directed against CMV epitopes can also be readily produced by one skilled in the art. The general methodology for making monoclonal antibodies by hybridomas is known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against CMV epitopes can be screened for various properties; i.e., for isotype, epitope affinity, etc.

Antibodies, both monoclonal and polyclonal, which are directed against CMV epitopes are particularly useful in diagnosis, and those which are neutralizing are useful in passive immunotherapy. Monoclonal antibodies, in particular, may be used to raise anti-idiotype antibodies.

Both the polypeptides which react immunologically with serum containing CMV antibodies, and the antibodies raised against these polypeptides, may be useful in immunoassays to detect the presence of CMV antibodies, or the presence of the virus, in biological samples, including for example, blood or serum samples. Design of the immunoassays is subject to a great deal of variation, and a variety of these are known in the art. For example, the immunoassay may utilize the polypeptide having the sequence set forth in any one of SEQ ID NOs: 2-106.

Alternatively, the immunoassay may use a combination of viral antigens derived from the polypeptides described herein. It may use, for example, a monoclonal antibody directed towards at least one polypeptide described herein, a combination of monoclonal antibodies directed towards the polypeptides described herein, monoclonal antibodies directed towards different viral antigens, polyclonal antibodies directed towards the polypeptides described herein, or polyclonal antibodies directed towards different viral antigens. Protocols may be based, for example, upon competition, or direct reaction, or may be sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the polypeptides of the invention containing CMV epitopes or antibodies directed against epitopes in suitable containers, along with the remaining reagents and materials required for the conduct of the assay, as well as a suitable set of assay instructions.

The polynucleotide probes can also be packaged into diagnostic kits. Diagnostic kits include the probe DNA, which may be labeled; alternatively, the probe DNA may be unlabeled and the ingredients for labeling may be included in the kit. The kit may also contain other suitably packaged reagents and materials needed for the particular hybridization protocol, for example, standards, as well as instructions for conducting the test.

Some embodiments of the present disclosure provide a HCMV vaccine that includes at least one ribonucleic acid (RNA) polynucleotide having an open reading frame encoding at least one HCMV antigenic polypeptide or an immunogenic fragment thereof and at least one 5' terminal cap. In some embodiments, a 5' terminal cap is 7mG(5')ppp(5') NlmpNp.

Some embodiments of the present disclosure provide a HCMV vaccine that includes at least one ribonucleic acid (RNA) polynucleotide having an open reading frame encoding at least one HCMV antigenic polypeptide or an immunogenic fragment thereof, wherein the at least one ribonucleic acid (RNA) polynucleotide has at least one chemical modification. In some embodiments, the at least one ribonucleic acid (RNA) polynucleotide further comprises a second chemical modification. In some embodiments, the at least one ribonucleic acid (RNA) polynucleotide having at least one chemical modification has a 5' terminal cap. In some embodiments, the at least one chemical modification is selected from pseudouridine, N1-methylpseudouridine, N1-ethylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine.

In some embodiments, the chemical modification is selected from the group consisting of pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine.

Some embodiments of the present disclosure provide a HCMV vaccine that includes at least one ribonucleic acid (RNA) polynucleotide having an open reading frame encoding at least one HCMV antigenic polypeptide or an immunogenic fragment thereof, wherein at least 80% (e.g., 85%, 90%, 95%, 98%, 99%, 100%) of the uracil in the open reading frame have a chemical modification, optionally wherein the vaccine is formulated in a lipid nanoparticle. In some embodiments, 100% of the uracil in the open reading frame have a chemical modification. In some embodiments, a chemical modification is in the 5-position of the uracil. In some embodiments, a chemical modification is a N1-methyl pseudouridine.

Some embodiments of the present disclosure provide a HCMV vaccine that is formulated within a cationic lipid nanoparticle, also referred to herein as ionizable cationic lipid nanoparticles, ionizable lipid nanoparticles and lipid nanoparticles, which are used interchangeably. In some embodiments, the lipid nanoparticle comprises a cationic lipid, a PEG-modified lipid, a sterol and a non-cationic lipid. In some embodiments, the cationic lipid is an ionizable cationic lipid and the non-cationic lipid is a neutral lipid, and the sterol is a cholesterol. In some embodiments, the cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). In some embodiments, the lipid nanoparticle has a molar ratio of about 20-60% cationic lipid, about 5-25% non-cationic lipid, about 25-55% sterol, and about 0.5-15% PEG-modified lipid. In some embodiments, the nanoparticle has a polydiversity value of less than 0.4. In some embodiments, the nanoparticle has a net neutral charge at a neutral pH. In some embodiments, the nanoparticle has a mean diameter of 50-200 nm.

In some embodiments, 80% of the uracil in the open reading frame have a chemical modification. In some embodiments, 100% of the uracil in the open reading frame have a chemical modification. In some embodiments, the chemical modification is in the 5-position of the uracil. In some embodiments, the chemical modification is N1-methylpseudouridine, N1-ethylpseudouridine. In some embodiments, the vaccine is formulated within a lipid nanoparticle. In some embodiments, the lipid nanoparticle comprises a cationic lipid, a PEG-modified lipid, a sterol and a non-cationic lipid. In some embodiments, the cationic lipid is an ionizable cationic lipid and the non-cationic lipid is a neutral lipid, and the sterol is a cholesterol. In some embodiments, the cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

Some embodiments of the present disclosure provide methods of inducing an antigen specific immune response in a subject, comprising administering to the subject a HCMV RNA vaccine in an amount effective to produce an antigen specific immune response. In some embodiments, an antigen specific immune response comprises a T cell response or a B cell response. In some embodiments, an antigen specific immune response comprises a T cell response and a B cell response. In some embodiments, a method of producing an antigen specific immune response involves a single administration of the vaccine. In some embodiments, a method further includes administering to the subject a booster dose of the vaccine. In some embodiments, a vaccine is administered to the subject by intradermal or intramuscular injection.

Also provided herein are HCMV RNA vaccines for use in a method of inducing an antigen specific immune response in a subject, the method comprising administering the vaccine to the subject in an amount effective to produce an antigen specific immune response.

Further provided herein are uses of HCMV RNA vaccines in the manufacture of a medicament for use in a method of inducing an antigen specific immune response in a subject, the method comprising administering the vaccine to the subject in an amount effective to produce an antigen specific immune response.

Further provided herein are methods of preventing or treating HCMV infection comprising administering to a subject the vaccine of the present disclosure. The HCMV vaccine disclosed herein may be formulated in an effective amount to produce an antigen specific immune response in a subject.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants possess at least 50% identity to a native or reference sequence. In some embodiments, variants share at least 80%, or at least 90% identity with a native or reference sequence.

In some embodiments "variant mimics" are provided. As used herein, the term "variant mimic" is one which contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic, for example, phenylalanine may act as an inactivating substitution for tyrosine; or alanine may act as an inactivating substitution for serine. "Orthologs" refers to genes in different species that evolved from a common ancestral gene by speciation. Normally, orthologs retain the same function in the course of evolution. Identification of orthologs is critical for reliable prediction of gene function in newly sequenced genomes. "Analogs" is meant to include polypeptide variants which differ by one or more amino acid alterations, for example, substitutions, additions or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is used synonymously with the term "variant" but generally refers to a molecule that has been modified and/or changed in any way relative to a reference molecule or starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. "Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule.

In some embodiments, the mutant CMV gB polypeptide is a truncated polypeptide lacking one or more of the following domain sequences as compard to SEQ ID NO: 1: (1) Domain V (residues 124-344), (2) MPR domain (residues 705-750), (3) TM domain (residues 751-772), or (3) the CT domain (residues 773-907). As used herein the term "truncated" shall mean that a sequence is missing some or all of the residues comprising a domain as set forth herein.

As described herein, CMV gB polypeptide comprises the following domains and residues (SEQ ID NO:1): (i) Domain I (residues 134-344), (ii) Domain II (residues 121-133 and 345-436), (iii) Domain III (residues 97-111, 475-539 and 640-648), (iv) Domain IV (residues 88-96, 540-639 and 551-641), (v) Domain V (residues 649-707), (vi) membrane-proximal region (MPR) (residues 705-750), (vii) transmembrane domain (TM) (residues 751-772), and (viii) cytoplasmic domain (CT) (residues 773-907). In another aspect, the ectodomain of CMV gB comprises residues 1-707 or 23-707 (without signal sequence) of SEQ ID NO: 1. In another aspect, the ectodomain is lacking Domain V and comprises residues 1-646 or 23-646 (without signal sequence).

EXAMPLES

The invention is further described by the following illustrative examples. The examples do not limit the invention in any way. They merely serve to clarify the invention.

Example 1: Isolation and Purification of Crosslinked and Native HCMV gB (Towne Strain) with Fusion Inhibitor During the sample preparation the HCMV fusion inhibitor (compound 28 described in Bloom et al., *Bioorganic & Medicinal Chemistry Letters* 14 (2004) 3401-3406; see also FIG. 5D) was added to each step during the virus concentration, processing, extraction and purification to inhibit conversion of gB to the postfusion form.

Following crosslinking of the proteins on the virion surface with bis(sulfosuccinimidyl) glutarate ($BS^2G$) and extraction of gB from the virion with detergent, the SM5-1 His/Strep-tagged Fab (Potzsch et al., *PLoS pathogens* 7(8): e1002172, 2011) was added to assist in purification and identification of gB by electron cryomicroscopy. The Fab-gB complexes were purified by an affinity column.

These extracted and purified proteins were then analyzed by electron cryomicroscopy for the presence of prefusion gB and used to solve the structure of a prefusion form.

Example 2: Electron Microscopy

Graphene oxide film-supported electron microscopy grids were prepared. The gB sample solutions were vitrified using a Vitrobot (ThermoFisher). The frozen grids were transferred to a FEI Titan Krios transmission electron microscope that operates at 300 kV. Target positions were set up in the SerialEM program, and high magnification (18000×) images were automatically collected with the program using a K2 direct detector camera (Gatan) using super resolution movie mode. The unbinned pixel size was 0.638 Å and the beam intensity was ~8 e/unbin pixel/s. The total electron dose on the sample for each movie was ~40 e/Å$^2$. A total of 7,771 movies, each with 28 frames, was collected in three sessions.

Image Processing

Drift correction was done using the MotionCor2 program (Zheng S et al. *Nature Methods* 14, 331-332 (2017)), and the final micrographs were binned 2× and averaged from all frames. Contrast transfer function parameters were calculated with Gctf (Kai Zhang, *Journal of Structural Biology* 193(1), 1-12 (2016)). For particle picking, the published structure of HCMV gB in postfusion conformation (PDB: 5CXF) was used to generate a 30 Å density map using pdb2mrc (EMAN) (Ludtke, S. et al. *Journal of Structural Biology* 128(1), 82-97 (1999)). Projection images from this density maps was generated with project3d (EMAN) (FIG. 1) and used as a template for the automatic particle picking using Gautomatch program (Urnavicius L, et al. *Science* 347(6229):1441-1446 (2015)). Relion v2.1-beta (Scheres, S. H. *Journal of Structural Biology* 180(3): 519-530 (2012)) was used to extract the resulting ~1.9 million particles and to carry out all subsequent image processing steps, including 2D classification, 3D classification, auto-refinement and post-processing. The 2D classes were put into three groups based on the image features: the first group consisted of the 2D classes that showed features that resemble the crystallographically determined postfusion gB structure (>50%); the second group contained 2D classes with well resolved protein features that do not resemble the structural features from postfusion gB (<10%); the third group contained 2D classes that did not contain clearly defined protein (~40%) (FIG. 1). The first and second groups were further processed with 3D classification, auto refinement and post processing procedures with Relion. Following this processing, a ~3.5 Å resolution electron density map showing the postfusion conformation structure was reconstructed from the first group; a ~3.6 Å resolution electron density map showing a prefusion conformation structure was reconstructed from the second group. Based on these density maps and the known HCMV gB amino acid sequence (Towne strain P13201, SEQ ID NO:1), atomic models were built with the Coot program (Emsley P. et al *Acta Crystallogr D Biol Crystallogr* 66(Pt 4): 486-501 (2010)) for the prefusion and postfusion conformation structures. The postfusion gB crystal structure (PDB accession code 5CXF) and a crystal structure of a complex between the SM5-1 fab and gB domain II (PDB accession code 4OT1) were used as initial models for both structures. For the postfusion structure model, small adjustment was enough to obtain a good fit to the electron density. For the prefusion conformation model, domains I, II, III and IV from the reference PDB model could be docked as rigid bodies into the electron density map as a starting point. Then, adjustments of individual residues were made for optimal fitting. The model for domains V, MPR and TM were built de novo. The models were iteratively refined with the Phenix.real_space_refine tool (Afonine P V et al. *Acta Crystallogr D Struct Biol* 74(Pt 6): 531-544 (2018)) followed by local manual adjusting for several rounds.

Results

Sample Screening by cryoEM

The prefusion conformation of gB is unstable, with a propensity to rearrange to the postfusion state, including during sample handling. Therefore, the samples studied contained a mixture of gB conformers, complicating structure determination. In addition, there was no pre-existing reliable information on the arrangement of domains or the unique structural features of prefusion gB. We used direct visualization by electron microscopy and image processing to screen different sample preparation conditions. Image sorting by 2D and 3D classification permits multiple structures to be determined from heterogeneous samples. However, it requires a large data set so that enough particles for each structure can be combined to produce a class average with good signal. This was especially the case for the gB samples because prefusion gB was a small population in the mixtures. Therefore, we collected ~1,000 movies for each condition, and decided whether to pursue image processing with more data from the same sample or switch to another at the 2D classification stage. The structure of antibody Fab-bound postfusion conformation gB was readily obtained from many datasets. The projection images from these Fab-bound postfusion conformation structures were used as a reference to avoid selecting images for the prefusion image reconstruction. We selected any good class average with protein features that did not resemble any of the postfusion gB projection images for further image processing. We screened dozens of conditions for sample preparation with this strategy and eventually found a sample that produced some alternative 2D classes as a minor species in the particle populations (FIG. 1B, circled). Then a total of 7,771 movies were collected from that sample and used for determination of a prefusion gB structure.

Figure 1A:
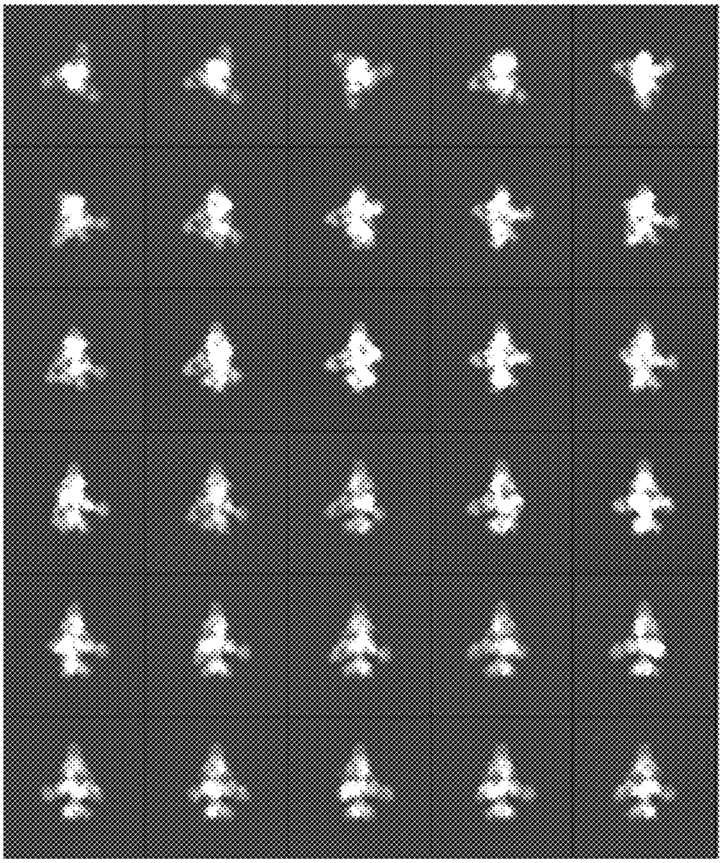
FIG. 1A-1B describe two-dimensional (2D) class averages of gB conformers.
Figure 1B:
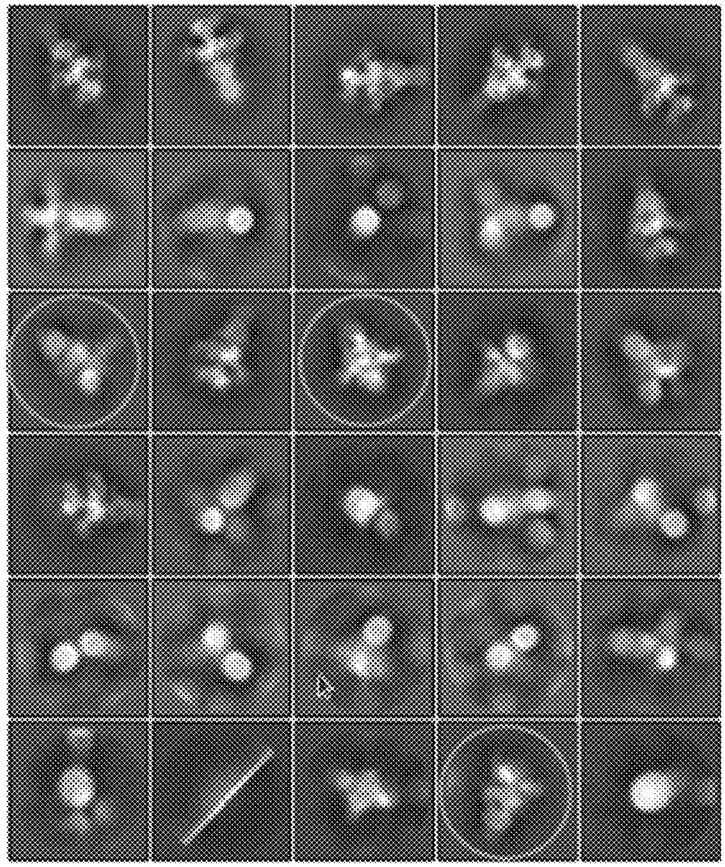

Projection images of the antibody Fab-bound postfusion gB structure are shown in FIG. 1A. The 2D class averages from the dataset collected are shown in FIG. 1B. Some classes that do not resemble any of the postfusion gB reference 2D projections are circled.

Obtaining a Prefusion Conformation Structure

Approximately 1.9 million raw particle images were automatically selected from the data set. After 2D classification, the images were grouped into a postfusion class (55% of the particle population) and a prefusion class (10% of the particle population). The two groups were further processed in 3D with C3 symmetry applied to yield a density map of SM5-1 Fab-bound postfusion gB at 3.5 Å resolution and a density map of SM5-1 Fab-bound prefusion gB at 3.6 Å resolution.

The X-ray crystallography-based models of the SM5-1 Fab and of the ectodomain of postfusion gB were fit to the postfusion density map with rigid body docking. Except for the constant domain of the Fab (which is likely too flexible to produce strong electron density), the density map of the postfusion gB-Fab complex and the model agreed well with each other (FIG. 3A). The membrane proximal region, transmembrane region and cytoplasmic domain were not resolved in our final postfusion gB density map, suggesting that these regions of postfusion gB are flexible either intrinsically or through detergent solubilization in the sample preparations (FIG. 2, lower line). The interaction of the Fab and DII of postfusion gB in the electron cryomicroscopy-based model agrees well with the previously determined crystal structure of the complex (PDB accession code 4OT1).

To build a prefusion gB model, guided by the known Fab binding position, domains I, II, III and part of domain IV from the postfusion gB crystal structure were docked into the density map of the prefusion gB-Fab complex individually and individual residues were manually adjusted as necessary for optimal fit of the electron density. The rest of the prefusion gB structure was built de novo. The amino acids of gB that were modeled in the prefusion structure are indicated in FIG. 2, the top line. The model of the prefusion gB-Fab complex fits most parts of the prefusion density map, and the presence of Fab density confirms the identity of gB in the novel structure (FIG. 3B).

The coordinates and structure factors for the model of the prefusion gB associated with the present Example are provided in Table 1A.

the Structure of gB in a Prefusion Conformation and Comparison to Postfusion gB

Figure 3B:
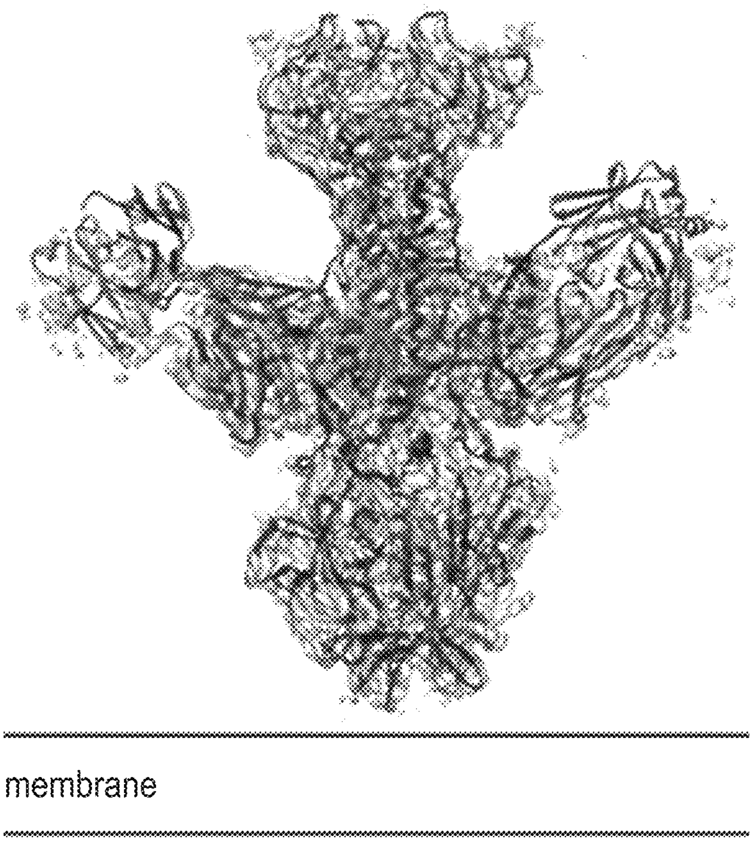
Figure 4A:
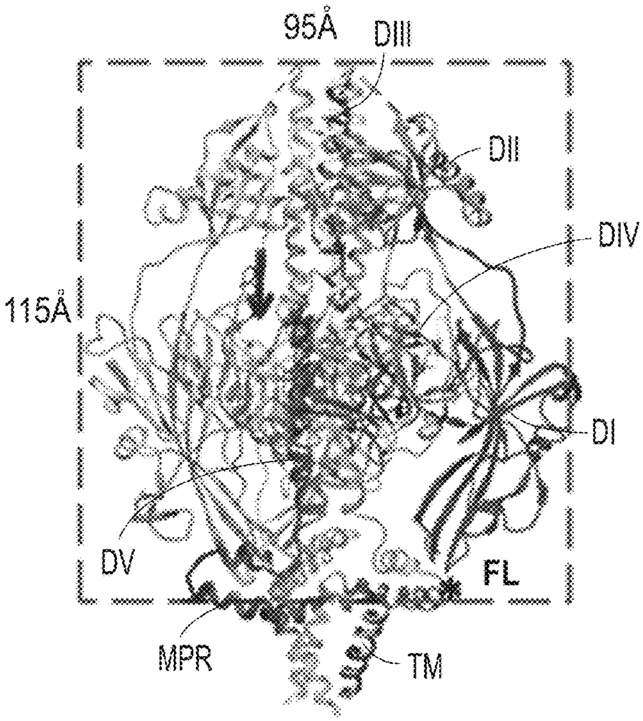
FIG. 4A-4B depict a comparison of the structures of gB in two conformations. The gB stabilized prefusion structure (FIG. 4A) and postfusion structure (FIG. 4B) are shown with one protomer to indicate the domains: I, II, III, IV, V, MPR and TM. The vertical black dashed line extending from the top of the prefusion structure represents residues missing from the model due to a less defined density map. The overall dimensions of the buildable ectodomain parts of the structure are indicated by the dashed line rectangles. The arrows indicate the direction pointed by the C-termini of the central 3-helix bundle in domain III of each conformation. The 115 Å dimension on the prefusion structure (FIG. 4A) indicates the height of the modeled part of the ectodomain.
Figure 4B:
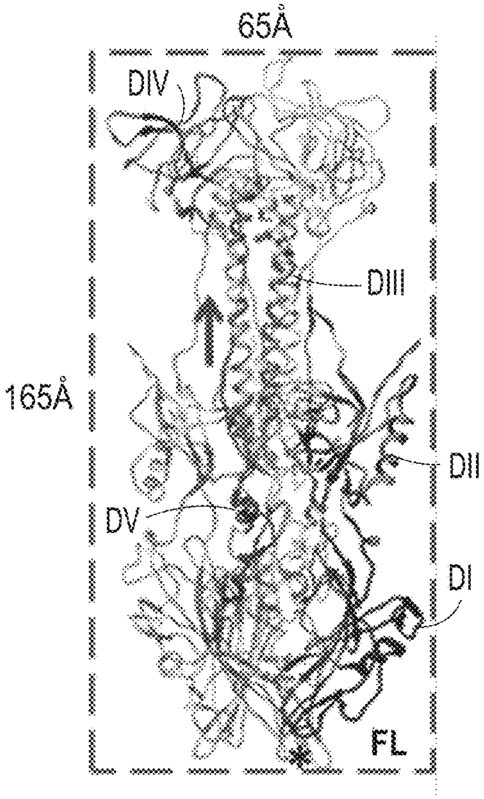

The electron density for the complex of prefusion gB and the SM5-1 Fab allowed the building of a prefusion gB model that includes the gB ectodomain, membrane proximal region (MPR—a helical region that is oriented parallel to the viral membrane), and single span transmembrane helix (TM) (FIG. 3B and FIG. 4B). The MPR and TM regions were not resolved in the structural data for postfusion gB or included in postfusion gB models.

The overall dimensions of prefusion and postfusion gB are different (FIG. 4A vs. FIG. 4B). The postfusion gB trimer ectodomain has a rod shape, with an approximate height of 165 Å (the distance between planes formed by proline 570 of each protomer at the membrane distal end and tryptophan 240 of the each protomer at the membrane proximal end; FIG. 4A). It has a width of approximately 65 Å (the distance between alanine 315 on adjacent protomers). The structures described here were derived from gB of HCMV strain Towne. Although there is some natural variations of gB amino acid sequence, the overall postfusion structure of Towne gB is almost identical to the postfusion structure of gB from the strain AD169 (PDB accession code 5CXF). Thus, the description of the postfusion gB structure applies to both strains with measurements from equivalent amino acids from sequence alignments.

The prefusion gB trimer has a more squat shape than the postfusion gB trimer (FIG. 4A vs. FIG. 4B). The distance between the plane formed by W240 of each protomer and the most membrane distal modeled residue in the prefusion structure, Q483, is roughly 115 Å. The prefusion model is 95 Å in width (measured by the distance between any two A315 from different protomers).

Figure 6A:
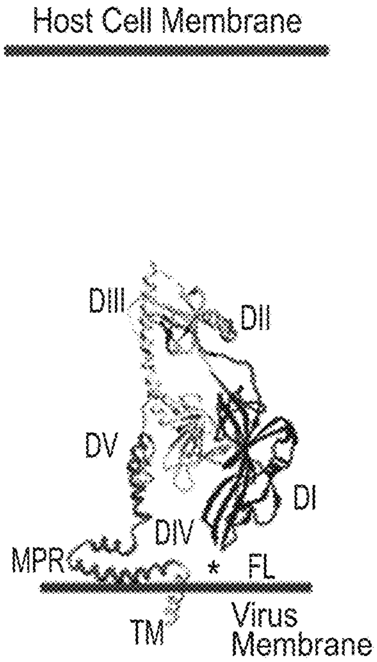
FIG. 6A-6C depict a model of structural rearrangements of gB during membrane fusion. FL (and asterisks)—fusion loop. DI—domain 1. DII—domain 2. DV—domain 5. TM—transmembrane region. The light blue line depicts the viral membrane. The lines depict membrane.

The individual subunit structures of domains I, II, III and IV are similar in the prefusion and postfusion conformations. However, the overall arrangement of these domains is very different in the two conformations (FIGS. 4A-4B and FIGS. 6A-6C). In the prefusion conformation, the fusion loops at the tip of DI and the C-termini of the central helix bundle in domain III all point in the same direction, toward the virion envelope, as identified by the position of the TM region (FIG. 4AI and FIG. 6A). In contrast, in the postfusion conformation, the fusion loops and the C-termini of the central helix bundle point in opposite directions (FIG. 4B and FIG. 6C).

In the prefusion structure, the hydrophobic residues in the fusion loops (residues Y155, I156, H157 and W240, L241) are in close proximity to the MPR and are likely surrounded by detergents (FIG. 4AI and FIG. 6A).

In the transition from prefusion to post fusion, domain II shifts from a position mid-way up the domain III central coiled-coil to a position at the membrane proximate end of the coiled-coil and near end of domain I opposite the fusion loops (FIG. 4A and FIG. 4B).

The structure of DIII (FIGS. 4A-4B and FIGS. 6A-6C) is very similar in the prefusion and postfusion conformations. The central helix in both conformations spans from L479 to P525, indicating a minimal rearrangement during the prefusion to postfusion transition. However, the other domains change their positions relative to the central helix of domain III, so that, as noted above, the direction of the DIII helix bundle (from N-terminal to C-terminal) points away from the fusion loops towards the distal end of the trimer in the postfusion conformation and toward the viral membrane, in the same direction as the fusion loops in the prefusion conformation.

In the prefusion structure, domain IV (FIG. 4A and FIG. 6A) is buried at the interface between domain I on the exterior of the trimer and domains III and V at the center of the trimer. In contrast, in the postfusion structure, domain IV forms a highly exposed "crown" at the membrane-distal tip of the trimer.

Domain V has different structures in prefusion gB (FIG. 4A and FIG. 6A) and postfusion gB (FIG. 4B and FIG. 6C). In prefusion gB, the N-terminal half of the domain (about residues 642-660) is sandwiched between domain I and domain IV of an adjacent protomer and is sequestered from solvent. The region between residue 683-704 of domain V forms a trimeric helix bundle with its counterpart in other protomers. This helix bundle is cuddled mostly inside of the pocket of the "crown" formed by domain IV. There is an additional short helix (approximately residues 710-719) linking the helix bundle from domain V to the MPR region. In contrast, in the postfusion conformation (FIG. 4B and FIG. 6C), domain V is solvent exposed and extends along the outside of domain III helix bundle and the groove formed by the interface between domain I from adjacent protomers.

Comparison of the prefusion and postfusion gB structures suggests a progression of conformational changes that is familiar from other well-studied fusion proteins (Harrison, S. C. *Virology* 0:498-507 (2015)). The comparison provides confidence that the structure described in this invention is, in fact, in a prefusion conformation. In the prefusion state (FIG. 6A), the fusion loops of domain I are buried by interaction with the MPR and potentially with the viral membrane. In the prefusion structure of the distant gB homolog, the vesicular stomatitis virus G glycoprotein, the fusion loops also point toward the viral membrane (also the anticipated position of an MPR region, which is not seen in that structure)(Roche et al. *Science* 315:843-8 (2007)).

Figure 6B:
Figure 6C:
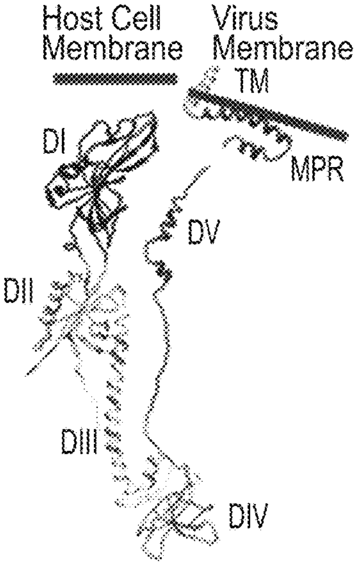
Figures 7A, 7B:
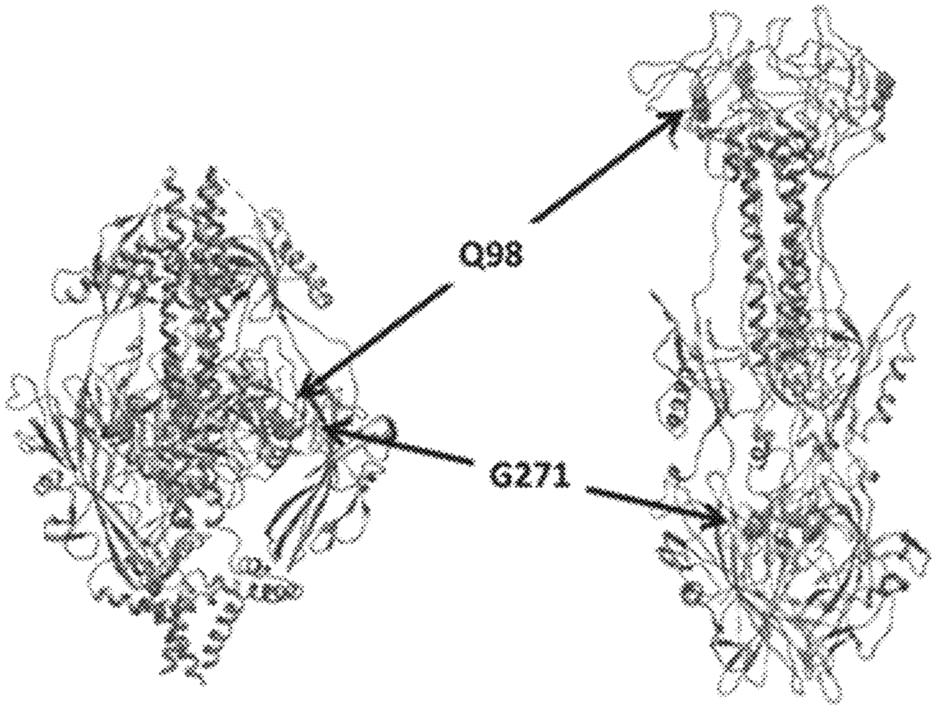
FIG. 7A-7B depict an exemplary disulfide bond mutation to stabilize gB in a prefusion conformation. The locations of the residues participating in the disulfide bond are depicted as gray spheres in a prefusion conformation (FIG. 7A) and postfusion conformation (FIG. 7B).

Based on analogy to other fusion proteins, it is likely that rearrangement proceeds with lengthening of the central helix as part of a transition to a proposed extended intermediate between the prefusion and postfusion states (FIG. 6B). In the proposed extended intermediate state, the TM region would still be anchored in the viral membrane, and the fusion loops, now extended far from the viral membrane at the tips of a rotated and translocated domain I, would interact with a cellular membrane. The transition from the proposed extended intermediate to the postfusion conformation would involve a fold-back so that the transmembrane region and the fusion loops are again in proximity to each other at the same end of the molecule, this time both interacting with the fused viral and cellular membrane (FIG. 6C).

We speculate that, in prefusion gB, there may be dynamic changes in the length of the central helix, with the prefusion structure we have determined representing a "snapshot" of a "breathing" molecule, locked into the conformation we see in the electron density by the fusion inhibitor and by the cross-linking agent used to prepare the sample studied by electron cryomicroscopy.

Stabilizing Factors for the Observed Prefusion Conformation

Figure 5A:
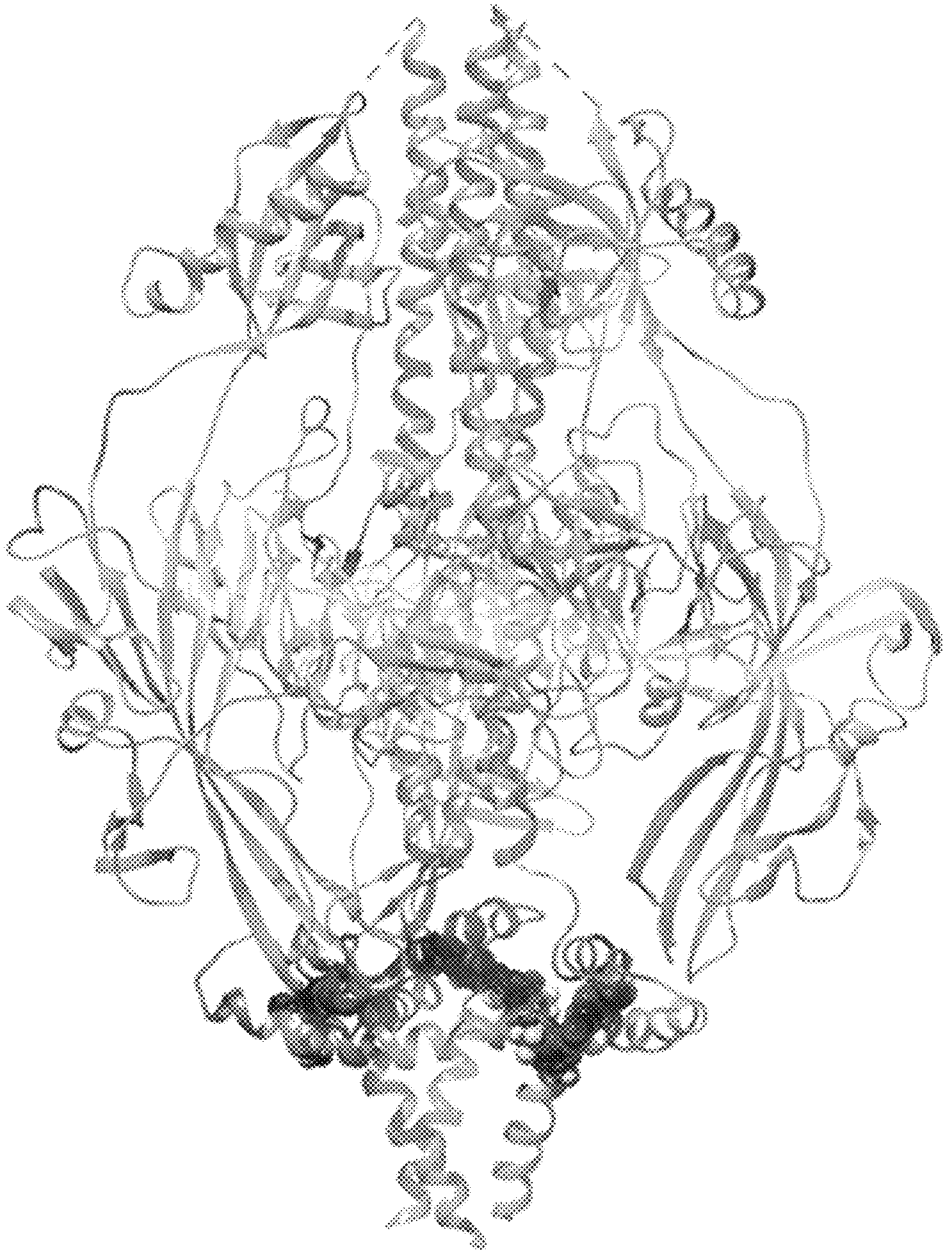
FIG. 5A-5D.
Figure 5B:
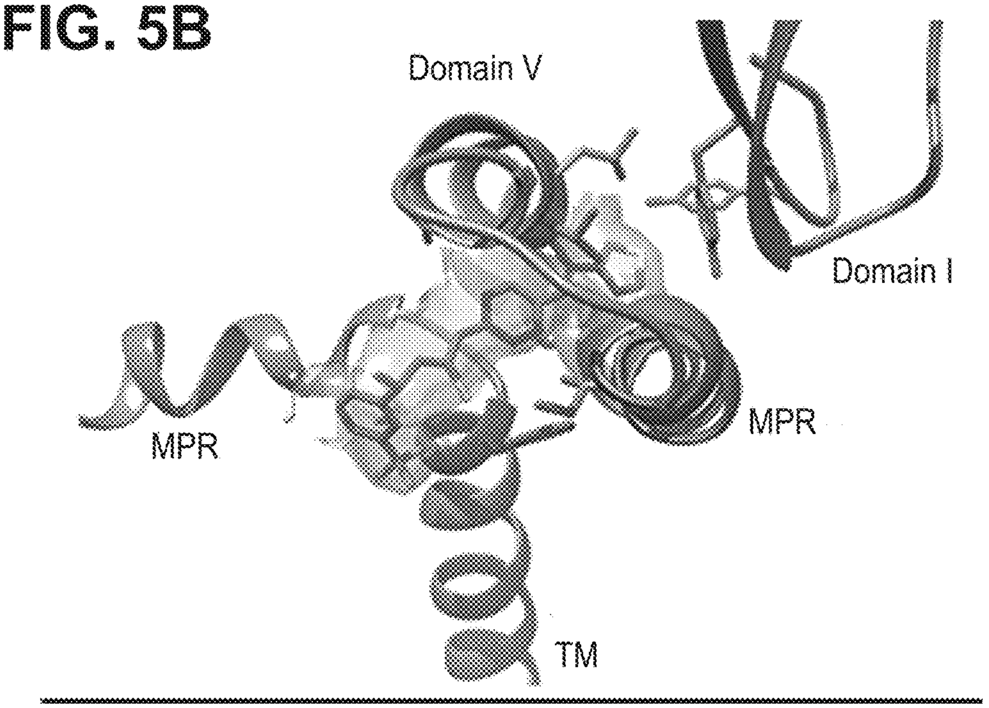
Figure 5C:
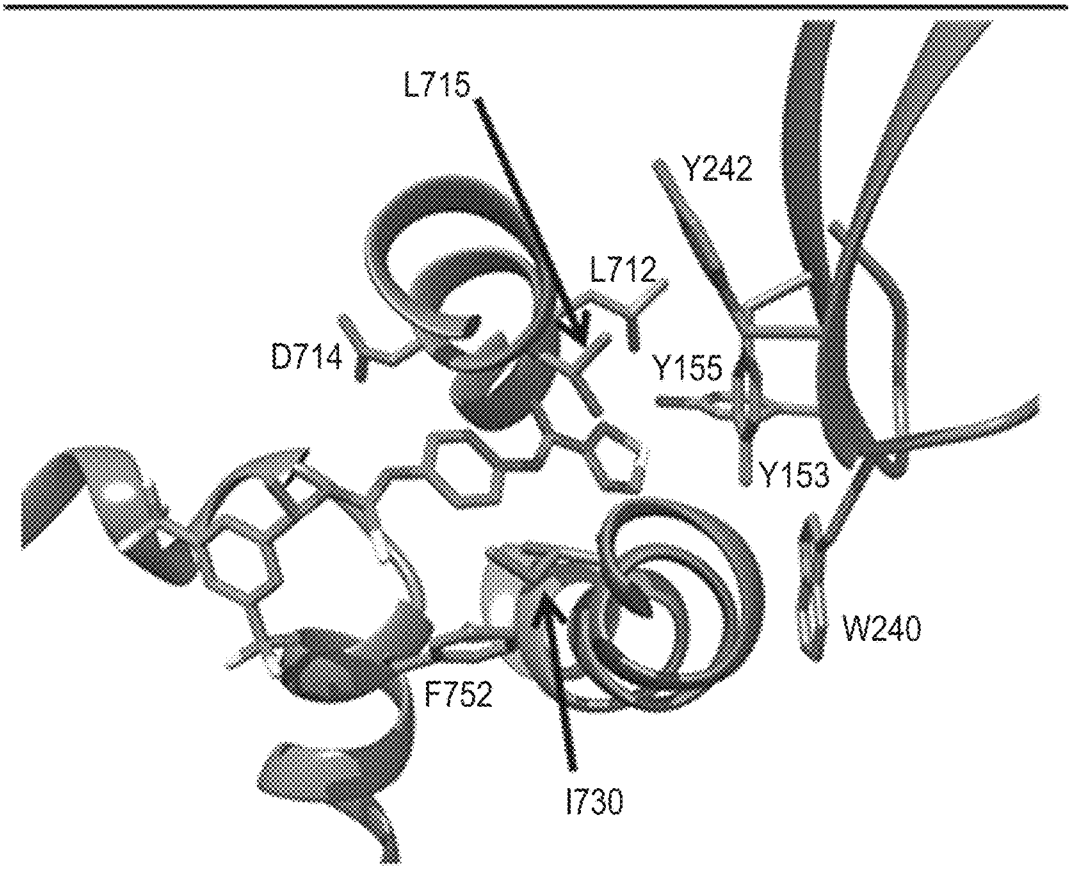

After modeling the gB amino acids into the electron density map, a region of density that was not filled by amino acid residues remained between the MPR, domain V, and the tip of domain I that contains the fusion loops (FIG. 5A). The size and shape of the unfilled density fits the chemical structure of the HCMV fusion inhibitor, N-{4-[({(1S)-1-[3, 5-bis(trifluoromethyl)phenyl]ethyl}carbamothioyl)amino] phenyl}-1,3-thiazole-4-carboxamide (FIG. 5D), which had been present throughout the production of the sample studied by electron cryomicroscopy (FIG. 5B). The compound adopted a pose with a kink between the trifluoromethyl phenyl moiety and the rest of the compound. The thiazole forms contacts with hydrophobic residues of L712, A738 and Y153, Y155 from an adjacent protomer. The phenyl is surrounded in a hydrophobic environment formed by residues of L715, the aliphatic hydrocarbon of D714 from domain V, G734 and I 730 from MPR, and F752 from the TM domain of an adjacent protomer. The trifluoromethyl phenyl resides in a hydrophobic environment near the hinge between MPR and TM helixes from another protomer. It may act as a hook to prevent the outward movement of MPR and TM domains. In addition to the interaction coordinated by the inhibitor compound, the W240, Y242 from other fusion loop are forming van der waals interactions with the hydrophobic patch from the MPR region and L715 in domain V respectively. (FIG. 5C). These specific interactions around the fusion inhibitor would be expected to hold domain I, domain V, and the MPR together and restrict movements among domain I, domain V, and the MPR during the fusion process (FIGS. 6A-6C).

The effects of cross linking on the stability of the prefusion conformation were also tested. During the sample preparation steps, $BS^2G$ cross linking reagents either were or were not added. In the absence of the cross linker, the ratio of particles in prefusion versus postfusion conformations was 1:100, while the ratio was 1:4 in the sample that had been cross linked by the $BS^2G$ reagent. The cross linker was not identified in the electron density.

The prefusion structure of CMV gB and color versions of the prefusion and postfusion structures set forth in the Figures described herein may also be found in Liu et al. *Science Advances* 7(10): eabf3178 (2021), which is hereby incorporated by reference herein in its entirety.

Example 3: Expression and Purification of gB1666

For the production of gB1666, the PSB1666 construct was transiently transfected into Expi293F cells. The cell pellets were harvested 96 hours after transfection. The PSB1666 protein was purified in 25 mM HEPES pH 7.5, 250 mM NaCl, 0.02% DDM, 0.002% CHS, 3 μg/ml WAY-174865 (inhibitor, see FIG. 5D) through a series or processes of solubilization, affinity column and size exclusion chromatography. The protein was analyzed on SDS-PAGE and by EM with negative staining to ensure at least 50% of the proteins displaying prefusion conformation. The PSB1666 protein is expressed efficiently in transfection of Expi293F cells and 1L expression would generate ~0.1 mg of purified PSB1666 in high quality.

The polypeptide gB1666 (PSB1666) (SEQ ID NO: 57) includes a mutation in Domains I and IV. The polypeptide includes the following mutations, D217C and Y589C, relative to the corresponding wild-type gB (Towne) set forth in SEQ ID NO: 1.

Example 4: DNA-Expressed gB1666 is Immunogenic in Balb/c Mice

Figure 5D:
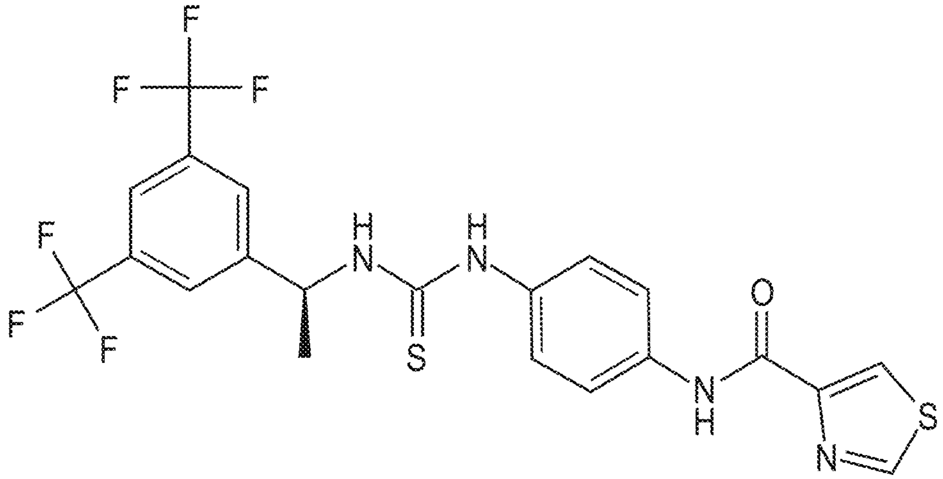

One of the proposed stabilized full length prefusion gB constructs, gB1666 (SEQ ID NO: 57), has been shown by EM to have an increased proportion of molecules in the prefusion conformation relative to wild type gB of the Towne strain after purification from transfected mammalian cells in the presence of a fusion inhibitor (WAY-174865; see FIG. 5D). To assess whether this molecule can elicit immune responses in vivo, the DNA sequence corresponding to gB1666 and wild type gB were cloned into an in-house mammalian expression vector. Ten Balb/c mice were electroporated with 100 ug of DNA encoding gB1666 twice at a three-week interval (DO and D21). An additional 10 mice were electroporated by the same protocol with DNA encoding wild type gB, and a third group was electroporated with a placebo, consisting of phosphate-buffered saline. Serum samples were collected at Day 28. ELISA was performed against recombinant gB protein produced from mammalian cells, based on the wild type sequence of Towne strain but with the transmembrane domain removed (Sino Biologicals) to determine the anti-gB IgG responses according to a standard protocol. Ten out of ten animals from the wild type gB DNA immunized mice and nine of ten gB1666 DNA immunized mice generated detectable anti-gB IgG titers (FIG. 11, showing mean±SD, LLOQ=25). The study demonstrates that gB1666 is immunogenic in Balb/c mice.

Example 5: Immunogenicity Study of Stabilized Prefusion gB1666 Protein

Immunogenicity study of gB1666 in mice. To evaluate the antibody response in mice, the following immunization scheme will be followed. At week 8, mice will be exsanguinated and the neutralization titers from the immunized animal serum will be determined and compared with those immunized with gB705 (postfuion) and/or gB wild type proteins.

TABLE 5

Mouse immunogenicity study design with gB1666 protein

| Group | No. of Mice | Immunogen | Adju-vant | Route | Dosing Schedule |
|---|---|---|---|---|---|
| 1 | 10 | gB705 (postfusion) (1.25 mcg/0.2 ml) | — | 0.2 ml/SC | Weeks 0, 3, 6 |
| 2 | 10 | gB705 (postfusion) (0.25 mcg/0.2 ml) | — | 0.2 ml/SC | Weeks 0, 3, 6 |
| 3 | 10 | gB1666 (in inhibitor-containing buffer) (1.25 mcg/0.2 ml) | — | 0.2 ml/SC | Weeks 0, 3, 6 |
| 4 | 10 | gB1666 (in inhibitor-containing buffer) (0.25 mcg/0.2 ml) | — | 0.2 ml/SC | Weeks 0, 3, 6 |
| 5 | 10 | gB wt (in inhibitor-containing buffer) (1.25 mcg/0.2 ml) | — | 0.2 ml/SC | Weeks 0, 3, 6 |
| 6 | 10 | gB wt (in inhibitor-containing buffer) (0.25 mcg/0.2 ml) | — | 0.2 ml/SC | Weeks 0, 3, 6 |
| 7 | 5 | Buffer (+Inhibitor) | — | 0.2 ml/SC | Weeks 0, 3, 6 |
| 8 | 5 | Buffer only | — | 0.2 ml/SC | Weeks 0, 3, 6 |

Example 6

In Example 2, we disclosed the electron cryomicroscopy (cryoEM) structure of prefusion human cytomegalovirus (HCMV) strain Towne glycoprotein B (gB) in complex with an antibody fragment. The gB used for structure determination was obtained by adding a small molecule fusion inhibitor, WAY-174865, to a fermentation of authentic HCMV in mammalian cell culture and maintaining the presence of the inhibitor throughout production and analysis of gB; purifying the virus; treating the virus with a chemical cross linker, bis(sulfosuccinimidyl) glutarate ($BS^2G$; 7.7 Å spacer arm); extracting gB from the virus with detergent; binding gB on the virion with an affinity tagged antibody fragment; and purifying the gB by affinity and sizing columns. We also disclosed the use of the prefusion gB cryoEM structure to engineer mutations that stabilize gB in the prefusion state. Specifically, we disclosed the recombinant gB protein gB1666, in which two residues are mutated to cysteine (D217C, Y589C). The resulting formation of an engineered disulfide bond between C217 and C589 increases the conformational stability of the recombinant gB in the prefusion state. gB1666 maintained prefusion structural features when it was expressed in Expi293F cells and purified in the presence of a fusion inhibitor, compound WAY-174865. In the absence of the inhibitor, gB1666 tends to undergo a conformational change and lose its prefusion structural state. Loss of prefusion conformational stability in the absence of inhibitor is not a desirable characteristic for use of the recombinant glycoprotein as an antigen for immunization. Even if gB1666 were formulated with the inhibitor, there is a risk that, upon injection into a person or animal, the dilution of the inhibitor in vivo would lead to its dissociation from gB1666 and the loss of prefusion conformation of gB1666. Thus, it is desired that HCMV gB be stabilized sufficiently in the prefusion conformation to remain in the prefusion state in the absence of WAY-174865. It is also preferable that a prefusion gB immunogen includes a soluble ectodomain to improve manufacturability, improve solubility, improve homogeneity, and reduce or eliminate the need for formulation with a detergent or other excipient to prevent aggregation or precipitation mediated by the gB transmembrane region.

We now report the invention, through a structure-based engineering approach, of new mutations in HCMV gB that confer these improved characteristics for use of prefusion gB as an immunogen. First, we determined the structure by cryoEM of gB1666, which was solubilized by anchoring in nanodiscs and stabilized in the prefusion conformation by the presence of WAY-174865 (FIG. 12). Most of the new structure of the recombinant, D217C and Y589C mutant gB is similar to the structure of the virion-derived, chemically cross-linked and antibody fragment bound HCMV Towne prefusion gB that we determined previously, but there are subtle differences between the two structures in certain local regions. The difference in the structures could reflect several differences in the preparations: first, the presence of the engineered disulfide bond in gB1666, which should restrict the breathing motion of the glycoprotein; second, the anchoring of gB1666 in a nanodisc, which provides a more natural local lipid environment for the transmembrane domain than the detergents used to extract and maintain gB in solution for the previous structure determination; third, the absence of chemical cross-linking of gB1666; fourth, the higher resolution of the new structure at 3.3 Å, compared to the 3.6 Å resolution of the previous structure, allowing more accurate modeling of amino acid side chains.

Based on the new structural information, we designed additional stabilizing mutations on the background of the full length gB construct pSB1666 (Table 6 and Table 7). We hypothesized that adding these additional mutations on the pSB1666 background would further stabilize the gB in a prefusion state (FIG. 13). For example, cysteine mutations at residues M371 and W506 may introduce a disulfide bond between domains II and III; cysteine mutations at the pairs of (F541, E681) and (N524, M684) may introduce disulfide bonds between domains IV and V; mutations of residues E686, D679 to hydrophobic residues could remove a locally destabilizing same charge repulsion patch and increase protein stability. Recombinant glycoproteins with a selection of the new, added mutations were expressed and purified in the absence of fusion inhibitor and without chemical cross-linking. The electrophoretic mobility of the expressed glycoproteins by SDS-PAGE showed the expected apparent molecular weight and heterogeneity consistent with glycosylation (FIG. 14). The samples were stored at 4° C., and aliquots were taken for negatively stained electron microscopy analysis on day 1 and day 7. In the 2D class averaged images, triangular shape features that resemble "top views" of the prefusion conformation of the gB were apparent. The ratio of particles in the population belonging to prefusion and postfusion classes were 5:1 on day 1 and 3:1 at day 7 (FIG. 15).

Based on the new structural information, we designed several soluble, detergent-free gB ectodomains (Table 8) with prefusion-stabilizing mutations as illustrated in FIGS. 16A-16D. The purified ectodomain of HCMV gB, residues 1-707, formed rosette-like aggregates, in which gB proteins associated through their exposed fusion loops. To eliminate aggregation and increase protein secretion to the condition media, we replaced four exposed hydrophobic residues within the fusion loops with the corresponding more hydrophilic amino acids from herpes simplex virus-1 (HSV-1) gB, e.g. YIH (155-157)→GHR, W240→A. We also mutated the exposed Cys246 to Ser (C246→S) to prevent formation of spurious disulfide bonds. To further stabilize the prefusion trimeric state of the antigen, we either introduced cysteine residues capable of forming inter-protomer disulfide bonds or appended C-terminal trimerization motifs, e.g. GCN4 or foldon from T4-bacteriophage fibritin. Disulfide mutations, e.g. D217C-Y589C, M317C-W506C, N524C-M684C, were further introduced to lock the proteins into the prefusion state. Recombinant glycoproteins were expressed, secreted to the conditioned media and purified in the absence of fusion inhibitor and without chemical detergent. Notably, the recombinant variant, fused to a GCN4 trimerization motif, showed optimal size-exclusion chromatography profile (FIG. 17). The negatively stained electron microscopy showed recombinant proteins, gB2555 and gB2556, as monodispersed proteins in the absence of inhibitor and detergents. Expected gB protein features are observed in the 2D class averaged images (FIG. 18 and FIG. 19). These results confirm that these engineered constructs are suitable to be used as a framework to add more stabilizing mutations towards a prefusion form of gB in the absence of inhibitor and detergents if needed.

The coordinates and structural factors for the model of the prefusion gB associated with the present Example are provided in Table 1B.

TABLE 6

Exemplary cysteine pair mutations for disulfide bond stabilization

| Row | Mutations |
|---|---|
| 1 | D217C, Y589C |
| 2 | I356C, A500C |
| 3 | S367C, A500C |
| 4 | S367C, A503C |
| 5 | M371C, A505C |
| 6 | M371C, W506C |
| 7 | T374C, A503C |
| 8 | Y160C, Y708C |
| 9 | L162C, M716C |
| 10 | N524C, M684C |

TABLE 6-continued

| Exemplary cysteine pair mutations for disulfide bond stabilization | |
|---|---|
| Row | Mutations |
| 11 | G99C, A267C |
| 12 | T100C, R258C |
| 13 | T221C, E657C |
| 14 | S223C, T659C |
| 15 | F541C, E681C |
| 16 | L603C, Y667C |
| 17 | N605C, K670C |
| 18 | R607C, N688C |
| 19 | E609C, K691C |

TABLE 7

| Exemplary charge mutations for stabilization | |
|---|---|
| Row | Mutations |
| 1 | E686L |
| 2 | E686I |
| 3 | D679A |
| 4 | R354F |
| 5 | R573F |
| 6 | D101L, K260L |

TABLE 8

| Construct mutations. | | | | |
|---|---|---|---|---|
| Construct | Mutation 1 | Mutation 2 | Mutation 3 | Mutation 4 |
| pSB1688 | N524C | M684C | | |
| pSB2455 | M371C | W506C | | |
| pSB2456 | F541C | E681C | | |
| pSB2457 | D217C | Y589C | M371C | W506C |
| pSB2459 | D217C | Y589C | N524C | M684C |
| pSB1666 | D217C | Y589C | | |

The constructs set forth in Table 8 were made for the purpose of testing the presence of prefusion gB in the purified recombinant protein preparation under different conditions.

TABLE 9

| Exemplary soluble, detergent-free gB ectodomain proteins | | | |
|---|---|---|---|
| Code | gB* | Mutations | C-Terminus Fusion Sequence |
| gB707 | gB (1-707) | D217C, Y589C | |
| gB2264 | gB (1-707) | D217C, Y589C, D703C, P704C | |
| gB2265 | gB (1-707) | D217C, Y589C, Y696C, V697C | |
| gB2266 | gB (1-702) | D217C, Y589C | RIKQIEDKIEEILSKQYHIENEIARIKKLIG (SEQ ID NO: 272) |
| gB2267 | gB (1-702) | D217C, Y589C | KIEEILSKQYHIENEIARIKKLIG (SEQ ID NO: 269) |
| gB2268 | gB (1-702) | D217C, Y589C | KIYHIENEIARIKKLIG (SEQ ID NO: 273) |
| gB2269 | gB (1-703) | D217C, Y589C | LSAIGGYIPEAPRDGQAYVRKDGEWVLLSTFL (SEQ ID NO: 274) |
| gB2555 | gB (1-702) | D217C, M371C, W506C, Y589C | KIEEILSKQYHIENEIARIKKLIG (SEQ ID NO: 269) |
| gB2556 | gB (1-702) | D217C, N524C, Y589C, M684C | KIEEILSKQYHIENEIARIKKLIG (SEQ ID NO: 269) |
| gB2557 | gB (1-707) | D217C, N524C, Y589C, M684C, D703C, P704C | |

*Mutations, including YIH (155-157)→GHR, W240→A and C246→S, had been incorporated in gB to decrease aggregation and increase protein secretion.

Example 7: Overall Strategies to Engineer a Stabilized Prefusion gB

To engineer a stabilized prefusion gB, two strategies were used:

i) the first strategy is to strengthen the interactions in the prefusion structure, which include engineering disulfide bonds between the residues that are in close proximity in the prefusion structure and grafting stable structure motifs to the C-terminal end without disrupting the structures from other parts of the molecule; and ii) the second strategy is to remove the energetically unfavorable local structures from the prefusion conformation. These include: (a) removal of surface exposed hydrophobic residues, (b) changes of proline to non-proline and hydrophilic residues in the loops regions, and (c) removal and reengineering Domain V, which undergoes large conformational changes during the fusion process. The combination of such designs was used to obtain enough stabilization for the prefusion gB. The proteins carrying such designed mutations were individually purified and screened by their properties in size exclusion chromatography (SEC), thermal melting assay (TM) and their features from the electron microscopy images (EM).

A panel of mutant cysteine pair constructs was screened against the CMV gB full length post-fusion construct pSB1764. For the first round, each new construct included one mutant cysteine pair. The complete list of mutants that were screened are in Table 10.

TABLE 10

| The list of one pair disulfide bond mutants that were screened on full length CMV gB | |
|---|---|
| Postfusion gB Full length Construct | pSB1764 |
| Construct Framework | CMV gB HAss FLAG/V23 . . . V907 (ACM48044.1) I675S/Thrombin His6 StrepTagII ** in pcDNA3.1(+) |

TABLE 10-continued

The list of one pair disulfide bond mutants that were screened on full length CMV gB

| Construct name | Mutation 1 | Mutation 2 |
|---|---|---|
| pSB01579 | G99C | A267C |
| pSB01581 | T100C | S269C |
| pSB01582 | Q98C | G271C |
| pSB01656 | M96C | D660C |
| pSB01657 | Q98C | N658C |
| pSB01658 | T100C | R258C |
| pSB01659 | T100C | L656C |
| pSB01660 | T100C | N658C |
| pSB01662 | I117C | S407C |
| pSB01663 | Y153C | L712C |
| pSB01664 | L162C | M716C |
| pSB01665 | D217C | S587C |
| pSB01666 | D217C | Y589C |
| pSB01667 | S219C | F584C |
| pSB01668 | S219C | A585C |
| pSB01669 | S219C | N586C |
| pSB01671 | S223C | T659C |
| pSB01672 | W240C | A732C |
| pSB01673 | W240C | G735C |
| pSB01674 | Y242C | V728C |
| pSB01675 | Y242C | G731C |
| pSB01678 | S269C | N658C |
| pSB01679 | D272C | P614C |
| pSB01680 | V273C | V629C |
| pSB01681 | W349C | A650C |
| pSB01682 | S367C | A500C |
| pSB01683 | S367C | A503C |
| pSB01684 | K370C | Q501C |
| pSB01686 | I523C | I683C |
| pSB01687 | I523C | M684C |
| pSB01688 | N524C | M684C |
| pSB01691 | F541C | L680C |
| pSB01692 | L548C | P655C |
| pSB01693 | A549C | N658C |
| pSB01694 | S550C | P655C |
| pSB01695 | S550C | E657C |
| pSB01696 | Q591C | S668C |
| pSB01697 | L603C | Y667C |
| pSB01698 | G604C | L672C |
| pSB01699 | R607C | N688C |
| pSB01700 | T608C | Q692C |
| pSB01702 | E610C | S674C |
| pSB01703 | E610C | S675C |
| pSB01704 | Q612C | V663C |
| pSB01705 | V737C | F755C |
| pSB01707 | V741C | F755C |
| pSB01708 | D679S | N/A |
| pSB01709 | D679N | N/A |
| pSB01712 | E686S | N/A |
| pSB01713 | E686Q | N/A |
| pSB01715 | D646P | N/A |
| pSB02041 | E686F | N/A |
| pSB02043 | E686I | N/A |
| pSB02044 | E686V | N/A |

It was determined from the screen that cysteine pair D217C-Y589C (pSB1666), in combination with inhibitor WAY-174865, stabilized CMV gB in the prefusion state.

In the presence of the fusion inhibitor, the construct gB1666 (engineered disulfide by mutating D217C and Y589C) showed a right shift in the in SEC retention volume and a distinct transition temperature at ~73° C. indicating a different conformation from that of the wild type gB (FIGS. 22A and 22B). gB1666 was further characterized by EM imaging experiments. From the cryoEM dataset 2D classification results, prefusion classes were observed as the dominant population and the 3D structure density map confirmed the prefusion gB structure (data not shown). However, in the absence of the inhibitor, the right shifted peak from SEC and the transition temperature peak at ~73° C. are less distinct (FIG. 23). This suggested a single disulfide bond has limited effect to retain gB1666 in a prefusion state.

Thus, a second round of mutations were screened in frame of gB1666 to create further stability of the prefusion conformation in the absence of the inhibitor (Table 11). A new mutant panel was cloned and screened in which a second cysteine pair was introduced into construct pSB1666. The goal was to add another stabilizing disulfide bridge, in order to further stabilize CMV gB in the prefusion state.

TABLE 11

The list of two pairs of disulfide bonds mutants that were screened on full length CMV gB

| | |
|---|---|
| Full length Prefusion construct | pSB1666 |
| Construct Description | CMV HAss FLAG/V23 . . . V907 (ACM48044.1)[D217C-Y589C] I675S/Thrombin His6 StrepTagII ** in pcDNA3.1(+). |

| Construct name | Mutation 1 | Mutation 2 |
|---|---|---|
| pSB02145 | T100C | N658C |
| pSB02146 | S367C | A500C |
| pSB02147 | D272C | P614C |
| pSB02148 | S219C | F584C |
| pSB02149 | E686V | |
| pSB02191 | D217C | F584C |
| pSB02193 | D217C | N586C |
| pSB02194 | D217C | S588C |
| pSB02195 | S219C | S587C |
| pSB02196 | S219C | S588C |
| pSB02197 | S219C | Y589C |
| pSB02455 | M371C | W506C |
| pSB02456 | F541C | E681C |
| pSB02457 | M371C | W506C |
| pSB02459 | N524C | M684C |

It was determined from this screen that cysteine pair D217C-Y589C, in combination with either pair M371C-W506C (pSB2457) or pair N524C-M684C (pSB2459) stabilized CMV gB in the prefusion state, without the need for a stabilizing inhibitor. gB2457 and gB2459 proteins showed similar profiles in SEC and TM results as the prefusion form (gB1666+inhibitor) (FIG. 24A-24B). gB2457 had a more distinct transition at ~73° C. in thermal stability assay (FIG. 24B). In addition, both gB2457 and gB2459 showed the prefusion gB feature in the negative staining EM 2D class averaged images (data not shown). In the absence of a fusion inhibitor, gB2457 and gB2459 represent more stable versions of prefusion gB than their parent design, i.e. gB1666. Such improvement also confirms that the right combination of stabilizing mutation sites can synergistically contribute to the overall stability of the prefusion conformation.

In comparison to the full length and membrane bound forms of prefusion gB, a soluble format prefusion gB does not require detergent which provides advantages in scalability of protein production and ease of purification. Based on the known structure, the membrane interaction domains from gB are the membrane proximal region (MPR), the transmembrane (TM) domain and fusion loops. The cytoplasmic tail domain may also interact with membrane from the cytosolic side. Thus, these membrane-interacting hydrophobic regions were either removed or converted to hydrophilic types in the designs for a soluble form prefusion gB. In addition, structurally stable trimerization tags (e.g. GCN4, cysteine rings, trimeric foldon) were added at the carboxy terminal of the protein that truncated at before the MPR domain. Several truncation designs were tested before the GCN4 tag (gB2267) was selected to be used as an ectodomain construct frame. The stabilizing mutation sites identified from full length frame were made on this ectodomain frame and screened (Table 12).

Figure 25B:
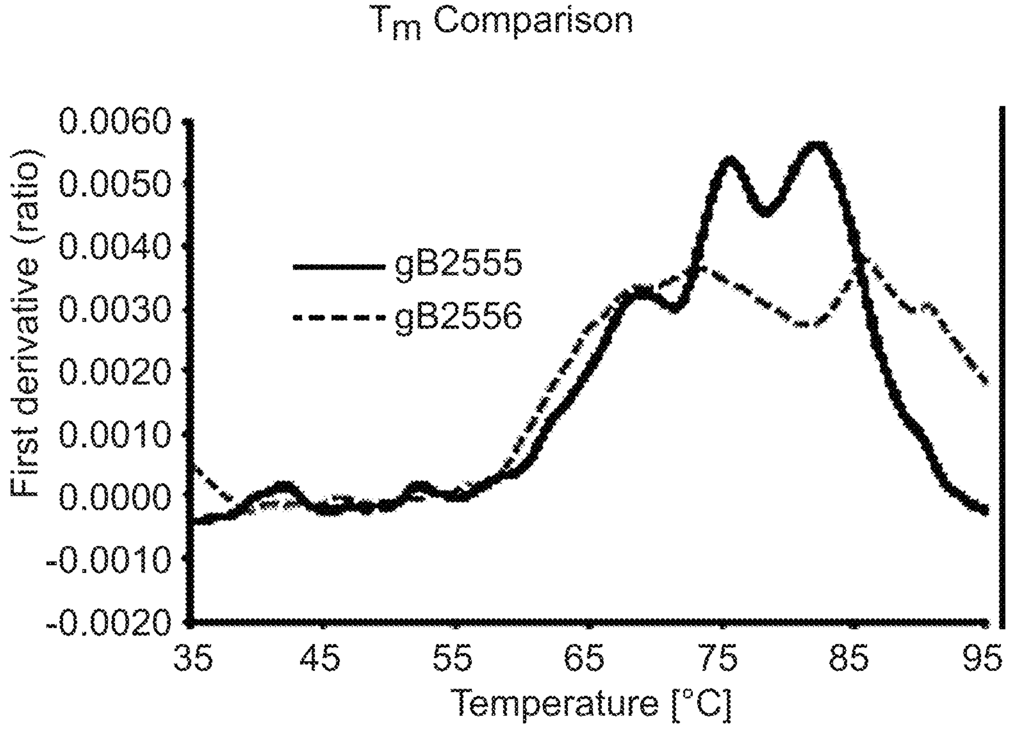

In the resulting gB2555 and gB2556, which were well behaved proteins after purification (FIG. 25A), the phase transition peak at a lower temperature ~73° was not obvious (FIG. 25B). But the 2D classification from negative staining EM images indicated that both prefusion and postfuiosn forms were present (data not shown) and further stabilization were still needed for the ectodomain prefusion gB. The third pair of disulfide bonds were screened on the pSB2556 background (Table 12), but not much improvement was observed.

TABLE 12

Ectodomain CMV gB mutants with triple disulfide bond pairs

| | | |
|---|---|---|
| Ectodomain construct | pSB2556 | |
| Construct Description | pSB2556: CMV HAss FLAG/V23 . . . V702 gB CMV (ACM48044) YIH to GHR (155-157)[D217C-Y589C] [N524C-M684C] W240A C246S I675S/ GCN4 CC tri2 ** in pcDNA3.1(+). | |
| construct name | mutation 1 | mutation 2 |
| pSB2558 | I356C | A500C |
| pSB2559 | S367C | A500C |
| pSB2560 | S367C | A503C |
| pSB2561 | M371C | A505C |
| pSB2562 | M371C | W506C |
| pSB2563 | T374C | A503C |
| pSB2564 | G99C | A267C |
| pSB2565 | T100C | R258C |
| pSB2567 | L603C | Y667C |
| pSB2568 | N605C | K670C |
| pSB2570 | E609C | K691C |
| pSB2571 | T221C | E657C |
| pSB2572 | S223C | T659C |

Since domain V undergoes large conformational changes and was expected to provide the energy to drive the membrane fusion between the viral and host cells, a new approach was to remove Domain V from the ectodomain gB. SB2562 was chosen as the starting construct (Table 13 and Table 14).

TABLE 13

Additional Ectodomain Designs

| | |
|---|---|
| pSB2795 | CMV HAss FLAG/V23 . . . D646 gB CMV (ACM48044) YIH to GHR (155-157) D217C W240A C246S M371C N524C W506C Y589C I675S ** in pcDNA3.1(+). |
| pSB2797 | CMV HAss FLAG/V23 . . . V702 gB CMV (ACM48044) YIH to GHR (155-157) 648 MIALDI to GSGKDG D217C W240A C246S M371C N524C W506C Y589C I675S M684C/GCN4 CC tri2 ** in pcDNA3.1(+). |
| pSB2968 | CMV HAss FLAG/V23 . . . V702 gB CMV (ACM48044) PI116117GS YIH to GHR (155-157) 648 MIALDI to GSGKDG D217C W240A C246S M371C N524C W506C Y589C I675S M684C/GCN4 CC tri2 ** in pcDNA3.1(+). |
| A | CMV HAss FLAG/V23 . . . V702 gB CMV (ACM48044) YIH to GHR (155-157) 648 MIALDI to GSGKDG D217C W240A C246S M371C N524C W506C Y589C I675S M684C R693V, last res L695 + KIKQIEDK IEEILSK IYHIENE IARIKKL IG ** in pcDNA3.1(+) |
| B | CMV HAss FLAG/V23 . . . V702 gB CMV (ACM48044) YIH to GHR (155-157) 648 MIALDI to GSGKDG D217C W240A C246S M371C N524C W506C Y589C I675S M684C R685A R693V, last res L695 + KIKQIEDK IEEILSK IYHIENE IARIKKL IG ** in pcDNA3.1(+) |
| C | CMV HAss FLAG/V23 . . . V702 gB CMV (ACM48044) YIH to GHR (155-157) 648 MIALDI to GSGKDG D217C W240A C246S M371C N524C W506C Y589C I675S M684C F678S, L680T R693V, last res L695 + KIKQIEDK IEEILSK IYHIENE IARIKKL IG ** in pcDNA3.1(+) |
| D | CMV HAss FLAG/V23 . . . V702 gB CMV (ACM48044) YIH to GHR (155-157) 648 MIALDI to GSGKDG D217C W240A C246S M371C N524C W506C Y589C I675S M684C P655S R693V, last res L695 + KIKQIEDK IEEILSK IYHIENE IARIKKL IG ** in pcDNA3.1(+) |

One of the designs removed the entire Domain V in which residues after D646 were truncated. Since the disulfide pair could no longer form at N524C and M684C, the N524C was reverted back to its wildtype asparagine residue (N) in order to remove the free cysteine (pSB2796) (Table 14). This construct was named gB2796 and showed a well-behaved protein as a single peak in SEC profile with a distinct phase transition temperature at ~70° C. (FIGS. 26A and 26B). From the cryoEM dataset, 2D class average showed clear expected protein densities that corresponded to the structural features from the model of ectodomain prefusion gB. The 3D reconstructed density envelope also corresponded to the expected ectodomain structure. (data not shown).

TABLE 14

Domain V truncated ectodomain CMV gB mutant with disulfide bond pairs

| | |
|---|---|
| CMV ectodomain gB prefusion | pSB2796 |
| Description | CMV HAss FLAG/V23 . . . D646 gB CMV (ACM48044) YIH to GHR (155-157) [D217C-Y589C] [M371C-W506C]W240A C246S I675S ** in pcDNA3.1(+). |

Construct pSB2796 was redesigned into different N-term tagged versions for use in animal studies (Table 15). The Flag tag was swapped out for a 6×His tag, which is more amenable for purification scale up. An untagged version was also created. The HA signal sequence was also replaced with the IgK signal sequence because it is more compatible with the His tag.

TABLE 15

| Construct Design for CMV gB ectodomain prefusion mouse study | |
|---|---|
| pSB3075 | CMV: IgKss 6xHis rTEV/V23 . . . D646 gB CMV (ACM48044) YIH to GHR (155-157) D217C W240A C246S M371C W506C Y589C I675S ** in pcDNA3.1(+). |
| pSB3076 | CMV: IgKss 6xHis PP/V23 . . . D646 gB CMV (ACM48044) YIH to GHR (155-157) D217C W240A C246S M371C W506C Y589C I675S ** in pcDNA3.1(+). |
| pSB3077 | CMV: IgKss 6xHis/V23 . . . D646 gB CMV (ACM48044) YIH to GHR (155-157) D217C W240A C246S M371C W506C Y589C I675S ** in pcDNA3.1(+). |
| pSB3078 | CMV: IgKss/V23 . . . D646 gB CMV (ACM48044) YIH to GHR (155-157) D217C W240A C246S M371C W506C Y589C I675S ** in pcDNA3.1(+). |

These data showed that the prefusion gB is metastable and stabilizing mutations at multiple sites are needed to achieve enough restraints to maintain its prefusion structure. The combination of disulfide bonds and the modifications of unstable Domain V provide examples of locking the prefusion conformation. The stabilized gB can be engineered in full length (gB1666, gB2457, gB2459) and ectodomain protein formats (gB2796), which are suitable for use as prefusion gB antigens. In addition, the SEC, the thermal shift assay and EM imaging approaches provided ways to evaluate the conformational state of the gB samples without the need for prefusion or postfusion specific antibodies.

Methods

Cysteine Mutants Construct Design and Cloning

All constructs were cloned into the pcDNA3.1(+) vector backbone (ThermoFisher Scientific, Waltham, MA). Primers, each containing a cysteine point mutation, were ordered from IDT (Coralville, Iowa). Site directed mutagenesis was performed using a QuikChange Multi Site-Directed Mutagenesis Kit (Agilent, Santa Clara, CA). The mutagenized DNA was transformed into DH5 alpha cells. Colonies were selected and sent for sequencing. Positive transformants were verified by DNA sequencing analysis. Plasmid DNA was amplified using DNA preparation kits.

Mammalian Cell Expression

EXPI293 cells were grown to an OD of $3\times10^6$ cells/mL. Plasmid DNA was diluted in OptiMem media and mixed 1:1 with PEI solution. The DNA-PEI mixture was then transfected into the EXPI293 cells at a concentration of lug DNA/mL culture. Enhancers were added 24 hours post transfection. Cells were monitored and harvested by centrifugation 4 to 5 days post transfection.

Protein Purification

CMVgB proteins were purified through a series or processes of solubilization, affinity column and size exclusion chromatography (SEC). SEC is run on Superose6 increase column in buffer 25 mM HEPES pH 7.5, 250 mM NaCl, 0.02% DDM, 0.002% CHS. For experiments with inhibitor, 3 ug/ml WAY-174865 was added.

Thermal Stability Assay

As a complementary biophysical study of the gB mutants to help identify prefusion stable mutants, thermal stability of the purified gB proteins was analyzed on Tycho NT.6 with 20° C./min heating rate from 35° C. to 95° C.

Negative Staining Grid Preparation

Thin carbon supported grids were glow discharged by EZ-glow with −20 mA current for 30 seconds before use. Aliquots of 4 ul sample solution at the protein concentration of 0.02 mg/ml were applied to the carbon surface of the grids and let sit for 45 seconds. The sample solution was then blotted away with filter paper and same carbon surface was rinsed with filtered water and excess water was blotted away with filter paper. The grid was stained with 2% uranyl acetate solution and air dried before being loaded to a TF20 electron microscope for imaging.

Cryo Grids Preparations

Quantifoil grids were plasma cleaned with Argon/Oxygen. Graphene oxide stock solution diluted to 0.2 mg/ml concentration (Sigma) was applied to the surface of the treated grid and let sit for 2 minutes. The excess solution was blotted with filter paper and washed with one droplet of water to remove excess graphene oxide. The grid was dried overnight before use. Aliquots of sample solution were vitrified on graphene oxide film-supported grids using a Vitrobot (ThermoFisher). The grids were stored in liquid nitrogen until loaded in the microscope under cryo conditions for imaging.

CryoEM Data Collection, Image Processing

Data collections were done on a Thermo Fisher Titan Krios transmission electron microscope that operates at 300 kV with SerialEM program at a nominal magnification (165,000×) using a K2 direct detector camera (Gatan) with super resolution movie mode. The unbinned pixel size was 0.434 Å, and the beam intensity was ~8 e/unbin pixels. The total electron dose on the sample for each movie was ~40 e/Å2. Both Relion and cisTEM programs were used for the data processing.

Example 8: gB2796 Immunogenicity

One of the designed prefusion stabilized ectodomain gB proteins (gB2796) containing amino acids 23-646 with mutations YIH to GHR (155-157), D217C, W240A, C246S, M371C, W506C and Y589C was purified from transfected mammalian via FLAG tag in the absence of fusion inhibitor. Briefly, the protein was purified by adding 20 mM Tris pH 7.5, 200 mM NaCl into the 3L cell media overexpressing SB2796. After incubation with 10 ml of M2 column at 4° C. with rotation for 4 hours, the supernatant was removed and the column was washed thoroughly with PBS. Then the protein was eluted with PBS containing 150 μg/ml FLAG peptide and subsequently concentrated. Size-exclusion chromatography was performed on Superose6 increase 10/300 in PBS at 0.5 ml/min, and the fractions were collected. The purified protein was analyzed on 4-20% Mini-PROTEAN® TGX Stain-Free™ Protein Gels (Biorad) in Tris/glycine/SDS buffer (FIG. 20A) as well as by electronic microscopy with negative staining (FIG. 20B). The EM image showed the triangular shape of the protein particles which is the typical prefusion conformation.

To assess whether gB2796 can elicit a better immune response compared to postfusion gB, a secreted postfusion gB was produced based on the same strain of HCMV with transmembrane domain removed. The protein was named Sanofi gB since it is equivalent to the gB protein used in previous clinical trial by Sanofi (Pass, et al. 2009). Purification of this tagless gB was achieved using affinity chromatography on Lentil Lectin-Sepharose (GE Healthcare) column, followed by anion-exchange chromatography on Toyopearl GigaCap Q-650M (Tosoh), and size-exclusion chromatography on Superdex 200 (GE Healthcare) column.

An in vivo immunogenicity study was conducted in mice with prefusion and postfusion gB described above, as shown in Table 16 below.

TABLE 16

| Immunization dose and schedule | | | | | |
|---|---|---|---|---|---|
| Group | No. of Mice | Immunogen | Adju-vant | Route | Dosing Schedule |
| 1 | 10 | gB2796 (4 mcg/0.2 ml) | — | 0.2 ml/SC | Weeks 0, 3, 6 |
| 2 | 10 | gB2796 (1 mcg/0.2 ml) | — | 0.2 ml/SC | Weeks 0, 3, 6 |
| 3 | 10 | gB2796 (0.25 mcg/0.2 ml) | — | 0.2 ml/SC | Weeks 0, 3, 6 |
| 6 | 10 | Sanofi gB (4 mcg/0.2 ml) | — | 0.2 ml/SC | Weeks 0, 3, 6 |

TABLE 16-continued

| Immunization dose and schedule | | | | | |
|---|---|---|---|---|---|
| Group | No. of Mice | Immunogen | Adju-vant | Route | Dosing Schedule |
| 7 | 10 | Sanofi gB (1 mcg/0.2 ml) | — | 0.2 ml/SC | Weeks 0, 3, 6 |
| 8 | 10 | Sanofi gB (0.25 mcg/0.2 ml) | — | 0.2 ml/SC | Weeks 0, 3, 6 |

At week 5 (2 weeks after second dose), mice sera samples were analyzed by ELISA to determine the IgG titers against gB2796. The results show dose-dependent IgG responses in both gB2796 and Sanofi gB immunized mice (FIG. 21).

| Listing of Raw Sequences | | |
|---|---|---|
| Construct | Sequence* | SEQ ID NO: |
| CMV gB1666: V23 . . . V907 of SEQ ID NO: 1 (Towne) (ACM48044.1) [D217C Y589C I675S] | VSSSSTRGTSATHSHHSSHTTSAAHSRSGSVSQRVTSSQTVSH<br>GVNETIYNTTLKYGDVVGVNTTKYPYRVCSMAQGTDLIRFER<br>NIVCTSMKPINEDLDEGIMVVYKRNIVAHTFKVRVYQKVLTFR<br>RSYAYIHTTYLLGSNTEYVAPPMWEIHHINSHSQCYSSYSRVIA<br>GTVFVAYHRDSYENKTMQLMPDCYSNTHSTRYVTVKDQWH<br>SRGSTWLYRETCNLNCMVTITTARSKYPYHFFATSTGDVVDIS<br>PFYNGTNRNASYFGENADKFFIFPNYTIVSDFGRPNSALETHRL<br>VAFLERADSVISWDIQDEKNVTCQLTFWEASERTIRSEAEDSY<br>HFSSAKMTATFLSKKQEVNMSDSALDCVRDEAINKLQQIFNT<br>SYNQTYEKYGNVSVFETTGGLVVFWQGIKQKSLVELERLANRS<br>SLNLTHNRTKRSTDGNNATHLSNMESVHNLVYAQLQFTYDTL<br>RGYINRALAQIAEAWCVDQRRTLEVFKELSKINPSAILSAIYNKP<br>IAARFMGDVLGLASCVTINQTSVKVLRDMNVKESPGRCYSRP<br>VVIFNFANSSCVQYGQLGEDNEILLGNHRTEECQLPSLKIFIAG<br>NSAYEYVDYLFKRMIDLSSISTVDSMIALDIDPLENTDFRVLELY<br>SQKELRSSNVFDLEEIMREFNSYKQRVKYVEDKVVDPLPPYLK<br>GLDDLMSGLGAAGKAVGVAIGAVGGAVASVVEGVATFLKNP<br>FGAFTIILVAIAVVIIIYLIYTRQRRLCMQPLQNLFPYLVSADGTT<br>VTSGNTKDTSLQAPPSYEESVYNSGRKGPGPPSSDASTAAPPY<br>TNEQAYQMLLALVRLDAEQRAQQNGTDSLDGQTGTQDKGQ<br>KPNLLDRLRHRKNGYRHLKDSDEEENV | 255 |
| | GTATCCTCCAGCTCTACTAGAGGAACGAGCGCGACCCATTC<br>ACACCACAGCTCCCACACTACGAGCGCTGCCCATTCTAGGA<br>GTGGCTCCGTGTCACAACGCGTTACTAGTAGCCAGACCGTG<br>TCTCACGGCGTCAACGAGACAATTTACAACACGACGCTGAA<br>ATACGGCGATGTCGTGGGTGTGAATACTACCAAGTACCCCT<br>ATAGAGTCTGTAGCATGGCCCAGGGCACCGACCTGATCAG<br>GTTCGAACGGAACATCGTTTGCACATCAATGAAGCCTATCA<br>ACGAAGACCTTGACGAGGGGATTATGGTGGTATACAAACG<br>GAATATCGTGGCTCACACCTTCAAAGTGCGAGTGTATCAGA<br>AGGTTCTGACATTCCGAAGAAGTTACGCCTACATCCATACC<br>ACCTATCTGCTGGGCTCCAACACTGAGTACGTGGCGCCCCC<br>AATGTGGGAAATCCACCACATCAACAGCCATTCACAGTGCT<br>ACTCTTCCTACAGCAGGGTGATTGCGGGCACAGTGTTTGTG<br>GCCTACCACAGGGACAGCTATGAGAACAAGACGATGCAGT<br>TGATGCCAGATTGTTACAGTAACACTCACAGTACACGGTAT<br>GTTACAGTTAAGGATCAGTGGCATTCACGCGGAAGCACAT<br>GGCTGTATAGAGAGACCTGTAATTTGAATTGTATGGTAACT<br>ATCACTACTGCACGGAGCAAGTACCCTTATCATTTCTTTGCT<br>ACAAGCACGGGCGATGTGGTAGACATCAGCCCCTTCTATAA<br>TGGCACAAATCGGAACGCAAGCTATTTCGGGGAGAACGCC<br>GACAAGTTTTTCATTTTTCCTAATTATACTATTGTTTCTGACT<br>TCGGGAGACCCAACTCCGCCCTGGAAACTCACAGACTGGTT<br>GCGTTCCTCGAAAGAGCAGATTCTGTGATATCCTGGGACAT<br>TCAGGATGAAAAGAACGTCACGTGTCAGCTGACCTTCTGG<br>GAGGCCTCAGAGCGGACGATCCGGTCTGAGGCCGAGGACT<br>CTTACCACTTTAGCAGCGCCAAGATGACCGCAACCTTCCTG<br>TCTAAAAAACAGGAAGTGAACATGTCCGATTCTGCTTTGGA<br>CTGCGTTCGCGATGAGGCCATCAACAAGCTTCAACAAATTT<br>TCAATACCTCCTACAATCAGACATATGAAAAATACGGAAAC<br>GTGAGTGTCTTTGAAACCACCGGGGGCCTGGTCGTGTTCTG<br>GCAGGGTATCAAACAGAAGAGCCTGGTGGAACTGGAACG<br>CCTGGCCAACAGAAGCAGTTTGAACCTCACGCACAACCGG<br>ACAAAGAGGAGCACCGACGGAAACAATGCTACACACCTTT<br>CCAACATGGAGTCTGTCCACAATCTGGTTTATGCACAGCTT<br>CAGTTCACTTATGACACACTGCGGGGCTACATAAACAGGGC | 256 |

-continued

Listing of Raw Sequences

| Construct | Sequence* | SEQ ID NO: |
|---|---|---|
| | TCTGGCACAGATAGCCGAGGCTTGGTGTGTGGACCAGCGG<br>AGAACCCTGGAGGTATTTAAAGAACTGTCTAAGATCAACCC<br>CTCTGCGATTCTGAGCGCTATTTACAACAAACCCATTGCCGC<br>ACGCTTCATGGGGGACGTCCTCGGTCTTGCCTCCTGTGTGA<br>CAATTAACCAGACGAGCGTGAAGGTGCTGCGAGATATGAA<br>CGTGAAGGAATCCCCTGGGCGGTGTTACAGTAGGCCTGTG<br>GTGATTTTCAACTTCGCCAACTCTTCCTGTGTCCAATACGGT<br>CAACTCGGTGAAGATAACGAGATTCTGCTGGGCAATCATC<br>GGACAGAAGAATGCCAGTTGCCAAGCCTTAAAATCTTTATT<br>GCAGGAAATTCAGCCTACGAGTACGTCGACTATCTGTTTAA<br>AAGAATGATTGATCTGAGCAGCATTTCCACTGTGGACAGTA<br>TGATCGCACTGGACATTGACCCTTTGGAAAACACCGATTTT<br>CGCGTCCTTGAGCTGTACTCCCAGAAAGAACTGCGCTCTAG<br>CAACGTCTTTGATCTTGAGGAGATCATGAGGGAGTTTAACT<br>CTTATAAACAGAGGGTGAAGTATGTGGAGGATAAAGTGGT<br>CGACCCTCTGCCACCCTACCTCAAAGGACTGGACGATCTGA<br>TGAGCGGACTTGGAGCTGCCGGCAAAGCCGTCGGGGGG<br>CTATCGGTGCCGTGGGCGGCGCCGTGGCTTCTGTGGTTGA<br>GGGAGTGGCCACTTTTCTTAAAAATCCTTTCGGAGCTTTTAC<br>CATTATTCTGGTCGCCATCGCCGTGGTGATCATCATTTATCT<br>GATCTACACCCGCCAGCGCCGCTTGTGCATGCAGCCACTTC<br>AGAACCTGTTTCCCTATCTGGTCAGTGCTGACGGTACAACC<br>GTGACCAGCGGCAACACAAAGGACACAAGCCTTCAGGCTC<br>CTCCAAGTTATGAAGAGTCCGTGTATAATTCTGGGAGGAA<br>GGGACCTGGTCCCCCCTCTTCCGACGCCTCAACAGCGGCAC<br>CCCCCTACACCAATGAGCAGGCATATCAGATGCTCCTGGCC<br>CTTGTGCGGCTCGATGCCGAGCAACGCGCACAACAGAACG<br>GGACGGATTCTCTCGACGGACAGACAGGCACTCAGGACAA<br>AGGCCAGAAGCCCAACCTTCTGGATCGGTTGCGGCATAGA<br>AAAAACGGCTATAGACACCTCAAGGACTCAGACGAAGAAG<br>AGAACGTC | |
| CMV gB2457 (Prefusion, Full length) V23 to V907 of SEQ ID NO: 1 (Towne) [D217C M371C W506C Y589C I675S] | VSSSSTRGTSATHSHHSSHTTSAAHSRSGSVSQRVTSSQTVSH<br>GVNETIYNTTLKYGDVVGVNTTKYPYRVCSMAQGTDLIRFER<br>NIVCTSMKPINEDLDEGIMVVYKRNIVAHTFKVRVYQKVLTFR<br>RSYAYIHTTYLLGSNTEYVAPPMWEIHHINSHSQCYSSYSRVIA<br>GTVFVAYHRDSYENKTMQLMPDCYSNTHSTRYVTVKDQWH<br>SRGSTWLYRETCNLNCMVTITTARSKYPYHFFATSTGDVVDIS<br>PFYNGTNRNASYFGENADKFFIFPNYTIVSDFGRPNSALETHRL<br>VAFLERADSVISWDIQDEKNVTCQLTFWEASERTIRSEAEDSY<br>HFSSAKCTATFLSKKQEVNMSDSALDCVRDEAINKLQQIFNTS<br>YNQTYEKYGNVSVFETTGGLVVFWQGIKQKSLVELERLANRSS<br>LNLTHNRTKRSTDGNNATHLSNMESVHNLVYAQLQFTYDTLR<br>GYINRALAQIAEACCVDQRRTLEVFKELSKINPSAILSAIYNKPIA<br>ARFMGDVLGLASCVTINQTSVKVLRDMNVKESPGRCYSRPVV<br>IFNFANSSCVQYGQLGEDNEILLGNHRTEECQLPSLKIFIAGNS<br>AYEYVDYLFKRMIDLSSISTVDSMIALDIDPLENTDFRVLELYSQ<br>KELRSSNVFDLEEIMREFNSYKQRVKYVEDKVVDPLPPYLKGL<br>DDLMSGLGAAGKAVGVAIGAVGGAVASVVEGVATFLKNPFG<br>AFTIILVAIAVVIIIYLIYTRQRRLCMQPLQNLFPYLVSADGTTVT<br>SGNTKDTSLQAPPSYEESVYNSGRKGPGPPSSDASTAAPPYTN<br>EQAYQMLLALVRLDAEQRAQQNGTDSLDGQTGTQDKGQKP<br>NLLDRLRHRKNGYRHLKDSDEEENV | 257 |
| | GTATCCTCCAGCTCTACTAGAGGAACGAGCGCGACCCATTC<br>ACACCACAGCTCCCACACTACGAGCGCTGCCCATTCTAGGA<br>GTGGCTCCGTGTCACAACGCGTTACTAGTAGCCAGACCGTG<br>TCTCACGGCGTCAACGAGACAATTTACAACACGACGCTGAA<br>ATACGGCGATGTCGTGGGTGTGAATACTACCAAGTACCCCT<br>ATAGAGTCTGTAGCATGGCCCAGGGCACCGACCTGATCAG<br>GTTCGAACGGAACATCGTTTGCACATCAATGAAGCCTATCA<br>ACGAAGACCTTGACGAGGGGATTATGGTGGTATACAAACG<br>GAATATCGTGGCTCACACCTTCAAAGTGCGAGTGTATCAGA<br>AGGTTCTGACATTCCGAAGAAGTTACGCCTACATCCATACC<br>ACCTATCTGCTGGGCTCCAACACTGAGTACGTGGCGCCCCC<br>AATGTGGGAAATCCACCACATCAACAGCCATTCACAGTGCT<br>ACTCTTCCTACAGCAGGGTGATTGCGGGCACAGTGTTTGTG<br>GCCTACCACAGGGACAGCTATGAGAACAAGACGATGCAGT<br>TGATGCCAGATTGTTACAGTAACACTCACAGTACACGGTAT<br>GTTACAGTTAAGGATCAGTGGCATTCACGCGGAAGCACAT<br>GGCTGTATAGAGAGACCTGTAATTTGAATTGTATGGTAACT<br>ATCACTACTGCACGGAGCAAGTACCCTTATCATTTCTTTGCT<br>ACAAGCACGGGCGATGTGGTAGACATCAGCCCCTTCTATAA<br>TGGCACAAATCGGAACGCAAGCTATTTCGGGGAGAACGCC<br>GACAAGTTTTTCATTTTTCCTAATTATACTATTGTTTCTGACT | 258 |

-continued

Listing of Raw Sequences

| Construct | Sequence* | SEQ ID NO: |
|---|---|---|
| | TCGGGAGACCCAACTCCGCCCTGGAAACTCACAGACTGGTT GCGTTCCTCGAAAGAGCAGATTCTGTGATATCCTGGGACAT TCAGGATGAAAAGAACGTCACGTGTCAGCTGACCTTCTGG GAGGCCTCAGAGCGGACGATCCGGTCTGAGGCCGAGGACT CTTACCACTTTAGCAGCGCCAAGTGCACCGCAACCTTCCTGT CTAAAAAACAGGAAGTGAACATGTCCGATTCTGCTTTGGAC TGCGTTCGCGATGAGGCCATCAACAAGCTTCAACAAATTTT CAATACCTCCTACAATCAGACATATGAAAAATACGGAAACG TGAGTGTCTTTGAAACCACCGGGGGCCTGGTCGTGTTCTGG CAGGGTATCAAACAGAAGAGCCTGGTGGAACTGGAACGCC TGGCCAACAGAAGCAGTTTGAACCTCACGCACAACCGGAC AAAGAGGAGCACCGACGGAAACAATGCTACACACCTTTCC AACATGGAGTCTGTCCACAATCTGGTTTATGCACAGCTTCA GTTCACTTATGACACACTGCGGGGCTACATAAACAGGGCTC TGGCACAGATAGCCGAGGCTTGCTGTGTGGACCAGCGGAG AACCCTGGAGGTATTTAAAGAACTGTCTAAGATCAACCCCT CTGCGATTCTGAGCGCTATTTACAACAAACCCATTGCCGCA CGCTTCATGGGGGACGTCCTCGGTCTTGCCTCCTGTGTGAC AATTAACCAGACGAGCGTGAAGGTGCTGCGAGATATGAAC GTGAAGGAATCCCCTGGGCGGTGTTACAGTAGGCCTGTGG TGATTTTCAACTTCGCCAACTCTTCCTGTGTCCAATACGGTC AACTCGGTGAAGATAACGAGATTCTGCTGGGCAATCATCG GACAGAAGAATGCCAGTTGCCAAGCCTTAAAATCTTTATTG CAGGAAATTCAGCCTACGAGTACGTCGACTATCTGTTTAAA AGAATGATTGATCTGAGCAGCATTTCCACTGTGGACAGTAT GATCGCACTGGACATTGACCCTTTGGAAAACACCGATTTTC GCGTCCTTGAGCTGTACTCCCAGAAAGAACTGCGCTCTAGC AACGTCTTTGATCTTGAGGAGATCATGAGGGAGTTTAACTC TTATAAACAGAGGGTGAAGTATGTGGAGGATAAAGTGGTC GACCCTCTGCCACCCTACCTCAAAGGACTGGACGATCTGAT GAGCGGACTTGGAGCTGCCGGCAAAGCCGTCGGGGTGGC TATCGGTGCCGTGGGCGGCGCCGTGGCTTCTGTGGTTGAG GGAGTGGCCACTTTTCTTAAAAATCCTTTCGGAGCTTTTACC ATTATTCTGGTCGCCATCGCCGTGGTGATCATCATTTATCTG ATCTACACCCGCCAGCGCCGCTTGTGCATGCAGCCACTTCA GAACCTGTTTCCCTATCTGGTCAGTGCTGACGGTACAACCG TGACCAGCGGCAACACAAAGGACACAAGCCTTCAGGCTCC TCCAAGTTATGAAGAGTCCGTGTATAATTCTGGGAGGAAG GGACCTGGTCCCCCCTCTTCCGACGCCTCAACAGCGGCACC CCCCTACACCAATGAGCAGGCATATCAGATGCTCCTGGCCC TTGTGCGGCTCGATGCCGAGCAACGCGCACAACAGAACGG GACGGATTCTCTCGACGGACAGACAGGCACTCAGGACAAA GGCCAGAAGCCCAACCTTCTGGATCGGTTGCGGCATAGAA AAAACGGCTATAGACACCTCAAGGACTCAGACGAAGAAGA GAACGTC | |
| CMV gB2459 (Prefusion, Full length) V23 to V907 of SEQ ID NO: 1 (Towne) [D217C N524C Y589C M684C I675S] | VSSSSTRGTSATHSHHSSHTTSAAHSRSGSVSQRVTSSQTVSH GVNETIYNTTLKYGDVVGVNTTKYPYRVCSMAQGTDLIRFER NIVCTSMKPINEDLDEGIMVVYKRNIVAHTFKVRVYQKVLTFR RSYAYIHTTYLLGSNTEYVAPPMWEIHHINSHSQCYSSYSRVIA GTVFVAYHRDSYENKTMQLMPDCYSNTHSTRYVTVKDQWH SRGSTWLYRETCNLNCMVTITTARSKYPYHFFATSTGDVVDIS PFYNGTNRNASYFGENADKFFIFPNYTIVSDFGRPNSALETHRL VAFLERADSVISWDIQDEKNVTCQLTFWEASERTIRSEAEDSY HFSSAKMTATFLSKKQEVNMSDSALDCVRDEAINKLQQIFNT SYNQTYEKYGNVSVFETTGGLVVFWQGIKQKSLVELERLANRS SLNLTHNRTKRSTDGNNATHLSNMESVHNLVYAQLQFTYDTL RGYINRALAQIAEAWCVDQRRTLEVFKELSKICPSAILSAIYNKP IAARFMGDVLGLASCVTINQTSVKVLRDMNVKESPGRCYSRP VVIFNFANSSCVQYGQLGEDNEILLGNHRTEECQLPSLKIFIAG NSAYEYVDYLFKRMIDLSSISTVDSMIALDIDPLENTDFRVLELY SQKELRSSNVFDLEEICREFNSYKQRVKYVEDKVVDPLPPYLKG LDDLMSGLGAAGKAVGVAIGAVGGAVASVVEGVATFLKNPF GAFTIILVAIAVVIIIYLIYTRQRRLCMQPLQNLFPYLVSADGTTV TSGNTKDTSLQAPPSYEESVYNSGRKGPGPPSSDASTAAPPYT NEQAYQMLLALVRLDAEQRAQQNGTDSLDGQTGTQDKGQK PNLLDRLRHRKNGYRHLKDSDEENV | 259 |
| | GTATCCTCCAGCTCTACTAGAGGAACGAGCGCGACCCATTC ACACCACAGCTCCCACACTACGAGCGCTGCCCATTCTAGGA GTGGCTCCGTGTCACAACGCGTTACTAGTAGCCAGACCGTG TCTCACGGCGTCAACGAGACAATTTACAACACGACGCTGAA ATACGGCGATGTCGTGGGTGTGAATACTACCAAGTACCCCT ATAGAGTCTGTAGCATGGCCCAGGGCACCGACCTGATCAG GTTCGAACGGAACATCGTTTGCACATCAATGAAGCCTATCA | 260 |

-continued

Listing of Raw Sequences

| Construct | Sequence* | SEQ ID NO: |
|---|---|---|
| | ACGAAGACCTTGACGAGGGGATTATGGTGGTATACAAACG<br>GAATATCGTGGCTCACACCTTCAAAGTGCGAGTGTATCAGA<br>AGGTTCTGACATTCCGAAGAAGTTACGCCTACATCCATACC<br>ACCTATCTGCTGGGCTCCAACACTGAGTACGTGGCGCCCCC<br>AATGTGGGAAATCCACCACATCAACAGCCATTCACAGTGCT<br>ACTCTTCCTACAGCAGGGTGATTGCGGGCACAGTGTTTGTG<br>GCCTACCACAGGGACAGCTATGAGAACAAGACGATGCAGT<br>TGATGCCAGATTGTTACAGTAACACTCACAGTACACGGTAT<br>GTTACAGTTAAGGATCAGTGGCATTCACGCGGAAGCACAT<br>GGCTGTATAGAGAGACCTGTAATTTGAATTGTATGGTAACT<br>ATCACTACTGCACGGAGCAAGTACCCTTATCATTTCTTTGCT<br>ACAAGCACGGGCGATGTGGTAGACATCAGCCCCTTCTATAA<br>TGGCACAAATCGGAACGCAAGCTATTTCGGGGAGAACGCC<br>GACAAGTTTTTCATTTTTCCTAATTATACTATTGTTTCTGACT<br>TCGGGAGACCCAACTCCGCCCTGGAAACTCACAGACTGGTT<br>GCGTTCCTCGAAAGAGCAGATTCTGTGATATCCTGGGACAT<br>TCAGGATGAAAAGAACGTCACGTGTCAGCTGACCTTCTGG<br>GAGGCCTCAGAGCGGACGATCCGGTCTGAGGCCGAGGACT<br>CTTACCACTTTAGCAGCGCCAAGATGACCGCAACCTTCCTG<br>TCTAAAAAACAGGAAGTGAACATGTCCGATTCTGCTTTGGA<br>CTGCGTTCGCGATGAGGCCATCAACAAGCTTCAACAAATTT<br>TCAATACCTCCTACAATCAGACATATGAAAAATACGGAAAC<br>GTGAGTGTCTTTGAAACCACCGGGGGCCTGGTCGTGTTCTG<br>GCAGGGTATCAAACAGAAGAGCCTGGTGGAACTGGAACG<br>CCTGGCCAACAGAAGCAGTTTGAACCTCACGCACAACCGG<br>ACAAAGAGGAGCACCGACGGAAACAATGCTACACACCTTT<br>CCAACATGGAGTCTGTCCACAATCTGGTTTATGCACAGCTT<br>CAGTTCACTTATGACACACTGCGGGGCTACATAAACAGGGC<br>TCTGGCACAGATAGCCGAGGCTTGGTGTGTGGACCAGCGG<br>AGAACCCTGGAGGTATTTAAAGAACTGTCTAAGATCTGTCC<br>CTCTGCGATTCTGAGCGCTATTTACAACAAACCCATTGCCGC<br>ACGCTTCATGGGGGACGTCCTCGGTCTTGCCTCCTGTGTGA<br>CAATTAACCAGACGAGCGTGAAGGTGCTGCGAGATATGAA<br>CGTGAAGGAATCCCCTGGGCGGTGTTACAGTAGGCCTGTG<br>GTGATTTTCAACTTCGCCAACTCTTCCTGTGTCCAATACGGT<br>CAACTCGGTGAAGATAACGAGATTCTGCTGGGCAATCATC<br>GGACAGAAGAATGCCAGTTGCCAAGCCTTAAAATCTTTATT<br>GCAGGAAATTCAGCCTACGAGTACGTCGACTATCTGTTTAA<br>AAGAATGATTGATCTGAGCAGCATTTCCACTGTGGACAGTA<br>TGATCGCACTGGACATTGACCCTTTGGAAAACACCGATTTT<br>CGCGTCCTTGAGCTGTACTCCCAGAAAGAACTGCGCTCTAG<br>CAACGTCTTTGATCTTGAGGAGATCTGTAGGGAGTTTAACT<br>CTTATAAACAGAGGGTGAAGTATGTGGAGGATAAAGTGGT<br>CGACCCTCTGCCACCCTACCTCAAAGGACTGGACGATCTGA<br>TGAGCGGACTTGGAGCTGCCGGCAAAGCCGTCGGGGTGG<br>CTATCGGTGCCGTGGGCGGCGCCGTGGCTTCTGTGGTTGA<br>GGGAGTGGCCACTTTTCTTAAAAATCCTTTCGGAGCTTTTAC<br>CATTATTCTGGTCGCCATCGCCGTGGTGATCATCATTTATCT<br>GATCTACACCCGCCAGCGCCGCTTGTGCATGCAGCCACTTC<br>AGAACCTGTTTCCCTATCTGGTCAGTGCTGACGGTACAACC<br>GTGACCAGCGGCAACACAAAGGACACAAGCCTTCAGGCTC<br>CTCCAAGTTATGAAGAGTCCGTGTATAATTCTGGGAGGAA<br>GGGACCTGGTCCCCCCTCTTCCGACGCCTCAACAGCGGCAC<br>CCCCCTACACCAATGAGCAGGCATATCAGATGCTCCTGGCC<br>CTTGTGCGGCTCGATGCCGAGCAACGCGCACAACAGAACG<br>GGACGGATTCTCTCGACGGACAGACAGGCACTCAGGACAA<br>AGGCCAGAAGCCCAACCTTCTGGATCGGTTGCGGCATAGA<br>AAAAACGGCTATAGACACCTCAAGGACTCAGACGAAGAAG<br>AGAACGTC | |
| CMV gB2555: V23 . . . V702 gB CMV (ACM48044) of SEQ ID NO: 1 (Towne) including trimerization domain (GCN4 CC tri2) [YIH to GHR (155-157) D217C W240A M371C C246S W506C Y589C I675S/GCN4 CC tri2] | VSSSSTRGTSATHSHHSSHTTSAAHSRSGSVSQRVTSSQTVSH<br>GVNETIYNTTLKYGDVVGVNTTKYPYRVCSMAQGTDLIRFER<br>NIVCTSMKPINEDLDEGIMVVYKRNIVAHTFKVRVYQKVLTFR<br>RSYAGHRTTYLLGSNTEYVAPPMWEIHHINSHSQCYSSYSRVI<br>AGTVFVAYHRDSYENKTMQLMPDCYSNTHSTRYVTVKDQW<br>HSRGSTALYRETSNLNCMVTITTARSKYPYHFFATSTGDVVDIS<br>PFYNGTNRNASYFGENADKFFIFPNYTIVSDFGRPNSALETHRL<br>VAFLERADSVISWDIQDEKNVTCQLTFWEASERTIRSEAEDSY<br>HFSSAKCTATFLSKKQEVNMSDSALDCVRDEAINKLQQIFNTS<br>YNQTYEKYGNVSVFETTGGLVVFWQGIKQKSLVELERLANRSS<br>LNLTHNRTKRSTDGNNATHLSNMESVHNLVYAQLQFTYDTLR<br>GYINRALAQIAEACCVDQRRTLEVFKELSKINPSAILSAIYNKPIA<br>ARFMGDVLGLASCVTINQTSVKVLRDMNVKESPGRCYSRPVV<br>IFNFANSSCVQYGQLGEDNEILLGNHRTEECQLPSLKIFIAGNS | 261 |

-continued

Listing of Raw Sequences

| Construct | Sequence* | SEQ ID NO: |
|---|---|---|
| | AYEYVDYLFKRMIDLSSISTVDSMIALDIDPLENTDFRVLELYSQ KELRSSNVFDLEEIMREFNSYKQRVKYVEDKVV**KIEEILSKQYHI ENEIARIKKLIG** | |
| | GTATCCTCCAGCTCTACTAGAGGAACGAGCGCGACCCATTC ACACCACAGCTCCCACACTACGAGCGCTGCCCATTCTAGGA GTGGCTCCGTGTCACAACGCGTTACTAGTAGCCAGACCGTG TCTCACGGCGTCAACGAGACAATTTACAACACGACGCTGAA ATACGGCGATGTCGTGGGTGTGAATACTACCAAGTACCCCT ATAGAGTCTGTAGCATGGCCCAGGGCACCGACCTGATCAG GTTCGAACGGAACATCGTTTGCACATCAATGAAGCCTATCA ACGAAGACCTTGACGAGGGGATTATGGTGGTATACAAACG GAATATCGTGGCTCACACCTTCAAAGTGCGAGTGTATCAGA AGGTTCTGACATTCCGAAGAAGTTACGCCGGTCATCGTACC ACCTATCTGCTGGGCTCCAACACTGAGTACGTGGCGCCCCC AATGTGGGAAATCCACCACATCAACAGCCATTCACAGTGCT ACTCTTCCTACAGCAGGGTGATTGCGGGCACAGTGTTTGTG GCCTACCACAGGGACAGCTATGAGAACAAGACGATGCAGT TGATGCCAGATTGTTACAGTAACACTCACAGTACACGGTAT GTTACAGTTAAGGATCAGTGGCATTCACGCGGAAGCACAG CACTGTATAGAGAGACCTCTAATTTGAATTGTATGGTAACT ATCACTACTGCACGGAGCAAGTACCCTTATCATTTCTTTGCT ACAAGCACGGGCGATGTGGTAGACATCAGCCCCTTCTATAA TGGCACAAATCGGAACGCAAGCTATTTCGGGGAGAACGCC GACAAGTTTTTCATTTTTCCTAATTATACTATTGTTTCTGACT TCGGGAGACCCAACTCCGCCCTGGAAACTCACAGACTGGTT GCGTTCCTCGAAAGAGCAGATTCTGTGATATCCTGGGACAT TCAGGATGAAAAGAACGTCACGTGTCAGCTGACCTTCTGG GAGGCCTCAGAGCGGACGATCCGGTCTGAGGCCGAGGACT CTTACCACTTTAGCAGCGCCAAGTGCACCGCAACCTTCCTGT CTAAAAAACAGGAAGTGAACATGTCCGATTCTGCTTTGGAC TGCGTTCGCGATGAGGCCATCAACAAGCTTCAACAAATTTT CAATACCTCCTACAATCAGACATATGAAAAATACGGAAACG TGAGTGTCTTTGAAACCACCGGGGGCCTGGTCGTGTTCTGG CAGGGTATCAAACAGAAGAGCCTGGTGGAACTGGAACGCC TGGCCAACAGAAGCAGTTTGAACCTCACGCACAACCGGAC AAAGAGGAGCACCGACGGAAACAATGCTACACACCTTTCC AACATGGAGTCTGTCCACAATCTGGTTTATGCACAGCTTCA GTTCACTTATGACACACTGCGGGGCTACATAAACAGGGCTC TGGCACAGATAGCCGAGGCTTGCTGTGTGGACCAGCGGAG AACCCTGGAGGTATTTAAAGAACTGTCTAAGATCAACCCCT CTGCGATTCTGAGCGCTATTTACAACAAACCCATTGCCGCA CGCTTCATGGGGGACGTCCTCGGTCTTGCCTCCTGTGTGAC AATTAACCAGACGAGCGTGAAGGTGCTGCGAGATATGAAC GTGAAGGAATCCCCTGGGCGGTGTTACAGTAGGCCTGTGG TGATTTTCAACTTCGCCAACTCTTCCTGTGTCCAATACGGTC AACTCGGTGAAGATAACGAGATTCTGCTGGGCAATCATCG GACAGAAGAATGCCAGTTGCCAAGCCTTAAAATCTTTATTG CAGGAAATTCAGCCTACGAGTACGTCGACTATCTGTTTAAA AGAATGATTGATCTGAGCAGCATTTCCACTGTGGACAGTAT GATCGCACTGGACATTGACCCTTTGGAAAACACCGATTTTC GCGTCCTTGAGCTGTACTCCCAGAAAGAACTGCGCTCTAGC AACGTCTTTGATCTTGAGGAGATCATGAGGGAGTTTAACTC TTATAAACAGAGGGTGAAGTATGTGGAGGATAAAGTGGTC **AAGATCGAGGAGATCCTGTCCAAGCAGTACCACATCGAG AACGAGATCGCCCGCATCAAGAAGCTGATCGGC** | 262 |
| CMV gB2556: V23 . . . V702 gB CMV (ACM48044) of SEQ ID NO: 1 (Towne) including trimerization domain (GCN4 CC tri2) [YIH to GHR (155-157) D217C W240A C246S N524C Y589C I675S M684C/GCN4 CC tri2] | VSSSSTRGTSATHSHHSSHTTSAAHSRSGSVSQRVTSSQTVSH GVNETIYNTTLKYGDVVGVNTTKYPYRVCSMAQGTDLIRFER NIVCTSMKPINEDLDEGIMVVYKRNIVAHTFKVRVYQKVLTFR RSYAGHRTTYLLGSNTEYVAPPMWEIHHINSHSQCYSSYSRVI AGTVFVAYHRDSYENKTMQLMPDCYSNTHSTRYVTVKDQW HSRGSTALYRETSNLNCMVTITTARSKYPYHFFATSTGDVVDIS PFYNGTNRNASYFGENADKFFIFPNYTIVSDFGRPNSALETHRL VAFLERADSVISWDIQDEKNVTCQLTFWEASERTIRSEAEDSY HFSSAKMTATFLSKKQEVNMSDSALDCVRDEAINKLQQIFNT SYNQTYEKYGNVSVFETTGGLVVFWQGIKQKSLVELERLANRS SLNLTHNRTKRSTDGNNATHLSNMESVHNLVYAQLQFTYDTL RGYINRALAQIAEAWCVDQRRTLEVFKELSKICPSAILSAIYNKP IAARFMGDVLGLASCVTINQTSVKVLRDMNVKESPGRCYSRP VVIFNFANSSCVQYGQLGEDNEILLGNHRTEECQLPSLKIFIAG NSAYEYVDYLFKRMIDLSSISTVDSMIALDIDPLENTDFRVLELY SQKELRSSNVFDLEEICREFNSYKQRVKYVEDKVV**KIEEILSKQY HIENEIARIKKLIG** | 263 |

-continued

Listing of Raw Sequences

| Construct | Sequence* | SEQ ID NO: |
|---|---|---|
| | GTATCCTCCAGCTCTACTAGAGGAACGAGCGCGACCCATTC<br>ACACCACAGCTCCCACACTACGAGCGCTGCCCATTCTAGGA<br>GTGGCTCCGTGTCACAACGCGTTACTAGTAGCCAGACCGTG<br>TCTCACGGCGTCAACGAGACAATTTACAACACGACGCTGAA<br>ATACGGCGATGTCGTGGGTGTGAATACTACCAAGTACCCCT<br>ATAGAGTCTGTAGCATGGCCCAGGGCACCGACCTGATCAG<br>GTTCGAACGGAACATCGTTTGCACATCAATGAAGCCTATCA<br>ACGAAGACCTTGACGAGGGGATTATGGTGGTATACAAACG<br>GAATATCGTGGCTCACACCTTCAAAGTGCGAGTGTATCAGA<br>AGGTTCTGACATTCCGAAGAAGTTACGCCGGTCATCGTACC<br>ACCTATCTGCTGGGCTCCAACACTGAGTACGTGGCGCCCCC<br>AATGTGGGAAATCCACCACATCAACAGCCATTCACAGTGCT<br>ACTCTTCCTACAGCAGGGTGATTGCGGGCACAGTGTTTGTG<br>GCCTACCACAGGGACAGCTATGAGAACAAGACGATGCAGT<br>TGATGCCAGATTGTTACAGTAACACTCACAGTACACGGTAT<br>GTTACAGTTAAGGATCAGTGGCATTCACGCGGAAGCACAG<br>CACTGTATAGAGAGACCTCTAATTTGAATTGTATGGTAACT<br>ATCACTACTGCACGGAGCAAGTACCCTTATCATTTCTTTGCT<br>ACAAGCACGGGCGATGTGGTAGACATCAGCCCCTTCTATAA<br>TGGCACAAATCGGAACGCAAGCTATTTCGGGGAGAACGCC<br>GACAAGTTTTTCATTTTTCCTAATTATACTATTGTTTCTGACT<br>TCGGGAGACCCAACTCCGCCCTGGAAACTCACAGACTGGTT<br>GCGTTCCTCGAAAGAGCAGATTCTGTGATATCCTGGGACAT<br>TCAGGATGAAAAGAACGTCACGTGTCAGCTGACCTTCTGG<br>GAGGCCTCAGAGCGGACGATCCGGTCTGAGGCCGAGGACT<br>CTTACCACTTTAGCAGCGCCAAGATGACCGCAACCTTCCTG<br>TCTAAAAAACAGGAAGTGAACATGTCCGATTCTGCTTTGGA<br>CTGCGTTCGCGATGAGGCCATCAACAAGCTTCAACAAATTT<br>TCAATACCTCCTACAATCAGACATATGAAAAATACGGAAAC<br>GTGAGTGTCTTTGAAACCACCGGGGGCCTGGTCGTGTTCTG<br>GCAGGGTATCAAACAGAAGAGCCTGGTGGAACTGGAACG<br>CCTGGCCAACAGAAGCAGTTTGAACCTCACGCACAACCGG<br>ACAAAGAGGAGCACCGACGGAAACAATGCTACACACCTTT<br>CCAACATGGAGTCTGTCCACAATCTGGTTTATGCACAGCTT<br>CAGTTCACTTATGACACACTGCGGGGCTACATAAACAGGGC<br>TCTGGCACAGATAGCCGAGGCTTGGTGTGTGGACCAGCGG<br>AGAACCCTGGAGGTATTTAAAGAACTGTCTAAGATCTGTCC<br>CTCTGCGATTCTGAGCGCTATTTACAACAAACCCATTGCCGC<br>ACGCTTCATGGGGGACGTCCTCGGTCTTGCCTCCTGTGTGA<br>CAATTAACCAGACGAGCGTGAAGGTGCTGCGAGATATGAA<br>CGTGAAGGAATCCCCTGGGCGGTGTTACAGTAGGCCTGTG<br>GTGATTTTCAACTTCGCCAACTCTTCCTGTGTCCAATACGGT<br>CAACTCGGTGAAGATAACGAGATTCTGCTGGGCAATCATC<br>GGACAGAAGAATGCCAGTTGCCAAGCCTTAAAATCTTTATT<br>GCAGGAAATTCAGCCTACGAGTACGTCGACTATCTGTTTAA<br>AAGAATGATTGATCTGAGCAGCATTTCCACTGTGGACAGTA<br>TGATCGCACTGGACATTGACCCTTTGGAAAACACCGATTTT<br>CGCGTCCTTGAGCTGTACTCCCAGAAAGAACTGCGCTCTAG<br>CAACGTCTTTGATCTTGAGGAGATCTGTAGGGAGTTTAACT<br>CTTATAAACAGAGGGTGAAGTATGTGGAGGATAAAGTGGT<br>**CAAGATCGAGGAGATCCTGTCCAAGCAGTACCACATCGA**<br>**GAACGAGATCGCCCGCATCAAGAAGCTGATCGGC** | 264 |
| CMV gB2796 (Prefusion, ectodomain) V23 to D646 of SEQ ID NO: 1 (Towne) [YIH to GHR (155-157) D217C W240A C246S M371C W506C Y589C] | VSSSSTRGTSATHSHHSSHTTSAAHSRSGSVSQRVTSSQTVSH<br>GVNETIYNTTLKYGDVVGVNTTKYPYRVCSMAQGTDLIRFER<br>NIVCTSMKPINEDLDEGIMVVYKRNIVAHTFKVRVYQKVLTFR<br>RSYAGHRTTYLLGSNTEYVAPPMWEIHHINSHSQCYSSYSRVI<br>AGTVFVAYHRDSYENKTMQLMPDCYSNTHSTRYVTVKDQW<br>HSRGSTALYRETSNLNCMVTITTARSKYPYHFFATSTGDVVDIS<br>PFYNGTNRNASYFGENADKFFIFPNYTIVSDFGRPNSALETHRL<br>VAFLERADSVISWDIQDEKNVTCQLTFWEASERTIRSEAEDSY<br>HFSSAKCTATFLSKKQEVNMSDSALDCVRDEAINKLQQIFNTS<br>YNQTYEKYGNVSVFETTGGLVVFWQGIKQKSLVELERLANRSS<br>LNLTHNRTKRSTDGNNATHLSNMESVHNLVYAQLQFTYDTLR<br>GYINRALAQIAEACCVDQRRTLEVFKELSKINPSAILSAIYNKPIA<br>ARFMGDVLGLASCVTINQTSVKVLRDMNVKESPGRCYSRPVV<br>IFNFANSSCVQYGQLGEDNEILLGNHRTEECQLPSLKIFIAGNS<br>AYEYVDYLFKRMIDLSSISTVD | 265 |
| | GTATCCTCCAGCTCTACTAGAGGAACGAGCGCGACCCATTC<br>ACACCACAGCTCCCACACTACGAGCGCTGCCCATTCTAGGA<br>GTGGCTCCGTGTCACAACGCGTTACTAGTAGCCAGACCGTG<br>TCTCACGGCGTCAACGAGACAATTTACAACACGACGCTGAA<br>ATACGGCGATGTCGTGGGTGTGAATACTACCAAGTACCCCT<br>ATAGAGTCTGTAGCATGGCCCAGGGCACCGACCTGATCAG | 266 |

-continued

| Listing of Raw Sequences | | |
|---|---|---|
| Construct | Sequence* | SEQ ID NO: |
| | GTTCGAACGGAACATCGTTTGCACATCAATGAAGCCTATCA<br>ACGAAGACCTTGACGAGGGGATTATGGTGGTATACAAACG<br>GAATATCGTGGCTCACACCTTCAAAGTGCGAGTGTATCAGA<br>AGGTTCTGACATTCCGAAGAAGTTACGCCGGTCATCGTACC<br>ACCTATCTGCTGGGCTCCAACACTGAGTACGTGGCGCCCCC<br>AATGTGGGAAATCCACCACATCAACAGCCATTCACAGTGCT<br>ACTCTTCCTACAGCAGGGTGATTGCGGGCACAGTGTTTGTG<br>GCCTACCACAGGGACAGCTATGAGAACAAGACGATGCAGT<br>TGATGCCAGATTGTTACAGTAACACTCACAGTACACGGTAT<br>GTTACAGTTAAGGATCAGTGGCATTCACGCGGAAGCACAG<br>CACTGTATAGAGAGACCTCTAATTTGAATTGTATGGTAACT<br>ATCACTACTGCACGGAGCAAGTACCCTTATCATTTCTTTGCT<br>ACAAGCACGGGCGATGTGGTAGACATCAGCCCCTTCTATAA<br>TGGCACAAATCGGAACGCAAGCTATTTCGGGGAGAACGCC<br>GACAAGTTTTTCATTTTTCCTAATTATACTATTGTTTCTGACT<br>TCGGGAGACCCAACTCCGCCCTGGAAACTCACAGACTGGTT<br>GCGTTCCTCGAAAGAGCAGATTCTGTGATATCCTGGGACAT<br>TCAGGATGAAAAGAACGTCACGTGTCAGCTGACCTTCTGG<br>GAGGCCTCAGAGCGGACGATCCGGTCTGAGGCCGAGGACT<br>CTTACCACTTTAGCAGCGCCAAGTGCACCGCAACCTTCCTGT<br>CTAAAAAACAGGAAGTGAACATGTCCGATTCTGCTTTGGAC<br>TGCGTTCGCGATGAGGCCATCAACAAGCTTCAACAAATTTT<br>CAATACCTCCTACAATCAGACATATGAAAAATACGGAAACG<br>TGAGTGTCTTTGAAACCACCGGGGGCCTGGTCGTGTTCTGG<br>CAGGGTATCAAACAGAAGAGCCTGGTGGAACTGGAACGCC<br>TGGCCAACAGAAGCAGTTTGAACCTCACGCACAACCGGAC<br>AAAGAGGAGCACCGACGGAAACAATGCTACACACCTTTCC<br>AACATGGAGTCTGTCCACAATCTGGTTTATGCACAGCTTCA<br>GTTCACTTATGACACACTGCGGGGCTACATAAACAGGGCTC<br>TGGCACAGATAGCCGAGGCTTGCTGTGTGGACCAGCGGAG<br>AACCCTGGAGGTATTTAAAGAACTGTCTAAGATCAACCCCT<br>CTGCGATTCTGAGCGCTATTTACAACAAACCCATTGCCGCA<br>CGCTTCATGGGGGACGTCCTCGGTCTTGCCTCCTGTGTGAC<br>AATTAACCAGACGAGCGTGAAGGTGCTGCGAGATATGAAC<br>GTGAAGGAATCCCCTGGGCGGTGTTACAGTAGGCCTGTGG<br>TGATTTTCAACTTCGCCAACTCTTCCTGTGTCCAATACGGTC<br>AACTCGGTGAAGATAACGAGATTCTGCTGGGCAATCATCG<br>GACAGAAGAATGCCAGTTGCCAAGCCTTAAAATCTTTATTG<br>CAGGAAATTCAGCCTACGAGTACGTCGACTATCTGTTTAAA<br>AGAATGATTGATCTGAGCAGCATTTCCACTGTGGAC | |
| CMV gB ectodomain, V23 to P707 of SEQ ID NO: 1 (Towne strain) | VSSSSTRGTSATHSHHSSHTTSAAHSRSGSVSQRVTSSQTVSH<br>GVNETIYNTTLKYGDVVGVNTTKYPYRVCSMAQGTDLIRFER<br>NIVCTSMKPINEDLDEGIMVVYKRNIVAHTFKVRVYQKVLTFR<br>RSYAYIHTTYLLGSNTEYVAPPMWEIHHINSHSQCYSSYSRVIA<br>GTVFVAYHRDSYENKTMQLMPDDYSNTHSTRYVTVKDQWH<br>SRGSTWLYRETCNLNCMVTITTARSKYPYHFFATSTGDVVDIS<br>PFYNGTNRNASYFGENADKFFIFPNYTIVSDFGRPNSALETHRL<br>VAFLERADSVISWDIQDEKNVTCQLTFWEASERTIRSEAEDSY<br>HFSSAKMTATFLSKKQEVNMSDSALDCVRDEAINKLQQIFNT<br>SYNQTYEKYGNVSVFETTGGLVVFWQGIKQKSLVELERLANRS<br>SLNLTHNRTKRSTDGNNATHLSNMESVHNLVYAQLQFTYDTL<br>RGYINRALAQIAEAWCVDQRRTLEVFKELSKINPSAILSAIYNKP<br>IAARFMGDVLGLASCVTINQTSVKVLRDMNVKESPGRCYSRP<br>VVIFNFANSSYVQYGQLGEDNEILLGNHRTEECQLPSLKIFIAG<br>NSAYEYVDYLFKRMIDLSSISTVDSMIALDIDPLENTDFRVLELY<br>SQKELRSSNVFDLEEIMREFNSYKQRVKYVEDKVVDPLPP | 267 |
| Signal Sequence of wt HCMV gB (Towne) | MESRIWCLVVCVNLCIVCLGAA | 268 |
| GCN4 CC tri2 trimerization domain (Table 9) | KIEEILSKQYHIENEIARIKKLIG | 269 |
| | AAGATCGAGGAGATCCTGTCCAAGCAGTACCACATCGA<br>GAACGAGATCGCCCGCATCAAGAAGCTGATCGGC | 270 |
| T4 fibritin foldon domain | GYIPEAPRDGQAYVRKDGEWVLLSTFL | 271 |
| GCN4 (Table 9) | RIKQIEDKIEEILSKQYHIENEIARIKKLIG | 272 |

-continued

| Listing of Raw Sequences | | |
|---|---|---|
| Construct | Sequence* | SEQ ID NO: |
| GCN4 (Table 9) | KIYHIENEIARIKKLIG | 273 |
| C-terminal fusion sequence (Table 9) | LSAIGGYIPEAPRDGQAYVRKDGEWVLLSTFL | 274 |

*signal sequence M1 . . . A22 (SEQ ID NO: 268) removed

Embodiments of the Present Invention are Set Out in the Following Numbered Clauses C1. A polypeptide comprising at least one introduced amino acid mutation relative to the amino acid sequence of the wild-type HCMV glycoprotein B (gB), wherein the polypeptide comprises a conformation that is not an HCMV gB postfusion conformation.

C2. A polypeptide that binds to an HCMV gB prefusion-specific antibody.

C3. A polypeptide comprising at least one introduced amino acid mutation relative to the amino acid sequence of the wild-type HCMV glycoprotein B (gB), wherein the polypeptide is capable of binding to an HCMV gB prefusion-specific antibody.

C4. A polypeptide comprising at least one introduced amino acid mutation relative to the amino acid sequence of the wild-type HCMV glycoprotein B (gB), wherein the polypeptide is capable of binding to a bis(aryl)thiourea compound.

C5. The polypeptide according to clause C3, wherein the compound is N-{4-[({(1S)-1-[3,5-bis(trifluoromethyl) phenyl]ethyl}carbamothioyl)amino]phenyl}-1,3-thiazole-4-carboxamide.

C6. The polypeptide according to clause C1, wherein said polypeptide is characterized by structure coordinates comprising a root mean square deviation (RMSD) of conserved residue backbone atoms when superimposed on backbone atoms described by structural coordinates of Table 1A.

C7. A polypeptide comprising at least one amino acid mutation relative to the amino acid sequence of the wild-type HCMV gB polypeptide, wherein the amino acid mutation comprises a cysteine substitution.

C8. A polypeptide comprising at least one amino acid mutation relative to the amino acid sequence of the wild-type HCMV gB polypeptide, wherein the amino acid mutation comprises a mutation that allows a disulfide bond to form.

C9. A polypeptide comprising at least one amino acid mutation relative to the amino acid sequence of the wild-type HCMV gB polypeptide, wherein the amino acid mutation comprises an electrostatic mutation.

C10. A polypeptide comprising at least one amino acid mutation relative to the amino acid sequence of the wild-type HCMV gB polypeptide, wherein the amino acid mutation comprises a phenylalanine substitution.

C11. A polypeptide comprising at least one amino acid mutation relative to the amino acid sequence of the wild-type HCMV gB polypeptide, wherein the amino acid mutation comprises a leucine substitution.

C12. A polypeptide comprising at least one amino acid mutation relative to the amino acid sequence of the wild-type HCMV gB polypeptide, wherein the mutation stabilizes prefusion conformation of the polypeptide, and wherein the polypeptide specifically binds to an HCMV gB prefusion-specific antibody.

C13. A polypeptide comprising a cysteine at any one of the amino acid positions listed in column (ii) of Table 2, as compared to SEQ ID NO: 1.

C14. A polypeptide comprising an amino acid substitution at any one of the amino acid positions listed in column (ii) of Table 2, as compared to SEQ ID NO: 1.

C15. A polypeptide comprising the mutations Q98C and I653C according to the numbering of SEQ ID NO: 1.

C16. A polypeptide comprising the mutations T100C and S269C according to the numbering of SEQ ID NO: 1.

C17. A polypeptide comprising the mutations D217C and F584C according to the numbering of SEQ ID NO: 1.

C18. A polypeptide comprising the mutations Y242C and K710C according to the numbering of SEQ ID NO: 1.

C19. A polypeptide comprising the mutations Y242C and D714C according to the numbering of SEQ ID NO: 1.

C20. A polypeptide comprising the mutations S367C and L499C according to the numbering of SEQ ID NO: 1.

C21. A polypeptide comprising the mutations T372C and W506C according to the numbering of SEQ ID NO: 1.

C22. A polypeptide comprising the mutations S550C and D652C according to the numbering of SEQ ID NO: 1.

C23. A polypeptide comprising the mutations T608C and D679C according to the numbering of SEQ ID NO: 1.

C24. A polypeptide comprising the mutations K695C and K724C according to the numbering of SEQ ID NO: 1.

C25. A polypeptide comprising an amino acid sequence that is at least about 90% identical to the amino acid sequence set forth in any one of SEQ ID NOs: 1-43, wherein the polypeptide comprises a mutation as compared to SEQ ID NO: 1.

C26. The polypeptide according to any one of clauses C1-C25, wherein the polypeptide does not comprise a mutation at any one of the following positions: R562, P577, S587, Y588, G592, G595, L601/H605, C610, L612, P613, Y625, Y627, F632, and K633.

C27. The polypeptide according to any one of clauses C1-C26, wherein the polypeptide does not comprise the cytoplasmic tail of HCMV gB.

C28. The polypeptide according to any one of clauses C1-C26, wherein the polypeptide does not comprise the transmembrane region.

C29. The polypeptide according to any one of clauses C1-C26, wherein the polypeptide comprises the cytoplasmic tail of HCMV gB and does not comprise the transmembrane region.

C30. The polypeptide according to any one of clauses C1-C29, wherein the polypeptide does not contain an insect cell pattern of glycosylation.

C31. The polypeptide according to any one of clauses C1-C30, wherein the polypeptide exhibits improved solubility or stability, as compared to a native gB in a postfusion conformation.

C32. The polypeptide according to any one of clauses C1-C31, wherein the polypeptide is immunogenic.

C33. A nucleic acid encoding the polypeptide according to any one of clauses C1-C32.

C34. The nucleic acid according to clause C33, wherein the nucleic acid comprises a self-replicating RNA molecule.

C35. The nucleic acid according to clause C33, wherein the nucleic acid comprises a modified RNA molecule.

C36. A composition comprising a nucleic acid according to any one of clauses C33-C35.

C37. A composition comprising the polypeptide according to any one of clauses C1-C32, and further comprising a CMV antigen.

C38. The composition according to any one of clauses C36-C37, further comprising any one of the following polypeptides: gO, gH, gL, pUL128, pUL130, pUL131, and any combination thereof.

C39. A composition comprising the polypeptide according to any one of clauses C1-C32, and a diluent.

C40. A composition comprising the polypeptide according to any one of clauses C1-C32, and an adjuvant.

C41. The composition according to any one of clauses C36-C40, wherein the composition is immunogenic.

C42. The composition according to any one of clauses C36-C41, for use in eliciting an immune response against cytomegalovirus.

C43. A method of eliciting an immune response in a mammal, the method comprising administering to the mammal an effective amount of the polypeptide according to any one of clauses C1-C32.

C44. A method for reducing cytomegalovirus viral shedding in a mammal, the method comprising administering to the mammal an effective amount of the polypeptide according to any one of clauses C1-C32.

C45. A polypeptide comprising at least one amino acid mutation relative to the amino acid sequence of the wild-type HCMV gB, wherein the polypeptide comprises an amino acid sequence having at least 95% identity to the amino acid sequence set forth in any one of SEQ ID NOs: 1-43.

C46. A polypeptide comprising at least one amino acid mutation relative to the amino acid sequence of the wild-type HCMV gB, wherein the polypeptide comprises an amino acid sequence having at least 95% identity to the amino acid sequence set forth in any one of SEQ ID NOs: 1-106.

C47. A polypeptide comprising at least one amino acid mutation relative to the amino acid sequence of the wild-type HCMV gB, wherein the polypeptide comprises an amino acid sequence having at least 95% identity to the amino acid sequence set forth in any one of SEQ ID NOs: 47-106.

C48. A polypeptide comprising an amino acid sequence having at least 95% identity to the sequence set forth in SEQ ID NO: 57.

C49. A composition comprising at least one polynucleotide encoding an HCMV polypeptide selected from any one of gH, gL, UL128, UL130, and UL131; a polynucleotide encoding HCMV gB or a fragment thereof; a polynucleotide encoding pp65 or a fragment thereof; and a pharmaceutically acceptable carrier or dilent.

C50. A composition comprising at least one polynucleotide comprising a sequence having at least 95% identity to a sequence selected from any one of SEQ ID NOS: 141-210; a polynucleotide encoding a polypeptide comprising an amino acid sequence having at least 95% identity to the amino acid sequence set forth in any one of SEQ ID NOs: 1-106; and a pharmaceutically acceptable carrier or dilent.

C51. A composition comprising at least one polynucleotide comprising a sequence having at least 95% identity to a sequence selected from any one of SEQ ID NOS: 224-254; a polynucleotide encoding a polypeptide comprising an amino acid sequence selected from any one of the amino acid sequences set forth in any one of SEQ ID NOs: 1-106; and a pharmaceutically acceptable carrier or dilent.

C52. A composition comprising at least one polypeptide comprising an amino acid sequence having at least 95% identity to an amino acid sequence selected from any one of SEQ ID NOS: 211-223; a polypeptide comprising an amino acid sequence having at least 95% identity to the amino acid sequence set forth in any one of SEQ ID NOs: 1-106; and a pharmaceutically acceptable carrier or dilent.

C53. A polypeptide comprising at least one amino acid mutation relative to the amino acid sequence of the wild-type HCMV gB, wherein the polypeptide comprises the amino acid sequence set forth in any one of SEQ ID NOs: 1-43, wherein the polypeptide comprises a mutation as compared to SEQ ID NO: 1.

C54. A polypeptide comprising at least one amino acid mutation relative to the amino acid sequence of the wild-type HCMV gB, wherein the polypeptide comprises the amino acid sequence set forth in any one of SEQ ID NOs: 1-106, wherein the polypeptide comprises a mutation as compared to SEQ ID NO: 1.

C55. A polypeptide comprising at least one amino acid mutation relative to the amino acid sequence of the wild-type HCMV gB, wherein the polypeptide comprises the amino acid sequence set forth in any one of SEQ ID NOs: 47-106, wherein the polypeptide comprises a mutation as compared to SEQ ID NO: 1.

C56. A polypeptide comprising the sequence set forth in SEQ ID NO: 57.

C57. A composition comprising at least one polynucleotide encoding an HCMV polypeptide selected from any one of gH, gL, UL128, UL130, and UL131; a polynucleotide encoding HCMV gB or a fragment thereof; a polynucleotide encoding pp65 or a fragment thereof; and a pharmaceutically acceptable carrier or dilent.

C58. A composition comprising at least one polynucleotide comprising a sequence selected from any one of SEQ ID NOS: 141-210; a polynucleotide encoding a polypeptide comprising the amino acid sequence set forth in any one of SEQ ID NOs: 1-106; and a pharmaceutically acceptable carrier or dilent.

C59. A composition comprising at least one polynucleotide comprising a sequence selected from any one of SEQ ID NOS: 224-254; a polynucleotide encoding a polypeptide comprising the amino acid sequence set forth in any one of SEQ ID NOs: 1-106; and a pharmaceutically acceptable carrier or dilent.

C60. A composition comprising at least one polypeptide comprising a sequence selected from any one of SEQ ID NOS: 211-223; a polypeptide comprising the amino acid sequence set forth in any one of SEQ ID NOs: 1-106; and a pharmaceutically acceptable carrier or dilent.

C61. The composition according to any one of clause C49-C51 and C57-C59, wherein the polynucleotide is DNA.

C62. The composition according to any one of clause C49-C51 and C57-C59, wherein the polynucleotide is RNA.

C63. The composition according to any one of clause C49-C51 and C57-C59, wherein at least one polynucleotide comprises at least one chemical modification.

C64. The composition according to clause C61, wherein the chemical modification is selected from the group consisting of pseudouridine, N1-methylpseudouridine, N1-ethylpseudouridine, N1-ethylpseudouridine, 2-thiouridine, 4'-thiouridine, 5-methylcytosine, 2-thio-I-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-0-methyl uridine.

C65. The composition according to any one of clause C49-C51 and C57-C59, wherein the composition is formulated within a cationic lipid nanoparticle.

C66. A composition comprising at least one polynucleotide comprising a sequence selected from any one of SEQ ID NO: 153, SEQ ID NO: 156, SEQ ID NO: 155, SEQ ID NO: 157, SEQ ID NO: 210, SEQ ID NO: 152, and SEQ ID NO: 158; a polynucleotide encoding a polypeptide comprising the amino acid sequence set forth in any one of SEQ ID NOs: 1-106; and a pharmaceutically acceptable carrier or dilent.

C67. A composition comprising at least one polypeptide comprising a sequence selected from any one of SEQ ID NO: 211, SEQ ID NO: 213, SEQ ID NO: 214, SEQ ID NO: 215, SEQ ID NO: 216, and SEQ ID NO: 217; a polypeptide comprising the amino acid sequence set forth in any one of SEQ ID NOs: 1-106; and a pharmaceutically acceptable carrier or dilent.

C68. A polypeptide comprising an amino acid sequence set forth in any one of SEQ ID NOs: 1-106.

C69. The polypeptide according to clause C68, wherein the sequence comprises SEQ ID NO: 56.

C70. The polypeptide according to clause C68, wherein the sequence comprises SEQ ID NO: 57.

C71. The polypeptide according to clause C68, wherein the sequence comprises SEQ ID NO: 58.

C72. The polypeptide according to clause C68, wherein the sequence comprises SEQ ID NO: 75.

C73. A polynucleotide encoding a polypeptide comprising an amino acid sequence set forth in any one of SEQ ID NOs: 1-106.

C74. A composition comprising a polypeptide comprising the sequence set forth in any one of SEQ ID NOs:1-106; and a diluent.

C75. The composition according to clause C74, wherein the sequence does not comprise any one of SEQ ID NO: 59, SEQ ID NO: 75, SEQ ID NO: 76, SEQ ID NO: 71, SEQ ID NO: 52, SEQ ID NO: 96, and SEQ ID NO: 50.

C76. The composition according to clause C74, further comprising a polypeptide comprising any one sequence selected from SEQ ID NOS: 211-224.

C77. A composition comprising a polynucleotide encoding a polypeptide comprising the sequence selected from any one of SEQ ID NOs:1-106; and a diluent.

C78. The composition according to clause C77, further comprising a polynucleotide comprising a sequence selected from any one of SEQ ID NOS: 141-210.

C79. The composition according to clause C77, further comprising a polynucleotide comprising a sequence selected from any one of SEQ ID NOS: 224-254.

C80. A method of eliciting an immune response in a mammal, comprising administering an effective amount of a composition comprising a polypeptide comprising the sequence set forth in any one of SEQ ID NOs:1-106; and a diluent.

C81. A method of eliciting an immune response in a mammal, comprising administering an effective amount of a composition comprising a polynucleotide encoding a polypeptide comprising the sequence set forth in any one of SEQ ID NOs:1-106; and a diluent.

SEQUENCE LISTING

```
Sequence total quantity: 276
SEQ ID NO: 1            moltype = AA  length = 907
FEATURE                 Location/Qualifiers
REGION                  1..907
                        note = Synthetic amino acid sequence: Original HCMV gB
                         (Towne) sequence
source                  1..907
                        mol_type = protein
                        organism = synthetic construct
SEQUENCE: 1
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
```

-continued

```
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 2           moltype = AA  length = 907
FEATURE                Location/Qualifiers
REGION                 1..907
                       note = Synthetic amino acid sequence: gB-001 Q98C, G271C
                        sequence
source                 1..907
                       mol_type = protein
                       organism = synthetic construct
SEQUENCE: 2
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMACGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST CDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 3           moltype = AA  length = 907
FEATURE                Location/Qualifiers
REGION                 1..907
                       note = Synthetic amino acid sequence: gB-002 Q98C, I653C
                        sequence
source                 1..907
                       mol_type = protein
                       organism = synthetic construct
SEQUENCE: 3
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMACGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDCDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 4           moltype = AA  length = 907
FEATURE                Location/Qualifiers
REGION                 1..907
                       note = Synthetic amino acid sequence: gB-003 G99C, A267C
source                 1..907
                       mol_type = protein
                       organism = synthetic construct
SEQUENCE: 4
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQCT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFCTST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
```

```
SDEEENV                                                          907

SEQ ID NO: 5            moltype = AA  length = 907
FEATURE                 Location/Qualifiers
REGION                  1..907
                        note = Synthetic amino acid sequence: gB-004 T100C, A267C
source                  1..907
                        mol_type = protein
                        organism = synthetic construct
SEQUENCE: 5
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGC DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFCTST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                          907

SEQ ID NO: 6            moltype = AA  length = 907
FEATURE                 Location/Qualifiers
REGION                  1..907
                        note = Synthetic amino acid sequence: gB-005 T100C, S269C
source                  1..907
                        mol_type = protein
                        organism = synthetic construct
SEQUENCE: 6
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGC DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATCT GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                          907

SEQ ID NO: 7            moltype = AA  length = 907
FEATURE                 Location/Qualifiers
REGION                  1..907
                        note = Synthetic amino acid sequence: gB-006 T100C, L651C
source                  1..907
                        mol_type = protein
                        organism = synthetic construct
SEQUENCE: 7
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGC DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA CDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                          907

SEQ ID NO: 8            moltype = AA  length = 907
FEATURE                 Location/Qualifiers
```

```
REGION                  1..907
                        note = Synthetic amino acid sequence: gB-007 D217C, F584C
source                  1..907
                        mol_type = protein
                        organism = synthetic construct
SEQUENCE: 8
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDCYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNCANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 9            moltype = AA  length = 907
FEATURE                 Location/Qualifiers
REGION                  1..907
                        note = Synthetic amino acid sequence: gB-008 Y218C, A585C
source                  1..907
                        mol_type = protein
                        organism = synthetic construct
SEQUENCE: 9
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDCSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFCNSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 10           moltype = AA  length = 907
FEATURE                 Location/Qualifiers
REGION                  1..907
                        note = Synthetic amino acid sequence: gB-009 S219C, D654C
source                  1..907
                        mol_type = protein
                        organism = synthetic construct
SEQUENCE: 10
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYCN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDICPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 11           moltype = AA  length = 907
FEATURE                 Location/Qualifiers
REGION                  1..907
                        note = Synthetic amino acid sequence: gB-010 N220C, D652C
source                  1..907
                        mol_type = protein
```

```
                        organism = synthetic construct
SEQUENCE: 11
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSC THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LCIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 12           moltype = AA  length = 907
FEATURE                 Location/Qualifiers
REGION                  1..907
                        note = Synthetic amino acid sequence: gB-011 T221C, D652C
source                  1..907
                        mol_type = protein
                        organism = synthetic construct
SEQUENCE: 12
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN CHSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LCIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 13           moltype = AA  length = 907
FEATURE                 Location/Qualifiers
REGION                  1..907
                        note = Synthetic amino acid sequence: gB-012 W240C, G718C
source                  1..907
                        mol_type = protein
                        organism = synthetic construct
SEQUENCE: 13
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTC  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSCLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 14           moltype = AA  length = 907
FEATURE                 Location/Qualifiers
REGION                  1..907
                        note = Synthetic amino acid sequence: gB-013 Y242C, K710C
source                  1..907
                        mol_type = protein
                        organism = synthetic construct
SEQUENCE: 14
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
```

-continued

```
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LCRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLC GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 15          moltype = AA  length = 907
FEATURE                Location/Qualifiers
REGION                 1..907
                       note = Synthetic amino acid sequence: gB-014 Y242C, D714C
source                 1..907
                       mol_type = protein
                       organism = synthetic construct
SEQUENCE: 15
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LCRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDCLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 16          moltype = AA  length = 907
FEATURE                Location/Qualifiers
REGION                 1..907
                       note = Synthetic amino acid sequence: gB-015 S269C, I653C
source                 1..907
                       mol_type = protein
                       organism = synthetic construct
SEQUENCE: 16
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATCT GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDCDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 17          moltype = AA  length = 907
FEATURE                Location/Qualifiers
REGION                 1..907
                       note = Synthetic amino acid sequence: gB-016 G271C, P614C
source                 1..907
                       mol_type = protein
                       organism = synthetic construct
SEQUENCE: 17
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST CDVVDISPFY NGTNRNASYF GENADKFFIF  300
PNYTIVSDFG RPNSALETHR LVAFLERADS VISWDIQDEK NVTCQLTFWE ASERTIRSEA  360
```

-continued

```
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLCSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 18          moltype = AA  length = 907
FEATURE                Location/Qualifiers
REGION                 1..907
                       note = Synthetic amino acid sequence: gB-017 S367C, L499C
source                 1..907
                       mol_type = protein
                       organism = synthetic construct
SEQUENCE: 18
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFCSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRACA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 19          moltype = AA  length = 907
FEATURE                Location/Qualifiers
REGION                 1..907
                       note = Synthetic amino acid sequence: gB-018 T372C, W506C
source                 1..907
                       mol_type = protein
                       organism = synthetic construct
SEQUENCE: 19
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MCATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEACCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 20          moltype = AA  length = 907
FEATURE                Location/Qualifiers
REGION                 1..907
                       note = Synthetic amino acid sequence: gB-019 F541C, Q669C
source                 1..907
                       mol_type = protein
                       organism = synthetic construct
SEQUENCE: 20
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
CMGDVLGLAS CVTINQTSVK VLRDMNVKES PGRCYSRPVV IFNFANSSYV QYGQLGEDNE  600
```

-continued

```
ILLGNHRTEE CQLPSLKIFI AGNSAYEYVD YLFKRMIDLS SISTVDSMIA LDIDPLENTD  660
FRVLELYSCK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 21          moltype = AA  length = 907
FEATURE                Location/Qualifiers
REGION                 1..907
                       note = Synthetic amino acid sequence: gB-020 L548C, A650C
source                 1..907
                       mol_type = protein
                       organism = synthetic construct
SEQUENCE: 21
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGCAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIC LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 22          moltype = AA  length = 907
FEATURE                Location/Qualifiers
REGION                 1..907
                       note = Synthetic amino acid sequence: gB-021 A549C, I653C
source                 1..907
                       mol_type = protein
                       organism = synthetic construct
SEQUENCE: 22
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLCS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDCDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 23          moltype = AA  length = 907
FEATURE                Location/Qualifiers
REGION                 1..907
                       note = Synthetic amino acid sequence: gB-022 S550C, D652C
source                 1..907
                       mol_type = protein
                       organism = synthetic construct
SEQUENCE: 23
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAC CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LCIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
```

-continued

```
TNEQAYQMLL ALVRLDAEQR AQQNGTDSLD GQTGTQDKGQ KPNLLDRLRH RKNGYRHLKD  900
SDEEENV                                                            907

SEQ ID NO: 24          moltype = AA  length = 907
FEATURE                Location/Qualifiers
REGION                 1..907
                       note = Synthetic amino acid sequence: gB-023 G604C, F661C
source                 1..907
                       mol_type = protein
                       organism = synthetic construct
SEQUENCE: 24
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLCNHRTEE CQLPSLKIFI AGNSAYEYVD YLFKRMIDLS SISTVDSMIA LDIDPLENTD  660
CRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 25          moltype = AA  length = 907
FEATURE                Location/Qualifiers
REGION                 1..907
                       note = Synthetic amino acid sequence: gB-024 N605C, E665C
source                 1..907
                       mol_type = protein
                       organism = synthetic construct
SEQUENCE: 25
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGCHRTEE CQLPSLKIFI AGNSAYEYVD YLFKRMIDLS SISTVDSMIA LDIDPLENTD  660
FRVLCLYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 26          moltype = AA  length = 907
FEATURE                Location/Qualifiers
REGION                 1..907
                       note = Synthetic amino acid sequence: gB-025 R607C, S675C
source                 1..907
                       mol_type = protein
                       organism = synthetic construct
SEQUENCE: 26
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHCTEE CQLPSLKIFI AGNSAYEYVD YLFKRMIDLS SISTVDSMIA LDIDPLENTD  660
FRVLELYSQK ELRSCNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 27          moltype = AA  length = 907
```

-continued

```
FEATURE                Location/Qualifiers
REGION                 1..907
                       note = Synthetic amino acid sequence: gB-026 T608C, D679C
source                 1..907
                       mol_type = protein
                       organism = synthetic construct
SEQUENCE: 27
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRCEE CQLPSLKIFI AGNSAYEYVD YLFKRMIDLS SISTVDSMIA LDIDPLENTD  660
FRVLELYSQK ELRSSNVFCL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                              907

SEQ ID NO: 28          moltype = AA  length = 907
FEATURE                Location/Qualifiers
REGION                 1..907
                       note = Synthetic amino acid sequence: gB-027 E609C, F678C
source                 1..907
                       mol_type = protein
                       organism = synthetic construct
SEQUENCE: 28
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTCE CQLPSLKIFI AGNSAYEYVD YLFKRMIDLS SISTVDSMIA LDIDPLENTD  660
FRVLELYSQK ELRSSNVCDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                              907

SEQ ID NO: 29          moltype = AA  length = 907
FEATURE                Location/Qualifiers
REGION                 1..907
                       note = Synthetic amino acid sequence: gB-028 R673C, S674C
source                 1..907
                       mol_type = protein
                       organism = synthetic construct
SEQUENCE: 29
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELCCSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                              907

SEQ ID NO: 30          moltype = AA  length = 907
FEATURE                Location/Qualifiers
REGION                 1..907
                       note = Synthetic amino acid sequence: gB-029 N676C, V677C
source                 1..907
```

```
                         mol_type = protein
                         organism = synthetic construct
SEQUENCE: 30
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSCCFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 31            moltype = AA  length = 907
FEATURE                  Location/Qualifiers
REGION                   1..907
                         note = Synthetic amino acid sequence: gB-030 L680C, E681C
source                   1..907
                         mol_type = protein
                         organism = synthetic construct
SEQUENCE: 31
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDC CEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 32            moltype = AA  length = 907
FEATURE                  Location/Qualifiers
REGION                   1..907
                         note = Synthetic amino acid sequence: gB-031 I683C, M684C
source                   1..907
                         mol_type = protein
                         organism = synthetic construct
SEQUENCE: 32
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EECCREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 33            moltype = AA  length = 907
FEATURE                  Location/Qualifiers
REGION                   1..907
                         note = Synthetic amino acid sequence: gB-032 F687C, N688C
source                   1..907
                         mol_type = protein
                         organism = synthetic construct
SEQUENCE: 33
MESRIWCLVV CVNLCIVCLG AAVSSSSTRG TSATHSHHSS HTTSAAHSRS GSVSQRVTSS  60
```

-continued

```
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMRECCSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 34           moltype = AA  length = 907
FEATURE                 Location/Qualifiers
REGION                  1..907
                        note = Synthetic amino acid sequence: gB-033 Y690C, K691C
source                  1..907
                        mol_type = protein
                        organism = synthetic construct
SEQUENCE: 34
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSC CQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 35           moltype = AA  length = 907
FEATURE                 Location/Qualifiers
REGION                  1..907
                        note = Synthetic amino acid sequence: gB-034 K695C, K724C
source                  1..907
                        mol_type = protein
                        organism = synthetic construct
SEQUENCE: 35
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVCYVEDK VVDPLPPYLK GLDDLMSGLG  720
AAGCAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 36           moltype = AA  length = 907
FEATURE                 Location/Qualifiers
REGION                  1..907
                        note = Synthetic amino acid sequence: gB-035 T746C, F747C
source                  1..907
                        mol_type = protein
                        organism = synthetic construct
SEQUENCE: 36
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
```

```
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVACCLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 37          moltype = AA  length = 907
FEATURE                Location/Qualifiers
REGION                 1..907
                       note = Synthetic amino acid sequence: gB-036 K749C, N750C
source                 1..907
                       mol_type = protein
                       organism = synthetic construct
SEQUENCE: 37
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLCC PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 38          moltype = AA  length = 907
FEATURE                Location/Qualifiers
REGION                 1..907
                       note = Synthetic amino acid sequence: gB-037 K670L
source                 1..907
                       mol_type = protein
                       organism = synthetic construct
SEQUENCE: 38
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQL ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 39          moltype = AA  length = 907
FEATURE                Location/Qualifiers
REGION                 1..907
                       note = Synthetic amino acid sequence: gB-038 K670F
source                 1..907
                       mol_type = protein
                       organism = synthetic construct
SEQUENCE: 39
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
```

-continued

```
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQF ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 40          moltype = AA  length = 907
FEATURE                Location/Qualifiers
REGION                 1..907
                       note = Synthetic amino acid sequence: gB-039 R673L
source                 1..907
                       mol_type = protein
                       organism = synthetic construct
SEQUENCE: 40
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELLSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 41          moltype = AA  length = 907
FEATURE                Location/Qualifiers
REGION                 1..907
                       note = Synthetic amino acid sequence: gB-040 R673F
source                 1..907
                       mol_type = protein
                       organism = synthetic construct
SEQUENCE: 41
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELFSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 42          moltype = AA  length = 907
FEATURE                Location/Qualifiers
REGION                 1..907
                       note = Synthetic amino acid sequence: gB-041 K691L
source                 1..907
                       mol_type = protein
                       organism = synthetic construct
SEQUENCE: 42
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY LQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
```

-continued

```
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 43           moltype = AA  length = 907
FEATURE                 Location/Qualifiers
REGION                  1..907
                        note = Synthetic amino acid sequence: gB-042 K691F
source                  1..907
                        mol_type = protein
                        organism = synthetic construct
SEQUENCE: 43
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY FQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 44           moltype = AA  length = 630
FEATURE                 Location/Qualifiers
source                  1..630
                        mol_type = protein
                        organism = Human cytomegalovirus
SEQUENCE: 44
YGDVVGVNTT KYPYRVCSMA QGTDLIRFER NIICTSMKPI NEDLDEGIMV VYKRNIVAHT  60
FKVRVYQKVL TFRRSYAGHR TTYLLGSNTE YVAPPMWEIH HINKFAQCYS SYSRVIGGTV  120
FVAYHRDSHE NKTMQLIPDD YSNTHSTRYV TVKDQWHSRG STATHRETCN LNCMLTITTA  180
RSKYPYHFFA TSTGDVVYIS PFYNGTNRNA SYFGENADKF FIFPNYTIVS DFGRPNAAPE  240
THRLVAFLER ADSVISWDIQ DEKNVTCQLT FWEASERTIR SEAEDSYHFS SAKMTATFLS  300
KKQEVNMSDS ALDCVRDEAI NKLQQIFNTS YNQTYEKYGN VSVFETSGGL VVFWQGIKQK  360
SLVELERLAN RSSLNITHDD DKKSTSDNNT THLSSMESVH NLVYAQLQFT YDTLRGYINR  420
ALAQIAEAWC VDQRRTLEVF KELSKINPSA ILSAIYNKPI AARFMGDVLG LASCVTINQT  480
SVKVLRDMNV KESPGRCYSR PVVIFNFANS SYVQYGQLGE DNEILLGNHR TEECQLPSLK  540
IFIAGNSAYE YVDYLFKRMI DLSSISTVDS MIALDIDPLE NTDFRVLELY SQKELRSSNV  600
FDLEEIMREF NSYKQRVKYV EDKVVDPLPP                                   630

SEQ ID NO: 45           moltype = AA  length = 705
FEATURE                 Location/Qualifiers
REGION                  1..705
                        note = Synthetic sequence: gB705
source                  1..705
                        mol_type = protein
                        organism = synthetic construct
SEQUENCE: 45
MESRIWCLVV CVNLCIVCLG AVVSSSSTSH ATSSAHNGSH TSRTTSAQTR SVSSQHVTSS  60
EAVSHRANET IYNTTLKYGD VVGVNTTKYP YRVCSMAQGT DLIRFERNIV CTPMKPINED  120
LDEGIMVVYK RNIVAHTFKV RVYQKVLTFR RSYAGHRTTY LLGSNTEYVA PPMWEIHHIN  180
RHSQCYSSYS RVIAGTVFVA YHRDSYENKT MQLMLDDYSN THSTRYVTVK DQWHSRGSTA  240
LYRETCNLNC MVTITTARSK YPYHFFATST GDVVDISPFY NGTNRNTSYF GENADKFFIF  300
PNYTIVSDFG RANSAPETHR LVAFLERADS VISWDIQDEK NVTCQLTFWE ASERTIRSEA  360
EDSYHFSSAK MTATFLSKKQ EVNMSDPVLD CVRDQALNKL QQIFNASYNQ TYEKYGNVSV  420
FETTGGLVVF WQGIKQKSLL ELERLANSSG VNSTRATKAS TGNTTTLSLE SESVRNVLYA  480
QLQFTYDTLR SYINRALAQI AEAWCVDQRR TLEVFKELSK INPSAILSAI YNKPIAARFM  540
GDVLGLASCV TINQTSVKVL RDMNVKESPG RCYSRPVVIF NFVNSSYVQY GQLGEDNEIL  600
LGNHRTEECQ FPSLKIFIAG NSAYEYVDYL FKRMIDLSSI STVDSMIALD IDPLENTDFR  660
VLELYSQKEL RSSNVFDLEE IMREFNSYKQ RVKYVEDKVV DPLPP                  705

SEQ ID NO: 46           moltype = AA  length = 907
FEATURE                 Location/Qualifiers
source                  1..907
                        mol_type = protein
                        organism = Human cytomegalovirus
SEQUENCE: 46
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
```

-continued

```
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GRTGTQDKGQ KPNLLDRLRH RKNGYRHLKD  900
SDEEENV                                                            907
```

```
SEQ ID NO: 47          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 47
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSCAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTC  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907
```

```
SEQ ID NO: 48          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 48
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMACGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLECTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907
```

```
SEQ ID NO: 49          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 49
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGC DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTACSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
```

```
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 50          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 50
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGC DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPCENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 51          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 51
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGC DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLECTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 52          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 52
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPCNED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNCSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
```

-continued

```
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 53          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 53
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPCNED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTCYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 54          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 54
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSCAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GCDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 55          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 55
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LCGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLCSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907
```

-continued

```
SEQ ID NO: 56           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 56
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDCYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANCSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 57           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 57
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDCYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSCV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 58           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 58
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYCN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNCANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 59           moltype = AA  length = 907
FEATURE                 Location/Qualifiers
REGION                  1..907
                        note = Synthetic amino acid sequence
```

-continued source 1..907
mol_type = protein
organism = synthetic construct
SEQUENCE: 59
MESRIWCLVV CVNLCIVCLG AAVSSSSTRG TSATHSHHSS HTTSAAHSRS GSVSQRVTSS 60
QTVSHGVNET IYNTTLKYGD VVGVNTTKYP YRVCSMAQGT DLIRFERNIV CTSMKPINED 120
LDEGIMVVYK RNIVAHTFKV RVYQKVLTFR RSYAYIHTTY LLGSNTEYVA PPMWEIHHIN 180
SHSQCYSSYS RVIAGTVFVA YHRDSYENKT MQLMPDDYCN THSTRYVTVK DQWHSRGSTW 240
LYRETCNLNC MVTITTARSK YPYHFFATST GDVVDISPFY NGTNRNASYF GENADKFFIF 300
PNYTIVSDFG RPNSALETHR LVAFLERADS VISWDIQDEK NVTCQLTFWE ASERTIRSEA 360
EDSYHFSSAK MTATFLSKKQ EVNMSDSALD CVRDEAINKL QQIFNTSYNQ TYEKYGNVSV 420
FETTGGLVVF WQGIKQKSLV ELERLANRSS LNLTHNRTKR STDGNNATHL SNMESVHNLV 480
YAQLQFTYDT LRGYINRALA QIAEAWCVDQ RRTLEVFKEL SKINPSAILS AIYNKPIAAR 540
FMGDVLGLAS CVTINQTSVK VLRDMNVKES PGRCYSRPVV IFNFCNSSYV QYGQLGEDNE 600
ILLGNHRTEE CQLPSLKIFI AGNSAYEYVD YLFKRMIDLS SISTVDSMIA LDIDPLENTD 660
FRVLELYSQK ELRSSNVFDL EEIMREFNSY KQRVKYVEDK VVDPLPPYLK GLDDLMSGLG 720
AAGKAVGVAI GAVGGAVASV VEGVATFLKN PFGAFTIILV AIAVVIIIYL IYTRQRRLCM 780
QPLQNLFPYL VSADGTTVTS GNTKDTSLQA PPSYEESVYN SGRKGPGPPS SDASTAAPPY 840
TNEQAYQMLL ALVRLDAEQR AQQNGTDSLD GQTGTQDKGQ KPNLLDRLRH RKNGYRHLKD 900
SDEEENV 907

SEQ ID NO: 60 moltype = AA length = 907
FEATURE Location/Qualifiers
REGION 1..907
note = Synthetic amino acid sequence
source 1..907
mol_type = protein
organism = synthetic construct
SEQUENCE: 60
MESRIWCLVV CVNLCIVCLG AAVSSSSTRG TSATHSHHSS HTTSAAHSRS GSVSQRVTSS 60
QTVSHGVNET IYNTTLKYGD VVGVNTTKYP YRVCSMAQGT DLIRFERNIV CTSMKPINED 120
LDEGIMVVYK RNIVAHTFKV RVYQKVLTFR RSYAYIHTTY LLGSNTEYVA PPMWEIHHIN 180
SHSQCYSSYS RVIAGTVFVA YHRDSYENKT MQLMPDDYCN THSTRYVTVK DQWHSRGSTW 240
LYRETCNLNC MVTITTARSK YPYHFFATST GDVVDISPFY NGTNRNASYF GENADKFFIF 300
PNYTIVSDFG RPNSALETHR LVAFLERADS VISWDIQDEK NVTCQLTFWE ASERTIRSEA 360
EDSYHFSSAK MTATFLSKKQ EVNMSDSALD CVRDEAINKL QQIFNTSYNQ TYEKYGNVSV 420
FETTGGLVVF WQGIKQKSLV ELERLANRSS LNLTHNRTKR STDGNNATHL SNMESVHNLV 480
YAQLQFTYDT LRGYINRALA QIAEAWCVDQ RRTLEVFKEL SKINPSAILS AIYNKPIAAR 540
FMGDVLGLAS CVTINQTSVK VLRDMNVKES PGRCYSRPVV IFNFACSSYV QYGQLGEDNE 600
ILLGNHRTEE CQLPSLKIFI AGNSAYEYVD YLFKRMIDLS SISTVDSMIA LDIDPLENTD 660
FRVLELYSQK ELRSSNVFDL EEIMREFNSY KQRVKYVEDK VVDPLPPYLK GLDDLMSGLG 720
AAGKAVGVAI GAVGGAVASV VEGVATFLKN PFGAFTIILV AIAVVIIIYL IYTRQRRLCM 780
QPLQNLFPYL VSADGTTVTS GNTKDTSLQA PPSYEESVYN SGRKGPGPPS SDASTAAPPY 840
TNEQAYQMLL ALVRLDAEQR AQQNGTDSLD GQTGTQDKGQ KPNLLDRLRH RKNGYRHLKD 900
SDEEENV 907

SEQ ID NO: 61 moltype = AA length = 907
FEATURE Location/Qualifiers
REGION 1..907
note = Synthetic amino acid sequence
source 1..907
mol_type = protein
organism = synthetic construct
SEQUENCE: 61
MESRIWCLVV CVNLCIVCLG AAVSSSSTRG TSATHSHHSS HTTSAAHSRS GSVSQRVTSS 60
QTVSHGVNET IYNTTLKYGD VVGVNTTKYP YRVCSMAQGT DLIRFERNIV CTSMKPINED 120
LDEGIMVVYK RNIVAHTFKV RVYQKVLTFR RSYAYIHTTY LLGSNTEYVA PPMWEIHHIN 180
SHSQCYSSYS RVIAGTVFVA YHRDSYENKT MQLMPDDYSC THSTRYVTVK DQWHSRGSTW 240
LYRETCNLNC MVTITTARSK YPYHFFATST GDVVDISPFY NGTNRNASYF GENADKFFIF 300
PNYTIVSDFG RPNSALETHR LVAFLERADS VISWDIQDEK NVTCQLTFWE ASERTIRSEA 360
EDSYHFSSAK MTATFLSKKQ EVNMSDSALD CVRDEAINKL QQIFNTSYNQ TYEKYGNVSV 420
FETTGGLVVF WQGIKQKSLV ELERLANRSS LNLTHNRTKR STDGNNATHL SNMESVHNLV 480
YAQLQFTYDT LRGYINRALA QIAEAWCVDQ RRTLEVFKEL SKINPSAILS AIYNKPIAAR 540
FMGDVLGLAS CVTINQTSVK VLRDMNVKES PGRCYSRPVV IFNFANSSYV QYGQLGEDNE 600
ILLGNHRTEE CQLPSLKIFI AGNSAYEYVD YLFKRMIDLS SISTVDSMIA LDIDPLENCD 660
FRVLELYSQK ELRSSNVFDL EEIMREFNSY KQRVKYVEDK VVDPLPPYLK GLDDLMSGLG 720
AAGKAVGVAI GAVGGAVASV VEGVATFLKN PFGAFTIILV AIAVVIIIYL IYTRQRRLCM 780
QPLQNLFPYL VSADGTTVTS GNTKDTSLQA PPSYEESVYN SGRKGPGPPS SDASTAAPPY 840
TNEQAYQMLL ALVRLDAEQR AQQNGTDSLD GQTGTQDKGQ KPNLLDRLRH RKNGYRHLKD 900
SDEEENV 907

SEQ ID NO: 62 moltype = AA length = 907
FEATURE Location/Qualifiers
REGION 1..907
note = Synthetic amino acid sequence
source 1..907
mol_type = protein
organism = synthetic construct
SEQUENCE: 62

```
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THCTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENCD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 63           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 63
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTC  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GCVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 64           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 64
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTC  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGCAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 65           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 65
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
```

```
LCRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGCAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 66          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 66
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LCRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI CAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 67          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 67
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTACSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPCENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 68          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 68
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATCT GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
```

-continued

```
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPCENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 69          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 69
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATCT GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLECTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 70          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 70
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GCVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLCSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 71          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 71
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDCVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYCD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
```

-continued

```
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 72          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 72
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFCE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIC LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 73          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 73
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFCSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALC QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 74          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 74
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFCSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QICEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907
```

```
SEQ ID NO: 75          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 75
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAC MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA CIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 76          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 76
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SCINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EECMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 77          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 77
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKCNPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EECMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 78          moltype = AA  length = 907
FEATURE                Location/Qualifiers
REGION                 1..907
```

```
                        note = Synthetic amino acid sequence
source                  1..907
                        mol_type = protein
                        organism = synthetic construct
SEQUENCE: 78
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKCNPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEICREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 79           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 79
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKICPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEICREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 80           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 80
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINCSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL CEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 81           moltype = AA  length = 907
FEATURE                 Location/Qualifiers
REGION                  1..907
                        note = Synthetic amino acid sequence
source                  1..907
                        mol_type = protein
                        organism = synthetic construct
```

```
SEQUENCE: 81
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAC  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDC EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 82          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 82
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
CMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDC EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 83          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 83
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGCAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDCLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 84          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 84
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
```

```
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLCS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLECTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 85          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 85
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAC CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDCLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 86          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 86
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAC CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLCNTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 87          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 87
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
```

-continued

```
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV CYGQLGEDNE  600
ILLGNHRTEE CQLPSLKIFI AGNSAYEYVD YLFKRMIDLS SISTVDSMIA LDIDPLENTD  660
FRVLELYCQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 88          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 88
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILCGNHRTEE CQLPSLKIFI AGNSAYEYVD YLFKRMIDLS SISTVDSMIA LDIDPLENTD  660
FRVLELCSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 89          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 89
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLCNHRTEE CQLPSLKIFI AGNSAYEYVD YLFKRMIDLS SISTVDSMIA LDIDPLENTD  660
FRVLELYSQK ECRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 90          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 90
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHCTEE CQLPSLKIFI AGNSAYEYVD YLFKRMIDLS SISTVDSMIA LDIDPLENTD  660
```

-continued

```
FRVLELYSQK ELRSSNVFDL EEIMREFCSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 91           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 91
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRCEE CQLPSLKIFI AGNSAYEYVD YLFKRMIDLS SISTVDSMIA LDIDPLENTD  660
FRVLELYSQK ELRSSNVFDL EEIMREFNSY KCRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 92           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 92
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTCE CQLPSLKIFI AGNSAYEYVD YLFKRMIDLS SISTVDSMIA LDIDPLENTD  660
FRVLELYSQK ELRSSNVFDL EEIMREFNSY CQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 93           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 93
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEC CQLPSLKIFI AGNSAYEYVD YLFKRMIDLS SISTVDSMIA LDIDPLENTD  660
FRVLELYSQK ELRCSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
```

```
SDEEENV                                                               907

SEQ ID NO: 94          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 94
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEC CQLPSLKIFI AGNSAYEYVD YLFKRMIDLS SISTVDSMIA LDIDPLENTD  660
FRVLELYSQK ELRSCNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                               907

SEQ ID NO: 95          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 95
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CCLPSLKIFI AGNSAYEYVD YLFKRMIDLS SISTVDSMIA LDIDPLENTD  660
FRCLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                               907

SEQ ID NO: 96          moltype = AA  length = 907
FEATURE                Location/Qualifiers
REGION                 1..907
                       note = Synthetic amino acid sequence
source                 1..907
                       mol_type = protein
                       organism = synthetic construct
SEQUENCE: 96
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGACASV VEGVATFLKN PFGACTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                               907

SEQ ID NO: 97          moltype = AA  length = 907
FEATURE                Location/Qualifiers
```

```
REGION                  1..907
                        note = Synthetic amino acid sequence
source                  1..907
                        mol_type = protein
                        organism = synthetic construct
SEQUENCE: 97
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV CEGVATFLKN PFGCFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 98           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 98
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV CEGVATFLKN PFGACTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 99           moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 99
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFSL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                           907

SEQ ID NO: 100          moltype = AA  length = 907
FEATURE                 Location/Qualifiers
REGION                  1..907
                        note = Synthetic amino acid sequence
source                  1..907
                        mol_type = protein
```

```
                         organism = synthetic construct
SEQUENCE: 100
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFNL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 101           moltype = AA  length = 907
FEATURE                  Location/Qualifiers
REGION                   1..907
                         note = Synthetic amino acid sequence
source                   1..907
                         mol_type = protein
                         organism = synthetic construct
SEQUENCE: 101
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL ESIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 102           moltype = AA  length = 907
FEATURE                  Location/Qualifiers
REGION                   1..907
                         note = Synthetic amino acid sequence
source                   1..907
                         mol_type = protein
                         organism = synthetic construct
SEQUENCE: 102
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EQIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 103           moltype = AA  length = 907
FEATURE                  Location/Qualifiers
REGION                   1..907
                         note = Synthetic amino acid sequence
source                   1..907
                         mol_type = protein
                         organism = synthetic construct
SEQUENCE: 103
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
```

```
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMRSFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 104          moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 104
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMRQFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 105          moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 105
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPIPED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 106          moltype = AA  length = 907
FEATURE                 Location/Qualifiers
REGION                  1..907
                        note = Synthetic amino acid sequence
source                  1..907
                        mol_type = protein
                        organism = synthetic construct
SEQUENCE: 106
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
```

-continued

```
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVPSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 107         moltype = AA  length = 630
FEATURE                Location/Qualifiers
REGION                 1..630
                       note = 5CXF:A[PD]BID[CH]AIN&QUENCE
source                 1..630
                       mol_type = protein
                       organism = synthetic construct
SEQUENCE: 107
YGDVVGVNTT KYPYRVCSMA QGTDLIRFER NIICTSMKPI NEDLDEGIMV VYKRNIVAHT  60
FKVRVYQKVL TFRRSYAGHR TTYLLGSNTE YVAPPMWEIH HINKFAQCYS SYSRVIGGTV  120
FVAYHRDSHE NKTMQLIPDD YSNTHSTRYV TVKDQWHSRG STATHRETCN LNCMLTITTA  180
RSKYPYHFFA TSTGDVVYIS PFYNGTNRNA SYFGENADKF FIFPNYTIVS DFGRPNAAPE  240
THRLVAFLER ADSVISWDIQ DEKNVTCQLT FWEASERTIR SEAEDSYHFS SAKMTATFLS  300
KKQEVNMSDS ALDCVRDEAI NKLQQIFNTS YNQTYEKYGN VSVFETSGGL VVFWQGIKQK  360
SLVELERLAN RSSLNITHDD DDKSTSDNNT THLSSMESVH NLVYAQLQFT YDTLRGYINR  420
ALAQIAEAWC VDQRRTLEVF KELSKINPSA ILSAIYNKPI AARFMGDVLG LASCVTINQT  480
SVKVLRDMNV KESPGRCYSR PVVIFNFANS SYVQYGQLGE DNEILLGNHR TEECQLPSLK  540
IFIAGNSAYE YVDYLFKRMI DLSSISTVDS MIALDIDPLE NTDFRVLELY SQKELRSSNV  600
FDLEEIMREF NSYKQRVKYV EDKVVDPLPP                                   630

SEQ ID NO: 108         moltype = AA  length = 630
FEATURE                Location/Qualifiers
REGION                 1..630
                       note = 5CXF:B[PD]BID[CH]AIN&QUENCE
source                 1..630
                       mol_type = protein
                       organism = synthetic construct
SEQUENCE: 108
YGDVVGVNTT KYPYRVCSMA QGTDLIRFER NIICTSMKPI NEDLDEGIMV VYKRNIVAHT  60
FKVRVYQKVL TFRRSYAGHR TTYLLGSNTE YVAPPMWEIH HINKFAQCYS SYSRVIGGTV  120
FVAYHRDSHE NKTMQLIPDD YSNTHSTRYV TVKDQWHSRG STATHRETCN LNCMLTITTA  180
RSKYPYHFFA TSTGDVVYIS PFYNGTNRNA SYFGENADKF FIFPNYTIVS DFGRPNAAPE  240
THRLVAFLER ADSVISWDIQ DEKNVTCQLT FWEASERTIR SEAEDSYHFS SAKMTATFLS  300
KKQEVNMSDS ALDCVRDEAI NKLQQIFNTS YNQTYEKYGN VSVFETSGGL VVFWQGIKQK  360
SLVELERLAN RSSLNITHDD DDKSTSDNNT THLSSMESVH NLVYAQLQFT YDTLRGYINR  420
ALAQIAEAWC VDQRRTLEVF KELSKINPSA ILSAIYNKPI AARFMGDVLG LASCVTINQT  480
SVKVLRDMNV KESPGRCYSR PVVIFNFANS SYVQYGQLGE DNEILLGNHR TEECQLPSLK  540
IFIAGNSAYE YVDYLFKRMI DLSSISTVDS MIALDIDPLE NTDFRVLELY SQKELRSSNV  600
FDLEEIMREF NSYKQRVKYV EDKVVDPLPP                                   630

SEQ ID NO: 109         moltype = AA  length = 630
FEATURE                Location/Qualifiers
REGION                 1..630
                       note = 5CXF:C[PD]BID[CH]AIN&QUENCE
source                 1..630
                       mol_type = protein
                       organism = synthetic construct
SEQUENCE: 109
YGDVVGVNTT KYPYRVCSMA QGTDLIRFER NIICTSMKPI NEDLDEGIMV VYKRNIVAHT  60
FKVRVYQKVL TFRRSYAGHR TTYLLGSNTE YVAPPMWEIH HINKFAQCYS SYSRVIGGTV  120
FVAYHRDSHE NKTMQLIPDD YSNTHSTRYV TVKDQWHSRG STATHRETCN LNCMLTITTA  180
RSKYPYHFFA TSTGDVVYIS PFYNGTNRNA SYFGENADKF FIFPNYTIVS DFGRPNAAPE  240
THRLVAFLER ADSVISWDIQ DEKNVTCQLT FWEASERTIR SEAEDSYHFS SAKMTATFLS  300
KKQEVNMSDS ALDCVRDEAI NKLQQIFNTS YNQTYEKYGN VSVFETSGGL VVFWQGIKQK  360
SLVELERLAN RSSLNITHDD DDKSTSDNNT THLSSMESVH NLVYAQLQFT YDTLRGYINR  420
ALAQIAEAWC VDQRRTLEVF KELSKINPSA ILSAIYNKPI AARFMGDVLG LASCVTINQT  480
SVKVLRDMNV KESPGRCYSR PVVIFNFANS SYVQYGQLGE DNEILLGNHR TEECQLPSLK  540
IFIAGNSAYE YVDYLFKRMI DLSSISTVDS MIALDIDPLE NTDFRVLELY SQKELRSSNV  600
FDLEEIMREF NSYKQRVKYV EDKVVDPLPP                                   630

SEQ ID NO: 110         moltype = AA  length = 905
FEATURE                Location/Qualifiers
source                 1..905
                       mol_type = protein
                       organism = Human cytomegalovirus
SEQUENCE: 110
MESRIWCLVV CVNLCIVCLG AAVSSSSTSH ATSSAHNGSH TSRTTSAQTR SVSSQHVTSS  60
EAVSHRANET IYNTTLKYGD VVGVNTTKYP YRVCSMAQGT DLIRFERNIV CTPMKPINED  120
```

-continued

```
LDEGIMVVYK RNIVAHTFKV RVYQKVLTFR RSYAYIHTTY LLGSNTEYVA PPMWEIHHIN  180
RHSQCYSSYS RVIAGTVFVA YHRDSYENKT MQLMLDDYSN THSTRYVTVK DQWHSRGSTW  240
LYRETCNLNC MVTITTARSK YPYHFFATST GDVVDISPFY NGTNRNTSYF GENADKFFIF  300
PNYTIVSDFG RANSAPETHR LVAFLERADS VISWDIQDEK NVTCQLTFWE ASERTIRSEA  360
EDSYHFSSAK MTATFLSKKQ EVNMSDPVLD CVRDQALNKL QQIFNASYNQ TYEKYGNVSV  420
FETTGGLVVF WQGIKQKSLL ELERLANSSG VNSTRRTKRS TGNTTTLSLE SESVRNVLYA  480
QLQFTYDTLR SYINRALAQI AEAWCVDQRR TLEVFKELSK INPSAILSAI YNKPIAARFM  540
GDVLGLASCV TINQTSVKVL RDMNVKESPG RCYSRPVVIF NFVNSSYVQY GQLGEDNEIL  600
LGNHRTEECQ FPSLKIFIAG NSAYEYVDYL FKRMIDLSSI STVDSMIALD IDPLENTDFR  660
VLELYSQKEL RSSNVFDLEE IMREFNSYKQ RVKYVEDKVV DPLPPYLKGL DDLMSGLGAA  720
GKAVGVAIGA VGGAVASVVE GVATFLKNPF GAFTIILVAI AVVIIIYLIY TRQRRLCMQP  780
LQNLFPYLVS ADGTTVTSGN TKDTSLQAPP SYEESVYNSG RKGPGPPSSD ASTAAPPYTN  840
EQAYQMLLAL ARLDAEQRAQ QNGTDSLDGQ TGTQDKGQKP NLLDRLRHRK NGYRHLKDSD  900
EEENV                                                              905

SEQ ID NO: 111         moltype = AA  length = 905
FEATURE                Location/Qualifiers
source                 1..905
                       mol_type = protein
                       organism = Human cytomegalovirus
SEQUENCE: 111
MESRIWCLVV CVNLCIVCLG AVVSSSSTSH ATSSAHNGSH TSRTTSAQTR SVSSQHVTSS  60
EAVSHRANET IYNTTLKYGD VVGVNTTKYP YRVCSMAQGT DLIRFERNIV CTPMKPINED  120
LDEGIMVVYK RNIVAHTFKV RVYQKVLTFR RSYAYIHTTY LLGSNTEYVA PPMWEIHHIN  180
RHSQCYSSYS RVIAGTVFVA YHRDSYENKT MQLMLDDYSN THSTRYVTVK DQWHSRGSTW  240
LYRETCNLNC MVTITTARSK YPYHFFATST GDVVDISPFY NGTNRNTSYF GENADKFFIF  300
PNYTIVSDFG RANSAPETHR LVAFLERADS VISWDIQDEK NVTCQLTFWE ASERTIRSEA  360
EDSYHFSSAK MTATFLSKKQ EVNMSDPVLD CVRDQALNKL QQIFNASYNQ TYEKYGNVSV  420
FETTGGLVVF WQGIKQKSLL ELERLANSSG VNSTRRTKRS TGNTTTLSLE SESVRNVLYA  480
QLQFTYDTLR SYINRALAQI AEAWCVDQRR TLEVFKELSK INPSAILSAI YNKPIAARFM  540
GDVLGLASCV TINQTSVKVL RDMNVKESPG RCYSRPVVIF NFVNSSYVQY GQLGEDNEIL  600
LGNHRTEECQ FPSLKIFIAG NSAYEYVDYL FKRMIDLSSI STVDSMIALD IDPLENTDFR  660
VLELYSQKEL RSSNVFDLEE IMREFNSYKQ RVKYVEDKVV DPLPPYLKGL DDLMSGLGAA  720
GKAVGVAIGA VGGAVASVVE GVATFLKNPF GAFTIILVAI AVVIIIYLIY TRQRRLCMQP  780
LQNLFPYLVS ADGTTVTSGN TKDTSLQAPP SYEESVYNSG RKGPGPPSSD ASTAAPPYTN  840
EQAYQMLLAL ARLDAEQRAQ QNGTDSLDGQ TGTQDKGQKP NLLDRLRHRK NGYRHLKDSD  900
EEENV                                                              905

SEQ ID NO: 112         moltype = AA  length = 905
FEATURE                Location/Qualifiers
source                 1..905
                       mol_type = protein
                       organism = Human cytomegalovirus
SEQUENCE: 112
MESRIWCLVV CVNLCIVCLG AVVSSSSTSH ATSSAHNGSH TSRTTSAQTR SVSSQHVTSS  60
EAVSHRANET IYNTTLKYGD VVGVNTTKYP YRVCSMAQGT DLIRFERNIV CTPMKPINED  120
LDEGIMVVYK RNIVAHTFKV RVYQKVLTFR RSYAYIHTTY LLGSNTEYVA PPMWEIHHIN  180
RHSQCYSSYS RVIAGTVFVA YHRDSYENKT MQLMLDDYSN THSTRYVTVK DQWHSRGSTW  240
LYRETCNLNC MVTITTARSK YPYHFFATST GDVVDISPFY NGTNRNTSYF GENADKFFIF  300
PNYTIVSDFG RANSAPETHR LVAFLERADS VISWDIQDEK NVTCQLTFWE ASERTIRSEA  360
EDSYHFSSAK MTATFLSKKQ EVNMSDPVLD CVRDQALNKL QQIFNASYNQ TYEKYGNVSV  420
FETTGGLVVF WQGIKQKSLL ELERLANSSG VNSTRRTKRS TGNTTTLSLE SESVRNVLYA  480
QLQFTYDTLR SYINRALAQI AEAWCVDQRR TLEVFKELSK INPSAILSAI YNKPIAARFM  540
GDVLGLASCV TINQTSVKVL RDMNVKESPG RCYSRPVVIF NFVNSSYVQY GQLGEDNEIL  600
LGNHRTEECQ FPSLKIFIAG NSAYEYVDYL FKRMIDLSSI STVDSMIALD IDPLENTDFR  660
VLELYSQKEL RSSNVFDLEE IMREFNSYKQ RVKYVEDKVV DPLPPYLKGL DDLMSGLGAA  720
GKAVGVAIGA VGGAVASVVE GVATFLKNPF GAFTIILVAI AVVIIIYLIY TRQRRLCMQP  780
LQNLFPYLVS ADGTTVTSGS TKDTSLQAPP SYEESVYNSG RKGPGPPSSD ASTAAPPYTN  840
EQAYQMLLAL ARLDAEQRAQ QNGTDSLDGR TGTQDKGQKP NLLDRLRHRK NGYRHLKDSD  900
EEENV                                                              905

SEQ ID NO: 113         moltype = AA  length = 905
FEATURE                Location/Qualifiers
source                 1..905
                       mol_type = protein
                       organism = Human cytomegalovirus
SEQUENCE: 113
MESRIWCLVV CVNLCYVCLG AVVSSSSTSH ATSSAHNGSH TSRTTSAQTR SVSSQHVTSS  60
EAVSHRANET IYNTTLKYGD VVGVNTTKYP YRVCSMAQGT DLIRFERNIV CTPMKPINED  120
LDEGIMVVYK RNIVAHTFKV RVYQKVLTFR RSYAYIHTTY LLGSNTEYVA PPMWEIHHIN  180
RHSQCYSSYS RVIAGTVFVA YHRDSYENKT MQLMLDDYSN THSTRYVTVK DQWHSRGSTW  240
LYRETCNLNC MVTITTARSK YPYHFFATST GDVVDISPFY NGTNRNTSYF GENADKFFIF  300
PNYTIVSDFG RANSAPETHR LVAFLERADS VISWDIQDEK NVTCQLTFWE ASERTIRSEA  360
EDSYHFSSAK MTATFLSKKQ EVNMSDPVLD CVRDQALNKL QQIFNASYNQ TYEKYGNVSV  420
FETTGGLVVF WQGIKQKSLL ELERLANSSG VNSTRRTKRS TGNTTTLSLE SESVRNVLYA  480
QLQFTYDTLR SYINRALAQI AEAWCVDQRR TLEVFKELSK INPSAILSAI YNKPIAARFM  540
GDVLGLASCV TINQTSVKVL RDMNVKESPG RCYSRPVVIF NFVNSSYVQY GQLGEDNEIL  600
LGNHRTEECQ FPSLKIFIAG NSAYEYVDYL FKRMIDLSSI STVDSMIALD IDPLENTDFR  660
VLELYSQKEL RSSNVFDLEE IMREFNSYKQ RVKYVEDKVV DPLPPYLKGL DDLMSGLGAA  720
```

-continued

```
GKAVGVAIGA VGGAVASVVE GVATFLKNPF GAFTIILVAI AVVIIIYLIY TRQRRLCMQP  780
LQNLFPYLVS ADGTTVTSGN TKDTSLQAPP SYEESVYNSG RKGPGPPSSD ASTAAPPYTN  840
EQAYQMLLAL ARLDAEQRAQ QNGTDSLDGQ TGTQDKGQKP NLLDRLRHRK NGYRHLKDSD  900
EEENV                                                              905

SEQ ID NO: 114          moltype = AA  length = 905
FEATURE                 Location/Qualifiers
source                  1..905
                        mol_type = protein
                        organism = Human cytomegalovirus
SEQUENCE: 114
MESRIWCLVV CVNLCIVCLG VAVSSSSTSH ATSSAHNGSH TSRTTSAQTR SVSSQHVTSS  60
EAVSHRANET IYNTTLKYGD VVGVNTTKYP YRVCSMAQGT DLIRFERNIV CTPMKPINED  120
LDEGIMVVYK RNIVAHTFKV RVYQKVLTFR RSYAYIHTTY LLGSNTEYVA PPMWEIHHIN  180
RHSQCYSSYS RVIAGTVFVA YHRDSYENKT MQLMLDDYSN THSTRYVTVK DQWHSRGSTW  240
LYRETCNLNC MVTITTARSK YPYHFFATST GDVVDISPFY NGTNRNTSYF GENADKFFIF  300
PNYTIVSDFG RANSAPETHR LVAFLERADS VISWDIQDEK NVTCQLTFWE ASERTIRSEA  360
EDSYHFSSAK MTATFLSKKQ EVNMSDPVLD CVRDQALNKL QQIFNASYNQ TYEKYGNVSV  420
FETTGGLVVF WQGIKQKSLL ELERLANSSG VNSTRRTKRS TGNTTTLSLE SESVRNVLYA  480
QLQFTYDTLR SYINRALAQI AEAWCVDQRR TLEVFKELSK INPSAILSAI YNKPIAARFM  540
GDVLGLASCV TINQTSVKVL RDMNVKESPG RCYSRPVVIF NFVNSSYVQY GQLGEDNEIL  600
LGNHRTEECQ FPSLKIFIAG NSAYEYVDYL FKRMIDLSSI STVDSMIALD IDPLENTDFR  660
VLELYSQKEL RSSNVFDLEE IMREFNSYKQ RVKYVEDKVV DPLPPYLKGL DDLMSGLGAA  720
GKAVGVAIGA VGGAVASVVE GVATFLKNPF GAFTIILVAI AVVIIIYLIY TRQRRLCMQP  780
LQNLFPYLVS ADGTTVTSGN TKDTSLQAPP SYEESVYNSG RKGPGPPSSD ASTAAPPYTN  840
EQAYQMLLAL ARLDAEQRAQ QNGTDSLDGQ TGTQDKGQKP NLLDRLRHRK NGYRHLKDSD  900
EEENV                                                              905

SEQ ID NO: 115          moltype = AA  length = 905
FEATURE                 Location/Qualifiers
source                  1..905
                        mol_type = protein
                        organism = Human cytomegalovirus
SEQUENCE: 115
MESRIWCLVV CVNLCIVCLG AAVSSSSTSH ATSSTHNGSH TSRTTSAQTR SVSSQHVTSS  60
EAVSHRANET IYNTTLKYGD VVGVNTTKYP YRVCSMAQGT DLIRFERNIV CTPMKPINED  120
LDEGIMVVYK RNIVAHTFKV RVYQKVLTFR RSYAYIHTTY LLGSNTEYVA PPMWEIHHIN  180
RNSQCYSSYS RVIAGTVFVA YHRDSYENKT MQLMLDDYSN THSTRYVTVK DQWHSRGSTW  240
LYRETCNLNC MVTITTARSK YPYHFFATST GDVVDISPFY NGTNRNTSYF GENADKFFIF  300
PNYTIVSDFG RANSAPETHR LVAFLERADS VISWDIQDEK NVTCQLTFWE ASERTIRSEA  360
EDSYHFSSAK MTATFLSKKQ EVNMSDPVLD CVRDQALNKL QQIFNASYNQ TYEKYGNVSV  420
FETTGGLVVF WQGIKQKSLL ELERLANSSG VNSTRRTKRS TGNTTTLSLE SESVRNVLYA  480
QLQFTYDTLR SYINRALAQI AEAWCVDQRR TLEVFRELSK INPSAILSAI YNKPIAARFM  540
GDVLGLASCV TINQTSVKVL RDMNVKESPG RCYSRPVVIF NFVNSSYVQY GQLGEDNEIL  600
LGNHRTEECQ FPSLKIFIAG NSAYEYVDYL FKRMIDLSSI STVDSMIALD IDPLENTDFR  660
VLELYSQKEL RSSNVFDLEE IMREFNSYKQ RVKYVEDKVV DPLPPYLKGL DDLMSGLGAA  720
GKAVGVAIGA VGGAVASVVE GVATFLKNPF GAFTIILVAI AVVIIIYLIY TRQRRLCMQP  780
LQNLFPYLVS ADGTTVTSGS TKDTSLQAPP SYEESVYNSG RKGPGPPSSD ASTAAPPYTN  840
EQAYQMLLAL ARLDAEQRAQ QNGTDSLDGQ TGTQDKGQKP NLLDRLRHRK NGYRHLKDSD  900
EEENV                                                              905

SEQ ID NO: 116          moltype = AA  length = 905
FEATURE                 Location/Qualifiers
source                  1..905
                        mol_type = protein
                        organism = Human cytomegalovirus
SEQUENCE: 116
MESRIWCLVV CVNLCIVCLG AAVSSSSTSH ATSSTHNGSH ASRTTSAQTR SVSSQHVTSS  60
KAVSHRANET IYNTTLKYGD VVGVNTTKYP YRVCSMAQGT DLIRFERNIV CTPMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMLDDYSN THSIRYVTVK DQWHSRGSTW  240
LYRETCNLNC MVTITTARSK YPYHFFATST GDVVDISPFY NGTNRNTSYF GENADKFFIF  300
PNYTIVSDFG RANSAPETHR LVAFLERADS VISWDIQDEK NVTCQLTFWE ASERTIRSEA  360
EDSYHFSSAK MTATFLSKKQ EVNMSDPVLD CVRNQALDKL QQIFNASYNQ TYEKYGNVSV  420
FETTGGLVVF WQGIKQKSLL ELERLANSSG VNSTRRTKRS TGNTTTLSPE SESVRNVLYA  480
QLQFTYDTLR SYINRALAQI AEAWCVDQRR TLEVFKELSK INPSAILSAI YNKPIAARFM  540
GDVLGLASCV TINQTSVKVL RDMNVKESPG RCYSRPVVIF NFVNSSYVQY GQLGEDNEIL  600
LGNHRTEECQ FPSLKIFIAG NSAYEYVDYL FKRMIDLSSI STVDSMIALD IDPLENTDFR  660
VLELYSQKEL RSSNVFDLEE IMREFNSYKQ RVKYVEDKVV DPLPPYLKGL DDLMSGLGAA  720
GKAVGVAIGA VGGAVASVVE GVATFLKNPF GAFTIILVAI AVVIIIYLIY TRQRRLCMQP  780
LQNLFPYLVS ADGTTVTSGN TKDTSLQAPP SYEESVYNSG RKGPGPPSSD ASTAAPPYTN  840
EQAYQMLLAL ARLDAEQRAQ QNGTDSLDGQ TGTQDKGQKP NLLDRLRHRK NGYRHLKDSD  900
EEENV                                                              905

SEQ ID NO: 117          moltype = AA  length = 904
FEATURE                 Location/Qualifiers
source                  1..904
                        mol_type = protein
                        organism = Human cytomegalovirus
```

```
SEQUENCE: 117
MESRIWCLVV CVNLCIVCLG AAVSSSSTRG TSATHNGSHT SHTTSAQTRS VSSQHVTSSE  60
AVSHRANETI YNTTLKYGDV VGVNTTKYPY RVCSMAQGTD LIRFERNIVC TPMKPINEDL  120
DEGIMVVYKR NIVAHTFKVR VYQKVLTFRR SYAYIHTTYL LGSNTEYVAP PMWEIHHINS  180
HSQCYSSYSR VIAGTVFVAY HRDSYENKTM QLMLDDYSNT HSTRYVTVKD QWHSRGSTWL  240
YRETCNLNCM VTITTARSKY PYHFFATSTG DVVDISPFYN GTNRNTSYFG ENADKFFIFP  300
NYTIVSDFGR ANSAPETHRL VAFLERADSV ISWDIQDEKN VTCQLTFWEA SERTIRSEAE  360
DSYHFSSAKM TATFLSKKQE VNMSDPVLDC VRNQALNKLQ QIFNASYNQT YEKYGNVSVF  420
ETTGGLVVFW QGIKQKSLLE LERLANSSGV NSTRRTKRST GNTTTLSLES ESVRNVLYAQ  480
LQFTYDTLRS YINRALAQIA EAWCVDQRRT LEVFKELSKI NPSAILSAIY NKPIAARFMG  540
DVLGLASCVT INQTSVKVLR DMNVKESPGR CYSRPVVIFN FVNSSYVQYG QLGEDNEILL  600
GNHRTEECQF PSLKIFIAGN SAYEYVDYLF KRMIDLSSIS TVDSMIALDI DPLENTDFRV  660
LELYSQKELR SSNVFDLEEI MREFNSYKQR VKYVEDKVVD PLPPYLKGLD DLMSGLGAAG  720
KAVGVAIGAV GGAVASVVEG VATFLKNPFG AFTIILVAIA VVIIIYLIYT RQRRLCMQPL  780
QNLFPYLVSA DGTTVTSSST KDTSLQAPPS YEESVYNSGR KGPGPPSSDA STAAPPYTNE  840
QAYQMLLALA RLDAEQRAQQ NGTDSLDGQT GTQDKGQKPN LLDRLRHRKN GYRHLKDSDE  900
EENV                                                              904

SEQ ID NO: 118         moltype = AA  length = 906
FEATURE                Location/Qualifiers
source                 1..906
                       mol_type = protein
                       organism = Human cytomegalovirus
SEQUENCE: 118
MESRIWCLVV CVNLCIVCLG AAVSSSSTSH ATSSTHNGSH TSRTTSAQTR SVYSQHVTSS  60
EAVSHRANET IYNTTLKYGD VVGVNTTKYP YRVCSMAQGT DLIRFERNII CTSMKPINED  120
LDEGIMVVYK RNIVAHTFKV RVYQKVLTFR RSYAYIYTTY LLGSNTEYVA PPMWEIHHIN  180
KFAQCYSSYS RVIGGTVFVA YHRDSYENKT MQLIPDDYSN THSTRYVTVK DQWHSRGSTW  240
LYRETCNLNC MLTITTARSK YPYHFFATST GDVVYISPFY NGTNRNASYF GENADKFFIF  300
PNYTIVSDFG RPNAAPETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETSGGLVVF WQGIKQKSLV ELERLANRSS LNITHRTRRS TSDNNTTHLS SMESVHNLVY  480
AQLQFTYDTL RGYINRALAQ IAEAWCVDQR RTLEVFKELS KINPSAILSA IYNKPIAARF  540
MGDVLGLASC VTINQTSVKV LRDMNVKESP GRCYSRPVVI FNFANSSYVQ YGQLGEDNEI  600
LLGNHRTEEC QLPSLKIFIA GNSAYEYVDY LFKRMIDLSS ISTVDSMIAL DIDPLENTDF  660
RVLELYSQKE LRSSNVFDLE EIMREFNSYK QRVKYVEDKV VDPLPPYLKG LDDLMSGLGA  720
AGKAVGVAIG AVGGAVASVV EGVATFLKNP FGAFTIILVA IAVVIITYLI YTRQRRLCTQ  780
PLQNLFPYLV SADGTTVTSG STKDTSLQAP PSYEESVYNS GRKGPGPPSS DASTAAPPYT  840
NEQAYQMLLA LARLDAEQRA QQNGTDSLDG QTGTQDKGQK PNLLDRLRHR KNGYRHLKDS  900
DEEENV                                                            906

SEQ ID NO: 119         moltype = AA  length = 906
FEATURE                Location/Qualifiers
source                 1..906
                       mol_type = protein
                       organism = Human cytomegalovirus
SEQUENCE: 119
MESRIWCLVV CVNLCIVCLG AAVSSSSTSH ATSSTHNGSH TSRTTSAQTR SVYSQHVTSS  60
EAVSHRANET IYNTTLKYGD VVGVNTTKYP YRVCSMAQGT DLIRFERNII CTSMKPINED  120
LDEGIMVVYK RNIVAHTFKV RVYQKVLTFR RSYAYIYTTY LLGSNTEYVA PPMWEIHHIN  180
KFAQCYSSYS RVIGGTVFVA YHRDSYENKT MQLIPDDYSN THSTRYVTVK DQWHSRGSTW  240
LYRETCNLNC MLTITTARSK YPYHFFATST GDVVDISPFY NGTNRNASYF GENADKFFIF  300
PNYTIVSDFG RPNAAPETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETSGGLVVF WQGIKQKSLV ELERLANRSS LNITHRTRRS TSDNNTTHLS SMESVHNLVY  480
AQLQFTYDTL RGYINRALAQ IAEAWCVDQR RTLEVFKELS KINPSAILSA IYNKPIAARF  540
MGDVLGLASC VTINQTSVKV LRDMNVKESP GRCYSRPVVI FNFANSSYVQ YGQLGEDNEI  600
LLGNHRTEEC QLPSLKIFIA GNSAYEYVDY LFKRMIDLSS ISTVDSMIAL DIDPLENTDF  660
RVLELYSQKE LRSSNVFDLE EIMREFNSYK QRVKYVEDKV VDPLPPYLKG LDDLMSGLGA  720
AGKAVGVAIG AVGGAVASVV EGVATFLKNP FGAFTIILVA IAVVIITYLI YTRQRRLCTQ  780
PLQNLFPYLV SADGTTVTSG STKDTSLQAP PSYEESVYNS GRKGPGPPSS DASTAAPPYT  840
NEQAYQMLLA LARLDAEQRA QQNGTDSLDG QTGTQDKGQK PNLLDRLRHR KNGYRHLKDS  900
DEEENV                                                            906

SEQ ID NO: 120         moltype = AA  length = 906
FEATURE                Location/Qualifiers
source                 1..906
                       mol_type = protein
                       organism = Human cytomegalovirus
SEQUENCE: 120
MESRIWCLVV CVNLCIVCLG AAVSSSSTSH ATSSTHNGSH TSRTTSAQTR SVYSQHVTSS  60
EAVSHRANET IYNTTLKYGD VVGVNTTKYP YRVCSMAQGT DLIRFERNII CTSMKPINED  120
LDEGIMVVYK RNIVAHTFKV RVYQKVLTFR RSYAYIYTTY LLGSNTEYVA PPMWEIHHIN  180
KFAQCYSSYS RVIGGTVFVA YHRDSYENKT MQLIPDDYSN THSTRYVTVK DQWHSRGSTW  240
LYRETCNLNC MLTITTARSK YPYHFFATST GDVVDISPFY NGTNRNASYF GENADKFFIF  300
PNYTIVSDFG RPNAAPETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETSGGLVVF WQGIKQKSLV ELERLANRSS LNITHRTRRS TSDNNTTHLS SMESVHNLVY  480
AQLQFTYDTL RGYINRALAQ IAEAWCVDQR RTLEVFKELS KINPSAILSA IYNKPIAARF  540
```

-continued

```
MGDVLGLASC VTINQTSVKV LRDMNVKESP GRCYSRPVVI FNFANSSYVQ YGQLGEDNEI  600
LLGNHRTEEC QLPSLKIFIA GNSAYEYVDY LFKRMIDLSS ISTVDSMIAL DIDPLENTDF  660
RVLELYSQKE LRSSNVFDLE EIMREFNSYK QRVKYVEDKV VDPLPPYLKG LDDLMSGLGA  720
AGKAVGVAIG AVGGAVASVV EGVATFLKNP FGAFTIILVA IAVVIITYLI YTRQRRLCTQ  780
PLQNLFPYLV SADGTTVTSG STKDTSLQAP PSYEESVYNS GRKGPGPPSS DASTAAPPYT  840
NEQAYQMLLA LARLDAEQRA QQNGTDSLDG QAGTQDKGQK PNLLDRLRHR KNGYRHLKDS  900
DEEENV                                                            906

SEQ ID NO: 121          moltype = AA  length = 906
FEATURE                 Location/Qualifiers
source                  1..906
                        mol_type = protein
                        organism = Human cytomegalovirus
SEQUENCE: 121
MESRIWCLVV CVNLCIVCLG AAVSSSSTSH ATSSTHNGSH TSRTTSAQTR SVSSQHVTSS  60
EAVSHRANET IYNTTLKYGD VVGVNTTKYP YRVCSMAQGT DLIRFERNIV CTPMKPINED  120
LDEGIMVVYK RNIVAHTFKV RVYQKVLTFR RSYAYIHTTY LLGSNTEYVA PPMWEIHHIN  180
KFAQCYSSYS RVIGGTVFVA YHRDSYENKT MQLMSDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNAAPETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETSGGLVVF WQGIKQKSLV ELERLANRSS LNITHRTRRS TSDNNTTHLS SMESVHNLVY  480
AQLQFTYDTL RGYINRALAQ IAEAWCVDQR RTLEVFKELS KINPSAILSA IYNKPIAARF  540
MGDVLGLASC VTINQTSVKV LRDMNVKESP GRCYSRPVVI FNFANSSYVQ YGQLGEDNEI  600
LLGNHRTEEC QLPSLKIFIA GNSAYEYVDY LFKRMIDLSS ISTVDSMIAL DIDPLENTDF  660
RVLELYSQKE LRSSNVFDLE EIMREFNSYK QRVKYVEDKV VDPLPPYLKG LDDLMSGLGA  720
AGKAVGVAIG AVGGAVASVV EGVATFLKNP FGAFTIILVA IAVVIITYLI YTRQRRLCTQ  780
PLQNLFPYLV SADGTTVTSG STKDTSLQAP PSYEESVYNS GRKGPGPPSS DASTAAPPYT  840
NEQAYQMLLA LARLDAEQRA QQNGTDSLDG QTGTQDKGQK PNLLDRLRHR KNGYRHLKDS  900
DEEENV                                                            906

SEQ ID NO: 122          moltype = AA  length = 906
FEATURE                 Location/Qualifiers
source                  1..906
                        mol_type = protein
                        organism = Human cytomegalovirus
SEQUENCE: 122
MESRIWCLVV CVNLCIVCLG AAVSSSSTSH ATSSTHNGSH TSRTTSAQTR SVSSQHVTSS  60
EAVSHRANET IYNTTLKYGD VVGVNTTKYP YRVCSMAQGT DLIRFERNIV CTPMKPINED  120
LDEGIMVVYK RNIVAHTFKV RVYQKVLTFR RSYAYIHTTY LLGSNTEYVA PPMWEIHHIN  180
KFAQCYSSYS RVIGGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNAAPETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETSGGLVVF WQGIKQKSLV ELERLANRSS LNITHRTRRS TSDNNTTHLS SMESVHNLVY  480
AQLQFTYDTL RGYINRALAQ IAEAWCVDQR RTLEVFKELS KINPSAILSA IYNKPIAARF  540
MGDVLGLASC VTINQTSVKV LRDMNVKESP GRCYSRPVVI FNFANSSYVQ YGQLGEDNEI  600
LLGNHRTEEC QLPSLKIFIA GNSAYEYVDY LFKRMIDLSS ISTVDSMIAL DIDPLENTDF  660
RVLELYSQKE LRSSNVFDLE EIMREFNSYK QRVKYVEDKV VDPLPPYLKG LDDLMSGLGA  720
AGKAVGVAIG AVGGAVASVV EGVATFLKNP FGAFTIILVA IAVVIITYLI YTRQRRLCTQ  780
PLQNLFPYLV SADGTTVTSG STKDTSLQAP PSYEESVYNS GRKGPGPPSS DASTAAPPYT  840
NEQAYQMLLA LARLDAEQRA QQNGTDSLDG QTGTQDKGQK PNLLDRLRHR KNGYRHLKDS  900
DEEENV                                                            906

SEQ ID NO: 123          moltype = AA  length = 907
FEATURE                 Location/Qualifiers
source                  1..907
                        mol_type = protein
                        organism = Human cytomegalovirus
SEQUENCE: 123
MESRIWCLVV CVNLCIVCLG AAVSSSSTHG TSATHSHHSS HTTSAAHSRS GSVSSQRVTS  60
SEAVSHRANE TIYNTTLKYG DVVGVNTTKY PYRVCSMAQG TDLIRFERNI VCTPMKPINE  120
DLDEGIMVVY KRNIVAHTFK VRVYQKVLTF RRSYAYIYTT YLLGSNTEYV APPMWEIHHI  180
NKFAQCYSSY SRVIGGTVFV AYHRDSYENK TMQLIPDDYS NTHSTRYVTV KDQWHSRGST  240
WLYRETCNLN CMLTITTARS KYPYHFFATS TGDVVDISPF YNGTNRNASY FGENADKFFI  300
FPNYTIVSDF GRPNAAPETH RLVAFLERAD SVISWDIQDE KNVTCQLTFW EASERTIRSE  360
AEDSYHFSSA KMTATFLSKK QEVNMSDSAL DCVRDEAINK LQQIFNTSYN QTYEKYGNVS  420
VFETSGGLVV FWQGIKQKSL VELERLANRS SLNITHRTRR STSDNNTTHL SSMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GQTGTQDKGQ KPNLLDRLRH RKNGYRHLKD  900
SDEEENV                                                           907

SEQ ID NO: 124          moltype = AA  length = 907
FEATURE                 Location/Qualifiers
```

-continued

```
source                  1..907
                        mol_type = protein
                        organism = Human cytomegalovirus
SEQUENCE: 124
MESRIWCLVV CVNLCIVCLG AAVSSSSTHG TSATHSHHSS HTTSAAHSRS GSVSSQRVTS  60
SEAVSHRANE TIYNTTLKYG DVVGVNTTKY PYRVCSMAQG TDLIRFERNI VCTPMKPINE  120
DLDEGIMVVY KRNIVAHTFK VRVYQKVLTF RRSYAYIYTT YLLGSNTEYV APPMWEIHHI  180
NKFAQCYSSY SRVIGGTVFV AYHRDSYENK TMQLIPDDYS NTHSTRYVTV KDQWHSRGST  240
WLYRETCNLN CMLTITTARS KYPYHFFATS TGDVVDISPF YNGTNRNASY FGENADKFFI  300
FPNYTIVSDF GRPNAAPETH RLVAFLERAD SVISWDIQDE KNVTCQLTFW EASERTIRSE  360
AEDSYHFSSA KMTATFLSKK QEVNMSDSAL DCVRDEAINK LQQIFNTSYN QTYEKYGNVS  420
VFETSGGLVV FWQGIKQKSL VELERLANRS SLNITHRTRR STSDNNTTHL SSMESVHNLV  480
YAQLQFTYDT LRGYINRALA QIAEAWCVDQ RRTLEVFKKL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GQTGTQDKGQ KPNLLDRLRH RKNGYRHLKD  900
SDEEENV                                                          907

SEQ ID NO: 125          moltype = AA  length = 906
FEATURE                 Location/Qualifiers
source                  1..906
                        mol_type = protein
                        organism = Human cytomegalovirus
SEQUENCE: 125
MESRIWCLVV CVNLCIVCLG AAVSSSTSHA TSSTHNGSHT SRTTSAQTRS VSSQHVTSSE  60
AVSHRANETI YNTTLKYGDV VGVNTTKYPY RVCSMAQGTD LIRFERNIVC TSMKPINEDL  120
DEGIMVVYKR NIVAHTFKVR VYQKVLTFRR SYAYIHTTYL LGSNTEYVAP PMWEIHHINS  180
HSQCYSSYSR VIAGTVFVAY HRDSYENKTM QLMPDDYSNT HSTRYVTVKD QWHSRGSTWL  240
YRETCNLNCM VTITTARSKY PYHFFATSTG DVVDISPFYN GTNRNASYFG ENADKFFIFP  300
NYTIVSDFGR PNSALETHRS VAFLERADSV ISWDIQDEKN VTCQLTFWEA SERTIRSEAE  360
DSYHFSSAKM TATFLSKKQE VNMSDSALDC VRDEAINKLQ QIFNTSYNQT YEKYGNVSVF  420
ETTGGLVVFW QGIKQKSLVE LERLANRSSL NLTHNRTKRS TNGNNATHLS NMESVHNLVY  480
AQLQFTYDTL RGYINRALAQ IAEAWCVDQR RSLEVFRELS KINPSAILSA IYNKPIAARF  540
MGDVLGLASC VTINQTSVKV LRDMNVKESP GRCYSRPVVI FNFANSSYVQ YGQLGEDNEI  600
LLGNHRTEEC QLPSLKIFIA GNSAYEYVDY LFKRMIDLSS ISTVDSMIAL DIDPLENTDF  660
RVLELYSQKE LRSSNVFDLE EIMREFNSYK QRVKYVEDKV VDPLPPYLKG LDDLMSGLGA  720
AGKAVGVAIG AVGGAVASVV EGVATFLKNP FGAFTIILVA IAVVIIIYLI YTRQRRLCTQ  780
PLQNLFPYLV SADGTTVTSG STKDTSLQAP PSYEESVYNS GRKGPGPPSS DASTAAPPYT  840
NEQAYQMLLA LARLDAEQRA QQNGTDSLDG QTGTQDKGQK PNLLDRLRHR KNGYRHLKDS  900
DEEENV                                                           906

SEQ ID NO: 126          moltype = AA  length = 906
FEATURE                 Location/Qualifiers
source                  1..906
                        mol_type = protein
                        organism = Human cytomegalovirus
SEQUENCE: 126
MESRIWCLVV CVNLCIVCLG AAVSSSTSHA TSSTHNGSHT SRTTSAQTRS VSSQHVTSSE  60
AVSHRANETI YNTTLKYGDV VGVNTTKYPY RVCSMAQGTD LIRFERNIVC TSMKPINEDL  120
DEGIMVVYKR NIVAHTFKVR VYQKVLTFRR SYAYIHTTYL LGSNTEYVAP PMWEIHHINS  180
HSQCYSSYSR VIAGTVFVAY HRDSYENKTM QLMPDDYSNT HSTRYVTVKD QWHSRGSTWL  240
YRETCNLNCM VTITTARSKY PYHFFATSTG DVVDISPFYN GTNRNASYFG ENADKFFIFP  300
NYTIVSDFGR PNSALETHRS VAFLERAESV ISWDIQDEKN VTCQLTFWEA SERTIRSEAE  360
DSYHFSSAKM TATFLSKKQE VNMSDSALDC VRDEAINKLQ QIFNTSYNQT YEKYGNVSVF  420
ETTGGLVVFW QGIKQKSLVE LERLANRSSL NLTHNRTKRS TNGSNATHLS NMESVHNLVY  480
AQLQFTYDTL RGYINRALAQ IAEAWCVDQR RSLEVFRELS KINPSAILSA IYNKPIAARF  540
MGDVLGLASC VTINQTSVKV LRDMNVKESP GRCYSRPVVI FNFANSSYVQ YGQLGEDNEI  600
LLGNHRTEEC QLPSLKIFIA GNSAYEYVDY LFKRMIDLSS ISTVDSMIAL DIDPLENTDF  660
RVLELYSQKE LRSSNVFDLE EIMREFNSYK QRVKYVEDKV VDPLPPYLKG LDDLMSGLGA  720
AGKAVGVAIG AVGGAVASVV EGVATFLKNP FGAFTIILVA IAVVIIIYLI YTRQRRLCTQ  780
PLQNLFPYLV SADGTTVTSG STKDTSLQAP PSYEESVYNS GRKGPGPPSS DASTAAPPYT  840
NEQAYQMLLA LARLDAEQRA QQNGTDSLDG QTGTQDKGQK PNLLDRLRHR KNGYRHLKDS  900
DEEENV                                                           906

SEQ ID NO: 127          moltype = AA  length = 907
FEATURE                 Location/Qualifiers
source                  1..907
                        mol_type = protein
                        organism = Human cytomegalovirus
SEQUENCE: 127
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
```

-continued

```
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GQTGTQDKGQ KPNLLDRLRH RKNGYRHLKD  900
SDEEENV                                                           907

SEQ ID NO: 128         moltype = AA  length = 907
FEATURE                Location/Qualifiers
source                 1..907
                       mol_type = protein
                       organism = Human cytomegalovirus
SEQUENCE: 128
MESRIWCLVV CVNLCIVRLG AAVSSSSTRG TSATHSHHSS RTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GNVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GQTGTQDKGQ KPNLLDRLRH RKNGYRHLKD  900
SDEEENV                                                           907

SEQ ID NO: 129         moltype = AA  length = 907
FEATURE                Location/Qualifiers
source                 1..907
                       mol_type = protein
                       organism = Human cytomegalovirus
SEQUENCE: 129
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GRTGTQDKGQ KPNLLDRLRH RKNGYRHLKD  900
SDEEENV                                                           907

SEQ ID NO: 130         moltype = AA  length = 907
FEATURE                Location/Qualifiers
source                 1..907
                       mol_type = protein
                       organism = Human cytomegalovirus
SEQUENCE: 130
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTL GSTKDTSLQA PPSYEESVYN SGRKGPGPPS SDASTAAPPY  840
TNEQAYQMLL ALARLDAEQR AQQNGTDSLD GQTGTQDKGQ KPNLLDRLRH RKNGYRHLKD  900
SDEEENV                                                           907
```

```
SEQ ID NO: 131          moltype = AA  length = 907
FEATURE                 Location/Qualifiers
source                  1..907
                        mol_type = protein
                        organism = Human cytomegalovirus
SEQUENCE: 131
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSVLD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GQTGTQDKGQ KPNLLDRLRH RKNGYRHLKD  900
SDEEENV                                                            907

SEQ ID NO: 132          moltype = AA  length = 908
FEATURE                 Location/Qualifiers
source                  1..908
                        mol_type = protein
                        organism = Human cytomegalovirus
SEQUENCE: 132
MESRIWCLVV CVNLCIVCLG AAVSSSSTSR GTSATHSHHS SHTTSAAHSR SGSVSQRVTS  60
SQTVSHGVNE TIYNTTLKYG DVVGVNTTKY PYRVCSMAQG TDLIRFERNI VCTSMKPINE  120
DLDEGIMVVY KRNIVAHTFK VRVYQKVLTF RRSYAYIHTT YLLGSNTEYV APPMWEIHHI  180
NSHSQCYSSY SRVIAGTVFV AYHRDSYENK TMQLMPDDYS NTHSTRYVTV KDQWHSRGST  240
WLYRETCNLN CMVTITTARS KYPYHFFATS TGDVVDISPF YNGTNRNASY FGENADKFFI  300
FPNYTIVSDF GRPNSALETH RLVAFLERAD SVISWDIQDE KNVTCQLTFW EASERTIRSE  360
AEDSYHFSSA KMTATFLSKK QEVNMSDSAL DCVRDEAINK LQQIFNTSYN QTYEKYGNVS  420
VFETTGGLVV FWQGIKQKSL VELERLANRS SLNLTHSRTK RSADGNNATH LSSMESVHNL  480
VYAQLQFTYD TLRGYINRAL AQIAEAWCVD QRRSLEVFKE LSKINPSAIL SAIYNKPIAA  540
RFMGDVLGLA SCVTINQTSV KVLRDMNVKD SPGRCYSRPV VIFNFANSSY VQYGQLGEDN  600
EILLGNHRTE ECQLPSLKIF IAGNSAYEYV DYLFKRMIDL SSISTVDSMI ALDIDPLENT  660
DFRVLELYSQ KELRSSNVFD LEEIMREFNS YKQRVKYVED KVVDPLPPYL KGLDDLMSGL  720
GAAGKAVGVA IGAVGGAVAS VVEGVATFLK NPFGAFTIIL VAIAVVIITY LIYTRQRRLC  780
MQPLQNLFPY LVSANGTTVT SGNTKDTSLQ APPSYEESVY NSGRKGSGPP SSDASTAAPP  840
YTNEQAYQML LALVRLDAEQ RAQQNGTDSL DGQTGTQDKG QKPNLLDRLR HRKNGYRHLK  900
DSDEEENV                                                           908

SEQ ID NO: 133          moltype = AA  length = 907
FEATURE                 Location/Qualifiers
source                  1..907
                        mol_type = protein
                        organism = Human cytomegalovirus
SEQUENCE: 133
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE APERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GRTGTQDKGQ KPNLLDRLRH RKNGYRHLKD  900
SDEEENV                                                            907

SEQ ID NO: 134          moltype = AA  length = 907
FEATURE                 Location/Qualifiers
source                  1..907
                        mol_type = protein
                        organism = Human cytomegalovirus
SEQUENCE: 134
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
```

-continued

```
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RANSAPETHR LVAFLERADS VISWDIQDEK NVTCQLTFWE ASERTIRSEA  360
EDSYHFSSAK MTATFLSKKQ EVNMSDSVLD CVRDEAINKL QQIFNTSYNQ TYEKYGNVSV  420
FETTGGLVVF WQGIKQKSLV ELERLANRSS LNLTHSRAKR SADGNNTTHL SNMESVHNLV  480
YAQLQFTYDT LRGYINRALA QIAEAWCVDQ RRSLEVFREL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GQTGTQDKGQ KPNLLDRLRH RKNGYRHLKD  900
SDEEENV                                                            907

SEQ ID NO: 135         moltype = AA  length = 905
FEATURE                Location/Qualifiers
source                 1..905
                       mol_type = protein
                       organism = Human cytomegalovirus
SEQUENCE: 135
MESRIWCLVV CVNLCIVCLG AAVSSSTSRA TSTHNGSHIS RTTSAQTRSI SSQRVTSSEA  60
VSHRANETIY NTTLKYGDVV GVNTTKYPYR VCSMAQGTDL IRFDRNIVCT PMKPINEDLD  120
EGIMVVYKRN IVAHTFKVRV YQKVLTFRRS YAYIHTTYLL GSNTEYVAPP MWEIHHINRH  180
SQCYSSYSRV IAGTVFVAYH RDSYENKTMQ LMPDDYSNTH STRYVTVKDQ WHSRGSTWLY  240
RETCNLNCMV TITTARSKYP YHFFATSTGD VVDISPFYNG TNRNASYFGE NADKFFIFPN  300
YTIVSDFGRP NSALETHRLV AFLERADSVI SWDIQDEKNV TCQLTFWEAS ERTIRSEAEE  360
SYHFSSAKMT ATFLSKKQEV NMSDSALDCV RDEALNKLQQ IFNTSYNQTY EKYGNVSVFE  420
TTGGLVVFWQ GIKQKSLVEL ERLANRSSLN LTHSRTRRST DGTNVTHLSN MDSVHNLVYA  480
QLQFTYDTLR GYINRALTQI AEAWCVDQRR TLEVFKELSK INPSAILSAI YNKPIAARFM  540
GDVLGLASCV TINQTSVKVL RDMNVKESPG RCYSRPVVIF NFANSSYVQY GQLGEDNEIL  600
LGNHRTEECQ LPSLKIFIAG NSAYEYVDYL FKRMIDLSSI STVDSMIALD IDPLENTDFR  660
VLELYSQKEL RSSNVFDLEE IMREFNSYKQ RVKYVEDKVV DPLPPYLKGL DDLMSGLGAA  720
GKAVGVAIGA VGGAVASVVE GVATFLKNPF GAFTIILVAI AVVIITYLIY TRQRRLCTQP  780
LQNLFPYLVS ADGTTVTSGS TKDTSLQAPP SYEESVYNSG RKGPGPPSSD ASTAAPPYTN  840
EQAYQMLLAL ARLDAEQRAQ QNGTDSLDGQ TGTQDKGQKP NLLDRLRHRK NGYRHLKDSD  900
EEENV                                                              905

SEQ ID NO: 136         moltype = AA  length = 905
FEATURE                Location/Qualifiers
source                 1..905
                       mol_type = protein
                       organism = Human cytomegalovirus
SEQUENCE: 136
MESRIWCLVV CVNLCIVCLG AAVSSSTSRA TSTHNGNHTS HTTSAQTRSI SSQRVTSSEA  60
VSHRANETIY NTTLKYGDVV GVNTTKYPYR VCSMAQGTDL IRFDRNIVCT PMKPINEDLD  120
EGIMVVYKRN IVAHTFKVRV YQKVLTFRRS YAYIHTTYLL GSNTEYVAPP MWEIHHINSH  180
SQCYSSYSRV IAGTVFVAYH RDSYENKTMQ LMPDDYSNTH STRYVTVKDQ WHSRGSTWLY  240
RETCNLNCMV TITTARSKYP YHFFATSTGD VVDISPFYNG TNRNASYFGE NADKFFIFPN  300
YTIVSDFGRP NSALETHRLV AFLERADSVI SWDIQDEKNV TCQLTFWEAS ERTIRSEAEE  360
SYHFSSAKMT ATFLSKKQEV NMSDSALDCV RDEALNKLQQ IFNASYNQTY EKYGNVSVFE  420
TTGGLVVFWQ GIKQKSLVEL ERLANRSSLN LTHSRTRRST DGTNVTHLSN MDSVHNLVYA  480
QLQFTYDTLR GYINRALTQI AEAWCVDQRR TLEVFKELSK INPSAILSAI YNKPIAARFM  540
GDVLGLASCV TINQTSVKVL RDMNVKESPG RCYSRPVVIF NFANSSYVQY GQLGEDNEIL  600
LGNHRTEECQ LPSLKIFIAG NSAYEYVDYL FKRMIDLSSI STVDSMIALD IDPLENTDFR  660
VLELYSQKEL RSSNVFDLEE IMREFNSYKQ RVKYVEDKVV DPLPPYLKGL DDLMSGLGAA  720
GKAVGVAIGA VGGAVASVVE GVATFLKNPF GAFTIILVAI AVVIIIYLIY TRQRRLCMQP  780
LQNLFPYLVS ADGTTVTSGN TKDTSLQAPP SYEESVYNSG RKGPGPPSSD ASTAAPPYTN  840
EQAYQMLLAL VRLDAEQRAQ QNGTDSLDGQ TGTQDKGQKP NLLDRLRHRK NGYRHLKDSD  900
EEENV                                                              905

SEQ ID NO: 137         moltype = AA  length = 907
FEATURE                Location/Qualifiers
source                 1..907
                       mol_type = protein
                       organism = Human cytomegalovirus
SEQUENCE: 137
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
```

```
QPLQNLFPYL VSADGTTVTS GNTKDTSLQA PPSYEESVYN SGRKGPGPPS SDASTAAPPY  840
TNEQAYQMLL ALVRLDAEQR AQQNGTDSLD GQTGTQDKGQ KPNLLDRLRH RKNGYRHLKD  900
SDEEENV                                                            907

SEQ ID NO: 138         moltype = AA  length = 907
FEATURE                Location/Qualifiers
source                 1..907
                       mol_type = protein
                       organism = Human cytomegalovirus
SEQUENCE: 138
MESRIWCLVV CVNLCIVCLG AAVSSSSTRG TSSTHSHHSS HTTSAAHSRS GSVSQRVTSS  60
QTVSHGVNET IYNTTLRYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR SIDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIIIYL IYTRQRRLCM  780
QPLQNLFPYL VSADGTTVTS GNTKDTSLQA PPSYEESVYN SGRKGPGPPS SDASTAAPPY  840
TNEQAYQMLL ALARLDAEQR AQQNGTDSLD GQTGTQDKGQ KPNLLDRLRH RKNGYRHLKD  900
SDEEENV                                                            907

SEQ ID NO: 139         moltype = AA  length = 907
FEATURE                Location/Qualifiers
source                 1..907
                       mol_type = protein
                       organism = Human cytomegalovirus
SEQUENCE: 139
MESRIWCLVV CVNLCIVCLG AAVSSSSTTG SRGTSTHNHH SSHTTSAARS QSGSVSHHVT  60
SSQTVSHDVN ETIYNTTLKY GDVVGVNTTK YPYRVCSMAQ GTDLIRFERN IVCTPVKPIN  120
EDLDEGIMVV YKRNIVAHTF KVRVYQKVLT FRRSYAYIYS TYLLGSNTEY VAPPMWEIHH  180
INKFAQCYSS YSRVIAGTLF VAYHRDSYEN KTMQLMSDDY SNTHSTRYVT VKDQWHSRGS  240
TWLYHETCNL NCMVTMTAAR SKYPYHFFAT STGDVVDISP FYNGTNRNTS YFGENADKFF  300
IFPNYTIVSD FGRPNAAQET HRLVAFLERA DSVISWDIQD EKNVTCQLTF WEASERTIRS  360
EAKDSYHFSS AKMTATFLSK KQEVNMSDPV LDCVRDQALN KLQQIFNASY NQTYEKYGNV  420
SVFETTGGLV VFWQGIKQKS LLELERLANS SGVNATRRSK RSTNNTTTLS LENDSVRSVL  480
YAQLQFTYDT LRNYINRALA QIAEAWCVDQ RRTLEVFKEL SKINPSAILS AIYNKPIAAR  540
FMGDVLGLAS CVTINQTSVK VLRDMTIKDS TGRCYSRPVV IFTFANSSHV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GQTGTQDKGQ KPNLLDRLRH RKNGYRHLKD  900
SDEEENV                                                            907

SEQ ID NO: 140         moltype = AA  length = 907
FEATURE                Location/Qualifiers
source                 1..907
                       mol_type = protein
                       organism = Human cytomegalovirus
SEQUENCE: 140
MESRIWCLVV CVNLCIVCLG AAVSSSSTTG SRGTSTHNHH SSHTTSAARS QSGSVSHHVT  60
SSQTVSHDVN ETIYNTTLKY GDVVGVNTTK YPYRVCSMAQ GTDLIRFERN IVCTPVKPIN  120
EDLDEGIMVV YKRNIVAHTF KVRVYQKVLT FRRSYAYIYS TYLLGSNTEY VAPPMWEIHH  180
INKFAQCYSS YSRVIAGTLF VAYHRDSYEN KTMQLMSDDY SNTHSTRYVT VKDQWHSRGS  240
TWLYHETCNL NCMVTMTAAR SKYPYHFFAT STGDVVDISP FYNGTNRNTS YFGENADKFF  300
IFPNYTIVSD FGRPNAAQET HRLVAFLERA DSVISWDIQD EKNVTCQLTF WEASERTIRS  360
EAKDSYHFSS AKMTATFLSK KQEVNMSDPV LDCVRDQALN KLQQIFNASY NQTYEKYGNV  420
SVFETTGGLV VFWQGIKQKS LLELERLANS SGVNATRRSK RSTNNTTTLS LENDSVRSVL  480
YAQLQFTYDT LRNYINRALA QIAEAWCVDQ RRTLEVFKEL SKINPSAILS AIYNKPIAAR  540
FMGDVLGLAS CVTINQTSVK VLRDMTIKDS TGRCYSRPVV IFTFANSSHV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAQPY  840
TNEQAYQMLL ALARLDAEQR AQQNGTDSLN GQTGTQDKGQ KPNLLDRLRH RKNGYRHLKD  900
SDEEENV                                                            907

SEQ ID NO: 141         moltype = DNA  length = 2437
FEATURE                Location/Qualifiers
misc_feature           1..2437
                       note = Synthetic polypeptide
source                 1..2437
                       mol_type = other DNA
```

```
                        organism = synthetic construct
SEQUENCE: 141
tcaagctttt ggaccctcgt acagaagcta atacgactca ctatagggaa ataagagaga  60
aaagaagagt aagaagaaat ataagagcca ccatgcggcc aggcctcccc tcctacctca  120
tcatcctcgc cgtctgtctc ttcagccacc tactttcgtc acgatatggc gcagaagccg  180
tatccgaacc gctggacaaa gcgtttcacc tactgctcaa cacctacggg agacccatcc  240
gcttcctgcg tgaaaatacc acccagtgta cctacaacag cagcctccgt aacagcacgg  300
tcgtcaggga aaacgccatc agtttcaact tcttccaaag ctataatcaa tactatgtat  360
tccatatgcc tcgatgtctc tttgcgggtc ctctggcgga gcagtttctg aaccaggtag  420
atctgaccga aaccctggaa agataccaac agagacttaa cacttacgcg ctggtatcca  480
aagacctggc cagctaccga tctttctcgc agcagctaaa ggcacaagac agcctaggtg  540
aacagcccac cactgtgcca ccgcccattg acctgtcaat acctcacgtt tggatgccac  600
cgcaaaccac tccacacggc tggacagaat cacataccac ctcaggacta caccgaccac  660
actttaacca gacctgtatc ctctttgatg gacacgatct actattcagc accgtcacac  720
cttgtttgca ccaaggcttt tacctcatcg acgaactacg ttacgttaaa ataacactga  780
ccgaggactt cttcgtagtt acggtgtcca tagacgacga cacacccatg ctgcttatct  840
tcggccatct tccacgcgta cttttcaaag cgccctatca acgcgacaac tttatactac  900
gacaaactga gaaacacgag ctcctggtgc tagttaagaa agatcaactg aaccgtcact  960
cttatctcaa agacccggac tttcttgacg ccgcacttga cttcaactac ctagacctca  1020
gcgcactact acgtaacagc tttcaccgtt acgccgtgga tgtactcaag agcggtcgat  1080
gtcagatgct ggaccgccgc acggtagaaa tggccttcgc ctacgcatta gcactgttcg  1140
cagcagcccg acaagaagag gccggcgccc aagtctccgt cccacgggcc ctagaccgcc  1200
aggccgcact cttacaaata caagaattta tgatcacctg cctctcacaa acaccaccac  1260
gcaccacgtt gctgctgtat cccacggccg tggacctggc caaacgagcc ctttggacac  1320
cgaatcagat caccgacatc accagcctcg tacgcctggt ctacatactc tctaaacaga  1380
atcagcaaca tctcatcccc caatgggcac tacgacagat cgccgacttt gccctaaaac  1440
tacacaaaac gcacctggcc tcttttcttt cagccttcgc acgccaagaa ctctacctca  1500
tgggcagcct cgtccactcc atgctggtac atacgacgga gagacgcgaa atcttcatcg  1560
tagaaacggg cctctgttca ttggccgagc tatcacactt tacgcagttg ttagctcatc  1620
cacaccacga atacctcagc gacctgtaca caccctgttc cagtagcggg cgacgcgatc  1680
actcgctcga acgcctcacg cgtctcttcc ccgatgccac cgtccccgct accgttcccg  1740
ccgccctctc catcctatct accatgcaac caagcacgct ggaaaccttc cccgacctgt  1800
tttgcttgcc gctcggcgaa tccttctccg cgctgaccgt ctccgaacac gtcagttata  1860
tcgtaacaaa ccagtacctg atcaaaggta tctcctaccc tgtctccacc accgtcgtag  1920
gccagagcct catcatcacc cagacggaca gtcaaactaa atgcgaactg acgcgcaaca  1980
tgcataccac acacagcatc acagtggcgc tcaacatttc gctagaaaac tgcgcctttt  2040
gccaaagcgc cctgctagaa tacgacgaca cgcaaggcgt catcaacatc atgtacatgc  2100
acgactcgga cgacgtcctt ttcgccctgg atccctacaa cgaagtggtg gtctcatctc  2160
cgcgaactca ctacctcatg cttttgaaga acggtacggt actagaagta actgacgtcg  2220
tcgtggacgc caccgacagt cgtctcctca tgatgtccgt ctacgcgcta tcggccatca  2280
tcggcatcta tctgctctac cgcatgctca agacatgctg ataataggct ggagcctcgg  2340
tggccatgct tcttgcccct tggcctcccc cccagcccct cctccccttc ctgcacccgt  2400
acccccgtgg tctttgaata aagtctgagt gggcggc                           2437

SEQ ID NO: 142          moltype = DNA  length = 1045
FEATURE                 Location/Qualifiers
misc_feature            1..1045
                        note = Synthetic polypeptide
source                  1..1045
                        mol_type = other DNA
                        organism = synthetic construct
SEQUENCE: 142
tcaagctttt ggaccctcgt acagaagcta atacgactca ctatagggaa ataagagaga  60
aaagaagagt aagaagaaat ataagagcca ccatgtgccg ccgcccggat tgcggcttct  120
ctttctcacc tggaccggtg atactgctgt ggtgttgcct tctgctgccc attgtttcct  180
cagccgccgt cagcgtcgct cctaccgccg ccgagaaagt ccccgcggag tgccccgaac  240
taacgcgccg atgcttgttg ggtgaggtgt ttgagggtga caagtatgaa agttggctgc  300
gcccgttggt gaatgttacc gggcgcgatg gcccgctatc gcaacttatc cgttaccgtc  360
ccgttacgcc ggaggccgcc aactccgtgc tgttggacga ggctttcctg gacactctgg  420
ccctgctgta caacaatccg gatcaattgc gggccctgct gacgctgttg agctcggaca  480
cagcgccgcg ctggatgacg gtgatgcgcg gctacagcga gtgcggcgat ggctcgccgg  540
ccgtgtacac gtgcgtggac gacctgtgcc gcggctacga cctcacgcga ctgtcatacg  600
ggcgcagcat cttcacggaa cacgtgttag gcttcgagct ggtgccaccg tctctcttta  660
acgtggtggt ggccatacgc aacgaagcca cgcgtaccaa ccgcgccgtg cgtctgcccg  720
tgagcaccgc tgccgcgccc gagggcatca cgctctttta cggcctgtac aacgcagtga  780
aggaattctg cctgcgtcac cagctggacc cgccgctgct acgccaccta gataaatact  840
acgccggact gccgcccgag ctgaagcaga cgcgcgtcaa cctgccggct cactcgcgct  900
atggccctca agcagtggat gctcgctgat aataggctgg agcctcggtg gccatgcttc  960
ttgccccttg ggcctccccc cagcccctcc tccccttcct gcacccgtac ccccgtggtc  1020
tttgaataaa gtctgagtgg gcggc                                        1045

SEQ ID NO: 143          moltype = DNA  length = 724
FEATURE                 Location/Qualifiers
misc_feature            1..724
                        note = Synthetic polypeptide
source                  1..724
                        mol_type = other DNA
                        organism = synthetic construct
SEQUENCE: 143
```

```
tcaagctttt ggaccctcgt acagaagcta atacgactca ctatagggaa ataagagaga  60
aaagaagagt aagaagaaat ataagagcca ccatgagtcc caaagatctg acgccgttct  120
tgacggcgtt gtggctgcta ttgggtcaca gccgcgtgcc gcgggtgcgc gcagaagaat  180
gttgcgaatt cataaacgtc aaccacccgc cggaacgctg ttacgatttc aaaatgtgca  240
atcgcttcac cgtcgcgctg cggtgtccgg acggcgaagt ctgctacagt cccgagaaaa  300
cggctgagat tcgcgggatc gtcaccacca tgacccattc attgacacgc caggtcgtac  360
acaacaaact gacgagctgc aactacaatc cgttatacct cgaagctgac gggcgaatac  420
gctgcggcaa agtaaacgac aaggcgcagt acctgctggg cgccgctggc agcgttccct  480
atcgatggat caatctggaa tacgacaaga taacccggat cgtgggcctg gatcagtacc  540
tggagagcgt taagaaacac aaacggctgg atgtgtgccg cgctaaaatg ggctatatgc  600
tgcagtgata ataggctgga gcctcggtgg ccatgcttct tgccccttgg gcctcccccc  660
agcccctcct ccccttcctg cacccgtacc cccgtggtct ttgaataaag tctgagtggg  720
cggc                                                              724
```

```
SEQ ID NO: 144         moltype = DNA  length = 846
FEATURE                Location/Qualifiers
misc_feature           1..846
                       note = Synthetic polypeptide
source                 1..846
                       mol_type = other DNA
                       organism = synthetic construct
SEQUENCE: 144
tcaagctttt ggaccctcgt acagaagcta atacgactca ctatagggaa ataagagaga  60
aaagaagagt aagaagaaat ataagagcca ccatgctgcg gcttctgctt cgtcaccact  120
ttcactgcct gcttctgtgc gcggtttggg caacgccctg tctggcgtct ccgtggtcga  180
cgctaacagc aaaccagaat ccgtccccgc catggtctaa actgacgtat tccaaaccgc  240
atgacgcggc gacgttttac tgtccttttc tctatccctc gcccccacga tccccccttgc  300
aattctcggg gttccagcgg gtatcaacgg gtcccgagtg tcgcaacgag accctgtatc  360
tgctgtacaa ccgggaaggc cagaccttgg tggagagaag ctccacctgg gtgaaaaagg  420
tgatctggta cctgagcggt cggaaccaaa ccatcctcca acggatgccc cgaacggctt  480
cgaaaccgag cgacggaaac gtgcagatca gcgtggaaga cgccaagatt tttggagcgc  540
acatggtgcc caagcgctgc tacgcttcgt cgtcaacgat ggcacacgtt atcagatgtg  600
tgtgatgaag ctggagagct gggctcacgt cttccgggac tacagcgtgt cttttcaggt  660
gcgattgacg ttcaccgagg ccaataacca gacttacacc ttctgcaccc atcccaatct  720
catcgtttga taataggctg gagcctcggt ggccatgctt cttgcccctt gggcctcccc  780
ccagcccctc ctccccttcc tgcacccgta cccccgtggt ctttgaataa agtctgagtg  840
ggcggc                                                            846
```

```
SEQ ID NO: 145         moltype = DNA  length = 598
FEATURE                Location/Qualifiers
misc_feature           1..598
                       note = Synthetic polypeptide
source                 1..598
                       mol_type = other DNA
                       organism = synthetic construct
SEQUENCE: 145
tcaagctttt ggaccctcgt acagaagcta atacgactca ctatagggaa ataagagaga  60
aaagaagagt aagaagaaat ataagagcca ccatgcggct gtgtcgggtg tggctgtctg  120
tttgtctgtg cgccgtggtg ctgggtcagt gccagcggga aaccgcggaa aagaacgatt  180
attaccgagt accgcattac tgggacgcgt gctctcgcgc gctgcccgac caaacccgtt  240
acaagtatgt ggaacagctc gtggacctca cgttgaacta ccactacgat gcgagccacg  300
gcttggacaa ctttgacgtg ctcaagagaa tcaacgtgac cgaggtgtcg ttgctcatca  360
gcgactttag acgtcagaac cgtcgcggcg gcaccaacaa aaggaccacg ttcaacgccg  420
ccggttcgct ggcgccacac gcccggagcc tcgagttcag cgtgcggctc tttgccaact  480
gataataggc tggagcctcg gtggccatgc ttcttgcccc ttgggcctcc ccccagcccc  540
tcctcccctt cctgcacccg tacccccgtg gtctttgaat aaagtctgag tgggcggc    598
```

```
SEQ ID NO: 146         moltype = DNA  length = 2933
FEATURE                Location/Qualifiers
misc_feature           1..2933
                       note = Synthetic polypeptide
source                 1..2933
                       mol_type = other DNA
                       organism = synthetic construct
SEQUENCE: 146
tcaagctttt ggaccctcgt acagaagcta atacgactca ctatagggaa ataagagaga  60
aaagaagagt aagaagaaat ataagagcca ccatggaatc caggatctgg tgcctggtag  120
tctgcgttaa cttgtgtatc gtctgtctgg gtgctgcggt ttcctcatct tctactcgtg  180
gaacttctgc tactcacagt caccattcct ctcatacgac gtctgctgct cactctcgat  240
ccggttcagt ctctcaacgc gtaacttctt cccaaacggt cagccatggt gttaacgaga  300
ccatctacaa cactaccctc aagtacggag atgtggtggg ggtcaatacc accaagtacc  360
cctatcgcgt gtgttctatg gcccaggggta cggatcttat tcgctttgaa cgtaatatcg  420
tctgcacctc gatgaagccc atcaatgaag acctggacga gggcatcatg gtggtctaca  480
aacgcaacat cgtcgcgcac acctttaagg tacgagtcta ccagaaggtt ttgacgtttc  540
gtcgtagcta cgcttacatc cacaccactt atctgctggg cagcaacacg gaatacgtgg  600
cgcctcctat gtgggagatt catcatatca acagccacag tcagtgctac agttcctaca  660
gccgcgttat agcaggcacg gttttcgtgg cttatcatag ggacagctat gaaaacaaaa  720
ccatgcaatt aatgcccgac gattattcca acacccacag tacccgttac gtgacggtca  780
aggatcaatg gcacagccgc ggcagcacct ggctctatcg tgagacctgt aatctgaatt  840
```

-continued

```
gtatggtgac catcactact gcgcgctcca aatatcctta tcattttttc gccacttcca  900
cgggtgacgt ggttgacatt tctcctttct acaacggaac caatcgcaat gccagctact  960
ttggagaaaa cgccgacaag tttttcattt ttccgaacta cactatcgtc tccgactttg  1020
gaagaccgaa ttctgcgtta gagacccaca ggttggtggc ttttcttgaa cgtgcggact  1080
cggtgatctc ctgggatata caggacgaaa agaatgtcac ttgtcaactc actttctggg  1140
aagcctcgga acgcaccatt cgttccgaag ccgaggactc gtatcacttt tcttctgcca  1200
aaatgaccgc cactttctta tctaagaagc aagaggtgaa catgtccgac tctgcgctgg  1260
actgcgtacg tgatgaggct ataaataagt tacagcagat tttcaatact tcatacaatc  1320
aaacatatga aaaatatgga aacgtgtccg tctttgaaac cactggtggt ttggtagtgt  1380
tctggcaagg tatcaagcaa aaatctctgg tggaactcga acgtttggcc aaccgctcca  1440
gtctgaatct tactcataat agaaccaaaa gaagtacaga tggcaacaat gcaactcatt  1500
tatccaacat ggaatcggtg cacaatctgg tctacgccca gctgcagttc acctatgaca  1560
cgttgcgcgg ttacatcaac cgggcgctgg cgcaaatcgc agaagcctgg tgtgtggatc  1620
aacggcgcac cctagaggtc ttcaaggaac tcagcaagat caacccgtca gccattctct  1680
cggccattta caacaaaccg attgccgcgc gtttcatggg tgatgtcttg ggcctggcca  1740
gctgcgtgac catcaaccaa accagcgtca aggtgctgcg tgatatgaac gtgaaggagt  1800
cgccaggacg ctgctactca cgacccgtgg tcatctttaa tttcgccaac agctcgtacg  1860
tgcagtacgg tcaactgggc gaggacaacg aaatcctgtt gggcaaccac cgcactgagg  1920
aatgtcagct tcccagcctc aagatcttca tcgccgggaa ctcggcctac gagtacgtgg  1980
actacctctt caaacgcatg attgacctca gcagtatctc caccgtcgac agcatgatcg  2040
ccctggatat cgacccgctg gaaaataccg acttcagggt actggaactt tactcgcaga  2100
aagagctgcg ttccagcaac gtttttgacc tcgaagagat catgcgcgaa ttcaactcgt  2160
acaagcagcg ggtaaagtac gtggaggaca aggtagtcga cccgctaccg ccctacctca  2220
agggtctgga cgacctcatg agcggcctgg gcgccgcggg aaaggccgtt ggcgtagcca  2280
ttggggccgt gggtggcgcg gtggcctccg tggtcgaagg cgttgccacc ttcctcaaaa  2340
accccttcgg agcgttcacc atcatcctcg tggccatagc tgtagtcatt atcacttatt  2400
tgatctatac tcgacagcgg cgtttgtgca cgcagccgct gcagaacctc tttccctatc  2460
tggtgtccgc cgacgggacc accgtgacgt cgggcagcac caaagacacg tcgttacagg  2520
ctccgccttc ctacgaggaa agtgtttata attctggtcg caaaggaccg ggaccaccgt  2580
cgtctgatgc atccacggcg gctccgcctt acaccaacga gcaggcttac cagatgcttc  2640
tggccctggc ccgtctggac gcagagcagc gagcgcagca gaacggtaca gattctttgg  2700
acggacggac tggcacgcag gacaagggac agaagcccaa cctactagac cgactgcgac  2760
atcgcaaaaa cggctaccga cacttgaaag actctgacga agaagagaac gtcttgataa  2820
taggctggag cctcggtggc catgcttctt gccccttggg cctcccccca gcccctcctc  2880
cccttcctgc acccgtaccc ccgtggtctt tgaataaagt ctgagtgggc ggc         2933

SEQ ID NO: 147         moltype = DNA  length = 1882
FEATURE                Location/Qualifiers
misc_feature           1..1882
                       note = Synthetic polypeptide
source                 1..1882
                       mol_type = other DNA
                       organism = synthetic construct
SEQUENCE: 147
tcaagctttt ggaccctcgt acagaagcta atacgactca ctatagggaa ataagagaga  60
aaagaagagt aagaagaaat ataagagcca ccatggagtc gcgcggtcgc cgttgtcccg  120
aaatgatatc cgtactgggt cccatttcgg ggcacgtgct gaaagccgtg tttagtcgcg  180
gcgatacgcc ggtgctgccg cacgagacga gactcctgca gacgggtatc cacgtacgcg  240
tgagccagcc ctcgctgatc ctggtgtcgc agtacacgcc cgactcgacg ccatgccacc  300
gcggcgacaa tcagctgcag gtgcagcaca cgtactttac gggcagcgag gtggagaacg  360
tgtcggtcaa cgtgcacaac cccacgggcc gaagcatctg ccccagccaa gagcccatgt  420
cgatctatgt gtacgcgctg ccgctcaaga tgctgaacat ccccagcatc aacgtgcacc  480
actacccgtc ggcggccgag cgcaaacacc gacacctgcc cgtagccgac gctgttattc  540
acgcgtcggg caagcagatg tggcaggcgc gtctcacggt ctcgggactg gcctggacgc  600
gtcagcagaa ccagtggaaa gagcccgacg tctactacac gtcagcgttc gtgtttccca  660
ccaaggacgt ggcactgcgg cacgtggtgt gcgcgcacga gctggtttgc tccatggaga  720
acacgcgcgc aaccaagatg caggtgatag gtgaccagta cgtcaaggtg tacctggagt  780
ccttctgcga ggacgtgccc tccggcaagc tctttatgca cgtcacgctg ggctctgacg  840
tggaagagga cctaacgatg acccgcaacc cgcaaccctt catgcgcccc cacgagcgca  900
acggctttac ggtgttgtgt cccaaaaata tgataatcaa accgggcaag atctcgcaca  960
tcatgctgga tgtggctttt acctcacacg agcattttgg gctgctgtgt cccaagagca  1020
tcccgggcct gagcatctca ggtaacctgt tgatgaacgg gcagcaaatc ttcctggagg  1080
tacaagcgat acgcgagacc gtggaactgc gtcagtacga tcccgtggct gcgctcttct  1140
ttttcgatat cgacttgttg ctgcagcgcg ggcctcagta cagcgagcac cccaccttca  1200
ccagccagta tcgcatccag ggcaagcttg agtaccgaca cacctgggac cggcacgacg  1260
agggtgccgc ccagggcgac gacgacgtct ggaccagcgg atcggactcc gacgaagaac  1320
tcgtaaccac cgagcgtaag acgccccgcg tcaccggcgg cggagccatg gcgagcgcct  1380
ccacttccgc gggctcagca tcctcggcga cggcgtgcac ggcgggcgtt atgacacgcg  1440
gccgccttaa ggccgagtcc accgtcgcgc ccgaagagga caccgacgag gattccgaca  1500
acgaaatcca caatccggcc gtgttcacct ggccgccctg gcaggccggc atcctggccc  1560
gcaacctggt gcccatggtg gctacggttc agggtcagaa tctgaagtac caggagttct  1620
tctgggacgc caacgacatc taccgcatct tcgccgaatt ggaaggcgta tggcagcccg  1680
ctgcgcaacc caaacgtcgc cgccaccggc aagacgcctt gcccgggcca tgcatcgcct  1740
cgacgcccaa aaagcaccga ggttgataat aggctggagc ctcggtggcc atgcttcttg  1800
ccccttgggc ctccccccag cccctcctcc ccttcctgca cccgtacccc cgtggtcttt  1860
gaataaagtc tgagtgggcg gc                                          1882

SEQ ID NO: 148         moltype = DNA  length = 3364
FEATURE                Location/Qualifiers
```

-continued

```
misc_feature            1..3364
                        note = Synthetic polypeptide
source                  1..3364
                        mol_type = other DNA
                        organism = synthetic construct
SEQUENCE: 148
tcaagctttt ggaccctcgt acagaagcta atacgactca ctatagggaa ataagagaga  60
aaagaagagt aagaagaaat ataagagcca ccatggagtc gcgcggtcgc cgttgtcccg  120
aaatgatatc cgtactgggt cccatttcgg ggcacgtgct gaaagccgtg tttagtcgcg  180
gcgatacgcc ggtgctgccg cacgagacgc gactcctgca gacgggtatc cacgtacgcg  240
tgagccagcc ctcgctgatc ctggtgtcgc agtacacgcc cgactcgacg ccatgccacc  300
gcggcgacaa tcagctgcag gtgcagcaca cgtactttac gggcagcgag gtggagaacg  360
tgtcggtcaa cgtgcacaac cccacgggcc gaagcatctg ccccagccaa gagcccatgt  420
cgatctatgt gtacgcgctg ccgctcaaga tgctgaacat ccccagcatc aacgtgcacc  480
actacccgtc ggcggccgag cgcaaacacc gacacctgcc cgtagccgac gctgttattc  540
acgcgtcggg caagcagatg tggcaggcgc gtctcacggt ctcgggactg gcctggacgc  600
gtcagcagaa ccagtggaaa gagcccgacg tctactacac gtcagcgttc gtgtttccca  660
ccaaggacgt ggcactgcgg cacgtggtgt gcgcgcacga gctggtttgc tccatggaga  720
acacgcgcgc aaccaagatg caggtgatag gtgaccagta cgtcaaggtg tacctggagt  780
ccttctgcga ggacgtgccc tccggcaagc tctttatgca cgtcacgctg ggctctgacg  840
tggaagagga cctaacgatg acccgcaacc cgcaaccctt catgcgcccc cacgagcgca  900
acggctttac ggtgttgtgt cccaaaaata tgataatcaa accgggcaag atctcgcaca  960
tcatgctgga tgtggctttt acctcacacg agcattttgg gctgctgtgt cccaagagca  1020
tcccgggcct gagcatctca ggtaacctgt tgatgaacgg gcagcaaatc ttcctggagg  1080
tacaagcgat acgcgagacc gtggaactgc gtcagtacga tcccgtggct gcgctcttct  1140
ttttcgatat cgacttgttg ctgcagcgcg ggcctcagta cagcgagcac ccccaccttca  1200
ccagccagta tcgcatccag ggcaagcttg agtaccgaca cacctgggac cggcacgacg  1260
agggtgccgc ccagggcgac gacgacgtct ggaccagcgg atcggactcc gacgaagaac  1320
tcgtaaccac cgagcgtaag acgccccgcg tcaccggcgg cggcgccatg gcgagcgcct  1380
ccacttccgc gggccgcaaa cgcaaatcag catcctcggc gacggcgtgc acggcgggcg  1440
ttatgacacg cggccgcctt aaggccgagt ccaccgtcgc gcccgaagag gacaccgacg  1500
aggattccga caacgaaatc cacaatccgg ccgtgttcac ctggccgccc tggcaggccg  1560
gcatcctggc ccgcaacctg gtgcccatgg tggctacggt tcagggtcag aatctgaagt  1620
accaggagtt cttctgggac gccaacgaca tctaccgcat cttcgccgaa ttggaaggcg  1680
tatggcagcc cgctgcgcaa cccaaacgtc gccgccaccg gcaagacgcc ttgcccgggc  1740
catgcatcgc ctcgacgccc aaaaagcacc gaggtgagtc ctctgccaag agaaagatgg  1800
accctgataa tcctgacgag ggcccttcct ccaaggtgcc acggcccgag acacccgtga  1860
ccaaggccac gacgttcctg cagactatgt taaggaagga ggttaacagt cagctgagcc  1920
tgggagaccc gctgttccca gaattggccg aagaatccct caaaaccttt gaacaagtga  1980
ccgaggattg caacgagaac cccgaaaaag atgtcctgac agaactcgtc aaacagatta  2040
aggttcgagt ggacatggtg cggcatagaa tcaaggagca catgctgaaa aaatataccc  2100
agacggaaga aaaattcact ggcgccttta atatgatggg aggatgtttg cagaatgcct  2160
tagatatctt agataaggtt catgagcctt tcgaggacat gaagtgtatt gggctaacta  2220
tgcagagcat gtatgagaac tacattgtac ctgaggataa gcgggagatg tggatggctt  2280
gtattaagga gctgcatgat gtgagcaagg gcgccgctaa caagttgggg ggtgcactgc  2340
aggctaaggc ccgtgctaaa aaggatgaac ttaggagaaa gatgatgtat atgtgctaca  2400
ggaatataga gttctttacc aagaactcag ccttccctaa gaccaccaat ggctgcagtc  2460
aggccatggc ggcattgcag aacttgcctc agtgctctcc tgatgagatt atgtcttatg  2520
cccagaaaat ctttaagatt ttggatgagg agagagacaa ggtgctcacg cacattgatc  2580
acatatttat ggatatcctc actacatgtg tggaaacaat gtgtaatgag tacaaggtca  2640
ctagtgacgc ttgtatgatg accatgtacg ggggcatctc tctcttaagt gagttctgtc  2700
gggtgctgtg ctgctatgtc ttagaggaga ctagtgtgat gctggccaag cggcctctga  2760
taaccaagcc tgaggttatc agtgtaatga agcgccgcat tgaggagatc tgcatgaagg  2820
tctttgccca gtacattctg ggggccgatc ctttgagagt ctgctctcct agtgtggatg  2880
acctacgggc catcgccgag gagtcagatg aggaagaggc tattgtagcc tacactttgg  2940
ccaccgctgg tgccagctcc tctgattctc tggtgtcacc tccagagtcc cctgtacccg  3000
cgactatccc tctgtcctca gtaattgtgg ctgagaacag tgatcaggaa gaaagtgaac  3060
agagtgatga ggaacaggag gagggtgctc aggaggagcg ggaggacact gtgtctgtca  3120
agtctgagcc agtgtctgag atagaggaag ttgcctcaga ggaagaggag gatggtgctg  3180
aggaacccac cgcctctgga ggcaagagca cccaccctat ggtgactaga agcaaggctg  3240
accagtgata ataggctgga gcctcggtgg ccatgcttct tgccccttgg gcctcccccc  3300
agcccctcct ccccttcctg cacccgtacc cccgtggtct ttgaataaag tctgagtggg  3360
cggc                                                              3364

SEQ ID NO: 149          moltype = DNA  length = 3352
FEATURE                 Location/Qualifiers
misc_feature            1..3352
                        note = Synthetic polypeptide
source                  1..3352
                        mol_type = other DNA
                        organism = synthetic construct
SEQUENCE: 149
tcaagctttt ggaccctcgt acagaagcta atacgactca ctatagggaa ataagagaga  60
aaagaagagt aagaagaaat ataagagcca ccatggagtc gcgcggtcgc cgttgtcccg  120
aaatgatatc cgtactgggt cccatttcgg gtcatgtgct gaaagcggtg tttagtcgcg  180
gcgatacgcc agtactgccg cacgagacgc gactcctgca gacaggtatc cacgtacgcg  240
tgagccagcc ctcgctcatc ctggtgtcgc agtacacgcc cgactcgacg ccatgccacc  300
gcggcgacaa tcagctgcag gtgcagcaca cgtactttac gggcagcgag gtggagaacg  360
tgtcggtcaa cgtccacaac cccacgggtc gaagcatctg cccctctcaa gagcccatgt  420
```

-continued

```
cgatctatgt gtacgcgctg ccgctcaaga tgctgaacat cccgagcatc aacgtgcacc  480
actacccgag cgcggccgag cgcaaacacc gacacctgcc cgtagccgac gctgttattc  540
acgcgtcggg caagcagatg tggcaagcgc gcctcacggt ctcgggacta gcctggacgc  600
gtcagcagaa ccagtggaaa gagcccgacg tctactacac gtcagcgttc gtgtttccca  660
ccaaggacgt ggcactgcgc cacgtggtgt gtgcgcacga gctggtttgc tccatggaga  720
atacgcgcgc aaccaagatg caggtgatag gtgatcaata cgtcaaggtg tacctggagt  780
ccttctgcga ggatgtgccc tccggtaagc tctttatgca cgtcacgctg ggctctgacg  840
tggaagagga cctaacgatg acccgcaatc cgcaaccctt catgcgcccc cacgagcgca  900
acggctttac ggtgttgtgt cctaaaaata tgataatcaa accaggcaag atctcgcaca  960
tcatgctgga tgtggctttt acctcacacg agcatttgg gctgctgtgt cccaagagca  1020
tcccgggcct gagcatctca ggtaacctgt tgatgaacgg gcagcaaatc tttctcgagg  1080
tgcaagctat acgcgagacc gtcgaactgc gtcagtacga tcccgtggct gcgctgttct  1140
ttttcgatat cgacttgttg ctgcagcgcg ggcctcagta cagcgagcac cccaccttca  1200
ccagccagta tcgcatccag ggcaagcttg agtaccgaca cacctgggac cggcacgacg  1260
agggagccgc ccagggcgac gacgacgtct ggacctctgg atcggactcc gacgaagaac  1320
tcgtaacgac cgagcgtaag accccccgcg tcaccggcgg cggcgccatg gcgtccgcct  1380
caacttccgc gggctcagca tcctcggcta cggcgtgcac ggcgggcgtt atgacacgtg  1440
gcagacttaa ggccgagtcc accgtcgcgc ccgaagagga caccgacgag gattccgaca  1500
acgaaatcca caatccggcc gtgttcacct ggccgccctg gcaggccggc atcctggccc  1560
gcaacctggt gcccatggtg gctacggttc agggtcagaa tctgaagtac caggagttct  1620
tctgggacgc caacgacatc taccgcatct tcgccgaatt ggaaggcgta tggcagcccg  1680
ctgcgcaacc caaacgtcgc cgccaccggc aagacgcctt gcccgggcca tgcatcgcct  1740
cgacgcccaa aaagcaccga ggtgagtcct ctgccaagag aaagatggac cctgataatc  1800
ctgacgaggg cccttcctcc aaggtgccac ggcccgagac acccgtgacc aaggccacga  1860
cgttcctgca gactatgtta aggaaggagg ttaacagtca gctgagcctg ggagacccgc  1920
tgttcccaga attggccgaa gaatccctca aaacctttga acaagtgacc gaggattgca  1980
acgagaaccc cgaaaaagat gtcctgacag aactcgtcaa acagattaag gttcgagtgg  2040
acatggtgcg gcatagaatc aaggagcaca tgctgaaaaa atatacccag acggaagaaa  2100
aattcactgg cgcctttaat atgatgggag gatgtttgca gaatgcctta gatatcttag  2160
ataaggttca tgagcctttc gaggacatga agtgtattgg gctaactatg cagagcatgt  2220
atgagaacta cattgtacct gaggataagc gggagatgtg gatggcttgt attaaggagc  2280
tgcatgatgt gagcaagggc gccgctaaca agttgggggg tgcactgcag gctaaggccc  2340
gtgctaaaaa ggatgaactt aggagaaaga tgatgtatat gtgctacagg aatatagagt  2400
tctttaccaa gaactcagcc ttccctaaga ccaccaatgg ctgctcgcag gccatggcgg  2460
cattgcagaa cttgcctcag tgctctcctg atgagattat gtcttatgcc cagaaaatct  2520
ttaagatttt ggatgaggag cgagacaagg tgcttacgca cattgatcac atatttatgg  2580
atatcctcac tacatgtgtt gaaacgatgt gcaatgagta caaggtcact agtgacgctt  2640
gtatgatgac catgtacggg ggcatatctc tcttaagtga attctgtcgg gtgctgtgct  2700
gctacgtctt agaggagact agtgtgatgc tggccaagcg gcctctgata accaagcctg  2760
aggtcatcag tgtaatgaag cgccgcattg aggagatctg catgaaggtc tttgcccagt  2820
acattctggg ggccgatcct ttgagagtct gctctccaag tgtggatgac ctacgggcca  2880
tcgccgagga gtcagacgag gaagaggcta ttgtagccta cactttggcc accgctggtg  2940
ccagctcctc tgactctctg gtgtcacctc cagaatcccc tgtgcccgcg acaatccctc  3000
tgtcctcagt aattgtggct gagaacagtg atcaggaaga aagtgaacag agtgatgagg  3060
aacaggagga gggtgctcag gaggagcggg aggatactgt gtctgtcaag tctgagccag  3120
tgtctgaaat tgaggaagtt gcctcagagg aagaggagga tggtgctgag gaacccaccg  3180
cctctggagg caagtccacc caccctatgg taactagatc aaaggctgac cagtgataat  3240
aggctggagc ctcggtggcc atgcttcttg ccccttgggc ctccccccag cccctcctcc  3300
ccttcctgca cccgtacccc cgtggtcttt gaataaagtc tgagtgggcg gc          3352

SEQ ID NO: 150          moltype = DNA  length = 1473
FEATURE                 Location/Qualifiers
misc_feature            1..1473
                        note = Synthetic polypeptide
source                  1..1473
                        mol_type = other DNA
                        organism = synthetic construct
SEQUENCE: 150
atggagtcct ctgccaagag aaagatggac cctgataatc ctgacgaggg cccttcctcc  60
aaggtgccac ggcccgagac acccgtgacc aaggccacga cgttcctgca gactatgtta  120
aggaaggagg ttaacagtca gctgagcctg ggagacccgc tgttcccaga attggccgaa  180
gaatccctca agacctttga acaagtgacc gaggattgca acgagaaccc cgagaaagat  240
gtcctgacag aactcgtcaa acagattaag gttcgagtgg acatggtgcg gcatagaatc  300
aaggagcaca tgctgaagaa atatacccag acggaagaga aattcactgg cgcctttaat  360
atgatgggag gatgtttgca gaatgcctta gatatcttag ataaggttca tgagcctttc  420
gaggacatga agtgtattgg gctaactatg cagagcatgt atgagaacta cattgtacct  480
gaggataagc gggagatgtg gatggcttgt attaaggagc tgcatgatgt gagcaagggc  540
gccgctaaca agttgggcgg tgcactgcag gctaaggccc gtgctaagaa ggatgaactt  600
aggagaaaga tgatgtatat gtgctacagg aatatagagt tctttaccaa gaactcagcc  660
ttccctaaga ccaccaatgg ctgcagtcag gccatggcgg cattgcagaa cttgcctcag  720
tgctctcctg atgagattat gtcttatgcc cagaagatct ttaagatttt ggatgaggag  780
agagacaagg tgctcacgca cattgatcac atatttatgg atatcctcac tacatgtgtg  840
gaaacaatgt gtaatgagta caaggtcact agtgacgctt gtatgatgac catgtacggc  900
ggcatctctc tcttaagtga gttctgtcgg gtgctgtgct gctatgtctt agaggagact  960
agtgtgatgc tggccaagcg gcctctgata accaagcctg aggttatcag tgtaatgaag  1020
cgccgcattg aggagatctg catgaaggtc tttgcccagt acattctggg agccgatcct  1080
ttgagagtct gctctcctag tgtggatgac ctacgggcca tcgccgagga gtcagatgag  1140
gaagaggcta ttgtagccta cactttggcc accgctggtg ccagctcctc tgattctctg  1200
gtgtcacctc cagagtcccc tgtacccgcg actatccctc tgtcctcagt aattgtggct  1260
```

```
gagaacagtg atcaggaaga aagtgaacag agtgatgagg aacaggagga gggtgctcag  1320
gaggagcggg aggacactgt gtctgtcaag tctgagccag tgtctgagat agaggaagtt  1380
gcctcagagg aagaggagga tggtgctgag gaacccaccg cctctggagg caagagcacc  1440
caccctatgg tgactagaag caaggctgac cag                               1473

SEQ ID NO: 151         moltype = DNA  length = 1740
FEATURE                Location/Qualifiers
misc_feature           1..1740
                       note = Synthetic polypeptide
source                 1..1740
                       mol_type = other DNA
                       organism = synthetic construct
SEQUENCE: 151
atggagtcct ctgccaagag aaagatggac cctgataatc ctgacgaggg cccttcctcc  60
aaggtgccac ggcccgagac acccgtgacc aaggccacga cgttcctgca gactatgtta  120
aggaaggagg ttaacagtca gctgagcctg ggagaccccgc tgttcccaga attggccgaa  180
gaatccctca agacctttga acaagtgacc gaggattgca acgagaaccc cgagaaagat  240
gtcctgacag aactcggtga catcctcgcc caggctgtca atcatgccgg tatcgattcc  300
agtagcaccg gccccacgct gacaacccac tcttgcagcg ttagcagcgc ccctcttaac  360
aagccgacgc ccaccagcgt cgcggttact aacactcctc tccccggggc atccgctact  420
cccgagctca gcccgcgtaa gaaaccgcgc aagaccacgc gtcctttcaa ggtgattatt  480
aaaccgcccg tgcctcccgc gcctatcatg ctgcccctca tcaaacagga agacatcaag  540
cccgagcccg actttaccat ccagtaccgc aacaagatta tcgataccgc cggctgtatc  600
gtgatctctg atagcgagga agaacagggt gaagaagtcg agacccgcgg tgctaccgcg  660
tcttcccctt ccaccggcag cggcacgccg cgagtgacct ctcccacgca cccgctctcc  720
cagatgaacc accctcctct tcccgatcct ttgggccggc ccgatgaaga tagttcctct  780
tcgtcttcct cctcctgcag ttcggcttcg gacagcgaga gtgagtccga ggagatgaaa  840
tgcagcagtg gcggaggagc atccgtgacc tcgagccacc atgggcgcgg cggttttggt  900
ggcgcggcct cctcctctct gctgagctgc ggacatcaga gcagcggcgg ggcgagcacc  960
ggacctcgca agaagaagag caaacgcatc tccgagttgg acaacgagaa ggtgcgcaat  1020
atcatgaaag ataagaacac gcccttctgc acacccaacg tgcagactcg gcggggtcgc  1080
gtcaagattg acgaggtgag ccgcatgttc cgtcacacca atcgttctct tgagtacaag  1140
aatctgccat tcatgatccc tagtatgcac caagtgttag aagaggccat caaagtttgc  1200
aagaccatgc aggtgaacaa caagggcatt cagatcatct acacccgcaa tcatgaagtg  1260
aagaatgagg tggatcaggt acggtgtcgc ctgggtagca tgtgcaacct ggccctctcc  1320
actcccttcc tcatggagca cactatgcct gtgacacacc ctcctgatgt ggcgcagcgc  1380
acggccgatg cttgtaacga cggtgtcaag gccgtgtgga acctcaaaga actgcacacc  1440
caccaattgt gcccgcgctc ttctgattac cgcaacatga ttatccacgc tgccacgccc  1500
gtggacctgt tgggcgctct caacctgtgc ctgcccctga tgcagaagtt tcccaaacag  1560
gtcatggtgc gcatcttctc caccaaccag ggtgggttca tgctgcctat ctacgagacg  1620
gccgcgaagg cctacgccgt ggggcagttt gagaagccca ccgagacccc tcccgaagac  1680
ctggacaccc tgagcctggc catcgaggca gccatccagg acctgaggaa caaatctcag  1740

SEQ ID NO: 152         moltype = DNA  length = 2721
FEATURE                Location/Qualifiers
misc_feature           1..2721
                       note = Synthetic polypeptide
source                 1..2721
                       mol_type = other DNA
                       organism = synthetic construct
SEQUENCE: 152
atggaatcca ggatctggtg cctggtagtc tgcgttaact tgtgtatcgt ctgtctgggt  60
gctgcggttt cctcatcttc tactcgtgga acttctgcta ctcacagtca ccattcctct  120
catacgacgt ctgctgctca ctctcgatcc ggttcagtct ctcaacgcgt aacttcttcc  180
caaacggtca gccatggtgt taacgagacc atctacaaca ctaccctcaa gtacggagat  240
gtggtggggg tcaataccac caagtacccc tatcgcgtgt gttctatggc ccagggtacg  300
gatcttattc gctttgaacg taatatcgtc tgcacctcga tgaagcccat caatgaagac  360
ctggacgagg gcatcatggt ggtctacaaa cgcaacatcg tcgcgcacac ctttaaggta  420
cgagtctacc agaaggtttt gacgtttcgt cgtagctacg cttacatcca caccacttat  480
ctgctgggca gcaacacgga atacgtggcg cctcctatgt gggagattca tcatatcaac  540
agccacagtc agtgctacag ttcctacagc cgcgttatag caggcacggt tttcgtggct  600
tatcataggg acagctatga aaacaaaacc atgcaattaa tgcccgacga ttattccaac  660
acccacagta cccgttacgt gacggtcaag gatcaatggc acagccgcgg cagcacctgg  720
ctctatcgtg agacctgtaa tctgaattgt atggtgacca tcactactgc gcgctccaaa  780
tatccttatc attttttcgc cacttccacg ggtgacgtgg ttgacatttc tcctttctac  840
aacggaacca atcgcaatgc cagctacttt ggagaaaacg ccgacaagtt tttcattttt  900
ccgaactaca ctatcgtctc cgactttgga agaccgaatt ctgcgttaga gacccacagg  960
ttggtggctt ttcttgaacg tgcggactcg gtgatctcct gggatataca ggacgaaaag  1020
aatgtcactt gtcaactcac tttctgggaa gcctcggaac gcaccattcg ttccgaagcc  1080
gaggactcgt atcacttttc ttctgccaaa atgaccgcca ctttcttatc taagaagcaa  1140
gaggtgaaca tgtccgactc tgcgctggac tgcgtacgtg atgaggctat aaataagtta  1200
cagcagattt tcaatacttc atacaatcaa acatatgaaa aatatggaaa cgtgtccgtc  1260
tttgaaacca ctggtggttt ggtagtgttc tggcaaggta tcaagcaaaa atctctggtg  1320
gaactcgaac gtttggccaa ccgctccagt ctgaatctta ctcataatag aaccaaaaga  1380
agtacagatg gcaacaatgc aactcattta tccaacatgg aatcggtgca caatctggtc  1440
tacgcccagc tgcagttcac ctatgacacg ttgcgcggtt acatcaaccg ggcgctggcg  1500
caaatcgcag aagcctggtg tgtggatcaa cggcgcaccc tagaggtctt caaggaactc  1560
agcaagatca acccgtcagc cattctctcg gccatttaca acaaaccgat tgccgcgcgt  1620
ttcatgggtg atgtcttggg cctggccagc tgcgtgacca tcaaccaaac cagcgtcaag  1680
```

```
gtgctgcgtg atatgaacgt gaaggagtcg ccaggacgct gctactcacg acccgtggtc  1740
atctttaatt tcgccaacag ctcgtacgtg cagtacggtc aactgggcga ggacaacgaa  1800
atcctgttgg gcaaccaccg cactgaggaa tgtcagcttc ccagcctcaa gatcttcatc  1860
gccgggaact cggcctacga gtacgtggac tacctcttca aacgcatgat tgacctcagc  1920
agtatctcca ccgtcgacag catgatcgcc ctggatatcg acccgctgga aaataccgac  1980
ttcagggtac tggaacttta ctcgcagaaa gagctgcgtt ccagcaacgt ttttgacctc  2040
gaagagatca tgcgcgaatt caactcgtac aagcagcggg taaagtacgt ggaggacaag  2100
gtagtcgacc cgctaccgcc ctacctcaag ggtctggacg acctcatgag cggcctgggc  2160
gccgcgggaa aggccgttgg cgtagccatt ggggccgtgg gtggcgcggt ggcctccgtg  2220
gtcgaaggcg ttgccacctt cctcaaaaac cccttcggag cgttcaccat catcctcgtg  2280
gccatagctg tagtcattat cacttatttg atctatactc gacagcggcg tttgtgcacg  2340
cagccgctgc agaacctctt tccctatctg gtgtccgccg acgggaccac cgtgacgtcg  2400
ggcagcacca aagacacgtc gttacaggct ccgccttcct acgaggaaag tgtttataat  2460
tctggtcgca aaggaccggg accaccgtcg tctgatgcat ccacggcggc tccgccttac  2520
accaacgagc aggcttacca gatgcttctg gccctggccc gtctggacgc agagcagcga  2580
gcgcagcaga acggtacaga ttctttggac ggacggactg gcacgcagga caagggacag  2640
aagcccaacc tactagaccg actgcgacat cgcaaaaacg gctaccgaca cttgaaagac  2700
tctgacgaag aagagaacgt c                                            2721
```

```
SEQ ID NO: 153          moltype = DNA  length = 2226
FEATURE                 Location/Qualifiers
misc_feature            1..2226
                        note = Synthetic polypeptide
source                  1..2226
                        mol_type = other DNA
                        organism = synthetic construct
SEQUENCE: 153
atgcggccag gcctcccctc ctacctcatc atcctcgccg tctgtctctt cagccaccta  60
ctttcgtcac gatatggcgc agaagccgta tccgaaccgc tggacaaagc gtttcaccta  120
ctgctcaaca cctacgggag acccatccgc ttcctgcgtg aaaataccac ccagtgtacc  180
tacaacagca gcctccgtaa cagcacggtc gtcagggaaa acgccatcag tttcaacttc  240
ttccaaagct ataatcaata ctatgtattc catatgcctc gatgtctctt tgcgggtcct  300
ctggcggagc agtttctgaa ccaggtagat ctgaccgaaa ccctggaaag ataccaacag  360
agacttaaca cttacgcgct ggtatccaaa gacctggcca gctaccgatc tttctcgcag  420
cagctaaagg cacaagacag cctaggtgaa cagcccacca ctgtgccacc gcccattgac  480
ctgtcaatac ctcacgtttg gatgccaccg caaaccactc cacacggctg gacagaatca  540
cataccacct caggactaca ccgaccacac tttaaccaga cctgtatcct ctttgatgga  600
cacgatctac tattcagcac cgtcacacct tgtttgcacc aaggctttta cctcatcgac  660
gaactacgtt acgttaaaat aacactgacc gaggacttct tcgtagttac ggtgtccata  720
gacgacgaca cacccatgct gcttatcttc ggccatcttc cacgcgtact tttcaaagcg  780
ccctatcaac gcgacaactt tatactacga caaactgaga aacacgagct cctggtgcta  840
gttaagaaag atcaactgaa ccgtcactct tatctcaaag acccggactt tcttgacgcc  900
gcacttgact tcaactacct agacctcagc gcactactac gtaacagctt tcaccgttac  960
gccgtggatg tactcaagag cggtcgatgt cagatgctgg accgccgcac ggtagaaatg  1020
gccttcgcct acgcattagc actgttcgca gcagcccgac aagaagaggc cggcgcccaa  1080
gtctccgtcc cacgggccct agaccgccag gccgcactct tacaaataca agaatttatg  1140
atcacctgcc tctcacaaac accaccacgc accacgttgc tgctgtatcc cacggccgtg  1200
gacctggcca aacgagccct ttggacaccg aatcagatca ccgacatcac cagcctcgta  1260
cgcctggtct acatactctc taaacagaat cagcaacatc tcatccccca atgggcacta  1320
cgacagatcg ccgactttgc cctaaaacta cacaaaacgc acctggcctc ttttctttca  1380
gccttcgcac gccaagaact ctacctcatg ggcagcctcg tccactccat gctggtacat  1440
acgacggaga gacgcgaaat cttcatcgta gaaacgggcc tctgttcatt ggccgagcta  1500
tcacacttta cgcagttgtt agctcatcca caccacgaat acctcagcga cctgtacaca  1560
ccctgttcca gtagcgggcg acgcgatcac tcgctcgaac gcctcacgcg tctcttcccc  1620
gatgccaccg tccccgctac cgttcccgcc gccctctcca tcctatctac catgcaacca  1680
agcacgctgg aaaccttccc cgacctgttt tgcttgccgc tcggcgaatc cttctccgcg  1740
ctgaccgtct ccgaacacgt cagttatatc gtaacaaacc agtacctgat caaaggtatc  1800
tcctaccctg tctccaccac cgtcgtaggc cagagcctca tcatcaccca gacggacagt  1860
caaactaaat gcgaactgac gcgcaacatg cataccacac acagcatcac agtggcgctc  1920
aacatttcgc tagaaaactg cgccttttgc caaagcgccc tgctagaata cgacgacacg  1980
caaggcgtca tcaacatcat gtacatgcac gactcggacg acgtcctttt cgccctggat  2040
ccctacaacg aagtggtggt ctcatctccg cgaactcact acctcatgct tttgaagaac  2100
ggtacggtac tagaagtaac tgacgtcgtc gtggacgcca ccgacagtcg tctcctcatg  2160
atgtccgtct acgcgctatc ggccatcatc ggcatctatc tgctctaccg catgctcaag  2220
acatgc                                                             2226
```

```
SEQ ID NO: 154          moltype = DNA  length = 2226
FEATURE                 Location/Qualifiers
misc_feature            1..2226
                        note = Synthetic polypeptide
source                  1..2226
                        mol_type = other DNA
                        organism = synthetic construct
SEQUENCE: 154
atgcggccag gcctcccctc ctacctcatc atcctcgccg tctgtctctt cagccaccta  60
ctttcgtcac gatatggcgc agaagccgta tccgaaccgc tggacaaagc gtttcaccta  120
ctgctcaaca cctacgggag acccatccgc ttcctgcgtg aaaataccac ccagtgtacc  180
tacaacagca gcctccgtaa cagcacggtc gtcagggaaa acgccatcag tttcaacttc  240
ttccaaagct ataatcaata ctatgtattc catatgcctc gatgtctctt tgcgggtcct  300
```

-continued

```
ctggcggagc agtttctgaa ccaggtagat ctgaccgaaa ccctggaaag ataccaacag  360
agacttaaca cttacgcgct ggtatccaaa gacctggcca gctaccgatc tttctcgcag  420
cagctaaagg cacaagacag cctaggtgaa cagcccacca ctgtgccacc gcccattgac  480
ctgtcaatac ctcacgtttg gatgccaccg caaaccactc cacacggctg gacagaatca  540
cataccacct caggactaca ccgaccacac tttaaccaga cctgtatcct ctttgatgga  600
cacgatctac tattcagcac cgtcacacct tgtttgcacc aaggctttta cctcatcgac  660
gaactacgtt acgttaaaat aacactgacc gaggacttct tcgtagttac ggtgtccata  720
gacgacgaca cacccatgct gcttatcttc ggccatcttc cacgcgtact tttcaaagcg  780
ccctatcaac gcgacaactt tatactacga caaactgaga aacacgagct cctggtgcta  840
gttaagaaag atcaactgaa ccgtcactct tatctcaaag acccggactt tcttgacgcc  900
gcacttgact tcaactacct agacctcagc gcactactac gtaacagctt tcaccgttac  960
gccgtggatg tactcaagag cggtcgatgt cagatgctgg accgccgcac ggtagaaatg  1020
gccttcgcct acgcattagc actgttcgca gcagcccgac aagaagaggc cggcgcccaa  1080
gtctccgtcc cacgggccct agaccgccag gccgcactct tacaaataca agaatttatg  1140
atcacctgcc tctcacaaac accaccacgc accacgttgc tgctgtatcc cacggccgtg  1200
gacctggcca aacgagccct ttggacaccg aatcagatca ccgacatcac cagcctcgta  1260
cgcctggtct acatactctc taaacagaat cagcaacatc tcatccccca atgggcacta  1320
cgacagatcg ccgactttgc cctaaaacta cacaaaacgc acctggcctc ttttctttca  1380
gccttcgcac gccaagaact ctacctcatg ggcagcctcg tccactccat gctggtacat  1440
acgacggaga gacgcgaaat cttcatcgta gaaacgggcc tctgttcatt ggccgagcta  1500
tcacacttta cgcagttgtt agctcatcca caccacgaat acctcagcga cctgtacaca  1560
ccctgttcca gtagcgggcg acgcgatcac tcgctcgaac gcctcacgcg tctcttcccc  1620
gatgccaccg tccccgctac cgttcccgcc gccctctcca tcctatctac catgcaacca  1680
agcacgctgg aaaccttccc cgacctgttt tgcttgccgc tcggcgaatc cttctccgcg  1740
ctgaccgtct ccgaacacgt cagttatatc gtaacaaacc agtacctgat caaaggtatc  1800
tcctaccctg tctccaccac cgtcgtaggc cagagcctca tcatcaccca gacggacagt  1860
caaactaaat gcgaactgac gcgcaacatg cataccacac acagcatcac agtggcgctc  1920
aacatttcgc tagaaaactg cgccttttgc caaagcgccc tgctagaata cgacgacacg  1980
caaggcgtca tcaacatcat gtacatgcac gactcggacg acgtcctttt cgccctggat  2040
ccctacaacg aagtggtggt ctcatctccg cgaactcact acctcatgct tttgaagaac  2100
ggtacggtac tagaagtaac tgacgtcgtc gtggacgcca ccgacagtcg tctcctcatg  2160
atgtccgtct acgcgctatc ggccatcatc ggcatctatc tgctctaccg catgctcaag  2220
acatgc                                                            2226

SEQ ID NO: 155         moltype = DNA  length = 513
FEATURE                Location/Qualifiers
misc_feature           1..513
                       note = Synthetic polypeptide
source                 1..513
                       mol_type = other DNA
                       organism = synthetic construct
SEQUENCE: 155
atgagtccca aagatctgac gccgttcttg acggcgttgt ggctgctatt gggtcacagc  60
cgcgtgccgc gggtgcgcgc agaagaatgt tgcgaattca taaacgtcaa ccacccgccg  120
gaacgctgtt acgatttcaa aatgtgcaat cgcttcaccg tcgcgctgcg gtgtccggac  180
ggcgaagtct gctacagtcc cgagaaaacg gctgagattc gcgggatcgt caccaccatg  240
acccattcat tgacacgcca ggtcgtacac aacaaactga cgagctgcaa ctacaatccg  300
ttatacctcg aagctgacgg gcgaatacgc tgcggcaaag taaacgacaa ggcgcagtac  360
ctgctgggcg ccgctggcag cgttccctat cgatggatca atctggaata cgacaagata  420
acccggatcg tgggcctgga tcagtacctg gagagcgtta agaaacacaa acggctggat  480
gtgtgccgcg ctaaaatggg ctatatgctg cag                               513

SEQ ID NO: 156         moltype = DNA  length = 834
FEATURE                Location/Qualifiers
misc_feature           1..834
                       note = Synthetic polypeptide
source                 1..834
                       mol_type = other DNA
                       organism = synthetic construct
SEQUENCE: 156
atgtgccgcc gcccggattg cggcttctct ttctcacctg gaccggtgat actgctgtgg  60
tgttgccttc tgctgcccat tgtttcctca gccgccgtca gcgtcgctcc taccgccgcc  120
gagaaagtcc ccgcggagtg ccccgaacta acgcgccgat gcttgttggg tgaggtgttt  180
gagggtgaca agtatgaaag ttggctgcgc ccgttggtga atgttaccgg gcgcgatggc  240
ccgctatcgc aacttatccg ttaccgtccc gttacgccgg aggccgccaa ctccgtgctg  300
ttggacgagg ctttcctgga cactctggcc ctgctgtaca acaatccgga tcaattgcgg  360
gccctgctga cgctgttgag ctcggacaca gcgccgcgct ggatgacggt gatgcgcggc  420
tacagcgagt gcggcgatgg ctcgccggcc gtgtacacgt gcgtggacga cctgtgccgc  480
ggctacgacc tcacgcgact gtcatacggg cgcagcatct tcacggaaca cgtgttaggc  540
ttcgagctgg tgccaccgtc tctctttaac gtggtggtgg ccatacgcaa cgaagccacg  600
cgtaccaacc gcgccgtgcg tctgcccgtg agcaccgctg ccgcgcccga gggcatcacg  660
ctcttttacg gcctgtacaa cgcagtgaag gaattctgcc tgcgtcacca gctggacccg  720
ccgctgctac gccacctaga taaatactac gccggactgc cgcccgagct gaagcagacg  780
cgcgtcaacc tgccggctca ctcgcgctat ggccctcaag cagtggatgc tcgc        834

SEQ ID NO: 157         moltype = DNA  length = 642
FEATURE                Location/Qualifiers
misc_feature           1..642
                       note = Synthetic polypeptide
```

```
source                  1..642
                        mol_type = other DNA
                        organism = synthetic construct
SEQUENCE: 157
atgctgcggc ttctgcttcg tcaccacttt cactgcctgc ttctgtgcgc ggtttgggca  60
acgccctgtc tggcgtctcc gtggtcgacg ctaacagcaa accagaatcc gtccccgcca  120
tggtctaaac tgacgtattc caaaccgcat gacgcggcga cgttttactg tccttttctc  180
tatccctcgc ccccacgatc ccccttgcaa ttctcggggt tccagcgggt atcaacgggt  240
cccgagtgtc gcaacgagac cctgtatctg ctgtacaacc gggaaggcca gaccttggtg  300
gagagaagct ccacctgggt gaaaaaggtg atctggtacc tgagcggtcg gaaccaaacc  360
atcctccaac ggatgccccg aacggcttcg aaaccgagcg acggaaacgt gcagatcagc  420
gtggaagacg ccaagatttt tggagcgcac atggtgccca agcagaccaa gctgctacgc  480
ttcgtcgtca acgatggcac acgttatcag atgtgtgtga tgaagctgga gagctgggct  540
cacgtcttcc gggactacag cgtgtctttt caggtgcgat tgacgttcac cgaggccaat  600
aaccagactt acaccttctg cacccatccc aatctcatcg tt                      642

SEQ ID NO: 158          moltype = DNA  length = 1671
FEATURE                 Location/Qualifiers
misc_feature            1..1671
                        note = Synthetic polypeptide
source                  1..1671
                        mol_type = other DNA
                        organism = synthetic construct
SEQUENCE: 158
atggagtcgc gcggtcgccg ttgtcccgaa atgatatccg tactgggtcc catttcgggg  60
cacgtgctga aagccgtgtt tagtcgcggc gatacgccgg tgctgccgca cgagacgaga  120
ctcctgcaga cgggtatcca cgtacgcgtg agccagccct cgctgatcct ggtgtcgcag  180
tacacgcccg actcgacgcc atgccaccgc ggcgacaatc agctgcaggt gcagcacacg  240
tactttacgg gcagcgaggt ggagaacgtg tcggtcaacg tgcacaaccc cacgggccga  300
agcatctgcc ccagccaaga gcccatgtcg atctatgtgt acgcgctgcc gctcaagatg  360
ctgaacatcc ccagcatcaa cgtgcaccac tacccgtcgg cggccgagcg caaacaccga  420
cacctgcccg tagccgacgc tgttattcac gcgtcgggca agcagatgtg gcaggcgcgt  480
ctcacggtct cgggactggc ctggacgcgt cagcagaacc agtggaaaga gcccgacgtc  540
tactacacgt cagcgttcgt gtttcccacc aaggacgtgg cactgcggca cgtggtgtgc  600
gcgcacgagc tggtttgctc catggagaac acgcgcgcaa ccaagatgca ggtgataggt  660
gaccagtacg tcaaggtgta cctggagtcc ttctgcgagg acgtgccctc cggcaagctc  720
tttatgcacg tcacgctggg ctctgacgtg gaagaggacc taacgatgac ccgcaacccg  780
caacccttca tgcgccccca cgagcgcaac ggctttacgg tgttgtgtcc caaaaatatg  840
ataatcaaac cgggcaagat ctcgcacatc atgctggatg tggcttttac ctcacacgag  900
cattttgggc tgctgtgtcc caagagcatc ccgggcctga gcatctcagg taacctgttg  960
atgaacgggc agcaaatctt cctggaggta caagcgatac gcgagaccgt ggaactgcgt  1020
cagtacgatc ccgtggctgc gctcttcttt ttcgatatcg acttgttgct gcagcgcggg  1080
cctcagtaca gcgagcaccc caccttcacc agccagtatc gcatccaggg caagcttgag  1140
taccgacaca cctgggaccg gcacgacgag ggtgccgccc agggcgacga cgacgtctgg  1200
accagcggat cggactccga cgaagaactc gtaaccaccg agcgtaagac gccccgcgtc  1260
accggcggcg gagccatggc gagcgcctcc acttccgcgg gctcagcatc ctcggcgacg  1320
gcgtgcacgg cgggcgttat gacacgcggc cgccttaagg ccgagtccac cgtcgcgccc  1380
gaagaggaca ccgacgagga ttccgacaac gaaatccaca atccggccgt gttcacctgg  1440
ccgccctggc aggccggcat cctggcccgc aacctggtgc ccatggtggc tacggttcag  1500
ggtcagaatc tgaagtacca ggagttcttc tgggacgcca acgacatcta ccgcatcttc  1560
gccgaattgg aaggcgtatg gcagcccgct gcgcaaccca aacgtcgccg ccaccggcaa  1620
gacgccttgc ccgggccatg catcgcctcg acgcccaaaa agcaccgagg t            1671

SEQ ID NO: 159          moltype = DNA  length = 1683
FEATURE                 Location/Qualifiers
misc_feature            1..1683
                        note = Synthetic polypeptide
source                  1..1683
                        mol_type = other DNA
                        organism = synthetic construct
SEQUENCE: 159
atggagtcgc gcggtcgccg ttgtcccgaa atgatatccg tactgggtcc catttcgggg  60
cacgtgctga aagccgtgtt tagtcgcggc gatacgccgg tgctgccgca cgagacgcga  120
ctcctgcaga cgggtatcca cgtacgcgtg agccagccct cgctgatcct ggtgtcgcag  180
tacacgcccg actcgacgcc atgccaccgc ggcgacaatc agctgcaggt gcagcacacg  240
tactttacgg gcagcgaggt ggagaacgtg tcggtcaacg tgcacaaccc cacgggccga  300
agcatctgcc ccagccaaga gcccatgtcg atctatgtgt acgcgctgcc gctcaagatg  360
ctgaacatcc ccagcatcaa cgtgcaccac tacccgtcgg cggccgagcg caaacaccga  420
cacctgcccg tagccgacgc tgttattcac gcgtcgggca agcagatgtg gcaggcgcgt  480
ctcacggtct cgggactggc ctggacgcgt cagcagaacc agtggaaaga gcccgacgtc  540
tactacacgt cagcgttcgt gtttcccacc aaggacgtgg cactgcggca cgtggtgtgc  600
gcgcacgagc tggtttgctc catggagaac acgcgcgcaa ccaagatgca ggtgataggt  660
gaccagtacg tcaaggtgta cctggagtcc ttctgcgagg acgtgccctc cggcaagctc  720
tttatgcacg tcacgctggg ctctgacgtg gaagaggacc taacgatgac ccgcaacccg  780
caacccttca tgcgccccca cgagcgcaac ggctttacgg tgttgtgtcc caagaatatg  840
ataatcaaac cgggcaagat ctcgcacatc atgctggatg tggcttttac ctcacacgag  900
cattttgggc tgctgtgtcc caagagcatc ccgggcctga gcatctcagg taacctgttg  960
atgaacgggc agcaaatctt cctggaggta caagcgatac gcgagaccgt ggaactgcgt  1020
cagtacgatc ccgtggctgc gctcttcttt ttcgatatcg acttgttgct gcagcgcggg  1080
```

```
cctcagtaca gcgagcaccc caccttcacc agccagtatc gcatccaggg caagcttgag  1140
taccgacaca cctgggaccg gcacgacgag ggtgccgccc agggcgacga cgacgtctgg  1200
accagcggat cggactccga cgaagaactc gtaaccaccg agcgtaagac gccccgcgtc  1260
accggcggcg gcgccatggc gagcgcctcc acttccgcgg gccgcaaacg caaatcagca  1320
tcctcggcga cggcgtgcac ggcgggcgtt atgacacgcg gccgccttaa ggccgagtcc  1380
accgtcgcgc ccgaagagga caccgacgag gattccgaca acgaaatcca caatccggcc  1440
gtgttcacct ggccgccctg gcaggccggc atcctggccc gcaacctggt gcccatggtg  1500
gctacggttc agggtcagaa tctgaagtac caggagttct tctgggacgc caacgacatc  1560
taccgcatct tcgccgaatt ggaaggcgta tggcagcccg ctgcgcaacc caaacgtcgc  1620
cgccaccggc aagacgcctt gcccgggcca tgcatcgcct cgacgcccaa gaagcaccga  1680
ggt                                                                1683
```

```
SEQ ID NO: 160          moltype = DNA  length = 2721
FEATURE                 Location/Qualifiers
misc_feature            1..2721
                        note = Synthetic polypeptide
source                  1..2721
                        mol_type = other DNA
                        organism = synthetic construct
SEQUENCE: 160
atggaaagcc ggatctggtg tcttgtggtg tgcgtgaatc tttgcatcgt gtgcttgggt  60
gccgccgtgt catctagcag cacaagaggc acctccgcca ctcactcaca ccacagcagc  120
cacacgacca gcgccgctca ctccagaagc ggctctgtaa gccagagagt gaccagttct  180
caaaccgtca gccacggcgt caatgagacg atatataata caaccctgaa gtatggagac  240
gtggtgggtg tcaataccac caagtaccct tatcgcgtgt gcagcatggc ccagggcact  300
gacctgatca gattcgagag aaatatcgtc tgcacctcca tgaagcctat caacgaggac  360
cttgacgagg gcatcatggt tgtctacaag agaaacattg tggctcacac cttcaaggtg  420
agagtgtatc agaaagtact gacctttagg agatcctacg cttacatcca caccacgtac  480
ctgctcggct ccaacaccga gtatgtggct ccacccatgt gggagattca tcacatcaat  540
tcccacagcc aatgttacag ttcctatagc agagtcattg ctggtaccgt gttcgtcgct  600
taccacagag acagctatga gaacaagacc atgcagttga tgcccgatga ctactccaat  660
acacactcta caaggtatgt gacagtcaaa gatcagtggc acagccgggg cagcacctgg  720
ctgtaccgag agacatgtaa tctgaattgt atggtgacta tcactacagc caggagcaaa  780
tatccatacc acttcttcgc cactagcacc ggggacgtcg tggacatttc cccattctac  840
aatggcacaa acagaaacgc cagctacttc ggcgagaatg ccgacaagtt ctttatattc  900
cccaactata ccatcgtgag cgacttcggc cgccccaaca gcgccctgga aacccaccgg  960
ctcgtggcct ttctcgagcg ggccgatagc gtcatatcct gggacatcca ggacgagaag  1020
aatgtgacat gccagctgac cttctgggag gcctccgagc gtaccatccg gtccgaggca  1080
gaggacagct accatttcag cagcgccaag atgaccgcaa ccttcctcag taagaaacag  1140
gaggttaaca tgtctgattc tgccctggac tgcgtgcgcg atgaggcaat caacaagctg  1200
cagcagatct tcaacacatc ttacaaccaa acttacgaga agtacggcaa cgtcagcgtg  1260
ttcgagacaa caggaggcct ggtagtgttc tggcaaggta tcaagcagaa gagtctggtg  1320
gagctcgagc gactggctaa ccgcagctcc ctcaacctga cccataatag gacaaagaga  1380
agcaccgacg gcaacaacgc tactcatttg agcaacatgg aatccgtgca caacctggtg  1440
tatgcccagc tgcagttcac ttacgacacc ctgagaggct acatcaatag agccttagct  1500
cagatcgcag aggcttggtg tgtggaccag cgaagaactc tggaggtgtt caaggagtta  1560
agtaagatca atccatccgc catcctgtct gctatctaca acaagcccat tgccgccagg  1620
ttcatgggag atgtgctcgg cctggctagt tgtgtcacca tcaaccagac ctccgtgaag  1680
gtgctgcggg acatgaatgt gaaggagagc cccggtcggt gttactccag accagtggtg  1740
attttcaact tcgccaacag ctcctatgtg cagtacggac agctcggaga ggataacgag  1800
atcttgctcg gcaatcacag aactgaggag tgtcagctgc catcactgaa gatatttatt  1860
gccgggaatt ccgcctacga atacgttgac taccttttca agagaatgat cgacctgagc  1920
agcatcagca ccgtcgacag catgattgct ctcgatatcg accctctgga gaacaccgac  1980
tttagagtcc ttgagctgta ttcacagaag gagctgagga gctccaatgt gttcgacctg  2040
gaggaaatca tgagagagtt caactcttac aagcagcggg tgaagtacgt ggaggataag  2100
gtagtggacc cactcccacc atacctgaaa ggactcgacg atctcatgag cggactgggc  2160
gcagccggga aggctgttgg cgtcgccatc ggagcggtcg gaggagcagt ggctagcgtg  2220
gtggagggcg tggccacctt cctgaagaac cctttcggcg cctttaccat catcctggtg  2280
gccatcgccg tggtcatcat tacatatctg atttatacaa gacagagaag gctctgcacc  2340
cagcccttgc agaacctgtt cccctacctg gtcagtgccg acggtacaac cgtgaccagc  2400
ggtagcacca aggacacctc cctgcaggca ccgccgagct acgaggagtc cgtgtataac  2460
agtggaagaa agggccccgg accgcccagc agcgacgcat ccaccgccgc tcctccctac  2520
acaaatgagc aggcctatca gatgttgctg gctctggcac gcctggacgc cgagcagcga  2580
gctcagcaga acggcaccga ttccctggat ggacgcacag gcacacagga caagggggcag  2640
aagcccaacc tcctcgacag actgagacac cggaagaacg gatacaggca tctgaaggac  2700
tccgatgagg aggagaacgt t                                           2721
```

```
SEQ ID NO: 161          moltype = DNA  length = 2721
FEATURE                 Location/Qualifiers
misc_feature            1..2721
                        note = Synthetic polypeptide
source                  1..2721
                        mol_type = other DNA
                        organism = synthetic construct
SEQUENCE: 161
atggaatcca ggatctggtg cctcgtggtc tgtgtgaact tgtgcatcgt gtgcttgggt  60
gccgccgtga gcagtagcag caccagaggc accagcgcaa cacactcaca ccacagctcc  120
cataccactt ccgccgccca ctccagatcg ggctccgtga gccagagggt caccagcagc  180
cagacggtgt cccacggagt gaatgaaacc atctacaaca ctactctgaa gtacggagac  240
```

```
gtcgtcggcg tgaataccac taagtacccc tacagggtct gctctatggc ccaaggcaca  300
gacctgatca gatttgaaag aaatatcgtc tgtacctcca tgaagcccat caatgaggac  360
ttagacgagg gcattatggt ggtgtataaa cgcaacattg tggcccacac tttcaaggtc  420
agagtgtatc agaaagtgct caccttcagg cgtagctatg cctatatcca caccacttat  480
ctcctcggca gcaacaccga gtatgttgcc ccgcctatgt gggagattca ccatataaat  540
agccatagcc agtgctacag ctcctattcg agagtaatcg ccggaaccgt tttcgtcgcc  600
taccacagag actcgtacga gaacaagaca atgcagctga tgccagatga ctattcgaac  660
acccacagca cgagatatgt caccgtgaaa gatcagtggc acagcagggg tagtacatgg  720
ttgtataggg aaacctgcaa tctcaattgc atggtgacca tcaccaccgc cagaagcaaa  780
taccccctatc atttcttcgc tacctcgaca ggagacgtgg tggacatatc tccctttttat  840
aatggcacaa atagaaatgc tagctacttt ggagagaacg ccgacaaatt cttcatcttc  900
cctaactata ccatcgtgag cgactttggg cgacctaaca gcgccctcga gactcacagg  960
ctggtggctt tcttagagag ggctgatagt gttatctctt gggacattca ggatgagaag  1020
aacgtgacat gccagctgac attttgggag gctagcgagc gaaccatcag gtccgaggcc  1080
gaggacagct accatttctc tagtgccaag atgaccgcca ccttcttgtc aaagaagcaa  1140
gaggtgaaca tgtccgactc tgcgctggac tgtgtccgcg acgaggcaat taataaactg  1200
cagcagatct ttaataccag ctacaaccag acatacgaga agtatggcaa cgtgagcgtc  1260
ttcgaaacca caggcggcct tgtcgtcttt tggcaaggca tcaagcagaa gagtctggtg  1320
gagctggaaa gactcgccaa ccggtcatcc ctgaatctga cccacaatag gacaaagcgc  1380
agcaccgatg ggaacaacgc cacccacctg tcgaacatgg agtcagtgca caacctggtg  1440
tacgcccagc tgcagttcac ttatgatacc ctcagaggct acattaaccg cgcactggct  1500
cagatcgccg aagcatggtg cgtggaccag cggcgaaccc tggaagtgtt taaagagctc  1560
tccaagatta atcctagcgc catcctgagt gctatctaca ataagcctat cgccgcaaga  1620
tttatgggcg acgtgctggg actggcttcc tgcgtgacaa ttaaccagac ctccgtcaag  1680
gtgctgaggg acatgaacgt gaaggagagc cccggcagat gctatagccg gccagtggtg  1740
atcttcaatt tcgccaacag ctcatacgtg cagtacggcc agctcgggga ggataatgaa  1800
atcctgctgg gaaatcacag aaccgaggag tgtcagctgc ccagtctgaa gattttcatc  1860
gcaggcaaca gtgcctatga atacgtggac tatctgttca aacgcatgat cgatctgagc  1920
tctatctcca ccgtggactc catgattgcc ttggatatcg acccactgga gaacaccgat  1980
ttcagagtgc tggagctgta cagccagaag gagctcaggt ccagcaatgt gttcgacctg  2040
gaggaaatca tgagagagtt caactcctac aaacagagag tcaagtacgt ggaggacaag  2100
gtggtggatc ccctgcctcc ctacctgaag ggctggacg acctgatgag tggcctggga  2160
gccgccggca aagctgtggg agtggccatc ggtgccgtcg gaggggctgt ggccagcgtc  2220
gtcgagggag ttgccacatt cctgaagaac cccttcgggg ccttcaccat tatcctagtc  2280
gccattgccg tggtcatcat tacctatctg atctacacgc ggcagagacg gctgtgcacc  2340
cagcctttgc agaacctgtt cccctattta gtgtccgctg acgggaccac tgtgacaagc  2400
ggaagcacca aggacacatc cctgcaggcc ccacccagct acgaggagtc tgtttacaat  2460
tctggccgga agggccccgg ccctccctct tctgacgcct ccaccgcagc ccctccttac  2520
acaaacgagc aggcttacca gatgctgttg gctttggccc gtctggacgc cgaacagagg  2580
gcccagcaga atggcaccga ctccttggac ggccggacag ggacccagga taagggtcag  2640
aagcctaacc tactggatcg gctccgccat cgcaagaatg gctacagaca tctcaaggac  2700
agcgacgaag aagagaatgt g                                           2721
```

```
SEQ ID NO: 162          moltype = DNA  length = 2721
FEATURE                 Location/Qualifiers
misc_feature            1..2721
                        note = Synthetic polypeptide
source                  1..2721
                        mol_type = other DNA
                        organism = synthetic construct
SEQUENCE: 162
atggaatcaa gaatctggtg tctcgtggtg tgcgtgaacc tgtgtatcgt ctgtcttggc  60
gccgccgtct cttcctcaag cacccggggt accagtgcca cccactcaca tcactcctcc  120
cacactacca gcgccgccca cagcagatcc ggctccgtgt cccagcgggt gaccagcagc  180
cagaccgtgt cacacggcgt taatgaaacc atttacaaca ccacactgaa gtacggggac  240
gtggtgggcg tgaacaccac caagtatccc tacagggtgt gcagcatggc ccagggcacc  300
gacctgattc ggttcgagag aaacatcgtg tgcacatcca tgaagcctat caatgaggac  360
ctcgacgagg gcatcatggt ggtttacaag aggaacattg tcgcacacac atttaaggtg  420
cgagtgtacc agaaggtgtt aaccttcaga aggtcctacg catacatcca caccacctac  480
ctcctgggct ctaacacaga atacgtcgcc cctcccatgt gggagattca ccacatcaac  540
agtcacagcc agtgctacag ctcgtatagc agagttatcg ctggcaccgt gttcgtggct  600
tatcaccgcg acagctacga gaacaagacg atgcaactta tgcccgacga ttactcaaac  660
acgcactcca ctagatacgt gactgtgaag gaccagtggc acagtagagg cagcacctgg  720
ctgtaccggg aaacatgcaa tctcaattgt atggtcacca ttaccaccgc caggtccaag  780
taccccttacc acttcttcgc cacctccact ggcgacgtgg tcgacatcag ccccttctac  840
aatggcacca acaggaacgc ctcttacttt ggggagaacg ccgataaatt ctttattttc  900
cccaactaca ctattgtctc cgactttggc agacccaact cagcattgga aacccacagg  960
ctcgtggcct tcctggagcg ggccgatagt gtgatcagct gggacatcca ggatgagaag  1020
aacgtgacat gccagctgac cttctgggag gccagcgaac gaaccatccg gtccgaggcc  1080
gaggactctt atcacttctc tagcgcaaag atgaccgcca ccttcctgtc taagaaacag  1140
gaggtgaaca tgagcgacag cgccctggac tgcgtcagag acgaggcaat caacaagctg  1200
cagcaaatct tcaacaccag ctacaaccaa acctacgaga aatacggcaa cgtcagcgtc  1260
ttcgagacta ccggagggct cgttgttttc tggcagggca ttaagcagaa gtctctggtc  1320
gagctggaaa ggctggccaa tagaagctcc ctaaacctca ctcacaacag aactaagaga  1380
agcaccgatg gcaataacgc cactcatctg agtaacatgg agtctgttca caacctggtg  1440
tatgcccagc tgcagtttac ttatgacaca ctgaggggct acatcaatcg agccctggcc  1500
cagatcgccg aggcttggtg cgtcgaccag agaagaacac tggaagtgtt caaggagctg  1560
agtaagatta atcccagcgc cattctgtcc gccatctaca ataagccaat cgccgcaaga  1620
ttcatgggtg acgtgctggg cctggcctcc tgcgtgacaa tcaaccagac aagcgtgaaa  1680
```

```
gtcctcagag acatgaacgt caaggagtct cctggcaggt gttactcccg gcccgtggtg  1740
atatttaatt tcgccaacag cagttacgtg cagtacggac agctgggcga ggataacgag  1800
atactgctcg gaaaccatag aacagaggag tgccaactgc cctccctgaa gattttcatc  1860
gccgggaaca gcgcctatga gtatgttgac tatctgttca agcggatgat cgacctgagt  1920
tctatcagca ccgttgactc catgattgct ctcgatatcg atcctctgga gaacaccgat  1980
ttcagagtgc tggaactcta ctctcagaaa gagctaagaa gctcgaacgt gttcgacctg  2040
gaagaaatca tgagagagtt caactcctac aaacagaggg ttaagtacgt agaggataag  2100
gtcgtggacc ctctgcctcc ataccttaag ggattagatg atctgatgag cggcctgggc  2160
gctgccggaa aggccgtggg agtggccatc ggcgcagtgg gtggtgccgt ggctagcgtc  2220
gtggaaggcg ttgccacatt cttgaagaac ccattcgggg ccttcacaat catcctggtg  2280
gctatcgccg ttgtgattat cacatatctg atctacactc gccagcggag gctctgcacc  2340
cagcctctgc agaacctttt cccctaccta gtgtccgctg atgggactac agtcactagc  2400
ggcagcacta aggacacatc cctgcaggct cctccatctt acgaggagag cgtgtataac  2460
tccgggcgca agggacctgg ccctcccagc agcgacgcca gcacggcggc tcctccctac  2520
accaacgagc aggcatacca gatgttgctt gcactggccc gtctggacgc tgagcagagg  2580
gcccagcaga atgggactga ttccctggac ggcagaaccg gcacacagga taaaggacag  2640
aaaccgaatc tgctcgacag gctgaggcac cggaagaatg gatacaggca tctgaaggac  2700
agtgacgagg aggagaacgt g                                            2721

SEQ ID NO: 163         moltype = DNA  length = 2721
FEATURE                Location/Qualifiers
misc_feature           1..2721
                       note = Synthetic polypeptide
source                 1..2721
                       mol_type = other DNA
                       organism = synthetic construct
SEQUENCE: 163
atggagtcaa gaatctggtg cttggtggtg tgtgtgaact tgtgtatcgt gtgccttgga  60
gccgccgtga gcagcagctc caccagaggc accagcgcca cccacagcca tcactcttcc  120
cacaccacaa gcgccgccca ctcgcggagc gggagtgttt cccaacgggt gacaagcagc  180
cagactgtga gccacggcgt taacgagaca atctacaaca caacactgaa gtacggcgac  240
gtggtgggtg taaatactac caagtatcct tacagggtgt gctctatggc ccagggtacc  300
gacctgatca ggtttgagag aaacattgtt tgcacaagca tgaagcccat caatgaggac  360
ttggatgagg gcatcatggt ggtttacaag agaaatatcg tggcccacac cttcaaagtg  420
agggtgtatc agaaggtgct gacctttaga aggagctacg cttatatcca cacaacctac  480
cttctgggca gcaacaccga gtacgtcgca ccacccatgt gggaaattca ccacatcaac  540
tctcactccc agtgctattc cagctacagc agagtgatag ccggcacagt cttcgtggcc  600
taccacaggg atagttacga gaataagacg atgcaactga tgcctgacga ttactccaac  660
acacacagca cccggtacgt caccgtgaag gaccagtggc actccagagg tagtacttgg  720
ctgtaccggg agacttgtaa cctgaactgc atggtgacaa ttaccactgc tcgaagcaag  780
taccettacc acttctttgc cacctctacc ggcgatgtcg tagacatatc tcctttctat  840
aacgggacca acagaaacgc ttcgtacttc ggcgagaacg ctgacaagtt cttcatcttc  900
ccgaactaca ctatagttag cgactttggt aggccgaaca gcgccctgga gacacaccga  960
cttgtggcct tcctcgagag agctgacagc gtgatctcct gggacatcca ggacgagaag  1020
aacgtcacct gccagctgac attctgggag gcctctgaga ggaccatcag atccgaggcc  1080
gaggattcat accactttag cagcgctaag atgaccgcta ccttcctgag taagaagcag  1140
gaagtgaaca tgtccgactc agccctcgac tgcgtgaggg acgaggccat caacaagctg  1200
cagcagatct tcaacacctc ctacaaccag acatatgaga agtatggtaa cgtgagcgtg  1260
ttcgagacaa ccggcggact ggtcgtgttt tggcagggca taaagcagaa gtctctggtc  1320
gagctggaga ggctggcgaa caggagcagc ctcaacctga cccataacag aaccaaacgc  1380
agcaccgacg gcaacaatgc tacccacctg tcaaacatgg agagcgtcca caacctggtg  1440
tatgcccagc tgcaatttac atacgacacg ctgcgcggct acatcaatag agccctggcc  1500
cagatcgccg aggcttggtg cgttgaccag cggcgtactc tggaagtctt caaggagctg  1560
agcaagatca atcccagcgc tatcctgagc gcgatctaca ataaacctat tgctgccaga  1620
ttcatgggag acgtgttggg gctggccagc tgcgtgacaa tcaatcagac cagcgtgaaa  1680
gtgctgagag acatgaatgt gaaggagtct cctggtaggt gctactcaag gcccgtcgta  1740
attttcaatt tcgccaacag ttcctacgtg cagtacggac agctgggcga agacaatgag  1800
atcctcctgg gcaaccatcg gacggaggag tgtcaactcc catcactgaa gatctttatc  1860
gcaggcaatt ccgcctatga gtatgtggac tatctgttca agaggatgat cgacctgtcc  1920
agcatcagca cagtggattc aatgattgcc cttgacatcg accctcttga gaataccgac  1980
tttagagtgc tggagcttta tagccagaaa gagctcagga gctccaatgt gttcgacctg  2040
gaagagatca tgcgggagtt taacagctac aagcagaggg ttaaatatgt ggaggacaag  2100
gttgtggatc cactgccgcc ctacctgaaa gggctggacg acctcatgtc cggcctagga  2160
gccgcaggga aagccgtggg cgtggccatc ggcgcagttg gaggcgccgt cgcctctgtg  2220
gttgaaggcg ttgcgacctt tctgaagaac ccattcggcg ccttcaccat tatcctggtg  2280
gccattgccg tggtcatcat cacctatctg atctacacca ggcaacgacg cctgtgcacc  2340
cagcccctgc agaacctgtt cccttacctg gtcagcgccg atgggaccac agtgacctct  2400
ggttctacta aagacaccag ccttcaggcc cctccatcct acgaggagtc tgtgtacaat  2460
agcggcagaa agggccccgg cccgcccagc agcgatgcca gcaccgccgc tcctccatac  2520
acgaacgagc aggcctatca gatgctgctg gcccttgccc gcctggacgc cgagcagcgt  2580
gctcagcaga atggcaccga ttctctggac ggccgaactg gaacgcaaga caagggacag  2640
aagccaaacc tgctggacag actgagacac aggaagaatg gctacaggca tctgaaggat  2700
tcagacgagg aggagaacgt g                                            2721

SEQ ID NO: 164         moltype = DNA  length = 2721
FEATURE                Location/Qualifiers
misc_feature           1..2721
                       note = Synthetic polypeptide
source                 1..2721
```

```
                         mol_type = other DNA
                         organism = synthetic construct
SEQUENCE: 164
atggagagcc ggatctggtg ccttgtggtg tgcgtgaacc tttgcatcgt gtgcctcggc  60
gccgccgtga gctcatcgag cacccggggc accagcgcca cccacagcca ccacagcagc  120
cacaccacca gcgcggccca cagtcggagc ggcagcgtga gccagcgggt gacctcctcc  180
cagaccgtct cccacggcgt gaacgaaacc atctacaaca ccaccctgaa gtacggcgac  240
gtggttgggg taaataccac taagtacccc taccgggtgt gcagcatggc ccagggcacc  300
gacctgatcc ggttcgagcg gaacatcgtc tgtaccagca tgaagcccat caacgaggac  360
ctggacgagg gcatcatggt tgtctacaag cggaatatcg tagcccacac cttcaaggtg  420
cgggtgtacc agaaggtgct gaccttccgg cggagctacg cctacattca cacgacttac  480
ctgctgggca gcaacaccga gtacgtggcg ccgcccatgt gggagatcca ccacatcaac  540
tctcactctc agtgctacag cagctacagc cgggtgatcg ccggcaccgt gttcgtggcc  600
taccaccggg acagctacga gaacaagacc atgcagctga tgcccgacga ctattctaac  660
acacactcca ctaggtacgt gaccgtgaag gaccagtggc actccagagg cagcacctgg  720
ctgtaccggg agacgtgcaa cctgaactgc atggtgacca tcaccaccgc ccggtcaaag  780
tacccttacc acttcttcgc caccagcact ggggatgtgg ttgacatcag ccccttctac  840
aacggcacca accggaacgc cagctacttc ggcgagaacg ccgacaagtt cttcatcttc  900
cccaactaca ccatcgtgag cgacttcggc cggcccaaca gcgccctgga aacacaccgg  960
ctggtggcct tcctggagcg ggccgacagc gtgatcagct gggacatcca ggacgagaag  1020
aacgtgacct gccaactcac attttgggag gccagcgagc ggaccatccg gagcgaggcc  1080
gaggactcct atcacttcag cagcgccaag atgaccgcca ccttcctgag caagaagcag  1140
gaggtgaaca tgagcgattc ggcattggac tgcgtgcggg acgaggccat caacaagctg  1200
cagcagatct tcaacaccag ctacaaccag acctatgaga aatacggcaa cgtgagcgtg  1260
ttcgaaacca ccggcggact ggttgttttc tggcagggta tcaagcagaa gagtttggtg  1320
gagctcgagc gcctggcaaa caggagcagc ctgaacctga cccacaaccg gaccaagcgg  1380
agcaccgacg gcaacaatgc aacgcaccta tccaacatgg agtccgtgca caacctggtg  1440
tacgcccagc tgcagttcac ctacgacacc ctgcggggct acatcaaccg ggccctggcc  1500
cagatcgccg aggcatggtg cgtggaccag cggcggaccc tggaggtgtt caaggagctt  1560
tccaagatca acccctctgc catcctgtct gctatctaca ataagccaat cgcggcacgc  1620
ttcatgggag acgtactggg cctggccagc tgcgtgacta ttaatcagac tagcgtcaaa  1680
gtgctacggg acatgaacgt aaaggagagc cccggccggt gctattctcg gcccgtggtc  1740
attttcaact tcgccaacag ttcctacgtg cagtacggac agttaggcga ggacaacgag  1800
attctgctgg gtaaccaccg gaccgaggag tgccaacttc ccagtctaaa gatatttatc  1860
gccgggaatt ccgcttatga gtatgtgcac tacctgttca agcggatgat cgacctgtcc  1920
agtatcagca ccgtggacag catgattgca ctggatatcg accctctcga gaacaccgac  1980
ttccgggtgc tggagctgta cagccagaaa gagctgagat caagtaatgt ctttgacctg  2040
gaggagatca tgcgggagtt caatagctac aagcagaggg tgaaatatgt cgaagacaag  2100
gtagtagacc cgctgcctcc ctacctgaag ggcttgacg acctcatgtc agggttaggg  2160
gcagctggca aggccgttgg cgtcgccatc ggcgcggtgg gcggtgccgt tgcctccgtg  2220
gtcgaaggcg tcgctacctt cctcaagaac cccttcggcg ccttcaccat catcctggtg  2280
gctattgcag ttgtcatcat tacctacctc atctacaccc ggcagcggag gctgtgcacc  2340
cagcccctgc agaacctgtt tccatacctg gtgagcgcag acggaactac cgtgacgagc  2400
ggatccacta aggacaccag cctgcaggcg cctccttcat acgaagagag tgtgtacaac  2460
agcggccgga agggccccgg acctccgagt agcgacgcaa gtaccgccgc cccaccctat  2520
accaacgagc aagcttacca gatgctgctg gcacttgctc ggctggacgc cgaacaacgc  2580
gcccagcaga acggaactga ttctctggac ggccggaccg gcacccagga caagggccag  2640
aagcccaacc tgttggaccg gctgcggcac cggaagaacg gctatcgtca cctgaaagac  2700
agcgacgagg aggagaacgt g                                            2721

SEQ ID NO: 165           moltype = DNA  length = 2721
FEATURE                  Location/Qualifiers
misc_feature             1..2721
                         note = Synthetic polypeptide
source                   1..2721
                         mol_type = other DNA
                         organism = synthetic construct
SEQUENCE: 165
atggagagcc ggatctggtg cctagtggtg tgcgtgaacc tctgcatcgt gtgcctaggc  60
gccgccgtga gcagttctag tacccggggc accagcgcca cccacagcca ccacagcagc  120
cacactacgt cagcagcgca tagtcggagc ggcagcgtga gccagcgggt gacgtcttcc  180
cagacagtgt cccacggcgt gaacgaaacc atctacaaca ccaccctgaa gtacggcgac  240
gtggtgggtg tcaatacaac taagtacccc taccgggtgt gcagcatggc ccagggcacc  300
gacctgatcc ggttcgagcg gaatattgtg tgtaccagca tgaagcccat caacgaggac  360
ctggacgagg gcatcatggt ggtatacaag agaaacattg tcgcccacac cttcaaggtg  420
cgggtgtatc agaaggtgct gaccttccgg cggagctacg cctacattca tacgacttac  480
ctgctgggca gcaacaccga gtacgtggcc ccgcccatgt gggagatcca ccacatcaac  540
agccactccc agtgctacag cagctacagc cgggtgatcg ccggcaccgt gttcgtggcc  600
taccaccggg acagctacga gaacaagacc atgcagctga tgcccgacga ctatagcaat  660
actcacagca cacggtacgt gaccgtgaag gaccagtggc acagccgcgg cagcacctgg  720
ctgtaccggg aaacgtgcaa cctgaactgc atggtgacca tcaccaccgc ccggtcgaag  780
tatccctatc acttcttcgc caccagcacg ggcgatgtgg ttgacatcag ccccttctac  840
aacggcacca accggaacgc cagctacttc ggcgagaacg ccgacaagtt cttcatcttc  900
cccaactaca ccatcgtgag cgacttcggc cggcccaaca gcgccctgga aacccaccgg  960
ctggtggcct tcctggagcg ggccgacagc gtgatcagct gggacatcca ggacgagaag  1020
aacgtgacct gccagcttac attctgggag gccagcgagc ggaccatccg gagcgaggcc  1080
gaggacagtt accacttctc gagcgccaag atgaccgcca ccttcctgag caagaagcag  1140
gaggtgaaca tgagcgacag tgctctggac tgcgtgcggg acgaggccat caacaagctg  1200
cagcagatct tcaacaccag ctacaaccag acctatgaga aatacgggaa cgtgagcgtg  1260
```

-continued

```
ttcgagacaa ccggcggctt agtagtgttc tggcagggga tcaagcagaa gagtttggtg  1320
gagctcgagc ggctggcgaa cagaagcagc ctgaacctga cccacaaccg gaccaagcgg  1380
agcaccgacg gcaacaacgc aacgcactta tcaaacatgg aaagtgtgca caacctggtg  1440
tacgcccagc tgcagttcac ctacgacacc ctgcggggct acatcaaccg ggccctggcc  1500
cagatcgccg aggcgtggtg cgtggaccag cggcggaccc tggaggtgtt caaggagttg  1560
tcgaagatca acccttctgc catcctgtca gcaatttaca ataaacctat tgccgcaagg  1620
ttcatgggag atgtcctggg cctggccagc tgcgtgacca taaaccagac aagcgtcaaa  1680
gtcctccggg acatgaatgt gaaagagagc cccggccggt gttacagtcg acccgtggtg  1740
atctttaact tcgccaattc ttcttatgtg cagtacggac agctcggcga ggacaacgag  1800
atcctgctcg gtaaccaccg gaccgaggag tgtcagcttc cctcactgaa gattttcatt  1860
gcggggaaca gtgcatacga gtatgttgac tacctgttca agcggatgat cgatctgtct  1920
agtatcagca ccgtggacag catgatcgct ctggatatcg acccattgga gaacaccgac  1980
ttccgggtgc tggagctgta cagccagaag gagcttcgca gcagtaatgt gtttgacctg  2040
gaggagatca tgcgggagtt caattcttac aagcagcgcg tgaaatacgt tgaggacaag  2100
gtggtcgatc cgctgcctcc ctacctgaag ggcctggatg atctcatgag cgggttaggg  2160
gctgccggca aggccgtcgg cgttgccatc ggcgcagtgg gcggagccgt cgccagcgtg  2220
gtggagggtg ttgcaacgtt cctgaagaac cccttcggcg ccttcaccat catcttggtt  2280
gcaatcgcgg ttgttatcat tacctacctt atctacaccc ggcaacggcg gctgtgcacc  2340
cagcccctgc agaacctgtt tccatacttg gtgagcgcgg atgggaccac cgtgacttca  2400
ggttccacca aggacaccag cctgcaggcg cctccctcat acgaggagtc cgtatacaac  2460
agcggccgga aggggccagg tcctcctagc tcggacgcaa gtactgccgc accgccttat  2520
accaacgagc aggcatatca gatgctgctt gccctggctc ggctggacgc cgaacagcgc  2580
gcccagcaga acggaacaga ttccctggac ggccggaccg gcacccagga taagggccag  2640
aagcccaact tgctggaccg gctgcggcac cggaagaacg gctataggca tctgaaggac  2700
agcgacgagg aggagaacgt g                                          2721

SEQ ID NO: 166          moltype = DNA  length = 2721
FEATURE                 Location/Qualifiers
misc_feature            1..2721
                        note = Synthetic polypeptide
source                  1..2721
                        mol_type = other DNA
                        organism = synthetic construct
SEQUENCE: 166
atggagagcc ggatctggtg cctagtggtg tgcgtgaacc tatgcatcgt gtgcttaggc  60
gccgccgtga gctcatcgtc cacccggggc accagcgcca cccacagcca ccacagcagc  120
cacacgacaa gcgccgccca ctcccggagc ggcagcgtga gccagcgggt gacttcttcc  180
cagacagtga gccacggcgt gaacgagact atctacaaca ccaccctgaa gtacggcgac  240
gtggtgggcg tcaacactac caagtacccc taccgggtgt gcagcatggc ccagggcacc  300
gacctgatcc ggttcgagcg gaacattgtg tgcaccagca tgaagcccat caacgaggac  360
ctggacgagg gcatcatggt tgtgtacaag cgtaatatcg tcgcccacac cttcaaggtg  420
cgggtgtacc agaaggtgct gaccttccgg cggagctacg cctacatcca tactacgtac  480
ctgctgggca gcaacaccga gtacgtggct cctcccatgt gggagatcca ccacatcaac  540
tcccatagcc agtgctacag cagctacagc cgggtgatcg ccggcaccgt gttcgtggcc  600
taccaccggg acagctacga gaacaagacc atgcagctga tgcccgacga ctattcgaac  660
acccactcaa ccagatacgt gaccgtgaag gaccagtggc attcacgggg cagcacctgg  720
ctgtaccggg aaacatgcaa cctgaactgc atggtgacca tcaccaccgc ccggagtaaa  780
taccccttatc acttcttcgc caccagcacg ggcgacgtcg tagacatcag cccctctac  840
aacggcacca accggaacgc cagctacttc ggcgagaacg ccgacaagtt cttcatcttc  900
cccaactaca ccatcgtgag cgacttcggc cggcccaaca gcgccctgga gacacaccgg  960
ctggtggcct tcctggagcg ggccgacagc gtgatcagct gggacatcca ggacgagaag  1020
aacgtgacct gccagctgac gttttgggag gccagcgagc ggaccatccg gagcgaggcc  1080
gaagattcct atcactttag cagcgccaag atgaccgcca ccttcctgag caagaagcag  1140
gaggtgaaca tgtctgattc cgcgctggac tgcgtgcggg acgaggccat caacaagctg  1200
cagcagatct tcaacaccag ctacaaccag acctatgaga agtatgggaa cgtgagcgtg  1260
ttcgagacaa ccggcgggct ggtcgtcttc tggcaaggca ttaagcagaa gtccctcgtg  1320
gagctggaac ggctggccaa ccgtagcagc ctgaacctga cccacaaccg gaccaagcgg  1380
agcaccgacg gcaacaatgc tactcatcta tcaaacatgg aaagcgtgca caacctggtg  1440
tacgcccagc tgcagttcac ctacgacacc ctgcggggct acatcaaccg ggccctggcc  1500
cagatcgccg aggcctggtg cgtggaccag cggcggaccc tggaggtgtt caaggagcta  1560
agtaagatca accccctccgc aatcctgagc gccatctata acaagcctat cgccgcccgg  1620
ttcatgggcg atgtgctggg cctggccagc tgcgtcacca tcaatcaaac tagcgtgaag  1680
gtcctacggg acatgaacgt gaaagagagc cccggccggt gctactcccg gcccgtggtc  1740
atcttcaatt tcgccaactc ttcctatgtg cagtacgggc agctgggcga ggacaacgag  1800
attctgctgg gtaaccaccg gaccgaggag tgccagcttc cctccctcaa gattttcata  1860
gcaggcaatt ctgcctatga atacgttgac tacctgttca agcggatgat cgatctctct  1920
agtatcagca ccgtggacag catgattgcg ttggacatcg acccgttaga gaacaccgac  1980
ttccgggtgc tggagctgta cagccagaaa gaactgcgtt caagcaacgt tttcgacctg  2040
gaggagatca tgcgggagtt caactcttac aagcagcggg tcaagtacgt cgaggataag  2100
gtcgtggacc cgctgccgcc ctacctgaag ggactggacg atctgatgtc cggattggga  2160
gctgcaggaa aggccgtggg agtagccatc ggcgctgttg gaggggcagt ggccagcgtg  2220
gtcgaaggcg tcgcgacgtt cctgaagaac cccttcggcg ccttcacaat aatcttggtt  2280
gccattgctg tcgtcattat tacatatctt atctacaccc ggcagagaag actgtgcacc  2340
cagcccctgc agaacctgtt cccttatttg gtgagcgccg acgggacaac cgtcacctcc  2400
ggctcaacga aggacaccag cctgcaggct ccgccttcat atgaagagtc agtatataac  2460
agcggccgga aggggccagg tcctccatct agcgacgcat caactgccgc acctccgtac  2520
accaacgagc aggcatacca gatgctgttg gccctcgcac ggctggacgc cgagcaacgc  2580
gcccagcaga acgggacgga ctctttggat ggccggaccg gcacccaaga caagggccag  2640
aagcccaatt tgctggaccg gctgcggcac cggaagaacg gctatagaca tctgaaggac  2700
```

```
agcgacgagg aggagaacgt g                                          2721

SEQ ID NO: 167          moltype = DNA  length = 2721
FEATURE                 Location/Qualifiers
misc_feature            1..2721
                        note = Synthetic polypeptide
source                  1..2721
                        mol_type = other DNA
                        organism = synthetic construct
SEQUENCE: 167
atggagagcc ggatctggtg cctagtggtg tgcgtgaacc tatgcatcgt gtgccttggc  60
gccgccgtga gctcgtccag tacccggggc acctccgcca cccactccca ccactcctcc  120
cacactacaa gcgccgccca ctcgcgctcc ggctccgtct cccagcgcgt caccagttcc  180
cagaccgtga gtcacggcgt caacgaaacc atctacaaca ccaccctcaa gtacggcgac  240
gtcgtgggcg tgaatacaac caagtacccc taccgcgtct gctccatggc ccagggcacc  300
gacctcatcc gcttcgagcg caacatcgtc tgcacctcca tgaagcccat caacgaggac  360
ctcgacgagg gcatcatggt cgtgtataag cgaaatattg tggcccacac cttcaaggtc  420
cgcgtctacc agaaggtcct caccttccgc cgctcctacg cctacattca cacaacctac  480
ctcctcggct ccaacaccga gtacgtcgcc cctcccatgt gggagatcca ccacatcaac  540
agtcacagcc agtgctactc ctcctactcc cgcgtcatcg ccggcaccgt cttcgtcgcc  600
taccaccgcg actcctacga gaacaagacc atgcagctca tgcccgacga ctatagcaat  660
acacatagta cccgctacgt caccgtcaag gaccagtggc acagcagggg ctccacctgg  720
ctctaccgcg agacttgcaa cctcaactgc atggtcacca tcaccaccgc ccgctcaaag  780
tacccgtatc acttcttcgc cacctccacg ggagacgtgg tggacatctc ccctttctac  840
aacggcacca accgcaacgc tagctatttc ggcgagaacg ccgacaagtt cttcatcttc  900
cccaactaca ccatcgtctc cgacttcggc cgccccaact ccgccctcga aacccacagg  960
cttgtggcct tcctcgagcg cgccgactcc gtcatctcct gggacatcca ggacgagaag  1020
aacgtcacct gccagctcac attctgggag gcctccgagc gcaccatccg ctccgaggcc  1080
gaggattcgt accactttag ctcagcaaag atgaccgcca ccttcctctc caagaagcag  1140
gaggtcaaca tgagcgactc tgctttggac tgcgtccgcg acgaggccat caacaagctc  1200
cagcagatct tcaacacctc ctacaaccag acttatgaga agtatggcaa cgtctcggtg  1260
ttcgagacta cgggcggtct ggtggtcttc tggcagggga ttaagcagaa gtccctcgtc  1320
gagttggaga gactcgccaa ccgctcctcc ctcaacctca cccacaaccg caccaagcgc  1380
tccaccgacg gcaacaacgc cacgcacctc tcaaacatgg agtccgtcca caacctcgtc  1440
tacgcccagc tccagttcac ctacgacacc ctccgcggct acatcaaccg cgccctcgcc  1500
cagatcgccg aggcctggtg cgtcgaccag cgccgcaccc tcgaggtctt caaggagctc  1560
agtaagatca acccaagtgc gatcctgtcg gccatttaca ataaaccgat tgcagcccgc  1620
ttcatgggtg acgtactcgg cctcgcctcc tgcgtgacga ttaatcagac cagcgtcaag  1680
gtgcttcgcg acatgaatgt gaaggagagc ccaggccgct gttacagtcg gcccgtcgtc  1740
attttcaatt tcgccaatag cagctatgtc cagtacggcc agctcggcga ggacaacgag  1800
atactccttg gcaaccaccg caccgaggag tgccagctgc cgtctctgaa gatattcata  1860
gccggcaaca gcgcttatga atacgtggac tacctcttca agcgcatgat cgacctctcc  1920
tccatctcca ccgtcgactc catgatcgca cttgatatcg acccactgga gaacaccgac  1980
ttccgcgttc tggaactcta ctcccagaag gagctacggt cctccaatgt tttcgacctc  2040
gaggagatca tgcgcgagtt caattcatac aagcaacggg tgaagtatgt ggaggacaag  2100
gtcgtcgatc ctctgcctcc ctacctcaag ggtcttgatg atctcatgtc cggcctcggc  2160
gctgccggga aggcagtggg agtcgccatc ggcgccgttg gaggggcgt cgcctctgtg  2220
gtggagggcg tggctacctt cctgaagaac cccttcggcg ccttcaccat tattctggtg  2280
gccatcgcag tggttatcat cacgtacctt atctacaccc ggcagagaag gctctgcacc  2340
cagcccctcc agaacctctt tccttatctc gtcagcgcag acggtacaac agttactagt  2400
ggaagtacca aggacacctc cctccaggcc ccgccaagct acgaggaaag tgtttacaac  2460
tccggccgca agggccccgg cccaccttct tccgacgctt ccaccgctgc tccaccatac  2520
accaacgagc aggcctacca gatgctcctg gcactggctc ggctggatgc cgagcagagg  2580
gcccagcaga acggtaccga ttccctcgac ggccgcaccg gcacccagga taagggccag  2640
aagcccaatt tactagacag actgcgccac cggaagaacg gctaccgcca tctgaaggac  2700
tccgacgagg aggagaacgt c                                          2721

SEQ ID NO: 168          moltype = DNA  length = 2721
FEATURE                 Location/Qualifiers
misc_feature            1..2721
                        note = Synthetic polypeptide
source                  1..2721
                        mol_type = other DNA
                        organism = synthetic construct
SEQUENCE: 168
atggagagcc ggatctggtg cctagtggtg tgcgtgaacc tctgcatcgt gtgcttgggc  60
gccgccgtga gtagttccag tacccggggc acctccgcca cccactccca ccactcctcc  120
cacactacga gtgccgccca ctcacgctcc ggctccgtct cccagcgcgt cactagttct  180
cagacagtgt ctcacggcgt caacgagaca atctacaaca ccaccctcaa gtacggcgac  240
gtcgtgggtg tgaatactac taagtacccc taccgcgtct gctccatggc ccagggcacc  300
gacctcatcc gcttcgagcg caacatcgtc tgcacctcca tgaagcccat caacgaggac  360
ctcgacgagg gcatcatggt cgtctacaag agaaatatag tggcccacac cttcaaggtc  420
cgcgtctacc agaaggtcct caccttccgc cgctcctacg cctacattca cactacctac  480
ctcctcggct ccaacaccga gtacgtcgcc ccacccatgt gggagatcca ccacatcaac  540
tctcacagtc agtgctactc ctcctactcc cgcgtcatcg ccggcaccgt cttcgtcgcc  600
taccaccgcg actcctacga gaacaagacc atgcagctca tgcccgacga ctactcaaac  660
actcacagca cccgctacgt caccgtcaag gaccagtggc acagccgcgg ctccacctgg  720
ctctaccgcg agacttgcaa cctcaactgc atggtcacca tcaccaccgc ccgctcgaag  780
tatccgtacc acttcttcgc cacctccacg ggcgatgtgg tcgacatcag tccattctac  840
```

-continued

```
aacggcacca accgcaacgc ttcatacttc ggcgagaacg ccgacaagtt cttcatcttc  900
cccaactaca ccatcgtctc cgacttcggc cgcccccaact ccgccctcga gacacaccgc  960
ctggtcgcct tcctcgagcg cgccgactcc gtcatctcct gggacatcca ggacgagaag  1020
aacgtcacct gccagttgac cttctgggag gcctccgagc gcaccatccg ctccgaggcc  1080
gaggacagtt accatttcag tagtgccaag atgaccgcca ccttcctctc caagaagcag  1140
gaggtcaaca tgtcggactc tgctcttgac tgcgtccgcg acgaggccat caacaagctc  1200
cagcagatct tcaacacctc ctacaaccag acttatgaga agtatggtaa cgtctctgtg  1260
tttgagacta caggcggtct tgtcgtcttc tggcagggta tcaagcagaa gtccctcgtc  1320
gagctggaac gcctcgccaa ccgctcctcc ctcaacctca cccacaaccg caccaagcgc  1380
tccaccgacg gcaacaacgc aacacatctt agcaacatgg agtccgtcca caacctcgtc  1440
tacgcccagc tccagttcac ctacgacacc ctccgcggct acatcaaccg cgccctcgcc  1500
cagatcgccg aggcctggtg cgtcgaccag cgccgcaccc tcgaggtctt caaggagctg  1560
agtaagatca acccaagtgc aatcctaagc gctatttaca acaaacctat cgcagccagg  1620
ttcatgggag acgtcctcgg cctcgcctcc tgcgtcacca ttaatcagac gtctgttaag  1680
gttctccgcg acatgaacgt gaaagagtct ccgggccgct gctacagcag gcccgtcgtc  1740
atcttcaatt tcgccaattc ttcatatgtc cagtacggcc agctcggcga ggacaacgag  1800
attctcttag ggaaccaccg caccgaggag tgtcagctac ccagcctgaa gatctttatt  1860
gccggcaata gcgcttatga gtatgttgac tacctcttca agcgcatgat cgacctctcc  1920
tccatctcca ccgtcgactc catgatcgct ctggatatcg accctctgga gaacaccgac  1980
ttccgcgtgc ttgagctcta ctcccagaaa gagcttaggt caagcaacgt tttcgacctc  2040
gaggagatca tgcgcgagtt caactcatat aagcaacgcg ttaaatatgt agaggataag  2100
gtggttgatc cacttcctcc ctacctcaag ggtctggatg acctcatgtc cggcctcggg  2160
gcagcaggca aggccgtcgg cgttgccatc ggcgccgtgg gaggtgctgt ggccagtgtt  2220
gtcgagggcg tagccacctt cttaaagaac cccttcggcg cctttacaat aatcctggtg  2280
gccatcgctg tggttatcat tacctatctt atctacacca ggcagcggag gctctgcacc  2340
cagcccctcc agaacctctt cccttacctc gtgagcgcgg acgggacgac cgtcacatct  2400
ggcagtacaa aggacacctc cctccaggcc ccgcctagtt atgaagagag cgtttacaac  2460
tccggccgca agggcccccgg tcctccctcc tccgacgcca gcaccgcagc gcctccatac  2520
accaacgagc aggcctacca gatgctcttg gccctggccc gactggatgc cgagcagcgc  2580
gcccagcaga acggaaccga ctccctcgac ggccgcaccg gcacccagga caaaggccag  2640
aagcccaatc tgctcgaccg cctgcgacac cgcaagaacg gctatcggca ccttaaagac  2700
tccgacgagg aggagaacgt c                                          2721

SEQ ID NO: 169         moltype = DNA  length = 2226
FEATURE                Location/Qualifiers
misc_feature           1..2226
                       note = Synthetic polypeptide
source                 1..2226
                       mol_type = other DNA
                       organism = synthetic construct
SEQUENCE: 169
atgcggccag gacttcctag ctacctaatc atccttgccg tgtgtctttt ctcacacctc  60
ctctctagta ggtacggcgc agaggccgtg tccgagccac tcgacaaggc cttccacctt  120
ttgttaaaca cctacggtcg gccaatcaga ttcctccgcg agaacaccac ccagtgcacg  180
tacaattcgt ctctccgcaa cagcacagtc gtgagggaga acgctatatc attcaacttc  240
ttccagtctt acaaccagta ttacgtgttc cacatgccaa gatgcctgtt cgctggccca  300
ctggccgagc agttccttaa ccaggtggat ctgacagaga ctctggagag ataccaacag  360
aggctgaaca cctacgcact ggtgagcaag gatctggcct cctacaggag cttcagccaa  420
cagctgaagg cccaggacag tctgggcgag caaccaacca ccgtacctcc acctattgac  480
ttatcaatac ctcacgtgtg gatgcctcct cagaccactc ctcacggctg gaccgaatcc  540
cacaccacct ccggcctgca caggcctcat ttcaaccaga cctgtattct cttcgacgga  600
cacgacctgc ttttcagcac cgtcacgcca tgcttgcacc agggcttcta cctgatcgac  660
gagctcaggt atgtgaagat cactctgacc gaggacttct tcgtggttac tgtgagcatc  720
gatgacgata ccccaatgtt actgatcttc ggccacctgc ctagggtgct gttcaaggca  780
ccataccaga gagacaattt catcctgaga caaaccgaga agcacgagct gctggtgctg  840
gtcaagaagg accagctgaa taggcactca tacctgaagg acccagattt cctggacgct  900
gcccttgatt tcaattacct ggacctgtcc gccctgctga gaaacagctt ccacagatac  960
gccgtggatg tgctgaagtc aggcagatgt cagatgttgg accgccgaac cgttgagatg  1020
gccttcgcct acgcgctggc cctgttcgc gccgctcggc aggaggaagc tggcgcacag  1080
gtgagcgtgc cgagggctct ggaccgacag gctgctctgc tacagattca ggaattcatg  1140
atcacctgcc tgtcacagac tccgcctcgg actaccctgc tgctgtatcc tacagcagtg  1200
gacctggcaa agagagctct ttggacccct aaccagatca ccgatatcac cagcctcgtc  1260
cggctggtct acattctgtc taagcagaat cagcagcacc tgatccctca gtgggctctc  1320
agacagatcg ccgatttcgc cctgaagctg cacaagaccc acctggcttc tttcctgagc  1380
gctttcgcca gacaggaact gtacctgatg ggatcgcttg tgcacagcat gctggtgcac  1440
acaactgaga ggagagagat tttcattgtg gagactggcc tgtgcagcct ggccgagctg  1500
tcccatttca cccagctcct cgctcatccg caccacgagt acctctccga cctctatacc  1560
ccttgctcct cttccggccg gcgcgatcac agcctggaaa gactcactag actgttccca  1620
gacgctaccg tgccggctac tgtcccggca gcactgagca tcctgagcac tatgcagcct  1680
tctacgctgg aaaccttccc ggacctgttc tgcctgccac tcggagaaag cttctctgcc  1740
ctgacggtga gtgagcacgt gtcgtacatc gtgacaaacc agtacctgat caagggtatc  1800
agctacccag tgtccacaac tgtggtgggc cagagcctga tcatcaccca gaccgatagc  1860
caaacaaagt gcgaactgac aagaaacatg cataccactc attccatcac tgtggcctta  1920
aacatctccc tggagaactg cgccttctgt cagtccgccc tgctggagta cgatgatacc  1980
cagggcgtta ttaatatcat gtacatgcat gatagcgacg atgtgctttt cgccctggac  2040
ccatacaacg aggtggtggt gtccagccct agaacccact acctcatgct gctgaagaac  2100
ggcacagtgc tggaggtgac cgacgtggtg gtggacgcta cggacagcag gctgctgatg  2160
atgagcgtgt acgccctgag cgccattatc ggaatatacc tgctgtacag gatgttgaag  2220
acctgt                                                           2226
```

```
SEQ ID NO: 170          moltype = DNA  length = 2226
FEATURE                 Location/Qualifiers
misc_feature            1..2226
                        note = Synthetic polypeptide
source                  1..2226
                        mol_type = other DNA
                        organism = synthetic construct
SEQUENCE: 170
atgcggccgg gactccctag ctacctcatc atcctcgccg tgtgcctttt ctctcacctt  60
ttgagctcca gatacggcgc cgaagcggtg tccgagcctc tcgacaaggc cttccacctc  120
cttctcaaca catacggcag accgatccgg ttcttgaggg agaacactac ccaatgcaca  180
tataacagta gcctgcggaa tagcactgtg gtgcgggaga acgccatcag cttcaatttc  240
ttccagagct acaatcagta ttacgtgttc cacatgccta gatgtctgtt cgcgggccct  300
ctggcagagc agttcctgaa ccaggttgat ctcacagaga cactggagag ataccagcaa  360
agactgaaca cctacgctct cgtctccaag gacctggcca gctataggag cttcagccag  420
cagctgaagg cccaggattc cctgggagag cagccaacca ccgtcccgcc gccaatcgac  480
ctctctatcc cacacgtgtg gatgcctcca caaaccacac cacacggatg gactgagtcc  540
cataccacca gcggactgca caggcctcac ttcaatcaga cctgcatttt gttcgacggc  600
cacgacctcc tgttcagcac tgtgaccccg tgtctgcatc agggcttcta cctgattgac  660
gagctgaggt acgtcaagat tacgctcacc gaagacttct tcgtggtcac agtgagtatc  720
gatgacgaca cccctatgct gctcatcttc ggccatctgc ctagggtgct gttcaaggcc  780
ccttaccaga gagataattt catcttgcgg cagactgaga agcacgaact gctggtactc  840
gtgaagaagg accagctgaa ccgccactct tacttaaagg atccagactt cctggatgca  900
gcacttgact tcaactatct cgacctctct gccctgctga ggaacagctt ccaccggtat  960
gccgtggacg tgctgaagag tggacggtgt cagatgctgg accgcagaac agtggaaatg  1020
gcgttcgcgt atgctctggc cctattcgcg gccgcaagac aggaggaggc cggcgctcag  1080
gtgtccgtcc ctagagctct ggacaggcag gccgccctgc tgcaaattca ggagttcatg  1140
ataacttgcc tgagccaaac ccctccgaga acaacactgc tgctgtatcc aacagccgta  1200
gatctggcca agcgggccct ttggactcct aaccagatca ccgatattac ctccctggtg  1260
agactggtgt acattctgtc caagcagaac cagcagcacc tgatcccgca gtgggccctg  1320
agacagatcg ctgatttcgc cttgaagctg cacaagactc atctggcctc cttcctgagt  1380
gctttcgccc gccaggaact gtatctgatg ggctctcttg tccattccat gctggttcat  1440
accacggaga gaagggagat cttcatcgtg gaaaccggcc tttgctccct cgctgagctg  1500
agccatttca ctcagctgct cgcccacccg caccacgagt acctgtcaga cctttatact  1560
ccgtgctcct ccagcggcag gagggaccac agcctggaac ggctcacaag actgttcccg  1620
gatgctaccg tgcctgctac tgtgccagcc gccctgagca tcctttccac catgcagcct  1680
tccacactgg agactttccc tgacctgttc tgcctgccac ttggcgaaag tttcagcgcc  1740
ctgaccgtgt ccgaacatgt gagctacatc gtgactaacc agtacctgat caagggcatc  1800
agctacccgg ttagcaccac tgtcgtcgga cagtcactga tcatcactca gaccgactcc  1860
cagaccaagt gcgaactgac cagaaatatg cacacaaccc atagcatcac cgtggccctg  1920
aacattagcc tggagaactg tgccttctgc cagagcgccc tcctcgagta cgacgatacc  1980
cagggtgtga taaacattat gtatatgcac gacagtgacg acgttctgtt cgcactggac  2040
ccttacaacg aagtggtcgt ttcctctcct cggacccatt acctgatgct gctgaagaac  2100
ggcaccgtgc tagaggttac tgatgtggta gtggacgcca cagacagcag actgctgatg  2160
atgagcgtgt acgccctgag cgccattatt ggcatctacc tgctgtacag gatgctgaag  2220
acatgt                                                            2226

SEQ ID NO: 171          moltype = DNA  length = 2226
FEATURE                 Location/Qualifiers
misc_feature            1..2226
                        note = Synthetic polypeptide
source                  1..2226
                        mol_type = other DNA
                        organism = synthetic construct
SEQUENCE: 171
atgcggccgg gactcccttc ctacctcatc atccttgccg tgtgtctttt ctcacacctc  60
ctcagcagcc gctacggcgc cgaggccgtg tcagagccac ttgacaaggc cttccatctt  120
ttgttgaaca cctacggcag acctattcgg ttcctgagag agaacacaac ccagtgcacc  180
tataacagct ctctgcgcaa ctccacagtg gttagagaga atgccatcag cttcaacttc  240
ttccagagtt acaaccagta ttacgtgttc catatgccta ggtgcctgtt cgctggcccg  300
ttagccgaac agttcctcaa ccaggtggat ctgaccgaaa cactggaaag gtaccagcag  360
cggctgaata catacgcctt ggtgtcaaag gatcttgctt cctacagaag cttcagccag  420
cagctgaagg cccaggacag ccttggagag cagccaacca ccgtgcctcc tcctattgac  480
ctgagcatcc ctcatgtgtg gatgcctcct cagaccaccc ctcacggctg gactgagagc  540
cataccacgt ccggcctgca caggcctcac ttcaatcaga cctgcatcct gttcgacggc  600
cacgatctgc ttttcagcac cgtcacccct tgcctgcacc agggattcta cctgatcgac  660
gagctccggt atgtgaagat tacactgacc gaggacttct tcgtggtgac cgtgtccatc  720
gacgatgaca ccccaatgct gctgatcttc ggccacctgc cgagagtcct gttcaaggcc  780
ccataccaga gagacaactt catcctgcgg cagaccgaga agcacgaact gctagtgctg  840
gtgaagaagg atcagctgaa ccggcactcc tacctgaagg accctgactt ccttgacgcc  900
gcactcgact tcaactacct ggacctcagt gctctactga ggaactcttt ccaccggtac  960
gccgtggacg tgctgaagtc tggaagatgc cagatgctgg ataggaggac agtggagatg  1020
gcgttcgcgt acgccctggc cctgttcgcc gccgccagac aggaggaggc cggcgcacag  1080
gtcagcgtcc caagggccct ggaccgccag gctgccctgc tgcagattca ggaattcatg  1140
atcacctgtc tcagccagac ccctccgaga acaaccctgc tgttgtaccc gaccgcagtg  1200
gatctggcta agagggccct gtggacccca aaccagatta ccgacatcac ctctctggtg  1260
agactggtgt acatcctgtc caagcagaac caacagcacc tcattccaca atgggccctg  1320
aggcaaatcg ccgatttcgc tctcaagttg cataagaccc atctggcctc attcctcagc  1380
```

```
gccttcgcaa gacaggagtt gtatctcatg ggctccctcg tgcatagcat gctggtgcac  1440
acaaccgagc gcagagaaat tttcatcgtt gaaaccggac tgtgcagcct cgccgagttg  1500
tctcatttca cccagctgct ggctcatcct caccatgagt atctttccga cctgtacacc  1560
ccgtgcagca gcagcggccg cagggatcac agcctcgaga gactgacaag actgttccca  1620
gacgccaccg tgcctgccac agtgccagcc gcgctgtcca tcctgagcac aatgcagcct  1680
agcacactgg agactttccc agatctgttc tgtcttccac tgggcgagag cttcagcgcc  1740
ctgaccgtga gcgagcacgt gagctacata gtgaccaacc aatatttgat taagggcatc  1800
tcctaccctg tgagcaccac agtggtgggc cagtctctga tcatcacaca aaccgacagt  1860
cagacgaagt gcgagctgac tagaaacatg cacacgaccc acagcataac cgtggcactc  1920
aacatctccc tggagaattg cgccttctgc cagagcgccc tcctggagta cgacgacact  1980
caaggagtga tcaacatcat gtacatgcac gatagcgatg acgtgctgtt cgccctggac  2040
ccatacaatg aagtggtggt gtccagccca cggacccact acctgatgct cctcaagaac  2100
ggcacagtgc tggaggttac agacgtggtg gtcgacgcta ccgatagcag acttcttatg  2160
atgtccgtgt acgccctgag cgccatcatc ggaatctatc tgctttacag gatgctgaag  2220
acttgc                                                             2226
```

```
SEQ ID NO: 172         moltype = DNA  length = 2226
FEATURE                Location/Qualifiers
misc_feature           1..2226
                       note = Synthetic polypeptide
source                 1..2226
                       mol_type = other DNA
                       organism = synthetic construct
SEQUENCE: 172
atgcggccag gcctcccttc gtaccttatc atcttggccg tgtgtctttt ctctcaccta  60
ctctcctcaa ggtacggcgc cgaggccgtg agtgagccgc tagacaaggc cttccaccta  120
ttacttaaca cctacggccg gcctatccga ttcctccggg agaataccac acagtgtaca  180
tacaactcta gcctgcgcaa cagcactgtg gtcagggaga acgccatcag cttcaatttc  240
ttccagagtt ataaccagta ctacgtgttc cacatgccaa gatgcctgtt cgccggacct  300
cttgccgagc agttcctgaa ccaggtggat ctgaccgaga cactggagag ataccagcaa  360
aggctcaata cctacgcttt agtgagcaag gaccttgctt cttacagatc tttctcacaa  420
cagcttaagg cgcaggacag cctcggcgag cagcctacca ccgtgcctcc tcctattgac  480
ttgagcatcc cacacgtatg gatgcctcca cagacgacac cacacggctg gaccgaatcc  540
catacaacca gcggactcca ccggcctcat ttcaatcaga cctgcatcct tttcgacggc  600
catgacctgc tattctctac cgtcaccccg tgcctgcacc agggcttcta ccttatcgac  660
gaactgagat acgtcaagat cacgctgacc gaagacttct tcgtcgttac agtcagcatc  720
gacgacgata cccctatgct gctgatattc ggccaccttc ctagagtcct gttcaaggca  780
ccgtaccaga gggacaactt catcctgaga cagacagaga agcacgagct cctggtgctg  840
gtgaagaagg atcagctgaa tagacacagt tacctgaagg atccagactt cctggacgcc  900
gcactggact tcaactatct ggatctgagc gccctgcttc gcaatagctt ccatagatac  960
gctgtggacg tgctgaagtc tggccggtgt cagatgctgg atcgtaggac cgtggagatg  1020
gccttcgcct acgcactcgc tctgttcgcc gccgctagac aggaggaggc cggagcccaa  1080
gtgagtgtgc ctcgggcact ggacagacag gcagccttac tgcagatcca ggagttcatg  1140
attacctgcc tgtctcagac tccaccacgg accacccttc tgctgtatcc taccgcggtt  1200
gatctggcta agagggccct gtggacccct aaccagatca ctgacatcac cagcctcgtg  1260
aggctggtgt acattcttag caagcagaac cagcagcacc taatacctca gtgggccctg  1320
cggcagatcg ccgacttcgc cctgaagctg cacaagaccc acctggcaag cttcctgtcc  1380
gccttcgccc gccaggagct gtacctcatg ggaagtctgg tacactccat gctggtgcac  1440
accaccgaga gaagagagat cttcatcgta gaaaccggac tctgctcact ggccgaattg  1500
tcacacttca cccagctgct ggcccatcct catcacgagt atctgtccga cctgtacacc  1560
ccttgcagct ctagcggcag gcgggaccat tccttggaga ggctgaccag gctgttcccg  1620
gatgccaccg ttccagcaac agtgcctgca gccctgagca ttctgtcaac aatgcagcct  1680
agcaccctcg aaactttccc ggatctgttc tgcctgcctc ttggtgagag cttcagcgcc  1740
ctgaccgtgt ccgagcatgt gtcttatatc gtaaccaatc agtacctgat caagggcatc  1800
agctaccctg tgtccacaac tgtcgtgggc caaagcctca tcataaccca gaccgattcc  1860
cagacaaagt gtgaactgac ccgcaacatg cacaccactc acagcattac tgtggccctg  1920
aacatctccc tggagaactg tgccttctgt cagagcgcgc ttctggagta tgatgacacc  1980
cagggtgtga ttaatatcat gtacatgcac gacagcgacg atgtgctgtt cgcgctggat  2040
ccttacaatg aggtggtcgt gagctcccct agaacccact atctcatgct gttaaagaac  2100
ggcaccgtcc tggaggtgac agacgtggtg gttgatgcca ccgacagcag gctgctgatg  2160
atgagcgttt atgccctgag cgccatcatc ggcatttacc tcctgtacag gatgttaaag  2220
acttgt                                                             2226
```

```
SEQ ID NO: 173         moltype = DNA  length = 2226
FEATURE                Location/Qualifiers
misc_feature           1..2226
                       note = Synthetic polypeptide
source                 1..2226
                       mol_type = other DNA
                       organism = synthetic construct
SEQUENCE: 173
atgcggccag gactccctag ctacctcatt atcctcgccg tgtgcctttt ctctcacctc  60
ttaagctccc ggtacggcgc cgaagccgtg agcgagccgc ttgacaaggc tttccacctc  120
ctccttaaca cctacggcag acctattaga ttcctgagag agaacaccac ccagtgtaca  180
tataattcta gcctgcggaa ctccaccgta gtgagggaga atgccattag cttcaacttc  240
ttccagagct acaaccagta ctatgtgttc catatgccga gatgtctgtt cgctggacct  300
ctcgcagaac agttcttgaa ccaggtggat ctgactgaaa ctctcgagcg gtaccagcaa  360
agactgaata cctatgcctt ggtaagcaag gatctggcta gctacaggag cttctcccag  420
cagctcaagg cccaggactc ccttggcgaa cagcctacca ccgtccctcc tccaattgac  480
```

```
ctgagcattc cgcacgtgtg gatgcctcct cagaccaccc cacacggctg gacagagtct  540
cataccacca gcggactgca tagaccgcat ttcaaccaga cttgcatcct gttcgatgga  600
catgatctcc tgttctctac agtgactcca tgcctgcacc agggcttcta cctgatcgat  660
gagctcagat acgtcaagat caccttgacc gaagatttct tcgtggtcac agtgagcatt  720
gacgacgaca ccccaatgct tctgatattc ggtcacctgc ctagggtcct cttcaaggct  780
ccataccaga gagacaattt catccttaga cagaccgaga agcacgagct gctcgtgctg  840
gtgaagaagg atcaactgaa cagacatagc tacctaaagg atccggattt cctggacgcc  900
gctctggact tcaactacct cgacctcagc gccctgctga ggaacagctt ccaccggtat  960
gcagtcgatg ttctcaagtc cggcagatgc cagatgctgg accgtagaac tgtggagatg  1020
gccttcgcct atgctctggc cctgttcgcc gccgcacgcc aggaagaggc tggagcccag  1080
gtgagcgtcc cacgggctct ggacagacag gctgctctgc tgcagatcca agagttcatg  1140
attacctgtc tgagccagac ccctcctaga accaccctcc tcctctatcc gaccgctgtg  1200
gacctggcca agagagcctt gtggacccct aatcagatta ctgacatcac aagcctggtc  1260
agactggtgt atatcctgag caagcagaat cagcagcacc tcattccaca gtgggcgctg  1320
cggcagatcg ctgatttcgc cctgaagctg cacaagaccc acctggccag cttcttgagc  1380
gcattcgcac ggcaggaact ctacctgatg ggctctctgg tgcacagcat gctcgtccac  1440
accacagaac ggcgagagat attcatcgtt gagacaggcc tgtgctctct ggccgagttg  1500
tcccacttca cccaactgct ggctcaccct catcacgagt acctcagcga cctgtacacc  1560
ccttgctcct ccagcggtag acgggatcac agcctggaaa gactgaccag actgttccca  1620
gacgccacgg tccctgcaac cgtgcctgcc gctctttcaa tcttgtccac catgcagcct  1680
agtacactgg aaacattccc tgacctcttc tgcctgcctc tcggagagtc cttctcagcc  1740
ctgaccgtga gcgaacacgt gtcctacatc gtgaccaacc agtacctgat caagggcatc  1800
tcctaccctg tgtcgaccac cgtcgtgggc cagagcctga tcattacaca gacggactct  1860
cagaccaagt gcgagttgac acggaacatg cacaccacac acagcatcac tgtggccctg  1920
aatattagcc tcgagaactg cgccttctgc cagagtgccc tgctagagta tgatgataca  1980
cagggcgtga ttaatatcat gtatatgcac gactctgatg acgtcctgtt cgccctggac  2040
ccatacaacg aggtggttgt gagctcccct cggacccact atctgatgct gctcaagaac  2100
ggcactgttc tcgaggtgac agatgtggtg gtcgatgcca cagattctcg gctgctgatg  2160
atgagcgtgt acgctcttag cgccatcatc ggaatctacc tcctgtacag gatgctgaag  2220
acttgt                                                            2226
```

```
SEQ ID NO: 174         moltype = DNA  length = 2226
FEATURE                Location/Qualifiers
misc_feature           1..2226
                       note = Synthetic polypeptide
source                 1..2226
                       mol_type = other DNA
                       organism = synthetic construct
SEQUENCE: 174
atgcggccgg gcctcccgtc ttacctcatc atcttggccg tgtgcctctt ctcccacctc  60
ttgagctccc ggtacggcgc agaggccgtg tcagagcctc tcgacaaggc cttccatttg  120
ctccttaaca catacggcag gccaatcagg ttcctgcgag agaataccac acaatgcacc  180
tacaactcca gcttgaggaa tagcaccgtg gtgcgggaga acgccatctc cttcaatttc  240
ttccagtcct acaatcagta ttatgtgttc catatgccta ggtgtctctt cgcaggccca  300
cttgccgaac aattcctgaa ccaagtggac ctgacagaga cactggagag ataccagcaa  360
cggctgaata cctacgcctt ggtgagcaag gatctcgcca gctacagatc tttctcacaa  420
caactgaagg cccaggattc tctcggtgag cagccaacga ctgtgcctcc tccaattgac  480
ctgtctatcc cacatgtgtg gatgccacct cagactaccc ctcacggatg gacagagtct  540
cataccacta gcggcctgca caggcctcac ttcaatcaga cctgtatcct cttcgacggt  600
cacgatctgt tgttcagcac cgtgacccca tgcctgcatc agggcttcta cctgattgac  660
gagctgagat atgtgaagat aacactgacc gaggatttct tcgtggtcac cgtgagcata  720
gacgacgaca caccgatgct cctgatcttc ggccatctgc cacgagttct gttcaaggca  780
ccttatcaga gagacaactt catcttgagg caaacagaga agcacgagct tctcgtgctg  840
gttaagaagg accagctcaa caggcatagc tacctgaagg acccagattt cctggacgcc  900
gctctggatt tcaattatct ggacctttct gctctgctga gaaacagctt ccatagatac  960
gccgtggacg tccttaagtc tggccgctgc cagatgctgg atagacggac tgtcgagatg  1020
gcattcgcct acgctctggc tctgttcgcc gccgccaggc aggaggaggc tggagcccaa  1080
gtgtcagtgc ctagggctct ggatagacaa gccgccttgc tccagatcca ggagttcatg  1140
attacctgtc tgagccagac cccaccaaga accacgttac tgctgtaccc taccgctgtg  1200
gacctggcta agcgagccct ctggacgcct aatcaaatca ccgacatcac cagcttagtc  1260
agactggtgt acattctgtc taagcagaac cagcagcact tgattccaca gtgggccctg  1320
agacagattg ccgacttcgc cctgaagctc cataagaccc atctggcgtc cttcctgagc  1380
gccttcgcca gacaggagct ctacctgatg ggcagcctgg ttcattccat gctggtccat  1440
acaacggaga gaagagagat cttcatcgtg gagacaggac tgtgctcttt ggccgaactt  1500
tcccacttca ctcagctgct ggcgcaccct catcacgagt acttatcgga cctgtacacc  1560
ccttgcagca gcagcggaag gagggaccat tctctcgaaa ggctgacaag actgttccct  1620
gacgccaccg tcccagccac agtgcctgcc gcactgagca tcctcagcac aatgcagcca  1680
agcactctgg agactttccc ggacttgttc tgcctgccgc tgggcgagtc cttcagcgcc  1740
cttacagtgt cagagcatgt gtcctacatc gtgaccaatc agtacctgat caagggaatc  1800
agctaccctg tgtctacaac cgtggttggc cagtccctca tcatcaccca gacagatagc  1860
caaactaagt gcgaactgac tagaaacatg cacacaaccc actccatcac agtggccctg  1920
aacatcagcc tcgagaattg cgccttctgc cagagcgcac tgttggagta cgacgatact  1980
cagggcgtga ttaacatcat gtacatgcat gatagcgacg atgtgctgtt cgccctggac  2040
ccttataacg aggtggtggt gagtagtcct aggacccatt accttatgct gctgaagaac  2100
ggaactgttc tggaggttac cgacgtcgtc gttgacgcta ccgactcacg cctgctcatg  2160
atgtctgtgt atgccctgtc tgccatcatc ggcatctacc tgctgtatag gatgctgaag  2220
acttgc                                                            2226
```

```
SEQ ID NO: 175         moltype = DNA  length = 2226
```

```
FEATURE                Location/Qualifiers
misc_feature           1..2226
                       note = Synthetic polypeptide
source                 1..2226
                       mol_type = other DNA
                       organism = synthetic construct
SEQUENCE: 175
atgcggcccg gccttcccag ctacctcatc atcctcgccg tgtgcttgtt cagccacctt  60
ctaagcagcc ggtacggcgc cgaggccgtg agcgagcccc tcgacaaggc cttccacttg  120
ttattgaaca cctacggccg gcccatccgg ttcctgcggg agaacaccac ccagtgcacc  180
tacaacagca gcctgcggaa cagcaccgtg gttcgggaga atgccatcag cttcaacttc  240
ttccagagct acaaccagta ctacgtgttc cacatgcccc ggtgtctttt cgccggaccg  300
ctggccgagc agttcctgaa ccaggtggac ctgaccgaaa ctctggagcg gtaccagcag  360
cggctgaata cctatgccct ggtgagcaag gacctggcct cataccggag cttcagccag  420
cagctgaagg cccaggacag cctgggcgag cagcccacca ccgtgcctcc acccatcgac  480
ctgagcatcc cgcacgtgtg gatgcctcca cagaccacac ctcacggctg gaccgagagc  540
cacaccacca gcggcctgca ccggccccac ttcaaccaga cctgcatcct gttcgacggc  600
cacgacctgc tgttcagcac agttacccct tgccttcatc agggcttcta tcttatagac  660
gagctgcggt acgtgaagat cacactcacc gaggacttct tcgtggtgac cgtgagcatc  720
gacgacgaca ctcctatgct cctcatcttc ggccatcttc cccgggttct gttcaaggct  780
ccataccagc gggacaactt catcctgcgg cagaccgaga agcacgagtt gctggtgctg  840
gtgaagaagg accagctgaa ccggcattcg taccttaagg accccgactt cctggacgcc  900
gccctggact tcaactacct agatctcagc gccctgttga ggaatagctt ccaccggtac  960
gccgtggacg tgttaaagag cggccggtgc cagatgctgg atcggcggac cgtggagatg  1020
gccttcgcct acgcgctggc cttgttcgct gccgcccggc aggaggaggc cggcgcccag  1080
gtgagcgtac cgcgggcact cgatcggcag gccgctctgc tgcagatcca ggagttcatg  1140
atcacctgcc tgagccagac ccctccgcgg accaccttac tgctttaccc cactgcagtt  1200
gacctggcta agcgcgcact ctggacccct aaccagatca ccgacatcac cagcctggtg  1260
cggctggtgt acatcctgag caagcagaac cagcaacacc tgataccaca gtgggctctg  1320
agacagatcg ccgacttcgc cctgaagctg cacaagaccc atctggccag cttcctgtcc  1380
gctttcgcac gacaggagct gtacctgatg ggatcactcg tgcacagcat gctcgtgcat  1440
accaccgagc ggcgggagat cttcatcgtg gaaacaggcc tgtgttcact agccgaactg  1500
agccacttca cccaactttt ggcccatcca caccacgagt atttgtcgga cctgtacacc  1560
ccttgttcct cttccggaag gcgggaccac tccctggaac ggctgacccg gctgttcccc  1620
gacgcaaccg taccggccac ggttccagct gccttaagca tcttaagtac catgcagccc  1680
agcacactgg aaaccttccc agatctgttc tgcctgccgc tgggtgagtc tttcagcgct  1740
ctcaccgtgt ccgagcacgt gagctacatc gtgacaaatc aatatctgat taagggcatc  1800
agctacccag tgtcaactac ggtggttggc cagagcttga ttataaccca gaccgactcg  1860
cagactaagt gcgagcttac gagaaacatg cacacaaccc acagcatcac cgtggccctg  1920
aacataagtc tggagaactg cgccttctgc cagtctgcct tgctcgagta tgatgacacc  1980
cagggcgtga tcaacatcat gtacatgcat gacagcgacg atgttctctt cgcgttggat  2040
ccatacaacg aggtggtggt gtccagtccg agaactcact atctgatgct cctaaagaac  2100
ggcaccgtgc tggaggtgac cgacgtcgtg gtcgatgcca cggactccag actgcttatg  2160
atgagcgtgt acgccctaag cgccatcatc ggcatctatc tcctgtatcg gatgcttaag  2220
acctgc                                                             2226

SEQ ID NO: 176         moltype = DNA  length = 2226
FEATURE                Location/Qualifiers
misc_feature           1..2226
                       note = Synthetic polypeptide
source                 1..2226
                       mol_type = other DNA
                       organism = synthetic construct
SEQUENCE: 176
atgcggcccg gccttcccag ctacctcatc atcctcgccg tgtgcttgtt cagccacttg  60
cttagcagcc ggtacggcgc cgaggccgtg agcgagccct tggacaaggc cttccactta  120
ctcctcaaca cctacggccg gcccatccgg ttcctgcggg agaacaccac ccagtgcacc  180
tacaacagca gcctgcggaa cagcaccgtg gtgcgtgaga acgccatcag cttcaacttc  240
ttccagagct acaaccagta ctacgtgttc cacatgccca ggtgcctttt cgccggacca  300
ctggccgagc agttcctgaa ccaggtggac ctgaccgaaa cactggagcg gtaccagcag  360
aggctgaaca catacgccct ggtgagcaag gacctggcct cctaccggag cttcagccag  420
cagctgaagg cccaggacag cctgggcgag cagcccacca ccgtgccgcc acccatcgac  480
ctgagcatcc cacacgtgtg gatgccacca cagaccaccc ctcacggctg gaccgagagc  540
cacaccacca gcggcctgca ccggccccac ttcaaccaga cctgcatcct gttcgacggc  600
cacgacctgc tgttctcgac cgtcacccct tgcttgcacc agggcttcta tctgatagac  660
gagctgcggt acgtgaagat caccttgacc gaggacttct tcgtggtgac cgtgagcatc  720
gacgacgaca cacctatgct gctcatcttc ggccatttac cccgggttct gttcaaggca  780
ccataccagc gggacaactt catcctgcgg cagaccgaga agcatgagct tctggtgctg  840
gtgaagaagg accagctgaa ccggcactca tatctgaagg accccgactt cctggacgcc  900
gccctggact tcaactacct ggatttaagc gccctgctcc gtaactcttt ccaccggtac  960
gccgtggacg tgttaaagtc aggccggtgc cagatgttgg accggcggac cgtggagatg  1020
gccttcgctt acgcattagc cctcttcgca gccgcccggc aggaggaggc cggcgcgcag  1080
gtgagcgtgc ctagagcgtt ggatagacag gcggccttgc tgcagatcca ggagttcatg  1140
atcacctgcc tgagccagac tcctccacgg accacattgc tgctctaccc caccgccgtt  1200
gacctggcaa agcgggcgct ctggactccg aaccagatca ccgacatcac cagcctggtg  1260
cggctggtgt acatcctgag caagcagaat cagcagcacc tgataccaca gtgggcacta  1320
cgccagatcg ccgacttcgc cctgaagctg cacaagaccc acctggccag cttcctgtct  1380
gctttcgcaa ggcaggaact gtacctgatg ggctctctag tgcacagcat gctcgtccat  1440
accacagagc ggcgggagat cttcatcgtg gagactggcc tgtgctctct tgcggaactg  1500
```

```
agccacttca cccagctcct agcccaccca caccacgagt acctttctga cctgtacacc  1560
ccgtgctcat caagtggacg gcgggaccac tcgctggaaa gactcacccg gctgttcccc  1620
gacgctactg tgccggcaac tgtgcctgcg gctctctcta tattatctac catgcagccc  1680
agcacactcg aaaccttccc tgatctgttc tgcctgcctc taggagagag cttctctgcc  1740
cttacagtgt ccgagcacgt gagctacatc gtgacaaacc aatacctcat taagggcatc  1800
agctaccctg ttagtactac cgtcgtaggc cagagcctaa ttatcaccca gaccgactcc  1860
cagacaaagt gcgaattaac gcgcaacatg cacacaaccc acagcatcac cgtggccctg  1920
aacattagcc tcgagaactg cgccttctgc cagagtgcct tgcttgagta tgatgatacc  1980
cagggcgtga tcaacatcat gtacatgcac gacagcgacg atgtgctgtt cgcactcgac  2040
ccctacaacg aggtggtcgt aagcagtcca aggacccatt atttgatgct gcttaagaac  2100
ggcaccgtgc tggaggtgac cgacgtggtg gtagacgcta cagactcccg gctgcttatg  2160
atgagcgtgt acgcgctcag tgcgatcatc ggcatctacc tgctttatcg gatgctaaag  2220
acctgc                                                             2226
```

```
SEQ ID NO: 177          moltype = DNA  length = 2226
FEATURE                 Location/Qualifiers
misc_feature            1..2226
                        note = Synthetic polypeptide
source                  1..2226
                        mol_type = other DNA
                        organism = synthetic construct
SEQUENCE: 177
atgcggcccg gcttgcccag ctacttgatc atcttggccg tgtgcttgtt cagccactta  60
cttagcagcc ggtacggcgc cgaggccgtg tccgagcccc tcgacaaggc cttccacctc  120
ctcctcaaca cctacggccg ccccatccgc ttcctccgcg agaacaccac ccagtgcacc  180
tacaactcct ccctccgcaa ctccaccgtc gtgcgggaga atgccatctc cttcaacttc  240
ttccagtcct acaaccagta ctacgtcttc cacatgcccc gctgcctctt cgccggacct  300
ctcgccgagc agttcctcaa ccaggtcgac ctcaccgaga cgctcgagcg ctaccagcag  360
aggttgaata cctatgccct cgtctccaag gacctcgcct cctaccgctc cttctcccag  420
cagctcaagg cccaggactc cctcggcgag cagcccacca ccgtgcctcc accaatcgac  480
ctctccatcc cgcacgtctg gatgcctccc cagaccactc cgcacggctg gaccgagtcc  540
cacaccacct ccggactgca tcgccctcac ttcaaccaga cctgcatcct cttcgacggc  600
cacgacctcc tcttcagtac cgtgacgcca tgcctgcacc agggcttcta cctcatcgac  660
gagctccgct acgtcaagat caccccttacc gaggacttct tcgtcgtcac cgtctcgatt  720
gacgacgaca caccaatgct cctcatcttc ggccacctcc cgcgcgtgct gttcaaggcg  780
ccctaccagc gcgacaactt catcctgagg cagaccgaga agcacgagct gctcgtcctc  840
gtcaagaagg accagctcaa ccgccactcc tacctcaagg accccgactt cctcgacgcc  900
gccctcgact tcaactacct cgatctgagt gctctgctga ggaattcatt ccaccgctac  960
gccgtcgacg tcctcaagtc cggccgctgc cagatgctcg accgccgcac cgtcgagatg  1020
gccttcgctt acgcgctggc actcttcgct gccgcccgcc aggaggaggc cggcgcccag  1080
gtcagtgtgc caagagcact ggatagacag gccgcacttt tgcagatcca ggagttcatg  1140
atcacctgcc tctcccagac tccgcctcgc accacgttgt tgttgtaccc cacagcagtc  1200
gatctggcta agagagcctt atggacacct aaccagatca ccgacatcac ctccctcgtt  1260
cggctggtct acatcctctc caagcagaat cagcagcacc tgatccctca gtgggcactc  1320
cgtcaaatcg ccgacttcgc cctcaagctc cacaagaccc acctggcgtc tttcctcagt  1380
gcattcgcta ggcaggagct gtacctgatg ggcagtctcg tccactccat gctggtgcac  1440
accacggagc gccgcgagat cttcatcgtc gagactggcc tctgtagttt agccgagctc  1500
agtcacttca cccaactgct cgcccaccct caccacgagt accttagtga cctctatacc  1560
ccttgctcta gttccggtcg ccgcgaccac agcctggaac gtctgacccg cctcttcccc  1620
gacgctacag taccagcaac cgtgccagcg gccctgtcta tcctgtctac catgcagccc  1680
tccaccttgg agacgttccc agatctgttc tgcctccctc taggcgaatc gttctctgca  1740
ctcacggtca gcgaacacgt ctcctacatc gtcacaaacc agtatctgat aaagggcatc  1800
tcctacccag tgtcgaccac tgttgtcggc cagtccctca tcatcacaca gactgattct  1860
cagactaagt gcgagttgac acggaacatg catactacac attctatcac cgttgcttta  1920
aacataagcc tggagaactg cgccttctgc cagtccgctc tgctcgagta cgacgatacg  1980
cagggcgtca tcaacatcat gtacatgcac gactccgatg acgttctgtt cgcactggac  2040
ccctacaacg aggtcgtcgt ctcctctcct aggactcact acttaatgct gttgaagaac  2100
ggcaccgtcc tcgaggtcac cgacgtggtc gtcgatgcta cagacagccg actgctcatg  2160
atgtccgtgt acgctctctc cgccatcatc ggcatctacc tgctctaccg catgctcaag  2220
acctgc                                                           2226
```

```
SEQ ID NO: 178          moltype = DNA  length = 2226
FEATURE                 Location/Qualifiers
misc_feature            1..2226
                        note = Synthetic polypeptide
source                  1..2226
                        mol_type = other DNA
                        organism = synthetic construct
SEQUENCE: 178
atgcggcccg gcctacccag ctaccttatc atcttagccg tgtgcttgtt cagccacttg  60
ctcagcagcc ggtacggcgc cgaggccgtg tccgagcccc tcgacaaggc cttccacctc  120
ctcctcaaca cctacggccg ccccatccgc ttcctccgcg agaacaccac ccagtgcacc  180
tacaactcct ccctccgcaa ctccaccgtc gtcagagaga atgccatctc cttcaacttc  240
ttccagtcct acaaccagta ctacgtcttc cacatgcccc gctgcctctt cgccggccca  300
ctcgccgagc agttcctcaa ccaggtcgac ctcaccgaaa ctctcgagcg ctaccagcag  360
cggctgaata cgtatgccct cgtctccaag gacctcgcct cctaccgctc cttctcccag  420
cagctcaagg cccaggactc cctcggcgag cagcccacca ccgtccctcc tccaatcgac  480
ctctccatcc cacacgtctg gatgcctccc cagaccactc ctcacggctg gaccgagtcc  540
cacaccacct ccggcctcca caggccacac ttcaaccaga cctgcatcct cttcgacggc  600
```

-continued

```
cacgacctcc tcttcagcac agtgacgcca tgtctgcatc agggcttcta cctcatcgac  660
gagctccgct acgtcaagat cactctgacg gaggacttct tcgtcgtcac cgtctctata  720
gatgacgaca ccccaatgct cctcatcttc ggccacttgc ctcgcgtgct gttcaaggct  780
ccctaccagc gcgacaactt catcctccgc cagaccgaga agcatgaatt actcgtcctc  840
gtcaagaagg accagctcaa ccgccactcc tacctcaagg accccgactt cctcgacgcc  900
gccctcgact tcaactacct ggatcttagc gccctgctgc gtaacagctt ccaccgctac  960
gccgtcgacg tcctcaagtc cggccgctgc cagatgctcg accgccgcac cgtcgagatg  1020
gccttcgcct atgctctggc cctgttcgct gccgcccgcc aggaggaggc cggcgcccag  1080
gtttccgttc ctcgggcttt agacagacag gctgccctgc ttcagatcca ggagttcatg  1140
atcacctgcc tctcccagac gccaccacgc accacactgt tgctgtaccc gacagcagtg  1200
gacctggcaa agagggcact ctggactcca aaccagatca ccgacatcac ctccctcgtc  1260
cgcctcgtct acatcctctc caagcagaac cagcaacacc tgatacctca gtgggctctg  1320
cggcagatcg ccgacttcgc cctcaagctc cacaagaccc atttggcctc cttcctgagt  1380
gccttcgcta gacaggagct gtacctgatg ggctccctgg tgcactccat gctggttcac  1440
accacagagc gccgcgagat cttcatcgtc gagacaggcc tctgttcatt ggcagaactc  1500
tcgcatttca cccagctgct ggcccacccg caccacgagt atctgagtga cctctacaca  1560
ccatgcagtt cgtcaggaag gcgcgaccac agcctggagc gactgacccg cctcttcccc  1620
gacgcaacag tccctgctac tgtccctgcc gcgctgagta ttttatcaac gatgcagccc  1680
tccacgctcg aaaccttccc tgacttgttc tgcctccctc ttggagagag tttcagtgcc  1740
ctgaccgtgt cagagcacgt ctcctacatc gtcacgaacc agtatcttat caagggcatc  1800
tcctacccag tatcgactac agtggttggc cagtccctca tcatcaccca gactgacagt  1860
caaactaagt gcgagcttac tagaaacatg cacacaaccc actccatcac cgttgcatta  1920
aacatcagcc tcgagaactg cgccttctgc cagagcgctc tgctggagta cgacgacaca  1980
cagggcgtca tcaacatcat gtacatgcac gactccgacg acgtcctgtt cgcgcttgat  2040
ccctacaacg aggtcgtcgt gtccagtcca cgaactcatt acctcatgct gcttaagaac  2100
ggcaccgtcc tcgaggtcac cgacgtggtc gtcgatgcta ccgactcccg cctcctcatg  2160
atgtccgttt acgcactctc tgcgatcatc ggcatctact tactatatcg catgctcaag  2220
acctgc                                                             2226
```

```
SEQ ID NO: 179          moltype = DNA  length = 834
FEATURE                 Location/Qualifiers
misc_feature            1..834
                        note = Synthetic polypeptide
source                  1..834
                        mol_type = other DNA
                        organism = synthetic construct
SEQUENCE: 179
atgtgcagaa gaccagactg cggattcagc ttctccccag gcccagtgat cttactttgg  60
tgctgcctcc tccttccgat tgtgagcagt gccgccgtga gcgtggctcc taccgcggcc  120
gagaaggtgc cggccgagtg cccagagctc acccgaaggt gccttctggg cgaggttttc  180
gagggagaca agtacgagtc ttggctccgg cctctggtca acgtgacggg cagagacggc  240
cctttgagcc agctcatcag atacagacca gtaacacctg aggccgccaa ttccgtcctg  300
ctggatgagg ccttcctgga caccctcgcc ctcctttaca ataacccaga ccagctgaga  360
gccctgttga cccttctcag cagcgacacc gctccacggt ggatgaccgt catgagaggc  420
tatagcgagt gcggagatgg cagccctgcc gtctatacct gcgttgacga cctgtgcagg  480
ggctacgatt tgacaaggct cagctacggc agatctatat tcacagagca tgtgctgggc  540
ttcgagctgg tgccgccatc cctgttcaac gtggtggtcg ctataaggaa cgaggccacc  600
agaacaaatc gcgccgtgag actgccggtg tccacggcag ccgcacctga gggcattaca  660
ctgttctatg gcctctacaa cgccgtgaag gagttctgtt tgcggcacca gctggaccca  720
ccactgctca gacacctgga taagtactac gctggcctgc ctccggagct gaagcaaaca  780
cgtgtgaatc tgccagccca ctctcggtac ggaccgcagg ccgtggacgc ccgg        834
```

```
SEQ ID NO: 180          moltype = DNA  length = 834
FEATURE                 Location/Qualifiers
misc_feature            1..834
                        note = Synthetic polypeptide
source                  1..834
                        mol_type = other DNA
                        organism = synthetic construct
SEQUENCE: 180
atgtgcagga ggccagactg cggcttctca ttcagcccag gcccagtcat cctcctttgg  60
tgttgcctcc ttctccctat agttagcagt gccgccgtga gcgtggcccc tacagccgcg  120
gagaaggtgc cagcggagtg cccggagtta accagacgtt gcctcttggg cgaggtgttc  180
gagggcgata agtatgagtc ctggctgcgg cctctggtga acgtgaccgg cagagacgga  240
cctctgtccc agctgatcag atacagacca gtgacccctg aagccgcaaa cagcgtgctg  300
ctggacgagg ccttcctgga caccctggcc ctgttataca acaaccctga ccagcttcgc  360
gcgctgctta cactgctgag cagcgatacc gccccaagat ggatgactgt gatgaggga  420
tatagcgagt gtggcgacgg cagccctgcc gtctacacct gtgtggacga cctctgcaga  480
ggctatgacc tgaccagact gtcatacggc cgaagcatct tcaccgagca cgtcttagga  540
ttcgagctgg tgcctccaag cctcttcaat gtggtggtgg ccattcggaa cgaggctacc  600
agaaccaacc gggcggtgcg tcttccagtt tctacagccg ccgcccccgga aggaattacc  660
ctgttctacg gcctgtacaa cgctgtcaag gagttctgcc tgagacacca gctggatcca  720
ccgctgctgc gccacttgga caagtactat gcgggcctcc ctcctgagct caagcagacg  780
agggtgaacc tccctgctca ctcacgttat ggaccacagg ccgtggacgc taga        834
```

```
SEQ ID NO: 181          moltype = DNA  length = 834
FEATURE                 Location/Qualifiers
misc_feature            1..834
                        note = Synthetic polypeptide
```

```
source                  1..834
                        mol_type = other DNA
                        organism = synthetic construct
SEQUENCE: 181
atgtgcagaa ggccagactg cggcttcagc ttctctccag gaccagtgat cctcctctgg  60
tgctgccttc tcctccctat tgtgtcctcc gccgccgtgt ccgtggcccc aaccgccgcc  120
gagaaggtgc cagcggagtg cccagagctc accaggcgct gtctgctggg cgaggtgttc  180
gagggcgata agtacgagag ttggctgagg ccgttggtga acgtgacggg cagggacggc  240
ccgctaagtc agttaataag gtaccggcca gtgaccccgg aggccgccaa cagcgtgctg  300
ctggatgagg ccttcttgga caccctggcc ctgttgtaca acaacccaga ccagctgaga  360
gccctgctga ctctgttgag cagcgacacc gccccaagat ggatgaccgt gatgagaggc  420
tatagcgagt gcggcgatgg cagccctgcc gtgtacacgt gcgtggacga tttgtgtaga  480
ggctacgacc tcaccagact gagctacggc agaagcatct tcactgagca tgtgctggga  540
ttcgagctgg tgcctcctag cctgttcaat gttgtggtgg ctatacgcaa cgaggccaca  600
agaacaaaca gggccgtaag actcccagtg agcaccgctg cagcccctga gggaatcacg  660
ctgttctacg gcctctacaa cgctgtgaag gagttctgtc tgaggcacca actggaccca  720
cctctgctta gacacctgga taagtactac gccggcctcc cacctgaact gaagcagacc  780
agggtgaatc ttcctgcaca ctcaaggtat ggcccacagg ccgtggatgc cagg        834

SEQ ID NO: 182          moltype = DNA  length = 834
FEATURE                 Location/Qualifiers
misc_feature            1..834
                        note = Synthetic polypeptide
source                  1..834
                        mol_type = other DNA
                        organism = synthetic construct
SEQUENCE: 182
atgtgcaggc ggccagactg cggcttcagc ttctcaccgg gcccagtcat cttgttgtgg  60
tgctgcctcc tcctccctat cgtaagctcg gcagccgtca gtgtggcccc aaccgccgcc  120
gagaaggttc cagccgagtg tccagaactc acaaggcggt gcctgctggg cgaggtcttc  180
gagggcgaca agtatgaaag ctggctcagg ccacttgtca atgtgacagg cagagacggc  240
ccactgagcc agcttatccg gtatagacct gtcactcctg aggccgctaa cagcgtgctt  300
ctggacgagg ctttcctgga cactctggct ctgctttaca acaacccaga ccagctgaga  360
gccctgctga ccctgctgag cagcgataca gccccaaggt ggatgacagt tatgagggga  420
tacagcgagt gtggcgacgg aagcccagcc gtgtatacct gcgtggatga cctgtgcaga  480
ggctacgacc tgacccgcct ctcctacgga agatccatct tcaccgagca cgtgctagga  540
ttcgagctcg tccctcctag cctgttcaat gtggtggtgg ccatcagaaa cgaggccact  600
cggaccaata gagcagtgag actgccagtg agcaccgcgg ccgcaccaga gggtatcaca  660
ctgttctacg gcctgtacaa cgccgtgaag gagttctgtc tgcgtcacca gctggaccca  720
cctctgctta gacatctgga taagtactat gccggcctgc ctcctgaact caagcagacc  780
cgtgtgaatc tgcctgccca ctccagatac ggccctcagg ccgtggacgc aagg        834

SEQ ID NO: 183          moltype = DNA  length = 834
FEATURE                 Location/Qualifiers
misc_feature            1..834
                        note = Synthetic polypeptide
source                  1..834
                        mol_type = other DNA
                        organism = synthetic construct
SEQUENCE: 183
atgtgtagac gaccagactg cggcttctct ttctctccag gcccggtgat cttactctgg  60
tgttgtttgc tccttcctat cgttagtagc gccgccgtga gcgtggctcc gacagccgcc  120
gagaaggtgc cagccgagtg cccagagctc accagaagat gtctgctggg cgaggtcttc  180
gaaggcgaca agtacgagtc ttggctgagg cctctcgtga atgttaccgg cagggacggc  240
ccactgagcc agctgattag gtaccggcca gtgaccccgg aagccgccaa cagcgtgctg  300
ctggatgaag ccttcctgga caccctggcc ctgctgtaca acaatcctga ccagctccgg  360
gccctgctga ccctcctcag cagcgacact gcccctcggt ggatgacagt catgagaggc  420
tactccgaat gtggagacgg cagccctgcc gtctacacct gtgtggacga cctctgtagg  480
ggctacgacc tgacaagact gtcctatggc agaagcattt tcaccgagca tgtgcttggc  540
ttcgagctgg tgcctccatc cctgttcaac gtggttgtgg ccattagaaa cgaggccacc  600
agaaccaaca gggccgtgcg gctgccagtg agtacagccg ctgctccaga gggcattacc  660
ctgttctacg gcctttacaa tgccgtgaag gagttctgtc tgcgccatca gctggaccct  720
cctctgctga gacacctgga taagtattac gcgggcctgc ctccagaact gaagcagacc  780
cgcgtcaacc tgccagctca tagccgttac ggcccgcaag cagtggacgc ccga        834

SEQ ID NO: 184          moltype = DNA  length = 834
FEATURE                 Location/Qualifiers
misc_feature            1..834
                        note = Synthetic polypeptide
source                  1..834
                        mol_type = other DNA
                        organism = synthetic construct
SEQUENCE: 184
atgtgccgaa gaccggactg cggcttcagc ttcagcccag gcccggttat cctcctctgg  60
tgctgcctcc ttctcccaat cgtgagcagc gccgccgtga gcgtggcgcc taccgccgcg  120
gagaaggtcc cagccgagtg cccagaattg acgaggagat gcttgctggg cgaagtgttc  180
gagggcgata agtatgagag ctggctgcgg cctctggtca acgtgaccgg ccgcgacggc  240
ccactgtccc agctgatcag gtacagacca gtgaccccag aggctgctaa cagcgtgctg  300
ctggatgagg ctttcctcga cacgctggct ctcctgtaca acaatccgga tcagctcaga  360
```

-continued

```
gccctgctca cactgctgtc cagcgacacc gctccaaggt ggatgacagt gatgcggggc  420
tactcagagt gcggcgacgg tagccctgcg gtgtatacat gtgtggacga cctgtgcaga  480
ggctacgact taaccaggct gtcctacggt agatccatct tcactgagca cgtgctgggc  540
ttcgagctgg tgccacctag cctgttcaat gtcgtggtag ccatccggaa cgaggctacc  600
agaacaaatc gggccgtgag gctcccagtg agcaccgccg ccgctcctga gggcatcact  660
ctgttctacg gactttacaa cgccgtcaag gagttctgcc tgcggcacca gctcgatcca  720
cctctgctga gacacctgga caagtactac gccggccttc cgcctgagct gaagcagacc  780
agagtcaacc tgcctgccca tagcagatac ggcccacagg ctgtggatgc caga        834

SEQ ID NO: 185         moltype = DNA  length = 834
FEATURE                Location/Qualifiers
misc_feature           1..834
                       note = Synthetic polypeptide
source                 1..834
                       mol_type = other DNA
                       organism = synthetic construct
SEQUENCE: 185
atgtgccggc ggcccgactg cggcttcagc ttcagccccg gccccgtgat cctattgtgg  60
tgctgcctac ttttgcccat cgtgagcagc gccgccgtga gcgtggctcc taccgccgcc  120
gagaaggtgc ccgccgagtg ccccgagcta acccggcggt gccttcttgg cgaggtgttc  180
gagggcgaca agtacgagag ctggctgcgg cccctggtga acgtgaccgg ccgggacggc  240
cctctgagcc agctgatccg gtaccggccc gtgacaccag aggccgccaa cagcgtgctg  300
ctggacgagg ccttcctgga caccctggcc ctgctgtaca acaaccccga ccagctgaga  360
gctctgctga cgctgctgtc aagcgacacc gcgccacggt ggatgaccgt gatgcggggc  420
tacagcgagt gcggcgacgg cagccccgcc gtgtacacct gcgtggacga cctgtgcagg  480
ggctatgacc tgacccgtct gagctacggc cggagcatct tcaccgagca cgtgctgggc  540
ttcgagctgg tgcctcccag cctgttcaac gtggtggtgg ccatccggaa cgaggccacc  600
cggaccaacc gggccgtgcg gctgcccgtg agcaccgcag cagccccaga aggcatcacc  660
ctgttctacg gcctgtacaa tgccgtgaag gagttctgcc tgcggcacca gctggaccca  720
cctcttctca ggcacctgga taagtactac gccggcctgc ctcctgaact gaagcagacc  780
cgggtgaacc tgcccgccca cagccggtat ggcccacagg ccgtggacgc ccgg        834

SEQ ID NO: 186         moltype = DNA  length = 834
FEATURE                Location/Qualifiers
misc_feature           1..834
                       note = Synthetic polypeptide
source                 1..834
                       mol_type = other DNA
                       organism = synthetic construct
SEQUENCE: 186
atgtgccggc ggcccgactg cggcttcagc ttcagccccg gccccgtgat cctcctctgg  60
tgctgcctct tgttgcccat cgtgagcagc gccgccgtga gcgtggctcc taccgccgcc  120
gagaaggtgc ccgccgagtg ccccgagctc acccggcggt gccttctggg cgaggtgttc  180
gagggcgaca agtacgagag ctggctgcgg cccctggtga acgtgaccgg ccgggacggc  240
cctctgagcc agctgatccg gtaccggccc gtgactccag aggccgccaa cagcgtgctg  300
ctggacgagg ccttcctgga caccctggcc ctgctgtaca acaaccccga ccagctgagg  360
gcccttctga ccctgctcag cagcgacacc gccccacggt ggatgaccgt gatgcggggc  420
tacagcgagt gcggcgacgg cagccccgcc gtgtacacct gcgtggacga cctgtgcagg  480
ggctacgacc tgaccaggct gagctacggc cggagcatct tcaccgagca cgtgctgggc  540
ttcgagctgg tgccgcccag cctgttcaac gtggtggtgg ccatccggaa cgaggccacc  600
cggaccaacc gggccgtgcg gctgcccgtg tcgacagccg ccgcccctga gggcatcacc  660
ctgttctacg gcctatataa cgccgtgaag gagttctgcc tgcggcacca gctggacccg  720
cccctgcttc gccacctgga caagtattac gccggcctgc ctccggagct gaagcagacc  780
cgggtgaacc tgcccgccca cagccggtac ggccctcagg ccgtggacgc ccgg        834

SEQ ID NO: 187         moltype = DNA  length = 834
FEATURE                Location/Qualifiers
misc_feature           1..834
                       note = Synthetic polypeptide
source                 1..834
                       mol_type = other DNA
                       organism = synthetic construct
SEQUENCE: 187
atgtgccggc ggcccgactg cggcttcagc ttcagccccg gccccgtgat cctcctttgg  60
tgctgcttgc tcttgcccat cgtgagcagc gccgccgtct ccgtcgctcc taccgccgcc  120
gagaaggtcc ccgccgagtg ccccgagctc acccgccgct gcctcctcgg cgaggtcttc  180
gagggcgaca agtacgagtc ctggctcaga cctctcgtca acgtcaccgg ccgcgacggc  240
ccactctccc agctcatccg ctaccgcccc gtcacaccgg aggccgccaa ctccgtcctc  300
ctcgacgagg ccttcctcga caccctcgcc ctcctctaca acaaccccga ccagctccga  360
gccctgctga ccctgctgtc ctccgacacc gctcctcgct ggatgaccgt catgcgcggc  420
tactccgagt gcggcgacgg ctccccagct gtgtacacct gcgtcgacga cctctgcaga  480
ggctacgacc tgacgcgcct ctcctacggc cgctccatct tcaccgagca cgtcctcggc  540
ttcgagctcg tgcctccctc cctcttcaac gtcgtcgtcg ccatccgcaa cgaggccacc  600
cgcaccaacc gcgccgtccg cctccccgtc agcacagccg ctgcaccaga gggcatcacc  660
ctcttctacg gactgtacaa cgccgtcaag gagttctgcc tccgccacca gctcgaccca  720
cctctgctga ggcatctgga caagtattac gccggcctcc caccagagct gaagcagacc  780
cgcgtcaacc tccccgccca ctcccgctac ggaccacagg ccgtcgacgc ccgc        834

SEQ ID NO: 188         moltype = DNA  length = 834
```

-continued

```
FEATURE                 Location/Qualifiers
misc_feature            1..834
                        note = Synthetic polypeptide
source                  1..834
                        mol_type = other DNA
                        organism = synthetic construct
SEQUENCE: 188
atgtgccggc ggcccgactg cggcttcagc ttcagccccg gccccgtgat cctcctctgg  60
tgctgccttt tgctccccat cgtgagcagc gccgccgtct ccgtcgctcc taccgccgcc  120
gagaaggtcc ccgccgagtg ccccgagctc acccgccgct gcctcctcgg cgaggtcttc  180
gagggcgaca agtacgagtc ctggctcaga cctctcgtca acgtcaccgg ccgcgacggc  240
ccactctccc agctcatccg ctaccgcccc gtcaccccag aggccgccaa ctccgtcctc  300
ctcgacgagg ccttcctcga caccctcgcc ctcctctaca acaaccccga ccagctcagg  360
gcccttctaa ccctgctgtc ctccgacacc gcccctcgct ggatgaccgt catgcgcggc  420
tactccgagt gcggcgacgg ctccccggcc gtgtacacct gcgtcgacga cctctgcaga  480
ggatacgacc tcacccggct ctcctacggc cgctccatct tcaccgagca cgtcctcggc  540
ttcgagctcg tcccaccctc cctcttcaac gtcgtcgtcg ccatccgcaa cgaggccacc  600
cgcaccaacc gcgccgtccg cctccccgtc agcacagccg cagccccaga gggcatcacc  660
ctcttctacg gcctgtataa cgccgtcaag gagttctgcc tccgccacca gctcgacccg  720
cctctgctga ggcacctgga caagtattac gccggcctcc ctcctgagct gaagcagacc  780
cgcgtcaacc tccccgccca ctcccgctat ggaccacagg ccgtcgacgc ccgc        834

SEQ ID NO: 189          moltype = DNA  length = 2094
FEATURE                 Location/Qualifiers
misc_feature            1..2094
                        note = Synthetic polypeptide
source                  1..2094
                        mol_type = other DNA
                        organism = synthetic construct
SEQUENCE: 189
atggagagca gaatttggtg cttggtggtg tgtgttaacc tctgcattgt ttgcctcggc  60
gcagcagtgt ctagcagctc tactcgggga acatccgcaa cccacagcca ccatagctca  120
cacaccacca gcgccgccca ctccagatcc ggtagcgtga gccagcgggt gactagcagc  180
cagactgtgt cccatggcgt caacgagaca atctacaaca ccaccctgaa gtacggcgac  240
gtcgtgggcg tgaacacaac gaagtaccct tacagggtgt gtagcatggc tcagggcacc  300
gacttgatcc ggttcgagag aaatattgta tgcaccagca tgaagccaat taacgaggat  360
ctggacgaag gcatcatggt agtgtataag agaaacatag ttgcacacac tttcaaggtg  420
agggtctacc agaaggtgct gaccttccgc cgaagctatg cttacatcca tactacctac  480
ctgctcggtt ctaacaccga gtatgtggca cctccaatgt gggagatcca ccacatcaat  540
tctcatagcc agtgttacag ctcttacagc cgggtgatag ccggcaccgt cttcgtggcc  600
taccatagag attcatacga gaacaagacc atgcagctga tgccagacga ctacagcaac  660
acccattcca ccaggtatgt gacagtcaag gaccaatggc actcacgcgg ctccacctgg  720
ctgtacaggg agacttgcaa cctcaattgc atggtgacca tcaccaccgc ccgcagcaag  780
tacccgtacc acttcttcgc caccagcacc ggagatgtcg tggacatcag ccctttctat  840
aacggcacta acagaaacgc cagttacttc ggagagaatg ccgacaagtt cttcatcttc  900
ccgaactaca ctattgtgag cgatttcggt cgccctaact ccgccctgga gacacaccgc  960
ctggttgcct tcctggagag agccgattcc gtgatcagct gggacatcca ggacgagaag  1020
aatgtgacct gtcagctcac tttctgggag gcctccgaga ggactatccg gagcgaggcc  1080
gaggactcat accatttcag cagcgccaag atgaccgcca ccttcctgtc aaagaagcag  1140
gaggtgaaca tgtcagatag cgctctggac tgtgtgcgcg acgaggctat taacaagctg  1200
cagcagatct tcaatacctc ctacaatcag acctacgaga agtatggtaa cgtgtcagta  1260
ttcgagacaa ctggcggcct cgtggtgttc tggcagggaa tcaagcagaa gtccctggtg  1320
gagcttgaaa gactcgccaa ccggagcagc ctgaacctga cccacaacag gacaaagaga  1380
tctacagatg gtaacaacgc cacccatctg agcaacatgg agtccgtgca caacctggtg  1440
tacgcccagc tccagttcac atacgacacc ctgagaggct acattaatag agccctcgcc  1500
caaatcgcag aggcctggtg cgtggaccag aggcgaaccc tggaggtgtt caaggaattg  1560
agcaagatca atccaagcgc catcttgagc gcaatctata acaagccgat tgcggccaga  1620
ttcatgggcg acgtgttggg cctggcctcc tgcgtcacta tcaaccagac ctctgtcaag  1680
gtgctcagag atatgaacgt taaggagtcc ccaggcagat gctatagcag acctgtcgtg  1740
attttcaatt tcgccaactc aagctacgtg cagtacggcc agctcggcga agataacgag  1800
atcctgctgg gcaaccacag aaccgaagag tgccagctgc cttccctgaa gatttcatc  1860
gctggcaact ccgcttacga gtacgtggat tacctgttca agagaatgat cgacctcagc  1920
agcatcagca ccgtggacag catgatcgcc ttagacattg accctctgga gaacacagat  1980
ttcagggtgc tggaactata ctctcagaag gagctccggt ctagcaacgt gttcgatctg  2040
gaggagatca tgcgggagtt caattcctac aagcagcacc accaccatca tcac        2094

SEQ ID NO: 190          moltype = DNA  length = 2094
FEATURE                 Location/Qualifiers
misc_feature            1..2094
                        note = Synthetic polypeptide
source                  1..2094
                        mol_type = other DNA
                        organism = synthetic construct
SEQUENCE: 190
atggagtcaa gaatctggtg tcttgtggtg tgcgtgaact tgtgtatcgt gtgtttgggc  60
gcagccgtgt cctcaagcag cactagaggc actagcgcca cccactccca tcatagctca  120
cacaccacaa gcgccgccca ctctaggtca ggcagcgtgt ctcagcgcgt gacctctagc  180
cagactgtga gtcacggagt caatgaaacc atctacaaca caacactgaa gtacggagac  240
gtcgtgggcg tgaatacaac caagtaccca tacagggtgt gcagcatggc tcagggcact  300
```

```
gacctcatca gattcgagcg gaacattgtg tgcacctcaa tgaagcctat caacgaggat  360
ttggatgaag gcatcatggt cgtgtacaag agaaacatcg tcgctcatac cttcaaggtg  420
agagtgtatc agaaggtgct gaccttcaga cgtagctacg cttacattca caccacctac  480
ctgctgggca gcaacaccga gtatgtggct cctcctatgt gggagataca tcacatcaac  540
agccattctc agtgctatag ttcttatagc agggtcatcg ccggcaccgt cttcgtggcc  600
taccatagag atagctacga gaacaagacc atgcagttga tgccggacga ttacagcaat  660
acccatagca ctaggtacgt gactgtgaag gaccagtggc actcccgggg tagcacctgg  720
ctttacaggg aaacctgcaa tctgaactgc atggtgacta ttaccaccgc caggagcaag  780
tatccttacc acttcttcgc tacatctact ggagacgtgg tcgatatctc tcctttctac  840
aatggcacaa acagaaatgc ttcatatttc ggcgagaatg ccgacaagtt cttcatcttc  900
ccaaactaca ccattgtgtc cgacttcgga agacctaatt ccgccctgga aacccataga  960
ctggtcgcat tcctggaaag ggccgactcc gtcatttcat gggacatcca ggatgagaag  1020
aacgtcacct gtcagctcac attctgggaa gcgagcgaaa gaacaattcg cagcgaagcc  1080
gaggacagct atcatttcag cagtgctaag atgaccgcca ctttcctgtc taagaagcag  1140
gaggtgaaca tgtccgacag cgccttggat tgcgtgagag acgaagctat taacaagctg  1200
cagcagatct tcaacacctc ctacaaccag acttacgaga agtatggcaa tgtgagtgtg  1260
ttcgagacaa ccggcggcct ggtagtattc tggcagggca tcaagcagaa gtcactggtg  1320
gagcttgaga ggctggccaa tagatccagc ctgaacctga cccacaaccg gacaaagaga  1380
tctaccgacg gaaacaacgc cactcatctt tccaatatgg agagcgtgca caacctggtg  1440
tacgcgcagc tccagttcac ctacgacaca ctgaggggct acataaacag ggccctggca  1500
cagatcgccg aagcctggtg cgtggaccag agaaggaccc tggaggtttt caaggagctg  1560
agcaagatta atccgtccgc tatcctgagc gcaatataca ataagccaat cgccgccaga  1620
ttcatgggcg acgtgttggg actggccagt tgcgtcacaa taaaccagac ctctgtaaag  1680
gtcctgaggg acatgaatgt caaggagagc ccgggcaggt gctacagccg tcctgtggtg  1740
attttcaact tcgctaattc atcttacgtc cagtacggcc agctgggcga agacaatgag  1800
atcttactgg gcaaccatag gactgaggag tgccagctgc cgagtctgaa gattttcata  1860
gccggcaata gcgcatatga atatgtagac tacctgttca agaggatgat tgacctctct  1920
agcatctcga ccgtggacag catgatcgcc ctcgacatcg accctctgga gaacacagac  1980
ttccgggtcc tcgaactgta cagccagaag gagcttagga gctccaacgt gttcgatctt  2040
gaggagatca tgagggagtt caatagctat aagcaacatc accaccatca tcac        2094
```

```
SEQ ID NO: 191         moltype = DNA  length = 2094
FEATURE                Location/Qualifiers
misc_feature           1..2094
                       note = Synthetic polypeptide
source                 1..2094
                       mol_type = other DNA
                       organism = synthetic construct
SEQUENCE: 191
atggagagca gaatttggtg tctcgtggtg tgtgttaatc tctgcatcgt gtgccttggc  60
gccgccgtgt ccagcagctc caccaggggc accagcgcaa cacacagcca ccactctagc  120
cacacaacca gcgccgccca ctctcgttca ggctccgttt cacagagggt gacctcctct  180
caaaccgtgt ctcatggagt gaatgaaacc atttataaca caacactgaa gtatggcgac  240
gtggtgggcg tcaacaccac caagtatcct taccgggttt gttcaatggc ccagggcacc  300
gatctcatca gattcgagcg aaatatcgtg tgtacatcca tgaagcctat caacgaagac  360
ctggacgagg gaattatggt cgtgtacaag agaaatattg tggcccacac tttcaaggtg  420
agagtgtacc agaaggtgtt gacattcagg cggtcctacg cctacatcca caccacttat  480
ctgttgggat ccaacacaga gtacgtcgca ccgcctatgt gggaaataca tcacatcaat  540
tcccattctc agtgctattc tagctactcc agagtgatcg ccggcaccgt gttcgtggcc  600
taccaccgcg atagctacga gaataagacc atgcagctga tgcctgacga ttacagcaac  660
actcattcca cacgctacgt gaccgtgaag gatcagtggc acagccgcgg cagcacctgg  720
ctgtaccggg aaacctgcaa cctgaactgc atggtgacaa taacaaccgc acgtagcaag  780
tacccatacc acttcttcgc cacctccacc ggtgacgtgg tcgacatcag ccctttctac  840
aatggcacca acagaaatgc ctcctacttc ggcgagaacg ccgacaagtt cttcatcttc  900
cctaattata caattgtgag cgacttcggc aggcctaaca gcgccctgga gactcatcgc  960
ttggtggctt tcctggaacg cgctgacagc gtcatctctt gggatatcca agatgagaag  1020
aacgtgacct gccagctgac cttctgggag gccagcgaga ggacaatcag aagcgaagcc  1080
gaggactctt accatttcag ttcagctaag atgaccgcca ccttcctgag caagaagcag  1140
gaagtgaata tgtccgattc cgctcttgac tgcgtcaggg acgaagccat caacaagctc  1200
cagcagattt tcaatacttc ttataatcag acctatgaga agtacggcaa tgtcagcgtc  1260
ttcgagacga ccggcggcct ggttgtgttc tggcaaggaa tcaagcagaa gtcactggtg  1320
gagcttgagc ggctggccaa cagatccagc ttgaacctga cccataatcg caccaagcgg  1380
agtaccgatg gcaacaacgc cacacacctc agcaatatgg aaagcgtgca caaccttgtg  1440
tacgctcagc tgcagttcac ctacgatacc cttagaggct acatcaacag agccctggcc  1500
cagatcgcag aggcatggtg cgtggaccag cggcggaccc tggaggtgtt caaggagctc  1560
tccaagatca acccatccgc cattctctcc gccatctaca acaagcctat tgccgctcgg  1620
ttcatgggcg atgtgctggg actggccagc tgcgtgacca tcaaccaaac ctcagtgaag  1680
gtgctcagag acatgaacgt caaggagtct ccaggcagat gttacagcag acctgtggtg  1740
atcttcaact tcgccaattc ttcctacgtg cagtacggcc aactgggtga agacaacgag  1800
attctgttag gcaaccacag gactgaggag tgtcagctgc cgagcctgaa gatcttcatc  1860
gctggaaaca gcgcatacga gtacgtggac tacctcttca agaggatgat cgacttgtca  1920
tctatctcca cggttgattc catgatcgcc ttggacatcg atcctctgga gaataccgac  1980
ttcagagtgc tggagctcta cagccagaag gagcttaggt ctagcaatgt gttcgacctg  2040
gaggagatca tgagggagtt caatagctat aagcagcatc accaccacca tcac        2094

SEQ ID NO: 192         moltype = DNA  length = 2094
FEATURE                Location/Qualifiers
misc_feature           1..2094
                       note = Synthetic polypeptide
```

```
source                  1..2094
                        mol_type = other DNA
                        organism = synthetic construct
SEQUENCE: 192
atggagagca gaatctggtg cctcgtggtg tgcgtgaacc tctgtatcgt ctgcttagga  60
gccgccgtga gcagtagctc taccagaggc acatccgcca cccacagcca ccactcttca  120
cacaccacca gcgccgccca ctccagatca ggcagcgtat cccagagagt gaccagcagc  180
cagaccgtgt cacatggagt gaatgaaaca atttacaaca ccaccctcaa gtacggcgac  240
gtagtgggag tgaacactac taagtaccca taccgcgtgt gtagcatggc ccagggcacc  300
gatctgatcc gattcgagag aaacatcgtt tgcaccagca tgaagcctat caacgaggac  360
ctggatgagg gcatcatggt ggtgtacaag aggaacatcg tggcccacac gttcaaggtt  420
agggtgtacc agaaggtgct gactttccga agaagctatg cctacattca cactacatac  480
ctgctcggca gtaacaccga gtacgtggcg ccaccgatgt gggaaataca ccatattaat  540
tctcatagtc agtgctattc cagctacagc agggtgatcg ccggaaccgt tttcgtggct  600
tatcatagag attcctacga gaacaagacc atgcagctga tgccagacga ctatagcaac  660
acgcatagca cccgctacgt gaccgtgaag gaccagtggc attcaagagg atccacctgg  720
ctctacagag agacatgcaa tctgaactgc atggtgacca tcaccaccgc ccggtccaag  780
taccccttatc acttcttcgc cacaagcacc ggcgatgtgg tggacatttc cccattctac  840
aacggaacca accggaacgc ctcttacttc ggcgagaacg ccgacaagtt cttcatcttc  900
ccaaattata ccatcgtgag cgacttcgga agacctaaca gcgccctgga gacacacaga  960
ctggtggcct tcctcgagcg cgccgactcc gtgatctcct gggacatcca ggacgagaag  1020
aacgtgactt gtcagctgac attctgggag gccagcgaac ggaccatcag aagcgaggct  1080
gaagactcct accacttcag ctccgccaag atgaccgcca ctttcctgtc aaagaagcag  1140
gaggtgaaca tgagcgacag cgccttggat tgcgtgagag atgaggccat caacaagctt  1200
caacagatct tcaacacatc ctacaaccag acgtacgaga agtacggaaa cgtgagcgtg  1260
ttcgaaacca ccggcggctt agtggtgttc tggcagggaa tcaagcagaa gtctctggtg  1320
gagctggaga gactggctaa cagatcctct ctaaacctga cacacaacag aaccaagcgg  1380
agcacagacg gcaataatgc cacacacctg agcaacatgg aaagcgtcca caacctcgtc  1440
tatgcccaac tgcagttcac ctacgacacc ctccgaggct acatcaacag agccctggcc  1500
cagatcgccg aggcttggtg tgtggatcag agacggaccc tggaggtgtt caaggagttg  1560
agcaagatca acccgtccgc catcttgagc gctatataca acaagccaat tgctgcgcgg  1620
ttcatgggcg acgtgctggg cctcgcctca tgtgtgacca ttaatcaaac aagcgtcaag  1680
gtcctgaggg atatgaacgt taaggagagc ccaggcaggt gctatagcag acctgtggtg  1740
attttcaact tcgccaacag cagctacgtg cagtacggcc agctgggcga ggacaacgag  1800
atcctgctgg gcaaccaccg cactgaggag tgccagctgc caagtctgaa gatattcatc  1860
gcgggaaatt cagcttacga gtatgtagac tacctgttca agagaatgat agatcttagc  1920
agcatctcca ctgtggacag tatgatagct cttgatattg acccactgga gaataccgac  1980
ttcagagtgt tggagctgta cagtcagaag gagctcagga gctccaatgt gttcgacctg  2040
gaggagatca tgagggaatt caatagctac aagcagcacc accaccatca tcac        2094

SEQ ID NO: 193          moltype = DNA  length = 2094
FEATURE                 Location/Qualifiers
misc_feature            1..2094
                        note = Synthetic polypeptide
source                  1..2094
                        mol_type = other DNA
                        organism = synthetic construct
SEQUENCE: 193
atggaatccc gaatctggtg cctcgttgtg tgcgtgaatt tgtgcatcgt gtgtttgggc  60
gccgccgtct cttcttcctc cacacgtggt accagcgcaa cacactccca ccactcaagc  120
cacaccacgt ccgcggcaca cagcagaagc ggcagtgtga gccaaagggt gaccagcagc  180
cagaccgtga gtcacggcgt gaacgagaca atctacaata ccacactcaa gtacggcgat  240
gtggtgggcg tcaacaccac caagtatcct tacagagtct gttccatggc ccagggcact  300
gacctgatcc ggttcgaaag aaacatagtg tgcacctcca tgaagcctat caatgaggac  360
ctcgatgaag gcattatggt ggtgtacaag aggaatattg tggcccatac cttcaaggtg  420
agagtgtacc agaaggtgct gaccttcaga cggagctacg cctacatcca tacaacctac  480
ctgctgggaa gcaacaccga gtacgtggct cctccaatgt gggagatcca ccacatcaat  540
agccacagcc agtgctactc cagctacagc agagtgattg ctggcaccgt cttcgtggct  600
taccacagag acagctatga gaacaagaca atgcagctca tgccagacga ctactctaac  660
acacattcaa cccggtatgt gaccgtgaag gaccagtggc actcaagagg cagcacatgg  720
ctctaccgag agacatgtaa cctgaactgc atggttacaa tcaccactgc aaggtctaag  780
tacccatatc acttcttcgc cacctctacc ggagacgtgg tggacatcag cccattctac  840
aatggcacca atcggaacgc aagctacttc ggagagaacg ccgacaagtt cttcatcttc  900
ccgaactaca ccatcgtgtc cgatttcggc aggccaaaca gcgccctgga gacacaccgg  960
ctggtggcct tcctggagcg cgctgactcc gttatctctt gggacatcca ggatgagaag  1020
aatgtgacct gccaactgac attctgggag gcatccgagc ggactatcag aagcgaggcc  1080
gaggacagct accacttcag cagcgctaag atgactgcta ccttcctgtc caagaagcag  1140
gaggtgaaca tgtctgattc cgctctggac tgcgtgaggg acgaggctat caacaagctc  1200
cagcagatat tcaatacttc ctacaaccag acctacgaga agtacggtaa cgtcagcgtt  1260
ttcgaaacca ccggcggcct ggtcgtgttc tggcagggaa tcaagcagaa gtcccttgtc  1320
gagctcgaga gactggccaa ccggtctagc ctcaatctga cacacaatag gaccaagaga  1380
tctactgacg gcaataacgc cacacacctc tccaacatgg agagtgttca taacctggtt  1440
tacgcccagc tgcagttcac ttacgatacc ctccgcggct acatcaacag ggccctggcg  1500
cagatcgccg aggcctggtg cgtggatcaa agaaggaccc tggaggtctt caaggaactc  1560
agcaagatca acccatctgc tatcctgagc gccatctaca acaagccaat cgccgcccgg  1620
ttcatgggcg acgtcctggg cttggctagc tgcgtgacca tcaatcagac cagcgtcaag  1680
gtgcttcgcg acatgaacgt caaggagtca cctggccgct gttactcaag gccagtcgtg  1740
atcttcaatt tcgccaatag ctcctacgtg cagtacggac agttgggcga ggacaatgaa  1800
atactcctgg gcaaccaccg caccgaggag tgtcagctgc caagcctgaa gatcttcatc  1860
```

```
gcgggaaact ccgcttacga gtatgtggac tacctgttca agagaatgat tgatctgagc  1920
agcatctcca ccgtggacag catgattgct ctggatattg atcctctgga gaacaccgat  1980
ttccgcgtgc tggagctgta cagccagaag gaattaagga gcagtaatgt gttcgacctg  2040
gaggagatca tgagggagtt caacagttac aagcagcacc accatcacca ccac        2094
```

```
SEQ ID NO: 194          moltype = DNA  length = 2094
FEATURE                 Location/Qualifiers
misc_feature            1..2094
                        note = Synthetic polypeptide
source                  1..2094
                        mol_type = other DNA
                        organism = synthetic construct
SEQUENCE: 194
atggagtcca gaatctggtg cttggtggtg tgcgtgaatc tttgcattgt gtgcctcggc  60
gccgccgtga gcagcagcag tactagaggt acctccgcta cccacagcca ccactcttcc  120
catacaacca gcgccgccca ctcacgtagc ggctctgtga gccagagggt gacaagctca  180
cagaccgtga gccacggcgt gaacgagact atctacaaca ctaccctgaa gtacggcgat  240
gtggtgggag tgaataccac aaagtacccg tacagggtgt gttccatggc ccagggcacc  300
gacctgattc gcttcgaaag aaacatcgtc tgcaccagca tgaagcctat caacgaggat  360
ttggatgagg gtattatggt ggtctacaag agaaatattg tggcccacac cttcaaggtc  420
agagtgtacc agaaggtcct gacgttcagg agatcttacg cttacatcca caccacctac  480
cttctgggct ccaacaccga gtatgtggcc ccgcctatgt gggagatcca ccacattaat  540
tcccactctc aatgctacag ctcctattcc agagtgatcg ccggcacagt cttcgtggcc  600
taccaccggg acagctatga gaacaagact atgcagctca tgccagacga ctatagcaat  660
actcatagca ctagatatgt gactgtgaag gaccagtggc atagcagagg cagcacttgg  720
ctgtaccggg aaacatgcaa tcttaattgc atggtcacca taaccaccgc gagatccaag  780
tacccttacc acttcttcgc cacctccact ggtgacgtcg tggacatctc ccctttctat  840
aacggaacaa atagaaacgc cagctacttc ggtgagaacg ccgacaagtt cttcatcttc  900
cctaactaca ccatagtgag cgatttcggc agaccgaact ccgctctgga gacacaccgg  960
ctggtggcct tcctggaacg ggccgatagt gttatctctt gggatattca agacgagaag  1020
aacgtcacct gtcagctgac tttctgggaa gccagcgaga ggaccatcag aagtgaagct  1080
gaggatagct accatttctc tagtgccaag atgactgcca ccttcctgtc caagaagcag  1140
gaggtcaaca tgtccgacag cgccctcgac tgtgtgagag acgaggctat taacaagctg  1200
cagcagattt tcaacactag ctacaatcag acatacgaga agtatggaaa cgtgagcgtg  1260
ttcgaaacta ccggtggcct ggtggtattc tggcagggca tcaagcagaa gtccctggtg  1320
gaattggaga gactggctaa caggtcgtcc ctgaacctga ctcacaatag aacgaagagg  1380
agcacagacg gcaataatgc cacccatctg tccaatatgg agagtgtgca caatttggtg  1440
tatgcccagc tgcagttcac ctacgacacc ctcaggggct acatcaacag agccctcgcc  1500
cagatcgctg aagcctggtg cgtggatcag aggaggaccc tggaggtctt caaggaactg  1560
agcaagataa acccatccgc catcctcagt gccatttata acaagcctat tgccgccagg  1620
ttcatgggcg acgtgctggg cctggcttcc tgtgtcacga ttaatcagac ctccgtgaag  1680
gtgctgaggg acatgaacgt gaaggaaagc cctggacggt gttacagccg accagtagtg  1740
atcttcaact tcgccaactc ctcatacgtg cagtatggcc agctgggcga ggacaatgaa  1800
attctgctgg gcaaccacag gaccgaagag tgccagctgc ctagcctgaa gatattcatc  1860
gccggtaata gcgcctacga gtacgtcgac tatcttttca agagaatgat cgatctgtct  1920
agcatttcta ccgtggattc catgatcgct cttgacattg acccactgga gaacacagac  1980
ttcagggtgc tcgagctgta ttcccagaag gaactcaggt ctagcaacgt tttcgacctc  2040
gaggaaatta tgagagagtt caactcgtac aagcaacacc atcaccacca tcac        2094
```

```
SEQ ID NO: 195          moltype = DNA  length = 2094
FEATURE                 Location/Qualifiers
misc_feature            1..2094
                        note = Synthetic polypeptide
source                  1..2094
                        mol_type = other DNA
                        organism = synthetic construct
SEQUENCE: 195
atggagagcc ggatctggtg cctcgtggtg tgcgtgaact tatgcatcgt gtgcctcggc  60
gccgccgtga gctctagctc tacccggggc accagcgcca cccacagcca ccacagcagc  120
cacaccacct cggccgctca cagccggagc ggcagcgtga gccagcgggt gacctccagc  180
cagaccgtgt cccacggcgt gaacgagacg atctacaaca ccaccctgaa gtacggcgac  240
gtggtgggag tgaacacgac caagtacccc taccgggtgt gcagcatggc ccagggcacc  300
gacctgatcc ggttcgagcg gaacattgtg tgcaccagca tgaagcccat caacgaggac  360
ctggacgagg gcatcatggt agtgtacaag agaaacatcg tggcccacac cttcaaggtg  420
cgggtgtacc agaaggtgct gaccttccgg cggagctacg cctacattca cacaacatac  480
ctgctgggca gcaacaccga gtacgtggct cctcccatgt gggagatcca ccacatcaac  540
tctcatagcc agtgctacag cagctacagc cgggtgatcg ccggcaccgt gttcgtggcc  600
taccaccggg acagctacga gaacaagacc atgcagctga tgcccgacga ctatagcaac  660
acacactcca ctcggtacgt gaccgtgaag gaccagtggc acagcagagg cagcacctgg  720
ctgtaccggg agacttgcaa cctgaactgc atggtgacca tcaccaccgc ccggtctaag  780
taccccttacc acttcttcgc caccagcacc ggcgatgtgg tggacatcag ccccttctac  840
aacggcacca accggaacgc cagctacttc ggcgagaacg ccgacaagtt cttcatcttc  900
cccaactaca ccatcgtgag cgacttcggc cggcccaaca gcgccctgga aactcaccgg  960
ctggtggcct tcctggagcg ggccgacagc gtgatcagct gggacatcca ggacgagaag  1020
aacgtgacct gccagctgac attctgggag gccagcgagc ggaccatccg gagcgaggcc  1080
gaggatagct atcacttcag cagcgccaag atgaccgcca ccttcctgag caagaagcag  1140
gaggtgaaca tgagcgattc tgcactggac tgcgtgcggg acgaggccat caacaagctg  1200
cagcagatct tcaacaccag ctacaaccag acctacgaga agtacggaaa cgtgagcgtg  1260
ttcgagacta ccggcggcct tgtcgtgttc tggcagggaa tcaagcagaa gtccctggtc  1320
```

```
gagctcgagc gactggccaa cagaagcagc ctgaacctga cccacaaccg gaccaagcgg  1380
agcaccgacg gcaacaacgc cacacacctg tctaacatgg agtctgtgca caacctggtg  1440
tacgcccagc tgcagttcac ctacgacacc ctgcggggct acatcaaccg ggccctggcc  1500
cagatcgccg aggcatggtg cgtggaccag cggcggaccc tggaggtgtt caaggagctc  1560
tctaagatca acccgtctgc catcctgagc gccatttaca acaagcctat cgccgcaaga  1620
ttcatgggcg acgtcctggg cctggccagc tgcgtgacga tcaatcagac cagcgtgaag  1680
gtcctgcggg acatgaacgt caaggagagc cccggcaggt gctatagccg gcccgtggtg  1740
attttcaact tcgccaatag ctcttacgtg cagtacggtc agttaggcga ggacaacgag  1800
atcttactgg gcaaccaccg gaccgaggag tgccaactcc cgagcctcaa gattttcatt  1860
gccggcaata gcgcatacga atatgtggac tacctgttca agcggatgat cgacctgagc  1920
agcatcagca ccgtggacag catgattgct ctggacatcg accctctgga gaacaccgac  1980
ttccgggtgc tggagctgta cagccagaag gagctgcgga gctctaatgt gttcgacctg  2040
gaggagatca tgcgggagtt caactcatat aagcagcacc accaccatca tcac        2094
```

```
SEQ ID NO: 196          moltype = DNA  length = 2094
FEATURE                 Location/Qualifiers
misc_feature            1..2094
                        note = Synthetic polypeptide
source                  1..2094
                        mol_type = other DNA
                        organism = synthetic construct
SEQUENCE: 196
atggagagcc ggatctggtg cctcgtggtg tgcgtgaacc tttgcatcgt gtgcttgggc  60
gccgccgtga gcagcagctc cacccggggc acctccgcca cccactccca ccactcctcc  120
cacaccacct cagccgccca ctctcgctcc ggctccgtct cccagcgcgt cacctccagc  180
cagaccgtta gccacggcgt caacgaaacc atctacaaca ccaccctcaa gtacggcgac  240
gtcgtcggcg taaacacaac caagtacccc taccgcgtct gctccatggc ccagggcacc  300
gacctcatcc gcttcgagcg caacatcgtc tgcacctcca tgaagcccat caacgaggac  360
ctcgacgagg gcatcatggt cgtctacaag cgcaatattg tggcccacac cttcaaggtc  420
cgcgtctacc agaaggtcct caccttccgc cgctcctacg cctacatcca cacaacctac  480
ctcctcggct ccaacaccga gtacgtcgcc cctcccatgt gggagatcca ccacatcaac  540
agccacagcc agtgctactc ctcctactcc cgcgtcatcg ccggcaccgt cttcgtcgcc  600
taccaccgcg actcctacga gaacaagacc atgcagctca tgcccgacga ctacagcaat  660
acccacagca cccgctacgt caccgtcaag gaccagtggc acagcagagg ctccacctgg  720
ctctaccgcg agacatgcaa cctcaactgc atggtcacca tcaccaccgc ccgctccaag  780
tatccttacc acttcttcgc cacctccacc ggcgatgtcg tggacatctc accattctac  840
aacggcacca accgcaacgc cagttacttc ggcgagaacg ccgacaagtt cttcatcttc  900
cccaactaca ccatcgtctc cgacttcggc cgccccaact ccgccctcga gacacacaga  960
ctggtggcct tcctcgagcg cgccgactcc gtcatctcct gggacatcca ggacgagaag  1020
aacgtcacct gccagctcac attctgggag gcctccgagc gcaccatccg ctccgaggcc  1080
gaggactcat accatttctc cagcgccaag atgaccgcca ccttcctctc caagaagcag  1140
gaggtcaaca tgagcgacag cgctctcgac tgcgtccgcg acgaggccat caacaagctc  1200
cagcagatct tcaacacctc ctacaaccag acgtacgaga agtatggaaa cgtcagtgtc  1260
ttcgaaacca cgggcggcct ggttgtattc tggcagggaa taaagcagaa gtccctcgtc  1320
gagcttgagc gcctcgccaa ccgctcctcc ctcaacctca cccacaaccg caccaagcgc  1380
tccaccgacg gcaacaacgc tacccacctg tccaacatgg agtccgtcca caacctcgtc  1440
tacgcccagc tccagttcac ctacgacacc ctccgcggct acatcaaccg cgccctcgcc  1500
cagatcgccg aggcctggtg cgtcgaccag cgccgcaccc tcgaggtctt caaggagctg  1560
agtaagatca accctagcgc gatcctcagc gctatctata acaagccaat cgctgctagg  1620
ttcatgggag acgtgctcgg cctcgcctcc tgcgtgacca tcaatcagac atccgtgaag  1680
gtgctgcgcg acatgaatgt caaggagagc ccaggccgct gttattcccg gcccgtcgtc  1740
attttcaatt tcgccaatag ctcttacgtc cagtacggcc agctcggcga ggacaacgag  1800
atcctgctgg gcaaccaccg caccgaggag tgccagctgc ctagcctcaa gattttcatt  1860
gccggcaatt ccgcttacga atacgtggac tacctcttca agcgcatgat cgacctctcc  1920
tccatctcca ccgtcgactc catgatcgcc ctggatatcg accctctcga gaacaccgac  1980
ttccgcgtgt tggagctcta ctcccagaag gagctcagat ccagcaacgt attcgacctc  2040
gaggagatca tgcgcgagtt caactcctat aagcagcacc accaccatca tcac        2094
```

```
SEQ ID NO: 197          moltype = DNA  length = 2094
FEATURE                 Location/Qualifiers
misc_feature            1..2094
                        note = Synthetic polypeptide
source                  1..2094
                        mol_type = other DNA
                        organism = synthetic construct
SEQUENCE: 197
atggagagcc ggatctggtg cttggtggtg tgcgtgaact tgtgcatcgt gtgcttgggc  60
gccgccgtga gcagctctag cacccggggc accagcgcca cccacagcca ccacagcagc  120
cacacgacct ccgccgccca ctcacggagc ggcagcgtga gccagcgggt gaccagctca  180
cagaccgtgt cccacggcgt gaacgagacg atctacaaca ccaccctgaa gtacggcgac  240
gtggtgggcg tcaacactac caagtacccc taccgggtgt gcagcatggc ccagggcacc  300
gacctgatcc ggttcgagcg gaatattgtg tgtaccagca tgaagcccat caacgaggac  360
ctggacgagg gcatcatggt ggtctacaag agaaacattg tggcccacac cttcaaggtg  420
cgggtgtacc agaaggtgct gaccttccgg cggagctacg cctacatcca tacaacctac  480
ctgctgggca gcaacaccga gtacgtggcg cctcccatgt gggagatcca ccacatcaac  540
tctcactcgc agtgctacag cagctacagc cgggtgatcg ccggcaccgt gttcgtggcc  600
taccaccggg acagctacga gaacaagacc atgcagctga tgcccgacga ctattctaac  660
acccactcca ccagatacgt gaccgtgaag gaccagtggc acagcagggg cagcacctgg  720
ctgtaccggg agacttgcaa cctgaactgc atggtgacca tcaccaccgc ccggagtaag  780
```

```
tatccatatc acttcttcgc caccagcacg ggcgacgttg tggacatcag ccccttctac  840
aacggcacca accggaacgc cagctacttc ggcgagaacg ccgacaagtt cttcatcttc  900
cccaactaca ccatcgtgag cgacttcggc cggcccaaca gcgccctgga aacccaccgg  960
ctggtggcct tcctggagcg ggccgacagc gtgatcagct gggacatcca ggacgagaag  1020
aacgtgacct gccagctgac tttctgggag gccagcgagc ggaccatccg gagcgaggcc  1080
gaagactcct accacttcag cagcgccaag atgaccgcca ccttcctgag caagaagcag  1140
gaggtgaaca tgagcgattc agctctggac tgcgtgcggg acgaggccat caacaagctg  1200
cagcagatct tcaacaccag ctacaaccag acttacgaga agtatggaaa cgtgagcgtg  1260
ttcgagacaa ccggcggcct cgtggtgttc tggcagggta tcaagcagaa gtctctcgtg  1320
gagctggaga gactggccaa cagaagcagc ctgaacctga cccacaaccg gaccaagcgg  1380
agcaccgacg gcaacaacgc tacccatctg tctaacatgg agtcagtgca caacctggtg  1440
tacgcccagc tgcagttcac ctacgacacc ctgcggggct acatcaaccg ggccctggcc  1500
cagatcgccg aggcctggtg cgtggaccag cggcggaccc tggaggtgtt caaggagctg  1560
tccaagatca acccttccgc catcctgagc gccatttata ataagccgat cgccgcccgg  1620
ttcatgggcg atgttctggg cctggccagc tgcgtcacca ttaatcagac cagcgttaag  1680
gtcctgcggg acatgaatgt caaggagagc cccggcaggt gctactcccg ccccgtggtg  1740
atattcaact tcgccaactc tagctacgtg cagtacggcc aactaggcga ggacaacgag  1800
atcttgctcg gtaaccaccg gaccgaggag tgccagttac cttccctgaa gattttcatc  1860
gcgggcaact ccgcctacga gtatgtggac tacctgttca agcggatgat cgatctttct  1920
agcatcagca ccgtggacag catgatagcc ctggacatcg acccactgga gaacaccgac  1980
ttccgggtgc tggagctgta cagccagaag gagcttcgga gcagcaatgt gttcgacctg  2040
gaggagatca tgcgggagtt caattcttac aagcagcacc accaccatca tcac        2094
```

```
SEQ ID NO: 198          moltype = DNA  length = 2094
FEATURE                 Location/Qualifiers
misc_feature            1..2094
                        note = Synthetic polypeptide
source                  1..2094
                        mol_type = other DNA
                        organism = synthetic construct
SEQUENCE: 198
atggagagcc ggatctggtg cctcgtggtg tgcgtgaacc tctgcatcgt gtgcctcggc  60
gccgccgtgt cttcatcctc cacccggggc acctccgcca cccactccca ccactcctcc  120
cacaccacta gtgccgccca ctcacgctcc ggctccgtct cccagcgcgt cacctcatcc  180
cagacagtga gccacggcgt caacgaaacc atctacaaca ccaccctcaa gtacggcgac  240
gtcgtgggcg tgaacactac aaagtacccc taccgcgtct gctccatggc ccagggcacc  300
gacctgatcc gcttcgagcg caacatcgtc tgcacctcca tgaagcccat caacgaggac  360
ctcgacgagg gcatcatggt cgtctacaag aggaacattg tggcccacac cttcaaggtc  420
cgcgtctacc agaaggtcct caccttccgc cgctcctacg cctacatcca cactacgtac  480
ctcctcggct ccaacaccga gtacgtcgcc cctcccatgt gggagatcca ccacatcaac  540
tcgcacagcc agtgctactc ctcctactcc cgcgtcatcg ccggcaccgt cttcgtcgcc  600
taccaccgcg actcctacga gaacaagacc atgcagctca tgcccgacga ctatagcaac  660
acacatagca cccgctacgt caccgtcaag gaccagtggc atagcagagg ctccacctgg  720
ctctaccgcg agacgtgcaa cctcaactgc atggtcacca tcaccaccgc ccgcagcaag  780
tatccatatc acttcttcgc cacctccaca ggagacgtgg tcgacatctc gcctttctac  840
aacggcacca accgcaacgc tagctacttc ggcgagaacg ccgacaagtt cttcatcttc  900
cccaactaca ccatcgtctc cgacttcggc cgccccaact ccgccctcga gactcaccgc  960
ttggtggcct tcctcgagcg cgccgactcc gtcatctcct gggacatcca ggacgagaag  1020
aacgtcacct gccagctgac cttctgggag gcctccgagc gcaccatccg ctccgaggcc  1080
gaggacagct accacttcag cagcgccaag atgaccgcca ccttcctctc caagaagcag  1140
gaggtcaaca tgagcgacag cgcccttgac tgcgtccgcg acgaggccat caacaagctc  1200
cagcagatct tcaacacctc ctacaaccag acttatgaga agtacggaaa cgtctccgtt  1260
ttcgagacaa caggaggcct ggttgtcttc tggcagggca ttaagcagaa gtccctcgtc  1320
gagctggaga gactcgccaa ccgctcctcc ctcaacctca cccacaaccg caccaagcgc  1380
tccaccgacg gcaacaatgc tacacacctg agcaacatgg agtccgtcca caacctcgtc  1440
tacgcccagc tccagttcac ctacgacacc ctccgcggct acatcaaccg cgccctcgcc  1500
cagatcgccg aggcgtggtg cgtcgaccag cgccgcaccc tcgaggtctt caaggagctg  1560
tccaagatca accctagcgc catcctgtcc gcaatctata acaagcctat cgcggctagg  1620
ttcatgggcg atgtgctcgg cctcgcctcc tgcgtgacta ttaatcagac cagcgtcaag  1680
gtgctgcgcg acatgaacgt gaaggagagc cctggccgct gctattccag gcccgtcgtc  1740
atcttcaatt tcgccaattc cagctatgtc cagtacggcc agctcggcga ggacaacgag  1800
atcctgcttg gcaaccaccg caccgaggag tgtcagctcc ctagcctgaa gattttcatt  1860
gccggcaata gcgcttatga gtatgtggac tacctcttca agcgcatgat cgacctctcc  1920
tccatctcca ccgtcgactc catgatcgcc ctggacatcg acccactgga gaacaccgac  1980
ttccgcgtgc tcgaactcta ctcccagaag gaactgagat caagcaacgt gttcgacctc  2040
gaggagatca tgcgcgagtt caactcttat aagcagcacc accaccatca tcac        2094
```

```
SEQ ID NO: 199          moltype = DNA  length = 642
FEATURE                 Location/Qualifiers
misc_feature            1..642
                        note = Synthetic polypeptide
source                  1..642
                        mol_type = other DNA
                        organism = synthetic construct
SEQUENCE: 199
atgctcagac ttctcctcag acaccacttc cactgcctct tgctttgtgc cgtctgggcc  60
acaccttgcc tcgccagccc ttggagcacc ttgacagcca accagaaccc ttcccctcct  120
tggtcaaagt tgacctacag caagcctcac gacgctgcta ccttctactg tccattcctg  180
taccctagcc ctccaagatc tccgctgcag ttcagcggct tccagagggt gtctaccgga  240
```

```
cctgagtgca ggaatgagac gctgtacctg ctgtacaaca gagagggcca gaccctggtg  300
gaaagaagct ccacctgggt caagaaggta atctggtacc tgagcggcag aaaccagaca  360
atactccaga gaatgccacg gaccgctagc aagcctagcg atggaaacgt gcagattagc  420
gtggaggacg caaagatttt cggcgcccac atggtgccaa agcagacaaa gctgctgcgg  480
ttcgtggtca acgacggcac ccggtaccag atgtgcgtga tgaagctgga gagctgggct  540
cacgtgttca gagattactc tgtgagcttc caagtgcggc tcaccttcac cgaagccaac  600
aatcagacct acactttctg tactcaccct aacctgatcg tg                      642

SEQ ID NO: 200          moltype = DNA  length = 642
FEATURE                 Location/Qualifiers
misc_feature            1..642
                        note = Synthetic polypeptide
source                  1..642
                        mol_type = other DNA
                        organism = synthetic construct
SEQUENCE: 200
atgcttagac tcctcctcag acaccacttc cattgtctcc ttttgtgcgc cgtgtgggcc  60
accccttgcc ttgcatcacc ttggtctacc ctcaccgcca accagaaccc tagccctcct  120
tggagtaagt taacatactc taagccgcac gacgccgcca ccttctactg tcctttcctc  180
tacccaagcc cacctcgtag cccacttcag ttctctggat tccagagagt ttcaacaggc  240
cctgagtgtc ggaacgagac tctgtacctg ttgtataaca gagagggaca gaccctggtg  300
gagcggtcct ccacctgggt gaagaaggtg atctggtatc tgagcggcag aaaccagacc  360
atcctgcagc ggatgccaag gaccgctagc aagccaagcg acggcaatgt gcagattagc  420
gtggaggatg ctaagatttt cggcgcacac atggttccta agcagaccaa gctgttacgg  480
ttcgtggtga acgatggaac tcggtaccaa atgtgcgtga tgaagctgga gtcatgggca  540
catgtgttcc gtgactactc tgtttctttc caggtgcgcc tgaccttcac cgaggccaat  600
aaccagacat acaccttctg tacgcaccca aatctgatcg ta                      642

SEQ ID NO: 201          moltype = DNA  length = 642
FEATURE                 Location/Qualifiers
misc_feature            1..642
                        note = Synthetic polypeptide
source                  1..642
                        mol_type = other DNA
                        organism = synthetic construct
SEQUENCE: 201
atgctcagac ttttgctcag acaccacttc cactgtttgt tgttatgtgc cgtgtgggct  60
accccttgcc tcgcatctcc gtggtccaca ctcacagcca accagaatcc ttctcctcct  120
tggagcaagc tcacatatag caagcctcac gacgcggcaa ccttctactg cccattcctg  180
tatccttctc ctccgcggag ccctctgcag ttctccggat tccagagagt gtccaccggt  240
cctgagtgca gaaatgaaac actgtatctt ctctacaaca gagagggcca gacccttgtg  300
gagagaagca gcacctgggt gaagaaggtc atttggtatc tgtctggcag aaaccagacc  360
atactgcagc ggatgccaag aacagcctcc aagccatccg acggtaacgt gcagatctcc  420
gtggaggacg ccaagatttt cggcgcccac atggtgccaa agcagaccaa gctgctgaga  480
ttcgtggtga acgatggcac caggtaccag atgtgcgtta tgaagcttga gtcctgggct  540
cacgtgttca gagactactc tgtgagcttc caggtgagac tgacattcac agaggccaac  600
aaccagactt acaccttctg cacgcatcct aatctgatcg tg                      642

SEQ ID NO: 202          moltype = DNA  length = 642
FEATURE                 Location/Qualifiers
misc_feature            1..642
                        note = Synthetic polypeptide
source                  1..642
                        mol_type = other DNA
                        organism = synthetic construct
SEQUENCE: 202
atgctcagac ttcttctcag acaccacttc cactgtttgc ttctctgcgc agtgtgggca  60
accccttgcc ttgcttcccc ttggtcgact ctcaccgcca accagaatcc aagccctcct  120
tggagcaagc tcacttacag caagccgcac gacgccgcca ccttctactg tcctttcctg  180
taccctagcc ctccaagatc tcctctgcaa ttctctggat tccagagagt gagcaccggc  240
ccagagtgcc ggaacgagac tctgtatctg ctgtacaata gggagggaca aaccctggtg  300
gagaggagca gcacatgggt gaagaaggtg atctggtacc tgagcggcag aaaccagacc  360
atcctgcaga gaatgccacg gaccgccagc aagccaagcg atggcaacgt ccagattagc  420
gtggaagacg ccaagatctt cggagcccac atggtgccta agcagaccaa gcttctgcga  480
ttcgtggtga acgacggtac ccgctaccaa atgtgcgtga tgaagctgga gtcatgggcc  540
cacgtcttcc gcgactacag cgtatccttc caggtgaggc ttaccttcac cgaggccaac  600
aaccaaacct acacattctg cacccatcca aatttgattg tg                      642

SEQ ID NO: 203          moltype = DNA  length = 642
FEATURE                 Location/Qualifiers
misc_feature            1..642
                        note = Synthetic polypeptide
source                  1..642
                        mol_type = other DNA
                        organism = synthetic construct
SEQUENCE: 203
atgctcagac tattgttgag acatcacttc cattgcctcc ttttgtgcgc cgtgtgggct  60
accccttgcc tcgcctcacc ttggagcacc ttgaccgcca accagaaccc gagccctccg  120
tggtcaaagc tcacctacag caagcctcac gacgccgcaa ccttctattg tccattcctg  180
```

```
tacccttctc cgccgaggtc ccctcttcag ttcagcggat tccagagagt gtctaccgga  240
ccagaatgca gaaacgaaac actgtatctg ctgtacaacc gggagggcca gaccctggtc  300
gagcggagct ctacctgggt caagaaggtt atatggtatc tgagcggcag gaaccagacc  360
atcctgcagc gcatgcctag aaccgctagc aagccaagcg acggcaacgt tcagatctcc  420
gtggaggacg ctaagatctt cggcgcccat atggtgccaa agcagactaa gctgctgaga  480
ttcgtggtaa acgacggcac aagatatcag atgtgcgtga tgaagctgga gagctgggct  540
catgtgttca gggactactc cgtgagtttc caggtgaggc tgacattcac cgaggctaat  600
aatcagacct acaccttctg cactcaccca aatctgatcg tg                     642

SEQ ID NO: 204         moltype = DNA  length = 642
FEATURE                Location/Qualifiers
misc_feature           1..642
                       note = Synthetic polypeptide
source                 1..642
                       mol_type = other DNA
                       organism = synthetic construct
SEQUENCE: 204
atgctcagat tattgctcag acaccacttc cactgcctcc tcttgtgcgc cgtgtgggcg  60
acaccgtgtc tcgcaagccc ttggtccaca ctaacggcca accagaaccc tagccctcct  120
tggagcaagc tcacttatag caagccacac gatgcggcca ctttctactg tcctttcctg  180
tatccatccc ctcctagatc tcctctgcag ttcagcggat tccagagagt atctactggc  240
cctgagtgca gaaatgaaac cctctatctc ctgtacaatc gggagggcca gactttggtg  300
gagcgcagct ccacctgggt gaagaaggtg atctggtacc tgagcggcag aaaccagacc  360
atcctacaga ggatgccaag gaccgccagc aagccatctg acggcaacgt gcagatctct  420
gtggaggacg ccaagatctt cggagcccat atggtgccta agcagacaaa gctgttgagg  480
ttcgtcgtga atgacggcac aagataccag atgtgtgtga tgaagctgga gagctgggct  540
cacgtgttcc gagactacag cgtctcgttc caggtgagac tgacattcac cgaggcaaac  600
aaccagacct acaccttctg tacgcaccct aacctgatcg tt                     642

SEQ ID NO: 205         moltype = DNA  length = 642
FEATURE                Location/Qualifiers
misc_feature           1..642
                       note = Synthetic polypeptide
source                 1..642
                       mol_type = other DNA
                       organism = synthetic construct
SEQUENCE: 205
atgcttcggc tcctccttcg gcaccacttc cactgcctcc tcctctgcgc cgtgtgggcc  60
acaccttgcc tcgccagccc ctggagcacc ctcaccgcca accagaaccc cagccctccg  120
tggtctaagt taacctacag caagccccac gacgccgcca ccttctactg ccccttcctg  180
tacccttcac cgccgcggag cccgctgcag ttcagcggct tccagcgggt gagcaccggc  240
cccgagtgcc ggaacgagac gctgtacctg ctgtacaacc gggagggcca gaccctggtg  300
gagcggagca gcacctgggt gaagaaggtg atctggtacc tgagcggccg gaaccagacc  360
atcctgcagc ggatgccccg gaccgcctca aagccaagcg acggcaacgt gcagatcagc  420
gtggaggacg ccaagatctt cggcgcccac atggtgccca agcagaccaa gttgctgcgc  480
ttcgtggtga acgacggcac ccggtaccag atgtgcgtga tgaagctgga gagctgggcc  540
cacgtgttcc gggactacag cgtgagcttc caggtgcggc tgacattcac cgaggccaac  600
aatcagacct acaccttctg cacccacccc aacctgatcg tg                     642

SEQ ID NO: 206         moltype = DNA  length = 642
FEATURE                Location/Qualifiers
misc_feature           1..642
                       note = Synthetic polypeptide
source                 1..642
                       mol_type = other DNA
                       organism = synthetic construct
SEQUENCE: 206
atgttacggc tccttctccg ccaccacttc cactgcctct tactctgcgc cgtgtgggcc  60
actccatgcc ttgccagccc ctggagcacc ttgaccgcca accagaaccc cagcccacct  120
tggagtaagc tcacctacag caagccccac gacgccgcca ccttctactg ccccttcctg  180
tatccgagcc caccgcggag cccgctgcag ttcagcggct tccagcgggt gagcaccggc  240
cccgagtgcc ggaacgaaac cctgtacctg ctgtacaacc gggagggcca gaccctggtg  300
gagcggagca gcacctgggt gaagaaggtg atctggtacc tgagcggccg gaaccagacc  360
atcctgcagc ggatgccccg gaccgctagt aagcctagcg acggcaacgt gcagatcagc  420
gtggaggacg ccaagatctt cggcgcccac atggtgccca agcagaccaa gctgcttagg  480
ttcgtggtga acgacggcac ccggtaccag atgtgcgtga tgaagctgga gagctgggcc  540
cacgtgttcc gggactacag cgtgagcttc caggtgcggc tgaccttcac cgaggccaac  600
aaccagacat acaccttctg cacccacccc aacctgatcg tg                     642

SEQ ID NO: 207         moltype = DNA  length = 642
FEATURE                Location/Qualifiers
misc_feature           1..642
                       note = Synthetic polypeptide
source                 1..642
                       mol_type = other DNA
                       organism = synthetic construct
SEQUENCE: 207
atgctacggc tcctactccg ccaccacttc cactgcttac ttttgtgcgc cgtgtgggcc  60
acaccatgct tggccagccc ctggagcacc ctcaccgcca accagaaccc ctcacctccc  120
```

-continued

```
tggtccaagc tcacctactc caagccccac gacgccgcca ccttctactg ccccttcctc  180
tatccatctc ctccacgcag cccactccag ttctccggct tccagcgcgt ctccaccggc  240
cccgagtgcc gcaacgagac gctctacctc ctctacaacc gcgagggcca gaccctcgtc  300
gagaggtcat ccacctgggt caagaaggtc atctggtacc tctccggccg caaccagacc  360
atcctccagc gcatgccccg caccgcgtct aagccgtccg acggcaacgt ccagatctcc  420
gtcgaggacg ccaagatctt cggcgcccac atggtcccca agcagaccaa gctcctccgc  480
ttcgtcgtca acgacggcac ccgctaccag atgtgcgtca tgaagctcga gtcctgggcc  540
cacgtcttcc gcgactactc cgtctccttc caggtccgcc tcaccttcac cgaggccaat  600
aaccagactt acaccttctg cacccacccc aacctcatcg tc                    642

SEQ ID NO: 208         moltype = DNA  length = 642
FEATURE                Location/Qualifiers
misc_feature           1..642
                       note = Synthetic polypeptide
source                 1..642
                       mol_type = other DNA
                       organism = synthetic construct
SEQUENCE: 208
atgctacggc tcctactccg ccaccacttc cactgcttac ttttgtgcgc cgtgtgggcc  60
acaccatgct tggccagccc ctggagcacc ctcaccgcca accagaaccc ctcacctccc  120
tggtccaagc tcacctactc caagccccac gacgccgcca ccttctactg ccccttcctc  180
tatccatctc ctccacgcag cccactccag ttctccggct tccagcgcgt ctccaccggc  240
cccgagtgcc gcaacgagac gctctacctc ctctacaacc gcgagggcca gaccctcgtc  300
gagaggtcat ccacctgggt caagaaggtc atctggtacc tctccggccg caaccagacc  360
atcctccagc gcatgccccg caccgcgtct aagccgtccg acggcaacgt ccagatctcc  420
gtcgaggacg ccaagatctt cggcgcccac atggtcccca agcagaccaa gctcctccgc  480
ttcgtcgtca acgacggcac ccgctaccag atgtgcgtca tgaagctcga gtcctgggcc  540
cacgtcttcc gcgactactc cgtctccttc caggtccgcc tcaccttcac cgaggccaat  600
aaccagactt acaccttctg cacccacccc aacctcatcg tc                    642

SEQ ID NO: 209         moltype = DNA  length = 642
FEATURE                Location/Qualifiers
misc_feature           1..642
                       note = Synthetic polypeptide
source                 1..642
                       mol_type = other DNA
                       organism = synthetic construct
SEQUENCE: 209
atgcttcggc tcctcctaag gcaccacttc cactgccttt tgctttgcgc cgtgtgggcc  60
accccttgct tggccagccc ctggagcacc ctcaccgcca accagaaccc ctcccctccc  120
tggtccaagc tcacctactc caagccccac gacgccgcca ccttctactg ccccttcctc  180
tacccgtccc ctccacgcag cccactccag ttctccggct tccagcgcgt ctccaccggc  240
cccgagtgcc gcaacgaaac actctacctc ctctacaacc gcgagggcca gaccctcgtc  300
gagcgctcct ccacctgggt caagaaggtc atctggtacc tctccggccg caaccagacc  360
atcctccagc gcatgccccg caccgcaagc aagccatccg acggcaacgt ccagatctcc  420
gtcgaggacg ccaagatctt cggcgcccac atggtcccca agcagaccaa gctcctccgc  480
ttcgtcgtca acgacggcac ccgctaccag atgtgcgtca tgaagctcga gtcctgggcc  540
cacgtcttcc gcgactactc cgtctccttc caggtccgcc tcaccttcac cgaggccaat  600
aatcagacat acaccttctg cacccacccc aacctcatcg tc                    642

SEQ ID NO: 210         moltype = DNA  length = 387
FEATURE                Location/Qualifiers
misc_feature           1..387
                       note = Synthetic polypeptide
source                 1..387
                       mol_type = other DNA
                       organism = synthetic construct
SEQUENCE: 210
atgcggctgt gtcgggtgtg gctgtctgtt tgtctgtgcg ccgtggtgct gggtcagtgc  60
cagcgggaaa ccgcggaaaa gaacgattat taccgagtac cgcattactg ggacgcgtgc  120
tctcgcgcgc tgcccgacca aacccgttac aagtatgtgg aacagctcgt ggacctcacg  180
ttgaactacc actacgatgc gagccacggc ttggacaact ttgacgtgct caagagaatc  240
aacgtgaccg aggtgtcgtt gctcatcagc gactttagac gtcagaaccg tcgcggcggc  300
accaacaaaa ggaccacgtt caacgccgcc ggttcgctgg cgccacacgc ccggagcctc  360
gagttcagcg tgcggctctt tgccaac                                     387

SEQ ID NO: 211         moltype = AA  length = 742
FEATURE                Location/Qualifiers
REGION                 1..742
                       note = Synthetic polypeptide
source                 1..742
                       mol_type = protein
                       organism = synthetic construct
SEQUENCE: 211
MRPGLPSYLI ILAVCLFSHL LSSRYGAEAV SEPLDKAFHL LLNTYGRPIR FLRENTTQCT  60
YNSSLRNSTV VRENAISFNF FQSYNQYYVF HMPRCLFAGP LAEQFLNQVD LTETLERYQQ  120
RLNTYALVSK DLASYRSFSQ QLKAQDSLGE QPTTVPPPID LSIPHVWMPP QTTPHGWTES  180
HTTSGLHRPH FNQTCILFDG HDLLFSTVTP CLHQGFYLID ELRYVKITLT EDFFVVTVSI  240
DDDTPMLLIF GHLPRVLFKA PYQRDNFILR QTEKHELLVL VKKDQLNRHS YLKDPDFLDA  300
```

```
ALDFNYLDLS ALLRNSFHRY AVDVLKSGRC QMLDRRTVEM AFAYALALFA AARQEEAGAQ  360
VSVPRALDRQ AALLQIQEFM ITCLSQTPPR TTLLLYPTAV DLAKRALWTP NQITDITSLV  420
RLVYILSKQN QQHLIPQWAL RQIADFALKL HKTHLASFLS AFARQELYLM GSLVHSMLVH  480
TTERREIFIV ETGLCSLAEL SHFTQLLAHP HHEYLSDLYT PCSSSGRRDH SLERLTRLFP  540
DATVPATVPA ALSILSTMQP STLETFPDLF CLPLGESFSA LTVSEHVSYI VTNQYLIKGI  600
SYPVSTTVVG QSLIITQTDS QTKCELTRNM HTTHSITVAL NISLENCAFC QSALLEYDDT  660
QGVINIMYMH DSDDVLFALD PYNEVVVSSP RTHYLMLLKN GTVLEVTDVV VDATDSRLLM  720
MSVYALSAII GIYLLYRMLK TC                                          742

SEQ ID NO: 212          moltype = AA  length = 278
FEATURE                 Location/Qualifiers
REGION                  1..278
                        note = Synthetic polypeptide
source                  1..278
                        mol_type = protein
                        organism = synthetic construct
SEQUENCE: 212
MCRRPDCGFS FSPGPVILLW CCLLLPIVSS AAVSVAPTAA EKVPAECPEL TRRCLLGEVF  60
EGDKYESWLR PLVNVTGRDG PLSQLIRYRP VTPEAANSVL LDEAFLDTLA LLYNNPDQLR  120
ALLTLLSSDT APRWMTVMRG YSECGDGSPA VYTCVDDLCR GYDLTRLSYG RSIFTEHVLG  180
FELVPPSLFN VVVAIRNEAT RTNRAVRLPV STAAAPEGIT LFYGLYNAVK EFCLRHQLDP  240
PLLRHLDKYY AGLPPELKQT RVNLPAHSRY GPQAVDAR                         278

SEQ ID NO: 213          moltype = AA  length = 171
FEATURE                 Location/Qualifiers
REGION                  1..171
                        note = Synthetic polypeptide
source                  1..171
                        mol_type = protein
                        organism = synthetic construct
SEQUENCE: 213
MSPKDLTPFL TALWLLLGHS RVPRVRAEEC CEFINVNHPP ERCYDFKMCN RFTVALRCPD  60
GEVCYSPEKT AEIRGIVTTM THSLTRQVVH NKLTSCNYNP LYLEADGRIR CGKVNDKAQY  120
LLGAAGSVPY RWINLEYDKI TRIVGLDQYL ESVKKHKRLD VCRAKMGYML Q           171

SEQ ID NO: 214          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 214
MLRLLLRHHF HCLLLCAVWA TPCLASPWST LTANQNPSPP WSKLTYSKPH DAATFYCPFL  60
YPSPPRSPLQ FSGFQRVSTG PECRNETLYL LYNREGQTLV ERSSTWVKKV IWYLSGRNQT  120
ILQRMPRTAS KPSDGNVQIS VEDAKIFGAH MVPKQTKLLR FVVNDGTRYQ MCVMKLESWA  180
HVFRDYSVSF QVRLTFTEAN NQTYTFCTHP NLIV                             214

SEQ ID NO: 215          moltype = AA  length = 129
FEATURE                 Location/Qualifiers
REGION                  1..129
                        note = Synthetic polypeptide
source                  1..129
                        mol_type = protein
                        organism = synthetic construct
SEQUENCE: 215
MRLCRVWLSV CLCAVVLGQC QRETAEKNDY YRVPHYWDAC SRALPDQTRY KYVEQLVDLT  60
LNYHYDASHG LDNFDVLKRI NVTEVSLLIS DFRRQNRRGG TNKRTTFNAA GSLAPHARSL  120
EFSVRLFAN                                                         129

SEQ ID NO: 216          moltype = AA  length = 907
FEATURE                 Location/Qualifiers
REGION                  1..907
                        note = Synthetic polypeptide
source                  1..907
                        mol_type = protein
                        organism = synthetic construct
SEQUENCE: 216
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
```

-continued

```
FRVLELYSQK ELRSSNVFDL EEIMREFNSY KQRVKYVEDK VVDPLPPYLK GLDDLMSGLG  720
AAGKAVGVAI GAVGGAVASV VEGVATFLKN PFGAFTIILV AIAVVIITYL IYTRQRRLCT  780
QPLQNLFPYL VSADGTTVTS GSTKDTSLQA PPSYEESVYN SGRKGPGPPS SDASTAAPPY  840
TNEQAYQMLL ALARLDAEQR AQQNGTDSLD GRTGTQDKGQ KPNLLDRLRH RKNGYRHLKD  900
SDEEENV                                                            907

SEQ ID NO: 217          moltype = AA  length = 557
FEATURE                 Location/Qualifiers
REGION                  1..557
                        note = Synthetic polypeptide
source                  1..557
                        mol_type = protein
                        organism = synthetic construct
SEQUENCE: 217
MESRGRRCPE MISVLGPISG HVLKAVFSRG DTPVLPHETR LLQTGIHVRV SQPSLILVSQ  60
YTPDSTPCHR GDNQLQVQHT YFTGSEVENV SVNVHNPTGR SICPSQEPMS IYVYALPLKM  120
LNIPSINVHH YPSAAERKHR HLPVADAVIH ASGKQMWQAR LTVSGLAWTR QQNQWKEPDV  180
YYTSAFVFPT KDVALRHVVC AHELVCSMEN TRATKMQVIG DQYVKVYLES FCEDVPSGKL  240
FMHVTLGSDV EEDLTMTRNP QPFMRPHERN GFTVLCPKNM IIKPGKISHI MLDVAFTSHE  300
HFGLLCPKSI PGLSISGNLL MNGQQIFLEV QAIRETVELR QYDPVAALFF FDIDLLLQRG  360
PQYSEHPTFT SQYRIQGKLE YRHTWDRHDE GAAQGDDDVW TSGSDSDEEL VTTERKTPRV  420
TGGGAMASAS TSAGSASSAT ACTAGVMTRG RLKAESTVAP EEDTDEDSDN EIHNPAVFTW  480
PPWQAGILAR NLVPMVATVQ GQNLKYQEFF WDANDIYRIF AELEGVWQPA AQPKRRRHRQ  540
DALPGPCIAS TPKKHRG                                                 557

SEQ ID NO: 218          moltype = AA  length = 900
FEATURE                 Location/Qualifiers
REGION                  1..900
                        note = Synthetic polypeptide
source                  1..900
                        mol_type = protein
                        organism = synthetic construct
SEQUENCE: 218
MESRGRRCPE MISVLGPISG HVLKAVFSRG DTPVLPHETR LLQTGIHVRV SQPSLILVSQ  60
YTPDSTPCHR GDNQLQVQHT YFTGSEVENV SVNVHNPTGR SICPSQEPMS IYVYALPLKM  120
LNIPSINVHH YPSAAERKHR HLPVADAVIH ASGKQMWQAR LTVSGLAWTR QQNQWKEPDV  180
YYTSAFVFPT KDVALRHVVC AHELVCSMEN TRATKMQVIG DQYVKVYLES FCEDVPSGKL  240
FMHVTLGSDV EEDLTMTRNP QPFMRPHERN GFTVLCPKNM IIKPGKISHI MLDVAFTSHE  300
HFGLLCPKSI PGLSISGNLL MNGQQIFLEV QAIRETVELR QYDPVAALFF FDIDLLLQRG  360
PQYSEHPTFT SQYRIQGKLE YRHTWDRHDE GAAQGDDDVW TSGSDSDEEL VTTERKTPRV  420
TGGGAMASAS TSAGRKRKSA SSATACTAGV MTRGRLKAES TVAPEEDTDE DSDNEIHNPA  480
VFTWPPWQAG ILARNLVPMV ATVQGQNLKY QEFFWDANDI YRIFAELEGV WQPAAQPKRR  540
RHRQDALPGP CIASTPKKHR GESSAKRKMD PDNPDEGPSS KVPRPETPVT KATTFLQTML  600
RKEVNSQLSL GDPLFPELAE ESLKTFEQVT EDCNENPEKD VLTELVKQIK VRVDMVRHRI  660
KEHMLKKYTQ TEEKFTGAFN MMGGCLQNAL DILDKVHEPF EDMKCIGLTM QSMYENYIVP  720
EDKREMWMAC IKELHDVSKG AANKLGGALQ AKARAKKDEL RRKMMYMCYR NIEFFTKNSA  780
FPKTTNGCSQ AMAALQNLPQ CSPDEIMSYA QKIFKILDEE RDKVLTHIDH IFMDILTTCV  840
ETMCNEYKVT SDACMMTMYG GISLLSEFCR VLCCYVLEET SVMLAKRPLI TKPEVISVMK  900

SEQ ID NO: 219          moltype = AA  length = 1047
FEATURE                 Location/Qualifiers
REGION                  1..1047
                        note = Synthetic polypeptide
source                  1..1047
                        mol_type = protein
                        organism = synthetic construct
SEQUENCE: 219
MESRGRRCPE MISVLGPISG HVLKAVFSRG DTPVLPHETR LLQTGIHVRV SQPSLILVSQ  60
YTPDSTPCHR GDNQLQVQHT YFTGSEVENV SVNVHNPTGR SICPSQEPMS IYVYALPLKM  120
LNIPSINVHH YPSAAERKHR HLPVADAVIH ASGKQMWQAR LTVSGLAWTR QQNQWKEPDV  180
YYTSAFVFPT KDVALRHVVC AHELVCSMEN TRATKMQVIG DQYVKVYLES FCEDVPSGKL  240
FMHVTLGSDV EEDLTMTRNP QPFMRPHERN GFTVLCPKNM IIKPGKISHI MLDVAFTSHE  300
HFGLLCPKSI PGLSISGNLL MNGQQIFLEV QAIRETVELR QYDPVAALFF FDIDLLLQRG  360
PQYSEHPTFT SQYRIQGKLE YRHTWDRHDE GAAQGDDDVW TSGSDSDEEL VTTERKTPRV  420
TGGGAMASAS TSAGSASSAT ACTAGVMTRG RLKAESTVAP EEDTDEDSDN EIHNPAVFTW  480
PPWQAGILAR NLVPMVATVQ GQNLKYQEFF WDANDIYRIF AELEGVWQPA AQPKRRRHRQ  540
DALPGPCIAS TPKKHRGESS AKRKMDPDNP DEGPSSKVPR PETPVTKATT FLQTMLRKEV  600
NSQLSLGDPL FPELAEESLK TFEQVTEDCN ENPEKDVLTE LVKQIKVRVD MVRHRIKEHM  660
LKKYTQTEEK FTGAFNMMGG CLQNALDILD KVHEPFEDMK CIGLTMQSMY ENYIVPEDKR  720
EMWMACIKEL HDVSKGAANK LGGALQAKAR AKKDELRRKM MYMCYRNIEF FTKNSAFPKT  780
TNGCSQAMAA LQNLPQCSPD EIMSYAQKIF KILDEERDKV LTHIDHIFMD ILTTCVETMC  840
NEYKVTSDAC MMTMYGGISL LSEFCRVLCC YVLEETSVML AKRPLITKPE VISVMKRRIE  900
EICMKVFAQY ILGADPLRVC SPSVDDLRAI AEESDEEEAI VAYTLATAGA SSSDSLVSPP  960
ESPVPATIPL SSVIVAENSD QEESEQSDEE QEEGAQEERE DTVSVKSEPV SEIEEVASEE  1020
EEDGAEEPTA SGGKSTHPMV TRSKADQ                                      1047

SEQ ID NO: 220          moltype = AA  length = 491
FEATURE                 Location/Qualifiers
REGION                  1..491
```

```
                         note = Synthetic polypeptide
source                   1..491
                         mol_type = protein
                         organism = synthetic construct
SEQUENCE: 220
MESSAKRKMD PDNPDEGPSS KVPRPETPVT KATTFLQTML RKEVNSQLSL GDPLFPELAE  60
ESLKTFEQVT EDCNENPEKD VLTELVKQIK VRVDMVRHRI KEHMLKKYTQ TEEKFTGAFN  120
MMGGCLQNAL DILDKVHEPF EDMKCIGLTM QSMYENYIVP EDKREMWMAC IKELHDVSKG  180
AANKLGGALQ AKARAKKDEL RRKMMYMCYR NIEFFTKNSA FPKTTNGCSQ AMAALQNLPQ  240
CSPDEIMSYA QKIFKILDEE RDKVLTHIDH IFMDILTTCV ETMCNEYKVT SDACMMTMYG  300
GISLLSEFCR VLCCYVLEET SVMLAKRPLI TKPEVISVMK RRIEEICMKV FAQYILGADP  360
LRVCSPSVDD LRAIAEESDE EEAIVAYTLA TAGASSSDSL VSPPESPVPA TIPLSSVIVA  420
ENSDQEESEQ SDEEQEEGAQ EEREDTVSVK SEPVSEIEEV ASEEEEDGAE EPTASGGKST  480
HPMVTRSKAD Q                                                       491

SEQ ID NO: 221           moltype = AA  length = 580
FEATURE                  Location/Qualifiers
REGION                   1..580
                         note = Synthetic polypeptide
source                   1..580
                         mol_type = protein
                         organism = synthetic construct
SEQUENCE: 221
MESSAKRKMD PDNPDEGPSS KVPRPETPVT KATTFLQTML RKEVNSQLSL GDPLFPELAE  60
ESLKTFEQVT EDCNENPEKD VLTELGDILA QAVNHAGIDS SSTGPTLTTH SCSVSSAPLN  120
KPTPTSVAVT NTPLPGASAT PELSPRKKPR KTTRPFKVII KPPVPPAPIM LPLIKQEDIK  180
PEPDFTIQYR NKIIDTAGCI VISDSEEEQG EEVETRGATA SSPSTGSGTP RVTSPTHPLS  240
QMNHPPLPDP LGRPDEDSSS SSSSSCSSAS DSESESEEMK CSSGGGASVT SSHHGRGGFG  300
GAASSSLLSC GHQSSGGAST GPRKKKSKRI SELDNEKVRN IMKDKNTPFC TPNVQTRRGR  360
VKIDEVSRMF RHTNRSLEYK NLPFMIPSMH QVLEEAIKVC KTMQVNNKGI QIIYTRNHEV  420
KNEVDQVRCR LGSMCNLALS TPFLMEHTMP VTHPPDVAQR TADACNDGVK AVWNLKELHT  480
HQLCPRSSDY RNMIIHAATP VDLLGALNLC LPLMQKFPKQ VMVRIFSTNQ GGFMLPIYET  540
AAKAYAVGQF EKPTETPPED LDTLSLAIEA AIQDLRNKSQ                        580

SEQ ID NO: 222           moltype = AA  length = 561
FEATURE                  Location/Qualifiers
REGION                   1..561
                         note = Synthetic polypeptide
source                   1..561
                         mol_type = protein
                         organism = synthetic construct
SEQUENCE: 222
MESRGRRCPE MISVLGPISG HVLKAVFSRG DTPVLPHETR LLQTGIHVRV SQPSLILVSQ  60
YTPDSTPCHR GDNQLQVQHT YFTGSEVENV SVNVHNPTGR SICPSQEPMS IYVYALPLKM  120
LNIPSINVHH YPSAAERKHR HLPVADAVIH ASGKQMWQAR LTVSGLAWTR QQNQWKEPDV  180
YYTSAFVFPT KDVALRHVVC AHELVCSMEN TRATKMQVIG DQYVKVYLES FCEDVPSGKL  240
FMHVTLGSDV EEDLTMTRNP QPFMRPHERN GFTVLCPKNM IIKPGKISHI MLDVAFTSHE  300
HFGLLCPKSI PGLSISGNLL MNGQQIFLEV QAIRETVELR QYDPVAALFF FDIDLLLQRG  360
PQYSEHPTFT SQYRIQGKLE YRHTWDRHDE GAAQGDDDVW TSGSDSDEEL VTTERKTPRV  420
TGGGAMASAS TSAGRKRKSA SSATACTAGV MTRGRLKAES TVAPEEDTDE DSDNEIHNPA  480
VFTWPPWQAG ILARNLVPMV ATVQGQNLKY QEFFWDANDI YRIFAELEGV WQPAAQPKRR  540
RHRQDALPGP CIASTPKKHR G                                            561

SEQ ID NO: 223           moltype = AA  length = 698
FEATURE                  Location/Qualifiers
REGION                   1..698
                         note = Synthetic polypeptide
source                   1..698
                         mol_type = protein
                         organism = synthetic construct
SEQUENCE: 223
MESRIWCLVV CVNLCIVCLG AAVSSSSTRG TSATHSHHSS HTTSAAHSRS GSVSQRVTSS  60
QTVSHGVNET IYNTTLKYGD VVGVNTTKYP YRVCSMAQGT DLIRFERNIV CTSMKPINED  120
LDEGIMVVYK RNIVAHTFKV RVYQKVLTFR RSYAYIHTTY LLGSNTEYVA PPMWEIHHIN  180
SHSQCYSSYS RVIAGTVFVA YHRDSYENKT MQLMPDDYSN THSTRYVTVK DQWHSRGSTW  240
LYRETCNLNC MVTITTARSK YPYHFFATST GDVVDISPFY NGTNRNASYF GENADKFFIF  300
PNYTIVSDFG RPNSALETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETTGGLVVF WQGIKQKSLV ELERLANRSS LNLTHNRTKR STDGNNATHL SNMESVHNLV  480
YAQLQFTYDT LRGYINRALA QIAEAWCVDQ RRTLEVFKEL SKINPSAILS AIYNKPIAAR  540
FMGDVLGLAS CVTINQTSVK VLRDMNVKES PGRCYSRPVV IFNFANSSYV QYGQLGEDNE  600
ILLGNHRTEE CQLPSLKIFI AGNSAYEYVD YLFKRMIDLS SISTVDSMIA LDIDPLENTD  660
FRVLELYSQK ELRSSNVFDL EEIMREFNSY KQHHHHHH                          698

SEQ ID NO: 224           moltype = AA  length = 742
FEATURE                  Location/Qualifiers
REGION                   1..742
                         note = Synthetic polypeptide
source                   1..742
```

```
                         mol_type = protein
                         organism = synthetic construct
SEQUENCE: 224
MRPGLPSYLI ILAVCLFSHL LSSRYGAEAV SEPLDKAFHL LLNTYGRPIR FLRENTTQCT  60
YNSSLRNSTV VRENAISFNF FQSYNQYYVF HMPRCLFAGP LAEQFLNQVD LTETLERYQQ  120
RLNTYALVSK DLASYRSFSQ QLKAQDSLGE QPTTVPPPID LSIPHVWMPP QTTPHGWTES  180
HTTSGLHRPH FNQTCILFDG HDLLFSTVTP CLHQGFYLID ELRYVKITLT EDFFVVTVSI  240
DDDTPMLLIF GHLPRVLFKA PYQRDNFILR QTEKHELLVL VKKDQLNRHS YLKDPDFLDA  300
ALDFNYLDLS ALLRNSFHRY AVDVLKSGRC QMLDRRTVEM AFAYALALFA AARQEEAGAQ  360
VSVPRALDRQ AALLQIQEFM ITCLSQTPPR TTLLLYPTAV DLAKRALWTP NQITDITSLV  420
RLVYILSKQN QQHLIPQWAL RQIADFALKL HKTHLASFLS AFARQELYLM GSLVHSMLVH  480
TTERREIFIV ETGLCSLAEL SHFTQLLAHP HHEYLSDLYT PCSSSGRRDH SLERLTRLFP  540
DATVPATVPA ALSILSTMQP STLETFPDLF CLPLGESFSA LTVSEHVSYI VTNQYLIKGI  600
SYPVSTTVVG QSLIITQTDS QTKCELTRNM HTTHSITVAL NISLENCAFC QSALLEYDDT  660
QGVINIMYMH DSDDVLFALD PYNEVVVSSP RTHYLMLLKN GTVLEVTDVV VDATDSRLLM  720
MSVYALSAII GIYLLYRMLK TC                                          742

SEQ ID NO: 225           moltype = DNA  length = 2464
FEATURE                  Location/Qualifiers
misc_feature             1..2464
                         note = Synthetic polypeptide
source                   1..2464
                         mol_type = other DNA
                         organism = synthetic construct
SEQUENCE: 225
tcaagctttt ggaccctcgt acagaagcta atacgactca ctatagggaa ataagagaga  60
aaagaagagt aagaagaaat ataagagcca ccatgcggcc aggcctcccc tcctacctca  120
tcatcctcgc cgtctgtctc ttcagccacc tactttcgtc acgatatggc gcagaagccg  180
tatccgaacc gctggacaaa gcgtttcacc tactgctcaa cacctacggg agacccatcc  240
gcttcctgcg tgaaaatacc acccagtgta cctacaacag cagcctccgt aacagcacgg  300
tcgtcaggga aaacgccatc agtttcaact ttttccaaag ctataatcaa tactatgtat  360
tccatatgcc tcgatgtctt tttgcgggtc ctctggcgga gcagtttctg aaccaggtag  420
atctgaccga aaccctggaa agataccaac agagacttaa cacttacgcg ctggtatcca  480
aagacctggc cagctaccga tctttttcgc agcagctaaa ggcacaagac agcctaggtg  540
aacagcccac cactgtgcca ccgcccattg acctgtcaat acctcacgtt tggatgccac  600
cgcaaaccac tccacacggc tggacagaat cacataccac ctcaggacta caccgaccac  660
actttaacca gacctgtatc ctctttgatg gacacgatct actattcagc accgtcacac  720
cttgtttgca ccaaggcttt tacctcatcg acgaactacg ttacgttaaa ataacactga  780
ccgaggactt cttcgtagtt acggtgtcca tagacgacga cacacccatg ctgcttatct  840
tcggccatct tccacgcgta cttttcaaag cgccctatca acgcgacaac tttatactac  900
gacaaactga aaaacacgag ctcctggtgc tagttaagaa agatcaactg aaccgtcact  960
cttatctcaa agacccggac tttcttgacg ccgcacttga cttcaactac ctagacctca  1020
gcgcactact acgtaacagc tttcaccgtt acgccgtgga tgtactcaag agcggtcgat  1080
gtcagatgct ggaccgccgc acggtagaaa tggccttcgc ctacgcatta gcactgttcg  1140
cagcagcccg acaagaagag gccggcgccc aagtctccgt cccacgggcc ctagaccgcc  1200
aggccgcact cttacaaata caagaattta tgatcacctg cctctcacaa acaccaccac  1260
gcaccacgtt gctgctgtat cccacggccg tggacctggc caaacgagcc ctttggacac  1320
cgaatcagat caccgacatc accagcctcg tacgcctggt ctacatactc tctaaacaga  1380
atcagcaaca tctcatcccc caatgggcac tacgacagat cgccgacttt gccctaaaac  1440
tacacaaaac gcacctggcc tcttttcttt cagccttcgc acgccaagaa ctctacctca  1500
tgggcagcct cgtccactcc atgctggtac atacgacgga gagacgcgaa atcttcatcg  1560
tagaaacggg cctctgttca ttggccgagc tatcacactt tacgcagttg ttagctcatc  1620
cacaccacga atacctcagc gacctgtaca caccctgttc cagtagcggg cgacgcgatc  1680
actcgctcga acgcctcacg cgtctcttcc ccgatgccac cgtccccgct accgttcccg  1740
ccgccctctc catcctatct accatgcaac caagcacgct ggaaaccttc cccgacctgt  1800
tttgcttgcc gctcggcgaa tccttctccg cgctgaccgt ctccgaacac gtcagttata  1860
tcgtaacaaa ccagtacctg atcaaaggta tctcctaccc tgtctccacc accgtcgtag  1920
gccagagcct catcatcacc cagacggaca gtcaaactaa atgcgaactg acgcgcaaca  1980
tgcataccac acacagcatc acagtggcgc tcaacatttc gctagaaaac tgcgcctttt  2040
gccaaagcgc cctgctagaa tacgacgaca cgcaaggcgt catcaacatc atgtacatgc  2100
acgactcgga cgacgtcctt ttcgccctgg atccctacaa cgaagtggtg gtctcatctc  2160
cgcgaactca ctacctcatg cttttgaaaa acggtacggt actagaagta actgacgtcg  2220
tcgtggacgc caccgacagt cgtctcctca tgatgtccgt ctacgcgcta tcggccatca  2280
tcggcatcta tctgctctac cgcatgctca agacatgcga ttacaaggac gatgacgata  2340
agtgatgata ataggctgga gcctcggtgg ccatgcttct tgccccttgg gcctcccccc  2400
agcccctcct ccccttcctg cacccgtacc cccgtggtct ttgaataaag tctgagtggg  2460
cggc                                                              2464

SEQ ID NO: 226           moltype = DNA  length = 1045
FEATURE                  Location/Qualifiers
misc_feature             1..1045
                         note = Synthetic polypeptide
source                   1..1045
                         mol_type = other DNA
                         organism = synthetic construct
SEQUENCE: 226
tcaagctttt ggaccctcgt acagaagcta atacgactca ctatagggaa ataagagaga  60
aaagaagagt aagaagaaat ataagagcca ccatgtgccg ccgcccggat tgcggcttct  120
ctttctcacc tggaccggtg atactgctgt ggtgttgcct tctgctgccc attgtttcct  180
```

```
cagccgccgt cagcgtcgct cctaccgccg ccgagaaagt ccccgcggag tgccccgaac  240
taacgcgccg atgcttgttg ggtgaggtgt ttgagggtga caagtatgaa agttggctgc  300
gcccgttggt gaatgttacc gggcgcgatg gcccgctatc gcaacttatc cgttaccgtc  360
ccgttacgcc ggaggccgcc aactccgtgc tgttggacga ggctttcctg gacactctgg  420
ccctgctgta caacaatccg gatcaattgc gggccctgct gacgctgttg agctcggaca  480
cagcgccgcg ctggatgacg gtgatgcgcg gctacagcga gtgcggcgat ggctcgccgg  540
ccgtgtacac gtgcgtggac gacctgtgcc gcggctacga cctcacgcga ctgtcatacg  600
ggcgcagcat cttcacggaa cacgtgttag gcttcgagct ggtgccaccg tctctcttta  660
acgtggtggt ggccatacgc aacgaagcca cgcgtaccaa ccgcgccgtg cgtctgcccg  720
tgagcaccgc tgccgcgccc gagggcatca cgctctttta cggcctgtac aacgcagtga  780
aggaattctg cctgcgtcac cagctggacc cgccgctgct acgccaccta gataaatact  840
acgccggact gccgcccgag ctgaagcaga cgcgcgtcaa cctgccggct cactcgcgct  900
atggccctca agcagtggat gctcgctgat aataggctgg agcctcggtg gccatgcttc  960
ttgccccttg ggcctccccc cagcccctcc tccccttcct gcacccgtac ccccgtggtc  1020
tttgaataaa gtctgagtgg gcggc                                      1045
```

```
SEQ ID NO: 227         moltype = DNA  length = 1072
FEATURE                Location/Qualifiers
misc_feature           1..1072
                       note = Synthetic polypeptide
source                 1..1072
                       mol_type = other DNA
                       organism = synthetic construct
SEQUENCE: 227
tcaagctttt ggaccctcgt acagaagcta atacgactca ctatagggaa ataagagaga  60
aaagaagagt aagaagaaat ataagagcca ccatgtgccg ccgcccggat tgcggcttct  120
ctttctcacc tggaccggtg atactgctgt ggtgttgcct tctgctgccc attgtttcct  180
cagccgccgt cagcgtcgct cctaccgccg ccgagaaagt ccccgcggag tgccccgaac  240
taacgcgccg atgcttgttg ggtgaggtgt ttgagggtga caagtatgaa agttggctgc  300
gcccgttggt gaatgttacc gggcgcgatg gcccgctatc gcaacttatc cgttaccgtc  360
ccgttacgcc ggaggccgcc aactccgtgc tgttggacga ggctttcctg gacactctgg  420
ccctgctgta caacaatccg gatcaattgc gggccctgct gacgctgttg agctcggaca  480
cagcgccgcg ctggatgacg gtgatgcgcg gctacagcga gtgcggcgat ggctcgccgg  540
ccgtgtacac gtgcgtggac gacctgtgcc gcggctacga cctcacgcga ctgtcatacg  600
ggcgcagcat cttcacggaa cacgtgttag gcttcgagct ggtgccaccg tctctcttta  660
acgtggtggt ggccatacgc aacgaagcca cgcgtaccaa ccgcgccgtg cgtctgcccg  720
tgagcaccgc tgccgcgccc gagggcatca cgctctttta cggcctgtac aacgcagtga  780
aggaattctg cctgcgtcac cagctggacc cgccgctgct acgccaccta gataaatact  840
acgccggact gccgcccgag ctgaagcaga cgcgcgtcaa cctgccggct cactcgcgct  900
atggccctca agcagtggat gctcgcgatt acaaggacga tgacgataag tgatgataat  960
aggctggagc ctcggtggcc atgcttcttg ccccttgggc ctccccccag cccctcctcc  1020
ccttcctgca cccgtacccc cgtggtcttt gaataaagtc tgagtgggcg gc        1072
```

```
SEQ ID NO: 228         moltype = DNA  length = 2932
FEATURE                Location/Qualifiers
misc_feature           1..2932
                       note = Synthetic polypeptide
source                 1..2932
                       mol_type = other DNA
                       organism = synthetic construct
SEQUENCE: 228
tcaagctttt ggaccctcgt acagaagcta atacgactca ctatagggaa ataagagaga  60
aaagaagagt aagaagaaat ataagagcca ccatggaatc caggatctgg tgcctggtag  120
tctgcgttaa cttgtgtatc gtctgtctgg gtgctgcggt ttcctcatct tctactcgtg  180
gaacttctgc tactcacagt caccattcct ctcatacgac gtctgctgct cactctcgat  240
ccggttcagt ctctcaacgc gtaacttctt cccaaacggt cagccatggt gttaacgaga  300
ccatctacaa cactaccctc aagtacggag atgtggtggg ggtcaatacc accaagtacc  360
cctatcgcgt gtgttctatg gcccagggta cggatcttat tcgctttgaa cgtaatatcg  420
tctgcacctc gatgaagccc atcaatgaag acctggacga gggcatcatg gtggtctaca  480
aacgcaacat cgtcgcgcac acctttaagg tacgagtcta ccagaaggtt ttgacgtttc  540
gtcgtagcta cgcttacatc cacaccactt atctgctggg cagcaacacg gaatacgtgg  600
cgcctcctat gtgggagatt catcatatca acagccacag tcagtgctac agttcctaca  660
gccgcgttat agcaggcacg gttttcgtgg cttatcatag ggacagctat gaaaacaaaa  720
ccatgcaatt aatgcccgac gattattcca acacccacag tacccgttac gtgacggtca  780
aggatcaatg gcacagccgc ggcagcacct ggctctatcg tgagacctgt aatctgaatt  840
gtatggtgac catcactact gcgcgctcca aatatcctta tcattttttc gccacttcca  900
cgggtgacgt ggttgacatt tctcctttct acaacggaac caatcgcaat gccagctact  960
ttggagaaaa cgccgacaag tttttcattt ttccgaacta cactatcgtc tccgactttg  1020
gaagaccgaa ttctgcgtta gagacccaca ggttggtggc ttttcttgaa cgtgcggact  1080
cggtgatctc ctgggatata caggacgaaa agaatgtcac ttgtcaactc actttctggg  1140
aagcctcgga acgcaccatt cgttccgaag ccgaggactc gtatcacttt tcttctgcca  1200
aaatgaccgc cactttctta tctaagaagc aagaggtgaa catgtccgac tctgcgctgg  1260
actgcgtacg tgatgaggct ataaataagt tacagcagat tttcaatact tcatacaatc  1320
aaacatatga aaaatatgga aacgtgtccg tctttgaaac cactggtggt ttggtagtgt  1380
tctggcaagg tatcaagcaa aaatctctgg tggaactcga acgtttggcc aaccgctcca  1440
gtctgaatct tactcataat agaaccaaaa gaagtacaga tggcaacaat gcaactcatt  1500
tatccaacat ggaatcggtg cacaatctgg tctacgccca gctgcagttc acctatgaca  1560
cgttgcgcgg ttacatcaac cgggcgctgg cgcaaatcgc agaagcctgg tgtgtggatc  1620
aacggcgcac cctagaggtc ttcaaggaac tcagcaagat caacccgtca gccattctct  1680
```

```
cggccattta caacaaaccg attgccgcgc gtttcatggg tgatgtcttg ggcctggcca  1740
gctgcgtgac catcaaccaa accagcgtca aggtgctgcg tgatatgaac gtgaaggagt  1800
cgccaggacg ctgctactca cgacccgtgg tcatctttaa tttcgccaac agctcgtacg  1860
tgcagtacgg tcaactgggc gaggacaacg aaatcctgtt gggcaaccac cgcactgagg  1920
aatgtcagct tcccagcctc aagatcttca tcgccgggaa ctcggcctac gagtacgtgg  1980
actacctctt caaacgcatg attgacctca gcagtatctc caccgtcgac agcatgatcg  2040
ccctggatat cgacccgctg gaaaataccg acttcagggt actggaactt tactcgcaga  2100
aagagctgcg ttccagcaac gtttttgacc tcgaagagat catgcgcgaa ttcaactcgt  2160
acaagcagcg ggtaaagtac gtggaggaca aggtagtcga cccgctaccg ccctacctca  2220
agggtctgga cgacctcatg agcggcctgg gcgccgcggg aaaggccgtt ggcgtagcca  2280
ttggggccgt gggtggcgcg gtggcctccg tggtcgaagg cgttgccacc ttcctcaaaa  2340
accccttcgg agcgttcacc atcatcctcg tggccatagc tgtagtcatt atcacttatt  2400
tgatctatac tcgacagcgg cgtttgtgca cgcagccgct gcagaacctc tttccctatc  2460
tggtgtccgc cgacgggacc accgtgacgt cgggcagcac caaagacacg tcgttacagg  2520
ctccgccttc ctacgaggaa agtgtttata attctggtcg caaaggaccg ggaccaccgt  2580
cgtctgatgc atccacggcg gctccgcctt acaccaacga gcaggcttac cagatgcttc  2640
tggccctggc ccgtctggac gcagagcagc gagcgcagca gaacggtaca gattctttgg  2700
acggacggac tggcacgcag gacaagggac agaagcccaa cctactagac cgactgcgac  2760
atcgcaaaaa cggctaccga cacttgaaag actctgacga agaagagaac gtctgataat  2820
aggctggagc ctcggtggcc atgcttcttg ccccttgggc ctccccccag cccctcctcc  2880
ccttcctgca cccgtacccc cgtggtcttt gaataaagtc tgagtgggcg gc          2932

SEQ ID NO: 229          moltype = DNA  length = 2956
FEATURE                 Location/Qualifiers
misc_feature            1..2956
                        note = Synthetic polypeptide
source                  1..2956
                        mol_type = other DNA
                        organism = synthetic construct
SEQUENCE: 229
tcaagctttt ggaccctcgt acagaagcta atacgactca ctatagggaa ataagagaga  60
aaagaagagt aagaagaaat ataagagcca ccatggaatc caggatctgg tgcctggtag  120
tctgcgttaa cttgtgtatc gtctgtctgg gtgctgcggt ttcctcatct tctactcgtg  180
gaacttctgc tactcacagt caccattcct ctcatacgac gtctgctgct cactctcgat  240
ccggttcagt ctctcaacgc gtaacttctt cccaaacggt cagccatggt gttaacgaga  300
ccatctacaa cactaccctc aagtacggag atgtggtggg ggtcaatacc accaagtacc  360
cctatcgcgt gtgttctatg gcccagggta cggatcttat tcgctttgaa cgtaatatcg  420
tctgcacctc gatgaagccc atcaatgaag acctggacga gggcatcatg gtggtctaca  480
aacgcaacat cgtcgcgcac acctttaagg tacgagtcta ccagaaggtt ttgacgtttc  540
gtcgtagcta cgcttacatc cacaccactt atctgctggg cagcaacacg gaatacgtgg  600
cgcctcctat gtgggagatt catcatatca acagccacag tcagtgctac agttcctaca  660
gccgcgttat agcaggcacg gttttcgtgg cttatcatag ggacagctat gaaaacaaaa  720
ccatgcaatt aatgcccgac gattattcca acacccacag tacccgttac gtgacggtca  780
aggatcaatg gcacagccgc ggcagcacct ggctctatcg tgagacctgt aatctgaatt  840
gtatggtgac catcactact gcgcgctcca aatatcctta tcattttttc gccacttcca  900
cgggtgacgt ggttgacatt tctccttct acaacggaac caatcgcaat gccagctact  960
ttggagaaaa cgccgacaag tttttcattt ttccgaacta cactatcgtc tccgactttg  1020
gaagaccgaa ttctgcgtta gagacccaca ggttggtggc ttttcttgaa cgtgcggact  1080
cggtgatctc ctgggatata caggacgaag agaatgtcac ttgtcaactc actttctggg  1140
aagcctcgga acgcaccatt cgttccgaag ccgaggactc gtatcacttt tcttctgcca  1200
aaatgaccgc cactttctta tctaagaagc aagaggtgaa catgtccgac tctgcgctgg  1260
actgcgtacg tgatgaggct ataaataagt tacagcagat tttcaatact tcatacaatc  1320
aaacatatga aaaatatgga aacgtgtccg tctttgaaac cactggtggt ttggtagtgt  1380
tctggcaagg tatcaagcaa aaatctctgg tggaactcga acgtttggcc aaccgctcca  1440
gtctgaatct tactcataat agaaccaaaa gaagtacaga tggcaacaat gcaactcatt  1500
tatccaacat ggaatcggtg cacaatctgg tctacgccca gctgcagttc acctatgaca  1560
cgttgcgcgg ttacatcaac cgggcgctgg cgcaaatcgc agaagcctgg tgtgtggatc  1620
aacggcgcac cctagaggtc ttcaaggaac tcagcaagat caacccgtca gccattctct  1680
cggccattta caacaaaccg attgccgcgc gtttcatggg tgatgtcttg ggcctggcca  1740
gctgcgtgac catcaaccaa accagcgtca aggtgctgcg tgatatgaac gtgaaggagt  1800
cgccaggacg ctgctactca cgacccgtgg tcatctttaa tttcgccaac agctcgtacg  1860
tgcagtacgg tcaactgggc gaggacaacg aaatcctgtt gggcaaccac cgcactgagg  1920
aatgtcagct tcccagcctc aagatcttca tcgccgggaa ctcggcctac gagtacgtgg  1980
actacctctt caaacgcatg attgacctca gcagtatctc caccgtcgac agcatgatcg  2040
ccctggatat cgacccgctg gaaaataccg acttcagggt actggaactt tactcgcaga  2100
aagagctgcg ttccagcaac gtttttgacc tcgaagagat catgcgcgaa ttcaactcgt  2160
acaagcagcg ggtaaagtac gtggaggaca aggtagtcga cccgctaccg ccctacctca  2220
agggtctgga cgacctcatg agcggcctgg gcgccgcggg aaaggccgtt ggcgtagcca  2280
ttggggccgt gggtggcgcg gtggcctccg tggtcgaagg cgttgccacc ttcctcaaaa  2340
accccttcgg agcgttcacc atcatcctcg tggccatagc tgtagtcatt atcacttatt  2400
tgatctatac tcgacagcgg cgtttgtgca cgcagccgct gcagaacctc tttccctatc  2460
tggtgtccgc cgacgggacc accgtgacgt cgggcagcac caaagacacg tcgttacagg  2520
ctccgccttc ctacgaggaa agtgtttata attctggtcg caaaggaccg ggaccaccgt  2580
cgtctgatgc atccacggcg gctccgcctt acaccaacga gcaggcttac cagatgcttc  2640
tggccctggc ccgtctggac gcagagcagc gagcgcagca gaacggtaca gattctttgg  2700
acggacggac tggcacgcag gacaagggac agaagcccaa cctactagac cgactgcgac  2760
atcgcaaaaa cggctaccga cacttgaaag actctgacga agaagagaac gtcgattaca  2820
aggacgatga cgataagtga taataggctg gagcctcggt ggccatgctt cttgcccctt  2880
gggcctcccc ccagcccctc ctccccttcc tgcacccgta cccccgtggt ctttgaataa  2940
```

```
agtctgagtg ggcggc                                                2956

SEQ ID NO: 230         moltype = DNA  length = 2356
FEATURE                Location/Qualifiers
misc_feature           1..2356
                       note = Synthetic polypeptide
source                 1..2356
                       mol_type = other DNA
                       organism = synthetic construct
SEQUENCE: 230
tcaagctttt ggaccctcgt acagaagcta atacgactca ctatagggaa ataagagaga  60
aaagaagagt aagaagaaat ataagagcca ccatgcggcc aggcctcccc tcctacctca  120
tcatcctcgc cgtctgtctc ttcagccacc tactttcgtc acgatatggc gcagaagccg  180
tatccgaacc gctggacaaa gcgtttcacc tactgctcaa cacctacggg agacccatcc  240
gcttcctgcg tgaaaatacc acccagtgta cctacaacag cagcctccgt aacagcacgg  300
tcgtcaggga aaacgccatc agtttcaact tttccaaag ctataatcaa tactatgtat  360
tccatatgcc tcgatgtctt tttgcgggtc ctctggcgga gcagtttctg aaccaggtag  420
atctgaccga aaccctggaa agataccaac agagacttaa cacttacgcg ctggtatcca  480
aagacctggc cagctaccga tctttttcgc agcagctaaa ggcacaagac agcctaggtg  540
aacagcccac cactgtgcca ccgcccattg acctgtcaat acctcacgtt tggatgccac  600
cgcaaaccac tccacacggc tggacagaat cacataccac ctcaggacta caccgaccac  660
actttaacca gacctgtatc ctctttgatg gacacgatct actattcagc accgtcacac  720
cttgtttgca ccaaggcttt tacctcatcg acgaactacg ttacgttaaa ataacactga  780
ccgaggactt cttcgtagtt acggtgtcca tagacgacga cacacccatg ctgcttatct  840
tcggccatct tccacgcgta cttttcaaag cgccctatca acgcgacaac tttatactac  900
gacaaactga aaaacacgag ctcctggtgc tagttaagaa agatcaactg aaccgtcact  960
cttatctcaa agacccggac tttcttgacg ccgcacttga cttcaactac ctagacctca  1020
gcgcactact acgtaacagc tttcaccgtt acgccgtgga tgtactcaag agcggtcgat  1080
gtcagatgct ggaccgccgc acggtagaaa tggccttcgc ctacgcatta gcactgttcg  1140
cagcagcccg acaagaagag gccggcgccc aagtctccgt cccacgggcc ctagaccgcc  1200
aggccgcact cttacaaata caagaattta tgatcacctg cctctcacaa acaccaccac  1260
gcaccacgtt gctgctgtat cccacggccg tggacctggc caaacgagcc ctttggacac  1320
cgaatcagat caccgacatc accagcctcg tacgcctggt ctacatactc tctaaacaga  1380
atcagcaaca tctcatcccc caatgggcac tacgacagat cgccgacttt gccctaaaac  1440
tacacaaaac gcacctggcc tcttttcttt cagccttcgc acgccaagaa ctctacctca  1500
tgggcagcct cgtccactcc atgctggtac atacgacgga gagacgcgaa atcttcatcg  1560
tagaaacggg cctctgttca ttggccgagc tatcacactt tacgcagttg ttagctcatc  1620
cacaccacga atacctcagc gacctgtaca caccctgttc cagtagcggg cgacgcgatc  1680
actcgctcga acgcctcacg cgtctcttcc ccgatgccac cgtccccgct accgttcccg  1740
ccgccctctc catcctatct accatgcaac caagcacgct ggaaaccttc cccgacctgt  1800
tttgcttgcc gctcggcgaa tccttctccg cgctgaccgt ctccgaacac gtcagttata  1860
tcgtaacaaa ccagtacctg atcaaaggta tctcctaccc tgtctccacc accgtcgtag  1920
gccagagcct catcatcacc cagacggaca gtcaaactaa atgcgaactg acgcgcaaca  1980
tgcataccac acacagcatc acagtggcgc tcaacatttc gctagaaaac tgcgcctttt  2040
gccaaagcgc cctgctagaa tacgacgaca cgcaaggcgt catcaacatc atgtacatgc  2100
acgactcgga cgacgtcctt ttcgccctgg atccctacaa cgaagtggtg gtctcatctc  2160
cgcgaactca ctacctcatg cttttgaaaa acggtacggt actagaagta actgacgtcg  2220
tcgtggacgc caccgactga taataggctg gagcctcggt ggccatgctt cttgcccctt  2280
gggcctcccc ccagcccctc ctccccttcc tgcacccgta cccccgtggt ctttgaataa  2340
agtctgagtg ggcggc                                                2356

SEQ ID NO: 231         moltype = DNA  length = 2383
FEATURE                Location/Qualifiers
misc_feature           1..2383
                       note = Synthetic polypeptide
source                 1..2383
                       mol_type = other DNA
                       organism = synthetic construct
SEQUENCE: 231
tcaagctttt ggaccctcgt acagaagcta atacgactca ctatagggaa ataagagaga  60
aaagaagagt aagaagaaat ataagagcca ccatgcggcc aggcctcccc tcctacctca  120
tcatcctcgc cgtctgtctc ttcagccacc tactttcgtc acgatatggc gcagaagccg  180
tatccgaacc gctggacaaa gcgtttcacc tactgctcaa cacctacggg agacccatcc  240
gcttcctgcg tgaaaatacc acccagtgta cctacaacag cagcctccgt aacagcacgg  300
tcgtcaggga aaacgccatc agtttcaact tttccaaag ctataatcaa tactatgtat  360
tccatatgcc tcgatgtctt tttgcgggtc ctctggcgga gcagtttctg aaccaggtag  420
atctgaccga aaccctggaa agataccaac agagacttaa cacttacgcg ctggtatcca  480
aagacctggc cagctaccga tctttttcgc agcagctaaa ggcacaagac agcctaggtg  540
aacagcccac cactgtgcca ccgcccattg acctgtcaat acctcacgtt tggatgccac  600
cgcaaaccac tccacacggc tggacagaat cacataccac ctcaggacta caccgaccac  660
actttaacca gacctgtatc ctctttgatg gacacgatct actattcagc accgtcacac  720
cttgtttgca ccaaggcttt tacctcatcg acgaactacg ttacgttaaa ataacactga  780
ccgaggactt cttcgtagtt acggtgtcca tagacgacga cacacccatg ctgcttatct  840
tcggccatct tccacgcgta cttttcaaag cgccctatca acgcgacaac tttatactac  900
gacaaactga aaaacacgag ctcctggtgc tagttaagaa agatcaactg aaccgtcact  960
cttatctcaa agacccggac tttcttgacg ccgcacttga cttcaactac ctagacctca  1020
gcgcactact acgtaacagc tttcaccgtt acgccgtgga tgtactcaag agcggtcgat  1080
gtcagatgct ggaccgccgc acggtagaaa tggccttcgc ctacgcatta gcactgttcg  1140
cagcagcccg acaagaagag gccggcgccc aagtctccgt cccacgggcc ctagaccgcc  1200
```

-continued

```
aggccgcact cttacaaata caagaattta tgatcacctg cctctcacaa acaccaccac  1260
gcaccacgtt gctgctgtat cccacggccg tggacctggc caaacgagcc ctttggacac  1320
cgaatcagat caccgacatc accagcctcg tacgcctggt ctacatactc tctaaacaga  1380
atcagcaaca tctcatcccc caatgggcac tacgacagat cgccgacttt gccctaaaac  1440
tacacaaaac gcacctggcc tcttttcttt cagccttcgc acgccaagaa ctctacctca  1500
tgggcagcct cgtccactcc atgctggtac atacgacgga gagacgcgaa atcttcatcg  1560
tagaaacggg cctctgttca ttggccgagc tatcacactt tacgcagttg ttagctcatc  1620
cacaccacga atacctcagc gacctgtaca caccctgttc cagtagcggg cgacgcgatc  1680
actcgctcga acgcctcacg cgtctcttcc ccgatgccac cgtccccgct accgttcccg  1740
ccgccctctc catcctatct accatgcaac caagcacgct ggaaaccttc cccgacctgt  1800
tttgcttgcc gctcggcgaa tccttctccg cgctgaccgt ctccgaacac gtcagttata  1860
tcgtaacaaa ccagtacctg atcaaaggta tctcctaccc tgtctccacc accgtcgtag  1920
gccagagcct catcatcacc cagacggaca gtcaaactaa atgcgaactg acgcgcaaca  1980
tgcataccac acacagcatc acagtggcgc tcaacatttc gctagaaaac tgcgcctttt  2040
gccaaagcgc cctgctagaa tacgacgaca cgcaaggcgt catcaacatc atgtacatgc  2100
acgactcgga cgacgtcctt ttcgccctgg atccctacaa cgaagtggtg gtctcatctc  2160
cgcgaactca ctacctcatg cttttgaaaa acggtacggt actagaagta actgacgtcg  2220
tcgtggacgc caccgacgat tacaaggacg atgacgataa gtgatgataa taggctggag  2280
cctcggtggc catgcttctt gccccttggg cctcccccca gcccctcctc cccttcctgc  2340
acccgtaccc ccgtggtctt tgaataaagt ctgagtgggc ggc                    2383

SEQ ID NO: 232         moltype = DNA  length = 2377
FEATURE                Location/Qualifiers
misc_feature           1..2377
                       note = Synthetic polypeptide
source                 1..2377
                       mol_type = other DNA
                       organism = synthetic construct
SEQUENCE: 232
tcaagctttt ggaccctcgt acagaagcta atacgactca ctatagggaa ataagagaga  60
aaagaagagt aagaagaaat ataagagcca ccatgcggcc aggcctcccc tcctacctca  120
tcatcctcgc cgtctgtctc ttcagccacc tactttcgtc acgatatggc gcagaagccg  180
tatccgaacc gctggacaaa gcgtttcacc tactgctcaa cacctacggg agacccatcc  240
gcttcctgcg tgaaaatacc acccagtgta cctacaacag cagcctccgt aacagcacgg  300
tcgtcaggga aaacgccatc agtttcaact ttttccaaag ctataatcaa tactatgtat  360
tccatatgcc tcgatgtctt tttgcgggtc ctctggcgga gcagtttctg aaccaggtag  420
atctgaccga aaccctggaa agataccaac agagacttaa cacttacgcg ctggtatcca  480
aagacctggc cagctaccga tctttttcgc agcagctaaa ggcacaagac agcctaggtg  540
aacagcccac cactgtgcca ccgcccattg acctgtcaat acctcacgtt tggatgccac  600
cgcaaaccac tccacacggc tggacagaat cacataccac ctcaggacta caccgaccac  660
actttaacca gacctgtatc ctctttgatg gacacgatct actattcagc accgtcacac  720
cttgtttgca ccaaggcttt tacctcatcg acgaactacg ttacgttaaa ataacactga  780
ccgaggactt cttcgtagtt acggtgtcca tagacgacga cacacccatg ctgcttatct  840
tcggccatct tccacgcgta cttttcaaag cgccctatca acgcgacaac tttatactac  900
gacaaactga aaaacacgag ctcctggtgc tagttaagaa agatcaactg aaccgtcact  960
cttatctcaa agacccggac tttcttgacg ccgcacttga cttcaactac ctagacctca  1020
gcgcactact acgtaacagc tttcaccgtt acgccgtgga tgtactcaag agcggtcgat  1080
gtcagatgct ggaccgccgc acggtagaaa tggccttcgc ctacgcatta gcactgttcg  1140
cagcagcccg acaagaagag gccggcgccc aagtctccgt cccacgggcc ctagaccgcc  1200
aggccgcact cttacaaata caagaattta tgatcacctg cctctcacaa acaccaccac  1260
gcaccacgtt gctgctgtat cccacggccg tggacctggc caaacgagcc ctttggacac  1320
cgaatcagat caccgacatc accagcctcg tacgcctggt ctacatactc tctaaacaga  1380
atcagcaaca tctcatcccc caatgggcac tacgacagat cgccgacttt gccctaaaac  1440
tacacaaaac gcacctggcc tcttttcttt cagccttcgc acgccaagaa ctctacctca  1500
tgggcagcct cgtccactcc atgctggtac atacgacgga gagacgcgaa atcttcatcg  1560
tagaaacggg cctctgttca ttggccgagc tatcacactt tacgcagttg ttagctcatc  1620
cacaccacga atacctcagc gacctgtaca caccctgttc cagtagcggg cgacgcgatc  1680
actcgctcga acgcctcacg cgtctcttcc ccgatgccac cgtccccgct accgttcccg  1740
ccgccctctc catcctatct accatgcaac caagcacgct ggaaaccttc cccgacctgt  1800
tttgcttgcc gctcggcgaa tccttctccg cgctgaccgt ctccgaacac gtcagttata  1860
tcgtaacaaa ccagtacctg atcaaaggta tctcctaccc tgtctccacc accgtcgtag  1920
gccagagcct catcatcacc cagacggaca gtcaaactaa atgcgaactg acgcgcaaca  1980
tgcataccac acacagcatc acagtggcgc tcaacatttc gctagaaaac tgcgcctttt  2040
gccaaagcgc cctgctagaa tacgacgaca cgcaaggcgt catcaacatc atgtacatgc  2100
acgactcgga cgacgtcctt ttcgccctgg atccctacaa cgaagtggtg gtctcatctc  2160
cgcgaactca ctacctcatg cttttgaaaa acggtacggt actagaagta actgacgtcg  2220
tcgtggacgc caccgaccac catcaccacc atcactgatg ataataggct ggagcctcgg  2280
tggccatgct tcttgcccct tggcctccc cccagcccct cctccccttc ctgcacccgt  2340
acccccgtgg tctttgaata aagtctgagt gggcggc                           2377

SEQ ID NO: 233         moltype = DNA  length = 2287
FEATURE                Location/Qualifiers
misc_feature           1..2287
                       note = Synthetic polypeptide
source                 1..2287
                       mol_type = other DNA
                       organism = synthetic construct
SEQUENCE: 233
tcaagctttt ggaccctcgt acagaagcta atacgactca ctatagggaa ataagagaga  60
```

```
aaagaagagt aagaagaaat ataagagcca ccatggaatc caggatctgg tgcctggtag  120
tctgcgttaa cttgtgtatc gtctgtctgg gtgctgcggt ttcctcatct tctactcgtg  180
gaacttctgc tactcacagt caccattcct ctcatacgac gtctgctgct cactctcgat  240
ccggttcagt ctctcaacgc gtaacttctt cccaaacggt cagccatggt gttaacgaga  300
ccatctacaa cactaccctc aagtacggag atgtggtggg ggtcaatacc accaagtacc  360
cctatcgcgt gtgttctatg gcccagggta cggatcttat tcgctttgaa cgtaatatcg  420
tctgcacctc gatgaagccc atcaatgaag acctggacga gggcatcatg gtggtctaca  480
aacgcaacat cgtcgcgcac acctttaagg tacgagtcta ccagaaggtt ttgacgtttc  540
gtcgtagcta cgcttacatc cacaccactt atctgctggg cagcaacacg gaatacgtgg  600
cgcctcctat gtgggagatt catcatatca acagccacag tcagtgctac agttcctaca  660
gccgcgttat agcaggcacg gttttcgtgg cttatcatag ggacagctat gaaaacaaaa  720
ccatgcaatt aatgcccgac gattattcca acacccacag tacccgttac gtgacggtca  780
aggatcaatg gcacagccgc ggcagcacct ggctctatcg tgagacctgt aatctgaatt  840
gtatggtgac catcactact gcgcgctcca aatatcctta tcattttttc gccacttcca  900
cgggtgacgt ggttgacatt tctcctttct acaacggaac caatcgcaat gccagctact  960
ttggagaaaa cgccgacaag tttttcattt ttccgaacta cactatcgtc tccgactttg  1020
gaagaccgaa ttctgcgtta gagacccaca ggttggtggc ttttcttgaa cgtgcggact  1080
cggtgatctc ctgggatata caggacgaaa agaatgtcac ttgtcaactc actttctggg  1140
aagcctcgga acgcaccatt cgttccgaag ccgaggactc gtatcacttt tcttctgcca  1200
aaatgaccgc cactttctta tctaagaagc aagaggtgaa catgtccgac tctgcgctgg  1260
actgcgtacg tgatgaggct ataaataagt tacagcagat tttcaatact tcatacaatc  1320
aaacatatga aaaatatgga aacgtgtccg tctttgaaac cactggtggt ttggtagtgt  1380
tctggcaagg tatcaagcaa aaatctctgg tggaactcga acgtttggcc aaccgctcca  1440
gtctgaatct tactcataat agaaccaaaa gaagtacaga tggcaacaat gcaactcatt  1500
tatccaacat ggaatcggtg cacaatctgg tctacgccca gctgcagttc acctatgaca  1560
cgttgcgcgg ttacatcaac cgggcgctgg cgcaaatcgc agaagcctgg tgtgtggatc  1620
aacggcgcac cctagaggtc ttcaaggaac tcagcaagat caacccgtca gccattctct  1680
cggccattta caacaaaccg attgccgcgc gtttcatggg tgatgtcttg ggcctggcca  1740
gctgcgtgac catcaaccaa accagcgtca aggtgctgcg tgatatgaac gtgaaggagt  1800
cgccaggacg ctgctactca cgacccgtgg tcatctttaa tttcgccaac agctcgtacg  1860
tgcagtacgg tcaactgggc gaggacaacg aaatcctgtt gggcaaccac cgcactgagg  1920
aatgtcagct tcccagcctc aagatcttca tcgccgggaa ctcggcctac gagtacgtgg  1980
actacctctt caaacgcatg attgacctca gcagtatctc caccgtcgac agcatgatcg  2040
ccctggatat cgacccgctg gaaaataccg acttcagggt actggaactt tactcgcaga  2100
aagagctgcg ttccagcaac gtttttgacc tcgaagagat catgcgcgaa ttcaactcgt  2160
acaagcagtg ataataggct ggagcctcgg tggccatgct tcttgcccct tgggcctccc  2220
cccagcccct cctccccttc ctgcacccgt acccccgtgg tctttgaata aagtctgagt  2280
gggcggc                                                           2287

SEQ ID NO: 234          moltype = DNA  length = 2311
FEATURE                 Location/Qualifiers
misc_feature            1..2311
                        note = Synthetic polypeptide
source                  1..2311
                        mol_type = other DNA
                        organism = synthetic construct
SEQUENCE: 234
tcaagctttt ggaccctcgt acagaagcta atacgactca ctatagggaa ataagagaga  60
aaagaagagt aagaagaaat ataagagcca ccatggaatc caggatctgg tgcctggtag  120
tctgcgttaa cttgtgtatc gtctgtctgg gtgctgcggt ttcctcatct tctactcgtg  180
gaacttctgc tactcacagt caccattcct ctcatacgac gtctgctgct cactctcgat  240
ccggttcagt ctctcaacgc gtaacttctt cccaaacggt cagccatggt gttaacgaga  300
ccatctacaa cactaccctc aagtacggag atgtggtggg ggtcaatacc accaagtacc  360
cctatcgcgt gtgttctatg gcccagggta cggatcttat tcgctttgaa cgtaatatcg  420
tctgcacctc gatgaagccc atcaatgaag acctggacga gggcatcatg gtggtctaca  480
aacgcaacat cgtcgcgcac acctttaagg tacgagtcta ccagaaggtt ttgacgtttc  540
gtcgtagcta cgcttacatc cacaccactt atctgctggg cagcaacacg gaatacgtgg  600
cgcctcctat gtgggagatt catcatatca acagccacag tcagtgctac agttcctaca  660
gccgcgttat agcaggcacg gttttcgtgg cttatcatag ggacagctat gaaaacaaaa  720
ccatgcaatt aatgcccgac gattattcca acacccacag tacccgttac gtgacggtca  780
aggatcaatg gcacagccgc ggcagcacct ggctctatcg tgagacctgt aatctgaatt  840
gtatggtgac catcactact gcgcgctcca aatatcctta tcattttttc gccacttcca  900
cgggtgacgt ggttgacatt tctcctttct acaacggaac caatcgcaat gccagctact  960
ttggagaaaa cgccgacaag tttttcattt ttccgaacta cactatcgtc tccgactttg  1020
gaagaccgaa ttctgcgtta gagacccaca ggttggtggc ttttcttgaa cgtgcggact  1080
cggtgatctc ctgggatata caggacgaaa agaatgtcac ttgtcaactc actttctggg  1140
aagcctcgga acgcaccatt cgttccgaag ccgaggactc gtatcacttt tcttctgcca  1200
aaatgaccgc cactttctta tctaagaagc aagaggtgaa catgtccgac tctgcgctgg  1260
actgcgtacg tgatgaggct ataaataagt tacagcagat tttcaatact tcatacaatc  1320
aaacatatga aaaatatgga aacgtgtccg tctttgaaac cactggtggt ttggtagtgt  1380
tctggcaagg tatcaagcaa aaatctctgg tggaactcga acgtttggcc aaccgctcca  1440
gtctgaatct tactcataat agaaccaaaa gaagtacaga tggcaacaat gcaactcatt  1500
tatccaacat ggaatcggtg cacaatctgg tctacgccca gctgcagttc acctatgaca  1560
cgttgcgcgg ttacatcaac cgggcgctgg cgcaaatcgc agaagcctgg tgtgtggatc  1620
aacggcgcac cctagaggtc ttcaaggaac tcagcaagat caacccgtca gccattctct  1680
cggccattta caacaaaccg attgccgcgc gtttcatggg tgatgtcttg ggcctggcca  1740
gctgcgtgac catcaaccaa accagcgtca aggtgctgcg tgatatgaac gtgaaggagt  1800
cgccaggacg ctgctactca cgacccgtgg tcatctttaa tttcgccaac agctcgtacg  1860
tgcagtacgg tcaactgggc gaggacaacg aaatcctgtt gggcaaccac cgcactgagg  1920
```

-continued

```
aatgtcagct tcccagcctc aagatcttca tcgccgggaa ctcggcctac gagtacgtgg  1980
actacctctt caaacgcatg attgacctca gcagtatctc caccgtcgac agcatgatcg  2040
ccctggatat cgacccgctg gaaaataccg acttcagggt actggaactt tactcgcaga  2100
aagagctgcg ttccagcaac gtttttgacc tcgaagagat catgcgcgaa ttcaactcgt  2160
acaagcagga ttacaaggac gatgacgata agtgataata ggctggagcc tcggtggcca  2220
tgcttcttgc cccttgggcc tccccccagc ccctcctccc cttcctgcac ccgtaccccc  2280
gtggtctttg aataaagtct gagtgggcgg c                                 2311
```

```
SEQ ID NO: 235         moltype = DNA  length = 2305
FEATURE                Location/Qualifiers
misc_feature           1..2305
                       note = Synthetic polypeptide
source                 1..2305
                       mol_type = other DNA
                       organism = synthetic construct
SEQUENCE: 235
tcaagctttt ggaccctcgt acagaagcta atacgactca ctatagggaa ataagagaga  60
aaagaagagt aagaagaaat ataagagcca ccatggaatc caggatctgg tgcctggtag  120
tctgcgttaa cttgtgtatc gtctgtctgg gtgctgcggt ttcctcatct tctactcgtg  180
gaacttctgc tactcacagt caccattcct ctcatacgac gtctgctgct cactctcgat  240
ccggttcagt ctctcaacgc gtaacttctt cccaaacggt cagccatggt gttaacgaga  300
ccatctacaa cactaccctc aagtacggag atgtggtggg ggtcaatacc accaagtacc  360
cctatcgcgt gtgttctatg gcccagggta cggatcttat tcgctttgaa cgtaatatcg  420
tctgcacctc gatgaagccc atcaatgaag acctggacga gggcatcatg gtggtctaca  480
aacgcaacat cgtcgcgcac acctttaagg tacgagtcta ccagaaggtt ttgacgtttc  540
gtcgtagcta cgcttacatc cacaccactt atctgctggg cagcaacacg gaatacgtgg  600
cgcctcctat gtgggagatt catcatatca acagccacag tcagtgctac agttcctaca  660
gccgcgttat agcaggcacg gttttcgtgg cttatcatag ggacagctat gaaaacaaaa  720
ccatgcaatt aatgcccgac gattattcca acacccacag tacccgttac gtgacggtca  780
aggatcaatg gcacagccgc ggcagcacct ggctctatcg tgagacctgt aatctgaatt  840
gtatggtgac catcactact gcgcgctcca aatatcctta tcatttttc gccacttcca  900
cgggtgacgt ggttgacatt tctcctttct acaacggaac caatcgcaat gccagctact  960
ttggagaaaa cgccgacaag tttttcattt ttccgaacta cactatcgtc tccgactttg  1020
gaagaccgaa ttctgcgtta gagacccaca ggttggtggc ttttcttgaa cgtgcggact  1080
cggtgatctc ctgggatata caggacgaaa agaatgtcac ttgtcaactc actttctggg  1140
aagcctcgga acgcaccatt cgttccgaag ccgaggactc gtatcacttt tcttctgcca  1200
aaatgaccgc cactttctta tctaagaagc aagaggtgaa catgtccgac tctgcgctgg  1260
actgcgtacg tgatgaggct ataaataagt tacagcagat tttcaatact tcatacaatc  1320
aaacatatga aaaatatgga aacgtgtccg tctttgaaac cactggtggt ttggtagtgt  1380
tctggcaagg tatcaagcaa aaatctctgg tggaactcga acgtttggcc aaccgctcca  1440
gtctgaatct tactcataat agaaccaaaa gaagtacaga tggcaacaat gcaactcatt  1500
tatccaacat ggaatcggtg cacaatctgg tctacgccca gctgcagttc acctatgaca  1560
cgttgcgcgg ttacatcaac cgggcgctgg cgcaaatcgc agaagcctgg tgtgtggatc  1620
aacggcgcac cctagaggtc ttcaaggaac tcagcaagat caacccgtca gccattctct  1680
cggccattta caacaaaccg attgccgcgc gtttcatggg tgatgtcttg ggcctggcca  1740
gctgcgtgac catcaaccaa accagcgtca aggtgctgcg tgatatgaac gtgaaggagt  1800
cgccaggacg ctgctactca cgacccgtgg tcatctttaa tttcgccaac agctcgtacg  1860
tgcagtacgg tcaactgggc gaggacaacg aaatcctgtt gggcaaccac cgcactgagg  1920
aatgtcagct tcccagcctc aagatcttca tcgccgggaa ctcggcctac gagtacgtgg  1980
actacctctt caaacgcatg attgacctca gcagtatctc caccgtcgac agcatgatcg  2040
ccctggatat cgacccgctg gaaaataccg acttcagggt actggaactt tactcgcaga  2100
aagagctgcg ttccagcaac gtttttgacc tcgaagagat catgcgcgaa ttcaactcgt  2160
acaagcagca ccatcaccac catcactgat aataggctgg agcctcggtg gccatgcttc  2220
ttgccccttg ggcctccccc cagcccctcc tccccttcct gcacccgtac ccccgtggtc  2280
tttgaataaa gtctgagtgg gcggc                                        2305
```

```
SEQ ID NO: 236         moltype = DNA  length = 724
FEATURE                Location/Qualifiers
misc_feature           1..724
                       note = Synthetic polypeptide
source                 1..724
                       mol_type = other DNA
                       organism = synthetic construct
SEQUENCE: 236
tcaagctttt ggaccctcgt acagaagcta atacgactca ctatagggaa ataagagaga  60
aaagaagagt aagaagaaat ataagagcca ccatgagtcc caaagatctg acgccgttct  120
tgacggcgtt gtggctgcta ttgggtcaca gccgcgtgcc gcgggtgcgc gcagaagaat  180
gttgcgaatt cataaacgtc aaccacccgc cggaacgctg ttacgatttc aaaatgtgca  240
atcgcttcac cgtcgcgctg cggtgtccgg acggcgaagt ctgctacagt cccgagaaaa  300
cggctgagat tcgcgggatc gtcaccacca tgacccattc attgacacgc caggtcgtac  360
acaacaaact gacgagctgc aactacaatc cgttatacct cgaagctgac gggcgaatac  420
gctgcggcaa agtaaacgac aaggcgcagt acctgctggg cgccgctggc agcgttccct  480
atcgatggat caatctggaa tacgacaaga taacccggat cgtgggcctg gatcagtacc  540
tggagagcgt taagaaacac aaacggctgg atgtgtgccg cgctaaaatg ggctatatgc  600
tgcagtgata ataggctgga gcctcggtgg ccatgcttct tgccccttgg gcctcccccc  660
agcccctcct ccccttcctg cacccgtacc cccgtggtct ttgaataaag tctgagtggg  720
cggc                                                               724
```

```
SEQ ID NO: 237         moltype = DNA  length = 748
```

```
FEATURE                 Location/Qualifiers
misc_feature            1..748
                        note = Synthetic polypeptide
source                  1..748
                        mol_type = other DNA
                        organism = synthetic construct
SEQUENCE: 237
tcaagctttt ggaccctcgt acagaagcta atacgactca ctatagggaa ataagagaga  60
aaagaagagt aagaagaaat ataagagcca ccatgagtcc caaagatctg acgccgttct  120
tgacggcgtt gtggctgcta ttgggtcaca gccgcgtgcc gcgggtgcgc gcagaagaat  180
gttgcgaatt cataaacgtc aaccacccgc cggaacgctg ttacgatttc aaaatgtgca  240
atcgcttcac cgtcgcgctg cggtgtccgg acggcgaagt ctgctacagt cccgagaaaa  300
cggctgagat tcgcgggatc gtcaccacca tgacccattc attgacacgc caggtcgtac  360
acaacaaact gacgagctgc aactacaatc cgttatacct cgaagctgac gggcgaatac  420
gctgcggcaa agtaaacgac aaggcgcagt acctgctggg cgccgctggc agcgttccct  480
atcgatggat caatctggaa tacgacaaga taacccggat cgtgggcctg gatcagtacc  540
tggagagcgt taagaaacac aaacggctgg atgtgtgccg cgctaaaatg ggctatatgc  600
tgcaggatta caaggacgat gacgataagt gataataggc tggagcctcg gtggccatgc  660
ttcttgcccc ttgggcctcc ccccagcccc tcctcccctt cctgcacccg tacccccgtg  720
gtctttgaat aaagtctgag tgggcggc                                     748

SEQ ID NO: 238          moltype = DNA  length = 853
FEATURE                 Location/Qualifiers
misc_feature            1..853
                        note = Synthetic polypeptide
source                  1..853
                        mol_type = other DNA
                        organism = synthetic construct
SEQUENCE: 238
tcaagctttt ggaccctcgt acagaagcta atacgactca ctatagggaa ataagagaga  60
aaagaagagt aagaagaaat ataagagcca ccatgctgcg gcttctgctt cgtcaccact  120
ttcactgcct gcttctgtgc gcggtttggg caacgccctg tctggcgtct ccgtggtcga  180
cgctaacagc aaaccagaat ccgtccccgc catggtctaa actgacgtat tccaaaccgc  240
atgacgcggc gacgttttac tgtccttttc tctatccctc gcccccacga tccccccttgc  300
aattctcggg gttccagcgg gtatcaacgg gtcccgagtg tcgcaacgag accctgtatc  360
tgctgtacaa ccgggaaggc cagaccttgg tggagagaag ctccacctgg gtgaaaaagg  420
tgatctggta cctgagcggt cggaaccaaa ccatcctcca acggatgccc cgaacggctt  480
cgaaaccgag cgacggaaac gtgcagatca gcgtggaaga cgccaagatt tttggagcgc  540
acatggtgcc caagcagacc aagctgctac gcttcgtcgt caacgatggc acacgttatc  600
agatgtgtgt gatgaagctg gagagctggg ctcacgtctt ccgggactac agcgtgtctt  660
ttcaggtgcg attgacgttc accgaggcca ataaccagac ttacaccttc tgcacccatc  720
ccaatctcat cgtttgataa taggctggag cctcggtggc catgcttctt gccccttggg  780
cctcccccca gcccctcctc cccttcctgc acccgtaccc ccgtggtctt tgaataaagt  840
ctgagtgggc ggc                                                     853

SEQ ID NO: 239          moltype = DNA  length = 880
FEATURE                 Location/Qualifiers
misc_feature            1..880
                        note = Synthetic polypeptide
source                  1..880
                        mol_type = other DNA
                        organism = synthetic construct
SEQUENCE: 239
tcaagctttt ggaccctcgt acagaagcta atacgactca ctatagggaa ataagagaga  60
aaagaagagt aagaagaaat ataagagcca ccatgctgcg gcttctgctt cgtcaccact  120
ttcactgcct gcttctgtgc gcggtttggg caacgccctg tctggcgtct ccgtggtcga  180
cgctaacagc aaaccagaat ccgtccccgc catggtctaa actgacgtat tccaaaccgc  240
atgacgcggc gacgttttac tgtccttttc tctatccctc gcccccacga tccccccttgc  300
aattctcggg gttccagcgg gtatcaacgg gtcccgagtg tcgcaacgag accctgtatc  360
tgctgtacaa ccgggaaggc cagaccttgg tggagagaag ctccacctgg gtgaaaaagg  420
tgatctggta cctgagcggt cggaaccaaa ccatcctcca acggatgccc cgaacggctt  480
cgaaaccgag cgacggaaac gtgcagatca gcgtggaaga cgccaagatt tttggagcgc  540
acatggtgcc caagcagacc aagctgctac gcttcgtcgt caacgatggc acacgttatc  600
agatgtgtgt gatgaagctg gagagctggg ctcacgtctt ccgggactac agcgtgtctt  660
ttcaggtgcg attgacgttc accgaggcca ataaccagac ttacaccttc tgcacccatc  720
ccaatctcat cgttgattac aaggacgatg acgataagtg atgataatag gctggagcct  780
cggtggccat gcttcttgcc ccttgggcct ccccccagcc cctcctcccc ttcctgcacc  840
cgtacccccg tggtctttga ataaagtctg agtgggcggc                       880

SEQ ID NO: 240          moltype = DNA  length = 598
FEATURE                 Location/Qualifiers
misc_feature            1..598
                        note = Synthetic polypeptide
source                  1..598
                        mol_type = other DNA
                        organism = synthetic construct
SEQUENCE: 240
tcaagctttt ggaccctcgt acagaagcta atacgactca ctatagggaa ataagagaga  60
aaagaagagt aagaagaaat ataagagcca ccatgcggct gtgtcgggtg tggctgtctg  120
```

```
tttgtctgtg cgccgtggtg ctgggtcagt gccagcggga aaccgcggaa aaaaacgatt  180
attaccgagt accgcattac tgggacgcgt gctctcgcgc gctgcccgac caaacccgtt  240
acaagtatgt ggaacagctc gtggacctca cgttgaacta ccactacgat gcgagccacg  300
gcttggacaa ctttgacgtg ctcaagagaa tcaacgtgac cgaggtgtcg ttgctcatca  360
gcgactttag acgtcagaac cgtcgcggcg gcaccaacaa aaggaccacg ttcaacgccg  420
ccggttcgct ggcgccacac gcccggagcc tcgagttcag cgtgcggctc tttgccaact  480
gataataggc tggagcctcg gtggccatgc ttcttgcccc ttgggcctcc ccccagcccc  540
tcctcccctt cctgcacccg tacccccgtg gtctttgaat aaagtctgag tgggcggc    598

SEQ ID NO: 241         moltype = DNA  length = 625
FEATURE                Location/Qualifiers
misc_feature           1..625
                       note = Synthetic polypeptide
source                 1..625
                       mol_type = other DNA
                       organism = synthetic construct
SEQUENCE: 241
tcaagctttt ggaccctcgt acagaagcta atacgactca ctatagggaa ataagagaga  60
aaagaagagt aagaagaaat ataagagcca ccatgcggct gtgtcgggtg tggctgtctg  120
tttgtctgtg cgccgtggtg ctgggtcagt gccagcggga aaccgcggaa aaaaacgatt  180
attaccgagt accgcattac tgggacgcgt gctctcgcgc gctgcccgac caaacccgtt  240
acaagtatgt ggaacagctc gtggacctca cgttgaacta ccactacgat gcgagccacg  300
gcttggacaa ctttgacgtg ctcaagagaa tcaacgtgac cgaggtgtcg ttgctcatca  360
gcgactttag acgtcagaac cgtcgcggcg gcaccaacaa aaggaccacg ttcaacgccg  420
ccggttcgct ggcgccacac gcccggagcc tcgagttcag cgtgcggctc tttgccaacg  480
attacaagga cgatgacgat aagtgatgat aataggctgg agcctcggtg gccatgcttc  540
ttgccccttg ggcctccccc cagcccctcc tccccttcct gcacccgtac ccccgtggtc  600
tttgaataaa gtctgagtgg gcggc                                       625

SEQ ID NO: 242         moltype = DNA  length = 2434
FEATURE                Location/Qualifiers
misc_feature           1..2434
                       note = Synthetic polypeptide
source                 1..2434
                       mol_type = other DNA
                       organism = synthetic construct
SEQUENCE: 242
tcaagctttt ggaccctcgt acagaagcta atacgactca ctatagggac agacgagaga  60
gaagcacgcc aattctgcct gcttaagcca tgcggccagg cctcccctcc tacctcatca  120
tcctcgccgt ctgtctcttc agccacctac tttcgtcacg atatggcgca gaagccgtat  180
ccgaaccgct ggacaaagcg tttcacctac tgctcaacac ctacgggaga cccatccgct  240
tcctgcgtga aaataccacc cagtgtacct acaacagcag cctccgtaac agcacggtcg  300
tcagggaaaa cgccatcagt ttcaactttt tccaaagcta taatcaatac tatgtattcc  360
atatgcctcg atgtcttttt gcgggtcctc tggcggagca gtttctgaac caggtagatc  420
tgaccgaaac cctggaaaga taccaacaga gacttaacac ttacgcgctg gtatccaaag  480
acctggccag ctaccgatct ttttcgcagc agctaaaggc acaagacagc ctaggtgaac  540
agcccaccac tgtgccaccg cccattgacc tgtcaatacc tcacgtttgg atgccaccgc  600
aaaccactcc acacggctgg acagaatcac ataccacctc aggactacac cgaccacact  660
ttaaccagac ctgtatcctc tttgatggac acgatctact attcagcacc gtcacacctt  720
gtttgcacca aggcttttac ctcatcgacg aactacgtta cgttaaaata acactgaccg  780
aggacttctt cgtagttacg gtgtccatag acgacgacac acccatgctg cttatcttcg  840
gccatcttcc acgcgtactt ttcaaagcgc cctatcaacg cgacaacttt atactacgac  900
aaactgaaaa acacgagctc ctggtgctag ttaagaaaga tcaactgaac cgtcactctt  960
atctcaaaga cccggacttt cttgacgccg cacttgactt caactaccta gacctcagcg  1020
cactactacg taacagcttt caccgttacg ccgtggatgt actcaagagc ggtcgatgtc  1080
agatgctgga ccgccgcacg gtagaaatgg ccttcgccta cgcattagca ctgttcgcag  1140
cagcccgaca agaagaggcc ggcgcccaag tctccgtccc acgggcccta gaccgccagg  1200
ccgcactctt acaaatacaa gaatttatga tcacctgcct ctcacaaaca ccaccacgca  1260
ccacgttgct gctgtatccc acggccgtgg acctggccaa acgagccctt tggacaccga  1320
atcagatcac cgacatcacc agcctcgtac gcctggtcta catactctct aaacagaatc  1380
agcaacatct catcccccaa tggcactac gacagatcgc cgactttgcc ctaaaactac  1440
acaaaacgca cctggcctct ttctttcag ccttcgcacg ccaagaactc tacctcatgg  1500
gcagcctcgt ccactccatg ctggtacata cgacggagag acgcgaaatc ttcatcgtag  1560
aaacgggcct ctgttcattg gccgagctat cacactttac gcagttgtta gctcatccac  1620
accacgaata cctcagcgac ctgtacacac cctgttccag tagcgggcga cgcgatcact  1680
cgctcgaacg cctcacgcgt ctcttccccg atgccaccgt ccccgctacc gttcccgccg  1740
ccctctccat cctatctacc atgcaaccaa gcacgctgga aaccttcccc gacctgtttt  1800
gcttgccgct cggcgaatcc ttctccgcgc tgaccgtctc cgaacacgtc agttatatcg  1860
taacaaacca gtacctgatc aaaggtatct cctaccctgt ctccaccacc gtcgtaggcc  1920
agagcctcat catcacccag acggacagtc aaactaaatg cgaactgacg cgcaacatgc  1980
ataccacaca cagcatcaca gtggcgctca acatttcgct agaaaactgc gccttttgcc  2040
aaagcgccct gctagaatac gacgacacgc aaggcgtcat caacatcatg tacatgcacg  2100
actcggacga cgtccttttc gccctggatc cctacaacga agtggtggtc tcatctccgc  2160
gaactcacta cctcatgctt ttgaaaaacg gtacggtact agaagtaact gacgtcgtcg  2220
tggacgccac cgacagtcgt ctcctcatga tgtccgtcta cgcgctatcg gccatcatcg  2280
gcatctatct gctctaccgc atgctcaaga catgctgata ataggctgga gcctcggtgg  2340
ccatgcttct tgccccttgg gcctccccc agcccctcct ccccttcctg cacccgtacc  2400
cccgtggtct ttgaataaag tctgagtggg cggc                             2434
```

```
SEQ ID NO: 243          moltype = DNA  length = 1044
FEATURE                 Location/Qualifiers
misc_feature            1..1044
                        note = Synthetic polypeptide
source                  1..1044
                        mol_type = other DNA
                        organism = synthetic construct
SEQUENCE: 243
tcaagctttt ggaccctcgt acagaagcta atacgactca ctatagggct taagcaggca  60
gaattggccc ttagcctgta ccagccgaac catgtgccgc cgcccggatt gcggcttctc  120
tttctcacct ggaccggtga tactgctgtg gtgttgcctt ctgctgccca ttgtttcctc  180
agccgccgtc agcgtcgctc ctaccgccgc cgagaaagtc cccgcggagt gccccgaact  240
aacgcgccga tgcttgttgg gtgaggtgtt tgagggtgac aagtatgaaa gttggctgcg  300
cccgttggtg aatgttaccg ggcgcgatgg cccgctatcg caacttatcc gttaccgtcc  360
cgttacgccg gaggccgcca actccgtgct gttggacgag gctttcctgg acactctggc  420
cctgctgtac aacaatccgg atcaattgcg ggccctgctg acgctgttga gctcggacac  480
agcgccgcgc tggatgacgg tgatgcgcgg ctacagcgag tgcggcgatg gctcgccggc  540
cgtgtacacg tgcgtggacg acctgtgccg cggctacgac ctcacgcgac tgtcatacgg  600
gcgcagcatc ttcacggaac acgtgttagg cttcgagctg gtgccaccgt ctctctttaa  660
cgtggtggtg gccatacgca acgaagccac gcgtaccaac cgcgccgtgc gtctgcccgt  720
gagcaccgct gccgcgcccg agggcatcac gctcttttac ggcctgtaca acgcagtgaa  780
ggaattctgc ctgcgtcacc agctggaccc gccgctgcta cgccacctag ataaatacta  840
cgccggactg ccgcccgagc tgaagcagac gcgcgtcaac ctgccggctc actcgcgcta  900
tggccctcaa gcagtggatg ctcgctgata ataggctgga gcctcggtgg ccatgcttct  960
tgccccttgg gcctcccccc agcccctcct ccccttcctg cacccgtacc cccgtggtct  1020
ttgaataaag tctgagtggg cggc                                        1044

SEQ ID NO: 244          moltype = DNA  length = 1045
FEATURE                 Location/Qualifiers
misc_feature            1..1045
                        note = Synthetic polypeptide
source                  1..1045
                        mol_type = other DNA
                        organism = synthetic construct
SEQUENCE: 244
tcaagctttt ggaccctcgt acagaagcta atacgactca ctatagggtg gctcttatat  60
ttcttcttac tcttcttttc tctcttattt ccatgtgccg ccgcccggat tgcggcttct  120
ctttctcacc tggaccggtg atactgctgt ggtgttgcct tctgctgccc attgtttcct  180
cagccgccgt cagcgtcgct cctaccgccg ccgagaaagt ccccgcggag tgccccgaac  240
taacgcgccg atgcttgttg ggtgaggtgt ttgagggtga caagtatgaa agttggctgc  300
gcccgttggt gaatgttacc gggcgcgatg gcccgctatc gcaacttatc cgttaccgtc  360
ccgttacgcc ggaggccgcc aactccgtgc tgttggacga ggctttcctg gacactctgg  420
ccctgctgta caacaatccg gatcaattgc gggccctgct gacgctgttg agctcggaca  480
cagcgccgcg ctggatgacg gtgatgcgcg gctacagcga gtgcggcgat ggctcgccgg  540
ccgtgtacac gtgcgtggac gacctgtgcc gcggctacga cctcacgcga ctgtcatacg  600
ggcgcagcat cttcacggaa cacgtgttag gcttcgagct ggtgccaccg tctctcttta  660
acgtggtggt ggccatacgc aacgaagcca cgcgtaccaa ccgcgccgtg cgtctgcccg  720
tgagcaccgc tgccgcgccc gagggcatca cgctctttta cggcctgtac aacgcagtga  780
aggaattctg cctgcgtcac cagctggacc cgccgctgct acgccaccta gataaatact  840
acgccggact gccgcccgag ctgaagcaga cgcgcgtcaa cctgccggct cactcgcgct  900
atggccctca agcagtggat gctcgctgat aataggctgg agcctcggtg gccatgcttc  960
ttgccccttg ggcctccccc cagcccctcc tccccttcct gcacccgtac ccccgtggtc  1020
tttgaataaa gtctgagtgg gcggc                                       1045

SEQ ID NO: 245          moltype = DNA  length = 722
FEATURE                 Location/Qualifiers
misc_feature            1..722
                        note = Synthetic polypeptide
source                  1..722
                        mol_type = other DNA
                        organism = synthetic construct
SEQUENCE: 245
tcaagctttt ggaccctcgt acagaagcta atacgactca ctatagggtt cggctggtac  60
aggctaacca gaagacagat aagagcctcc atgagtccca aagatctgac gccgttcttg  120
acggcgttgt ggctgctatt gggtcacagc cgcgtgccgc gggtgcgcgc agaagaatgt  180
tgcgaattca taaacgtcaa ccacccgccg gaacgctgtt acgatttcaa aatgtgcaat  240
cgcttcaccg tcgcgctgcg gtgtccggac ggcgaagtct gctacagtcc cgagaaaacg  300
gctgagattc gcgggatcgt caccaccatg acccattcat tgacacgcca ggtcgtacac  360
aacaaactga cgagctgcaa ctacaatccg ttatacctcg aagctgacgg gcgaatacgc  420
tgcggcaaag taaacgacaa ggcgcagtac ctgctgggcg ccgctggcag cgttccctat  480
cgatggatca atctggaata cgacaagata acccggatcg tgggcctgga tcagtacctg  540
gagagcgtta agaaacacaa acggctggat gtgtgccgcg ctaaaatggg ctatatgctg  600
cagtgataat aggctggagc ctcggtggcc atgcttcttg ccccttgggc ctccccccag  660
cccctcctcc ccttcctgca cccgtacccc cgtggtcttt gaataaagtc tgagtgggcg  720
gc                                                                722

SEQ ID NO: 246          moltype = DNA  length = 853
FEATURE                 Location/Qualifiers
misc_feature            1..853
```

-continued

```
                         note = Synthetic polypeptide
source                   1..853
                         mol_type = other DNA
                         organism = synthetic construct
SEQUENCE: 246
tcaagctttt ggaccctcgt acagaagcta atacgactca ctatagggtg gctcttatat  60
ttcttcttag tccgaattcg aagtacggct acatgctgcg gcttctgctt cgtcaccact  120
ttcactgcct gcttctgtgc gcggtttggg caacgccctg tctggcgtct ccgtggtcga  180
cgctaacagc aaaccagaat ccgtccccgc catggtctaa actgacgtat tccaaaccgc  240
atgacgcggc gacgttttac tgtccttttc tctatccctc gcccccacga tccccccttgc  300
aattctcggg gttccagcgg gtatcaacgg gtcccgagtg tcgcaacgag accctgtatc  360
tgctgtacaa ccgggaaggc cagaccttgg tggagagaag ctccacctgg gtgaaaaagg  420
tgatctggta cctgagcggt cggaaccaaa ccatcctcca acggatgccc cgaacggctt  480
cgaaaccgag cgacggaaac gtgcagatca gcgtggaaga cgccaagatt tttggagcgc  540
acatggtgcc caagcagacc aagctgctac gcttcgtcgt caacgatggc acacgttatc  600
agatgtgtgt gatgaagctg gagagctggg ctcacgtctt ccgggactac agcgtgtctt  660
ttcaggtgcg attgacgttc accgaggcca ataaccagac ttacaccttc tgcacccatc  720
ccaatctcat cgtttgataa taggctggag cctcggtggc catgcttctt gccccttggg  780
cctcccccca gcccctcctc cccttcctgc acccgtaccc ccgtggtctt tgaataaagt  840
ctgagtgggc ggc                                                     853

SEQ ID NO: 247           moltype = DNA  length = 853
FEATURE                  Location/Qualifiers
misc_feature             1..853
                         note = Synthetic polypeptide
source                   1..853
                         mol_type = other DNA
                         organism = synthetic construct
SEQUENCE: 247
tcaagctttt ggaccctcgt acagaagcta atacgactca ctatagggtg gctcttatat  60
ttcttcttag tccgaattcg aagtacggct acatgctgcg gcttctgctt cgtcaccact  120
ttcactgcct gcttctgtgc gcggtttggg caacgccctg tctggcgtct ccgtggtcga  180
cgctaacagc aaaccagaat ccgtccccgc catggtctaa actgacgtat tccaaaccgc  240
atgacgcggc gacgttttac tgtccttttc tctatccctc gcccccacga tccccccttgc  300
aattctcggg gttccagcgg gtatcaacgg gtcccgagtg tcgcaacgag accctgtatc  360
tgctgtacaa ccgggaaggc cagaccttgg tggagagaag ctccacctgg gtgaaaaagg  420
tgatctggta cctgagcggt cggaaccaaa ccatcctcca acggatgccc cgaacggctt  480
cgaaaccgag cgacggaaac gtgcagatca gcgtggaaga cgccaagatt tttggagcgc  540
acatggtgcc caagcagacc aagctgctac gcttcgtcgt caacgatggc acacgttatc  600
agatgtgtgt gatgaagctg gagagctggg ctcacgtctt ccgggactac agcgtgtctt  660
ttcaggtgcg attgacgttc accgaggcca ataaccagac ttacaccttc tgcacccatc  720
ccaatctcat cgtttgataa taggctggag cctcggtggc catgcttctt gccccttggg  780
cctcccccca gcccctcctc cccttcctgc acccgtaccc ccgtggtctt tgaataaagt  840
ctgagtgggc ggc                                                     853

SEQ ID NO: 248           moltype = DNA  length = 597
FEATURE                  Location/Qualifiers
misc_feature             1..597
                         note = Synthetic polypeptide
source                   1..597
                         mol_type = other DNA
                         organism = synthetic construct
SEQUENCE: 248
tcaagctttt ggaccctcgt acagaagcta atacgactca ctatagggta gccgtacttc  60
gaattcggac aagcttctct ctcgtctgtc catgcggctg tgtcgggtgt ggctgtctgt  120
ttgtctgtgc gccgtggtgc tgggtcagtg ccagcgggaa accgcggaaa aaaacgatta  180
ttaccgagta ccgcattact gggacgcgtg ctctcgcgcg ctgcccgacc aaacccgtta  240
caagtatgtg gaacagctcg tggacctcac gttgaactac cactacgatg cgagccacgg  300
cttggacaac tttgacgtgc tcaagagaat caacgtgacc gaggtgtcgt tgctcatcag  360
cgactttaga cgtcagaacc gtcgcggcgg caccaacaaa aggaccacgt tcaacgccgc  420
cggttcgctg gcgccacacg cccggagcct cgagttcagc gtgcggctct ttgccaactg  480
ataataggct ggagcctcgg tggccatgct tcttgcccct tgggcctccc cccagcccct  540
cctccccttc ctgcacccgt acccccgtgg tctttgaata aagtctgagt gggcggc     597

SEQ ID NO: 249           moltype = DNA  length = 597
FEATURE                  Location/Qualifiers
misc_feature             1..597
                         note = Synthetic polypeptide
source                   1..597
                         mol_type = other DNA
                         organism = synthetic construct
SEQUENCE: 249
tcaagctttt ggaccctcgt acagaagcta atacgactca ctatagggta gccgtacttc  60
gaattcggac tttcttttct ctcttatttc catgcggctg tgtcgggtgt ggctgtctgt  120
ttgtctgtgc gccgtggtgc tgggtcagtg ccagcgggaa accgcggaaa aaaacgatta  180
ttaccgagta ccgcattact gggacgcgtg ctctcgcgcg ctgcccgacc aaacccgtta  240
caagtatgtg gaacagctcg tggacctcac gttgaactac cactacgatg cgagccacgg  300
cttggacaac tttgacgtgc tcaagagaat caacgtgacc gaggtgtcgt tgctcatcag  360
cgactttaga cgtcagaacc gtcgcggcgg caccaacaaa aggaccacgt tcaacgccgc  420
```

-continued

```
cggttcgctg gcgccacacg cccggagcct cgagttcagc gtgcggctct ttgccaactg  480
ataataggct ggagcctcgg tggccatgct tcttgcccct tgggcctccc cccagcccct  540
cctccccttc ctgcacccgt acccccgtgg tctttgaata aagtctgagt gggcggc     597

SEQ ID NO: 250         moltype = DNA  length = 3364
FEATURE                Location/Qualifiers
misc_feature           1..3364
                       note = Synthetic polypeptide
source                 1..3364
                       mol_type = other DNA
                       organism = synthetic construct
SEQUENCE: 250
tcaagctttt ggaccctcgt acagaagcta atacgactca ctatagggaa ataagagaga  60
aaagaagagt aagaagaaat ataagagcca ccatggagtc gcgcggtcgc cgttgtcccg  120
aaatgatatc cgtactgggt cccatttcgg ggcacgtgct gaaagccgtg tttagtcgcg  180
gcgatacgcc ggtgctgccg cacgagacgc gactcctgca gacgggtatc cacgtacgcg  240
tgagccagcc ctcgctgatc ctggtgtcgc agtacacgcc cgactcgacg ccatgccacc  300
gcggcgacaa tcagctgcag gtgcagcaca cgtactttac gggcagcgag gtggagaacg  360
tgtcggtcaa cgtgcacaac cccacgggcc gaagcatctg ccccagccaa gagcccatgt  420
cgatctatgt gtacgcgctg ccgctcaaga tgctgaacat ccccagcatc aacgtgcacc  480
actacccgtc ggcggccgag cgcaaacacc gacacctgcc cgtagccgac gctgttattc  540
acgcgtcggg caagcagatg tggcaggcgc gtctcacggt ctcgggactg gcctggacgc  600
gtcagcagaa ccagtggaaa gagcccgacg tctactacac gtcagcgttc gtgtttccca  660
ccaaggacgt ggcactgcgg cacgtggtgt gcgcgcacga gctggtttgc tccatggaga  720
acacgcgcgc aaccaagatg caggtgatag gtgaccagta cgtcaaggtg tacctggagt  780
ccttctgcga ggacgtgccc tccggcaagc tctttatgca cgtcacgctg ggctctgacg  840
tggaagagga cctaacgatg acccgcaacc cgcaaccctt catgcgcccc cacgagcgca  900
acggctttac ggtgttgtgt cccaaaaata tgataatcaa accgggcaag atctcgcaca  960
tcatgctgga tgtggctttt acctcacacg agcattttgg gctgctgtgt cccaagagca  1020
tcccgggcct gagcatctca ggtaacctgt tgatgaacgg gcagcaaatc ttcctggagg  1080
tacaagcgat acgcgagacc gtggaactgc gtcagtacga tcccgtggct gcgctcttct  1140
ttttcgatat cgacttgttg ctgcagcgcg ggcctcagta cagcgagcac cccaccttca  1200
ccagccagta tcgcatccag ggcaagcttg agtaccgaca cacctgggac cggcacgacg  1260
agggtgccgc ccagggcgac gacgacgtct ggaccagcgg atcggactcc gacgaagaac  1320
tcgtaaccac cgagcgtaag acgccccgcg tcaccggcgg cggcgccatg gcgagcgcct  1380
ccacttccgc gggccgcaaa cgcaaatcag catcctcggc gacggcgtgc acggcgggcg  1440
ttatgacacg cggccgcctt aaggccgagt ccaccgtcgc gcccgaagag gacaccgacg  1500
aggattccga caacgaaatc cacaatccgg ccgtgttcac ctggccgccc tggcaggccg  1560
gcatcctggc ccgcaacctg gtgcccatgg tggctacggt tcagggtcag aatctgaagt  1620
accaggagtt cttctgggac gccaacgaca tctaccgcat cttcgccgaa ttggaaggcg  1680
tatggcagcc cgctgcgcaa cccaaacgtc gccgccaccg gcaagacgcc ttgcccgggc  1740
catgcatcgc ctcgacgccc aaaaagcacc gaggtgagtc ctctgccaag agaaagatgg  1800
accctgataa tcctgacgag ggcccttcct ccaaggtgcc acggcccgag acacccgtga  1860
ccaaggccac gacgttcctg cagactatgt taaggaagga ggttaacagt cagctgagcc  1920
tgggagaccc gctgttccca gaattggccg aagaatccct caaaaccttt gaacaagtga  1980
ccgaggattg caacgagaac cccgaaaaag atgtcctgac agaactcgtc aaacagatta  2040
aggttcgagt ggacatggtg cggcatagaa tcaaggagca catgctgaaa aaatataccc  2100
agacggaaga aaaattcact ggcgccttta atatgatggg aggatgtttg cagaatgcct  2160
tagatatctt agataaggtt catgagcctt tcgaggacat gaagtgtatt gggctaacta  2220
tgcagagcat gtatgagaac tacattgtac ctgaggataa gcgggagatg tggatggctt  2280
gtattaagga gctgcatgat gtgagcaagg gcgccgctaa caagttgggg ggtgcactgc  2340
aggctaaggc ccgtgctaaa aaggatgaac ttaggagaaa gatgatgtat atgtgctaca  2400
ggaatataga gttctttacc aagaactcag ccttccctaa gaccaccaat ggctgcagtc  2460
aggccatggc ggcattgcag aacttgcctc agtgctctcc tgatgagatt atgtcttatg  2520
cccagaaaat ctttaagatt ttggatgagg agagagacaa ggtgctcacg cacattgatc  2580
acatatttat ggatatcctc actacatgtg tggaaacaat gtgtaatgag tacaaggtca  2640
ctagtgacgc ttgtatgatg accatgtacg ggggcatctc tctcttaagt gagttctgtc  2700
gggtgctgtg ctgctatgtc ttagaggaga ctagtgtgat gctggccaag cggcctctga  2760
taaccaagcc tgaggttatc agtgtaatga agcgccgcat tgaggagatc tgcatgaagg  2820
tctttgccca gtacattctg gggcgccgatc ctttgagagt ctgctctcct agtgtggatg  2880
acctacgggc catcgccgag gagtcagatg aggaagaggc tattgtagcc tacactttgg  2940
ccaccgctgg tgccagctcc tctgattctc tggtgtcacc tccagagtcc cctgtacccg  3000
cgactatccc tctgtcctca gtaattgtgg ctgagaacag tgatcaggaa gaaagtgaac  3060
agagtgatga ggaacaggag gagggtgctc aggaggagcg ggaggacact gtgtctgtca  3120
agtctgagcc agtgtctgag atagaggaag ttgcctcaga ggaagaggag gatggtgctg  3180
aggaacccac cgcctctgga ggcaagagca cccaccctat ggtgactaga agcaaggctg  3240
accagtgata ataggctgga gcctcggtgg ccatgcttct tgccccttgg gcctcccccc  3300
agcccctcct ccccttcctg cacccgtacc cccgtggtct ttgaataaag tctgagtggg  3360
cggc                                                               3364

SEQ ID NO: 251         moltype = DNA  length = 3388
FEATURE                Location/Qualifiers
misc_feature           1..3388
                       note = Synthetic polypeptide
source                 1..3388
                       mol_type = other DNA
                       organism = synthetic construct
SEQUENCE: 251
tcaagctttt ggaccctcgt acagaagcta atacgactca ctatagggaa ataagagaga  60
```

```
aaagaagagt aagaagaaat ataagagcca ccatggagtc gcgcggtcgc cgttgtcccg  120
aaatgatatc cgtactgggt cccatttcgg ggcacgtgct gaaagccgtg tttagtcgcg  180
gcgatacgcc ggtgctgccg cacgagacgc gactcctgca gacgggtatc cacgtacgcg  240
tgagccagcc ctcgctgatc ctggtgtcgc agtacacgcc cgactcgacg ccatgccacc  300
gcggcgacaa tcagctgcag gtgcagcaca cgtactttac gggcagcgag gtggagaacg  360
tgtcggtcaa cgtgcacaac cccacgggcc gaagcatctg ccccagccaa gagcccatgt  420
cgatctatgt gtacgcgctg ccgctcaaga tgctgaacat ccccagcatc aacgtgcacc  480
actacccgtc ggcggccgag cgcaaacacc gacacctgcc cgtagccgac gctgttattc  540
acgcgtcggg caagcagatg tggcaggcgc gtctcacggt ctcgggactg gcctggacgc  600
gtcagcagaa ccagtggaaa gagcccgacg tctactacac gtcagcgttc gtgtttccca  660
ccaaggacgt ggcactgcgg cacgtggtgt gcgcgcacga gctggtttgc tccatggaga  720
acacgcgcgc aaccaagatg caggtgatag gtgaccagta cgtcaaggtg tacctggagt  780
ccttctgcga ggacgtgccc tccggcaagc tctttatgca cgtcacgctg ggctctgacg  840
tggaagagga cctaacgatg acccgcaacc cgcaaccctt catgcgcccc cacgagcgca  900
acggctttac ggtgttgtgt cccaaaaaata tgataatcaa accgggcaag atctcgcaca  960
tcatgctgga tgtggctttt acctcacacg agcattttgg gctgctgtgt cccaagagca  1020
tcccgggcct gagcatctca ggtaacctgt tgatgaacgg gcagcaaatc ttcctggagg  1080
tacaagcgat acgcgagacc gtggaactgc gtcagtacga tcccgtggct gcgctcttct  1140
ttttcgatat cgacttgttg ctgcagcgcg ggcctcagta cagcgagcac cccaccttca  1200
ccagccagta tcgcatccag ggcaagcttg agtaccgaca cacctgggac cggcacgacg  1260
agggtgccgc ccagggcgac gacgacgtct ggaccagcgg atcggactcc gacgaagaac  1320
tcgtaaccac cgagcgtaag acgccccgcg tcaccggcgg cggcgccatg gcgagcgcct  1380
ccacttccgc gggccgcaaa cgcaaatcag catcctcggc gacggcgtgc acggcgggcg  1440
ttatgacacg cggccgcctt aaggccgagt ccaccgtcgc gcccgaagag gacaccgacg  1500
aggattccga caacgaaatc cacaatccgg ccgtgttcac ctggccgccc tggcaggccg  1560
gcatcctggc ccgcaacctg gtgcccatgg tggctacggt tcagggtcag aatctgaagt  1620
accaggagtt cttctgggac gccaacgaca tctaccgcat cttcgccgaa ttggaaggcg  1680
tatggcagcc cgctgcgcaa cccaaacgtc gccgccaccg gcaagacgcc ttgcccgggc  1740
catgcatcgc ctcgacgccc aaaaagcacc gaggtgagtc ctctgccaag agaaagatgg  1800
accctgataa tcctgacgag ggcccttcct ccaaggtgcc acggcccgag acacccgtga  1860
ccaaggccac gacgttcctg cagactatgt taaggaagga ggttaacagt cagctgagcc  1920
tgggagaccc gctgttccca gaattggccg aagaatccct caaaaccttt gaacaagtga  1980
ccgaggattg caacgagaac cccgaaaaag atgtcctgac agaactcgtc aaacagatta  2040
aggttcgagt ggacatggtg cggcatagaa tcaaggagca catgctgaaa aaatataccc  2100
agacggaaga aaaattcact ggcgccttta atatgatggg aggatgtttg cagaatgcct  2160
tagatatctt agataaggtt catgagcctt tcgaggacat gaagtgtatt gggctaacta  2220
tgcagagcat gtatgagaac tacattgtac ctgaggataa gcgggagatg tggatggctt  2280
gtattaagga gctgcatgat gtgagcaagg gcgccgctaa caagttgggg ggtgcactgc  2340
aggctaaggc ccgtgctaaa aaggatgaac ttaggagaaa gatgatgtat atgtgctaca  2400
ggaatataga gttctttacc aagaactcag ccttccctaa gaccaccaat ggctgcagtc  2460
aggccatggc ggcattgcag aacttgcctc agtgctctcc tgatgagatt atgtcttatg  2520
cccagaaaat ctttaagatt ttggatgagg agagagacaa ggtgctcacg cacattgatc  2580
acatatttat ggatatcctc actacatgtg tggaaacaat gtgtaatgag tacaaggtca  2640
ctagtgacgc ttgtatgatg accatgtacg ggggcatctc tctcttaagt gagttctgtc  2700
gggtgctgtg ctgctatgtc ttagaggaga ctagtgtgat gctggccaag cggcctctga  2760
taaccaagcc tgaggttatc agtgtaatga agcgccgcat tgaggagatc tgcatgaagg  2820
tctttgccca gtacattctg gggcgccgatc ctttgagagt ctgctctcct agtgtggatg  2880
acctacgggc catcgccgag gagtcagatg aggaagaggc tattgtagcc tacactttgg  2940
ccaccgctgg tgccagctcc tctgattctc tggtgtcacc tccagagtcc cctgtacccg  3000
cgactatccc tctgtcctca gtaattgtgg ctgagaacag tgatcaggaa gaaagtgaac  3060
agagtgatga ggaacaggag gagggtgctc aggaggagcg ggaggacact gtgtctgtca  3120
agtctgagcc agtgtctgag atagaggaag ttgcctcaga ggaagaggag gatggtgctg  3180
aggaacccac cgcctctgga ggcaagagca cccaccctat ggtgactaga agcaaggctg  3240
accaggatta caaggacgat gacgataagt gataataggc tggagcctcg gtggccatgc  3300
ttcttgcccc ttgggcctcc ccccagcccc tcctcccctt cctgcacccg taccccccgtg  3360
gtctttgaat aaagtctgag tgggcggc                                    3388
```

```
SEQ ID NO: 252          moltype = DNA  length = 3352
FEATURE                 Location/Qualifiers
misc_feature            1..3352
                        note = Synthetic polypeptide
source                  1..3352
                        mol_type = other DNA
                        organism = synthetic construct
SEQUENCE: 252
tcaagctttt ggaccctcgt acagaagcta atacgactca ctatagggaa ataagagaga  60
aaagaagagt aagaagaaat ataagagcca ccatgcggcc aggcctcccc tcctacctca  120
tcatcctcgc cgtctgtctc ttcagccacc tactttcgtc acgatatggc gcagaagccg  180
tatccgaacc gctggacaaa gcgtttcacc tactgctcaa cacctacggg agacccatcc  240
gcttcctgcg tgaaaatacc acccagtgta cctacaacag cagcctccgt aacagcacgg  300
tcgtcaggga aaacgccatc agtttcaact tttccaaag ctataatcaa tactatgtat  360
tccatatgcc tcgatgtctt tttgcgggtc ctctggcgga gcagtttctg aaccaggtag  420
atctgaccga aaccctggaa agataccaac agagacttaa cacttacgcg ctggtatcca  480
aagacctggc cagctaccga tctttttcgc agcagctaaa ggcacaagac agcctaggtg  540
aacagcccac cactgtgcca ccgcccattg acctgtcaat acctcacgtt tggatgccac  600
cgcaaaccac tccacacggc tggacagaat cacataccac ctcaggacta caccgaccac  660
actttaacca gacctgtatc ctctttgatg gacacgatct actattcagc accgtcacac  720
cttgtttgca ccaaggcttt tacctcatcg acgaactacg ttacgttaaa ataacactga  780
ccgaggactt cttcgtagtt acggtgtcca tagacgacga cacacccatg ctgcttatct  840
```

```
tcggccatct tccacgcgta cttttcaaag cgccctatca acgcgacaac tttatactac  900
gacaaactga aaaacacgag ctcctggtgc tagttaagaa agatcaactg aaccgtcact  960
cttatctcaa agacccggac tttcttgacg ccgcacttga cttcaactac ctagacctca  1020
gcgcactact acgtaacagc tttcaccgtt acgccgtgga tgtactcaag agcggtcgat  1080
gtcagatgct ggaccgccgc acggtagaaa tggccttcgc ctacgcatta gcactgttcg  1140
cagcagcccg acaagaagag gccggcgccc aagtctccgt cccacgggcc ctagaccgcc  1200
aggccgcact cttacaaata caagaattta tgatcacctg cctctcacaa acaccaccac  1260
gcaccacgtt gctgctgtat cccacggccg tggacctggc caaacgagcc ctttggacac  1320
cgaatcagat caccgacatc accagcctcg tacgcctggt ctacatactc tctaaacaga  1380
atcagcaaca tctcatcccc caatgggcac tacgacagat cgccgacttt gccctaaaac  1440
tacacaaaac gcacctggcc tcttttcttt cagccttcgc acgccaagaa ctctacctca  1500
tgggcagcct cgtccactcc atgctggtac atacgacgga gagacgcgaa atcttcatcg  1560
tagaaacggg cctctgttca ttggccgagc tatcacactt tacgcagttg ttagctcatc  1620
cacaccacga atacctcagc gacctgtaca caccctgttc cagtagcggg cgacgcgatc  1680
actcgctcga acgcctcacg cgtctcttcc ccgatgccac cgtccccgct accgttcccg  1740
ccgccctctc catcctatct accatgcaac caagcacgct ggaaaccttc cccgacctgt  1800
tttgcttgcc gctcggcgaa tccttctccg cgctgaccgt ctccgaacac gtcagttata  1860
tcgtaacaaa ccagtacctg atcaaaggta tctcctaccc tgtctccacc accgtcgtag  1920
gccagagcct catcatcacc cagacggaca gtcaaactaa atgcgaactg acgcgcaaca  1980
tgcataccac acacagcatc acagtggcgc tcaacatttc gctagaaaac tgcgcctttt  2040
gccaaagcgc cctgctagaa tacgacgaca cgcaaggcgt catcaacatc atgtacatgc  2100
acgactcgga cgacgtcctt ttcgccctgg atccctacaa cgaagtggtg gtctcatctc  2160
cgcgaactca ctacctcatg cttttgaaaa acggtacggt actagaagta actgacgtcg  2220
tcgtggacgc caccgacagt cgtctcctca tgatgtccgt ctacgcgcta tcggccatca  2280
tcggcatcta tctgctctac cgcatgctca agacatgccg cgccaagagg agcggaagcg  2340
gagctactaa cttcagcctg ctgaagcagg ctggagacgt ggaggagaac cctggaccta  2400
tgtgccgccg cccggattgc ggcttctctt tctcacctgg accggtgata ctgctgtggt  2460
gttgccttct gctgcccatt gtttcctcag ccgccgtcag cgtcgctcct accgccgccg  2520
agaaagtccc cgcggagtgc cccgaactaa cgcgccgatg cttgttgggt gaggtgtttg  2580
agggtgacaa gtatgaaagt tggctgcgcc cgttggtgaa tgttaccggg cgcgatggcc  2640
cgctatcgca acttatccgt taccgtcccg ttacgccgga ggccgccaac tccgtgctgt  2700
tggacgaggc tttcctggac actctggccc tgctgtacaa caatccggat caattgcggg  2760
ccctgctgac gctgttgagc tcggacacag cgccgcgctg gatgacggtg atgcgcggct  2820
acagcgagtg cggcgatggc tcgccggccg tgtacacgtg cgtggacgac ctgtgccgcg  2880
gctacgacct cacgcgactg tcatacgggc gcagcatctt cacggaacac gtgttaggct  2940
tcgagctggt gccaccgtct ctctttaacg tggtggtggc catacgcaac gaagccacgc  3000
gtaccaaccg cgccgtgcgt ctgcccgtga gcaccgctgc cgcgcccgag ggcatcacgc  3060
tcttttacgg cctgtacaac gcagtgaagg aattctgcct gcgtcaccag ctggacccgc  3120
cgctgctacg ccacctagat aaatactacg ccggactgcc gcccgagctg aagcagacgc  3180
gcgtcaacct gccggctcac tcgcgctatg gccctcaagc agtggatgct cgctgataat  3240
aggctggagc ctcggtggcc atgcttcttg ccccttgggc ctccccccag cccctcctcc  3300
ccttcctgca cccgtacccc cgtggtcttt gaataaagtc tgagtgggcg gc          3352
```

```
SEQ ID NO: 253          moltype = DNA  length = 1924
FEATURE                 Location/Qualifiers
misc_feature            1..1924
                        note = Synthetic polypeptide
source                  1..1924
                        mol_type = other DNA
                        organism = synthetic construct
SEQUENCE: 253
tcaagctttt ggaccctcgt acagaagcta atacgactca ctatagggaa ataagagaga  60
aaagaagagt aagaagaaat ataagagcca ccatgagtcc caaagatctg acgccgttct  120
tgacggcgtt gtggctgcta ttgggtcaca gccgcgtgcc gcgggtgcgc gcagaagaat  180
gttgcgaatt cataaacgtc aaccacccgc cggaacgctg ttacgatttc aaaatgtgca  240
atcgcttcac cgtcgcgctg cggtgtccgg acggcgaagt ctgctacagt cccgagaaaa  300
cggctgagat tcgcgggatc gtcaccacca tgacccattc attgacacgc caggtcgtac  360
acaacaaact gacgagctgc aactacaatc cgttatacct cgaagctgac gggcgaatac  420
gctgcggcaa agtaaacgac aaggcgcagt acctgctggg cgccgctggc agcgttccct  480
atcgatggat caatctggaa tacgacaaga taacccggat cgtgggcctg gatcagtacc  540
tggagagcgt taagaaacac aaacggctgg atgtgtgccg cgctaaaatg ggctatatgc  600
tgcagcgcgc caagaggagc ggaagcggag ctactaactt cagcctgctg aagcaggctg  660
gagacgtgga ggagaaccct ggacctatgc tgcggcttct gcttcgtcac cactttcact  720
gcctgcttct gtgcgcggtt tgggcaacgc cctgtctggc gtctccgtgg tcgacgctaa  780
cagcaaacca gaatccgtcc ccgccatggt ctaaactgac gtattccaaa ccgcatgacg  840
cggcgacgtt ttactgtcct tttctctatc cctcgccccc acgatccccc ttgcaattct  900
cggggttcca gcgggtatca acgggtcccg agtgtcgcaa cgagaccctg tatctgctgt  960
acaaccggga aggccagacc ttggtggaga gaagctccac ctgggtgaaa aaggtgatct  1020
ggtacctgag cggtcggaac caaaccatcc tccaacggat gccccgaacg gcttcgaaac  1080
cgagcgacgg aaacgtgcag atcagcgtgg aagacgccaa gatttttgga gcgcacatgg  1140
tgcccaagca gaccaagctg ctacgcttcg tcgtcaacga tggcacacgt tatcagatgt  1200
gtgtgatgaa gctggagagc tggctcacg tcttccggga ctacagcgtg tcttttcagg  1260
tgcgattgac gttcaccgag gccaataacc agacttacac cttctgcacc catcccaatc  1320
tcatcgttcg cgccaagagg agcggaagcg gagtgaaaca gactttgaat tttgaccttc  1380
tcaagttggc gggagacgtg gagtccaacc ctggacctat gcggctgtgt cgggtgtggc  1440
tgtctgtttg tctgtgcgcc gtggtgctgg gtcagtgcca gcgggaaacc gcggaaaaaa  1500
acgattatta ccgagtaccg cattactggg acgcgtgctc tcgcgcgctg cccgaccaaa  1560
cccgttacaa gtatgtggaa cagctcgtgg acctcacgtt gaactaccac tacgatgcga  1620
gccacggctt ggacaacttt gacgtgctca agagaatcaa cgtgaccgag gtgtcgttgc  1680
```

```
tcatcagcga ctttagacgt cagaaccgtc gcggcggcac caacaaaagg accacgttca  1740
acgccgccgg ttcgctggcg ccacacgccc ggagcctcga gttcagcgtg cggctctttg  1800
ccaactgata ataggctgga gcctcggtgg ccatgcttct tgccccttgg gcctcccccc  1860
agcccctcct ccccttcctg cacccgtacc cccgtggtct ttgaataaag tctgagtggg  1920
cggc                                                                1924

SEQ ID NO: 254         moltype = DNA  length = 5146
FEATURE                Location/Qualifiers
misc_feature           1..5146
                       note = Synthetic polypeptide
source                 1..5146
                       mol_type = other DNA
                       organism = synthetic construct
SEQUENCE: 254
tcaagctttt ggaccctcgt acagaagcta atacgactca ctatagggaa ataagagaga  60
aaagaagagt aagaagaaat ataagagcca ccatgcggcc aggcctcccc tcctacctca  120
tcatcctcgc cgtctgtctc ttcagccacc tactttcgtc acgatatggc gcagaagccg  180
tatccgaacc gctggacaaa gcgtttcacc tactgctcaa cacctacggg agacccatcc  240
gcttcctgcg tgaaaatacc acccagtgta cctacaacag cagcctccgt aacagcacgg  300
tcgtcaggga aaacgccatc agtttcaact ttttccaaag ctataatcaa tactatgtat  360
tccatatgcc tcgatgtctt tttgcgggtc ctctggcgga gcagtttctg aaccaggtag  420
atctgaccga aaccctggaa agataccaac agagacttaa cacttacgcg ctggtatcca  480
aagacctggc cagctaccga tctttttcgc agcagctaaa ggcacaagac agcctaggtg  540
aacagcccac cactgtgcca ccgcccattg acctgtcaat acctcacgtt tggatgccac  600
cgcaaaccac tccacacggc tggacagaat cacataccac ctcaggacta caccgaccac  660
actttaacca gacctgtatc ctctttgatg gacacgatct actattcagc accgtcacac  720
cttgtttgca ccaaggcttt tacctcatcg acgaactacg ttacgttaaa ataacactga  780
ccgaggactt cttcgtagtt acggtgtcca tagacgacga cacacccatg ctgcttatct  840
tcggccatct tccacgcgta cttttcaaag cgccctatca acgcgacaac tttatactac  900
gacaaactga aaaacacgag ctcctggtgc tagttaagaa agatcaactg aaccgtcact  960
cttatctcaa agacccggac tttcttgacg ccgcacttga cttcaactac ctagacctca  1020
gcgcactact acgtaacagc tttcaccgtt acgccgtgga tgtactcaag agcggtcgat  1080
gtcagatgct ggaccgccgc acggtagaaa tggccttcgc ctacgcatta gcactgttcg  1140
cagcagcccg acaagaagag gccggcgccc aagtctccgt cccacgggcc ctagaccgcc  1200
aggccgcact cttacaaata caagaattta tgatcacctg cctctcacaa acaccaccac  1260
gcaccacgtt gctgctgtat cccacggccg tggacctggc caaacgagcc ctttggacac  1320
cgaatcagat caccgacatc accagcctcg tacgcctggt ctacatactc tctaaacaga  1380
atcagcaaca tctcatcccc caatgggcac tacgacagat cgccgacttt gccctaaaac  1440
tacacaaaac gcacctggcc tcttttcttt cagccttcgc acgccaagaa ctctacctca  1500
tgggcagcct cgtccactcc atgctggtac atacgacgga gagacgcgaa atcttcatcg  1560
tagaaacggg cctctgttca ttggccgagc tatcacactt tacgcagttg ttagctcatc  1620
cacaccacga atacctcagc gacctgtaca caccctgttc cagtagcggg cgacgcgatc  1680
actcgctcga acgcctcacg cgtctcttcc ccgatgccac cgtccccgct accgttcccg  1740
ccgccctctc catcctatct accatgcaac caagcacgct ggaaaccttc cccgacctgt  1800
tttgcttgcc gctcggcgaa tccttctccg cgctgaccgt ctccgaacac gtcagttata  1860
tcgtaacaaa ccagtacctg atcaaaggta tctcctaccc tgtctccacc accgtcgtag  1920
gccagagcct catcatcacc cagacggaca gtcaaactaa atgcgaactg acgcgcaaca  1980
tgcataccac acacagcatc acagtggcgc tcaacatttc gctagaaaac tgcgcctttt  2040
gccaaagcgc cctgctagaa tacgacgaca cgcaaggcgt catcaacatc atgtacatgc  2100
acgactcgga cgacgtcctt ttcgccctgg atccctacaa cgaagtggtg gtctcatctc  2160
cgcgaactca ctacctcatg cttttgaaaa acggtacggt actagaagta actgacgtcg  2220
tcgtggacgc caccgacagt cgtctcctca tgatgtccgt ctacgcgcta tcggccatca  2280
tcggcatcta tctgctctac cgcatgctca agacatgccg cgccaagagg agcggaagcg  2340
gagctactaa cttcagcctg ctgaagcagg ctggagacgt ggaggagaac cctggaccta  2400
tgtgccgccg cccggattgc ggcttctctt tctcacctgg accggtgata ctgctgtggt  2460
gttgccttct gctgcccatt gtttcctcag ccgccgtcag cgtcgctcct accgccgccg  2520
agaaagtccc cgcggagtgc cccgaactaa cgcgccgatg cttgttgggt gaggtgtttg  2580
agggtgacaa gtatgaaagt tggctgcgcc cgttggtgaa tgttaccggg cgcgatggcc  2640
cgctatcgca acttatccgt taccgtcccg ttacgccgga ggccgccaac tccgtgctgt  2700
tggacgaggc tttcctggac actctggccc tgctgtacaa caatccggat caattgcggg  2760
ccctgctgac gctgttgagc tcggacacag cgccgcgctg gatgacggtg atgcgcggct  2820
acagcgagtg cggcgatggc tcgccggccg tgtacacgtg cgtggacgac ctgtgccgcg  2880
gctacgacct cacgcgactg tcatacgggc gcagcatctt cacggaacac gtgttaggct  2940
tcgagctggt gccaccgtct ctctttaacg tggtggtggc catacgcaac gaagccacgc  3000
gtaccaaccg cgccgtgcgt ctgcccgtga gcaccgctgc cgcgcccgag ggcatcacgc  3060
tcttttacgg cctgtacaac gcagtgaagg aattctgcct gcgtcaccag ctggacccgc  3120
cgctgctacg ccacctagat aaatactacg ccggactgcc gcccgagctg aagcagacgc  3180
gcgtcaacct gccggctcac tcgcgctatg gccctcaagc agtggatgct cgccgcgcca  3240
agaggagcgg aagcggagtg aaacagactt tgaattttga ccttctcaag ttggcgggag  3300
acgtggagtc caaccctgga cctatgagtc ccaaagatct gacgccgttc ttgacggcgt  3360
tgtggctgct attgggtcac agccgcgtgc cgcgggtgcg cgcagaagaa tgttgcgaat  3420
tcataaacgt caaccacccg ccggaacgct gttacgattt caaaatgtgc aatcgcttca  3480
ccgtcgcgct gcggtgtccg gacggcgaag tctgctacag tcccgagaaa acggctgaga  3540
ttcgcgggat cgtcaccacc atgacccatt cattgacacg ccaggtcgta cacaacaaac  3600
tgacgagctg caactacaat ccgttatacc tcgaagctga cgggcgaata cgctgcggca  3660
aagtaaacga caaggcgcag tacctgctgg gcgccgctgg cagcgttccc tatcgatgga  3720
tcaatctgga atacgacaag ataacccgga tcgtgggcct ggatcagtac ctggagagcg  3780
ttaagaaaca caaacggctg gatgtgtgcc gcgctaaaat gggctatatg ctgcagcgcg  3840
ccaagaggag cggaagcgga cagtgtacta attatgctct cttgaaattg gctggagatg  3900
```

-continued

```
ttgagagcaa ccctggacct atgctgcggc ttctgcttcg tcaccacttt cactgcctgc  3960
ttctgtgcgc ggtttgggca acgccctgtc tggcgtctcc gtggtcgacg ctaacagcaa  4020
accagaatcc gtccccgcca tggtctaaac tgacgtattc caaaccgcat gacgcggcga  4080
cgttttactg tccttttctc tatccctcgc ccccacgatc cccctgcaa ttctcggggt  4140
tccagcgggt atcaacgggt cccgagtgtc gcaacgagac cctgtatctg ctgtacaacc  4200
gggaaggcca gaccttggtg gagagaagct ccacctgggt gaaaaaggtg atctggtacc  4260
tgagcggtcg gaaccaaacc atcctccaac ggatgccccg aacggcttcg aaaccgagcg  4320
acggaaacgt gcagatcagc gtggaagacg ccaagatttt tggagcgcac atggtgccca  4380
agcagaccaa gctgctacgc ttcgtcgtca acgatggcac acgttatcag atgtgtgtga  4440
tgaagctgga gagctgggct cacgtcttcc gggactacag cgtgtctttt caggtgcgat  4500
tgacgttcac cgaggccaat aaccagactt acaccttctg cacccatccc aatctcatcg  4560
ttcgcgccaa gaggaggcgga agcggagagg gcagaggaag tctgctaaca tgcggtgacg  4620
tcgaggagaa tcctggacct atgcggctgt gtcgggtgtg gctgtctgtt tgtctgtgcg  4680
ccgtggtgct gggtcagtgc cagcgggaaa ccgcggaaaa aaacgattat taccgagtac  4740
cgcattactg ggacgcgtgc tctcgcgcgc tgcccgacca aacccgttac aagtatgtgg  4800
aacagctcgt ggacctcacg ttgaactacc actacgatgc gagccacggc ttggacaact  4860
ttgacgtgct caagagaatc aacgtgaccg aggtgtcgtt gctcatcagc gactttagac  4920
gtcagaaccg tcgcggcggc accaacaaaa ggaccacgtt caacgccgcc ggttcgctgg  4980
cgccacacgc ccggagcctc gagttcagcg tgcggctctt tgccaactga taataggctg  5040
gagcctcggt ggccatgctt cttgcccctt gggcctcccc ccagcccctc ctccccttcc  5100
tgcacccgta cccccgtggt ctttgaataa agtctgagtg ggcggc                5146

SEQ ID NO: 255         moltype = AA  length = 885
FEATURE                Location/Qualifiers
REGION                 1..885
                       note = Synthetic peptide sequence
source                 1..885
                       mol_type = protein
                       organism = synthetic construct
SEQUENCE: 255
VSSSSTRGTS ATHSHHSSHT TSAAHSRSGS VSQRVTSSQT VSHGVNETIY NTTLKYGDVV  60
GVNTTKYPYR VCSMAQGTDL IRFERNIVCT SMKPINEDLD EGIMVVYKRN IVAHTFKVRV  120
YQKVLTFRRS YAYIHTTYLL GSNTEYVAPP MWEIHHINSH SQCYSSYSRV IAGTVFVAYH  180
RDSYENKTMQ LMPDCYSNTH STRYVTVKDQ WHSRGSTWLY RETCNLNCMV TITTARSKYP  240
YHFFATSTGD VVDISPFYNG TNRNASYFGE NADKFFIFPN YTIVSDFGRP NSALETHRLV  300
AFLERADSVI SWDIQDEKNV TCQLTFWEAS ERTIRSEAED SYHFSSAKMT ATFLSKKQEV  360
NMSDSALDCV RDEAINKLQQ IFNTSYNQTY EKYGNVSVFE TTGGLVVFWQ GIKQKSLVEL  420
ERLANRSSLN LTHNRTKRST DGNNATHLSN MESVHNLVYA QLQFTYDTLR GYINRALAQI  480
AEAWCVDQRR TLEVFKELSK INPSAILSAI YNKPIAARFM GDVLGLASCV TINQTSVKVL  540
RDMNVKESPG RCYSRPVVIF NFANSSCVQY GQLGEDNEIL LGNHRTEECQ LPSLKIFIAG  600
NSAYEYVDYL FKRMIDLSSI STVDSMIALD IDPLENTDFR VLELYSQKEL RSSNVFDLEE  660
IMREFNSYKQ RVKYVEDKVV DPLPPYLKGL DDLMSGLGAA GKAVGVAIGA VGGAVASVVE  720
GVATFLKNPF GAFTIILVAI AVVIIIYLIY TRQRRLCMQP LQNLFPYLVS ADGTTVTSGN  780
TKDTSLQAPP SYEESVYNSG RKGPGPPSSD ASTAAPPYTN EQAYQMLLAL VRLDAEQRAQ  840
QNGTDSLDGQ TGTQDKGQKP NLLDRLRHRK NGYRHLKDSD EEENV                 885

SEQ ID NO: 256         moltype = DNA  length = 2655
FEATURE                Location/Qualifiers
misc_feature           1..2655
                       note = Synthetic nucleotide sequence
source                 1..2655
                       mol_type = other DNA
                       organism = synthetic construct
SEQUENCE: 256
gtatcctcca gctctactag aggaacgagc gcgacccatt cacaccacag ctcccacact  60
acgagcgctg cccattctag gagtggctcc gtgtcacaac gcgttactag tagccagacc  120
gtgtctcacg gcgtcaacga gacaatttac aacacgacgc tgaaatacgg cgatgtcgtg  180
ggtgtgaata ctaccaagta cccctataga gtctgtagca tggcccaggg caccgacctg  240
atcaggttcg aacggaacat cgtttgcaca tcaatgaagc ctatcaacga agaccttgac  300
gaggggatta tggtggtata caaacggaat atcgtggctc acaccttcaa agtgcgagtg  360
tatcagaagg ttctgacatt ccgaagaagt tacgcctaca tccataccac ctatctgctg  420
ggctccaaca ctgagtacgt ggcgccccca atgtgggaaa tccaccacat caacagccat  480
tcacagtgct actcttccta cagcagggtg attgcgggca cagtgtttgt ggcctaccac  540
agggacagct atgagaacaa gacgatgcag ttgatgccag attgttacag taacactcac  600
agtacacggt atgttacagt taaggatcag tggcattcac gcggaagcac atggctgtat  660
agagagacct gtaatttgaa ttgtatggta actatcacta ctgcacggag caagtaccct  720
tatcatttct ttgctacaag cacgggcgat gtggtagaca tcagcccctt ctataatggc  780
acaaatcgga acgcaagcta tttcggggag aacgccgaca agtttttcat ttttcctaat  840
tatactattg tttctgactt cgggagaccc aactccgccc tggaaactca cagactggtt  900
gcgttcctcg aaagagcaga ttctgtgata tcctgggaca ttcaggatga aaagaacgtc  960
acgtgtcagc tgaccttctg ggaggcctca gagcggacga tccggtctga ggccgaggac  1020
tcttaccact ttagcagcgc caagatgacc gcaaccttcc tgtctaaaaa acaggaagtg  1080
aacatgtccg attctgcttt ggactgcgtt cgcgatgagg ccatcaacaa gcttcaacaa  1140
attttcaata cctcctacaa tcagacatat gaaaaatacg gaaacgtgag tgtctttgaa  1200
accaccgggg gcctggtcgt gttctggcag ggtatcaaac agaagagcct ggtggaactg  1260
gaacgcctgg ccaacagaag cagtttgaac ctcacgcaca accggacaaa gaggagcacc  1320
gacggaaaca atgctacaca cctttccaac atggagtctg tccacaatct ggtttatgca  1380
cagcttcagt tcacttatga cacactgcgg ggctacataa acagggctct ggcacagata  1440
gccgaggctt ggtgtgtgga ccagcggaga accctggagg tatttaaaga actgtctaag  1500
```

```
atcaacccct ctgcgattct gagcgctatt tacaacaaac ccattgccgc acgcttcatg  1560
ggggacgtcc tcggtcttgc ctcctgtgtg acaattaacc agacgagcgt gaaggtgctg  1620
cgagatatga acgtgaagga atcccctggg cggtgttaca gtaggcctgt ggtgattttc  1680
aacttcgcca actcttcctg tgtccaatac ggtcaactcg gtgaagataa cgagattctg  1740
ctgggcaatc atcggacaga agaatgccag ttgccaagcc ttaaaatctt tattgcagga  1800
aattcagcct acgagtacgt cgactatctg tttaaaagaa tgattgatct gagcagcatt  1860
tccactgtgg acagtatgat cgcactggac attgaccctt tggaaaacac cgattttcgc  1920
gtccttgagc tgtactccca gaaagaactg cgctctagca acgtctttga tcttgaggag  1980
atcatgaggg agtttaactc ttataaacag agggtgaagt atgtggagga taaagtggtc  2040
gaccctctgc caccctacct caaaggactg gacgatctga tgagcggact tggagctgcc  2100
ggcaaagccg tcggggtggc tatcggtgcc gtgggcggcg ccgtggcttc tgtggttgag  2160
ggagtggcca ctttcttaa aaatcctttc ggagctttta ccattattct ggtcgccatc  2220
gccgtggtga tcatcattta tctgatctac acccgccagc gccgcttgtg catgcagcca  2280
cttcagaacc tgtttcccta tctggtcagt gctgacggta caaccgtgac cagcggcaac  2340
acaaaggaca caagccttca ggctcctcca agttatgaag agtccgtgta taattctggg  2400
aggaagggac ctggtccccc ctcttccgac gcctcaacag cggcaccccc ctacaccaat  2460
gagcaggcat atcagatgct cctggccctt gtgcggctcg atgccgagca acgcgcacaa  2520
cagaacggga cggattctct cgacggacag acaggcactc aggacaaagg ccagaagccc  2580
aaccttctgg atcggttgcg gcatagaaaa aacggctata gacacctcaa ggactcagac  2640
gaagaagaga acgtc                                                    2655

SEQ ID NO: 257          moltype = AA  length = 885
FEATURE                 Location/Qualifiers
REGION                  1..885
                        note = Synthetic peptide sequence
source                  1..885
                        mol_type = protein
                        organism = synthetic construct
SEQUENCE: 257
VSSSSTRGTS ATHSHHSSHT TSAAHSRSGS VSQRVTSSQT VSHGVNETIY NTTLKYGDVV  60
GVNTTKYPYR VCSMAQGTDL IRFERNIVCT SMKPINEDLD EGIMVVYKRN IVAHTFKVRV  120
YQKVLTFRRS YAYIHTTYLL GSNTEYVAPP MWEIHHINSH SQCYSSYSRV IAGTVFVAYH  180
RDSYENKTMQ LMPDCYSNTH STRYVTVKDQ WHSRGSTWLY RETCNLNCMV TITTARSKYP  240
YHFFATSTGD VVDISPFYNG TNRNASYFGE NADKFFIFPN YTIVSDFGRP NSALETHRLV  300
AFLERADSVI SWDIQDEKNV TCQLTFWEAS ERTIRSEAED SYHFSSAKCT ATFLSKKQEV  360
NMSDSALDCV RDEAINKLQQ IFNTSYNQTY EKYGNVSVFE TTGGLVVFWQ GIKQKSLVEL  420
ERLANRSSLN LTHNRTKRST DGNNATHLSN MESVHNLVYA QLQFTYDTLR GYINRALAQI  480
AEACCVDQRR TLEVFKELSK INPSAILSAI YNKPIAARFM GDVLGLASCV TINQTSVKVL  540
RDMNVKESPG RCYSRPVVIF NFANSSCVQY GQLGEDNEIL LGNHRTEECQ LPSLKIFIAG  600
NSAYEYVDYL FKRMIDLSSI STVDSMIALD IDPLENTDFR VLELYSQKEL RSSNVFDLEE  660
IMREFNSYKQ RVKYVEDKVV DPLPPYLKGL DDLMSGLGAA GKAVGVAIGA VGGAVASVVE  720
GVATFLKNPF GAFTIILVAI AVVIIIYLIY TRQRRLCMQP LQNLFPYLVS ADGTTVTSGN  780
TKDTSLQAPP SYEESVYNSG RKGPGPPSSD ASTAAPPYTN EQAYQMLLAL VRLDAEQRAQ  840
QNGTDSLDGQ TGTQDKGQKP NLLDRLRHRK NGYRHLKDSD EEENV                  885

SEQ ID NO: 258          moltype = DNA  length = 2655
FEATURE                 Location/Qualifiers
misc_feature            1..2655
                        note = Synthetic nucleotide sequence
source                  1..2655
                        mol_type = other DNA
                        organism = synthetic construct
SEQUENCE: 258
gtatcctcca gctctactag aggaacgagc gcgacccatt cacaccacag ctcccacact  60
acgagcgctg cccattctag gagtggctcc gtgtcacaac gcgttactag tagccagacc  120
gtgtctcacg gcgtcaacga gacaatttac aacacgacgc tgaaatacgg cgatgtcgtg  180
ggtgtgaata ctaccaagta cccctataga gtctgtagca tggcccaggg caccgacctg  240
atcaggttcg aacggaacat cgtttgcaca tcaatgaagc ctatcaacga agaccttgac  300
gaggggatta tggtggtata caaacggaat atcgtggctc acaccttcaa agtgcgagtg  360
tatcagaagg ttctgacatt ccgaagaagt tacgcctaca tccataccac ctatctgctg  420
ggctccaaca ctgagtacgt ggcgccccca atgtgggaaa tccaccacat caacagccat  480
tcacagtgct actcttccta cagcagggtg attgcgggca cagtgtttgt ggcctaccac  540
agggacagct atgagaacaa gacgatgcag ttgatgccag attgttacag taacactcac  600
agtacacggt atgttacagt taaggatcag tggcattcac gcggaagcac atggctgtat  660
agagagacct gtaatttgaa ttgtatggta actatcacta ctgcacggag caagtaccct  720
tatcatttct ttgctacaag cacgggcgat gtggtagaca tcagcccctt ctataatggc  780
acaaatcgga acgcaagcta tttcggggag aacgccgaca agtttttcat ttttcctaat  840
tatactattg tttctgactt cgggagaccc aactccgccc tggaaactca cagactggtt  900
gcgttcctcg aaagagcaga ttctgtgata tcctgggaca ttcaggatga aaagaacgtc  960
acgtgtcagc tgaccttctg ggaggcctca gagcggacga tccggtctga ggccgaggac  1020
tcttaccact ttagcagcgc caagtgcacc gcaaccttcc tgtctaaaaa acaggaagtg  1080
aacatgtccg attctgcttt ggactgcgtt cgcgatgagg ccatcaacaa gcttcaacaa  1140
attttcaata cctcctacaa tcagacatat gaaaaatacg gaaacgtgag tgtctttgaa  1200
accaccgggg gcctggtcgt gttctggcag ggtatcaaac agaagagcct ggtggaactg  1260
gaacgcctgg ccaacagaag cagtttgaac ctcacgcaca accggacaaa gaggagcacc  1320
gacggaaaca atgctacaca cctttccaac atggagtctg tccacaatct ggtttatgca  1380
cagcttcagt tcacttatga cacactgcgg ggctacataa acagggctct ggcacagata  1440
gccgaggctt gctgtgtgga ccagcggaga accctggagg tatttaaaga actgtctaag  1500
atcaacccct ctgcgattct gagcgctatt tacaacaaac ccattgccgc acgcttcatg  1560
```

-continued

```
ggggacgtcc tcggtcttgc ctcctgtgtg acaattaacc agacgagcgt gaaggtgctg  1620
cgagatatga acgtgaagga atcccctggg cggtgttaca gtaggcctgt ggtgattttc  1680
aacttcgcca actcttcctg tgtccaatac ggtcaactcg gtgaagataa cgagattctg  1740
ctgggcaatc atcggacaga agaatgccag ttgccaagcc ttaaaatctt tattgcagga  1800
aattcagcct acgagtacgt cgactatctg tttaaaagaa tgattgatct gagcagcatt  1860
tccactgtgg acagtatgat cgcactggac attgaccctt tggaaaacac cgattttcgc  1920
gtccttgagc tgtactccca gaaagaactg cgctctagca acgtctttga tcttgaggag  1980
atcatgaggg agtttaactc ttataaacag agggtgaagt atgtggagga taaagtggtc  2040
gaccctctgc caccctacct caaaggactg gacgatctga tgagcggact tggagctgcc  2100
ggcaaagccg tcggggtggc tatcggtgcc gtgggcggcg ccgtggcttc tgtggttgag  2160
ggagtggcca ctttcttaa aaatcctttc ggagctttta ccattattct ggtcgccatc  2220
gccgtggtga tcatcattta tctgatctac acccgccagc gccgcttgtg catgcagcca  2280
cttcagaacc tgtttcccta tctggtcagt gctgacggta caaccgtgac cagcggcaac  2340
acaaaggaca caagccttca ggctcctcca agttatgaag agtccgtgta taattctggg  2400
aggaagggac ctggtccccc ctcttccgac gcctcaacag cggcaccccc ctacaccaat  2460
gagcaggcat atcagatgct cctggccctt gtgcggctcg atgccgagca acgcgcacaa  2520
cagaacggga cggattctct cgacggacag acaggcactc aggacaaagg ccagaagccc  2580
aaccttctgg atcggttgcg gcatagaaaa aacggctata gacacctcaa ggactcagac  2640
gaagaagaga acgtc                                                    2655

SEQ ID NO: 259         moltype = AA  length = 885
FEATURE                Location/Qualifiers
REGION                 1..885
                       note = Synthetic peptide sequence
source                 1..885
                       mol_type = protein
                       organism = synthetic construct
SEQUENCE: 259
VSSSSTRGTS ATHSHHSSHT TSAAHSRSGS VSQRVTSSQT VSHGVNETIY NTTLKYGDVV  60
GVNTTKYPYR VCSMAQGTDL IRFERNIVCT SMKPINEDLD EGIMVVYKRN IVAHTFKVRV  120
YQKVLTFRRS YAYIHTTYLL GSNTEYVAPP MWEIHHINSH SQCYSSYSRV IAGTVFVAYH  180
RDSYENKTMQ LMPDCYSNTH STRYVTVKDQ WHSRGSTWLY RETCNLNCMV TITTARSKYP  240
YHFFATSTGD VVDISPFYNG TNRNASYFGE NADKFFIFPN YTIVSDFGRP NSALETHRLV  300
AFLERADSVI SWDIQDEKNV TCQLTFWEAS ERTIRSEAED SYHFSSAKMT ATFLSKKQEV  360
NMSDSALDCV RDEAINKLQQ IFNTSYNQTY EKYGNVSVFE TTGGLVVFWQ GIKQKSLVEL  420
ERLANRSSLN LTHNRTKRST DGNNATHLSN MESVHNLVYA QLQFTYDTLR GYINRALAQI  480
AEAWCVDQRR TLEVFKELSK ICPSAILSAI YNKPIAARFM GDVLGLASCV TINQTSVKVL  540
RDMNVKESPG RCYSRPVVIF NFANSSCVQY GQLGEDNEIL LGNHRTEECQ LPSLKIFIAG  600
NSAYEYVDYL FKRMIDLSSI STVDSMIALD IDPLENTDFR VLELYSQKEL RSSNVFDLEE  660
ICREFNSYKQ RVKYVEDKVV DPLPPYLKGL DDLMSGLGAA GKAVGVAIGA VGGAVASVVE  720
GVATFLKNPF GAFTIILVAI AVVIIIYLIY TRQRRLCMQP LQNLFPYLVS ADGTTVTSGN  780
TKDTSLQAPP SYEESVYNSG RKGPGPPSSD ASTAAPPYTN EQAYQMLLAL VRLDAEQRAQ  840
QNGTDSLDGQ TGTQDKGQKP NLLDRLRHRK NGYRHLKDSD EEENV                   885

SEQ ID NO: 260         moltype = DNA  length = 2655
FEATURE                Location/Qualifiers
misc_feature           1..2655
                       note = Synthetic nucleotide sequence
source                 1..2655
                       mol_type = other DNA
                       organism = synthetic construct
SEQUENCE: 260
gtatcctcca gctctactag aggaacgagc gcgacccatt cacaccacag ctcccacact  60
acgagcgctg cccattctag gagtggctcc gtgtcacaac gcgttactag tagccagacc  120
gtgtctcacg gcgtcaacga gacaatttac aacacgacgc tgaaatacgg cgatgtcgtg  180
ggtgtgaata ctaccaagta cccctataga gtctgtagca tggcccaggg caccgacctg  240
atcaggttcg aacggaacat cgtttgcaca tcaatgaagc ctatcaacga agaccttgac  300
gaggggatta tggtggtata caaacggaat atcgtggctc acaccttcaa agtgcgagtg  360
tatcagaagg ttctgacatt ccgaagaagt tacgcctaca tccataccac ctatctgctg  420
ggctccaaca ctgagtacgt ggcgccccca atgtgggaaa tccaccacat caacagccat  480
tcacagtgct actcttccta cagcagggtg attgcgggca cagtgtttgt ggcctaccac  540
agggacagct atgagaacaa gacgatgcag ttgatgccag attgttacag taacactcac  600
agtacacggt atgttacagt taaggatcag tggcattcac gcggaagcac atggctgtat  660
agagagacct gtaatttgaa ttgtatggta actatcacta ctgcacggag caagtaccct  720
tatcatttct ttgctacaag cacgggcgat gtggtagaca tcagcccctt ctataatggc  780
acaaatcgga acgcaagcta tttcggggag aacgccgaca agtttttcat ttttcctaat  840
tatactattg tttctgactt cgggagaccc aactccgccc tggaaactca cagactggtt  900
gcgttcctcg aaagagcaga ttctgtgata tcctgggaca ttcaggatga aaagaacgtc  960
acgtgtcagc tgaccttctg ggaggcctca gagcggacga tccggtctga ggccgaggac  1020
tcttaccact ttagcagcgc caagatgacc gcaaccttcc tgtctaaaaa acaggaagtg  1080
aacatgtccg attctgcttt ggactgcgtt cgcgatgagg ccatcaacaa gcttcaacaa  1140
attttcaata cctcctacaa tcagacatat gaaaaatacg gaaacgtgag tgtctttgaa  1200
accaccgggg gcctggtcgt gttctggcag ggtatcaaac agaagagcct ggtggaactg  1260
gaacgcctgg ccaacagaag cagtttgaac ctcacgcaca accggacaaa gaggagcacc  1320
gacggaaaca atgctacaca cctttccaac atggagtctg tccacaatct ggtttatgca  1380
cagcttcagt tcacttatga cacactgcgg ggctacataa acagggctct ggcacagata  1440
gccgaggctt ggtgtgtgga ccagcggaga accctggagg tatttaaaga actgtctaag  1500
atctgtccct ctgcgattct gagcgctatt tacaacaaac ccattgccgc acgcttcatg  1560
ggggacgtcc tcggtcttgc ctcctgtgtg acaattaacc agacgagcgt gaaggtgctg  1620
```

```
cgagatatga acgtgaagga atcccctggg cggtgttaca gtaggcctgt ggtgattttc  1680
aacttcgcca actcttcctg tgtccaatac ggtcaactcg gtgaagataa cgagattctg  1740
ctgggcaatc atcggacaga agaatgccag ttgccaagcc ttaaaatctt tattgcagga  1800
aattcagcct acgagtacgt cgactatctg tttaaaagaa tgattgatct gagcagcatt  1860
tccactgtgg acagtatgat cgcactggac attgaccctt tggaaaacac cgattttcgc  1920
gtccttgagc tgtactccca gaaagaactg cgctctagca acgtctttga tcttgaggag  1980
atctgtaggg agtttaactc ttataaacag agggtgaagt atgtggagga taaagtggtc  2040
gaccctctgc caccctacct caaaggactg gacgatctga tgagcggact tggagctgcc  2100
ggcaaagccg tcggggtggc tatcggtgcc gtgggcggcg ccgtggcttc tgtggttgag  2160
ggagtggcca cttttcttaa aaatcctttc ggagctttta ccattattct ggtcgccatc  2220
gccgtggtga tcatcattta tctgatctac acccgccagc gccgcttgtg catgcagcca  2280
cttcagaacc tgtttcccta tctggtcagt gctgacggta caaccgtgac cagcggcaac  2340
acaaaggaca caagccttca ggctcctcca agttatgaag agtccgtgta taattctggg  2400
aggaagggac ctggtccccc ctcttccgac gcctcaacag cggcaccccc ctacaccaat  2460
gagcaggcat atcagatgct cctggccctt gtgcggctcg atgccgagca acgcgcacaa  2520
cagaacggga cggattctct cgacggacag acaggcactc aggacaaagg ccagaagccc  2580
aaccttctgg atcggttgcg gcatagaaaa aacggctata gacacctcaa ggactcagac  2640
gaagaagaga acgtc                                                    2655
```

```
SEQ ID NO: 261         moltype = AA  length = 704
FEATURE                Location/Qualifiers
REGION                 1..704
                       note = Synthetic peptide sequence
source                 1..704
                       mol_type = protein
                       organism = synthetic construct
SEQUENCE: 261
VSSSSTRGTS ATHSHHSSHT TSAAHSRSGS VSQRVTSSQT VSHGVNETIY NTTLKYGDVV  60
GVNTTKYPYR VCSMAQGTDL IRFERNIVCT SMKPINEDLD EGIMVVYKRN IVAHTFKVRV  120
YQKVLTFRRS YAGHRTTYLL GSNTEYVAPP MWEIHHINSH SQCYSSYSRV IAGTVFVAYH  180
RDSYENKTMQ LMPDCYSNTH STRYVTVKDQ WHSRGSTALY RETSNLNCMV TITTARSKYP  240
YHFFATSTGD VVDISPFYNG TNRNASYFGE NADKFFIFPN YTIVSDFGRP NSALETHRLV  300
AFLERADSVI SWDIQDEKNV TCQLTFWEAS ERTIRSEAED SYHFSSAKCT ATFLSKKQEV  360
NMSDSALDCV RDEAINKLQQ IFNTSYNQTY EKYGNVSVFE TTGGLVVFWQ GIKQKSLVEL  420
ERLANRSSLN LTHNRTKRST DGNNATHLSN MESVHNLVYA QLQFTYDTLR GYINRALAQI  480
AEACCVDQRR TLEVFKELSK INPSAILSAI YNKPIAARFM GDVLGLASCV TINQTSVKVL  540
RDMNVKESPG RCYSRPVVIF NFANSSCVQY GQLGEDNEIL LGNHRTEECQ LPSLKIFIAG  600
NSAYEYVDYL FKRMIDLSSI STVDSMIALD IDPLENTDFR VLELYSQKEL RSSNVFDLEE  660
IMREFNSYKQ RVKYVEDKVV KIEEILSKQY HIENEIARIK KLIG                    704
```

```
SEQ ID NO: 262         moltype = DNA  length = 2112
FEATURE                Location/Qualifiers
misc_feature           1..2112
                       note = Synthetic nucleotide sequence
source                 1..2112
                       mol_type = other DNA
                       organism = synthetic construct
SEQUENCE: 262
gtatcctcca gctctactag aggaacgagc gcgacccatt cacaccacag ctcccacact  60
acgagcgctg cccattctag gagtggctcc gtgtcacaac gcgttactag tagccagacc  120
gtgtctcacg gcgtcaacga gacaatttac aacacgacgc tgaaatacgg cgatgtcgtg  180
ggtgtgaata ctaccaagta cccctataga gtctgtagca tggcccaggg caccgacctg  240
atcaggttcg aacggaacat cgtttgcaca tcaatgaagc ctatcaacga agaccttgac  300
gaggggatta tggtggtata caaacggaat atcgtggctc acaccttcaa agtgcgagtg  360
tatcagaagg ttctgacatt ccgaagaagt tacgccggtc atcgtaccac ctatctgctg  420
ggctccaaca ctgagtacgt ggcgccccca atgtgggaaa tccaccacat caacagccat  480
tcacagtgct actcttccta cagcagggtg attgcgggca cagtgtttgt ggcctaccac  540
agggacagct atgagaacaa gacgatgcag ttgatgccag attgttacag taacactcac  600
agtacacggt atgttacagt taaggatcag tggcattcac gcggaagcac agcactgtat  660
agagagacct ctaatttgaa ttgtatggta actatcacta ctgcacggag caagtaccct  720
tatcatttct ttgctacaag cacgggcgat gtggtagaca tcagcccctt ctataatggc  780
acaaatcgga acgcaagcta tttcggggag aacgccgaca agtttttcat ttttcctaat  840
tatactattg tttctgactt cgggagaccc aactccgccc tggaaactca cagactggtt  900
gcgttcctcg aaagagcaga ttctgtgata tcctgggaca ttcaggatga aaagaacgtc  960
acgtgtcagc tgaccttctg ggaggcctca gagcggacga tccggtctga ggccgaggac  1020
tcttaccact ttagcagcgc caagtgcacc gcaaccttcc tgtctaaaaa acaggaagtg  1080
aacatgtccg attctgcttt ggactgcgtt cgcgatgagg ccatcaacaa gcttcaacaa  1140
attttcaata cctcctacaa tcagacatat gaaaaatacg gaaacgtgag tgtctttgaa  1200
accaccgggg gcctggtcgt gttctggcag ggtatcaaac agaagagcct ggtggaactg  1260
gaacgcctgg ccaacagaag cagtttgaac ctcacgcaca accggacaaa gaggagcacc  1320
gacggaaaca atgctacaca cctttccaac atggagtctg tccacaatct ggtttatgca  1380
cagcttcagt tcacttatga cacactgcgg ggctacataa acagggctct ggcacagata  1440
gccgaggctt gctgtgtgga ccagcggaga accctggagg tatttaaaga actgtctaag  1500
atcaacccct ctgcgattct gagcgctatt tacaacaaac ccattgccgc acgcttcatg  1560
ggggacgtcc tcggtcttgc ctcctgtgtg acaattaacc agacgagcgt gaaggtgctg  1620
cgagatatga acgtgaagga atcccctggg cggtgttaca gtaggcctgt ggtgattttc  1680
aacttcgcca actcttcctg tgtccaatac ggtcaactcg gtgaagataa cgagattctg  1740
ctgggcaatc atcggacaga agaatgccag ttgccaagcc ttaaaatctt tattgcagga  1800
aattcagcct acgagtacgt cgactatctg tttaaaagaa tgattgatct gagcagcatt  1860
```

```
tccactgtgg acagtatgat cgcactggac attgaccctt tggaaaacac cgattttcgc  1920
gtccttgagc tgtactccca gaaagaactg cgctctagca acgtctttga tcttgaggag  1980
atcatgaggg agtttaactc ttataaacag agggtgaagt atgtggagga taaagtggtc  2040
aagatcgagg agatcctgtc caagcagtac cacatcgaga acgagatcgc ccgcatcaag  2100
aagctgatcg gc                                                      2112

SEQ ID NO: 263         moltype = AA  length = 704
FEATURE                Location/Qualifiers
REGION                 1..704
                       note = Synthetic peptide sequence
source                 1..704
                       mol_type = protein
                       organism = synthetic construct
SEQUENCE: 263
VSSSSTRGTS ATHSHHSSHT TSAAHSRSGS VSQRVTSSQT VSHGVNETIY NTTLKYGDVV  60
GVNTTKYPYR VCSMAQGTDL IRFERNIVCT SMKPINEDLD EGIMVVYKRN IVAHTFKVRV  120
YQKVLTFRRS YAGHRTTYLL GSNTEYVAPP MWEIHHINSH SQCYSSYSRV IAGTVFVAYH  180
RDSYENKTMQ LMPDCYSNTH STRYVTVKDQ WHSRGSTALY RETSNLNCMV TITTARSKYP  240
YHFFATSTGD VVDISPFYNG TNRNASYFGE NADKFFIFPN YTIVSDFGRP NSALETHRLV  300
AFLERADSVI SWDIQDEKNV TCQLTFWEAS ERTIRSEAED SYHFSSAKMT ATFLSKKQEV  360
NMSDSALDCV RDEAINKLQQ IFNTSYNQTY EKYGNVSVFE TTGGLVVFWQ GIKQKSLVEL  420
ERLANRSSLN LTHNRTKRST DGNNATHLSN MESVHNLVYA QLQFTYDTLR GYINRALAQI  480
AEAWCVDQRR TLEVFKELSK ICPSAILSAI YNKPIAARFM GDVLGLASCV TINQTSVKVL  540
RDMNVKESPG RCYSRPVVIF NFANSSCVQY GQLGEDNEIL LGNHRTEECQ LPSLKIFIAG  600
NSAYEYVDYL FKRMIDLSSI STVDSMIALD IDPLENTDFR VLELYSQKEL RSSNVFDLEE  660
ICREFNSYKQ RVKYVEDKVV KIEEILSKQY HIENEIARIK KLIG                   704

SEQ ID NO: 264         moltype = DNA  length = 2112
FEATURE                Location/Qualifiers
misc_feature           1..2112
                       note = Synthetic nucleotide sequence
source                 1..2112
                       mol_type = other DNA
                       organism = synthetic construct
SEQUENCE: 264
gtatcctcca gctctactag aggaacgagc gcgacccatt cacaccacag ctcccacact  60
acgagcgctg cccattctag gagtggctcc gtgtcacaac gcgttactag tagccagacc  120
gtgtctcacg gcgtcaacga gacaatttac aacacgacgc tgaaatacgg cgatgtcgtg  180
ggtgtgaata ctaccaagta cccctataga gtctgtagca tggcccaggg caccgacctg  240
atcaggttcg aacggaacat cgtttgcaca tcaatgaagc ctatcaacga agaccttgac  300
gaggggatta tggtggtata caaacggaat atcgtggctc acaccttcaa agtgcgagtg  360
tatcagaagg ttctgacatt ccgaagaagt tacgccggtc atcgtaccac ctatctgctg  420
ggctccaaca ctgagtacgt ggcgccccca atgtgggaaa tccaccacat caacagccat  480
tcacagtgct actcttccta cagcagggtg attgcgggca cagtgtttgt ggcctaccac  540
agggacagct atgagaacaa gacgatgcag ttgatgccag attgttacag taacactcac  600
agtacacggt atgttacagt taaggatcag tggcattcac gcggaagcac agcactgtat  660
agagagacct ctaatttgaa ttgtatggta actatcacta ctgcacggag caagtaccct  720
tatcatttct ttgctacaag cacgggcgat gtggtagaca tcagcccctt ctataatggc  780
acaaatcgga acgcaagcta tttcggggag aacgccgaca agtttttcat ttttcctaat  840
tatactattg tttctgactt cgggagaccc aactccgccc tggaaactca cagactggtt  900
gcgttcctcg aaagagcaga ttctgtgata tcctgggaca ttcaggatga aaagaacgtc  960
acgtgtcagc tgaccttctg ggaggcctca gagcggacga tccggtctga ggccgaggac  1020
tcttaccact ttagcagcgc caagatgacc gcaaccttcc tgtctaaaaa acaggaagtg  1080
aacatgtccg attctgcttt ggactgcgtt cgcgatgagg ccatcaacaa gcttcaacaa  1140
attttcaata cctcctacaa tcagacatat gaaaaatacg gaaacgtgag tgtctttgaa  1200
accaccgggg gcctggtcgt gttctggcag ggtatcaaac agaagagcct ggtggaactg  1260
gaacgcctgg ccaacagaag cagtttgaac ctcacgcaca accggacaaa gaggagcacc  1320
gacggaaaca atgctacaca cctttccaac atggagtctg tccacaatct ggtttatgca  1380
cagcttcagt tcacttatga cacactgcgg ggctacataa acagggctct ggcacagata  1440
gccgaggctt ggtgtgtgga ccagcggaga accctggagg tatttaaaga actgtctaag  1500
atctgtccct ctgcgattct gagcgctatt tacaacaaac ccattgccgc acgcttcatg  1560
ggggacgtcc tcggtcttgc ctcctgtgtg acaattaacc agacgagcgt gaaggtgctg  1620
cgagatatga acgtgaagga atcccctggg cggtgttaca gtaggcctgt ggtgattttc  1680
aacttcgcca actcttcctg tgtccaatac ggtcaactcg gtgaagataa cgagattctg  1740
ctgggcaatc atcggacaga agaatgccag ttgccaagcc ttaaaatctt tattgcagga  1800
aattcagcct acgagtacgt cgactatctg tttaaaagaa tgattgatct gagcagcatt  1860
tccactgtgg acagtatgat cgcactggac attgaccctt tggaaaacac cgattttcgc  1920
gtccttgagc tgtactccca gaaagaactg cgctctagca acgtctttga tcttgaggag  1980
atctgtaggg agtttaactc ttataaacag agggtgaagt atgtggagga taaagtggtc  2040
aagatcgagg agatcctgtc caagcagtac cacatcgaga acgagatcgc ccgcatcaag  2100
aagctgatcg gc                                                      2112

SEQ ID NO: 265         moltype = AA  length = 624
FEATURE                Location/Qualifiers
REGION                 1..624
                       note = Synthetic peptide sequence
source                 1..624
                       mol_type = protein
                       organism = synthetic construct
```

SEQUENCE: 265
VSSSSTRGTS ATHSHHSSHT TSAAHSRSGS VSQRVTSSQT VSHGVNETIY NTTLKYGDVV 60
GVNTTKYPYR VCSMAQGTDL IRFERNIVCT SMKPINEDLD EGIMVVYKRN IVAHTFKVRV 120
YQKVLTFRRS YAGHRTTYLL GSNTEYVAPP MWEIHHINSH SQCYSSYSRV IAGTVFVAYH 180
RDSYENKTMQ LMPDCYSNTH STRYVTVKDQ WHSRGSTALY RETSNLNCMV TITTARSKYP 240
YHFFATSTGD VVDISPFYNG TNRNASYFGE NADKFFIFPN YTIVSDFGRP NSALETHRLV 300
AFLERADSVI SWDIQDEKNV TCQLTFWEAS ERTIRSEAED SYHFSSAKCT ATFLSKKQEV 360
NMSDSALDCV RDEAINKLQQ IFNTSYNQTY EKYGNVSVFE TTGGLVVFWQ GIKQKSLVEL 420
ERLANRSSLN LTHNRTKRST DGNNATHLSN MESVHNLVYA QLQFTYDTLR GYINRALAQI 480
AEACCVDQRR TLEVFKELSK INPSAILSAI YNKPIAARFM GDVLGLASCV TINQTSVKVL 540
RDMNVKESPG RCYSRPVVIF NFANSSCVQY GQLGEDNEIL LGNHRTEECQ LPSLKIFIAG 600
NSAYEYVDYL FKRMIDLSSI STVD 624

SEQ ID NO: 266 moltype = DNA length = 1872
FEATURE Location/Qualifiers
misc_feature 1..1872
note = Synthetic nucleotide sequence
source 1..1872
mol_type = other DNA
organism = synthetic construct
SEQUENCE: 266
gtatcctcca gctctactag aggaacgagc gcgacccatt cacaccacag ctcccacact 60
acgagcgctg cccattctag gagtggctcc gtgtcacaac gcgttactag tagccagacc 120
gtgtctcacg gcgtcaacga gacaatttac aacacgacgc tgaaatacgg cgatgtcgtg 180
ggtgtgaata ctaccaagta cccctataga gtctgtagca tggcccaggg caccgacctg 240
atcaggttcg aacggaacat cgtttgcaca tcaatgaagc ctatcaacga agaccttgac 300
gaggggatta tggtggtata caaacggaat atcgtggctc acaccttcaa agtgcgagtg 360
tatcagaagg ttctgacatt ccgaagaagt tacgccggtc atcgtaccac ctatctgctg 420
ggctccaaca ctgagtacgt ggcgccccca atgtgggaaa tccaccacat caacagccat 480
tcacagtgct actcttccta cagcagggtg attgcgggca cagtgtttgt ggcctaccac 540
agggacagct atgagaacaa gacgatgcag ttgatgccag attgttacag taacactcac 600
agtacacggt atgttacagt taaggatcag tggcattcac gcggaagcac agcactgtat 660
agagagacct ctaatttgaa ttgtatggta actatcacta ctgcacggag caagtaccct 720
tatcatttct ttgctacaag cacgggcgat gtggtagaca tcagcccctt ctataatggc 780
acaaatcgga acgcaagcta tttcggggag aacgccgaca agtttttcat ttttcctaat 840
tatactattg tttctgactt cgggagaccc aactccgccc tggaaactca cagactggtt 900
gcgttcctcg aaagagcaga ttctgtgata tcctgggaca ttcaggatga aaagaacgtc 960
acgtgtcagc tgaccttctg ggaggcctca gagcggacga tccggtctga ggccgaggac 1020
tcttaccact ttagcagcgc caagtgcacc gcaaccttcc tgtctaaaaa acaggaagtg 1080
aacatgtccg attctgcttt ggactgcgtt cgcgatgagg ccatcaacaa gcttcaacaa 1140
attttcaata cctcctacaa tcagacatat gaaaaatacg gaaacgtgag tgtctttgaa 1200
accaccgggg gcctggtcgt gttctggcag ggtatcaaac agaagagcct ggtggaactg 1260
gaacgcctgg ccaacagaag cagtttgaac ctcacgcaca accggacaaa gaggagcacc 1320
gacggaaaca atgctacaca cctttccaac atggagtctg tccacaatct ggtttatgca 1380
cagcttcagt tcacttatga cacactgcgg ggctacataa acagggctct ggcacagata 1440
gccgaggctt gctgtgtgga ccagcggaga accctggagg tatttaaaga actgtctaag 1500
atcaacccct ctgcgattct gagcgctatt tacaacaaac ccattgccgc acgcttcatg 1560
ggggacgtcc tcggtcttgc ctcctgtgtg acaattaacc agacgagcgt gaaggtgctg 1620
cgagatatga acgtgaagga atcccctggg cggtgttaca gtaggcctgt ggtgattttc 1680
aacttcgcca actcttcctg tgtccaatac ggtcaactcg gtgaagataa cgagattctg 1740
ctgggcaatc atcggacaga agaatgccag ttgccaagcc ttaaaatctt tattgcagga 1800
aattcagcct acgagtacgt cgactatctg tttaaaagaa tgattgatct gagcagcatt 1860
tccactgtgg ac 1872

SEQ ID NO: 267 moltype = AA length = 685
FEATURE Location/Qualifiers
REGION 1..685
note = Synthetic peptide sequence
source 1..685
mol_type = protein
organism = synthetic construct
SEQUENCE: 267
VSSSSTRGTS ATHSHHSSHT TSAAHSRSGS VSQRVTSSQT VSHGVNETIY NTTLKYGDVV 60
GVNTTKYPYR VCSMAQGTDL IRFERNIVCT SMKPINEDLD EGIMVVYKRN IVAHTFKVRV 120
YQKVLTFRRS YAYIHTTYLL GSNTEYVAPP MWEIHHINSH SQCYSSYSRV IAGTVFVAYH 180
RDSYENKTMQ LMPDDYSNTH STRYVTVKDQ WHSRGSTWLY RETCNLNCMV TITTARSKYP 240
YHFFATSTGD VVDISPFYNG TNRNASYFGE NADKFFIFPN YTIVSDFGRP NSALETHRLV 300
AFLERADSVI SWDIQDEKNV TCQLTFWEAS ERTIRSEAED SYHFSSAKMT ATFLSKKQEV 360
NMSDSALDCV RDEAINKLQQ IFNTSYNQTY EKYGNVSVFE TTGGLVVFWQ GIKQKSLVEL 420
ERLANRSSLN LTHNRTKRST DGNNATHLSN MESVHNLVYA QLQFTYDTLR GYINRALAQI 480
AEAWCVDQRR TLEVFKELSK INPSAILSAI YNKPIAARFM GDVLGLASCV TINQTSVKVL 540
RDMNVKESPG RCYSRPVVIF NFANSSYVQY GQLGEDNEIL LGNHRTEECQ LPSLKIFIAG 600
NSAYEYVDYL FKRMIDLSSI STVDSMIALD IDPLENTDFR VLELYSQKEL RSSNVFDLEE 660
IMREFNSYKQ RVKYVEDKVV DPLPP 685

SEQ ID NO: 268 moltype = AA length = 22
FEATURE Location/Qualifiers
REGION 1..22
note = Synthetic peptide sequence

```
source                1..22
                      mol_type = protein
                      organism = synthetic construct
SEQUENCE: 268
MESRIWCLVV CVNLCIVCLG AA                                            22

SEQ ID NO: 269        moltype = AA  length = 24
FEATURE               Location/Qualifiers
REGION                1..24
                      note = Synthetic peptide sequence
source                1..24
                      mol_type = protein
                      organism = synthetic construct
SEQUENCE: 269
KIEEILSKQY HIENEIARIK KLIG                                          24

SEQ ID NO: 270        moltype = DNA  length = 72
FEATURE               Location/Qualifiers
misc_feature          1..72
                      note = Synthetic nucleotide sequence
source                1..72
                      mol_type = other DNA
                      organism = synthetic construct
SEQUENCE: 270
aagatcgagg agatcctgtc caagcagtac cacatcgaga acgagatcgc ccgcatcaag  60
aagctgatcg gc                                                       72

SEQ ID NO: 271        moltype = AA  length = 27
FEATURE               Location/Qualifiers
REGION                1..27
                      note = Synthetic peptide sequence
source                1..27
                      mol_type = protein
                      organism = synthetic construct
SEQUENCE: 271
GYIPEAPRDG QAYVRKDGEW VLLSTFL                                       27

SEQ ID NO: 272        moltype = AA  length = 31
FEATURE               Location/Qualifiers
REGION                1..31
                      note = Synthetic peptide sequence
source                1..31
                      mol_type = protein
                      organism = synthetic construct
SEQUENCE: 272
RIKQIEDKIE EILSKQYHIE NEIARIKKLI G                                  31

SEQ ID NO: 273        moltype = AA  length = 17
FEATURE               Location/Qualifiers
REGION                1..17
                      note = Synthetic peptide sequence
source                1..17
                      mol_type = protein
                      organism = synthetic construct
SEQUENCE: 273
KIYHIENEIA RIKKLIG                                                  17

SEQ ID NO: 274        moltype = AA  length = 32
FEATURE               Location/Qualifiers
REGION                1..32
                      note = Synthetic peptide sequence
source                1..32
                      mol_type = protein
                      organism = synthetic construct
SEQUENCE: 274
LSAIGGYIPE APRDGQAYVR KDGEWVLLST FL                                 32

SEQ ID NO: 275        moltype = AA  length = 6
FEATURE               Location/Qualifiers
source                1..6
                      mol_type = protein
                      organism = Human cytomegalovirus
SEQUENCE: 275
MIALDI                                                              6
```

-continued

```
SEQ ID NO: 276          moltype = AA  length = 6
FEATURE                 Location/Qualifiers
source                  1..6
                        mol_type = protein
                        organism = synthetic construct
SEQUENCE: 276
GSGKDG                                                        6
```

The invention claimed is:

1. A human cytomegalovirus (HCMV) immunogenic composition comprising: RNA formulated in a lipid nanoparticle, wherein the RNA encodes an amino acid sequence for a glycoprotein B (gB) protein comprising at least one engineered disulfide mutation, wherein the gB protein comprises a cysteine mutation selected from the group consisting of: D217C, Y589C, M371C, W506C, N524C, and M684C, numbered according to SEQ ID NO:1.

2. The HCMV immunogenic composition of claim 1, wherein the lipid nanoparticle comprises a cationic lipid, a polyethylene glycol (PEG)-modified lipid, a sterol, and a non-cationic lipid.

3. The HCMV immunogenic composition of claim 2, wherein the cationic lipid is an ionizable cationic lipid, the non-cationic lipid is a neutral lipid, and the sterol is a cholesterol.

4. The HCMV immunogenic composition of claim 2, wherein the cationic lipid is selected from the group consisting of: 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

5. The HCMV immunogenic composition of claim 2, wherein the lipid nanoparticle has a molar ratio of about 20-60% cationic lipid, about 5-25% non-cationic lipid, about 25-55% sterol, and about 0.5-15% PEG-modified lipid.

6. The HCMV immunogenic composition of claim 1, wherein the lipid nanoparticle has a polydispersity value of less than 0.4.

7. The HCMV immunogenic composition of claim 1, wherein the lipid nanoparticle has a net neutral charge at a neutral pH.

8. The HCMV immunogenic composition of claim 1, wherein the lipid nanoparticle has a mean diameter of 50-200 nm.

9. A human cytomegalovirus (HCMV) immunogenic composition comprising: RNA formulated in a lipid nanoparticle, wherein the RNA encodes an amino acid sequence for a glycoprotein B (gB) protein comprising at least two amino acid mutations, and wherein said at least two amino acid mutations comprise:

a) at least one engineered disulfide mutation selected from the group consisting of: D217C and Y589C, and M371C and W506C, numbered according to SEQ ID NO:1; and b) at least one additional mutation selected from the group consisting of:

i) substitution of YIH at positions 155-157 with GHR;

ii) substitution of W at position 240 with A;

iii) substitution of C at position 246 with S;

iv) substitution of P at position 655 with S;

v) substitution of F at position 678 with S;

vi) substitution of L at position 680 with T;

vii) substitution of R at position 685 with A;

viii) substitution of MIALDI (SEQ ID NO: 275) at positions 648-653 with GSGKDG (SEQ ID NO: 276);

ix) substitution of R at position 693 with V;

x) substitution of I at positions 767 and 768 with C;

xi) substitution of D at position 703 and P at position 704 with C; and xii) substitution of Y at position 696 and V at position 697 with C, wherein the positions are numbered according to SEQ ID NO: 1.

10. The HCMV immunogenic composition of claim 9, wherein the lipid nanoparticle comprises a cationic lipid, a PEG-modified lipid, a sterol, and a non-cationic lipid.

11. The HCMV immunogenic composition of claim 10, wherein the cationic lipid is an ionizable cationic lipid, the non-cationic lipid is a neutral lipid, and the sterol is a cholesterol.

12. The HCMV immunogenic composition of claim 10, wherein the cationic lipid is selected from the group consisting of: 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

13. The HCMV immunogenic composition of claim 10, wherein the lipid nanoparticle has a molar ratio of about 20-60% cationic lipid, about 5-25% non-cationic lipid, about 25-55% sterol, and about 0.5-15% PEG-modified lipid.

14. A human cytomegalovirus (HCMV) immunogenic composition comprising: RNA formulated in a lipid nanoparticle, wherein the RNA encodes an amino acid sequence for a glycoprotein B (gB) protein comprising at least one engineered disulfide mutation selected from the group consisting of: D217C and Y589C, and M371C and W506C, numbered according to SEQ ID NO:1.

15. The HCMV immunogenic composition of claim 14, wherein the gB protein comprises at least two engineered disulfide mutations.

16. The HCMV immunogenic composition of claim 14, wherein the gB protein comprises an additional mutation selected from the group consisting of:

(1) substitution of YIH at positions 155-157 with GHR;

(2) substitution of W at position 240 with A; and (3) substitution of C at position 246 with S, wherein the positions are numbered according to SEQ ID NO: 1.

17. The HCMV immunogenic composition of claim 14, wherein the gB comprises the following mutations: D217C, Y589C, M371C, W506C, Y155G, I156H, H157R, W240A, and C246S, wherein the positions are numbered according to SEQ ID NO: 1.

18. The HCMV immunogenic composition of claim 14, wherein the lipid nanoparticle comprises a cationic lipid, a PEG-modified lipid, a sterol, and a non-cationic lipid.

19. The HCMV immunogenic composition of claim 18, wherein the cationic lipid is an ionizable cationic lipid, the non-cationic lipid is a neutral lipid, and the sterol is a cholesterol.

20. The HCMV immunogenic composition of claim 18, wherein the lipid nanoparticle has a molar ratio of about 20-60% cationic lipid, about 5-25% non-cationic lipid, about 25-55% sterol, and about 0.5-15% PEG-modified lipid.

* * * * *